US012509672B2

(12) United States Patent
Babe et al.

(10) Patent No.: US 12,509,672 B2
(45) Date of Patent: Dec. 30, 2025

(54) SUBTILISIN VARIANTS HAVING IMPROVED STABILITY

(71) Applicant: DANISCO US INC, Palo Alto, CA (US)

(72) Inventors: Lilia Maria Babe, Palo Alto, CA (US); Viktor Yuryevich Alekseyev, Leiden (NL); Joshua Roy Basler, Palo Alto, CA (US); H. Billur Engin, Palo Alto, CA (US); David A. Estell, Palo Alto, CA (US); Roopa Santosh Ghirnikar, Palo Alto, CA (US); Frits Goedegebuur, Oegstgeest (NL); Thijs Kaper, Palo Alto, CA (US); Harm Mulder, Oegstgeest (NL); Sina Pricelius, Oegstgeest (NL); Nils Henning Redestig, Oegstgeest (NL); Sander Van Stigt Thans, Oegstgeest (NL)

(73) Assignee: Danisco US Inc., Palo Alto, CA (US)

( * ) Notice: Subject to any disclaimer, the term of this patent is extended or adjusted under 35 U.S.C. 154(b) by 983 days.

(21) Appl. No.: 17/295,959

(22) PCT Filed: Nov. 25, 2019

(86) PCT No.: PCT/US2019/062939
§ 371 (c)(1),
(2) Date: May 21, 2021

(87) PCT Pub. No.: WO2020/112599
PCT Pub. Date: Jun. 4, 2020

(65) Prior Publication Data

US 2023/0028935 A1 Jan. 26, 2023

Related U.S. Application Data

(60) Provisional application No. 62/772,271, filed on Nov. 28, 2018.

(51) Int. Cl.
*C12N 9/54* (2006.01)
*C11D 3/386* (2006.01)

(52) U.S. Cl.
CPC ............ *C12N 9/54* (2013.01); *C11D 3/38636* (2013.01); *C12Y 304/21062* (2013.01); *C11D 3/386* (2013.01)

(58) Field of Classification Search
CPC ...... C12N 9/54; C11D 3/38636; C11D 3/386; C12Y 304/21062
See application file for complete search history.

(56) References Cited

U.S. PATENT DOCUMENTS

| | | | | |
|---|---|---|---|---|
| 6,929,939 | B2 * | 8/2005 | Estell | A61Q 19/10 435/222 |
| 7,476,528 | B2 * | 1/2009 | Estell | A61P 37/08 435/219 |
| 8,183,024 | B2 * | 5/2012 | Cascao-Pereira | C11D 17/0086 435/212 |
| 8,530,219 | B2 * | 9/2013 | Estell | C11D 3/3942 435/219 |
| 8,728,790 | B2 * | 5/2014 | Basler | C12N 9/52 435/226 |
| 8,753,861 | B2 * | 6/2014 | Cascao-Pereira | C12N 9/54 435/221 |
| 9,096,838 | B2 * | 8/2015 | Cascao-Pereira | C11D 3/38681 |
| 9,434,915 | B2 * | 9/2016 | Estell | C11D 3/38618 |
| 9,856,466 | B2 * | 1/2018 | Amin | C11D 3/386 |
| 10,093,887 | B2 * | 10/2018 | Aehle | C12N 9/50 |
| 10,563,189 | B2 * | 2/2020 | Basler | C12N 9/54 |
| 11,447,762 | B2 * | 9/2022 | Alekseyev | C11D 3/38681 |
| 11,473,075 | B2 * | 10/2022 | Estell | C12Y 304/21062 |
| 11,499,146 | B2 * | 11/2022 | Babe | C12Y 304/21062 |
| 11,661,567 | B2 * | 5/2023 | Marquez | C11D 3/386 510/392 |
| 11,946,080 | B2 * | 4/2024 | Bott | C11D 3/386 |
| 11,946,081 | B2 * | 4/2024 | Babe | C12N 9/54 |
| 12,104,187 | B2 * | 10/2024 | Babe | C11D 3/38618 |

FOREIGN PATENT DOCUMENTS

| | | | | |
|---|---|---|---|---|
| EP | 0398539 B1 | | 8/1996 | |
| WO | WO-2016145428 A1 | * | 9/2016 | C11D 3/386 |
| WO | 2017/192692 A1 | | 11/2017 | |

OTHER PUBLICATIONS

UniProt Database Accession No. A0A384HMRO (Nov. 2018, 1 page) (Year: 2018).*
GenPept Accession No. WP_013351733 (Jan. 12, 2017, 1 page) (Year: 2017).*
Goddette et al. (J Mol Biol, 1992, 228:580) (Year: 1992).*
UniProt Accession No. SUBB_BACLE (Nov. 2, 2016, 2 pages) (Year: 2016).*
Database Accession No. AAR08307, Modified substilin gene product, XP002797090, Feb. 18, 1991.
Database Accession No. BDJ32510, *Bacillus* sp. AprL subtilisin protein, SEQ ID 35, XP002797091, Dec. 29, 2016.
Huimin Zhao et al., Molecular evolution by staggered extension process (StEP) in vitro recombination.
International Search Report and Written Opinion—PCT/US2019/062939—mailed Jan. 4, 2020.

* cited by examiner

*Primary Examiner* — David Steadman
*Assistant Examiner* — Joseph R Spangler

(57) ABSTRACT

Disclosed herein is one or more subtilisin variant, nucleic acid encoding same, and compositions and methods related to the production and use thereof, including one or more subtilisin variant that has improved stability compared to one or more reference subtilisin.

21 Claims, 6 Drawing Sheets

Specification includes a Sequence Listing.

SEQUENCE LISTING

```
<160> NUMBER OF SEQ ID NOS: 49

<210> SEQ ID NO 1
<211> LENGTH: 275
<212> TYPE: PRT
<213> ORGANISM: Bacillus amyloliquefaciens

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110
```

```
Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275


<210> SEQ ID NO 2
<211> LENGTH: 274
<212> TYPE: PRT
<213> ORGANISM: Bacillus licheniformis

<400> SEQUENCE: 2

Ala Gln Thr Val Pro Tyr Gly Ile Pro Leu Ile Lys Ala Asp Lys Val
1               5                   10                  15

Gln Ala Gln Gly Phe Lys Gly Ala Asn Val Lys Val Ala Val Leu Asp
            20                  25                  30

Thr Gly Ile Gln Ala Ser His Pro Asp Leu Asn Val Val Gly Gly Ala
        35                  40                  45

Ser Phe Val Ala Gly Glu Ala Tyr Asn Thr Asp Gly Asn Gly His Gly
    50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                85                  90                  95

Ser Ser Gly Ser Gly Ser Tyr Ser Gly Ile Val Ser Gly Ile Glu Trp
            100                 105                 110

Ala Thr Thr Asn Gly Met Asp Val Ile Asn Met Ser Leu Gly Gly Ala
        115                 120                 125

Ser Gly Ser Thr Ala Met Lys Gln Ala Val Asp Asn Ala Tyr Ala Arg
    130                 135                 140

Gly Val Val Val Val Ala Ala Ala Gly Asn Ser Gly Ser Ser Gly Asn
145                 150                 155                 160

Thr Asn Thr Ile Gly Tyr Pro Ala Lys Tyr Asp Ser Val Ile Ala Val
                165                 170                 175

Gly Ala Val Asp Ser Asn Ser Asn Arg Ala Ser Phe Ser Ser Val Gly
            180                 185                 190

Ala Glu Leu Glu Val Met Ala Pro Gly Ala Gly Val Tyr Ser Thr Tyr
```

```
        195                 200                 205

Pro Thr Asn Thr Tyr Ala Thr Leu Asn Gly Thr Ser Met Ala Ser Pro
    210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                245                 250                 255

Gly Ser Ser Phe Tyr Tyr Gly Lys Gly Leu Ile Asn Val Glu Ala Ala
            260                 265                 270

Ala Gln


<210> SEQ ID NO 3
<211> LENGTH: 269
<212> TYPE: PRT
<213> ORGANISM: Bacillus lentus

<400> SEQUENCE: 3

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265


<210> SEQ ID NO 4
<211> LENGTH: 269
<212> TYPE: PRT
```

<213> ORGANISM: Bacillus gibsonii

<400> SEQUENCE: 4

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Ala His Ser Asp Leu Asn Ile Arg Gly Gly Ala Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Asn Ala Glu Leu Tyr Ala Val Lys Val Leu Gly Ala
                85                  90                  95

Asn Gly Ser Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Phe
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 5
<211> LENGTH: 269
<212> TYPE: PRT
<213> ORGANISM: artificial sequence
<220> FEATURE:
<223> OTHER INFORMATION: Synthesized sequence- amino acid sequence of mature BSP-00801 protease

<400> SEQUENCE: 5

```
Gln Gln Thr Val Pro Trp Gly Ile Thr Arg Val Gln Ala Pro Ala Val
1               5                   10                  15

His Asn Arg Gly Ile Thr Gly Ser Gly Val Arg Val Ala Ile Leu Asp
            20                  25                  30

Ser Gly Ile Ser Thr His Glu Asp Leu Asn Val Arg Gly Gly Val Ser
        35                  40                  45

Phe Val Pro Gly Glu Pro Thr Thr Ala Asp Leu Asn Gly His Gly Thr
    50                  55                  60

His Val Ala Gly Thr Val Ala Ala Leu Asn Asn Ser Ile Gly Val Val
```

```
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Ser Thr Leu Glu Arg Ala Val Asn Tyr Ala Thr Ser Arg Asp
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Ala
    210                 215                 220

Ala Ala Leu Val Lys Gln Arg Tyr Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Glu Ala Ala Thr Arg
            260                 265
```

<210> SEQ ID NO 6
<211> LENGTH: 275
<212> TYPE: PRT
<213> ORGANISM: artificial sequence
<220> FEATURE:
<223> OTHER INFORMATION: Synthesized sequence- amino acid sequence of mature LG12 protease from Bacillus sp.

<400> SEQUENCE: 6

```
Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
    50                  55                  60

Gly Thr His Val Ala Gly Thr Val Ala Ala Leu Asn Asn Thr Thr Gly
65                  70                  75                  80

Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ser Asn Gly Met Asn Val Ile Asn Met Ser Leu Gly Gly
        115                 120                 125

Ser Ser Gly Ser Thr Ala Leu Gln Gln Ala Cys Asn Asn Ala Tyr Asn
    130                 135                 140

Arg Gly Ile Val Val Ile Ala Ala Ala Gly Asn Ser Gly Ser Ser Gly
145                 150                 155                 160
```

```
Asn Arg Asn Thr Met Gly Tyr Pro Ala Arg Tyr Ser Ser Val Ile Ala
                165                 170                 175

Val Gly Ala Val Ser Ser Asn Asn Thr Arg Ala Ser Phe Ser Ser Val
            180                 185                 190

Gly Ser Glu Leu Glu Val Met Ala Pro Gly Val Asn Ile Leu Ser Thr
        195                 200                 205

Thr Pro Gly Asn Asn Tyr Ala Ser Phe Asn Gly Thr Ser Met Ala Ala
    210                 215                 220

Pro His Val Ala Gly Ala Ala Ala Leu Ile Lys Ala Lys Tyr Pro Ser
225                 230                 235                 240

Met Thr Asn Val Gln Ile Arg Glu Arg Leu Lys Asn Thr Ala Thr Asn
                245                 250                 255

Leu Gly Asp Pro Phe Phe Tyr Gly Lys Gly Val Ile Asn Val Glu Ser
            260                 265                 270

Ala Leu Gln
        275


<210> SEQ ID NO 7
<211> LENGTH: 275
<212> TYPE: PRT
<213> ORGANISM: artificial sequence
<220> FEATURE:
<223> OTHER INFORMATION: Synthesized sequence- amino acid sequence of
      mature WP_010192403 protease from Bacillus sp. m3-13

<400> SEQUENCE: 7

Ala Gln Thr Val Pro Trp Gly Ile Pro His Ile Lys Ala Asp Lys Ala
1               5                   10                  15

His Ala Ser Gly Val Thr Gly Ser Gly Val Lys Val Ala Val Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
    50                  55                  60

Gly Thr His Val Ala Gly Thr Val Ala Ala Leu Asn Asn Thr Thr Gly
65                  70                  75                  80

Val Leu Gly Val Ala Tyr Asn Ala Asp Leu Tyr Ala Val Lys Val Leu
                85                  90                  95

Ser Ala Ser Gly Ser Gly Thr Leu Ser Gly Ile Ala Gln Gly Ile Glu
            100                 105                 110

Trp Ser Ile Ala Asn Asp Met Asp Val Ile Asn Met Ser Leu Gly Gly
        115                 120                 125

Ser Thr Gly Ser Thr Ala Leu Gln Gln Ala Cys Asp Asn Ala Tyr Ala
    130                 135                 140

Ser Gly Ile Val Val Val Ala Ala Ala Gly Asn Ser Gly Ser Lys Gly
145                 150                 155                 160

Lys Arg Asn Thr Met Gly Tyr Pro Ala Arg Tyr Ser Ser Val Ile Ala
                165                 170                 175

Val Gly Ala Val Asp Ser Ser Asn Asn Arg Ala Ser Phe Ser Ser Val
            180                 185                 190

Gly Ser Glu Leu Glu Val Met Ala Pro Gly Val Ser Ile Leu Ser Thr
        195                 200                 205

Thr Pro Gly Asn Asn Tyr Ser Ser Phe Asn Gly Thr Ser Met Ala Ser
    210                 215                 220

Pro His Val Ala Gly Ala Ala Ala Leu Ile Lys Ala Lys Tyr Pro Ser
225                 230                 235                 240
```

```
Met Thr Asn Val Gln Ile Arg Glu Lys Leu Lys Asn Thr Ala Thr Asn
                245                 250                 255

Leu Gly Asp Ala Phe Tyr Tyr Gly His Gly Val Ile Asn Val Glu Ser
            260                 265                 270

Ala Leu Gln
        275


<210> SEQ ID NO 8
<211> LENGTH: 275
<212> TYPE: PRT
<213> ORGANISM: Bacillus subtilis

<400> SEQUENCE: 8

Ala Gln Ser Val Pro Tyr Gly Ile Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Asn Val Arg Gly Gly Ala
        35                  40                  45

Ser Phe Val Pro Ser Glu Thr Asn Pro Tyr Gln Asp Gly Ser Ser His
    50                  55                  60

Gly Thr His Val Ala Gly Thr Ile Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
        275


<210> SEQ ID NO 9
<211> LENGTH: 275
<212> TYPE: PRT
<213> ORGANISM: Bacillus xiamenensis

<400> SEQUENCE: 9
```

```
Ala Gln Thr Val Pro Tyr Gly Ile Pro Gln Ile Lys Ala Pro Ala Val
1               5                   10                  15

His Ala Gln Gly Tyr Lys Gly Ala Asn Val Lys Val Ala Val Leu Asp
            20                  25                  30

Thr Gly Ile His Ala Ala His Pro Asp Leu Asn Val Ala Gly Gly Ala
        35                  40                  45

Ser Phe Val Pro Ser Glu Pro Asn Ala Thr Gln Asp Phe Gln Ser His
    50                  55                  60

Gly Thr His Val Ala Gly Thr Ile Ala Ala Leu Asp Asn Thr Ile Gly
65                  70                  75                  80

Val Leu Gly Val Ala Pro Ser Ala Ser Leu Tyr Ala Val Lys Val Leu
                85                  90                  95

Asp Arg Asn Gly Asp Gly Gln Tyr Ser Trp Ile Ile Ser Gly Ile Glu
            100                 105                 110

Trp Ala Val Ala Asn Asn Met Asp Val Ile Asn Met Ser Leu Gly Gly
        115                 120                 125

Pro Ser Gly Ser Thr Ala Leu Lys Asn Ala Val Asp Thr Ala Asn Asn
    130                 135                 140

Arg Gly Val Val Val Val Ala Ala Ala Gly Asn Ser Gly Ser Ser Gly
145                 150                 155                 160

Ser Thr Ser Thr Val Gly Tyr Pro Ala Lys Tyr Asp Ser Thr Ile Ala
                165                 170                 175

Val Ala Asn Val Asn Ser Asn Asn Val Arg Asn Ser Ser Ser Ser Ala
            180                 185                 190

Gly Pro Glu Leu Asp Val Ser Ala Pro Gly Thr Ser Ile Leu Ser Thr
        195                 200                 205

Val Pro Ser Ser Gly Tyr Ala Ser Tyr Thr Gly Thr Ser Met Ala Ser
    210                 215                 220

Pro His Val Ala Gly Ala Ala Ala Leu Ile Leu Ser Lys His Pro Asn
225                 230                 235                 240

Leu Thr Asn Thr Gln Val Arg Gln Arg Leu Glu Asn Thr Ala Thr Pro
                245                 250                 255

Leu Gly Ser Ser Phe Tyr Tyr Gly Lys Gly Leu Ile Asn Val Gln Ala
            260                 265                 270

Ala Ala Asn
        275


<210> SEQ ID NO 10
<211> LENGTH: 275
<212> TYPE: PRT
<213> ORGANISM: Bacillus subtilus

<400> SEQUENCE: 10

Ala Gln Thr Thr Pro Trp Gly Ile Thr His Ile Asn Ala His Lys Ala
1               5                   10                  15

His Ser Ser Ser Val Thr Gly Ser Gly Val Lys Val Ala Val Leu Asp
            20                  25                  30

Thr Gly Ile Asp Ala Ser His Pro Asp Leu Asn Val Lys Gly Gly Ala
        35                  40                  45

Ser Phe Ile Ser Gly Glu Pro Asn Ala Leu Val Asp Thr Asn Gly His
    50                  55                  60

Gly Thr His Val Ala Gly Thr Val Ala Ala Leu Asn Asn Thr Ile Gly
65                  70                  75                  80

Val Val Gly Val Ala Tyr Asn Ala Asp Leu Tyr Ala Val Lys Val Leu
```

```
                85                  90                  95

Ser Ala Ser Gly Ser Gly Thr Leu Ser Gly Ile Ala Gln Gly Val Glu
            100                 105                 110

Trp Ala Ile Ala Asn Asn Met Asp Val Ile Asn Met Ser Leu Gly Gly
        115                 120                 125

Ser Ser Gly Ser Thr Ala Leu Lys Gln Ala Val Asp Asn Ala Tyr Ala
    130                 135                 140

Ser Gly Ile Val Val Val Ala Ala Ala Gly Asn Ser Gly Thr Arg Gly
145                 150                 155                 160

Arg Gln Asn Thr Met Gly Tyr Pro Ala Arg Tyr Ser Ser Val Ile Ala
                165                 170                 175

Val Gly Ala Val Asp Ser Asn Asn Asn Arg Ala Ser Phe Ser Ser Val
            180                 185                 190

Gly Ala Glu Leu Glu Val Met Ala Pro Gly Val Ser Val Leu Ser Thr
        195                 200                 205

Val Pro Gly Gly Gly Tyr Ala Ser Tyr Asn Gly Thr Ser Met Ala Ser
    210                 215                 220

Pro His Val Ala Gly Ala Ala Ala Leu Ile Lys Ala Lys Tyr Pro Ser
225                 230                 235                 240

Leu Ser Ala Ser Gln Ile Arg Asp Arg Leu Arg Asn Thr Ala Thr Tyr
                245                 250                 255

Leu Gly Asp Pro Phe Tyr Tyr Gly Asn Gly Val Ile Asn Val Glu Arg
            260                 265                 270

Ala Leu Gln
        275


<210> SEQ ID NO 11
<211> LENGTH: 271
<212> TYPE: PRT
<213> ORGANISM: artificial sequence
<220> FEATURE:
<223> OTHER INFORMATION: Synthesized sequence - amino acid sequence of
      mature CP474 protease

<400> SEQUENCE: 11

Ala Gln Thr Val Pro Trp Gly Ile Pro His Ile Lys Ala Asp Lys Ala
1               5                   10                  15

His Ala Ala Gly Val Thr Gly Ser Gly Val Lys Val Ala Ile Leu Asp
            20                  25                  30

Thr Gly Ile Asp Ala Asn His Ala Asp Leu Asn Val Lys Gly Gly Ala
        35                  40                  45

Ser Phe Val Ala Gly Glu Pro Asn Ala Leu Gln Asp Gly Asn Gly His
    50                  55                  60

Gly Thr His Val Ala Gly Thr Val Ala Ala Leu Asp Asn Thr Thr Gly
65                  70                  75                  80

Val Leu Gly Val Ala Pro Ser Val Ser Leu Tyr Ala Val Lys Val Leu
                85                  90                  95

Gly Ala Ser Gly Ser Gly Ser Val Ser Ser Ile Ala Gln Gly Leu Glu
            100                 105                 110

Trp Ala Gly Asn Asn Gly Met His Val Ala Asn Leu Ser Leu Gly Ser
        115                 120                 125

Pro Ser Pro Ser Ala Thr Leu Glu Gln Ala Val Asn Ser Ala Thr Ser
    130                 135                 140

Arg Gly Val Leu Val Val Ala Ala Ser Gly Asn Ser Gly Ala Gly Ser
145                 150                 155                 160
```

```
Ile Ser Tyr Pro Ala Arg Tyr Ala Asn Ala Met Ala Val Gly Ala Thr
                165                 170                 175

Asp Gln Asn Asn Asn Arg Ala Ser Phe Ser Gln Tyr Gly Ala Gly Leu
            180                 185                 190

Asp Ile Val Ala Pro Gly Val Asn Ile Leu Ser Thr Thr Pro Gly Asn
        195                 200                 205

Asn Tyr Ala Ser Leu Asn Gly Thr Ser Met Ala Ala Pro His Val Ala
    210                 215                 220

Gly Ala Ala Ala Leu Ile Lys Ala Lys Tyr Pro Ser Met Thr Asn Val
225                 230                 235                 240

Gln Ile Arg Asn Arg Leu Lys Asn Thr Ala Thr Asn Leu Gly Asp Pro
                245                 250                 255

Phe Phe Tyr Gly Lys Gly Val Ile Asn Val Glu Ser Ala Leu Gln
            260                 265                 270


<210> SEQ ID NO 12
<211> LENGTH: 275
<212> TYPE: PRT
<213> ORGANISM: artificial sequence
<220> FEATURE:
<223> OTHER INFORMATION: Synthesized sequence - amino acid sequence of
      mature ZP_00454 protease

<400> SEQUENCE: 12

Ala Gln Val Val Pro Trp Gly Ile Pro His Ile Lys Ala Asp Lys Ala
1               5                   10                  15

His Ala Ser Gly Val Thr Gly Ser Gly Val Lys Val Ala Val Leu Asp
            20                  25                  30

Thr Gly Ile Asp Ala Asn His Ala Asp Leu Asn Val Lys Gly Gly Ala
        35                  40                  45

Ser Phe Val Ser Gly Glu Pro Asn Ala Leu Gln Asp Gly Asn Gly His
    50                  55                  60

Gly Thr His Val Ala Gly Thr Val Ala Ala Leu Asn Asn Thr Thr Gly
65                  70                  75                  80

Val Leu Gly Val Ala Tyr Asn Ala Phe Leu Tyr Ala Val Lys Val Leu
                85                  90                  95

Gly Ala Ser Gly Ser Gly Thr Leu Ser Gly Ile Ala Gln Gly Ile Glu
            100                 105                 110

Trp Ser Ile Ala Asn Asp Met Asp Val Ile Asn Met Ser Leu Gly Ile
        115                 120                 125

Ser Thr Gly Ser Thr Ala Leu Gln Gln Ala Cys Asn Asn Ala Tyr Ala
    130                 135                 140

Ser Gly Ile Val Val Val Ala Ala Ala Gly Asn Ser Gly Ser Asn Gly
145                 150                 155                 160

Lys Arg Asn Thr Met Gly Tyr Pro Ala Arg Tyr Ser Ser Val Ile Ala
                165                 170                 175

Val Gly Ala Val Asp Ser Ser Asn Asn Arg Ala Ser Phe Ser Ser Val
            180                 185                 190

Gly Ser Glu Leu Glu Val Met Ala Pro Gly Val Ser Ile Leu Ser Thr
        195                 200                 205

Thr Pro Gly Asn Asn Tyr Glu Ser Phe Asn Gly Thr Ser Met Ala Ser
    210                 215                 220

Pro His Val Ala Gly Ala Ala Ala Leu Ile Lys Ala Lys Tyr Pro Ser
225                 230                 235                 240

Met Thr Asn Val Gln Ile Arg Asn Lys Leu Lys Asn Thr Ala Thr Asn
                245                 250                 255
```

```
Leu Gly Asp Ala Phe Tyr Tyr Gly His Gly Val Ile Asn Val Glu Lys
            260                 265                 270

Ala Leu Gln
        275


<210> SEQ ID NO 13
<211> LENGTH: 269
<212> TYPE: PRT
<213> ORGANISM: Bacillus patagoniensis

<400> SEQUENCE: 13

Ala Gln Ser Val Pro Trp Gly Ile Ser Arg Val Gln Ala Gln Ser Ala
1               5                   10                  15

His Asn Arg Gly Ile Thr Gly Ser Gly Val Lys Val Ala Val Leu Asp
            20                  25                  30

Thr Gly Ile Ser Thr His Glu Asp Leu Asn Val Arg Gly Gly Ala Ser
        35                  40                  45

Phe Val Ala Gly Glu Pro Gly Tyr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Asn Ala Glu Leu Tyr Ala Val Lys Val Leu Gly Ala
                85                  90                  95

Ser Gly Ser Gly Ser Ile Ser Gly Ile Ala Gln Gly Leu Gln Trp Ala
            100                 105                 110

Gly Asn Asn Gly Met His Ile Ala Asn Met Ser Leu Gly Thr Ser Ala
        115                 120                 125

Pro Ser Ala Thr Leu Glu Gln Ala Val Asn Ala Ala Thr Ser Arg Gly
    130                 135                 140

Val Leu Val Ile Ala Ala Ser Gly Asn Ser Gly Ala Gly Ser Val Gly
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Gly Val Gln Ser Thr Tyr Pro Gly Asn Arg Tyr
        195                 200                 205

Ala Ser Leu Asn Gly Thr Ser Met Ala Thr Pro His Val Ala Gly Val
    210                 215                 220

Ala Ala Leu Val Lys Gln Lys Asn Pro Ser Trp Ser Asn Val Gln Val
225                 230                 235                 240

Arg Asn His Leu Lys Asn Thr Ala Thr Asn Leu Gly Asn Thr Asn Leu
                245                 250                 255

Tyr Gly Ser Gly Leu Val Asn Ala Glu Ala Ala Thr Arg
            260                 265


<210> SEQ ID NO 14
<211> LENGTH: 269
<212> TYPE: PRT
<213> ORGANISM: Bacillus gibsonii

<400> SEQUENCE: 14

Gln Gln Thr Val Pro Trp Gly Ile Thr Arg Val Gln Ala Pro Thr Val
1               5                   10                  15

His Asn Arg Gly Ile Thr Gly Ser Gly Val Lys Val Ala Ile Leu Asp
            20                  25                  30
```

```
Thr Gly Ile Ala Gln His Ser Asp Leu Thr Ile Arg Gly Gly Ala Ser
        35                  40                  45

Phe Val Pro Gly Glu Ser Thr Thr Ala Asp Leu Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Thr Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Arg Gly
    130                 135                 140

Val Leu Val Ile Ala Ala Thr Gly Asn Asn Gly Thr Gly Ser Ile Gly
145                 150                 155                 160

Tyr Pro Ala Arg Tyr Ala Asn Ala Met Ala Val Gly Ala Thr Asp Gln
                165                 170                 175

Asn Asn Arg Arg Ala Ser Phe Ser Gln Tyr Gly Thr Gly Ile Asp Ile
            180                 185                 190

Val Ala Pro Gly Val Gly Ile Gln Ser Thr Tyr Leu Asn Asn Ser Tyr
        195                 200                 205

Ala Ser Met Pro Gly Thr Ser Met Ala Thr Pro His Val Ala Gly Val
    210                 215                 220

Ala Ala Leu Val Lys Gln Lys Asn Pro Ser Trp Asn Ala Thr Gln Ile
225                 230                 235                 240

Arg Asn His Leu Lys Asn Thr Ala Thr Asn Leu Gly Asn Ser Ser Gln
                245                 250                 255

Phe Gly Ser Gly Leu Val Asn Ala Asp Ala Ala Thr Arg
            260                 265


<210> SEQ ID NO 15
<211> LENGTH: 269
<212> TYPE: PRT
<213> ORGANISM: artificial sequence
<220> FEATURE:
<223> OTHER INFORMATION: Synthesized sequence - amino acid sequence of
      mature BspAK01305 protease from Bacillus sp. DSM 8717

<400> SEQUENCE: 15

Ala Gln Ser Ile Pro Trp Gly Ile Glu Arg Ile Gly Thr Pro Ala Ala
1               5                   10                  15

His Ala Ser Gly Phe Thr Gly Ser Gly Val Ser Val Ala Val Leu Asp
            20                  25                  30

Thr Gly Ile Asp Pro His Ser Asp Leu Asn Val Gln Gly Gly Val Ser
        35                  40                  45

Phe Val Pro Gly Glu Ser Gly Ala Asp Asp Gly Asn Gly His Gly Thr
    50                  55                  60

His Val Ala Gly Thr Ile Ala Ala Leu Asp Asn Asp Glu Gly Val Leu
65                  70                  75                  80

Gly Val Ala Pro Glu Val Asp Leu Phe Ala Val Lys Val Leu Ser Ala
                85                  90                  95

Ser Gly Ser Gly Ser Ile Ser Ser Ile Ala Gln Gly Leu Glu Trp Thr
            100                 105                 110

Ala Glu Asn Asn Ile Asp Val Ala Asn Leu Ser Leu Gly Ser Pro Ser
```

```
        115                 120                 125

Pro Ser Gln Thr Leu Glu Gln Ala Val Asn Asp Ala Thr Asp Ser Gly
    130                 135                 140

Val Leu Val Val Ala Ala Ala Gly Asn Ser Gly Thr Ser Ser Leu Gly
145                 150                 155                 160

Tyr Pro Ala Arg Tyr Asp Asn Ala Met Ala Val Gly Ala Thr Asp Gln
                165                 170                 175

Ser Asp Ser Leu Ala Ser Phe Ser Gln Tyr Gly Glu Gly Leu Asp Leu
            180                 185                 190

Val Ala Pro Gly Val Gly Val Glu Ser Thr Tyr Pro Gly Gly Gly Tyr
        195                 200                 205

Asp Ser Leu Ser Gly Thr Ser Met Ala Ala Pro His Val Ala Gly Ala
    210                 215                 220

Ala Ala Leu Val Lys Gln Lys Asn Pro Gly Trp Thr Asn Glu Gln Ile
225                 230                 235                 240

Arg Ser His Leu Asn Asp Thr Ala Asn Asp Leu Gly Asp Ser Phe Arg
                245                 250                 255

Phe Gly Ser Gly Leu Leu Asn Ala Glu Asn Ala Val Gln
            260                 265


<210> SEQ ID NO 16
<211> LENGTH: 269
<212> TYPE: PRT
<213> ORGANISM: artificial sequence
<220> FEATURE:
<223> OTHER INFORMATION: Synthesized sequence - amino acid sequence of
      mature BspAI02518 protease from Bacillus sp. C-M2-3

<400> SEQUENCE: 16

Ala Gln Ser Thr Pro Trp Gly Ile Ser Arg Ile Asn Ala Pro Ala Val
1               5                   10                  15

His Ser Thr Gly Asn Phe Gly Gln Gly Val Arg Val Ala Val Leu Asp
            20                  25                  30

Ser Gly Val Ala Ser His Glu Asp Leu Arg Ile Ala Gly Gly Val Ser
        35                  40                  45

Phe Val Ala Ser Glu Pro Ser Tyr Gln Asp Tyr Asn Gly His Gly Thr
    50                  55                  60

His Val Ala Gly Thr Ile Ala Gly Leu Asn Asn Ser Val Gly Val Leu
65                  70                  75                  80

Gly Val Ala Pro Ser Val Gln Leu Tyr Ala Val Lys Val Leu Asp Arg
                85                  90                  95

Asn Gly Gly Gly Asn His Ser Asp Ile Ala Arg Gly Ile Glu Trp Ser
            100                 105                 110

Val Asn Asn Gly Met His Val Val Asn Met Ser Leu Gly Gly Pro Thr
        115                 120                 125

Gly Ser Thr Thr Leu Gln Arg Ala Ala Asp Asn Ala Tyr Asn Arg Gly
    130                 135                 140

Val Leu Leu Ile Ala Ala Ala Gly Asn Thr Gly Thr Ser Gly Val Ser
145                 150                 155                 160

Phe Pro Ala Arg Tyr Ser Ser Val Met Ala Val Ala Ala Thr Asp Ser
                165                 170                 175

Asn Asn Asn Arg Ala Ser Phe Ser Thr Tyr Gly Ser Gln Ile Glu Ile
            180                 185                 190

Ser Ala Pro Gly Val Gly Ile Asn Ser Thr Tyr Pro Thr Asn Gly Tyr
        195                 200                 205
```

```
Ser Ser Leu Asn Gly Thr Ser Met Ala Ser Pro His Val Ala Gly Val
    210                 215                 220

Ala Ala Leu Val Lys Ala Arg Tyr Pro Ser Ala Thr Asn Ala Gln Ile
225                 230                 235                 240

Arg Gln His Leu Arg Ser Thr Ser Thr Tyr Leu Gly Asn Ser Thr Tyr
                245                 250                 255

Tyr Gly Ser Gly Leu Val Asp Ala Gln Arg Ala Thr Asn
            260                 265


<210> SEQ ID NO 17
<211> LENGTH: 281
<212> TYPE: PRT
<213> ORGANISM: artificial sequence
<220> FEATURE:
<223> OTHER INFORMATION: Synthesized sequence - amino acid sequence of
      mature BspZ00056 protease from Bacillus sp. WDG291

<400> SEQUENCE: 17

Gly Gln Thr Val Pro Trp Gly Ile Pro His Val Gln Gly Thr Ala Ala
1               5                   10                  15

Gln Asp Ala Gly Tyr Thr Gly Ala Gly Leu Lys Val Ala Ile Leu Asp
            20                  25                  30

Thr Gly Ile Asp Arg Asn His Glu Asp Leu Phe Ala Asn Val Lys Gly
        35                  40                  45

Gly His Ser Val Phe Thr Asp Ser Ala Asn Ser Asp Pro Phe Tyr Asp
    50                  55                  60

Ala Asp Gly His Gly Thr His Val Ala Gly Thr Val Ala Ala Val Asp
65                  70                  75                  80

Asn Asp Leu Gly Val Val Gly Val Ala Ser Gln Ala Glu Leu Tyr Ala
                85                  90                  95

Val Lys Val Leu Asn Asn Ser Gly Ser Gly Ser Tyr Ala Gly Ile Ala
            100                 105                 110

Glu Gly Ile Glu Trp Ser Ile Asn Asn Gly Met Asp Ile Ile Asn Met
        115                 120                 125

Ser Leu Gly Gly Ser Gln Ser Ser Ser Ile Leu Lys Gln Phe Ser Asp
    130                 135                 140

Leu Ala Tyr Glu Glu Gly Leu Leu Val Val Ala Ala Ala Gly Asn Ser
145                 150                 155                 160

Gly Asn Arg Gly Gly Asn Asn Asp Thr Val Gly Tyr Pro Ala Lys Tyr
                165                 170                 175

Asp Ser Val Ile Ala Val Ala Ala Val Asp Gln Asn Asn Asn Arg Ala
            180                 185                 190

Thr Phe Ser Ser Thr Gly Pro Ala Val Glu Ile Ser Ala Pro Gly Val
        195                 200                 205

Ser Ile Leu Ser Thr Thr Pro Gly Asn Asn Tyr Ala Ala Phe Asn Gly
    210                 215                 220

Thr Ser Met Ala Ser Pro His Val Ala Gly Val Ala Ala Gln Val Trp
225                 230                 235                 240

Gln Ala Lys Pro Glu Leu Ser Asn Val Glu Leu Arg Asn Leu Leu Asn
                245                 250                 255

Glu Thr Ala Val Asn Leu Gly Gly Ser Asn Gln Phe Gly His Gly Leu
            260                 265                 270

Val Gln Ser Leu Asp Ala Ile Gln His
        275                 280


<210> SEQ ID NO 18
```

```
<211> LENGTH: 307
<212> TYPE: PRT
<213> ORGANISM: artificial sequence
<220> FEATURE:
<223> OTHER INFORMATION: Synthesized sequence - amino acid sequence of
      mature Bad02409 protease from Bacillus sp. KSM-LD1

<400> SEQUENCE: 18

Ala Gln Thr Val Pro Trp Gly Val Pro His Val Gln Gly Thr Asp Ala
1               5                   10                  15

His Ala Ala Gly His Thr Gly Ser Gly Val Lys Val Ala Ile Leu Asp
            20                  25                  30

Thr Gly Ile Asp Arg Asn His Glu Asp Leu Asn Val Arg Gly Gly His
        35                  40                  45

Ser Val Phe Thr Asp Ser Ala Asn Arg Asp Pro Tyr Tyr Asp Gly Ser
    50                  55                  60

Gly His Gly Thr His Val Ala Gly Thr Val Ala Ala Leu Asn Asn Ser
65                  70                  75                  80

Val Gly Val Leu Gly Val Ala Tyr Asn Ala Glu Leu Tyr Ala Val Lys
                85                  90                  95

Val Leu Asn Asn Ser Gly Ser Gly Ser Tyr Ala Gly Ile Ala Glu Gly
            100                 105                 110

Ile Glu Trp Ala Val Asn Asn Gly Met Asp Ile Ile Asn Met Ser Leu
        115                 120                 125

Gly Gly Ser Met Ser Ser Ser Ile Leu Glu Glu Trp Cys Asn Ile Ala
    130                 135                 140

Tyr Asn Ser Gly Val Leu Val Val Ala Ala Ala Gly Asn Ser Gly Arg
145                 150                 155                 160

Thr Asn Gly Arg Gly Asp Thr Val Gly Tyr Pro Ala Lys Tyr Asp Ser
                165                 170                 175

Val Ile Ala Val Ala Ala Val Asp Ser Ser Asn Asn Arg Ala Ser Phe
            180                 185                 190

Ser Ser Thr Gly Pro Ala Val Glu Ile Ala Ala Pro Gly Val Asn Ile
        195                 200                 205

Leu Ser Thr Thr Pro Gly Asn Ser Tyr Ala Ser Tyr Asn Gly Thr Ser
    210                 215                 220

Met Ala Ser Pro His Val Ala Gly Val Ala Ala Leu Val Leu Ala Ala
225                 230                 235                 240

Asn Pro Asn Leu Ser Asn Val Glu Leu Arg Asn Arg Leu Asn Asp Thr
                245                 250                 255

Ala Gln Asn Leu Gly Asp Ala Asn His Phe Gly Asn Gly Leu Val Arg
            260                 265                 270

Ala Val Asp Ala Ile Asn Gly Thr Ser Ser Gly Asp Asn Gly Gly Gly
        275                 280                 285

Asp Asp Gly Gly Ser Glu Pro Thr Lys Pro Gly Asn Gly Lys Gly Asn
    290                 295                 300

Gly Arg Asn
305


<210> SEQ ID NO 19
<211> LENGTH: 277
<212> TYPE: PRT
<213> ORGANISM: Bacillus agaradhaerens

<400> SEQUENCE: 19

Gln Gln Gln Thr Pro Trp Gly Ile Thr Arg Val Gln Gly Ile Ala Ala
1               5                   10                  15
```

```
Gln Ser Gln Gly Tyr Thr Gly Asn Asn Val Lys Val Ala Val Leu Asp
            20                  25                  30

Ser Gly Ile Asp Arg Ser His Pro Asp Leu Ser Ala Asn Val Arg Gly
        35                  40                  45

Gly Tyr Ser Val Phe Gly Asp Ser Pro Tyr Asn Asp Gly Asn Gly His
    50                  55                  60

Gly Thr His Val Ala Gly Thr Val Gly Ala Val Asn Asn Asn Ile Gly
65                  70                  75                  80

Val Ile Gly Val Ala Pro Gln Ala Asp Leu Tyr Ala Val Lys Val Leu
                85                  90                  95

Asn Asn Ser Gly Ser Gly Ser Tyr Ala Gly Ile Ala Gln Gly Ile Glu
            100                 105                 110

Trp Ser Ile Asn Asn Gly Met Asp Ile Ile Asn Met Ser Leu Gly Gly
        115                 120                 125

Ser Ser Ser Ser Ser Ile Leu Glu Gln Tyr Cys Asn Leu Ala Tyr Asn
    130                 135                 140

Arg Gly Leu Leu Val Val Ala Ala Ala Gly Asn Ser Gly Thr Ala Ala
145                 150                 155                 160

Gly Asn Thr Asn Thr Val Gly Tyr Pro Ala Arg Tyr Asn Ser Val Ile
                165                 170                 175

Ala Val Ala Ala Thr Asn Ser Asn Asn Val Arg Gly Asn Phe Ser Ser
            180                 185                 190

Thr Gly Pro Thr Val Glu Leu Ser Ala Pro Gly Val Ser Val Leu Ser
        195                 200                 205

Thr Thr Pro Gly Gly Asn Tyr Ala Ser Tyr Asn Gly Thr Ser Met Ala
    210                 215                 220

Ser Pro His Val Ala Gly Val Ala Ala Gln Val Trp Gln Ala Arg Pro
225                 230                 235                 240

Asn Leu Ser Asn Ala Gln Leu Arg Gln Ile Leu Asn Ala Ser Ala Gln
                245                 250                 255

Asn Leu Gly Ser Ser Tyr Gln Tyr Gly Asn Gly Leu Val Arg Ser Leu
            260                 265                 270

Asn Ala Ile Gln Tyr
        275


<210> SEQ ID NO 20
<211> LENGTH: 255
<212> TYPE: PRT
<213> ORGANISM: Bacillus amyloliquefaciens

<400> SEQUENCE: 20

Tyr Thr Gly Ser Asn Val Lys Val Ala Val Ile Asp Ser Gly Ile Asp
1               5                   10                  15

Ser Ser His Pro Asp Leu Lys Val Ala Gly Gly Ala Ser Met Val Pro
            20                  25                  30

Ser Glu Thr Asn Pro Phe Gln Asp Asn Asn Ser His Gly Thr His Val
        35                  40                  45

Ala Gly Thr Val Ala Ala Leu Asn Asn Ser Ile Gly Val Leu Gly Val
    50                  55                  60

Ala Pro Ser Ala Ser Leu Tyr Ala Val Lys Val Leu Gly Ala Asp Gly
65                  70                  75                  80

Ser Gly Gln Tyr Ser Trp Ile Ile Asn Gly Ile Glu Trp Ala Ile Ala
                85                  90                  95

Asn Asn Met Asp Val Ile Asn Met Ser Leu Gly Gly Pro Ser Gly Ser
```

```
            100                 105                 110

Ala Ala Leu Lys Ala Ala Val Asp Lys Ala Val Ala Ser Gly Val Val
        115                 120                 125

Val Val Ala Ala Ala Gly Asn Glu Gly Thr Ser Gly Ser Ser Ser Thr
    130                 135                 140

Val Gly Tyr Pro Gly Lys Tyr Pro Ser Val Ile Ala Val Gly Ala Val
145                 150                 155                 160

Asp Ser Ser Asn Gln Arg Ala Ser Phe Ser Ser Val Gly Pro Glu Leu
                165                 170                 175

Asp Val Met Ala Pro Gly Val Ser Ile Gln Ser Thr Leu Pro Gly Asn
            180                 185                 190

Lys Tyr Gly Ala Tyr Asn Gly Thr Ser Met Ala Ser Pro His Val Ala
        195                 200                 205

Gly Ala Ala Ala Leu Ile Leu Ser Lys His Pro Asn Trp Thr Asn Thr
    210                 215                 220

Gln Val Arg Ser Ser Leu Glu Asn Thr Thr Thr Lys Leu Gly Asp Ser
225                 230                 235                 240

Phe Tyr Tyr Gly Lys Gly Leu Ile Asn Val Gln Ala Ala Ala Gln
                245                 250                 255


<210> SEQ ID NO 21
<211> LENGTH: 254
<212> TYPE: PRT
<213> ORGANISM: Bacillus licheniformis

<400> SEQUENCE: 21

Phe Lys Gly Ala Asn Val Lys Val Ala Val Leu Asp Thr Gly Ile Gln
1               5                   10                  15

Ala Ser His Pro Asp Leu Asn Val Val Gly Gly Ala Ser Phe Val Ala
            20                  25                  30

Gly Glu Ala Tyr Asn Thr Asp Gly Asn Gly His Gly Thr His Val Ala
        35                  40                  45

Gly Thr Val Ala Ala Leu Asp Asn Thr Thr Gly Val Leu Gly Val Ala
    50                  55                  60

Pro Ser Val Ser Leu Tyr Ala Val Lys Val Leu Asn Ser Ser Gly Ser
65                  70                  75                  80

Gly Ser Tyr Ser Gly Ile Val Ser Gly Ile Glu Trp Ala Thr Thr Asn
                85                  90                  95

Gly Met Asp Val Ile Asn Met Ser Leu Gly Gly Ala Ser Gly Ser Thr
            100                 105                 110

Ala Met Lys Gln Ala Val Asp Asn Ala Tyr Ala Arg Gly Val Val Val
        115                 120                 125

Val Ala Ala Ala Gly Asn Ser Gly Ser Ser Gly Asn Thr Asn Thr Ile
    130                 135                 140

Gly Tyr Pro Ala Lys Tyr Asp Ser Val Ile Ala Val Gly Ala Val Asp
145                 150                 155                 160

Ser Asn Ser Asn Arg Ala Ser Phe Ser Ser Val Gly Ala Glu Leu Glu
                165                 170                 175

Val Met Ala Pro Gly Ala Gly Val Tyr Ser Thr Tyr Pro Thr Asn Thr
            180                 185                 190

Tyr Ala Thr Leu Asn Gly Thr Ser Met Ala Ser Pro His Val Ala Gly
        195                 200                 205

Ala Ala Ala Leu Ile Leu Ser Lys His Pro Asn Leu Ser Ala Ser Gln
    210                 215                 220
```

```
Val Arg Asn Arg Leu Ser Ser Thr Ala Thr Tyr Leu Gly Ser Ser Phe
225                 230                 235                 240

Tyr Tyr Gly Lys Gly Leu Ile Asn Val Glu Ala Ala Ala Gln
                245                 250


<210> SEQ ID NO 22
<211> LENGTH: 277
<212> TYPE: PRT
<213> ORGANISM: artificial sequence
<220> FEATURE:
<223> OTHER INFORMATION: Synthesized sequence - amino acid sequence of
      mature BspZ00258 protease; from Bacillus sp. WDG291

<400> SEQUENCE: 22

Ala Gln Glu Val Pro Tyr Gly Ile Glu Gln Ile Gly Ala Ile Asp Val
1               5                   10                  15

Gln Val Asn Asp Gly Asn Thr Gly Asn Gly Val Ser Val Ala Val Leu
            20                  25                  30

Asp Thr Gly Ile Ala Ala His Glu Asp Leu Asn Val Val Asp Gly Ala
        35                  40                  45

Ser Phe Ile Ala Gly Glu Pro Asp Tyr Glu Asp Tyr Asn Gly His Gly
    50                  55                  60

Thr His Val Ala Gly Thr Val Ala Ala Leu Asp Asn Asp Leu Gly Val
65                  70                  75                  80

Leu Gly Val Ser Pro Asp Val Asp Leu Tyr Ala Val Lys Val Leu Gly
                85                  90                  95

Ala Asp Gly Gly Gly Ser His Ala Ser Ile Ala Gln Gly Ile Glu Trp
            100                 105                 110

Ala Val Asp Asn Asn Ile Asp Val Val Asn Met Ser Leu Gly Gly Ala
        115                 120                 125

Val Gly Ser Thr Thr Leu Glu Gln Ala Val Asn Tyr Ala His Ser Gln
    130                 135                 140

Gly Val Thr Leu Ile Ala Ala Ala Gly Asn Glu Gly Ser Leu Ile Pro
145                 150                 155                 160

Gly Leu Asn Thr Ile Gly Tyr Pro Ala Lys Tyr Asp Asn Val Ile Ala
                165                 170                 175

Val Gly Ala Val Asp Ser Asn Asn Asn Arg Ala Ser Phe Ser Ser Val
            180                 185                 190

Gly Asn Glu Leu Asp Val Val Ala Pro Gly Val Ser Ile Leu Ser Thr
        195                 200                 205

Tyr Leu Gly Asn Asp Tyr Ala Ala Leu Asn Gly Thr Ser Met Ala Ser
    210                 215                 220

Pro His Val Ala Gly Ala Ala Ala Leu Leu Leu Ala Glu Asn Pro Gly
225                 230                 235                 240

Leu Thr Asn Asp Gln Val Arg Ala Val Phe Asn Glu Thr Ala Val Pro
                245                 250                 255

Leu Gly Asp His Phe Tyr Tyr Gly Asn Gly Leu Ile Asp Val Arg Ala
            260                 265                 270

Ala Ile Asp Ala Gln
        275


<210> SEQ ID NO 23
<211> LENGTH: 70
<212> TYPE: PRT
<213> ORGANISM: artificial sequence
<220> FEATURE:
<223> OTHER INFORMATION: Synthesized sequence - amino acid sequence of
      Bad02409 pro-peptide from Bacillus sp. KSM-LD1
```

<400> SEQUENCE: 23

```
Gln Ala Glu Lys Gln Glu Tyr Leu Val Gln Phe Asn Asp Lys Val Asn
1               5                   10                  15

Lys Gly Ile Leu Asn Ala Phe Gly Val Asp Asn Ser Asp Val Leu His
            20                  25                  30

Thr Tyr Asn Leu Leu Pro Val Asn Leu Val Lys Met Thr Glu Gln Gln
        35                  40                  45

Ala Lys Ala Leu Gln Asn Asn Pro His Ile Lys Ala Val Glu Pro Asn
    50                  55                  60

Phe Glu Ala Gln Ala Phe
65                  70
```

<210> SEQ ID NO 24
<211> LENGTH: 1059
<212> TYPE: DNA
<213> ORGANISM: artificial sequence
<220> FEATURE:
<223> OTHER INFORMATION: Synthesized sequence - synthetic gene for expression of AprE protease

<400> SEQUENCE: 24

```
gccggaaaaa gcagtacaga aaagaaatac attgtcggat ttaaacagac aatgagtgcc     60

atgagttccg ccaagaaaaa ggatgttatt tctgaaaaag gcggaaaggt tcaaaagcaa    120

tttaagtatg ttaacgcggc tgcagcaaca ttggatgaaa aagctgtaaa agaattgaaa    180

aaagatccga gcgttgcata tgtggaagaa gatcatattg cacatgaata tgcgcaatct    240

gttccttatg gcatttctca aattaaagcg ccggctcttc actctcaagg ctacacaggc    300

tctaacgtaa aagtagctgt tatcgacagc ggaattgact cttctcatcc tgacttaaac    360

gtcagaggcg gagcgagctt cgtaccttct gaaacaaacc cataccagga cggcagttct    420

cacggtacgc atgtagccgg tacgattgcc gctcttaata actcaatcgg tgttctgggc    480

gttgcgccaa gcgcatcatt atatgcagta aaagtgcttg attcaacagg aagcggccaa    540

tatagctgga ttattaacgg cattgagtgg gccatttcca acaatatgga tgttatcaac    600

atgagccttg gcggacctac tggttctaca gcgctgaaaa cagtcgttga caaagccgtt    660

tccagcggta tcgtcgttgc tgccgcagcc ggaaacgaag gttcatccgg aagcacaagc    720

acagtcggct accctgcaaa atatccttct actattgcag taggtgcggt aaacagcagc    780

aaccaaagag cttcattctc cagcgcaggt tctgagcttg atgtgatggc tcctggcgtg    840

tccatccaaa gcacacttcc tggaggcact tacggcgctt ataacggaac gtccatggcg    900

actcctcacg ttgccggagc agcagcgtta attctttcta agcacccgac ttggacaaac    960

gcgcaagtcc gtgatcgttt agaaagcact gcaacatatc ttggaaactc tttctactat   1020

ggaaaagggt taatcaacgt acaagcagct gcacaataa                          1059
```

<210> SEQ ID NO 25
<211> LENGTH: 1059
<212> TYPE: DNA
<213> ORGANISM: artificial sequence
<220> FEATURE:
<223> OTHER INFORMATION: Synthesized sequence - synthetic gene for expression of WP_082194748 protease

<400> SEQUENCE: 25

```
gaaacggcta gcaagtcaga aagtgaaaaa agctatattg ttggcttcaa agcatctgcc     60

accacaaaca gctctaaaaa acaagcggtc actcaaaatg gtgggacatt agaaaagcaa    120
```

```
tatcgcctca tcaatgctgc acaagtaaaa atgtccgaac aagccgcaaa aaaacttgaa    180
catgacccta gcattgatta tgtagaagaa gactacaaag cagaagcata tgcacaaacc    240
gtcccttatg gtatccctca aatcaaagct ccagcagtac acgctcaagg ttataaaggt    300
gctaatgtga aagtagctgt ccttgatact ggtatccacg ctgcacaccc tgacttaaat    360
gttgcaggcg gtgcttcttt cgtcccttca gagccaaatg ccacccaaga ttttcaatca    420
cacggaactc acgtagcagg aaccattgct gcccttgata acacaattgg tgttcttggt    480
gtcgcaccaa gtgcctcctt gtatgccgtt aaagtgttag accgtaacgg cgatggacaa    540
tacagctgga ttattagcgg tattgaatgg gctgttgcca ataatatgga tgtgatcaat    600
atgagtttag gcggaccaag tggttccaca gcgcttaaaa atgctgtaga tacagcaaat    660
aatcgcggag tggtggttgt tgccgcagca ggaaattcag gttccagtgg ctctacaagc    720
accgttggct atccagcaaa atatgattct acgattgccg ttgctaatgt gaacagcaac    780
aatgtaagaa actcatcttc tagtgcaggt cctgaattag atgtttctgc acctggtacg    840
tccattttaa gtacagtacc aagcagtgga tatgcatctt ataccgggac atctatggct    900
tctcctcatg tagcaggagc agcagcgctt attctgtcta agcacccgaa cctaacaaat    960
acgcaggtgc gccagcgttt agaaaataca gccactccgc ttggtagctc gttctattac   1020
ggaaagggat taatcaacgt tcaagctgca gctaactaa                          1059
```

```
<210> SEQ ID NO 26
<211> LENGTH: 1050
<212> TYPE: DNA
<213> ORGANISM: artificial sequence
<220> FEATURE:
<223> OTHER INFORMATION: synthesized sequence - synthetic gene for
      expression of Chemgen_164A protease

<400> SEQUENCE: 26
```

```
agcgggaaaa atgctgaaat taagaaagat tacttagttg gttttaaaac gaatgtaacc     60
aatgaatcta aaaatatagt aaactcacta ggtggaagcg tacatcatca atataagtat    120
atggacgtat tgcatgtatc tctcccagaa aaagcagcag aagcattaaa aaacaatccg    180
aatgtagcat ttgtcgattt agatgctgaa gttcaagcat ttgcacaaac tactccttgg    240
ggaattacgc atattaatgc gcataaagca cacagctcta gcgttactgg atctggtgtg    300
aaagttgccg ttcttgatac tggaattgat gctagtcatc cagatttaaa tgtaaaaggt    360
ggagcaagtt ttatctctgg tgagcccaat gcacttgttg atacaaatgg tcatggtaca    420
catgtagctg gtacggtagc tgcattaaac aatacaatcg gtgttgtagg agttgcatac    480
aatgcagatt tatatgctgt taaagtatta agtgcttcag gaagtggaac gttaagtgga    540
attgctcaag gtgttgaatg ggcaattgct aataatatgg atgtaattaa catgagtctt    600
ggtgggagtt ctggatctac agcattaaag caagctgttg ataatgctta tgcaagcgga    660
attgttgtag tagcagcggc tggtaatagc ggaacaagag gaagacagaa cacaatgggc    720
tacccagcaa gatatagttc agtaattgct gttggtgcgg tagactcaaa taacaatcgt    780
gcatcattct ctagcgtagg tgctgaacta gaagtaatgg ctcctggtgt aagtgtttta    840
agtacagtac caggtggtgg ttatgcttct tataatggaa catcaatggc ttctccacat    900
gtagcaggag cagcagcttt aatcaaagct aaatacccta gcttaagcgc ttcacaaatt    960
cgtgatagat taagaaacac agctacttac ttaggtgatc cattctatta tggaaacgga   1020
gttataaatg tagagagagc attacaataa                                    1050
```

<210> SEQ ID NO 27
<211> LENGTH: 1068
<212> TYPE: DNA
<213> ORGANISM: artificial sequence
<220> FEATURE:
<223> OTHER INFORMATION: Synthesized sequence - synthetic gene for expression of CP474 protease

<400> SEQUENCE: 27

```
gctgaagaag caaaagaaaa atatttaatt ggctttaatg agcaggaagc tgtcagtgag     60
tttgtagaac aagtagaggc aaatgacgag gtcgccattc tctctgagga agaggaagtc    120
gaaattgaat tgcttcatga atttgaaacg attcctgttt tatccgttga gttaagccca    180
gaagatgtgg acgcgcttga gctcgatcca gcgatttctt atattgaaga ggatgcagaa    240
gtaacgacaa tggcgcaaac agtgccatgg ggaattcctc atatcaaagc cgacaaagcc    300
catgctgctg gagtgacagg ttctggtgta aaagttgcta tcctcgatac aggtattgac    360
gcaaaccatg ccgacttaaa tgtaaaaggt ggcgctagct ttgtagctgg ggaaccaaat    420
gctcttcaag atgggaatgg gcatggcacg catgtggctg ggacggtagc tgctttagac    480
aatacaacgg gcgttcttgg cgtagcaccg agcgtatccc tatacgctgt taaagtatta    540
ggggcgagcg gttcaggttc ggtcagctcg attgcccaag gattggaatg ggcagggaac    600
aatggcatgc acgttgctaa tttgagttta ggaagccctt cgccaagtgc cacacttgag    660
caagctgtta atagcgcgac ttctagaggc gttcttgttg tagcggcatc tgggaattca    720
ggtgcaggct caatcagcta tccggcccgt tatgcgaacg caatggcagt cggagccact    780
gaccaaaaca acaaccgcgc cagcttttca cagtatggcg cagggcttga cattgtcgca    840
ccaggtgtaa acattttgag cacaactcct ggtaacaatt atgccagctt aaacggtaca    900
tcgatggctg ctcctcatgt tgcaggtgca gcagccctta tcaaagcgaa gtacccatct    960
atgacaaatg tacaaatccg caatcgtcta aagaatacgg caacgaattt aggagatcct   1020
ttcttctatg gaaaaggagt catcaatgtg gaaagtgcat tacaataa                 1068
```

<210> SEQ ID NO 28
<211> LENGTH: 1065
<212> TYPE: DNA
<213> ORGANISM: artificial sequence
<220> FEATURE:
<223> OTHER INFORMATION: Synthesized sequence - synthetic gene for expression of ZP_00454 protease

<400> SEQUENCE: 28

```
gcagcttctg gtccgagtgc taatgccaag aaagagtact tagtgggatt tgctaaagga     60
aacaaagcga atgctcagtc ttccaaaaat ttaattacag ctgctggtgg cgatattcaa    120
catacattcc agtacatgga tgtagtggaa gtgagcttgc ctgaaaaagc ggctgaagca    180
ttagcgaaaa atcctaacat tgcatttgta gaggtaaacg cagaagttca agctactgca    240
caagttgttc cttggggaat ccctcacatt aaagcagaca aagcgcacgc ttcaggtgta    300
acaggaagtg gagtgaaagt tgcggtcctt gatacaggaa ttgatgcaaa ccatgcggat    360
ttgaatgtta aaggtggagc atcatttgtt tctggtgaac caaatgccct tcaagatgga    420
aacgggcacg gaacacacgt agcaggaacg gttgctgcat tgaataatac gacaggagtg    480
cttggtgtag cttataatgc gtttctttat gcagttaaag ttcttggcgc ttccggaagc    540
ggtacattaa gtggaatcgc acaaggaatt gagtggtcca ttgctaatga tatggacgtt    600
```

```
atcaatatga gccttggtat tagtaccggt tccacagcac ttcagcaagc atgtaataat    660

gcatatgcaa gtggaattgt agtggttgca gctgctggaa actccggttc taatggtaag    720

agaaacacaa tgggttaccc tgctagatac agttctgtaa ttgcagttgg tgcggtcgac    780

agcagtaaca accgtgcatc tttctcaagt gttggaagtg agcttgaagt aatggctcca    840

ggtgtaagta tccttagcac gactcctgga aacaactacg aatccttcaa tggtacgtct    900

atggcttctc cacatgttgc aggagcagct gcattaatca aagcaaaata tcctagcatg    960

acgaatgtcc aaattcgtaa taaactaaaa aatactgcca ctaaccttgg cgatgcgttc   1020

tattatggac atggtgtaat taacgttgaa aaagctttgc aataa                   1065
```

<210> SEQ ID NO 29
<211> LENGTH: 1056
<212> TYPE: DNA
<213> ORGANISM: artificial sequence
<220> FEATURE:
<223> OTHER INFORMATION: Synthesized sequence - synthetic gene for expression of Bpan01744 protease

<400> SEQUENCE: 29

```
gcagaggaag cgaaagagaa atatttaatt ggtttcacag agcaggaagc ggtatctact     60

tttgtagaac aaattgaaga agaagaggtt agtatttcag aagtcgatga cgttgaaatt    120

gatcttttat atgaatttga aacgattcca gttttatcag tagaattaaa tcctgaagat    180

gtggcttctt tggaatcaga cccagcaatt tcttatattg aagaagatgc tgaagtgact    240

acaatggctc aatcagttcc ttgggggata agccgtgttc aagctcaatc tgctcataat    300

cgaggtataa caggatcagg agtgaaggtg gcggttcttg atacaggtat ttcaacacat    360

gaagatttaa atgtacgggg aggggcaagc ttcgtagcag gtgaacctgg ttatcaagat    420

gggaatggac acgggacaca tgtagcagga acgatagccg ctctaaataa ttcaataggc    480

gtacttggtg ttgcaccgaa tgcagaatta tatgcagtta aagtacttgg agctagtggt    540

tctggatcaa ttagtggaat tgcacaaggg ttgcaatggg ctggcaataa tggaatgcat    600

atagctaata tgagccttgg tacttctgca ccgagcgcaa ctcttgaaca agctgttaac    660

gcggcgacat ctcgtggtgt acttgttatc gcagcctctg gtaattctgg tgctggctca    720

gttggttatc ctgcacgtta cgcgaatgcg atggcagtag gtgcaactga tcaaaataac    780

aaccgtgcaa gcttctctca atatggtgca ggtcttgata ttgtcgctcc tggcgtaggt    840

gttcaaagca catatccagg gaaccgttat gcgagtttga atggtacttc aatggcaact    900

cctcacgtag ctggtgttgc agcacttgtt aaacagaaaa acccttcatg gtctaatgta    960

caagttagaa atcacttgaa aaatactgca actaatcttg gcaatacgaa tctttatggt   1020

agcggactag taaacgcaga agcagcaaca cgttaa                             1056
```

<210> SEQ ID NO 30
<211> LENGTH: 1062
<212> TYPE: DNA
<213> ORGANISM: artificial sequence
<220> FEATURE:
<223> OTHER INFORMATION: Synthesized sequence - synthetic gene for expression of DSM14391 protease

<400> SEQUENCE: 30

```
gctgaagaag caaaagaaaa atatttaatt ggctttaatg agcaggaagc tgtcagtgag     60

tttgtagaac aagtagaggc aaatgacgag gtcgccattc tctctgagga agaggaagtc    120

gaaattgaat tgcttcatga atttgaaacg attcctgttt tatccgttga gttaagccca    180
```

gaagatgtgg acgcgcttga gctcgatcca gcgatttctt atattgaaga ggatgcagaa 240
gtaacgacaa tgcaacaaac agtgccatgg ggaattactc gtgtgcaagc cccaacagtt 300
cataaccgtg gaattacagg ttctggtgta aaagttgcta tcctcgatac aggtattgca 360
caacattcag acttaacaat tcgtggtggc gcaagctttg taccagggga atcaacgaca 420
gctgatttaa atgggcatgg cacgcatgtg gctgggacgg tagctgcttt aaacaattcg 480
attggcgtta ttggcgtagc accgtcagcg gatctatacg ctgttaaagt attaggggcg 540
aatggtagag gttcggtcag cgggattgcc caaggattgg aatgggcagc aacaaataac 600
atgcacattg ctaatatgag tttaggatca gatgcaccaa gtacaacact tgagcgtgct 660
gttaattatg cgacttctag aggcgttctt gttattgcgg caactgggaa taacggtaca 720
ggctcaattg gctatccggc ccgttatgcg aacgcaatgg cagtcggagc tactgaccaa 780
aacaacagac gcgcctcatt ttcacagtat ggcacgggga ttgacattgt cgcaccaggt 840
gtaggcattc agagcacata cctgaataac tcatatgcaa gcatgccggg tacatcgatg 900
gctactcctc atgttgcagg tgttgcagcc cttgttaaac aaaaaaatcc atcttggaat 960
gcgactcaaa tccgcaatca tctaaagaat acggcaacga atttaggaaa ctcttcacaa 1020
tttggaagcg gacttgtcaa tgcagatgcg gcaacacgct aa 1062

<210> SEQ ID NO 31
<211> LENGTH: 1044
<212> TYPE: DNA
<213> ORGANISM: artificial sequence
<220> FEATURE:
<223> OTHER INFORMATION: Synthesized sequence - synthetic gene for expression of BspAK01305 protease

<400> SEQUENCE: 31
gcagaggaaa aaaaatctta tttaattggc tttgatgaac ctcaagaagt tgagcaattt 60
acaacaaatt tggaagaaga gattcgtaca caagcagatg atgctattga tgtaacgtac 120
gagtttaaag atattcctgt tcttgccgta gatatgacgg aagaagaaat gactgaactc 180
aaaaatgaag agagcatttc ttatattgaa gaagatcaag aagtgacaac gatggcgcaa 240
agcattccat ggggaattga aagaattggc acgccagcag cacacgcatc aggattcaca 300
ggtagcggtg taagtgtcgc ggtccttgat acagggattg atccacattc tgacttaaac 360
gtacaagggg gggttagctt cgtaccaggc gaaagcggag cagatgatgg aaatggacac 420
ggtactcatg tagcaggaac gattgcagcg ttagataatg atgaaggcgt tttaggcgtt 480
gctccagagg ttgatctctt tgcagtaaaa gttttaagtg catctggatc aggatcaatt 540
agctctattg cgcaaggttt agagtggaca gctgaaaaca acattgatgt ggctaatctt 600
agcttaggca gtccctctcc tagtcagacg cttgaacaag cggttaatga cgccacagat 660
agtggtgtgc ttgtagtagc agcagcaggg aactctggaa caagctcatt aggttatcca 720
gctcgttatg ataatgcaat ggctgttggc gctaccgacc aatccgatag cctggctagc 780
ttctcacagt atggcgaggg tcttgactta gtcgctcctg gtgttggtgt agaaagcacg 840
tacccaggtg gaggttatga cagcttaagc ggcacatcta tggctgctcc acatgttgca 900
ggtgcagcag cactcgttaa acaaaaaaat ccaggctgga caaacgaaca aataagaagc 960
catttaaacg atacagccaa tgacctaggc gattcgttcc gcttcggtag tggcttattg 1020
aatgccgaaa atgccgttca ataa 1044

<210> SEQ ID NO 32
<211> LENGTH: 1023
<212> TYPE: DNA
<213> ORGANISM: artificial sequence
<220> FEATURE:
<223> OTHER INFORMATION: Synthesized sequence - synthetic gene for expression of BspAI02518 protease

<400> SEQUENCE: 32

```
aactctgcag tagaaaaaga ggactatctg atcggtttta agcagaaagg gaatgttagc     60
gcacaagttg tgaatatgag cggaggagaa gtcgtccatg aatatgaaca tatgccagtc    120
ttgcacgtta aattacctcc acaagctgct aaagcattag aaaagaaccg caatattgaa    180
tacatcgaaa aagatgaaaa agtccaagca acagcacaat cgacaccttg gggatttca    240
cgtattaatg ctcctgctgt tcactcgact ggtaattttg gacaaggtgt cagagttgcc    300
gttttagata gtggagttgc ttctcatgaa gacttacgca ttgctggggg agtgagcttt    360
gtcgcttcag aacctagtta tcaagattat aatggtcacg gaacacatgt tgctggaacc    420
attgctggtt taaataatag cgttggggtc cttggtgtag ctccatctgt ccaattatat    480
gcggttaagg tgttggatcg taatggcggt ggaaatcata gcgacattgc tagaggaatt    540
gagtggtcag ttaataatgg tatgcatgtg gtgaatatga gtttaggtgg accaacaggg    600
tcaaccactc ttcaacgagc agcggataat gcttataata gaggagttct tttaattgct    660
gcggctggta acacgggaac tagcggagtt agcttccctg cgcgttacag ctcagtaatg    720
gcagtagccg caacagattc taataataac cgtgcttcat tttcaactta tggatcacaa    780
attgaaattt cagcacctgg agttggcatt aatagcacgt atccaacgaa tggttattca    840
agtttaaatg gaacatcaat ggcttcacct catgtcgctg gtgtagcggc cctagtgaag    900
gcgagatatc caagtgcgac gaatgctcag attagacaac atcttcgtag cacttctacg    960
tatctaggaa actcaactta ctatggtagt ggtctagtcg acgcacagcg tgcaactaac   1020
taa                                                                 1023
```

<210> SEQ ID NO 33
<211> LENGTH: 1062
<212> TYPE: DNA
<213> ORGANISM: artificial sequence
<220> FEATURE:
<223> OTHER INFORMATION: Synthesized sequence - synthetic gene for expression of BspZ00056 protease

<400> SEQUENCE: 33

```
ggtggtaacg atcaaagtca ggattatttg gtccaattta acggacctgc aagtaaaggg     60
ctgattaaag cgttcggtgt cgatgaaggg gacattcttc atacatacga ccaccttcca    120
gtcgtccacg tgaacttgac tgaaaaccag gcacggggcc ttgccaatca cccacacatc    180
acaacagttg aagaaaacgc tgaagtaaaa gcgctcggtc aaacggtccc atggggcatt    240
ccacacgtgc aaggaactgc ggctcaagat gctgggtata ctggtgccgg tcttaaagta    300
gcgattcttg atacggggat cgaccgtaac cacgaagact tgtttgctaa cgtaaaaggc    360
ggtcattccg tatttacgga ttccgcaaac agcgatccat tttatgatgc tgacggtcac    420
ggtacacacg ttgcaggtac agtcgcagct gttgataacg accttggcgt tgtaggcgtg    480
gcttcccaag ctgagctgta tgcggtaaaa gttctgaaca actccggaag cggatcttat    540
gcaggtatcg ctgaaggaat tgaatggtcg atcaacaacg gaatggacat catcaacatg    600
agccttggtg gttcccaaag ctcgtccatc ctgaaacagt tctctgactt agcttacgaa    660
```

```
gaaggacttc ttgtcgtagc cgcagcgggt aacagcggaa accgcggtgg aaacaacgac    720

actgtcggct acccggcgaa atatgactct gtaatcgcgg tcgctgccgt cgatcaaaac    780

aacaaccgtg ctacattctc tagtaccggt cctgctgttg aaatttcagc tcctggtgtg    840

agcattctca gcacaacgcc aggcaacaac tacgctgcgt tcaacggaac ttccatggct    900

tctcctcacg tagccggcgt ggcagctcaa gtttggcagg caaaacctga actatcaaac    960

gtagagcttc gtaatctatt aaacgaaact gcagtgaacc tgggcggatc aaaccaattc   1020

ggtcacggtc tagttcagtc gctggatgcg attcagcact aa                      1062
```

<210> SEQ ID NO 34
<211> LENGTH: 1134
<212> TYPE: DNA
<213> ORGANISM: artificial sequence
<220> FEATURE:
<223> OTHER INFORMATION: Synthesized sequence - synthetic gene for
expression of Bad02409 protease

<400> SEQUENCE: 34

```
caggcagaaa aacaggagta ccttgttcaa tttaatgaca aggtaaataa ggggatatta     60

aacgcgtttg gtgtagataa tagtgatgtt cttcatactt acaatctact acctgttaat    120

ctagtaaaaa tgacagagca acaagcgaaa gcattacaaa ataatccgca tattaaagcg    180

gtggaaccta actttgaggc gcaagcattt gctcaaaccg taccgtgggg agttcctcat    240

gttcaaggta ctgatgctca tgcagcgggg catactggaa gtggtgtaaa agtagctata    300

ctcgatacgg gaattgatcg aaatcatgaa gatttaaatg taagaggagg gcactctgta    360

ttcacagaca gtgcaaacag agatccttat tacgatggta gtggtcatgg cacgcacgtt    420

gctggaacag tagcggcctt aaataatagt gtaggtgtgt taggtgtagc ctacaacgcg    480

gagctatatg cggtaaaagt attaaataac agtggaagtg gttcttatgc gggaattgct    540

gaaggaattg aatgggctgt taataacgga atggacatta taaatatgag tttaggaggt    600

tcgatgagtt cttctatttt agaagagtgg tgtaatattg cctacaattc tggtgtgctt    660

gtagtggcgg cagctggaaa cagtggacgt acgaatggcc gaggggatac tgttggttat    720

ccagcaaaat atgattctgt tatcgcagta gcagcagttg attctagcaa caatcgtgca    780

agtttctcta gtacaggacc tgcagtggaa attgcagctc ctggtgtaaa cattcttagt    840

acgactcctg gaaacagcta tgcatcttac aacggaactt cgatggcatc tccacatgta    900

gctggtgtgg cagcgcttgt cttggcagcg aatccgaacc tttcaaacgt ggagcttcgt    960

aatcgattaa acgatacagc gcaaaactta ggtgatgcaa accactttgg aaacggctta   1020

gtgcgtgcag ttgatgccat taacggcact agctccggtg ataacggtgg cggcgacgat   1080

ggtggaagcg aaccaacaaa accaggtaac ggcaaaggaa acggaagaaa ctaa         1134
```

<210> SEQ ID NO 35
<211> LENGTH: 1068
<212> TYPE: DNA
<213> ORGANISM: artificial sequence
<220> FEATURE:
<223> OTHER INFORMATION: Synthesized sequence - synthetic gene for
expression of Bba02069 protease

<400> SEQUENCE: 35

```
gactcaacag atagaaactc tggcagcggt accaaagaat atctcgtcat gtttgaggaa     60

gacagcgctg acatgagtgt catgaagtct attggtattt ctcaaagcaa tatactttat    120

gagttcgagt tactgcctgt tttacatgtg gagctcagtg agactcaagt aaacagcctt    180
```

```
gagaatcatc ctcaaattaa aacggtagaa gaaaatgccg aagcgaaggc ctaccaacaa    240

caaacaccat ggggtatcac tcgcgttcaa ggcattgccg ctcaatcaca aggttataca    300

ggtaataacg tcaaagtagc tgtcttggat tctggtattg atcgctctca tccagattta    360

tcagccaatg tacgtggagg ctactcagtg tttggcgact ctccttacaa cgatggtaac    420

ggacatggaa cccatgtagc tggtactgtc ggtgccgtta acaacaacat cggcgttatc    480

ggtgtggctc ctcaagcaga cctctatgct gtaaaagtac tcaataactc tggtagtggc    540

tcatatgccg gtatcgccca aggaattgaa tggtcaatta ataacggtat ggacatcatt    600

aatatgagct taggtgggtc ttcaagctcc tcaatccttg agcagtattg taaccttgcc    660

tacaatcgtg gccttctcgt agttgctgcc gctgggaaca gtggaacagc tgctggaaac    720

acaaacacag taggttatcc agcgcgttat aattcagtta tcgctgtggc tgcaacaaat    780

tctaataatg tgcgggggaa cttctctagt acaggcccta cagtggaact atcagctcct    840

ggcgtaagtg tcctaagtac aacacctggt ggaaactatg cttcatacaa tggtacttca    900

atggcttctc cgcatgttgc aggtgtggct gcccaagtat ggcaagcaag accaaatcta    960

tcaaatgctc aattaagaca aatcttaaat gcttccgcac aaaaccttgg tagttcatat   1020

caatatggta acgggctcgt cagatctttg aatgccatcc aatactaa                1068
```

<210> SEQ ID NO 36
<211> LENGTH: 75
<212> TYPE: PRT
<213> ORGANISM: artificial sequence
<220> FEATURE:
<223> OTHER INFORMATION: Synthesized sequence - amino acid sequence of
      BspZ00258 pro-peptide from Bacillus sp. WDG291

<400> SEQUENCE: 36

```
Asn Gly Ser Gly Glu Thr Lys Glu Tyr Leu Val Gly Phe Gln Pro Gly
1               5                   10                  15

Ala Ala Ser Asp Asn Val Asn Ala Leu Ser Gln Val Thr Ala Leu Gly
            20                  25                  30

Gly Glu Val Glu His Glu Phe Asp Phe Ala Asp Ile Ile His Val Ser
        35                  40                  45

Leu Pro Glu Gln Ala Val Arg Gly Leu Glu Asn Asn Pro Asn Val Ala
    50                  55                  60

Phe Val Glu Glu Asn His Glu Val Gln Ala Tyr
65                  70                  75
```

<210> SEQ ID NO 37
<211> LENGTH: 250
<212> TYPE: PRT
<213> ORGANISM: Bacillus lentus

<400> SEQUENCE: 37

```
Gly Leu Thr Gly Ser Gly Val Lys Val Ala Val Leu Asp Thr Gly Ile
1               5                   10                  15

Ser Thr His Pro Asp Leu Asn Ile Arg Gly Gly Ala Ser Phe Val Pro
            20                  25                  30

Gly Glu Pro Ser Thr Gln Asp Gly Asn Gly His Gly Thr His Val Ala
        35                  40                  45

Gly Thr Ile Ala Ala Leu Asn Asn Ser Ile Gly Val Leu Gly Val Ala
    50                  55                  60

Pro Ser Ala Glu Leu Tyr Ala Val Lys Val Leu Gly Ala Ser Gly Ser
65                  70                  75                  80
```

```
Gly Ser Val Ser Ser Ile Ala Gln Gly Leu Glu Trp Ala Gly Asn Asn
                85                  90                  95

Gly Met His Val Ala Asn Leu Ser Leu Gly Ser Pro Ser Pro Ser Ala
            100                 105                 110

Thr Leu Glu Gln Ala Val Asn Ser Ala Thr Ser Arg Gly Val Leu Val
        115                 120                 125

Val Ala Ala Ser Gly Asn Ser Gly Ala Gly Ser Ile Ser Tyr Pro Ala
    130                 135                 140

Arg Tyr Ala Asn Ala Met Ala Val Gly Ala Thr Asp Gln Asn Asn Asn
145                 150                 155                 160

Arg Ala Ser Phe Ser Gln Tyr Gly Ala Gly Leu Asp Ile Val Ala Pro
                165                 170                 175

Gly Val Asn Val Gln Ser Thr Tyr Pro Gly Ser Thr Tyr Ala Ser Leu
            180                 185                 190

Asn Gly Thr Ser Met Ala Thr Pro His Val Ala Gly Ala Ala Ala Leu
        195                 200                 205

Val Lys Gln Lys Asn Pro Ser Trp Ser Asn Val Gln Ile Arg Asn His
    210                 215                 220

Leu Lys Asn Thr Ala Thr Ser Leu Gly Ser Thr Asn Leu Tyr Gly Ser
225                 230                 235                 240

Gly Leu Val Asn Ala Glu Ala Ala Thr Arg
                245                 250
```

<210> SEQ ID NO 38
<211> LENGTH: 1059
<212> TYPE: DNA
<213> ORGANISM: artificial sequence
<220> FEATURE:
<223> OTHER INFORMATION: Synthesized sequence - synthetic gene for expression of BspZ00258 protease

<400> SEQUENCE: 38

```
aacggatcag gagagacgaa ggagtatttg gttggttttc aacctggagc agcatcagat     60

aacgtgaatg cgttaagtca ggttaccgct cttggtggag aggtggagca tgaatttgat    120

tttgcggata tcatccatgt ttctttacct gaacaagcgg ttcgtggttt agaaaacaat    180

ccgaatgtag cgtttgtaga agaaaatcac gaagttcaag catatgctca agaagtccct    240

tatggtattg aacaaattgg cgctattgat gttcaggtca atgacggaaa cacaggtaat    300

ggcgtgagtg tggctgtgtt ggatacgggg attgccgctc atgaggattt gaatgtggtt    360

gatggtgcga gttttatcgc aggtgaacct gattacgaag actataatgg tcatggtaca    420

cacgttgctg gaaccgtcgc agcccttgat aatgacttag gtgttctcgg tgtgagccct    480

gacgttgatc tctatgctgt caaagtatta ggtgctgatg gggcggttc ccacgcatcc     540

attgctcaag gcatcgagtg ggcggttgat aataatatcg atgttgtgaa catgagtctt    600

ggtggtgctg taggttcgac gacacttgag caagcagtaa attacgctca tagccaaggt    660

gtaaccctta ttgcagcagc cggtaatgaa ggatcgctta ttccaggttt gaacacgatc    720

ggctacccag caaagtatga taatgtgatc gcggttgggg cggttgactc aaataacaac    780

cgtgcctcgt tctctagcgt tggaaatgag ctagatgtgg tcgcaccagg cgtgagcata    840

ttgagtacct acttgggcaa tgactacgca gcgttgaacg gtacgtctat ggcttctcca    900

cacgtggcag gagcagctgc gctgttactt gcagaaaatc caggattgac gaacgatcaa    960

gttcgcgcgg tatttaacga aactgcagtt ccactgggag atcacttcta ctatggaaat   1020
```

ggattaattg atgtaagagc tgcgattgat gcgcagtaa 1059

<210> SEQ ID NO 39
<211> LENGTH: 78
<212> TYPE: PRT
<213> ORGANISM: Bacillus agaradhaerens

<400> SEQUENCE: 39

Asp Ser Thr Asp Arg Asn Ser Gly Ser Gly Thr Lys Glu Tyr Leu Val
1 5 10 15

Met Phe Glu Glu Asp Ser Ala Asp Met Ser Val Met Lys Ser Ile Gly
20 25 30

Ile Ser Gln Ser Asn Ile Leu Tyr Glu Phe Glu Leu Leu Pro Val Leu
35 40 45

His Val Glu Leu Ser Glu Thr Gln Val Asn Ser Leu Glu Asn His Pro
50 55 60

Gln Ile Lys Thr Val Glu Glu Asn Ala Glu Ala Lys Ala Tyr
65 70 75

<210> SEQ ID NO 40
<211> LENGTH: 84
<212> TYPE: PRT
<213> ORGANISM: Bacillus lentus

<400> SEQUENCE: 40

Ala Glu Glu Ala Lys Glu Lys Tyr Leu Ile Gly Phe Asn Glu Gln Glu
1 5 10 15

Ala Val Ser Glu Phe Val Glu Gln Val Glu Ala Asn Asp Glu Val Ala
20 25 30

Ile Leu Ser Glu Glu Glu Glu Val Glu Ile Glu Leu Leu His Glu Phe
35 40 45

Glu Thr Ile Pro Val Leu Ser Val Glu Leu Ser Pro Glu Asp Val Asp
50 55 60

Ala Leu Glu Leu Asp Pro Ala Ile Ser Tyr Ile Glu Glu Asp Ala Glu
65 70 75 80

Val Thr Thr Met

<210> SEQ ID NO 41
<211> LENGTH: 77
<212> TYPE: PRT
<213> ORGANISM: Bacillus subtilis

<400> SEQUENCE: 41

Ala Gly Lys Ser Ser Thr Glu Lys Lys Tyr Ile Val Gly Phe Lys Gln
1 5 10 15

Thr Met Ser Ala Met Ser Ser Ala Lys Lys Lys Asp Val Ile Ser Glu
20 25 30

Lys Gly Gly Lys Val Gln Lys Gln Phe Lys Tyr Val Asn Ala Ala Ala
35 40 45

Ala Thr Leu Asp Glu Lys Ala Val Lys Glu Leu Lys Lys Asp Pro Ser
50 55 60

Val Ala Tyr Val Glu Glu Asp His Ile Ala His Glu Tyr
65 70 75

<210> SEQ ID NO 42
<211> LENGTH: 77
<212> TYPE: PRT
<213> ORGANISM: Bacillus xiamenensis

<400> SEQUENCE: 42

Glu Thr Ala Ser Lys Ser Glu Ser Glu Lys Ser Tyr Ile Val Gly Phe
1 5 10 15

Lys Ala Ser Ala Thr Thr Asn Ser Ser Lys Lys Gln Ala Val Thr Gln
20 25 30

Asn Gly Gly Thr Leu Glu Lys Gln Tyr Arg Leu Ile Asn Ala Ala Gln
35 40 45

Val Lys Met Ser Glu Gln Ala Ala Lys Lys Leu Glu His Asp Pro Ser
50 55 60

Ile Asp Tyr Val Glu Glu Asp Tyr Lys Ala Glu Ala Tyr
65 70 75

<210> SEQ ID NO 43
<211> LENGTH: 74
<212> TYPE: PRT
<213> ORGANISM: artificial sequence
<220> FEATURE:
<223> OTHER INFORMATION: synthesized sequence - amino acid sequence of Chemgen_164A pro-peptide; Bacillus strain 164A

<400> SEQUENCE: 43

Ser Gly Lys Asn Ala Glu Ile Lys Lys Asp Tyr Leu Val Gly Phe Lys
1 5 10 15

Thr Asn Val Thr Asn Glu Ser Lys Asn Ile Val Asn Ser Leu Gly Gly
20 25 30

Ser Val His His Gln Tyr Lys Tyr Met Asp Val Leu His Val Ser Leu
35 40 45

Pro Glu Lys Ala Ala Glu Ala Leu Lys Asn Asn Pro Asn Val Ala Phe
50 55 60

Val Asp Leu Asp Ala Glu Val Gln Ala Phe
65 70

<210> SEQ ID NO 44
<211> LENGTH: 79
<212> TYPE: PRT
<213> ORGANISM: artificial sequence
<220> FEATURE:
<223> OTHER INFORMATION: synthesized sequence -amino acid sequence of ZP_00454 pro-peptide; Bacillus sp. m3-13

<400> SEQUENCE: 44

Ala Ala Ser Gly Pro Ser Ala Asn Ala Lys Lys Glu Tyr Leu Val Gly
1 5 10 15

Phe Ala Lys Gly Asn Lys Ala Asn Ala Gln Ser Ser Lys Asn Leu Ile
20 25 30

Thr Ala Ala Gly Gly Asp Ile Gln His Thr Phe Gln Tyr Met Asp Val
35 40 45

Val Glu Val Ser Leu Pro Glu Lys Ala Ala Glu Ala Leu Ala Lys Asn
50 55 60

Pro Asn Ile Ala Phe Val Glu Val Asn Ala Glu Val Gln Ala Thr
65 70 75

<210> SEQ ID NO 45
<211> LENGTH: 82
<212> TYPE: PRT
<213> ORGANISM: Bacillus patagoniensis

<400> SEQUENCE: 45

Ala Glu Glu Ala Lys Glu Lys Tyr Leu Ile Gly Phe Thr Glu Gln Glu
1 5 10 15

```
Ala Val Ser Thr Phe Val Glu Gln Ile Glu Glu Glu Glu Val Ser Ile
            20                  25                  30

Ser Glu Val Asp Asp Val Glu Ile Asp Leu Leu Tyr Glu Phe Glu Thr
        35                  40                  45

Ile Pro Val Leu Ser Val Glu Leu Asn Pro Glu Asp Val Ala Ser Leu
    50                  55                  60

Glu Ser Asp Pro Ala Ile Ser Tyr Ile Glu Glu Asp Ala Glu Val Thr
65                  70                  75                  80

Thr Met


<210> SEQ ID NO 46
<211> LENGTH: 87
<212> TYPE: PRT
<213> ORGANISM: Bacillus gibsonii

<400> SEQUENCE: 46

Ala Glu Glu Lys Val Lys Tyr Leu Ile Gly Phe Glu Glu Glu Ala Glu
1               5                   10                  15

Leu Glu Ala Phe Thr Glu Glu Val Asp Gln Val Gly Val Phe Ser Val
            20                  25                  30

Glu Glu Gln Ser Leu Val Glu Asp Thr Leu Asp Ile Asp Val Asp Ile
        35                  40                  45

Ile Asp Glu Tyr Asp Tyr Ile Asp Val Leu Ser Val Glu Leu Asp Pro
    50                  55                  60

Glu Asp Val Asp Ala Leu Ser Glu Glu Glu Gly Ile Ser Tyr Ile Glu
65                  70                  75                  80

Glu Asp Phe Glu Leu Ser Ile
                85


<210> SEQ ID NO 47
<211> LENGTH: 78
<212> TYPE: PRT
<213> ORGANISM: artificial sequence
<220> FEATURE:
<223> OTHER INFORMATION: synthesized sequence - amino acid sequence of
      BspAK01305 pro-peptide; Bacillus sp. DSM 8717

<400> SEQUENCE: 47

Ala Glu Glu Lys Lys Ser Tyr Leu Ile Gly Phe Asp Glu Pro Gln Glu
1               5                   10                  15

Val Glu Gln Phe Thr Thr Asn Leu Glu Glu Glu Ile Arg Thr Gln Ala
            20                  25                  30

Asp Asp Ala Ile Asp Val Thr Tyr Glu Phe Lys Asp Ile Pro Val Leu
        35                  40                  45

Ala Val Asp Met Thr Glu Glu Glu Met Thr Glu Leu Lys Asn Glu Glu
    50                  55                  60

Ser Ile Ser Tyr Ile Glu Glu Asp Gln Glu Val Thr Thr Met
65                  70                  75


<210> SEQ ID NO 48
<211> LENGTH: 71
<212> TYPE: PRT
<213> ORGANISM: artificial sequence
<220> FEATURE:
<223> OTHER INFORMATION: synthesized sequence - amino acid sequence of
      BspAI02518 pro-peptide; Bacillus  sp. C-M2-3

<400> SEQUENCE: 48

Asn Ser Ala Val Glu Lys Glu Asp Tyr Leu Ile Gly Phe Lys Gln Lys
```

-continued

```
1               5                   10                  15

Gly Asn Val Ser Ala Gln Val Val Asn Met Ser Gly Gly Glu Val Val
            20                  25                  30

His Glu Tyr Glu His Met Pro Val Leu His Val Lys Leu Pro Pro Gln
        35                  40                  45

Ala Ala Lys Ala Leu Glu Lys Asn Arg Asn Ile Glu Tyr Ile Glu Lys
    50                  55                  60

Asp Glu Lys Val Gln Ala Thr
65                  70


<210> SEQ ID NO 49
<211> LENGTH: 72
<212> TYPE: PRT
<213> ORGANISM: artificial sequence
<220> FEATURE:
<223> OTHER INFORMATION: synthesized sequence - amino acid sequence of
      BspZ00056 pro-peptide; Bacillus sp. WDG291

<400> SEQUENCE: 49

Gly Gly Asn Asp Gln Ser Gln Asp Tyr Leu Val Gln Phe Asn Gly Pro
1               5                   10                  15

Ala Ser Lys Gly Leu Ile Lys Ala Phe Gly Val Asp Glu Gly Asp Ile
            20                  25                  30

Leu His Thr Tyr Asp His Leu Pro Val Val His Val Asn Leu Thr Glu
        35                  40                  45

Asn Gln Ala Arg Gly Leu Ala Asn His Pro His Ile Thr Thr Val Glu
    50                  55                  60

Glu Asn Ala Glu Val Lys Ala Leu
65                  70
```

SUBTILISIN VARIANTS HAVING IMPROVED STABILITY

The present application claims priority to U.S. Provisional Application 62/772,271, filed Nov. 28, 2018, the entirety of which is hereby incorporated by reference.

Disclosed herein is one or more subtilisin variant, and compositions and methods related to the production and use thereof, including one or more subtilisin variant that has improved stability and/or soil removal compared to one or more reference subtilisin.

REFERENCE TO SEQUENCE LISTING SUBMITTED ELECTRONICALLY

The content of the sequence listing electronically submitted with the application as an ASCII text file (Name: 20191120_NB41589PCT_ST25_SeqLst.txt; Size: 84,000 bytes; Created: Nov. 20, 2019) forms part of the application and is hereby incorporated herein by reference in its entirety.

BACKGROUND

A protease (also known as a proteinase) is an enzyme that has the ability to break down other proteins. A protease has the ability to conduct proteolysis, by hydrolysis of peptide bonds that link amino acids together in a peptide or polypeptide chain forming the protein. This activity of a protease as a protein-digesting enzyme is termed a proteolytic activity. Many well-known procedures exist for measure ng proteolytic activity (Kalisz, "Microbial Proteinases," In: Fiechter (ed.), *Advances in Biochemical Engineering/Biotechnology*, (1988)). For example, proteolytic activity may be ascertained by comparative assays which analyze the respective protease's ability to hydrolyze a commercial substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and Keratin Azure (Sigma-Aldrich K8500). Colorimetric assays utilizing these substrates are well known in the art (see, e.g., WO 99/34011 and U.S. Pat. No. 6,376,450, both of which are incorporated herein by reference).

Serine proteases are enzymes (EC No. 3.4.21) possessing an active site serine that initiates hydrolysis of peptide bonds of proteins. Serine proteases comprise a diverse class of enzymes having a wide range of specificities and biological functions that are further divided based on their structure into chymotrypsin-like (trypsin-like) and subtilisin-like. The prototypical subtilisin (EC No. 3.4.21.62) was initially obtained from *Bacillus subtilis*. Subtilisins (also sometimes referred to as subtilases) and their homologues are members of the S8 peptidase family of the MEROPS classification scheme. Members of family S8 have a catalytic triad in the order Asp, His and Ser in their amino acid sequence. Although a number of useful variant proteases have been developed for cleaning applications, there remains a need for improved subtilisin variants.

BRIEF SUMMARY

In one embodiment, the present disclosure provides one or more subtilisin variant having at least 70% amino acid sequence identity to SEQ ID NO: 8, 9, 10, 11, 12, 13, 14, 15, 16, 17, 18, 19, or 22, where the variant has at least one, two, three, four, or more features selected from the group consisting of: X003T, X003V, X009E, X024Q, X040E, X069S, X076D, X078N, X079I, X087D, X118R, X124I, X128R, X128S, X129P, X130S, X145R, X166Q, X182E, X185Q, X210I, X211P, X217L, X218S, X248D, and X259P, where the positions are numbered by correspondence with the amino acid sequence of SEQ ID NO:1 (BPN'), where the variant does not have 100% sequence identity to a naturally-occurring amino acid sequence.

In another embodiment, the disclosure provides one or more subtilisin variant having at least 70% amino acid sequence identity to SEQ ID NO: 8, 9, 10, 11, 12, 13, 14, 15, 16, 17, 18, 19, or 22, where the variant has at least one, two or more features selected from the group consisting of X003V, X009E, X024Q, X040E, X069S, X076D, X078N, X079I, X087D, X118R, X124I, X128S, X129P, X130S, X145R, X166Q, X182E, X185Q, X210I, X217L, X218S, X248D, and X259P, where the positions are numbered by correspondence with the amino acid sequence of SEQ ID NO:1 (BPN'), where the variant does not have 100% sequence identity to a naturally-occurring amino acid sequence.

In another embodiment, the disclosure provides one or more subtilisin variant having at least 70% amino acid sequence identity to SEQ ID NO: 8, 10, 13, 14, 16, 17, or 19, where the variant has at least one, two or more features selected from the group consisting of X003V, X009E, X040E, X069S, X076D, X078N, X166Q, X185Q, X218S, and X259P, where the positions are numbered by correspondence with the amino acid sequence of SEQ ID NO:1 (BPN'), where the variant does not have 100% sequence identity to a naturally-occurring amino acid sequence. In another embodiment, the disclosure provides one or more subtilisin variant having at least 70% amino acid sequence identity to SEQ ID NO: 8, 9, 10, 11, 12, 13, 14, 15, 16, 17, 18, 19, or 22, where the variant has at least one feature selected from the group consisting of X003V-X009E, X003V-X024Q, X003V-X040E, X003V-X069S, X003V-X076D, X003V-X078N, X003V-X079I, X003V-X087D, X003V-X118R, X003V-X124I, X003V-X128S, X003V-X129P, X003V-X130S, X003V-X145R, X003V-X166Q, X003V-X185Q, X003V-X210I, X003V-X217L, X003V-X218S, X003V-X248D, X003V-X259P, X009E-X024Q, X009E-X040E, X009E-X069S, X009E-X076D, X009E-X078N, X009E-X079I, X009E-X087D, X009E-X118R, X009E-X124I, X009E-X128S, X009E-X129P, X009E-X130S, X009E-X145R, X009E-X166Q, X009E-X185Q, X009E-X210I, X009E-X217L, X009E-X218S, X009E-X248D, X009E-X259P, X024Q-X040E, X024Q-X069S, X024Q-X076D, X024Q-X078N, X024Q-X079I, X024Q-X087D, X024Q-X118R, X024Q-X124I, X024Q-X128S, X024Q-X129P, X024Q-X130S, X024Q-X145R, X024Q-X166Q, X024Q-X185Q, X024Q-X210I, X024Q-X217L, X024Q-X218S, X024Q-X248D, X024Q-X259P, X040E-X069S, X040E-X076D, X040E-X078N, X040E-X079I, X040E-X087D, X040E-X118R, X040E-X124I, X040E-X128S, X040E-X129P, X040E-X130S, X040E-X145R, X040E-X166Q, X040E-X185Q, X040E-X210I, X040E-X217L, X040E-X218S, X040E-X248D, X040E-X259P, X069S-X076D, X069S-X078N, X069S-X079I, X069S-X087D, X069S-X118R, X069S-X124I, X069S-X128S, X069S-X129P, X069S-X130S, X069S-X145R, X069S-X166Q, X069S-X185Q, X069S-X210I, X069S-X217L, X069S-X218S, X069S-X248D, X069S-X259P, X076D-X078N, X076D-X079I, X076D-X087D, X076D-X118R, X076D-X124I, X076D-X128S, X076D-X129P, X076D-X130S, X076D-X145R, X076D-X166Q, X076D-X185Q, X076D-X210I, X076D-X217L, X076D-X218S, X076D-X248D, X076D-X259P, X078N-X079I, X078N-X087D, X078N-X118R, X078N-X124I, X078N-X128S, X078N-X129P, X078N-X130S, X078N-X145R, X078N-X166Q, X078N-X185Q, X078N-X210I, X078N-X217L, X078N-X218S, X078N-X248D, X078N-X259P, X079I-X087D, X079I-X118R, X079I-X124I, X079I-X128S, X079I-X129P, X079I-X130S, X079I-X145R, X079I-X166Q, X079I-X185Q, X079I-X210I, X079I-X217L, X079I-X218S, X079I-X248D, X079I-X259P, X087D-X118R, X087D-X124I, X087D-X128S, X087D-X129P, X087D-X130S, X087D-X145R, X087D-X166Q, X087D-X185Q, X087D-X210I, X087D-X217L, X087D-X218S, X087D-X248D, X087D-X259P, X118R-X124I, X118R-X128S, X118R-X129P, X118R-X130S, X118R-X145R, X118R-X166Q, X118R-X185Q, X118R-X210I, X118R-X217L, X118R-X218S, X118R-X248D, X118R-X259P, X124I-X128S, X124I-X129P, X124I-X130S, X124I-X145R, X124I-X166Q, X124I-X185Q, X124I-X210I, X124I-X217L, X124I-X218S, X124I-X248D, X124I-X259P, X128S-X129P, X128S-X130S, X128S-X145R, X128S-X166Q, X128S-X185Q, X128S-X210I, X128S-X217L, X128S-X218S, X128S-X248D, X128S-X259P, X129P-X130S, X129P-X145R, X129P-X166Q, X129P-X185Q, X129P-X210I, X129P-X217L, X129P-X218S, X129P-X248D, X129P-X259P, X130S-X145R, X130S-X166Q, X130S-X185Q, X130S-X210I, X130S-X217L, X130S-X218S, X130S-X248D, X130S-X259P, X145R-X166Q, X145R-X185Q, X145R-X210I, X145R-X217L, X145R-X218S, X145R-X248D, X145R-X259P, X166Q-X185Q, X166Q-X210I, X166Q-X217L, X166Q-X218S, X166Q-X248D, X166Q-X259P, X185Q-X210I, X185Q-X217L, X185Q-X218S, X185Q-X248D, X185Q-X259P, X210I-X217L, X210I-X218S, X210I-X248D, X210I-X259P, X217L-X218S, X217L-X248D, X217L-X259P, X218S-X248D, X218S-X259P, and X248D-X259P, where the positions are numbered by correspondence with the amino acid sequence of SEQ ID NO:1 (BPN'), where the variant does not have 100% sequence identity to a naturally-occurring amino acid sequence.

Some further embodiments are directed to a composition comprising one or more subtilisin variant described herein. Further embodiments are directed to a method of cleaning comprising contacting a surface or an item in need of cleaning with an effective amount of one or more subtilisin variant described herein or one or more composition described herein.

Still other embodiments are directed to a method for producing a variant described herein, comprising stably transforming a host cell with an expression vector comprising a polynucleotide encoding one or more subtilisin variant described herein. Still further embodiments are directed to a polynucleotide comprising a nucleic acid sequence encoding one or more subtilisin variant described herein.

DETAILED DESCRIPTION

Figure 1:
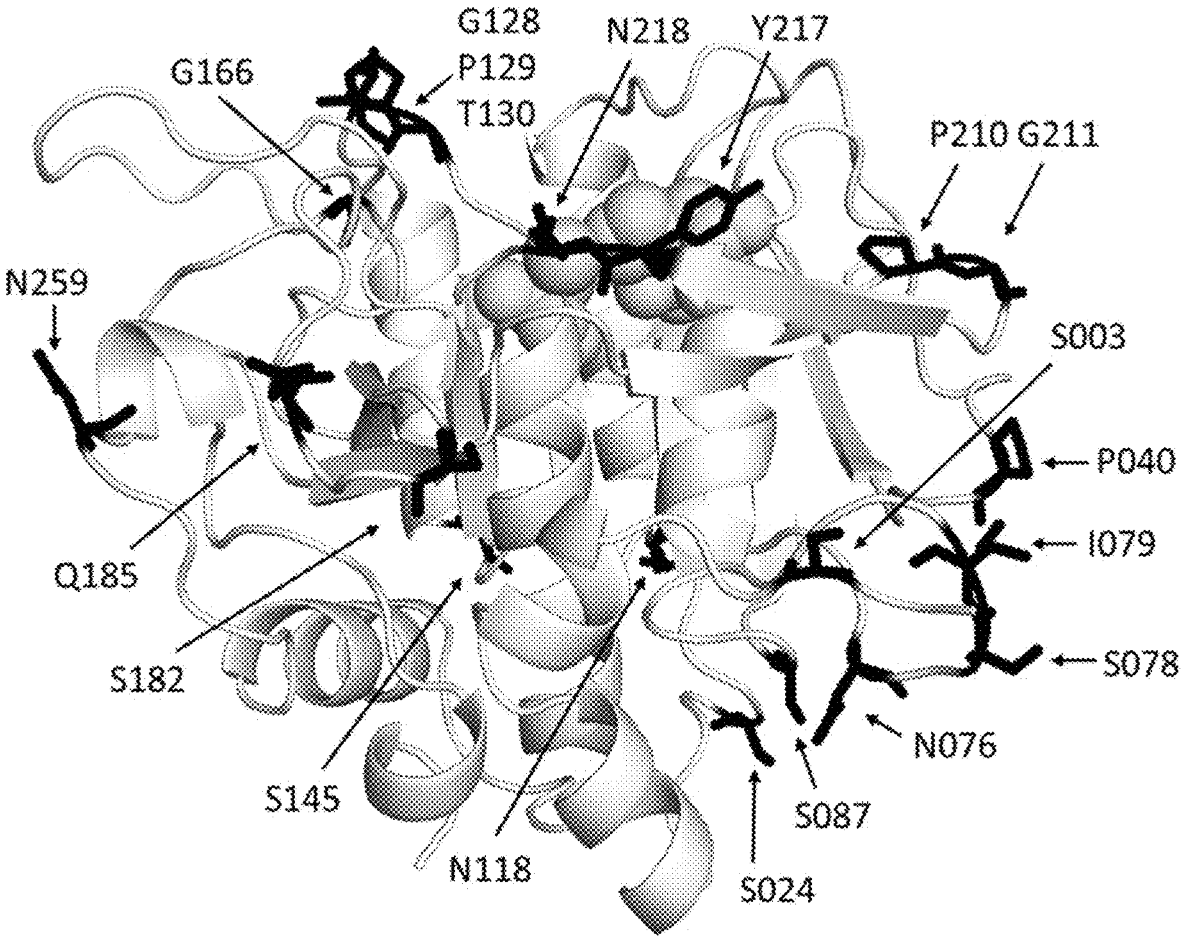
FIG. 1 depicts the locations on the structure of AprE (Subtilisin E from *B. subtilis*, strain 168) (PDB entry 1SCJ) for a subset of sites where certain amino acid residues evaluated in this study show benefit in increasing stability. The main chain fold of AprE (Subtilisin E) is schematically represented in light gray (only mature polypeptide region is shown, excluding the propeptide segment), the catalytic tried is shown as gray spheres, and the sites evaluated for stability improvement are shown as black stick figures (numbered with respect to BPN' subtilisin sequence, SEQ ID NO:1).

The present disclosure provides subtilisin variants having amino acid sequences with one, two, three or more features (e.g. substitutions) at positions in the polypeptide sequence that provide for improved stability of the variant subtilisin when compared to a reference subtilisin lacking the one, two, three, or more features. As provided in more detail below, the features are found at positions selected from 3, 9, 24, 40, 69, 76, 78, 79, 87, 118, 124, 128, 129, 130, 145, 166, 182, 185, 210, 211, 217, 218, 248, and 259, where positions are numbered by correspondence to the amino acid positions of BPN' (SEQ ID NO: 1) using the multiple protein sequence alignment shown on Table 28 of this application. The features can be combinations at the positions listed above, and include substitutions or, in some cases, combinations of wildtype amino acids and substitutions at the identified positions that provide improved stability in comparison to a parent or reference subtilisin polypeptide. Also provided are compositions (e.g. enzyme compositions or detergent compositions (e.g. dishwashing and laundry detergent compositions)) containing such subtilisin variants and methods using such variants and compositions.

Terms and abbreviations not defined should be accorded their ordinary meaning as used in the art. Unless defined otherwise herein, all technical and scientific terms used herein have the same meaning as commonly understood by one of ordinary skill in the art. Any definitions provided herein are to be interpreted in the context of the specification as a whole. As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. Each numerical range used herein includes every narrower numerical range that falls within such broader numerical range, as if such narrower numerical ranges were all expressly written herein.

As used herein in connection with a numerical value, the term "about" refers to a range of +/−0.5 of the numerical value, unless the term is otherwise specifically defined in context. For instance, the phrase a "pH value of about 6" refers to pH values of from 5.5 to 6.5, unless the pH value is specifically defined otherwise.

The nomenclature of the amino acid substitutions of the one or more subtilisin variants described herein uses one or more of the following: position; position:amino acid or amino acid substitution(s); or starting amino acid(s):position:amino acid substitution(s). Reference to a "position" (i.e. 5, 8, 17, 22, etc) encompasses any starting amino acid that may be present at such position, and any substitution that may be present at such position. Reference to a position can be recited in several forms, for example, position 003 can also be referred to as position 3. Reference to a "position: amino acid substitution(s)" (i.e. 1S/T/G, 3G, 17T, etc) encompasses any starting amino acid that may be present at such position and the one or more amino acid(s) with which such starting amino acid may be substituted. Reference to a starting or substituted amino acid may be further expressed as several starting, or substituted amino acids separated by a foreslash ("/"). For example, D275S/K indicates position 275 is substituted with serine (S) or lysine (K) and P/S197K indicates that starting amino acid proline (P) or serine (S) at position 197 is substituted with lysine (K). Reference to an X as the amino acid in a position, refers to any amino acid at the recited position.

Unless otherwise indicated, the position of an amino acid residue in a given amino acid sequence is numbered by correspondence with the amino acid sequence of SEQ ID NO:1. That is, the amino acid sequence of BPN' shown in SEQ ID NO:1 serves as a reference sequence. In one embodiment, the amino acid sequence of one or more subtilisin variant described herein is aligned with the amino acid sequence of SEQ ID NO:1 in accordance with Table 28 using an alignment algorithm as described herein, and each amino acid residue in the given amino acid sequence that aligns (preferably optimally aligns) with an amino acid residue in SEQ ID NO:1 is conveniently numbered by reference to the numerical position of that corresponding amino acid residue. Sequence alignment algorithms, such as, for example, those described herein will identify the location or locations where insertions or deletions occur in a subject sequence when compared to a query sequence (also sometimes referred to as "reference sequence").

The terms "protease" and "proteinase" refer to an enzyme that has the ability to break down proteins and peptides. A protease has the ability to conduct "proteolysis," by hydrolysis of peptide bonds that link amino acids together in a peptide or polypeptide chain forming the protein. This activity of a protease as a protein-digesting enzyme is referred to as "proteolytic activity." Many well-known procedures exist for measuring proteolytic activity. For example, proteolytic activity may be ascertained by comparative assays that analyze the respective protease's ability to hydrolyze a suitable substrate. Exemplary substrates useful in the analysis of protease or proteolytic activity, include, but are not limited to, di-methyl casein (Sigma C-9801), bovine collagen (Sigma C-9879), bovine elastin (Sigma E-1625), and Keratin Azure (Sigma-Aldrich K8500). Colorimetric assays utilizing these substrates are well known in the art (See e.g., WO99/34011 and U.S. Pat. No. 6,376,450). The pNA peptidyl assay (See e.g., Del Mar et al., Anal Biochem, 99:316-320, 1979) also finds use in determining the active enzyme concentration. This assay measures the rate at which p-nitroaniline is released as the enzyme hydrolyzes a soluble synthetic substrate, such as succinyl-alanine-alanine-proline-phenylalanine-p-nitroanilide (suc-AAPF-pNA). The rate of production of yellow color from the hydrolysis reaction is measured at 405 or 410 nm on a spectrophotometer and is proportional to the active enzyme concentration. In addition, absorbance measurements at 280 nanometers (nm) can be used to determine the total protein concentration in a sample of purified protein. The activity on substrate divided by protein concentration gives the enzyme specific activity.

The phrase "composition(s) substantially-free of boron" or "detergent(s) substantially-free of boron" refers to composition(s) or detergent(s), respectively, that contain trace amounts of boron, for example, less than about 1000 ppm (1 mg/kg or liter equals 1 ppm), less than about 100 ppm, less than about 50 ppm, less than about 10 ppm, or less than about 5 ppm, or less than about 1 ppm, perhaps from other compositions or detergent constituents.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. gibsonii*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*", or *B. polymyxa*, which is now "*Paenibacillus polymyxa*". The production of resistant endospores under stressful environmental conditions is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus, and Virgibacillus.*

The term "vector" refers to a nucleic acid construct used to introduce or transfer nucleic acid(s) into a target cell or tissue. A vector is typically used to introduce foreign DNA into a cell or tissue. Vectors include plasmids, cloning vectors, bacteriophages, viruses (e.g., viral vector), cosmids, expression vectors, shuttle vectors, and the like. A vector typically includes an origin of replication, a multicloning site, and a selectable marker. The process of inserting a vector into a target cell is typically referred to as transformation. The present invention includes, in some embodiments, a vector that comprises a DNA sequence encoding a serine protease polypeptide (e.g., precursor or mature serine protease polypeptide) that is operably linked to a suitable prosequence (e.g., secretory, signal peptide sequence, etc.) capable of effecting the expression of the DNA sequence in a suitable host, and the folding and translocation of the recombinant polypeptide chain.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, electroporation, conjugation, and transduction. Transformation refers to the genetic alteration of a cell which results from the uptake, optional genomic incorporation, and expression of genetic material (e.g., DNA).

The term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the "production of the polypeptide" including, but not limited to, transcription, post-transcriptional modifications, translation, post-translational modifications, secretion and the like.

The phrases "expression cassette" or "expression vector" refer to a nucleic acid construct or vector generated recombinantly or synthetically for the expression of a nucleic acid of interest (e.g., a foreign nucleic acid or transgene) in a target cell. The nucleic acid of interest typically expresses a protein of interest. An expression vector or expression cassette typically comprises a promoter nucleotide sequence that drives or promotes expression of the foreign nucleic acid. The expression vector or cassette also typically includes other specified nucleic acid elements that permit transcription of a particular nucleic acid in a target cell. A recombinant expression cassette can be incorporated into a plasmid, chromosome, mitochondrial DNA, plastid DNA, virus, or nucleic acid fragment. Some expression vectors have the ability to incorporate and express heterologous DNA fragments in a host cell or genome of the host cell. Many prokaryotic and eukaryotic expression vectors are commercially available. Selection of appropriate expression vectors for expression of a protein from a nucleic acid sequence incorporated into the expression vector is within the knowledge of those of skill in the art.

As used herein, a nucleic acid is "operably linked" with another nucleic acid sequence when it is placed into a functional relationship with another nucleic acid sequence. For example, a promoter or enhancer is operably linked to a nucleotide coding sequence if the promoter affects the transcription of the coding sequence. A ribosome binding site may be operably linked to a coding sequence if it is positioned so as to facilitate translation of the coding sequence. Typically, "operably linked" DNA sequences are contiguous. However, enhancers do not have to be contiguous. Linking is accomplished by ligation at convenient restriction sites. If such sites do not exist, synthetic oligonucleotide adaptors or linkers may be used in accordance with conventional practice.

The term "gene" refers to a polynucleotide (e.g., a DNA segment), that encodes a polypeptide and includes regions preceding and following the coding regions. In some instances a gene includes intervening sequences (introns) between individual coding segments (exons).

The term "recombinant", when used with reference to a cell typically indicates that the cell has been modified by the introduction of a foreign nucleic acid sequence or that the cell is derived from a cell so modified. For example, a recombinant cell may comprise a gene not found in identical form within the native (non-recombinant) form of the cell, or a recombinant cell may comprise a native gene (found in the native form of the cell) that has been modified and re-introduced into the cell. A recombinant cell may comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide. "Recombination" and "recombining" of polynucleotides or nucleic acids refer generally to the assembly or combining of two or more nucleic acid or polynucleotide strands or fragments to generate a new polynucleotide or nucleic acid.

A nucleic acid or polynucleotide is said to "encode" a polypeptide if, in its native state or when manipulated by methods known to those of skill in the art, it can be transcribed and/or translated to produce the polypeptide or a fragment thereof. The anti-sense strand of such a nucleic acid is also said to encode the sequence.

The terms "host strain" and "host cell" refer to a suitable host for an expression vector comprising a DNA sequence of interest.

A "protein" or "polypeptide" comprises a polymeric sequence of amino acid residues. The terms "protein" and "polypeptide" are used interchangeably herein. The single and three-letter code for amino acids as defined in conformity with the IUPAC-IUB Joint Commission on Biochemical Nomenclature (JCBN) is used throughout this disclosure. The single letter X refers to any of the twenty amino acids. It is also understood that a polypeptide may be coded for by more than one nucleotide sequence due to the degeneracy of the genetic code.

The terms "prosequence" or "propeptide sequence" refer to an amino acid sequence between the signal peptide sequence and mature protease sequence that is involved in the proper folding and secretion of the protease; they are sometimes referred to as intramolecular chaperones. Cleavage of the prosequence or propeptide sequence results in a mature active protease. Bacterial serine proteases are often expressed as pro-enzymes. Examples of modified propeptides are provided, for example, in WO 2016/205710.

The terms "signal sequence" and "signal peptide" refer to a sequence of amino acid residues that may participate in the secretion or direct transport of the mature or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "mature" form of a protein, polypeptide, or peptide refers to the functional form of the protein, polypeptide, or peptide without the signal peptide sequence and propeptide sequence.

The term "precursor" form of a protein or peptide refers to a mature form of the protein having a prosequence operably linked to the amino or carbonyl terminus of the protein. The precursor may also have a "signal" sequence operably linked to the amino terminus of the prosequence. The precursor may also have additional polypeptides that are involved in post-translational activity (e.g., polypeptides cleaved therefrom to leave the mature form of a protein or peptide).

The term "wildtype", with respect to a polypeptide, refers to a naturally-occurring polypeptide that does not include a man-made substitution, insertion, or deletion at one or more amino acid positions. Similarly, the term "wildtype", with respect to a polynucleotide, refers to a naturally-occurring polynucleotide that does not include a man-made substitution, insertion, or deletion at one or more nucleotides. A polynucleotide encoding a wildtype polypeptide is, however, not limited to a naturally-occurring polynucleotide, and encompasses any polynucleotide encoding the wildtype or parental polypeptide.

The term "parent", with respect to a polypeptide, includes reference to a naturally-occurring, or wildtype, polypeptide or to a naturally-occurring polypeptide in which a man-made substitution, insertion, or deletion at one or more amino acid positions has been made. The term "parent" with respect to a polypeptide also includes any polypeptide that has protease activity that serves as the starting polypeptide for alteration, such as substitutions, additions, and/or deletions, to result in a variant having one or more alterations in comparison to the starting polypeptide. That is, a parental, or reference polypeptide is not limited to a naturally-occurring wildtype polypeptide, and encompasses any wildtype, parental, or reference polypeptide. Similarly, the term "parent," with respect to a polynucleotide, can refer to a naturally-occurring polynucleotide or to a polynucleotide that does include a man-made substitution, insertion, or deletion at one or more nucleotides. The term "parent" with respect to a polynucleotide also includes any polynucleotide that encodes a polypeptide having protease activity that serves as the starting polynucleotide for alteration to result in a variant protease having a modification, such as substitutions, additions, and/or deletions, in comparison to the starting polynucleotide. That is, a polynucleotide encoding a wildtype, parental, or reference polypeptide is not limited to a naturally-occurring polynucleotide, and encompasses any polynucleotide encoding the wildtype, parental, or reference polypeptide.

The term "naturally-occurring" refers to, for example, a sequence and residues contained therein (e.g., polypeptide sequence and amino acids contained therein or nucleic acid sequence and nucleotides contained therein) that are found in nature. Conversely, the term "non-naturally occurring" refers to, for example, a sequence and residues contained therein (e.g., polypeptide sequences and amino acids contained therein or nucleic acid sequence and nucleotides contained therein) that are not found in nature.

As used herein with regard to amino acid residue positions, "corresponding to" or "corresponds to" or "corresponds" refers to an amino acid residue at the enumerated position in a protein or peptide, or an amino acid residue that is analogous, homologous, or equivalent to an enumerated residue in a protein or peptide. As used herein, "corresponding region" generally refers to an analogous position in a related protein or a reference protein.

The terms "derived from" and "obtained from" refer to not only a protein produced or producible by a strain of the organism in question, but also a protein encoded by a DNA sequence isolated from such strain and produced in a host organism containing such DNA sequence. Additionally, the term refers to a protein which is encoded by a DNA sequence of synthetic and/or cDNA origin and which has the identifying characteristics of the protein in question. To exemplify, "proteases derived from *Bacillus*" refers to those enzymes having proteolytic activity that are naturally produced by *Bacillus*, as well as to serine proteases like those produced by *Bacillus* sources but which through the use of genetic engineering techniques are produced by other host cells transformed with a nucleic acid encoding the serine proteases.

The term "identical" in the context of two polynucleotide or polypeptide sequences refers to nucleotides or amino acids in the two sequences that are the same when aligned for maximum correspondence, as measured using sequence comparison or analysis algorithms described below and known in the art.

The phrases "% identity" or "percent identity" or "PID" refer to protein sequence identity. Percent identity may be determined using standard techniques known in the art. The percent amino acid identity shared by sequences of interest can be determined by aligning the sequences to directly compare the sequence information, e.g., by using a program such as BLAST, MUSCLE, or CLUSTAL. The BLAST algorithm is described, for example, in Altschul et al., *J Mol Biol,* 215:403-410 (1990) and Karlin et al., *Proc Natl Acad Sci USA,* 90:5873-5787 (1993). A percent (%) amino acid sequence identity value is determined by the number of matching identical residues divided by the total number of residues of the "reference" sequence including any gaps created by the program for optimal/maximum alignment. BLAST algorithms refer to the "reference" sequence as the "query" sequence.

As used herein, "homologous proteins" or "homologous proteases" refers to proteins that have distinct similarity in primary, secondary, and/or tertiary structure. Protein homology can refer to the similarity in linear amino acid sequence when proteins are aligned. Homology can be determined by amino acid sequence alignment, e.g., using a program such as BLAST, MUSCLE, or CLUSTAL. Homologous search of protein sequences can be done using BLASTP and PSI-BLAST from NCBI BLAST with threshold (E-value cut-off) at 0.001. (Altschul et al., "Gapped BLAST and PSI BLAST a new generation of protein database search programs", *Nucleic Acids Res, Set* 1; 25(17):3389-402(1997)). The BLAST program uses several search parameters, most of which are set to the default values. The NCBI BLAST algorithm finds the most relevant sequences in terms of biological similarity but is not recommended for query sequences of less than 20 residues (Altschul et al., *Nucleic Acids Res,* 25:3389-3402, 1997 and Schaffer et al., *Nucleic Acids Res,* 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1. Using this information, protein sequences can be grouped and/or a phylogenetic tree built therefrom. Amino acid sequences can be entered in a program such as the Vector NTI Advance suite and a Guide Tree can be created using the Neighbor Joining (NJ) method (Saitou and Nei, *Mol Biol Evol,* 4:406-425, 1987). The tree construction can be calculated using Kimura's correction for sequence distance and ignoring positions with gaps. A program such as AlignX can display the calculated distance values in parentheses following the molecule name displayed on the phylogenetic tree.

In embodiments where three-dimensional structures of proteins have been determined or homology models created, structurally homologous amino acid positions between two or more molecules can be determined. For molecules with significant structural similarities, it might be expected that introducing substitutions that confer improvement in one molecule at structurally homologous sites in another molecule could confer similar improvements in performance and/or stability to these molecules. Structurally homologous amino acid positions can be identified by performing a structural alignment, which attempts to determine homology between two or more protein structures based on their shape and three-dimensional conformation. Structural alignment can produce a superposition of the atomic coordinate sets and a minimal root mean square deviation between the structures. Examples of methods for creating structural alignments are the distance alignment matrix method (DALI) (Holm L, Sander C (1996) "Mapping the protein universe", *Science,* 273 (5275): 595-603), combinatorial extension (CE) (Shindyalov, I. N.; Bourne P. E. (1998) "Protein structure alignment by incremental combinatorial extension (CE) of the optimal path", *Protein Engineering,* 11 (9): 739-747), and Sequential Structure Alignment Program (S SAP) (Taylor W R, Flores T P, Orengo C A (1994) "Multiple protein structure alignment", *Protein Sci.,* 3 (10): 1858-70). By combining multiple sequence alignments with structural alignments, structurally homologous amino acid positions can be identified in molecules for which the three-dimensional structure has not been determined. Examples of methods for creating multiple sequence alignment-based structural alignments are 3DCoffee (Poirot O et al (2004) "3DCoffee@igs: a web server for combining sequences and structures into a multiple sequence alignment" *Nucleic Acids Res.,* 2004 Jul. 1; 32:W37-40), PROMALS3D (Pei J et al. (2008) "PROMALS3D: a tool for multiple protein sequence and structure alignments." *Nucleic Acids Res.,* 36(7):2295-300), and 3DM (Kuipers, R K et al (2010) "3DM: Systematic analysis of heterogeneous superfamily data to discover protein functionalities" Proteins, 78(9):2101-13). Understanding the homology between molecules can reveal the evolutionary history of the molecules, as well as information about their function; if a newly sequenced protein is homologous to an already characterized protein, there is a strong indication of the new protein's biochemical function. Two molecules are said to be homologous if they have been derived from a common ancestor. Homologous molecules, or homologs, can be divided into two classes, paralogs and orthologs. Paralogs are homologs that are present within one species. Paralogs often differ in their detailed biochemical functions. Orthologs are homologs that are present within different species and have very similar or identical functions. A protein superfamily is the largest grouping (clade) of proteins for which common ancestry can be inferred. Usually this common ancestry is based on sequence alignment and mechanistic similarity. Superfamilies typically contain several protein families which show sequence similarity within the family. The term "protein clan" is commonly used for protease superfamilies based on the MEROPS protease classification system. As used herein, the term "subtilisin" includes any member of the S8 serine protease family as described in MEROPS—The Peptidase Data base (Rawlings, N. D. et al (2016) Twenty years of the MEROPS database of proteolytic enzymes, their substrates and inhibitors. *Nucleic Acids Res* 44, D343-D350).

The CLUSTAL W algorithm is another example of a sequence alignment algorithm (See, Thompson et al., *Nucleic Acids Res,* 22:4673-4680, 1994). Default parameters for the CLUSTAL W algorithm include: Gap opening penalty=10.0; Gap extension penalty=0.05; Protein weight matrix=BLOSUM series; DNA weight matrix=IUB; Delay divergent sequences %=40; Gap separation distance=8; DNA transitions weight=0.50; List hydrophilic residues=GPSNDQEKR; Use negative matrix=OFF; Toggle Residue specific penalties=ON; Toggle hydrophilic penalties=ON; and Toggle end gap separation penalty=OFF. In CLUSTAL algorithms, deletions occurring at either terminus are included. For example, a variant with a five amino acid deletion at either terminus (or within the polypeptide) of a polypeptide of 500 amino acids would have a percent sequence identity of 99% (495/500 identical residues x 100) relative to the "reference" polypeptide. Such a variant would be encompassed by a variant having "at least 99% sequence identity" to the polypeptide.

A nucleic acid or polynucleotide is "isolated" when it is at least partially or completely separated from other components, including but not limited to for example, other proteins, nucleic acids, cells, etc. Similarly, a polypeptide, protein or peptide is "isolated" when it is at least partially or completely separated from other components, including but not limited to for example, other proteins, nucleic acids, cells, etc. On a molar basis, an isolated species is more abundant than are other species in a composition. For example, an isolated species may comprise at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or about 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.6%, about 99.7%, about 99.8% or more pure (e.g., percent by weight on a molar basis). In a related sense, a composition is enriched for a molecule when there is a substantial increase in the concentration of the molecule after application of a purification or enrichment technique. The term "enriched" refers to a compound, polypeptide, cell, nucleic acid, amino acid, or other specified material or component that is present in a composition at a relative or absolute concentration that is higher than in a starting composition.

The term "cleaning activity" refers to a cleaning performance achieved by a serine protease polypeptide, variant, or reference subtilisin under conditions prevailing during the proteolytic, hydrolyzing, cleaning, or other process of the disclosure. In some embodiments, cleaning performance of a serine protease or reference subtilisin may be determined by using various assays for cleaning one or more enzyme sensitive stain on an item or surface (e.g., a stain resulting from food, grass, blood, ink, milk, oil, and/or egg protein). Cleaning performance of one or more subtilisin variant described herein or reference subtilisin can be determined by subjecting the stain on the item or surface to standard wash condition(s) and assessing the degree to which the stain is removed by using various chromatographic, spectrophotometric, or other quantitative methodologies. Exemplary cleaning assays and methods are known in the art and include, but are not limited to those described in WO99/34011 and U.S. Pat. No. 6,605,458, as well as those cleaning assays and methods included in the Examples provided below.

The terms "stable" and "stability" with regard to a protease variant refer to a protease that retains a greater amount of residual activity when compared to the parent or reference protease after exposure to altered temperatures over a given period of time under conditions (or "stress conditions") prevailing during proteolytic, hydrolysing, cleaning or other process. Residual activity is the amount of activity remaining after the test compared to the initial activity of the sample and can be reported as a percentage e.g. % remaining activity. "Altered temperatures" encompass increased or decreased temperatures. In some embodiments, the proteases retain at least about 10%, about 15%, about 20%, about 25%, about 30%, about 35%, about 40%, about 50%, about 60%, about 70%, about 80%, about 85%, about 90%, about 92%, about 95%, about 96%, about 97%, about 98%, or about 99% proteolytic activity (residual activity) in comparison to the respective parent or reference protease after exposure to altered temperatures over a given time period, for example, at least about 20 minutes, at least about 40 minutes, at least about 60 minutes, about 90 minutes, about 120 minutes, about 180 minutes, about 240 minutes, about 300 minutes, about 360 minutes, about 420 minutes, about 480 minutes, about 540 minutes, about 600 minutes, about 660 minutes, about 720 minutes, about 780 minutes, about 840 minutes, about 900 minutes, about 960 minutes, about 1020 minutes, about 1080 minutes, about 1140 minutes, or about 1200 minutes.

Alternatively, the terms "stable" and "stability" with regard to a protease variant also refer to a protease that, after exposure to altered temperatures over a given period of time under conditions (or "stress conditions") prevailing during proteolytic, hydrolysing, cleaning or other process, retains a higher residual activity than a parent, or reference, protease. "Altered temperatures" encompass increased or decreased temperatures. A stability Performance Index (PI) for a variant protease can be obtained by dividing the residual activity of the variant protease by the residual activity of the parent, or reference protease when tested under the same conditions, stressed and non-stressed. In some embodiments, the protease variants have a PI of about 1.1, about 1.2, about 1.3, about 1.4, about 1.5, about 2, about 2.5, about 3, about 4, or higher than 4, after exposure to altered temperatures over a given time period, for example, at least about 5 minutes, at least about 10 minutes, at least about 20 minutes, at least about 40 minutes, at least about 60 minutes, about 90 minutes, about 120 minutes, about 180 minutes, about 240 minutes, about 300 minutes, about 360 minutes, about 420 minutes, about 480 minutes, about 540 minutes, about 600 minutes, about 660 minutes, about 720 minutes, about 780 minutes, about 840 minutes, about 900 minutes, about 960 minutes, about 1020 minutes, about 1080 minutes, about 1140 minutes, or about 1200 minutes. Altered temperatures for evaluation of protein stability can be between 28-85° C., e.g. 30, 35, 40, 45, 50, 55, 60, 65, 70, 75, or 80° C. In some embodiments, stability (e.g. residual activity or performance index) may be measured in the presence of one or more protease stabilizers.

Alternatively, the terms "stable" and "stability" with regard to a protease variant also refer to a protease that, after exposure to altered temperatures over a given period of time under conditions (or "stress conditions") prevailing during proteolytic, hydrolysing, cleaning or other process, exhibits longer half-lives for inactivation ($T_{1/2}$) than a parent, or reference, protease. "Altered temperatures" encompass increased or decreased temperatures. "Half-lives for inactivation" with regard to a protease variant refers to the time period after which the protease retains one half of the initial enzymatic activity.

The term "stability" includes storage stability and stability during use, e.g. during a wash process and reflects the stability of the subtilisin variant according to the invention as a function of time, e.g. how much activity is retained when the subtilisin variants is kept in solution in particular in a detergent solution. The stability is influenced by many factors e.g. pH, temperature, detergent composition, e.g. amount of builder, surfactant, water content, protease inhibitors/stabilizers etc. The stability of the subtilisin variant may be measured using the assays described in Example 2. The term "improved stability" or "increased stability" is defined herein as a variant subtilisin displaying an increased stability in solutions, relative to the stability of the parent subtilisin. The terms "improved stability" and "increased stability" includes "improved chemical stability" or "improved detergent stability".

The term "improved detergent stability" is defined herein as a variant subtilisin displaying retention of enzymatic activity after a period of incubation in the presence of a detergent or chemical component of a detergent, which reduces the enzymatic activity of the parent enzyme. Improved detergent stability may also result in variants being more able to catalyze a reaction in the presence of such detergent or chemical components. The term "detergent stability" or "improved detergent stability" is in particular an improved stability of the protease activity when a subtilisin variant of the present invention is mixed into a liquid detergent formulation and incubated at temperatures between 30-70° C., e.g. 35, 40, 45, 50, 55, 60, or 65° C. Detergent stability can be evaluated in a diluted liquid detergent composition, such as 10% detergent, where the commercial liquid detergent is diluted 10 fold in water or a liquid buffer solution prepared at a relevant pH.

The term "enhanced stability" or "improved stability" in the context of an oxidation, chelator, denaturant, surfactant, thermal and/or pH stable protease refers to a higher retained proteolytic activity over time as compared to a reference protease, for example, a wildtype protease or parent protease. Autolysis has been identified as one mode of subtilisin activity loss in liquid detergents. (Stoner et al., 2004 Protease autolysis in heavy-duty liquid detergent formulations: effects of thermodynamic stabilizers and protease inhibitors, *Enzyme and Microbial Technology* 34:114-125.)

The term "effective amount" of one or more subtilisin variant described herein or reference subtilisin refers to the amount of protease that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, tablet, bar) composition is required, etc.

The term "adjunct material" refers to any liquid, solid, or gaseous material included in a cleaning composition, other than one or more subtilisin variant described herein, or recombinant polypeptide or active fragment thereof. In some embodiments, the cleaning compositions of the present disclosure include one or more cleaning adjunct materials. Each cleaning adjunct material is typically selected depending on the particular type and form of cleaning composition (e.g., liquid, granule, powder, bar, paste, spray, tablet, gel, foam, or other composition). Preferably, each cleaning adjunct material is compatible with the protease enzyme used in the composition.

Cleaning compositions and cleaning formulations include any composition that is suited for cleaning, bleaching, disinfecting, and/or sterilizing any object, item, and/or surface. Such compositions and formulations include, but are not limited to, for example, liquid and/or solid compositions, including cleaning or detergent compositions (e.g., liquid, tablet, gel, bar, granule, and/or solid laundry cleaning or detergent compositions and fine fabric detergent compositions); hard surface cleaning compositions and formulations, such as for glass, wood, ceramic and metal counter tops and windows; carpet cleaners; oven cleaners; fabric fresheners; fabric softeners; and textile, laundry booster cleaning or detergent compositions, laundry additive cleaning compositions, and laundry pre-spotter cleaning compositions; dishwashing compositions, including hand or manual dishwashing compositions (e.g., "hand" or "manual" dishwashing detergents) and automatic dishwashing compositions (e.g., "automatic dishwashing detergents"). Single dosage unit forms also find use with the present invention, including but not limited to pills, tablets, gelcaps, or other single dosage units such as pre-measured powders or liquids.

Cleaning composition or cleaning formulations, as used herein, include, unless otherwise indicated, granular or powder-form all-purpose or heavy-duty washing agents, especially cleaning detergents; liquid, granular, gel, solid, tablet, paste, or unit dosage form all-purpose washing agents, especially the so-called heavy-duty liquid (HDL) detergent or heavy-duty dry (HDD) detergent types; liquid fine-fabric detergents; hand or manual dishwashing agents, including those of the high-foaming type; hand or manual dishwashing, automatic dishwashing (ADW), or dishware or tableware washing agents, including the various tablet, powder, solid, granular, liquid, gel, and rinse-aid types for household and institutional use; liquid cleaning and disinfecting agents, including antibacterial hand-wash types, cleaning bars, mouthwashes, denture cleaners, car shampoos, carpet shampoos, bathroom cleaners; hair shampoos and/or hair-rinses for humans and other animals; shower gels and foam baths and metal cleaners; as well as cleaning auxiliaries, such as bleach additives and "stain-stick" or pre-treat types. In some embodiments, granular compositions are in "compact" form; in some embodiments, liquid compositions are in a "concentrated" form.

The term "detergent composition" or "detergent formulation" is used in reference to a composition intended for use in a wash medium for the cleaning of soiled or dirty objects, including particular fabric and/or non-fabric objects or items. In some embodiments, the detergents of the disclosure comprise one or more subtilisin variant described herein and, in addition, one or more surfactants, transferase (s), hydrolytic enzymes, oxido reductases, builders (e.g., a builder salt), bleaching agents, bleach activators, bluing agents, fluorescent dyes, caking inhibitors, masking agents, enzyme stabilizers, calcium, enzyme activators, antioxidants, and/or solubilizers. In some instances, a builder salt is a mixture of a silicate salt and a phosphate salt, preferably with more silicate (e.g., sodium metasilicate) than phosphate (e.g., sodium tripolyphosphate). Some embodiments are directed to cleaning compositions or detergent compositions that do not contain any phosphate (e.g., phosphate salt or phosphate builder).

The term "bleaching" refers to the treatment of a material (e.g., fabric, laundry, pulp, etc.) or surface for a sufficient length of time and/or under appropriate pH and/or temperature conditions to effect a brightening (i.e., whitening) and/or cleaning of the material. Examples of chemicals suitable for bleaching include, but are not limited to, for example, $ClO_2$, $H_2O_2$, peracids, $NO_2$, etc. Bleaching agents also include enzymatic bleaching agents such as perhydrolase and arylesterases. Another embodiment is directed to a composition comprising one or more subtilisin variant described herein, and one or more perhydrolase, such as, for example, is described in WO2005/056782, WO2007/106293, WO 2008/063400, WO2008/106214, and WO2008/106215.

The term "wash performance" of a protease (e.g., one or more subtilisin variant described herein, or recombinant polypeptide or active fragment thereof) refers to the contribution of one or more subtilisin variant described herein to washing that provides additional cleaning performance to the detergent as compared to the detergent without the addition of the one or more subtilisin variant described herein to the composition. Wash performance is compared under relevant washing conditions. In some test systems, other relevant factors, such as detergent composition, sud concentration, water hardness, washing mechanics, time, pH, and/or temperature, can be controlled in such a way that condition(s) typical for household application in a certain market segment (e.g., hand or manual dishwashing, automatic dishwashing, dishware cleaning, tableware cleaning, fabric cleaning, etc.) are imitated.

The phrase "relevant washing conditions" is used herein to indicate the conditions, particularly washing temperature, time, washing mechanics, sud concentration, type of detergent and water hardness, actually used in households in a hand dishwashing, automatic dishwashing, or laundry detergent market segment.

The term "disinfecting" refers to the removal of contaminants from the surfaces, as well as the inhibition or killing of microbes on the surfaces of items.

The term "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically about 17 to about 35% by weight of the total composition. In contrast, in compact compositions, the filler salt is present in amounts not exceeding about 15% of the total composition. In some embodiments, the filler salt is present in amounts that do not exceed about 10%, or more preferably, about 5%, by weight of the composition. In some embodiments, the inorganic filler salts are selected from the alkali and alkaline-earth-metal salts of sulfates and chlorides. In some embodiments, the filler salt is sodium sulfate.

Disclosed herein is one or more subtilisin variants useful, for example, in cleaning compositions and applications and in methods of cleaning, as well as in a variety of industrial applications. Disclosed herein is one or more isolated, recombinant, substantially pure, or non-naturally occurring subtilisin variants. In some embodiments, one or more subtilisin variants described herein is useful in cleaning applications and can be incorporated into cleaning compositions that are useful in methods of cleaning an item or a surface in need thereof.

In one embodiment, the disclosure provides one or more subtilisin variant having at least 70%, 75%, 80%, 85%, 90%, 91%, 92%, 93%, 94%, 95%, 96%, 97%, 98%, or 99% amino acid sequence identity to SEQ ID NO: 8, 9, 10, 11, 12, 13, 14, 15, 16, 17, 18, 19, or 22, where the variant has at least one, two, three, four, or more features selected from the group consisting of: X003T, X003V, X009E, X024Q, X040E, X069S, X076D, X078N, X079I, X087D, X118R, X124I, X128R, X128S, X129P, X130S, X145R, X166Q, X182E, X185Q, X210I, X211P, X217L, X218S, X248D, and X259P, where the positions are numbered by correspondence with the amino acid sequence of SEQ ID NO:1 (BPN'). In one embodiment, the variant does not have 100% sequence identity to a wildtype amino acid sequence (SEQ ID NO: 8, 9, 10, 11, 12, 13, 14, 15, 16, 17, 18, 19, or 22).

In another embodiment, the disclosure provides one or more subtilisin variants having at least one, two, three or more features selected from the group consisting of X003V, X009E, X024Q, X040E, X069S, X076D, X078N, X079I, X087D, X118R, X124I, X128S, X129P, X130S, X166Q, X182E, X185Q, X217L, X218S, X248D, and X259P, where the positions are numbered by correspondence with the amino acid sequence of SEQ ID NO:1 (BPN').

In another embodiment, the subtilisin variant has at least one, two, three or more features selected from the group consisting of X003V, X009E, X040E, X069S, X076D, X078N, X166Q, X185Q, X218S, and X259P, where the positions are numbered by correspondence with the amino acid sequence of SEQ ID NO:1 (BPN'), where the variant does not have 100% sequence identity to a wildtype amino acid sequence.

In still another embodiment, the subtilisin variant has at least two or more features, where the combination of two more features are selected from the group consisting of X003V-X009E, X003V-X024Q, X003V-X040E, X003V-X069S, X003V-X076D, X003V-X078N, X003V-X079I, X003V-X087D, X003V-X118R, X003V-X124I, X003V-X128S, X003V-X129P, X003V-X130S, X003V-X145R, X003V-X166Q, X003V-X185Q, X003V-X210I, X003V-X217L, X003V-X218S, X003V-X248D, X003V-X259P, X009E-X024Q, X009E-X040E, X009E-X069S, X009E-X076D, X009E-X078N, X009E-X079I, X009E-X087D, X009E-X118R, X009E-X124I, X009E-X128S, X009E-X129P, X009E-X130S, X009E-X145R, X009E-X166Q, X009E-X185Q, X009E-X210I, X009E-X217L, X009E-X218S, X009E-X248D, X009E-X259P, X024Q-X040E, X024Q-X069S, X024Q-X076D, X024Q-X078N, X024Q-X079I, X024Q-X087D, X024Q-X118R, X024Q-X124I, X024Q-X128S, X024Q-X129P, X024Q-X130S, X024Q-X145R, X024Q-X166Q, X024Q-X185Q, X024Q-X210I, X024Q-X217L, X024Q-X218S, X024Q-X248D, X024Q-X259P, X040E-X069S, X040E-X076D, X040E-X078N, X040E-X079I, X040E-X087D, X040E-X118R, X040E-X124I, X040E-X128S, X040E-X129P, X040E-X130S, X040E-X145R, X040E-X166Q, X040E-X185Q, X040E-X210I, X040E-X217L, X040E-X218S, X040E-X248D, X040E-X259P, X069S-X076D, X069S-X078N, X069S-X079I, X069S-X087D, X069S-X118R, X069S-X124I, X069S-X128S, X069S-X129P, X069S-X130S, X069S-X145R, X069S-X166Q, X069S-X185Q, X069S-X210I, X069S-X217L, X069S-X218S, X069S-X248D, X069S-X259P, X076D-X078N, X076D-X079I, X076D-X087D, X076D-X118R, X076D-X124I, X076D-X128S, X076D-X129P, X076D-X130S, X076D-X145R, X076D-X166Q, X076D-X185Q, X076D-X210I, X076D-X217L, X076D-X218S, X076D-X248D, X076D-X259P, X078N-X079I, X078N-X087D, X078N-X118R, X078N-X124I, X078N-X128S, X078N-X129P, X078N-X130S, X078N-X145R, X078N-X166Q, X078N-X185Q, X078N-X210I, X078N-X217L, X078N-X218S, X078N-X248D, X078N-X259P, X079I-X087D, X079I-X118R, X079I-X124I, X079I-X128S, X079I-X129P, X079I-X130S, X079I-X145R, X079I-X166Q, X079I-X185Q, X079I-X210I, X079I-X217L, X079I-X218S, X079I-X248D, X079I-X259P, X087D-X118R, X087D-X124I, X087D-X128S, X087D-X129P, X087D-X130S, X087D-X145R, X087D-X166Q, X087D-X185Q, X087D-X210I, X087D-X217L, X087D-X218S, X087D-X248D, X087D-X259P, X118R-X124I, X118R-X128S, X118R-X129P, X118R-X130S, X118R-X145R, X118R-X166Q, X118R-X185Q, X118R-X210I, X118R-X217L, X118R-X218S, X118R-X248D, X118R-X259P, X124I-X128S, X124I-X129P, X124I-X130S, X124I-X145R, X124I-X166Q, X124I-X185Q, X124I-X210I, X124I-X217L, X124I-X218S, X124I-X248D, X124I-X259P, X128S-X129P, X128S-X130S, X128S-X145R, X128S-X166Q, X128S-X185Q, X128S-X210I, X128S-X217L, X128S-X218S, X128S-X248D, X128S-X259P, X129P-X130S, X129P-X145R, X129P-X166Q, X129P-X185Q, X129P-X210I, X129P-X217L, X129P-X218S, X129P-X248D, X129P-X259P, X130S-X145R, X130S-X166Q, X130S-X185Q, X130S-X210I, X130S-X217L, X130S-X218S, X130S-X248D, X130S-X259P, X145R-X166Q, X145R-X185Q, X145R-X210I, X145R-X217L, X145R-X218S, X145R-X248D, X145R-X259P, X166Q-X185Q, X166Q-X210I, X166Q-X217L, X166Q-X218S, X166Q-X248D, X166Q-X259P, X185Q-X210I, X185Q-X217L, X185Q-X218S, X185Q-X248D, X185Q-X259P, X210I-X217L, X210I-X218S, X210I-X248D, X210I-X259P, X217L-X218S, X217L-X248D, X217L-X259P, X218S-X248D, X218S-X259P, X248D-X259P where the positions are numbered by correspondence with the amino acid sequence of SEQ ID NO:1 (BPN').

In other embodiments, the subtilisin variants disclosed herein contain a combination of two or more features with respect to SEQ ID NO: 1, where the combination of two or more features are selected from the group consisting of X003V-X009E, X003V-X040E, X003V-X069S, X003V-X076D, X003V-X078N, X003V-X079I, X003V-X124I, X003V-X128S, X003V-X129P, X003V-X166Q, X003V-X185Q, X003V-X218S, X003V-X259P, X003V-X262L, X009E-X040E, X009E-X069S, X009E-X076D, X009E-X078N, X009E-X166Q, X009E-X185Q, X009E-X218S, X009E-X259P, X040E-X069S, X040E-X076D, X040E-X078N, X040E-X079I, X040E-X124I, X040E-X128S, X040E-X129P, X040E-X166Q, X040E-X185Q, X040E-X218S, X040E-X259P, X069S-X076D, X069S-X078N, X069S-X079I, X069S-X124I, X069S-X128S, X069S-X129P, X069S-X166Q, X069S-X185Q, X069S-X218S, X069S-X259P, X076D-X078N, X076D-X079I, X076D-X124I, X076D-X128S, X076D-X129P, X076D-X166Q, X076D-X185Q, X076D-X218S, X076D-X259P, X078N-X079I, X078N-X124I, X078N-X128S, X078N-X129P, X078N-X166Q, X078N-X185Q, X078N-X218S, X078N-X259P, X078T-X124I, X079I-X124I, X079I-X128S, X079I-X129P, X079I-X166Q, X079I-X185Q, X079I-X218S, X079I-X259P, X124I-X128S, X124I-X129P, X124I-X166Q, X124I-X185Q, X124I-X218S, X124I-X259K, X124I-X259P, X128S-X129P, X128S-X166Q, X128S-X185Q, X128S-X218S, X128S-X259P, X129P-X166Q, X129P-X185Q, X129P-X218S, X129P-X259P, X166Q-X185Q, X166Q-X218S, X166Q-X259P, X185Q-X218S, X185Q-X259P, and X218S-X259P, where the positions are numbered by correspondence with the amino acid sequence of SEQ ID NO:1 (BPN').

In other embodiments, the subtilisin variants disclosed herein contain a combination of three or more features with respect to SEQ ID NO: 1, where the combination of three or more features are selected from the group consisting of X003V-X009E-X024Q, X003V-X009E-X040E, X003V-X009E-X069S, X003V-X009E-X076D, X003V-X009E-X078N, X003V-X009E-X079I, X003V-X009E-X087D, X003V-X009E-X118R, X003V-X009E-X124I, X003V-X009E-X128S, X003V-X009E-X129P, X003V-X009E-X130S, X003V-X009E-X145R, X003V-X009E-X166Q, X003V-X009E-X185Q, X003V-X009E-X210I, X003V-X009E-X217L, X003V-X009E-X218S, X003V-X009E-X248D, X003V-X009E-X259P, X003V-X024Q-X040E, X003V-X024Q-X069S, X003V-X024Q-X076D, X003V-X024Q-X078N, X003V-X024Q-X079I, X003V-X024Q-X087D, X003V-X024Q-X118R, X003V-X024Q-X124I, X003V-X024Q-X128S, X003V-X024Q-X129P, X003V-X024Q-X130S, X003V-X024Q-X145R, X003V-X024Q-X166Q, X003V-X024Q-X185Q, X003V-X024Q-X210I, X003V-X024Q-X217L, X003V-X024Q-X218S, X003V-X024Q-X248D, X003V-X024Q-X259P, X003V-X040E-X069S, X003V-X040E-X076D, X003V-X040E-X078N, X003V-X040E-X079I, X003V-X040E-X087D, X003V-X040E-X118R, X003V-X040E-X124I, X003V-X040E-X128S, X003V-X040E-X129P, X003V-X040E-X130S, X003V-X040E-X145R, X003V-X040E-X166Q, X003V-X040E-X185Q, X003V-X040E-X210I, X003V-X040E-X217L, X003V-X040E-X218S, X003V-X040E-X248D, X003V-X040E-X259P, X003V-X069S-X076D, X003V-X069S-X078N, X003V-X069S-X079I, X003V-X069S-X087D, X003V-X069S-X118R, X003V-X069S-X124I, X003V-X069S-X128S, X003V-X069S-X129P, X003V-X069S-X130S, X003V-X069S-X145R, X003V-X069S-X166Q, X003V-X069S-X185Q, X003V-X069S-X210I, X003V-X069S-X217L, X003V-X069S-X218S, X003V-X069S-X248D, X003V-X069S-X259P, X003V-X076D-X078N, X003V-X076D-X079I, X003V-X076D-X087D, X003V-X076D-X118R, X003V-X076D-X124I, X003V-X076D-X128S, X003V-X076D-X129P, X003V-X076D-X130S, X003V-X076D-X145R, X003V-X076D-X166Q, X003V-X076D-X185Q, X003V-X076D-X210I, X003V-X076D-X217L, X003V-X076D-X218S, X003V-X076D-X248D, X003V-X076D-X259P, X003V-X078N-X079I, X003V-X078N-X087D, X003V-X078N-X118R, X003V-X078N-X124I, X003V-X078N-X128S, X003V-X078N-X129P, X003V-X078N-X130S, X003V-X078N-X145R, X003V-X078N-X166Q, X003V-X078N-X185Q, X003V-X078N-X210I, X003V-X078N-X217L, X003V-X078N-X218S, X003V-X078N-X248D, X003V-X078N-X259P, X003V-X079I-X087D, X003V-X079I-X118R, X003V-X079I-X124I, X003V-X079I-X128S, X003V-X079I-X129P, X003V-X079I-X130S, X003V-X079I-X145R, X003V-X079I-X166Q, X003V-X079I-X185Q, X003V-X079I-X210I, X003V-X079I-X217L, X003V-X079I-X218S, X003V-X079I-X248D, X003V-X079I-X259P, X003V-X087D-X118R, X003V-X087D-X124I, X003V-X087D-X128S, X003V-X087D-X129P, X003V-X087D-X130S, X003V-X087D-X145R, X003V-X087D-X166Q, X003V-X087D-X185Q, X003V-X087D-X210I, X003V-X087D-X217L, X003V-X087D-X218S, X003V-X087D-X248D, X003V-X087D-X259P, X003V-X118R-X124I, X003V-X118R-X128S, X003V-X118R-X129P, X003V-X118R-X130S, X003V-X118R-X145R, X003V-X118R-X166Q, X003V-X118R-X185Q, X003V-X118R-X210I, X003V-X118R-X217L, X003V-X118R-X218S, X003V-X118R-X248D, X003V-X118R-X259P, X003V-X124I-X128S, X003V-X124I-X129P, X003V-X124I-X130S, X003V-X124I-X145R, X003V-X124I-X166Q, X003V-X124I-X185Q, X003V-X124I-X210I, X003V-X124I-X217L, X003V-X124I-X218S, X003V-X124I-X248D, X003V-X124I-X259P, X003V-X128S-X129P, X003V-X128S-X130S, X003V-X128S-X145R, X003V-X128S-X166Q, X003V-X128S-X185Q, X003V-X128S-X210I, X003V-X128S-X217L, X003V-X128S-X218S, X003V-X128S-X248D, X003V-X128S-X259P, X003V-X129P-X130S, X003V-X129P-X145R, X003V-X129P-X166Q, X003V-X129P-X185Q, X003V-X129P-X210I, X003V-X129P-X217L, X003V-X129P-X218S, X003V-X129P-X248D, X003V-X129P-X259P, X003V-X130S-X145R, X003V-X130S-X166Q, X003V-X130S-X185Q, X003V-X130S-X210I, X003V-X130S-X217L, X003V-X130S-X218S, X003V-X130S-X248D, X003V-X130S-X259P, X003V-X145R-X166Q, X003V-X145R-X185Q, X003V-X145R-X210I, X003V-X145R-X217L, X003V-X145R-X218S, X003V-X145R-X248D, X003V-X145R-X259P, X003V-X166Q-X185Q, X003V-X166Q-X210I, X003V-X166Q-X217L, X003V-X166Q-X218S, X003V-X166Q-X248D, X003V-X166Q-X259P, X003V-X185Q-X210I, X003V-X185Q-X217L, X003V-X185Q-X218S, X003V-X185Q-X248D, X003V-X185Q-X259P, X003V-X210I-X217L, X003V-X210I-X218S, X003V-X210I-X248D, X003V-X210I-X259P, X003V-X217L-X218S, X003V-X217L-X248D, X003V-X217L-X259P, X003V-X218S-X248D, X003V-X218S-X259P, X003V-X248D-X259P, X009E-X024Q-X040E, X009E-X024Q-X069S, X009E-X024Q-X076D, X009E-X024Q-X078N, X009E-X024Q-X079I, X009E-X024Q-X087D, X009E-X024Q-X118R, X009E-X024Q-X124I, X009E-X024Q-X128S, X009E-X024Q-X129P, X009E-X024Q-X130S, X009E-X024Q-X145R, X009E-X024Q-X166Q, X009E-X024Q-X185Q, X009E-X024Q-X210I, X009E-X024Q-X217L, X009E-X024Q-X218S, X009E-X024Q-X248D, X009E-X024Q-X259P, X009E-X040E-X069S, X009E-X040E-X076D, X009E-X040E-X078N, X009E-X040E-X079I, X009E-X040E-X087D, X009E-X040E-X118R, X009E-X040E-X124I, X009E-X040E-X128S, X009E-X040E-X129P, X009E-X040E-X130S, X009E-X040E-X145R, X009E-X040E-X166Q, X009E-X040E-X185Q, X009E-X040E-X210I, X009E-X040E-X217L, X009E-X040E-X218S, X009E-X040E-X248D, X009E-X040E-X259P, X009E-X069S-X076D, X009E-X069S-X078N, X009E-X069S-X079I, X009E-X069S-X087D, X009E-X069S-X118R, X009E-X069S-X124I, X009E-X069S-X128S, X009E-X069S-X129P, X009E-X069S-X130S, X009E-X069S-X145R, X009E-X069S-X166Q, X009E-X069S-X185Q, X009E-X069S-X210I, X009E-X069S-X217L, X009E-

X069S-X218S, X009E-X069S-X248D, X009E-X069S-X259P, X009E-X076D-X078N, X009E-X076D-X079I, X009E-X076D-X087D, X009E-X076D-X118R, X009E-X076D-X124I, X009E-X076D-X128S, X009E-X076D-X129P, X009E-X076D-X130S, X009E-X076D-X145R, X009E-X076D-X166Q, X009E-X076D-X185Q, X009E-X076D-X210I, X009E-X076D-X217L, X009E-X076D-X218S, X009E-X076D-X248D, X009E-X076D-X259P, X009E-X078N-X079I, X009E-X078N-X087D, X009E-X078N-X118R, X009E-X078N-X124I, X009E-X078N-X128S, X009E-X078N-X129P, X009E-X078N-X130S, X009E-X078N-X145R, X009E-X078N-X166Q, X009E-X078N-X185Q, X009E-X078N-X210I, X009E-X078N-X217L, X009E-X078N-X218S, X009E-X078N-X248D, X009E-X078N-X259P, X009E-X079I-X087D, X009E-X079I-X118R, X009E-X079I-X124I, X009E-X079I-X128S, X009E-X079I-X129P, X009E-X079I-X130S, X009E-X079I-X145R, X009E-X079I-X166Q, X009E-X079I-X185Q, X009E-X079I-X210I, X009E-X079I-X217L, X009E-X079I-X218S, X009E-X079I-X248D, X009E-X079I-X259P, X009E-X087D-X118R, X009E-X087D-X124I, X009E-X087D-X128S, X009E-X087D-X129P, X009E-X087D-X130S, X009E-X087D-X145R, X009E-X087D-X166Q, X009E-X087D-X185Q, X009E-X087D-X210I, X009E-X087D-X217L, X009E-X087D-X218S, X009E-X087D-X248D, X009E-X087D-X259P, X009E-X118R-X124I, X009E-X118R-X128S, X009E-X118R-X129P, X009E-X118R-X130S, X009E-X118R-X145R, X009E-X118R-X166Q, X009E-X118R-X185Q, X009E-X118R-X210I, X009E-X118R-X217L, X009E-X118R-X218S, X009E-X118R-X248D, X009E-X118R-X259P, X009E-X124I-X128S, X009E-X124I-X129P, X009E-X124I-X130S, X009E-X124I-X145R, X009E-X124I-X166Q, X009E-X124I-X185Q, X009E-X124I-X210I, X009E-X124I-X217L, X009E-X124I-X218S, X009E-X124I-X248D, X009E-X124I-X259P, X009E-X128S-X129P, X009E-X128S-X130S, X009E-X128S-X145R, X009E-X128S-X166Q, X009E-X128S-X185Q, X009E-X128S-X210I, X009E-X128S-X217L, X009E-X128S-X218S, X009E-X128S-X248D, X009E-X128S-X259P, X009E-X129P-X130S, X009E-X129P-X145R, X009E-X129P-X166Q, X009E-X129P-X185Q, X009E-X129P-X210I, X009E-X129P-X217L, X009E-X129P-X218S, X009E-X129P-X248D, X009E-X129P-X259P, X009E-X130S-X145R, X009E-X130S-X166Q, X009E-X130S-X185Q, X009E-X130S-X210I, X009E-X130S-X217L, X009E-X130S-X218S, X009E-X130S-X248D, X009E-X130S-X259P, X009E-X145R-X166Q, X009E-X145R-X185Q, X009E-X145R-X210I, X009E-X145R-X217L, X009E-X145R-X218S, X009E-X145R-X248D, X009E-X145R-X259P, X009E-X166Q-X185Q, X009E-X166Q-X210I, X009E-X166Q-X217L, X009E-X166Q-X218S, X009E-X166Q-X248D, X009E-X166Q-X259P, X009E-X185Q-X210I, X009E-X185Q-X217L, X009E-X185Q-X218S, X009E-X185Q-X248D, X009E-X185Q-X259P, X009E-X210I-X217L, X009E-X210I-X218S, X009E-X210I-X248D, X009E-X210I-X259P, X009E-X217L-X218S, X009E-X217L-X248D, X009E-X217L-X259P, X009E-X218S-X248D, X009E-X218S-X259P, X009E-X248D-X259P, X024Q-X040E-X069S, X024Q-X040E-X076D, X024Q-X040E-X078N, X024Q-X040E-X079I, X024Q-X040E-X087D, X024Q-X040E-X118R, X024Q-X040E-X124I, X024Q-X040E-X128S, X024Q-X040E-X129P, X024Q-X040E-X130S, X024Q-X040E-X145R, X024Q-X040E-X166Q, X024Q-X040E-X185Q, X024Q-X040E-X210I, X024Q-X040E-X217L, X024Q-X040E-X218S, X024Q-X040E-X248D, X024Q-X040E-X259P, X024Q-X069S-X076D, X024Q-X069S-X078N, X024Q-X069S-X079I, X024Q-X069S-X087D, X024Q-X069S-X118R, X024Q-X069S-X124I, X024Q-X069S-X128S, X024Q-X069S-X129P, X024Q-X069S-X130S, X024Q-X069S-X145R, X024Q-X069S-X166Q, X024Q-X069S-X185Q, X024Q-X069S-X210I, X024Q-X069S-X217L, X024Q-X069S-X218S, X024Q-X069S-X248D, X024Q-X069S-X259P, X024Q-X076D-X078N, X024Q-X076D-X079I, X024Q-X076D-X087D, X024Q-X076D-X118R, X024Q-X076D-X124I, X024Q-X076D-X128S, X024Q-X076D-X129P, X024Q-X076D-X130S, X024Q-X076D-X145R, X024Q-X076D-X166Q, X024Q-X076D-X185Q, X024Q-X076D-X210I, X024Q-X076D-X217L, X024Q-X076D-X218S, X024Q-X076D-X248D, X024Q-X076D-X259P, X024Q-X078N-X079I, X024Q-X078N-X087D, X024Q-X078N-X118R, X024Q-X078N-X124I, X024Q-X078N-X128S, X024Q-X078N-X129P, X024Q-X078N-X130S, X024Q-X078N-X145R, X024Q-X078N-X166Q, X024Q-X078N-X185Q, X024Q-X078N-X210I, X024Q-X078N-X217L, X024Q-X078N-X218S, X024Q-X078N-X248D, X024Q-X078N-X259P, X024Q-X079I-X087D, X024Q-X079I-X118R, X024Q-X079I-X124I, X024Q-X079I-X128S, X024Q-X079I-X129P, X024Q-X079I-X130S, X024Q-X079I-X145R, X024Q-X079I-X166Q, X024Q-X079I-X185Q, X024Q-X079I-X210I, X024Q-X079I-X217L, X024Q-X079I-X218S, X024Q-X079I-X248D, X024Q-X079I-X259P, X024Q-X087D-X118R, X024Q-X087D-X124I, X024Q-X087D-X128S, X024Q-X087D-X129P, X024Q-X087D-X130S, X024Q-X087D-X145R, X024Q-X087D-X166Q, X024Q-X087D-X185Q, X024Q-X087D-X210I, X024Q-X087D-X217L, X024Q-X087D-X218S, X024Q-X087D-X248D, X024Q-X087D-X259P, X024Q-X118R-X124I, X024Q-X118R-X128S, X024Q-X118R-X129P, X024Q-X118R-X130S, X024Q-X118R-X145R, X024Q-X118R-X166Q, X024Q-X118R-X185Q, X024Q-X118R-X210I, X024Q-X118R-X217L, X024Q-X118R-X218S, X024Q-X118R-X248D, X024Q-X118R-X259P, X024Q-X124I-X128S, X024Q-X124I-X129P, X024Q-X124I-X130S, X024Q-X124I-X145R, X024Q-X124I-X166Q, X024Q-X124I-X185Q, X024Q-X124I-X210I, X024Q-X124I-X217L, X024Q-X124I-X218S, X024Q-X124I-X248D, X024Q-X124I-X259P, X024Q-X128S-X129P, X024Q-X128S-X130S, X024Q-X128S-X145R, X024Q-X128S-X166Q, X024Q-X128S-X185Q, X024Q-X128S-X210I, X024Q-X128S-X217L, X024Q-X128S-X218S, X024Q-X128S-X248D, X024Q-X128S-X259P, X024Q-X129P-X130S, X024Q-X129P-X145R, X024Q-X129P-X166Q, X024Q-X129P-X185Q, X024Q-X129P-X210I, X024Q-X129P-X217L, X024Q-X129P-X218S, X024Q-X129P-X248D, X024Q-X129P-X259P, X024Q-X130S-X145R, X024Q-X130S-X166Q, X024Q-X130S-X185Q, X024Q-X130S-X210I, X024Q-X130S-X217L, X024Q-X130S-X218S, X024Q-X130S-X248D, X024Q-X130S-X259P, X024Q-X145R-X166Q, X024Q-X145R-X185Q, X024Q-X145R-X210I, X024Q-X145R-X217L, X024Q-X145R-X218S, X024Q-X145R-X248D, X024Q-X145R-X259P, X024Q-X166Q-X185Q, X024Q-X166Q-X210I, X024Q-X166Q-X217L, X024Q-X166Q-X218S, X024Q-X166Q-X248D, X024Q-X166Q-X259P, X024Q-X185Q-X210I, X024Q-X185Q-X217L, X024Q-X185Q-X218S, X024Q-X185Q-X248D, X024Q-X185Q-X259P, X024Q-X210I-X217L, X024Q-X210I-X218S, X024Q-X210I-X248D, X024Q-X210I-X259P, X024Q-X217L-X218S, X024Q-X217L-X248D, X024Q-X217L-X259P, X024Q-X218S-X248D, X024Q-X218S-X259P, X024Q-X248D-X259P, X040E-X069S-X076D, X040E-X069S-X078N, X040E-X069S-X079I,

X040E-X069S-X087D, X040E-X069S-X118R, X040E-X069S-X124I, X040E-X069S-X128S, X040E-X069S-X129P, X040E-X069S-X130S, X040E-X069S-X145R, X040E-X069S-X166Q, X040E-X069S-X185Q, X040E-X069S-X210I, X040E-X069S-X217L, X040E-X069S-X218S, X040E-X069S-X248D, X040E-X069S-X259P, X040E-X076D-X078N, X040E-X076D-X079I, X040E-X076D-X087D, X040E-X076D-X118R, X040E-X076D-X124I, X040E-X076D-X128S, X040E-X076D-X129P, X040E-X076D-X130S, X040E-X076D-X145R, X040E-X076D-X166Q, X040E-X076D-X185Q, X040E-X076D-X210I, X040E-X076D-X217L, X040E-X076D-X218S, X040E-X076D-X248D, X040E-X076D-X259P, X040E-X078N-X079I, X040E-X078N-X087D, X040E-X078N-X118R, X040E-X078N-X124I, X040E-X078N-X128S, X040E-X078N-X129P, X040E-X078N-X130S, X040E-X078N-X145R, X040E-X078N-X166Q, X040E-X078N-X185Q, X040E-X078N-X210I, X040E-X078N-X217L, X040E-X078N-X218S, X040E-X078N-X248D, X040E-X078N-X259P, X040E-X079I-X087D, X040E-X079I-X118R, X040E-X079I-X124I, X040E-X079I-X128S, X040E-X079I-X129P, X040E-X079I-X130S, X040E-X079I-X145R, X040E-X079I-X166Q, X040E-X079I-X185Q, X040E-X079I-X210I, X040E-X079I-X217L, X040E-X079I-X218S, X040E-X079I-X248D, X040E-X079I-X259P, X040E-X087D-X118R, X040E-X087D-X124I, X040E-X087D-X128S, X040E-X087D-X129P, X040E-X087D-X130S, X040E-X087D-X145R, X040E-X087D-X166Q, X040E-X087D-X185Q, X040E-X087D-X210I, X040E-X087D-X217L, X040E-X087D-X218S, X040E-X087D-X248D, X040E-X087D-X259P, X040E-X118R-X124I, X040E-X118R-X128S, X040E-X118R-X129P, X040E-X118R-X130S, X040E-X118R-X145R, X040E-X118R-X166Q, X040E-X118R-X185Q, X040E-X118R-X210I, X040E-X118R-X217L, X040E-X118R-X218S, X040E-X118R-X248D, X040E-X118R-X259P, X040E-X124I-X128S, X040E-X124I-X129P, X040E-X124I-X130S, X040E-X124I-X145R, X040E-X124I-X166Q, X040E-X124I-X185Q, X040E-X124I-X210I, X040E-X124I-X217L, X040E-X124I-X218S, X040E-X124I-X248D, X040E-X124I-X259P, X040E-X128S-X129P, X040E-X128S-X130S, X040E-X128S-X145R, X040E-X128S-X166Q, X040E-X128S-X185Q, X040E-X128S-X210I, X040E-X128S-X217L, X040E-X128S-X218S, X040E-X128S-X248D, X040E-X128S-X259P, X040E-X129P-X130S, X040E-X129P-X145R, X040E-X129P-X166Q, X040E-X129P-X185Q, X040E-X129P-X210I, X040E-X129P-X217L, X040E-X129P-X218S, X040E-X129P-X248D, X040E-X129P-X259P, X040E-X130S-X145R, X040E-X130S-X166Q, X040E-X130S-X185Q, X040E-X130S-X210I, X040E-X130S-X217L, X040E-X130S-X218S, X040E-X130S-X248D, X040E-X130S-X259P, X040E-X145R-X166Q, X040E-X145R-X185Q, X040E-X145R-X210I, X040E-X145R-X217L, X040E-X145R-X218S, X040E-X145R-X248D, X040E-X145R-X259P, X040E-X166Q-X185Q, X040E-X166Q-X210I, X040E-X166Q-X217L, X040E-X166Q-X218S, X040E-X166Q-X248D, X040E-X166Q-X259P, X040E-X185Q-X210I, X040E-X185Q-X217L, X040E-X185Q-X218S, X040E-X185Q-X248D, X040E-X185Q-X259P, X040E-X210I-X217L, X040E-X210I-X218S, X040E-X210I-X248D, X040E-X210I-X259P, X040E-X217L-X218S, X040E-X217L-X248D, X040E-X217L-X259P, X040E-X218S-X248D, X040E-X218S-X259P, X040E-X248D-X259P, X069S-X076D-X078N, X069S-X076D-X079I, X069S-X076D-X087D, X069S-X076D-X118R, X069S-X076D-X124I, X069S-X076D-X128S, X069S-X076D-X129P, X069S-X076D-X130S, X069S-X076D-X145R, X069S-X076D-X166Q, X069S-X076D-X185Q, X069S-X076D-X210I, X069S-X076D-X217L, X069S-X076D-X218S, X069S-X076D-X248D, X069S-X076D-X259P, X069S-X078N-X079I, X069S-X078N-X087D, X069S-X078N-X118R, X069S-X078N-X124I, X069S-X078N-X128S, X069S-X078N-X129P, X069S-X078N-X130S, X069S-X078N-X145R, X069S-X078N-X166Q, X069S-X078N-X185Q, X069S-X078N-X210I, X069S-X078N-X217L, X069S-X078N-X218S, X069S-X078N-X248D, X069S-X078N-X259P, X069S-X079I-X087D, X069S-X079I-X118R, X069S-X079I-X124I, X069S-X079I-X128S, X069S-X079I-X129P, X069S-X079I-X130S, X069S-X079I-X145R, X069S-X079I-X166Q, X069S-X079I-X185Q, X069S-X079I-X210I, X069S-X079I-X217L, X069S-X079I-X218S, X069S-X079I-X248D, X069S-X079I-X259P, X069S-X087D-X118R, X069S-X087D-X124I, X069S-X087D-X128S, X069S-X087D-X129P, X069S-X087D-X130S, X069S-X087D-X145R, X069S-X087D-X166Q, X069S-X087D-X185Q, X069S-X087D-X210I, X069S-X087D-X217L, X069S-X087D-X218S, X069S-X087D-X248D, X069S-X087D-X259P, X069S-X118R-X124I, X069S-X118R-X128S, X069S-X118R-X129P, X069S-X118R-X130S, X069S-X118R-X145R, X069S-X118R-X166Q, X069S-X118R-X185Q, X069S-X118R-X210I, X069S-X118R-X217L, X069S-X118R-X218S, X069S-X118R-X248D, X069S-X118R-X259P, X069S-X124I-X128S, X069S-X124I-X129P, X069S-X124I-X130S, X069S-X124I-X145R, X069S-X124I-X166Q, X069S-X124I-X185Q, X069S-X124I-X210I, X069S-X124I-X217L, X069S-X124I-X218S, X069S-X124I-X248D, X069S-X124I-X259P, X069S-X128S-X129P, X069S-X128S-X130S, X069S-X128S-X145R, X069S-X128S-X166Q, X069S-X128S-X185Q, X069S-X128S-X210I, X069S-X128S-X217L, X069S-X128S-X218S, X069S-X128S-X248D, X069S-X128S-X259P, X069S-X129P-X130S, X069S-X129P-X145R, X069S-X129P-X166Q, X069S-X129P-X185Q, X069S-X129P-X210I, X069S-X129P-X217L, X069S-X129P-X218S, X069S-X129P-X248D, X069S-X129P-X259P, X069S-X130S-X145R, X069S-X130S-X166Q, X069S-X130S-X185Q, X069S-X130S-X210I, X069S-X130S-X217L, X069S-X130S-X218S, X069S-X130S-X248D, X069S-X130S-X259P, X069S-X145R-X166Q, X069S-X145R-X185Q, X069S-X145R-X210I, X069S-X145R-X217L, X069S-X145R-X218S, X069S-X145R-X248D, X069S-X145R-X259P, X069S-X166Q-X185Q, X069S-X166Q-X210I, X069S-X166Q-X217L, X069S-X166Q-X218S, X069S-X166Q-X248D, X069S-X166Q-X259P, X069S-X185Q-X210I, X069S-X185Q-X217L, X069S-X185Q-X218S, X069S-X185Q-X248D, X069S-X185Q-X259P, X069S-X210I-X217L, X069S-X210I-X218S, X069S-X210I-X248D, X069S-X210I-X259P, X069S-X217L-X218S, X069S-X217L-X248D, X069S-X217L-X259P, X069S-X218S-X248D, X069S-X218S-X259P, X069S-X248D-X259P, X076D-X078N-X079I, X076D-X078N-X087D, X076D-X078N-X118R, X076D-X078N-X124I, X076D-X078N-X128S, X076D-X078N-X129P, X076D-X078N-X130S, X076D-X078N-X145R, X076D-X078N-X166Q, X076D-X078N-X185Q, X076D-X078N-X210I, X076D-X078N-X217L, X076D-X078N-X218S, X076D-X078N-X248D, X076D-X078N-X259P, X076D-X079I-X087D, X076D-X079I-X118R, X076D-X079I-X124I, X076D-X079I-X128S, X076D-X079I-X129P, X076D-X079I-X130S, X076D-X079I-X145R, X076D-X079I-X166Q, X076D-X079I-X185Q, X076D-X079I-X210I, X076D-X079I-X217L, X076D-X079I-

X218S, X076D-X079I-X248D, X076D-X079I-X259P, X076D-X087D-X118R, X076D-X087D-X124I, X076D-X087D-X128S, X076D-X087D-X129P, X076D-X087D-X130S, X076D-X087D-X145R, X076D-X087D-X166Q, X076D-X087D-X185Q, X076D-X087D-X210I, X076D-X087D-X217L, X076D-X087D-X218S, X076D-X087D-X248D, X076D-X087D-X259P, X076D-X118R-X124I, X076D-X118R-X128S, X076D-X118R-X129P, X076D-X118R-X130S, X076D-X118R-X145R, X076D-X118R-X166Q, X076D-X118R-X185Q, X076D-X118R-X210I, X076D-X118R-X217L, X076D-X118R-X218S, X076D-X118R-X248D, X076D-X118R-X259P, X076D-X124I-X128S, X076D-X124I-X129P, X076D-X124I-X130S, X076D-X124I-X145R, X076D-X124I-X166Q, X076D-X124I-X185Q, X076D-X124I-X210I, X076D-X124I-X217L, X076D-X124I-X218S, X076D-X124I-X248D, X076D-X124I-X259P, X076D-X128S-X129P, X076D-X128S-X130S, X076D-X128S-X145R, X076D-X128S-X166Q, X076D-X128S-X185Q, X076D-X128S-X210I, X076D-X128S-X217L, X076D-X128S-X218S, X076D-X128S-X248D, X076D-X128S-X259P, X076D-X129P-X130S, X076D-X129P-X145R, X076D-X129P-X166Q, X076D-X129P-X185Q, X076D-X129P-X210I, X076D-X129P-X217L, X076D-X129P-X218S, X076D-X129P-X248D, X076D-X129P-X259P, X076D-X130S-X145R, X076D-X130S-X166Q, X076D-X130S-X185Q, X076D-X130S-X210I, X076D-X130S-X217L, X076D-X130S-X218S, X076D-X130S-X248D, X076D-X130S-X259P, X076D-X145R-X166Q, X076D-X145R-X185Q, X076D-X145R-X210I, X076D-X145R-X217L, X076D-X145R-X218S, X076D-X145R-X248D, X076D-X145R-X259P, X076D-X166Q-X185Q, X076D-X166Q-X210I, X076D-X166Q-X217L, X076D-X166Q-X218S, X076D-X166Q-X248D, X076D-X166Q-X259P, X076D-X185Q-X210I, X076D-X185Q-X217L, X076D-X185Q-X218S, X076D-X185Q-X248D, X076D-X185Q-X259P, X076D-X210I-X217L, X076D-X210I-X218S, X076D-X210I-X248D, X076D-X210I-X259P, X076D-X217L-X218S, X076D-X217L-X248D, X076D-X217L-X259P, X076D-X218S-X248D, X076D-X218S-X259P, X076D-X248D-X259P, X078N-X079I-X087D, X078N-X079I-X118R, X078N-X079I-X124I, X078N-X079I-X128S, X078N-X079I-X129P, X078N-X079I-X130S, X078N-X079I-X145R, X078N-X079I-X166Q, X078N-X079I-X185Q, X078N-X079I-X210I, X078N-X079I-X217L, X078N-X079I-X218S, X078N-X079I-X248D, X078N-X079I-X259P, X078N-X087D-X118R, X078N-X087D-X124I, X078N-X087D-X128S, X078N-X087D-X129P, X078N-X087D-X130S, X078N-X087D-X145R, X078N-X087D-X166Q, X078N-X087D-X185Q, X078N-X087D-X210I, X078N-X087D-X217L, X078N-X087D-X218S, X078N-X087D-X248D, X078N-X087D-X259P, X078N-X118R-X124I, X078N-X118R-X128S, X078N-X118R-X129P, X078N-X118R-X130S, X078N-X118R-X145R, X078N-X118R-X166Q, X078N-X118R-X185Q, X078N-X118R-X210I, X078N-X118R-X217L, X078N-X118R-X218S, X078N-X118R-X248D, X078N-X118R-X259P, X078N-X124I-X128S, X078N-X124I-X129P, X078N-X124I-X130S, X078N-X124I-X145R, X078N-X124I-X166Q, X078N-X124I-X185Q, X078N-X124I-X210I, X078N-X124I-X217L, X078N-X124I-X218S, X078N-X124I-X248D, X078N-X124I-X259P, X078N-X128S-X129P, X078N-X128S-X130S, X078N-X128S-X145R, X078N-X128S-X166Q, X078N-X128S-X185Q, X078N-X128S-X210I, X078N-X128S-X217L, X078N-X128S-X218S, X078N-X128S-X248D, X078N-X128S-X259P, X078N-X129P-X130S, X078N-X129P-X145R, X078N-X129P-X166Q, X078N-X129P-X185Q, X078N-X129P-X210I, X078N-X129P-X217L, X078N-X129P-X218S, X078N-X129P-X248D, X078N-X129P-X259P, X078N-X130S-X145R, X078N-X130S-X166Q, X078N-X130S-X185Q, X078N-X130S-X210I, X078N-X130S-X217L, X078N-X130S-X218S, X078N-X130S-X248D, X078N-X130S-X259P, X078N-X145R-X166Q, X078N-X145R-X185Q, X078N-X145R-X210I, X078N-X145R-X217L, X078N-X145R-X218S, X078N-X145R-X248D, X078N-X145R-X259P, X078N-X166Q-X185Q, X078N-X166Q-X210I, X078N-X166Q-X217L, X078N-X166Q-X218S, X078N-X166Q-X248D, X078N-X166Q-X259P, X078N-X185Q-X210I, X078N-X185Q-X217L, X078N-X185Q-X218S, X078N-X185Q-X248D, X078N-X185Q-X259P, X078N-X210I-X217L, X078N-X210I-X218S, X078N-X210I-X248D, X078N-X210I-X259P, X078N-X217L-X218S, X078N-X217L-X248D, X078N-X217L-X259P, X078N-X218S-X248D, X078N-X218S-X259P, X078N-X248D-X259P, X079I-X087D-X118R, X079I-X087D-X124I, X079I-X087D-X128S, X079I-X087D-X129P, X079I-X087D-X130S, X079I-X087D-X145R, X079I-X087D-X166Q, X079I-X087D-X185Q, X079I-X087D-X210I, X079I-X087D-X217L, X079I-X087D-X218S, X079I-X087D-X248D, X079I-X087D-X259P, X079I-X118R-X124I, X079I-X118R-X128S, X079I-X118R-X129P, X079I-X118R-X130S, X079I-X118R-X145R, X079I-X118R-X166Q, X079I-X118R-X185Q, X079I-X118R-X210I, X079I-X118R-X217L, X079I-X118R-X218S, X079I-X118R-X248D, X079I-X118R-X259P, X079I-X124I-X128S, X079I-X124I-X129P, X079I-X124I-X130S, X079I-X124I-X145R, X079I-X124I-X166Q, X079I-X124I-X185Q, X079I-X124I-X210I, X079I-X124I-X217L, X079I-X124I-X218S, X079I-X124I-X248D, X079I-X124I-X259P, X079I-X128S-X129P, X079I-X128S-X130S, X079I-X128S-X145R, X079I-X128S-X166Q, X079I-X128S-X185Q, X079I-X128S-X210I, X079I-X128S-X217L, X079I-X128S-X218S, X079I-X128S-X248D, X079I-X128S-X259P, X079I-X129P-X130S, X079I-X129P-X145R, X079I-X129P-X166Q, X079I-X129P-X185Q, X079I-X129P-X210I, X079I-X129P-X217L, X079I-X129P-X218S, X079I-X129P-X248D, X079I-X129P-X259P, X079I-X130S-X145R, X079I-X130S-X166Q, X079I-X130S-X185Q, X079I-X130S-X210I, X079I-X130S-X217L, X079I-X130S-X218S, X079I-X130S-X248D, X079I-X130S-X259P, X079I-X145R-X166Q, X079I-X145R-X185Q, X079I-X145R-X210I, X079I-X145R-X217L, X079I-X145R-X218S, X079I-X145R-X248D, X079I-X145R-X259P, X079I-X166Q-X185Q, X079I-X166Q-X210I, X079I-X166Q-X217L, X079I-X166Q-X218S, X079I-X166Q-X248D, X079I-X166Q-X259P, X079I-X185Q-X210I, X079I-X185Q-X217L, X079I-X185Q-X218S, X079I-X185Q-X248D, X079I-X185Q-X259P, X079I-X210I-X217L, X079I-X210I-X218S, X079I-X210I-X248D, X079I-X210I-X259P, X079I-X217L-X218S, X079I-X217L-X248D, X079I-X217L-X259P, X079I-X218S-X248D, X079I-X218S-X259P, X079I-X248D-X259P, X087D-X118R-X124I, X087D-X118R-X128S, X087D-X118R-X129P, X087D-X118R-X130S, X087D-X118R-X145R, X087D-X118R-X166Q, X087D-X118R-X185Q, X087D-X118R-X210I, X087D-X118R-X217L, X087D-X118R-X218S, X087D-X118R-X248D, X087D-X118R-X259P, X087D-X124I-X128S, X087D-X124I-X129P, X087D-X124I-X130S, X087D-X124I-X145R, X087D-X124I-X166Q, X087D-X124I-X185Q, X087D-X124I-X210I, X087D-X124I-X217L, X087D-X124I-X218S, X087D-X124I-X248D, X087D-X124I-X259P, X087D-X128S-X129P, X087D-

X128S-X130S, X087D-X128S-X145R, X087D-X128S-X166Q, X087D-X128S-X185Q, X087D-X128S-X210I, X087D-X128S-X217L, X087D-X128S-X218S, X087D-X128S-X248D, X087D-X128S-X259P, X087D-X129P-X130S, X087D-X129P-X145R, X087D-X129P-X166Q, X087D-X129P-X185Q, X087D-X129P-X210I, X087D-X129P-X217L, X087D-X129P-X218S, X087D-X129P-X248D, X087D-X129P-X259P, X087D-X130S-X145R, X087D-X130S-X166Q, X087D-X130S-X185Q, X087D-X130S-X210I, X087D-X130S-X217L, X087D-X130S-X218S, X087D-X130S-X248D, X087D-X130S-X259P, X087D-X145R-X166Q, X087D-X145R-X185Q, X087D-X145R-X210I, X087D-X145R-X217L, X087D-X145R-X218S, X087D-X145R-X248D, X087D-X145R-X259P, X087D-X166Q-X185Q, X087D-X166Q-X210I, X087D-X166Q-X217L, X087D-X166Q-X218S, X087D-X166Q-X248D, X087D-X166Q-X259P, X087D-X185Q-X210I, X087D-X185Q-X217L, X087D-X185Q-X218S, X087D-X185Q-X248D, X087D-X185Q-X259P, X087D-X210I-X217L, X087D-X210I-X218S, X087D-X210I-X248D, X087D-X210I-X259P, X087D-X217L-X218S, X087D-X217L-X248D, X087D-X217L-X259P, X087D-X218S-X248D, X087D-X218S-X259P, X087D-X248D-X259P, X118R-X124I-X128S, X118R-X124I-X129P, X118R-X124I-X130S, X118R-X124I-X145R, X118R-X124I-X166Q, X118R-X124I-X185Q, X118R-X124I-X210I, X118R-X124I-X217L, X118R-X124I-X218S, X118R-X124I-X248D, X118R-X124I-X259P, X118R-X128S-X129P, X118R-X128S-X130S, X118R-X128S-X145R, X118R-X128S-X166Q, X118R-X128S-X185Q, X118R-X128S-X210I, X118R-X128S-X217L, X118R-X128S-X218S, X118R-X128S-X248D, X118R-X128S-X259P, X118R-X129P-X130S, X118R-X129P-X145R, X118R-X129P-X166Q, X118R-X129P-X185Q, X118R-X129P-X210I, X118R-X129P-X217L, X118R-X129P-X218S, X118R-X129P-X248D, X118R-X129P-X259P, X118R-X130S-X145R, X118R-X130S-X166Q, X118R-X130S-X185Q, X118R-X130S-X210I, X118R-X130S-X217L, X118R-X130S-X218S, X118R-X130S-X248D, X118R-X130S-X259P, X118R-X145R-X166Q, X118R-X145R-X185Q, X118R-X145R-X210I, X118R-X145R-X217L, X118R-X145R-X218S, X118R-X145R-X248D, X118R-X145R-X259P, X118R-X166Q-X185Q, X118R-X166Q-X210I, X118R-X166Q-X217L, X118R-X166Q-X218S, X118R-X166Q-X248D, X118R-X166Q-X259P, X118R-X185Q-X210I, X118R-X185Q-X217L, X118R-X185Q-X218S, X118R-X185Q-X248D, X118R-X185Q-X259P, X118R-X210I-X217L, X118R-X210I-X218S, X118R-X210I-X248D, X118R-X210I-X259P, X118R-X217L-X218S, X118R-X217L-X248D, X118R-X217L-X259P, X118R-X218S-X248D, X118R-X218S-X259P, X118R-X248D-X259P, X124I-X128S-X129P, X124I-X128S-X130S, X124I-X128S-X145R, X124I-X128S-X166Q, X124I-X128S-X185Q, X124I-X128S-X210I, X124I-X128S-X217L, X124I-X128S-X218S, X124I-X128S-X248D, X124I-X128S-X259P, X124I-X129P-X130S, X124I-X129P-X145R, X124I-X129P-X166Q, X124I-X129P-X185Q, X124I-X129P-X210I, X124I-X129P-X217L, X124I-X129P-X218S, X124I-X129P-X248D, X124I-X129P-X259P, X124I-X130S-X145R, X124I-X130S-X166Q, X124I-X130S-X185Q, X124I-X130S-X210I, X124I-X130S-X217L, X124I-X130S-X218S, X124I-X130S-X248D, X124I-X130S-X259P, X124I-X145R-X166Q, X124I-X145R-X185Q, X124I-X145R-X210I, X124I-X145R-X217L, X124I-X145R-X218S, X124I-X145R-X248D, X124I-X145R-X259P, X124I-X166Q-X185Q, X124I-X166Q-X210I, X124I-X166Q-X217L, X124I-X166Q-X218S, X124I-X166Q-X248D, X124I-X166Q-X259P, X124I-X185Q-X210I, X124I-X185Q-X217L, X124I-X185Q-X218S, X124I-X185Q-X248D, X124I-X185Q-X259P, X124I-X210I-X217L, X124I-X210I-X218S, X124I-X210I-X248D, X124I-X210I-X259P, X124I-X217L-X218S, X124I-X217L-X248D, X124I-X217L-X259P, X124I-X218S-X248D, X124I-X218S-X259P, X124I-X248D-X259P, X128S-X129P-X130S, X128S-X129P-X145R, X128S-X129P-X166Q, X128S-X129P-X185Q, X128S-X129P-X210I, X128S-X129P-X217L, X128S-X129P-X218S, X128S-X129P-X248D, X128S-X129P-X259P, X128S-X130S-X145R, X128S-X130S-X166Q, X128S-X130S-X185Q, X128S-X130S-X210I, X128S-X130S-X217L, X128S-X130S-X218S, X128S-X130S-X248D, X128S-X130S-X259P, X128S-X145R-X166Q, X128S-X145R-X185Q, X128S-X145R-X210I, X128S-X145R-X217L, X128S-X145R-X218S, X128S-X145R-X248D, X128S-X145R-X259P, X128S-X166Q-X185Q, X128S-X166Q-X210I, X128S-X166Q-X217L, X128S-X166Q-X218S, X128S-X166Q-X248D, X128S-X166Q-X259P, X128S-X185Q-X210I, X128S-X185Q-X217L, X128S-X185Q-X218S, X128S-X185Q-X248D, X128S-X185Q-X259P, X128S-X210I-X217L, X128S-X210I-X218S, X128S-X210I-X248D, X128S-X210I-X259P, X128S-X217L-X218S, X128S-X217L-X248D, X128S-X217L-X259P, X128S-X218S-X248D, X128S-X218S-X259P, X128S-X248D-X259P, X129P-X130S-X145R, X129P-X130S-X166Q, X129P-X130S-X185Q, X129P-X130S-X210I, X129P-X130S-X217L, X129P-X130S-X218S, X129P-X130S-X248D, X129P-X130S-X259P, X129P-X145R-X166Q, X129P-X145R-X185Q, X129P-X145R-X210I, X129P-X145R-X217L, X129P-X145R-X218S, X129P-X145R-X248D, X129P-X145R-X259P, X129P-X166Q-X185Q, X129P-X166Q-X210I, X129P-X166Q-X217L, X129P-X166Q-X218S, X129P-X166Q-X248D, X129P-X166Q-X259P, X129P-X185Q-X210I, X129P-X185Q-X217L, X129P-X185Q-X218S, X129P-X185Q-X248D, X129P-X185Q-X259P, X129P-X210I-X217L, X129P-X210I-X218S, X129P-X210I-X248D, X129P-X210I-X259P, X129P-X217L-X218S, X129P-X217L-X248D, X129P-X217L-X259P, X129P-X218S-X248D, X129P-X218S-X259P, X129P-X248D-X259P, X130S-X145R-X166Q, X130S-X145R-X185Q, X130S-X145R-X210I, X130S-X145R-X217L, X130S-X145R-X218S, X130S-X145R-X248D, X130S-X145R-X259P, X130S-X166Q-X185Q, X130S-X166Q-X210I, X130S-X166Q-X217L, X130S-X166Q-X218S, X130S-X166Q-X248D, X130S-X166Q-X259P, X130S-X185Q-X210I, X130S-X185Q-X217L, X130S-X185Q-X218S, X130S-X185Q-X248D, X130S-X185Q-X259P, X130S-X210I-X217L, X130S-X210I-X218S, X130S-X210I-X248D, X130S-X210I-X259P, X130S-X217L-X218S, X130S-X217L-X248D, X130S-X217L-X259P, X130S-X218S-X248D, X130S-X218S-X259P, X130S-X248D-X259P, X145R-X166Q-X185Q, X145R-X166Q-X210I, X145R-X166Q-X217L, X145R-X166Q-X218S, X145R-X166Q-X248D, X145R-X166Q-X259P, X145R-X185Q-X210I, X145R-X185Q-X217L, X145R-X185Q-X218S, X145R-X185Q-X248D, X145R-X185Q-X259P, X145R-X210I-X217L, X145R-X210I-X218S, X145R-X210I-X248D, X145R-X210I-X259P, X145R-X217L-X218S, X145R-X217L-X248D, X145R-X217L-X259P, X145R-X218S-X248D, X145R-X218S-X259P, X145R-X248D-X259P, X166Q-X185Q-X210I, X166Q-X185Q-X217L, X166Q-X185Q-X218S, X166Q-X185Q-X248D, X166Q-X185Q-X259P, X166Q-X210I-X217L, X166Q-X210I-X218S, X166Q-X210I-X248D, X166Q-

X210I-X259P, X166Q-X217L-X218S, X166Q-X217L-X248D, X166Q-X217L-X259P, X166Q-X218S-X248D, X166Q-X218S-X259P, X166Q-X248D-X259P, X185Q-X210I-X217L, X185Q-X210I-X218S, X185Q-X210I-X248D, X185Q-X210I-X259P, X185Q-X217L-X218S, X185Q-X217L-X248D, X185Q-X217L-X259P, X185Q-X218S-X248D, X185Q-X218S-X259P, X185Q-X248D-X259P, X210I-X217L-X218S, X210I-X217L-X248D, X210I-X217L-X259P, X210I-X218S-X248D, X210I-X218S-X259P, X210I-X248D-X259P, X217L-X218S-X248D, X217L-X218S-X259P, X217L-X248D-X259P, X218S-X248D-X259P, where the positions are numbered by correspondence with the amino acid sequence of SEQ ID NO:1 (BPN').

In other embodiments, the subtilisin variants disclosed herein contain a combination of three or more features with respect to SEQ ID NO: 1, where the combination of three or more features are selected from the group consisting of X003V-X009E-X040E, X003V-X009E-X069S, X003V-X009E-X076D, X003V-X009E-X078N, X003V-X009E-X166Q, X003V-X009E-X185Q, X003V-X009E-X218S, X003V-X009E-X259P, X003V-X040E-X069S, X003V-X040E-X076D, X003V-X040E-X078N, X003V-X040E-X166Q, X003V-X040E-X185Q, X003V-X040E-X218S, X003V-X040E-X259P, X003V-X069S-X076D, X003V-X069S-X078N, X003V-X069S-X128S, X003V-X069S-X129P, X003V-X069S-X166Q, X003V-X069S-X185Q, X003V-X069S-X218S, X003V-X069S-X259P, X003V-X076D-X078N, X003V-X076D-X129P, X003V-X076D-X166Q, X003V-X076D-X185Q, X003V-X076D-X218S, X003V-X076D-X259P, X003V-X078N-X128S, X003V-X078N-X166Q, X003V-X078N-X185Q, X003V-X078N-X218S, X003V-X078N-X259P, X003V-X124I-X128S, X003V-X124I-X259P, X003V-X128S-X166Q, X003V-X128S-X259P, X003V-X129P-X166Q, X003V-X129P-X185Q, X003V-X129P-X259P, X003V-X166Q-X185Q, X003V-X166Q-X218S, X003V-X166Q-X259P, X003V-X185Q-X218S, X003V-X185Q-X259P, X003V-X218S-X259P, X009E-X040E-X069S, X009E-X040E-X076D, X009E-X040E-X078N, X009E-X040E-X166Q, X009E-X040E-X185Q, X009E-X040E-X218S, X009E-X040E-X259P, X009E-X069S-X076D, X009E-X069S-X078N, X009E-X069S-X166Q, X009E-X069S-X185Q, X009E-X069S-X218S, X009E-X069S-X259P, X009E-X076D-X078N, X009E-X076D-X166Q, X009E-X076D-X185Q, X009E-X076D-X218S, X009E-X076D-X259P, X009E-X078N-X166Q, X009E-X078N-X185Q, X009E-X078N-X218S, X009E-X078N-X259P, X009E-X166Q-X185Q, X009E-X166Q-X218S, X009E-X166Q-X259P, X009E-X185Q-X218S, X009E-X185Q-X259P, X009E-X218S-X259P, X040E-X069S-X076D, X040E-X069S-X078N, X040E-X069S-X166Q, X040E-X069S-X185Q, X040E-X069S-X218S, X040E-X069S-X259P, X040E-X076D-X078N, X040E-X076D-X166Q, X040E-X076D-X185Q, X040E-X076D-X218S, X040E-X076D-X259P, X040E-X078N-X129P, X040E-X078N-X166Q, X040E-X078N-X185Q, X040E-X078N-X218S, X040E-X078N-X259P, X040E-X166Q-X185Q, X040E-X166Q-X218S, X040E-X166Q-X259P, X040E-X185Q-X218S, X040E-X185Q-X259P, X040E-X218S-X259P, X069S-X076D-X078N, X069S-X076D-X128S, X069S-X076D-X166Q, X069S-X076D-X185Q, X069S-X076D-X218S, X069S-X076D-X259P, X069S-X078N-X124I, X069S-X078N-X166Q, X069S-X078N-X185Q, X069S-X078N-X218S, X069S-X078N-X259P, X069S-X128S-X185Q, X069S-X129P-X166Q, X069S-X129P-X185Q, X069S-X129P-X218S, X069S-X129P-X259P, X069S-X166Q-X185Q, X069S-X166Q-X218S, X069S-X166Q-X259P, X069S-X185Q-X218S, X069S-X185Q-X259P, X069S-X218S-X259P, X076D-X078N-X166Q, X076D-X078N-X185Q, X076D-X078N-X218S, X076D-X078N-X259P, X076D-X128S-X166Q, X076D-X129P-X218S, X076D-X166Q-X185Q, X076D-X166Q-X218S, X076D-X166Q-X259P, X076D-X185Q-X218S, X076D-X185Q-X259P, X076D-X218S-X259P, X078N-X124I-X166Q, X078N-X128S-X166Q, X078N-X129P-X259P, X078N-X166Q-X185Q, X078N-X166Q-X218S, X078N-X166Q-X259P, X078N-X185Q-X218S, X078N-X185Q-X259P, X078N-X218S-X259P, X124I-X128S-X166Q, X124I-X128S-X185Q, X124I-X129P-X185Q, X124I-X129P-X259P, X124I-X166Q-X259P, X124I-X185Q-X259P, X124I-X218S-X259P, X128S-X129P-X218S, X128S-X166Q-X185Q, X128S-X166Q-X259P, X128S-X185Q-X218S, X128S-X185Q-X259P, X166Q-X185Q-X218S, X166Q-X185Q-X259P, X166Q-X218S-X259P, and X185Q-X218S-X259P, where the positions are numbered by correspondence with the amino acid sequence of SEQ ID NO:1 (BPN').

In other embodiments, the subtilisin variants disclosed herein contain a combination of four or more features with respect to SEQ ID NO: 1, where the combination of four or more features are selected from the group consisting of X003V-X009E-X024Q-X040E, X003V-X009E-X024Q-X069S, X003V-X009E-X024Q-X076D, X003V-X009E-X024Q-X078N, X003V-X009E-X024Q-X079I, X003V-X009E-X024Q-X087D, X003V-X009E-X024Q-X118R, X003V-X009E-X024Q-X124I, X003V-X009E-X024Q-X128S, X003V-X009E-X024Q-X129P, X003V-X009E-X024Q-X130S, X003V-X009E-X024Q-X145R, X003V-X009E-X024Q-X166Q, X003V-X009E-X024Q-X185Q, X003V-X009E-X024Q-X210I, X003V-X009E-X024Q-X217L, X003V-X009E-X024Q-X218S, X003V-X009E-X024Q-X248D, X003V-X009E-X024Q-X259P, X003V-X009E-X040E-X069S, X003V-X009E-X040E-X076D, X003V-X009E-X040E-X078N, X003V-X009E-X040E-X079I, X003V-X009E-X040E-X087D, X003V-X009E-X040E-X118R, X003V-X009E-X040E-X124I, X003V-X009E-X040E-X128S, X003V-X009E-X040E-X129P, X003V-X009E-X040E-X130S, X003V-X009E-X040E-X145R, X003V-X009E-X040E-X166Q, X003V-X009E-X040E-X185Q, X003V-X009E-X040E-X210I, X003V-X009E-X040E-X217L, X003V-X009E-X040E-X218S, X003V-X009E-X040E-X248D, X003V-X009E-X040E-X259P, X003V-X009E-X069S-X076D, X003V-X009E-X069S-X078N, X003V-X009E-X069S-X079I, X003V-X009E-X069S-X087D, X003V-X009E-X069S-X118R, X003V-X009E-X069S-X124I, X003V-X009E-X069S-X128S, X003V-X009E-X069S-X129P, X003V-X009E-X069S-X130S, X003V-X009E-X069S-X145R, X003V-X009E-X069S-X166Q, X003V-X009E-X069S-X185Q, X003V-X009E-X069S-X210I, X003V-X009E-X069S-X217L, X003V-X009E-X069S-X218S, X003V-X009E-X069S-X248D, X003V-X009E-X069S-X259P, X003V-X009E-X076D-X078N, X003V-X009E-X076D-X079I, X003V-X009E-X076D-X087D, X003V-X009E-X076D-X118R, X003V-X009E-X076D-X124I, X003V-X009E-X076D-X128S, X003V-X009E-X076D-X129P, X003V-X009E-X076D-X130S, X003V-X009E-X076D-X145R, X003V-X009E-X076D-X166Q, X003V-X009E-X076D-X185Q, X003V-X009E-X076D-X210I, X003V-X009E-X076D-X217L, X003V-X009E-X076D-X218S, X003V-X009E-X076D-X248D, X003V-X009E-X076D-X259P, X003V-X009E-X078N-X079I, X003V-X009E-X078N-X087D, X003V-X009E-X078N-X118R, X003V-X009E-X078N-X124I, X003V-X009E-X078N-X128S, X003V-

X009E-X078N-X129P, X003V-X009E-X078N-X130S, X003V-X009E-X078N-X145R, X003V-X009E-X078N-X166Q, X003V-X009E-X078N-X185Q, X003V-X009E-X078N-X210I, X003V-X009E-X078N-X217L, X003V-X009E-X078N-X218S, X003V-X009E-X078N-X248D, X003V-X009E-X078N-X259P, X003V-X009E-X079I-X087D, X003V-X009E-X079I-X118R, X003V-X009E-X079I-X124I, X003V-X009E-X079I-X128S, X003V-X009E-X079I-X129P, X003V-X009E-X079I-X130S, X003V-X009E-X079I-X145R, X003V-X009E-X079I-X166Q, X003V-X009E-X079I-X185Q, X003V-X009E-X079I-X210I, X003V-X009E-X079I-X217L, X003V-X009E-X079I-X218S, X003V-X009E-X079I-X248D, X003V-X009E-X079I-X259P, X003V-X009E-X087D-X118R, X003V-X009E-X087D-X124I, X003V-X009E-X087D-X128S, X003V-X009E-X087D-X129P, X003V-X009E-X087D-X130S, X003V-X009E-X087D-X145R, X003V-X009E-X087D-X166Q, X003V-X009E-X087D-X185Q, X003V-X009E-X087D-X210I, X003V-X009E-X087D-X217L, X003V-X009E-X087D-X218S, X003V-X009E-X087D-X248D, X003V-X009E-X087D-X259P, X003V-X009E-X118R-X124I, X003V-X009E-X118R-X128S, X003V-X009E-X118R-X129P, X003V-X009E-X118R-X130S, X003V-X009E-X118R-X145R, X003V-X009E-X118R-X166Q, X003V-X009E-X118R-X185Q, X003V-X009E-X118R-X210I, X003V-X009E-X118R-X217L, X003V-X009E-X118R-X218S, X003V-X009E-X118R-X248D, X003V-X009E-X118R-X259P, X003V-X009E-X124I-X128S, X003V-X009E-X124I-X129P, X003V-X009E-X124I-X130S, X003V-X009E-X124I-X145R, X003V-X009E-X124I-X166Q, X003V-X009E-X124I-X185Q, X003V-X009E-X124I-X210I, X003V-X009E-X124I-X217L, X003V-X009E-X124I-X218S, X003V-X009E-X124I-X248D, X003V-X009E-X124I-X259P, X003V-X009E-X128 S-X129P, X003V-X009E-X128 S-X130S, X003V-X009E-X128 S-X145R, X003V-X009E-X128 S-X166Q, X003V-X009E-X128 S-X185Q, X003V-X009E-X128 S-X210I, X003V-X009E-X128S-X217L, X003V-X009E-X128S-X218S, X003V-X009E-X128S-X248D, X003V-X009E-X128S-X259P, X003V-X009E-X129P-X130S, X003V-X009E-X129P-X145R, X003V-X009E-X129P-X166Q, X003V-X009E-X129P-X185Q, X003V-X009E-X129P-X210I, X003V-X009E-X129P-X217L, X003V-X009E-X129P-X218S, X003V-X009E-X129P-X248D, X003V-X009E-X129P-X259P, X003V-X009E-X130S-X145R, X003V-X009E-X130S-X166Q, X003V-X009E-X130S-X185Q, X003V-X009E-X130S-X210I, X003V-X009E-X130S-X217L, X003V-X009E-X130S-X218S, X003V-X009E-X130S-X248D, X003V-X009E-X130S-X259P, X003V-X009E-X145R-X166Q, X003V-X009E-X145R-X185Q, X003V-X009E-X145R-X210I, X003V-X009E-X145R-X217L, X003V-X009E-X145R-X218S, X003V-X009E-X145R-X248D, X003V-X009E-X145R-X259P, X003V-X009E-X166Q-X185Q, X003V-X009E-X166Q-X210I, X003V-X009E-X166Q-X217L, X003V-X009E-X166Q-X218S, X003V-X009E-X166Q-X248D, X003V-X009E-X166Q-X259P, X003V-X009E-X185Q-X210I, X003V-X009E-X185Q-X217L, X003V-X009E-X185Q-X218S, X003V-X009E-X185Q-X248D, X003V-X009E-X185Q-X259P, X003V-X009E-X210I-X217L, X003V-X009E-X210I-X218S, X003V-X009E-X210I-X248D, X003V-X009E-X210I-X259P, X003V-X009E-X217L-X218S, X003V-X009E-X217L-X248D, X003V-X009E-X217L-X259P, X003V-X009E-X218S-X248D, X003V-X009E-X218S-X259P, X003V-X009E-X248D-X259P, X003V-X024Q-X040E-X069S, X003V-X024Q-X040E-X076D, X003V-X024Q-X040E-X078N, X003V-X024Q-X040E-X079I, X003V-X024Q-X040E-X087D, X003V-X024Q-X040E-X118R, X003V-X024Q-X040E-X124I, X003V-X024Q-X040E-X128S, X003V-X024Q-X040E-X129P, X003V-X024Q-X040E-X130S, X003V-X024Q-X040E-X145R, X003V-X024Q-X040E-X166Q, X003V-X024Q-X040E-X185Q, X003V-X024Q-X040E-X210I, X003V-X024Q-X040E-X217L, X003V-X024Q-X040E-X218S, X003V-X024Q-X040E-X248D, X003V-X024Q-X040E-X259P, X003V-X024Q-X069S-X076D, X003V-X024Q-X069S-X078N, X003V-X024Q-X069S-X079I, X003V-X024Q-X069S-X087D, X003V-X024Q-X069S-X118R, X003V-X024Q-X069S-X124I, X003V-X024Q-X069S-X128S, X003V-X024Q-X069S-X129P, X003V-X024Q-X069S-X130S, X003V-X024Q-X069S-X145R, X003V-X024Q-X069S-X166Q, X003V-X024Q-X069S-X185Q, X003V-X024Q-X069S-X210I, X003V-X024Q-X069S-X217L, X003V-X024Q-X069S-X218S, X003V-X024Q-X069S-X248D, X003V-X024Q-X069S-X259P, X003V-X024Q-X076D-X078N, X003V-X024Q-X076D-X079I, X003V-X024Q-X076D-X087D, X003V-X024Q-X076D-X118R, X003V-X024Q-X076D-X124I, X003V-X024Q-X076D-X128S, X003V-X024Q-X076D-X129P, X003V-X024Q-X076D-X130S, X003V-X024Q-X076D-X145R, X003V-X024Q-X076D-X166Q, X003V-X024Q-X076D-X185Q, X003V-X024Q-X076D-X210I, X003V-X024Q-X076D-X217L, X003V-X024Q-X076D-X218S, X003V-X024Q-X076D-X248D, X003V-X024Q-X076D-X259P, X003V-X024Q-X078N-X079I, X003V-X024Q-X078N-X087D, X003V-X024Q-X078N-X118R, X003V-X024Q-X078N-X124I, X003V-X024Q-X078N-X128S, X003V-X024Q-X078N-X129P, X003V-X024Q-X078N-X130S, X003V-X024Q-X078N-X145R, X003V-X024Q-X078N-X166Q, X003V-X024Q-X078N-X185Q, X003V-X024Q-X078N-X210I, X003V-X024Q-X078N-X217L, X003V-X024Q-X078N-X218S, X003V-X024Q-X078N-X248D, X003V-X024Q-X078N-X259P, X003V-X024Q-X079I-X087D, X003V-X024Q-X079I-X118R, X003V-X024Q-X079I-X124I, X003V-X024Q-X079I-X128S, X003V-X024Q-X079I-X129P, X003V-X024Q-X079I-X130S, X003V-X024Q-X079I-X145R, X003V-X024Q-X079I-X166Q, X003V-X024Q-X079I-X185Q, X003V-X024Q-X079I-X210I, X003V-X024Q-X079I-X217L, X003V-X024Q-X079I-X218S, X003V-X024Q-X079I-X248D, X003V-X024Q-X079I-X259P, X003V-X024Q-X087D-X118R, X003V-X024Q-X087D-X124I, X003V-X024Q-X087D-X128S, X003V-X024Q-X087D-X129P, X003V-X024Q-X087D-X130S, X003V-X024Q-X087D-X145R, X003V-X024Q-X087D-X166Q, X003V-X024Q-X087D-X185Q, X003V-X024Q-X087D-X210I, X003V-X024Q-X087D-X217L, X003V-X024Q-X087D-X218S, X003V-X024Q-X087D-X248D, X003V-X024Q-X087D-X259P, X003V-X024Q-X118R-X124I, X003V-X024Q-X118R-X128S, X003V-X024Q-X118R-X129P, X003V-X024Q-X118R-X130S, X003V-X024Q-X118R-X145R, X003V-X024Q-X118R-X166Q, X003V-X024Q-X118R-X185Q, X003V-X024Q-X118R-X210I, X003V-X024Q-X118R-X217L, X003V-X024Q-X118R-X218S, X003V-X024Q-X118R-X248D, X003V-X024Q-X118R-X259P, X003V-X024Q-X124I-X128S, X003V-X024Q-X124I-X129P, X003V-X024Q-X124I-X130S, X003V-X024Q-X124I-X145R, X003V-X024Q-X124I-X166Q, X003V-X024Q-X124I-X185Q, X003V-X024Q-X124I-X210I, X003V-X024Q-X124I-X217L, X003V-X024Q-X124I-X218S, X003V-X024Q-X124I-X248D, X003V-X024Q-X124I-X259P, X003V-X024Q-X128S-X129P, X003V-X024Q-X128S-X130S, X003V-X024Q-X128S-X145R, X003V-X024Q-X128S-

X166Q, X003V-X024Q-X128S-X185Q, X003V-X024Q-X128S-X210I, X003V-X024Q-X128S-X217L, X003V-X024Q-X128S-X218S, X003V-X024Q-X128S-X248D, X003V-X024Q-X128S-X259P, X003V-X024Q-X129P-X130S, X003V-X024Q-X129P-X145R, X003V-X024Q-X129P-X166Q, X003V-X024Q-X129P-X185Q, X003V-X024Q-X129P-X210I, X003V-X024Q-X129P-X217L, X003V-X024Q-X129P-X218S, X003V-X024Q-X129P-X248D, X003V-X024Q-X129P-X259P, X003V-X024Q-X130S-X145R, X003V-X024Q-X130S-X166Q, X003V-X024Q-X130S-X185Q, X003V-X024Q-X130S-X210I, X003V-X024Q-X130S-X217L, X003V-X024Q-X130S-X218S, X003V-X024Q-X130S-X248D, X003V-X024Q-X130S-X259P, X003V-X024Q-X145R-X166Q, X003V-X024Q-X145R-X185Q, X003V-X024Q-X145R-X210I, X003V-X024Q-X145R-X217L, X003V-X024Q-X145R-X218S, X003V-X024Q-X145R-X248D, X003V-X024Q-X145R-X259P, X003V-X024Q-X166Q-X185Q, X003V-X024Q-X166Q-X210I, X003V-X024Q-X166Q-X217L, X003V-X024Q-X166Q-X218S, X003V-X024Q-X166Q-X248D, X003V-X024Q-X166Q-X259P, X003V-X024Q-X185Q-X210I, X003V-X024Q-X185Q-X217L, X003V-X024Q-X185Q-X218S, X003V-X024Q-X185Q-X248D, X003V-X024Q-X185Q-X259P, X003V-X024Q-X210I-X217L, X003V-X024Q-X210I-X218S, X003V-X024Q-X210I-X248D, X003V-X024Q-X210I-X259P, X003V-X024Q-X217L-X218S, X003V-X024Q-X217L-X248D, X003V-X024Q-X217L-X259P, X003V-X024Q-X218S-X248D, X003V-X024Q-X218S-X259P, X003V-X024Q-X248D-X259P, X003V-X040E-X069S-X076D, X003V-X040E-X069S-X078N, X003V-X040E-X069S-X079I, X003V-X040E-X069S-X087D, X003V-X040E-X069S-X118R, X003V-X040E-X069S-X124I, X003V-X040E-X069S-X128S, X003V-X040E-X069S-X129P, X003V-X040E-X069S-X130S, X003V-X040E-X069S-X145R, X003V-X040E-X069S-X166Q, X003V-X040E-X069S-X185Q, X003V-X040E-X069S-X210I, X003V-X040E-X069S-X217L, X003V-X040E-X069S-X218S, X003V-X040E-X069S-X248D, X003V-X040E-X069S-X259P, X003V-X040E-X076D-X078N, X003V-X040E-X076D-X079I, X003V-X040E-X076D-X087D, X003V-X040E-X076D-X118R, X003V-X040E-X076D-X124I, X003V-X040E-X076D-X128S, X003V-X040E-X076D-X129P, X003V-X040E-X076D-X130S, X003V-X040E-X076D-X145R, X003V-X040E-X076D-X166Q, X003V-X040E-X076D-X185Q, X003V-X040E-X076D-X210I, X003V-X040E-X076D-X217L, X003V-X040E-X076D-X218S, X003V-X040E-X076D-X248D, X003V-X040E-X076D-X259P, X003V-X040E-X078N-X079I, X003V-X040E-X078N-X087D, X003V-X040E-X078N-X118R, X003V-X040E-X078N-X124I, X003V-X040E-X078N-X128S, X003V-X040E-X078N-X129P, X003V-X040E-X078N-X130S, X003V-X040E-X078N-X145R, X003V-X040E-X078N-X166Q, X003V-X040E-X078N-X185Q, X003V-X040E-X078N-X210I, X003V-X040E-X078N-X217L, X003V-X040E-X078N-X218S, X003V-X040E-X078N-X248D, X003V-X040E-X078N-X259P, X003V-X040E-X079I-X087D, X003V-X040E-X079I-X118R, X003V-X040E-X079I-X124I, X003V-X040E-X079I-X128S, X003V-X040E-X079I-X129P, X003V-X040E-X079I-X130S, X003V-X040E-X079I-X145R, X003V-X040E-X079I-X166Q, X003V-X040E-X079I-X185Q, X003V-X040E-X079I-X210I, X003V-X040E-X079I-X217L, X003V-X040E-X079I-X218S, X003V-X040E-X079I-X248D, X003V-X040E-X079I-X259P, X003V-X040E-X087D-X118R, X003V-X040E-X087D-X124I, X003V-X040E-X087D-X128S, X003V-X040E-X087D-X129P, X003V-X040E-X087D-X130S, X003V-X040E-X087D-X145R, X003V-X040E-X087D-X166Q, X003V-X040E-X087D-X185Q, X003V-X040E-X087D-X210I, X003V-X040E-X087D-X217L, X003V-X040E-X087D-X218S, X003V-X040E-X087D-X248D, X003V-X040E-X087D-X259P, X003V-X040E-X118R-X124I, X003V-X040E-X118R-X128S, X003V-X040E-X118R-X129P, X003V-X040E-X118R-X130S, X003V-X040E-X118R-X145R, X003V-X040E-X118R-X166Q, X003V-X040E-X118R-X185Q, X003V-X040E-X118R-X210I, X003V-X040E-X118R-X217L, X003V-X040E-X118R-X218S, X003V-X040E-X118R-X248D, X003V-X040E-X118R-X259P, X003V-X040E-X124I-X128S, X003V-X040E-X124I-X129P, X003V-X040E-X124I-X130S, X003V-X040E-X124I-X145R, X003V-X040E-X124I-X166Q, X003V-X040E-X124I-X185Q, X003V-X040E-X124I-X210I, X003V-X040E-X124I-X217L, X003V-X040E-X124I-X218S, X003V-X040E-X124I-X248D, X003V-X040E-X124I-X259P, X003V-X040E-X128S-X129P, X003V-X040E-X128S-X130S, X003V-X040E-X128S-X145R, X003V-X040E-X128S-X166Q, X003V-X040E-X128S-X185Q, X003V-X040E-X128S-X210I, X003V-X040E-X128S-X217L, X003V-X040E-X128S-X218S, X003V-X040E-X128S-X248D, X003V-X040E-X128S-X259P, X003V-X040E-X129P-X130S, X003V-X040E-X129P-X145R, X003V-X040E-X129P-X166Q, X003V-X040E-X129P-X185Q, X003V-X040E-X129P-X210I, X003V-X040E-X129P-X217L, X003V-X040E-X129P-X218S, X003V-X040E-X129P-X248D, X003V-X040E-X129P-X259P, X003V-X040E-X130S-X145R, X003V-X040E-X130S-X166Q, X003V-X040E-X130S-X185Q, X003V-X040E-X130S-X210I, X003V-X040E-X130S-X217L, X003V-X040E-X130S-X218S, X003V-X040E-X130S-X248D, X003V-X040E-X130S-X259P, X003V-X040E-X145R-X166Q, X003V-X040E-X145R-X185Q, X003V-X040E-X145R-X210I, X003V-X040E-X145R-X217L, X003V-X040E-X145R-X218S, X003V-X040E-X145R-X248D, X003V-X040E-X145R-X259P, X003V-X040E-X166Q-X185Q, X003V-X040E-X166Q-X210I, X003V-X040E-X166Q-X217L, X003V-X040E-X166Q-X218S, X003V-X040E-X166Q-X248D, X003V-X040E-X166Q-X259P, X003V-X040E-X185Q-X210I, X003V-X040E-X185Q-X217L, X003V-X040E-X185Q-X218S, X003V-X040E-X185Q-X248D, X003V-X040E-X185Q-X259P, X003V-X040E-X210I-X217L, X003V-X040E-X210I-X218S, X003V-X040E-X210I-X248D, X003V-X040E-X210I-X259P, X003V-X040E-X217L-X218S, X003V-X040E-X217L-X248D, X003V-X040E-X217L-X259P, X003V-X040E-X218S-X248D, X003V-X040E-X218S-X259P, X003V-X040E-X248D-X259P, X003V-X069S-X076D-X078N, X003V-X069S-X076D-X079I, X003V-X069S-X076D-X087D, X003V-X069S-X076D-X118R, X003V-X069S-X076D-X124I, X003V-X069S-X076D-X128S, X003V-X069S-X076D-X129P, X003V-X069S-X076D-X130S, X003V-X069S-X076D-X145R, X003V-X069S-X076D-X166Q, X003V-X069S-X076D-X185Q, X003V-X069S-X076D-X210I, X003V-X069S-X076D-X217L, X003V-X069S-X076D-X218S, X003V-X069S-X076D-X248D, X003V-X069S-X076D-X259P, X003V-X069S-X078N-X079I, X003V-X069S-X078N-X087D, X003V-X069S-X078N-X118R, X003V-X069S-X078N-X124I, X003V-X069S-X078N-X128S, X003V-X069S-X078N-X129P, X003V-X069S-X078N-X130S, X003V-X069S-X078N-X145R, X003V-X069S-X078N-X166Q, X003V-X069S-X078N-X185Q, X003V-X069S-X078N-X210I, X003V-X069S-X078N-X217L, X003V-X069S-X078N-X218S, X003V-X069S-X078N-X248D, X003V-

X069S-X078N-X259P, X003V-X069S-X079I-X087D, X003V-X069S-X079I-X118R, X003V-X069S-X079I-X124I, X003V-X069S-X079I-X128S, X003V-X069S-X079I-X129P, X003V-X069S-X079I-X130S, X003V-X069S-X079I-X145R, X003V-X069S-X079I-X166Q, X003V-X069S-X079I-X185Q, X003V-X069S-X079I-X210I, X003V-X069S-X079I-X217L, X003V-X069S-X079I-X218S, X003V-X069S-X079I-X248D, X003V-X069S-X079I-X259P, X003V-X069S-X087D-X118R, X003V-X069S-X087D-X124I, X003V-X069S-X087D-X128S, X003V-X069S-X087D-X129P, X003V-X069S-X087D-X130S, X003V-X069S-X087D-X145R, X003V-X069S-X087D-X166Q, X003V-X069S-X087D-X185Q, X003V-X069S-X087D-X210I, X003V-X069S-X087D-X217L, X003V-X069S-X087D-X218S, X003V-X069S-X087D-X248D, X003V-X069S-X087D-X259P, X003V-X069S-X118R-X124I, X003V-X069S-X118R-X128S, X003V-X069S-X118R-X129P, X003V-X069S-X118R-X130S, X003V-X069S-X118R-X145R, X003V-X069S-X118R-X166Q, X003V-X069S-X118R-X185Q, X003V-X069S-X118R-X210I, X003V-X069S-X118R-X217L, X003V-X069S-X118R-X218S, X003V-X069S-X118R-X248D, X003V-X069S-X118R-X259P, X003V-X069S-X124I-X128S, X003V-X069S-X124I-X129P, X003V-X069S-X124I-X130S, X003V-X069S-X124I-X145R, X003V-X069S-X124I-X166Q, X003V-X069S-X124I-X185Q, X003V-X069S-X124I-X210I, X003V-X069S-X124I-X217L, X003V-X069S-X124I-X218S, X003V-X069S-X124I-X248D, X003V-X069S-X124I-X259P, X003V-X069S-X128S-X129P, X003V-X069S-X128S-X130S, X003V-X069S-X128S-X145R, X003V-X069S-X128S-X166Q, X003V-X069S-X128S-X185Q, X003V-X069S-X128S-X210I, X003V-X069S-X128S-X217L, X003V-X069S-X128S-X218S, X003V-X069S-X128S-X248D, X003V-X069S-X128S-X259P, X003V-X069S-X129P-X130S, X003V-X069S-X129P-X145R, X003V-X069S-X129P-X166Q, X003V-X069S-X129P-X185Q, X003V-X069S-X129P-X210I, X003V-X069S-X129P-X217L, X003V-X069S-X129P-X218S, X003V-X069S-X129P-X248D, X003V-X069S-X129P-X259P, X003V-X069S-X130S-X145R, X003V-X069S-X130S-X166Q, X003V-X069S-X130S-X185Q, X003V-X069S-X130S-X210I, X003V-X069S-X130S-X217L, X003V-X069S-X130S-X218S, X003V-X069S-X130S-X248D, X003V-X069S-X130S-X259P, X003V-X069S-X145R-X166Q, X003V-X069S-X145R-X185Q, X003V-X069S-X145R-X210I, X003V-X069S-X145R-X217L, X003V-X069S-X145R-X218S, X003V-X069S-X145R-X248D, X003V-X069S-X145R-X259P, X003V-X069S-X166Q-X185Q, X003V-X069S-X166Q-X210I, X003V-X069S-X166Q-X217L, X003V-X069S-X166Q-X218S, X003V-X069S-X166Q-X248D, X003V-X069S-X166Q-X259P, X003V-X069S-X185Q-X210I, X003V-X069S-X185Q-X217L, X003V-X069S-X185Q-X218S, X003V-X069S-X185Q-X248D, X003V-X069S-X185Q-X259P, X003V-X069S-X210I-X217L, X003V-X069S-X210I-X218S, X003V-X069S-X210I-X248D, X003V-X069S-X210I-X259P, X003V-X069S-X217L-X218S, X003V-X069S-X217L-X248D, X003V-X069S-X217L-X259P, X003V-X069S-X218S-X248D, X003V-X069S-X218S-X259P, X003V-X069S-X248D-X259P, X003V-X076D-X078N-X079I, X003V-X076D-X078N-X087D, X003V-X076D-X078N-X118R, X003V-X076D-X078N-X124I, X003V-X076D-X078N-X128S, X003V-X076D-X078N-X129P, X003V-X076D-X078N-X130S, X003V-X076D-X078N-X145R, X003V-X076D-X078N-X166Q, X003V-X076D-X078N-X185Q, X003V-X076D-X078N-X210I, X003V-X076D-X078N-X217L, X003V-X076D-X078N-X218S, X003V-X076D-X078N-X248D, X003V-X076D-X078N-X259P, X003V-X076D-X079I-X087D, X003V-X076D-X079I-X118R, X003V-X076D-X079I-X124I, X003V-X076D-X079I-X128S, X003V-X076D-X079I-X129P, X003V-X076D-X079I-X130S, X003V-X076D-X079I-X145R, X003V-X076D-X079I-X166Q, X003V-X076D-X079I-X185Q, X003V-X076D-X079I-X210I, X003V-X076D-X079I-X217L, X003V-X076D-X079I-X218S, X003V-X076D-X079I-X248D, X003V-X076D-X079I-X259P, X003V-X076D-X087D-X118R, X003V-X076D-X087D-X124I, X003V-X076D-X087D-X128S, X003V-X076D-X087D-X129P, X003V-X076D-X087D-X130S, X003V-X076D-X087D-X145R, X003V-X076D-X087D-X166Q, X003V-X076D-X087D-X185Q, X003V-X076D-X087D-X210I, X003V-X076D-X087D-X217L, X003V-X076D-X087D-X218S, X003V-X076D-X087D-X248D, X003V-X076D-X087D-X259P, X003V-X076D-X118R-X124I, X003V-X076D-X118R-X128S, X003V-X076D-X118R-X129P, X003V-X076D-X118R-X130S, X003V-X076D-X118R-X145R, X003V-X076D-X118R-X166Q, X003V-X076D-X118R-X185Q, X003V-X076D-X118R-X210I, X003V-X076D-X118R-X217L, X003V-X076D-X118R-X218S, X003V-X076D-X118R-X248D, X003V-X076D-X118R-X259P, X003V-X076D-X124I-X128S, X003V-X076D-X124I-X129P, X003V-X076D-X124I-X130S, X003V-X076D-X124I-X145R, X003V-X076D-X124I-X166Q, X003V-X076D-X124I-X185Q, X003V-X076D-X124I-X210I, X003V-X076D-X124I-X217L, X003V-X076D-X124I-X218S, X003V-X076D-X124I-X248D, X003V-X076D-X124I-X259P, X003V-X076D-X128S-X129P, X003V-X076D-X128S-X130S, X003V-X076D-X128S-X145R, X003V-X076D-X128S-X166Q, X003V-X076D-X128S-X185Q, X003V-X076D-X128S-X210I, X003V-X076D-X128S-X217L, X003V-X076D-X128S-X218S, X003V-X076D-X128S-X248D, X003V-X076D-X128S-X259P, X003V-X076D-X129P-X130S, X003V-X076D-X129P-X145R, X003V-X076D-X129P-X166Q, X003V-X076D-X129P-X185Q, X003V-X076D-X129P-X210I, X003V-X076D-X129P-X217L, X003V-X076D-X129P-X218S, X003V-X076D-X129P-X248D, X003V-X076D-X129P-X259P, X003V-X076D-X130S-X145R, X003V-X076D-X130S-X166Q, X003V-X076D-X130S-X185Q, X003V-X076D-X130S-X210I, X003V-X076D-X130S-X217L, X003V-X076D-X130S-X218S, X003V-X076D-X130S-X248D, X003V-X076D-X130S-X259P, X003V-X076D-X145R-X166Q, X003V-X076D-X145R-X185Q, X003V-X076D-X145R-X210I, X003V-X076D-X145R-X217L, X003V-X076D-X145R-X218S, X003V-X076D-X145R-X248D, X003V-X076D-X145R-X259P, X003V-X076D-X166Q-X185Q, X003V-X076D-X166Q-X210I, X003V-X076D-X166Q-X217L, X003V-X076D-X166Q-X218S, X003V-X076D-X166Q-X248D, X003V-X076D-X166Q-X259P, X003V-X076D-X185Q-X210I, X003V-X076D-X185Q-X217L, X003V-X076D-X185Q-X218S, X003V-X076D-X185Q-X248D, X003V-X076D-X185Q-X259P, X003V-X076D-X210I-X217L, X003V-X076D-X210I-X218S, X003V-X076D-X210I-X248D, X003V-X076D-X210I-X259P, X003V-X076D-X217L-X218S, X003V-X076D-X217L-X248D, X003V-X076D-X217L-X259P, X003V-X076D-X218S-X248D, X003V-X076D-X218S-X259P, X003V-X076D-X248D-X259P, X003V-X078N-X079I-X087D, X003V-X078N-X079I-X118R, X003V-X078N-X079I-X124I, X003V-X078N-X079I-X128S, X003V-X078N-X079I-X129P, X003V-X078N-X079I-X130S, X003V-X078N-X079I-X145R, X003V-X078N-X079I-X166Q, X003V-X078N-X079I-

X185Q, X003V-X078N-X079I-X210I, X003V-X078N-X079I-X217L, X003V-X078N-X079I-X218S, X003V-X078N-X079I-X248D, X003V-X078N-X079I-X259P, X003V-X078N-X087D-X118R, X003V-X078N-X087D-X124I, X003V-X078N-X087D-X128S, X003V-X078N-X087D-X129P, X003V-X078N-X087D-X130S, X003V-X078N-X087D-X145R, X003V-X078N-X087D-X166Q, X003V-X078N-X087D-X185Q, X003V-X078N-X087D-X210I, X003V-X078N-X087D-X217L, X003V-X078N-X087D-X218S, X003V-X078N-X087D-X248D, X003V-X078N-X087D-X259P, X003V-X078N-X118R-X124I, X003V-X078N-X118R-X128S, X003V-X078N-X118R-X129P, X003V-X078N-X118R-X130S, X003V-X078N-X118R-X145R, X003V-X078N-X118R-X166Q, X003V-X078N-X118R-X185Q, X003V-X078N-X118R-X210I, X003V-X078N-X118R-X217L, X003V-X078N-X118R-X218S, X003V-X078N-X118R-X248D, X003V-X078N-X118R-X259P, X003V-X078N-X124I-X128S, X003V-X078N-X124I-X129P, X003V-X078N-X124I-X130S, X003V-X078N-X124I-X145R, X003V-X078N-X124I-X166Q, X003V-X078N-X124I-X185Q, X003V-X078N-X124I-X210I, X003V-X078N-X124I-X217L, X003V-X078N-X124I-X218S, X003V-X078N-X124I-X248D, X003V-X078N-X124I-X259P, X003V-X078N-X128S-X129P, X003V-X078N-X128S-X130S, X003V-X078N-X128S-X145R, X003V-X078N-X128S-X166Q, X003V-X078N-X128S-X185Q, X003V-X078N-X128S-X210I, X003V-X078N-X128S-X217L, X003V-X078N-X128S-X218S, X003V-X078N-X128S-X248D, X003V-X078N-X128S-X259P, X003V-X078N-X129P-X130S, X003V-X078N-X129P-X145R, X003V-X078N-X129P-X166Q, X003V-X078N-X129P-X185Q, X003V-X078N-X129P-X210I, X003V-X078N-X129P-X217L, X003V-X078N-X129P-X218S, X003V-X078N-X129P-X248D, X003V-X078N-X129P-X259P, X003V-X078N-X130S-X145R, X003V-X078N-X130S-X166Q, X003V-X078N-X130S-X185Q, X003V-X078N-X130S-X210I, X003V-X078N-X130S-X217L, X003V-X078N-X130S-X218S, X003V-X078N-X130S-X248D, X003V-X078N-X130S-X259P, X003V-X078N-X145R-X166Q, X003V-X078N-X145R-X185Q, X003V-X078N-X145R-X210I, X003V-X078N-X145R-X217L, X003V-X078N-X145R-X218S, X003V-X078N-X145R-X248D, X003V-X078N-X145R-X259P, X003V-X078N-X166Q-X185Q, X003V-X078N-X166Q-X210I, X003V-X078N-X166Q-X217L, X003V-X078N-X166Q-X218S, X003V-X078N-X166Q-X248D, X003V-X078N-X166Q-X259P, X003V-X078N-X185Q-X210I, X003V-X078N-X185Q-X217L, X003V-X078N-X185Q-X218S, X003V-X078N-X185Q-X248D, X003V-X078N-X185Q-X259P, X003V-X078N-X210I-X217L, X003V-X078N-X210I-X218 S, X003V-X078N-X210I-X248D, X003V-X078N-X210I-X259P, X003V-X078N-X217L-X218S, X003V-X078N-X217L-X248D, X003V-X078N-X217L-X259P, X003V-X078N-X218S-X248D, X003V-X078N-X218S-X259P, X003V-X078N-X248D-X259P, X003V-X079I-X087D-X118R, X003V-X079I-X087D-X124I, X003V-X079I-X087D-X128S, X003V-X079I-X087D-X129P, X003V-X079I-X087D-X130S, X003V-X079I-X087D-X145R, X003V-X079I-X087D-X166Q, X003V-X079I-X087D-X185Q, X003V-X079I-X087D-X210I, X003V-X079I-X087D-X217L, X003V-X079I-X087D-X218S, X003V-X079I-X087D-X248D, X003V-X079I-X087D-X259P, X003V-X079I-X118R-X124I, X003V-X079I-X118R-X128S, X003V-X079I-X118R-X129P, X003V-X079I-X118R-X130S, X003V-X079I-X118R-X145R, X003V-X079I-X118R-X166Q, X003V-X079I-X118R-X185Q, X003V-X079I-X118R-X210I, X003V-X079I-X118R-X217L, X003V-X079I-X118R-X218S, X003V-X079I-X118R-X248D, X003V-X079I-X118R-X259P, X003V-X079I-X124I-X128S, X003V-X079I-X124I-X129P, X003V-X079I-X124I-X130S, X003V-X079I-X124I-X145R, X003V-X079I-X124I-X166Q, X003V-X079I-X124I-X185Q, X003V-X079I-X124I-X210I, X003V-X079I-X124I-X217L, X003V-X079I-X124I-X218S, X003V-X079I-X124I-X248D, X003V-X079I-X124I-X259P, X003V-X079I-X128S-X129P, X003V-X079I-X128S-X130S, X003V-X079I-X128S-X145R, X003V-X079I-X128S-X166Q, X003V-X079I-X128S-X185Q, X003V-X079I-X128S-X210I, X003V-X079I-X128S-X217L, X003V-X079I-X128S-X218S, X003V-X079I-X128S-X248D, X003V-X079I-X128S-X259P, X003V-X079I-X129P-X130S, X003V-X079I-X129P-X145R, X003V-X079I-X129P-X166Q, X003V-X079I-X129P-X185Q, X003V-X079I-X129P-X210I, X003V-X079I-X129P-X217L, X003V-X079I-X129P-X218S, X003V-X079I-X129P-X248D, X003V-X079I-X129P-X259P, X003V-X079I-X130S-X145R, X003V-X079I-X130S-X166Q, X003V-X079I-X130S-X185Q, X003V-X079I-X130S-X210I, X003V-X079I-X130S-X217L, X003V-X079I-X130S-X218S, X003V-X079I-X130S-X248D, X003V-X079I-X130S-X259P, X003V-X079I-X145R-X166Q, X003V-X079I-X145R-X185Q, X003V-X079I-X145R-X210I, X003V-X079I-X145R-X217L, X003V-X079I-X145R-X218S, X003V-X079I-X145R-X248D, X003V-X079I-X145R-X259P, X003V-X079I-X166Q-X185Q, X003V-X079I-X166Q-X210I, X003V-X079I-X166Q-X217L, X003V-X079I-X166Q-X218S, X003V-X079I-X166Q-X248D, X003V-X079I-X166Q-X259P, X003V-X079I-X185Q-X210I, X003V-X079I-X185Q-X217L, X003V-X079I-X185Q-X218S, X003V-X079I-X185Q-X248D, X003V-X079I-X185Q-X259P, X003V-X079I-X210I-X217L, X003V-X079I-X210I-X218S, X003V-X079I-X210I-X248D, X003V-X079I-X210I-X259P, X003V-X079I-X217L-X218S, X003V-X079I-X217L-X248D, X003V-X079I-X217L-X259P, X003V-X079I-X218S-X248D, X003V-X079I-X218S-X259P, X003V-X079I-X248D-X259P, X003V-X087D-X118R-X124I, X003V-X087D-X118R-X128S, X003V-X087D-X118R-X129P, X003V-X087D-X118R-X130S, X003V-X087D-X118R-X145R, X003V-X087D-X118R-X166Q, X003V-X087D-X118R-X185Q, X003V-X087D-X118R-X210I, X003V-X087D-X118R-X217L, X003V-X087D-X118R-X218S, X003V-X087D-X118R-X248D, X003V-X087D-X118R-X259P, X003V-X087D-X124I-X128S, X003V-X087D-X124I-X129P, X003V-X087D-X124I-X130S, X003V-X087D-X124I-X145R, X003V-X087D-X124I-X166Q, X003V-X087D-X124I-X185Q, X003V-X087D-X124I-X210I, X003V-X087D-X124I-X217L, X003V-X087D-X124I-X218S, X003V-X087D-X124I-X248D, X003V-X087D-X124I-X259P, X003V-X087D-X128S-X129P, X003V-X087D-X128S-X130S, X003V-X087D-X128S-X145R, X003V-X087D-X128S-X166Q, X003V-X087D-X128S-X185Q, X003V-X087D-X128S-X210I, X003V-X087D-X128S-X217L, X003V-X087D-X128S-X218S, X003V-X087D-X128S-X248D, X003V-X087D-X128S-X259P, X003V-X087D-X129P-X130S, X003V-X087D-X129P-X145R, X003V-X087D-X129P-X166Q, X003V-X087D-X129P-X185Q, X003V-X087D-X129P-X210I, X003V-X087D-X129P-X217L, X003V-X087D-X129P-X218S, X003V-X087D-X129P-X248D, X003V-X087D-X129P-X259P, X003V-X087D-X130S-X145R, X003V-X087D-X130S-X166Q, X003V-X087D-X130S-X185Q, X003V-X087D-X130S-X210I, X003V-X087D-X130S-X217L, X003V-

X087D-X130S-X218S, X003V-X087D-X130S-X248D, X003V-X087D-X130S-X259P, X003V-X087D-X145R-X166Q, X003V-X087D-X145R-X185Q, X003V-X087D-X145R-X210I, X003V-X087D-X145R-X217L, X003V-X087D-X145R-X218S, X003V-X087D-X145R-X248D, X003V-X087D-X145R-X259P, X003V-X087D-X166Q-X185Q, X003V-X087D-X166Q-X210I, X003V-X087D-X166Q-X217L, X003V-X087D-X166Q-X218S, X003V-X087D-X166Q-X248D, X003V-X087D-X166Q-X259P, X003V-X087D-X185Q-X210I, X003V-X087D-X185Q-X217L, X003V-X087D-X185Q-X218S, X003V-X087D-X185Q-X248D, X003V-X087D-X185Q-X259P, X003V-X087D-X210I-X217L, X003V-X087D-X210I-X218S, X003V-X087D-X210I-X248D, X003V-X087D-X210I-X259P, X003V-X087D-X217L-X218S, X003V-X087D-X217L-X248D, X003V-X087D-X217L-X259P, X003V-X087D-X218S-X248D, X003V-X087D-X218S-X259P, X003V-X087D-X248D-X259P, X003V-X118R-X124I-X128S, X003V-X118R-X124I-X129P, X003V-X118R-X124I-X130S, X003V-X118R-X124I-X145R, X003V-X118R-X124I-X166Q, X003V-X118R-X124I-X185Q, X003V-X118R-X124I-X210I, X003V-X118R-X124I-X217L, X003V-X118R-X124I-X218S, X003V-X118R-X124I-X248D, X003V-X118R-X124I-X259P, X003V-X118R-X128S-X129P, X003V-X118R-X128S-X130S, X003V-X118R-X128S-X145R, X003V-X118R-X128S-X166Q, X003V-X118R-X128S-X185Q, X003V-X118R-X128S-X210I, X003V-X118R-X128S-X217L, X003V-X118R-X128S-X218S, X003V-X118R-X128S-X248D, X003V-X118R-X128S-X259P, X003V-X118R-X129P-X130S, X003V-X118R-X129P-X145R, X003V-X118R-X129P-X166Q, X003V-X118R-X129P-X185Q, X003V-X118R-X129P-X210I, X003V-X118R-X129P-X217L, X003V-X118R-X129P-X218S, X003V-X118R-X129P-X248D, X003V-X118R-X129P-X259P, X003V-X118R-X130S-X145R, X003V-X118R-X130S-X166Q, X003V-X118R-X130S-X185Q, X003V-X118R-X130S-X210I, X003V-X118R-X130S-X217L, X003V-X118R-X130S-X218S, X003V-X118R-X130S-X248D, X003V-X118R-X130S-X259P, X003V-X118R-X145R-X166Q, X003V-X118R-X145R-X185Q, X003V-X118R-X145R-X210I, X003V-X118R-X145R-X217L, X003V-X118R-X145R-X218S, X003V-X118R-X145R-X248D, X003V-X118R-X145R-X259P, X003V-X118R-X166Q-X185Q, X003V-X118R-X166Q-X210I, X003V-X118R-X166Q-X217L, X003V-X118R-X166Q-X218S, X003V-X118R-X166Q-X248D, X003V-X118R-X166Q-X259P, X003V-X118R-X185Q-X210I, X003V-X118R-X185Q-X217L, X003V-X118R-X185Q-X218S, X003V-X118R-X185Q-X248D, X003V-X118R-X185Q-X259P, X003V-X118R-X210I-X217L, X003V-X118R-X210I-X218S, X003V-X118R-X210I-X248D, X003V-X118R-X210I-X259P, X003V-X118R-X217L-X218S, X003V-X118R-X217L-X248D, X003V-X118R-X217L-X259P, X003V-X118R-X218S-X248D, X003V-X118R-X218S-X259P, X003V-X118R-X248D-X259P, X003V-X124I-X128S-X129P, X003V-X124I-X128S-X130S, X003V-X124I-X128S-X145R, X003V-X124I-X128S-X166Q, X003V-X124I-X128S-X185Q, X003V-X124I-X128S-X210I, X003V-X124I-X128S-X217L, X003V-X124I-X128S-X218S, X003V-X124I-X128S-X248D, X003V-X124I-X128S-X259P, X003V-X124I-X129P-X130S, X003V-X124I-X129P-X145R, X003V-X124I-X129P-X166Q, X003V-X124I-X129P-X185Q, X003V-X124I-X129P-X210I, X003V-X124I-X129P-X217L, X003V-X124I-X129P-X218S, X003V-X124I-X129P-X248D, X003V-X124I-X129P-X259P, X003V-X124I-X130S-X145R, X003V-X124I-X130S-X166Q, X003V-X124I-X130S-X185Q, X003V-X124I-X130S-X210I, X003V-X124I-X130S-X217L, X003V-X124I-X130S-X218S, X003V-X124I-X130S-X248D, X003V-X124I-X130S-X259P, X003V-X124I-X145R-X166Q, X003V-X124I-X145R-X185Q, X003V-X124I-X145R-X210I, X003V-X124I-X145R-X217L, X003V-X124I-X145R-X218S, X003V-X124I-X145R-X248D, X003V-X124I-X145R-X259P, X003V-X124I-X166Q-X185Q, X003V-X124I-X166Q-X210I, X003V-X124I-X166Q-X217L, X003V-X124I-X166Q-X218S, X003V-X124I-X166Q-X248D, X003V-X124I-X166Q-X259P, X003V-X124I-X185Q-X210I, X003V-X124I-X185Q-X217L, X003V-X124I-X185Q-X218S, X003V-X124I-X185Q-X248D, X003V-X124I-X185Q-X259P, X003V-X124I-X210I-X217L, X003V-X124I-X210I-X218S, X003V-X124I-X210I-X248D, X003V-X124I-X210I-X259P, X003V-X124I-X217L-X218S, X003V-X124I-X217L-X248D, X003V-X124I-X217L-X259P, X003V-X124I-X218S-X248D, X003V-X124I-X218S-X259P, X003V-X124I-X248D-X259P, X003V-X128S-X129P-X130S, X003V-X128S-X129P-X145R, X003V-X128S-X129P-X166Q, X003V-X128S-X129P-X185Q, X003V-X128S-X129P-X210I, X003V-X128S-X129P-X217L, X003V-X128S-X129P-X218S, X003V-X128S-X129P-X248D, X003V-X128S-X129P-X259P, X003V-X128S-X130S-X145R, X003V-X128S-X130S-X166Q, X003V-X128S-X130S-X185Q, X003V-X128S-X130S-X210I, X003V-X128S-X130S-X217L, X003V-X128S-X130S-X218S, X003V-X128S-X130S-X248D, X003V-X128S-X130S-X259P, X003V-X128S-X145R-X166Q, X003V-X128S-X145R-X185Q, X003V-X128S-X145R-X210I, X003V-X128S-X145R-X217L, X003V-X128S-X145R-X218S, X003V-X128S-X145R-X248D, X003V-X128S-X145R-X259P, X003V-X128S-X166Q-X185Q, X003V-X128S-X166Q-X210I, X003V-X128S-X166Q-X217L, X003V-X128S-X166Q-X218S, X003V-X128S-X166Q-X248D, X003V-X128S-X166Q-X259P, X003V-X128S-X185Q-X210I, X003V-X128S-X185Q-X217L, X003V-X128S-X185Q-X218S, X003V-X128S-X185Q-X248D, X003V-X128S-X185Q-X259P, X003V-X128S-X210I-X217L, X003V-X128S-X210I-X218S, X003V-X128S-X210I-X248D, X003V-X128S-X210I-X259P, X003V-X128S-X217L-X218S, X003V-X128S-X217L-X248D, X003V-X128S-X217L-X259P, X003V-X128S-X218S-X248D, X003V-X128S-X218S-X259P, X003V-X128S-X248D-X259P, X003V-X129P-X130S-X145R, X003V-X129P-X130S-X166Q, X003V-X129P-X130S-X185Q, X003V-X129P-X130S-X210I, X003V-X129P-X130S-X217L, X003V-X129P-X130S-X218S, X003V-X129P-X130S-X248D, X003V-X129P-X130S-X259P, X003V-X129P-X145R-X166Q, X003V-X129P-X145R-X185Q, X003V-X129P-X145R-X210I, X003V-X129P-X145R-X217L, X003V-X129P-X145R-X218S, X003V-X129P-X145R-X248D, X003V-X129P-X145R-X259P, X003V-X129P-X166Q-X185Q, X003V-X129P-X166Q-X210I, X003V-X129P-X166Q-X217L, X003V-X129P-X166Q-X218S, X003V-X129P-X166Q-X248D, X003V-X129P-X166Q-X259P, X003V-X129P-X185Q-X210I, X003V-X129P-X185Q-X217L, X003V-X129P-X185Q-X218S, X003V-X129P-X185Q-X248D, X003V-X129P-X185Q-X259P, X003V-X129P-X210I-X217L, X003V-X129P-X210I-X218S, X003V-X129P-X210I-X248D, X003V-X129P-X210I-X259P, X003V-X129P-X217L-X218S, X003V-X129P-X217L-X248D, X003V-X129P-X217L-X259P, X003V-X129P-X218S-X248D, X003V-X129P-X218S-X259P, X003V-X129P-X248D-X259P, X003V-X130S-X145R-X166Q, X003V-X130S-X145R-

X185Q, X003V-X130S-X145R-X210I, X003V-X130S-X145R-X217L, X003V-X130S-X145R-X218S, X003V-X130S-X145R-X248D, X003V-X130S-X145R-X259P, X003V-X130S-X166Q-X185Q, X003V-X130S-X166Q-X210I, X003V-X130S-X166Q-X217L, X003V-X130S-X166Q-X218S, X003V-X130S-X166Q-X248D, X003V-X130S-X166Q-X259P, X003V-X130S-X185Q-X210I, X003V-X130S-X185Q-X217L, X003V-X130S-X185Q-X218S, X003V-X130S-X185Q-X248D, X003V-X130S-X185Q-X259P, X003V-X130S-X210I-X217L, X003V-X130S-X210I-X218S, X003V-X130S-X210I-X248D, X003V-X130S-X210I-X259P, X003V-X130S-X217L-X218S, X003V-X130S-X217L-X248D, X003V-X130S-X217L-X259P, X003V-X130S-X218S-X248D, X003V-X130S-X218S-X259P, X003V-X130S-X248D-X259P, X003V-X145R-X166Q-X185Q, X003V-X145R-X166Q-X210I, X003V-X145R-X166Q-X217L, X003V-X145R-X166Q-X218S, X003V-X145R-X166Q-X248D, X003V-X145R-X166Q-X259P, X003V-X145R-X185Q-X210I, X003V-X145R-X185Q-X217L, X003V-X145R-X185Q-X218S, X003V-X145R-X185Q-X248D, X003V-X145R-X185Q-X259P, X003V-X145R-X210I-X217L, X003V-X145R-X210I-X218S, X003V-X145R-X210I-X248D, X003V-X145R-X210I-X259P, X003V-X145R-X217L-X218S, X003V-X145R-X217L-X248D, X003V-X145R-X217L-X259P, X003V-X145R-X218S-X248D, X003V-X145R-X218S-X259P, X003V-X145R-X248D-X259P, X003V-X166Q-X185Q-X210I, X003V-X166Q-X185Q-X217L, X003V-X166Q-X185Q-X218S, X003V-X166Q-X185Q-X248D, X003V-X166Q-X185Q-X259P, X003V-X166Q-X210I-X217L, X003V-X166Q-X210I-X218S, X003V-X166Q-X210I-X248D, X003V-X166Q-X210I-X259P, X003V-X166Q-X217L-X218S, X003V-X166Q-X217L-X248D, X003V-X166Q-X217L-X259P, X003V-X166Q-X218S-X248D, X003V-X166Q-X218S-X259P, X003V-X166Q-X248D-X259P, X003V-X185Q-X210I-X217L, X003V-X185Q-X210I-X218S, X003V-X185Q-X210I-X248D, X003V-X185Q-X210I-X259P, X003V-X185Q-X217L-X218S, X003V-X185Q-X217L-X248D, X003V-X185Q-X217L-X259P, X003V-X185Q-X218S-X248D, X003V-X185Q-X218S-X259P, X003V-X185Q-X248D-X259P, X003V-X210I-X217L-X218S, X003V-X210I-X217L-X248D, X003V-X210I-X217L-X259P, X003V-X210I-X218S-X248D, X003V-X210I-X218S-X259P, X003V-X210I-X248D-X259P, X003V-X217L-X218S-X248D, X003V-X217L-X218S-X259P, X003V-X217L-X248D-X259P, X003V-X218S-X248D-X259P, X009E-X024Q-X040E-X069S, X009E-X024Q-X040E-X076D, X009E-X024Q-X040E-X078N, X009E-X024Q-X040E-X079I, X009E-X024Q-X040E-X087D, X009E-X024Q-X040E-X118R, X009E-X024Q-X040E-X124I, X009E-X024Q-X040E-X128S, X009E-X024Q-X040E-X129P, X009E-X024Q-X040E-X130S, X009E-X024Q-X040E-X145R, X009E-X024Q-X040E-X166Q, X009E-X024Q-X040E-X185Q, X009E-X024Q-X040E-X210I, X009E-X024Q-X040E-X217L, X009E-X024Q-X040E-X218S, X009E-X024Q-X040E-X248D, X009E-X024Q-X040E-X259P, X009E-X024Q-X069S-X076D, X009E-X024Q-X069S-X078N, X009E-X024Q-X069S-X079I, X009E-X024Q-X069S-X087D, X009E-X024Q-X069S-X118R, X009E-X024Q-X069S-X124I, X009E-X024Q-X069S-X128S, X009E-X024Q-X069S-X129P, X009E-X024Q-X069S-X130S, X009E-X024Q-X069S-X145R, X009E-X024Q-X069S-X166Q, X009E-X024Q-X069S-X185Q, X009E-X024Q-X069S-X210I, X009E-X024Q-X069S-X217L, X009E-X024Q-X069S-X218S, X009E-X024Q-X069S-X248D, X009E-X024Q-X069S-X259P, X009E-X024Q-X076D-X078N, X009E-X024Q-X076D-X079I, X009E-X024Q-X076D-X087D, X009E-X024Q-X076D-X118R, X009E-X024Q-X076D-X124I, X009E-X024Q-X076D-X128S, X009E-X024Q-X076D-X129P, X009E-X024Q-X076D-X130S, X009E-X024Q-X076D-X145R, X009E-X024Q-X076D-X166Q, X009E-X024Q-X076D-X185Q, X009E-X024Q-X076D-X210I, X009E-X024Q-X076D-X217L, X009E-X024Q-X076D-X218S, X009E-X024Q-X076D-X248D, X009E-X024Q-X076D-X259P, X009E-X024Q-X078N-X079I, X009E-X024Q-X078N-X087D, X009E-X024Q-X078N-X118R, X009E-X024Q-X078N-X124I, X009E-X024Q-X078N-X128S, X009E-X024Q-X078N-X129P, X009E-X024Q-X078N-X130S, X009E-X024Q-X078N-X145R, X009E-X024Q-X078N-X166Q, X009E-X024Q-X078N-X185Q, X009E-X024Q-X078N-X210I, X009E-X024Q-X078N-X217L, X009E-X024Q-X078N-X218S, X009E-X024Q-X078N-X248D, X009E-X024Q-X078N-X259P, X009E-X024Q-X079I-X087D, X009E-X024Q-X079I-X118R, X009E-X024Q-X079I-X124I, X009E-X024Q-X079I-X128S, X009E-X024Q-X079I-X129P, X009E-X024Q-X079I-X130S, X009E-X024Q-X079I-X145R, X009E-X024Q-X079I-X166Q, X009E-X024Q-X079I-X185Q, X009E-X024Q-X079I-X210I, X009E-X024Q-X079I-X217L, X009E-X024Q-X079I-X218S, X009E-X024Q-X079I-X248D, X009E-X024Q-X079I-X259P, X009E-X024Q-X087D-X118R, X009E-X024Q-X087D-X124I, X009E-X024Q-X087D-X128S, X009E-X024Q-X087D-X129P, X009E-X024Q-X087D-X130S, X009E-X024Q-X087D-X145R, X009E-X024Q-X087D-X166Q, X009E-X024Q-X087D-X185Q, X009E-X024Q-X087D-X210I, X009E-X024Q-X087D-X217L, X009E-X024Q-X087D-X218S, X009E-X024Q-X087D-X248D, X009E-X024Q-X087D-X259P, X009E-X024Q-X118R-X124I, X009E-X024Q-X118R-X128S, X009E-X024Q-X118R-X129P, X009E-X024Q-X118R-X130S, X009E-X024Q-X118R-X145R, X009E-X024Q-X118R-X166Q, X009E-X024Q-X118R-X185Q, X009E-X024Q-X118R-X210I, X009E-X024Q-X118R-X217L, X009E-X024Q-X118R-X218S, X009E-X024Q-X118R-X248D, X009E-X024Q-X118R-X259P, X009E-X024Q-X124I-X128S, X009E-X024Q-X124I-X129P, X009E-X024Q-X124I-X130S, X009E-X024Q-X124I-X145R, X009E-X024Q-X124I-X166Q, X009E-X024Q-X124I-X185Q, X009E-X024Q-X124I-X210I, X009E-X024Q-X124I-X217L, X009E-X024Q-X124I-X218S, X009E-X024Q-X124I-X248D, X009E-X024Q-X124I-X259P, X009E-X024Q-X128S-X129P, X009E-X024Q-X128S-X130S, X009E-X024Q-X128S-X145R, X009E-X024Q-X128S-X166Q, X009E-X024Q-X128S-X185Q, X009E-X024Q-X128S-X210I, X009E-X024Q-X128S-X217L, X009E-X024Q-X128S-X218S, X009E-X024Q-X128S-X248D, X009E-X024Q-X128S-X259P, X009E-X024Q-X129P-X130S, X009E-X024Q-X129P-X145R, X009E-X024Q-X129P-X166Q, X009E-X024Q-X129P-X185Q, X009E-X024Q-X129P-X210I, X009E-X024Q-X129P-X217L, X009E-X024Q-X129P-X218S, X009E-X024Q-X129P-X248D, X009E-X024Q-X129P-X259P, X009E-X024Q-X130S-X145R, X009E-X024Q-X130S-X166Q, X009E-X024Q-X130S-X185Q, X009E-X024Q-X130S-X210I, X009E-X024Q-X130S-X217L, X009E-X024Q-X130S-X218S, X009E-X024Q-X130S-X248D, X009E-X024Q-X130S-X259P, X009E-X024Q-X145R-X166Q, X009E-X024Q-X145R-X185Q, X009E-X024Q-X145R-X210I, X009E-X024Q-X145R-X217L, X009E-X024Q-X145R-X218S, X009E-X024Q-X145R-X248D, X009E-X024Q-X145R-X259P, X009E-X024Q-X166Q-X185Q, X009E-X024Q-X166Q-X210I, X009E-

X024Q-X166Q-X217L, X009E-X024Q-X166Q-X218S, X009E-X024Q-X166Q-X248D, X009E-X024Q-X166Q-X259P, X009E-X024Q-X185Q-X210I, X009E-X024Q-X185Q-X217L, X009E-X024Q-X185Q-X218S, X009E-X024Q-X185Q-X248D, X009E-X024Q-X185Q-X259P, X009E-X024Q-X210I-X217L, X009E-X024Q-X210I-X218S, X009E-X024Q-X210I-X248D, X009E-X024Q-X210I-X259P, X009E-X024Q-X217L-X218S, X009E-X024Q-X217L-X248D, X009E-X024Q-X217L-X259P, X009E-X024Q-X218S-X248D, X009E-X024Q-X218S-X259P, X009E-X024Q-X248D-X259P, X009E-X040E-X069S-X076D, X009E-X040E-X069S-X078N, X009E-X040E-X069S-X079I, X009E-X040E-X069S-X087D, X009E-X040E-X069S-X118R, X009E-X040E-X069S-X124I, X009E-X040E-X069S-X128S, X009E-X040E-X069S-X129P, X009E-X040E-X069S-X130S, X009E-X040E-X069S-X145R, X009E-X040E-X069S-X166Q, X009E-X040E-X069S-X185Q, X009E-X040E-X069S-X210I, X009E-X040E-X069S-X217L, X009E-X040E-X069S-X218S, X009E-X040E-X069S-X248D, X009E-X040E-X069S-X259P, X009E-X040E-X076D-X078N, X009E-X040E-X076D-X079I, X009E-X040E-X076D-X087D, X009E-X040E-X076D-X118R, X009E-X040E-X076D-X124I, X009E-X040E-X076D-X128S, X009E-X040E-X076D-X129P, X009E-X040E-X076D-X130S, X009E-X040E-X076D-X145R, X009E-X040E-X076D-X166Q, X009E-X040E-X076D-X185Q, X009E-X040E-X076D-X210I, X009E-X040E-X076D-X217L, X009E-X040E-X076D-X218S, X009E-X040E-X076D-X248D, X009E-X040E-X076D-X259P, X009E-X040E-X078N-X079I, X009E-X040E-X078N-X087D, X009E-X040E-X078N-X118R, X009E-X040E-X078N-X124I, X009E-X040E-X078N-X128S, X009E-X040E-X078N-X129P, X009E-X040E-X078N-X130S, X009E-X040E-X078N-X145R, X009E-X040E-X078N-X166Q, X009E-X040E-X078N-X185Q, X009E-X040E-X078N-X210I, X009E-X040E-X078N-X217L, X009E-X040E-X078N-X218S, X009E-X040E-X078N-X248D, X009E-X040E-X078N-X259P, X009E-X040E-X079I-X087D, X009E-X040E-X079I-X118R, X009E-X040E-X079I-X124I, X009E-X040E-X079I-X128S, X009E-X040E-X079I-X129P, X009E-X040E-X079I-X130S, X009E-X040E-X079I-X145R, X009E-X040E-X079I-X166Q, X009E-X040E-X079I-X185Q, X009E-X040E-X079I-X210I, X009E-X040E-X079I-X217L, X009E-X040E-X079I-X218S, X009E-X040E-X079I-X248D, X009E-X040E-X079I-X259P, X009E-X040E-X087D-X118R, X009E-X040E-X087D-X124I, X009E-X040E-X087D-X128S, X009E-X040E-X087D-X129P, X009E-X040E-X087D-X130S, X009E-X040E-X087D-X145R, X009E-X040E-X087D-X166Q, X009E-X040E-X087D-X185Q, X009E-X040E-X087D-X210I, X009E-X040E-X087D-X217L, X009E-X040E-X087D-X218S, X009E-X040E-X087D-X248D, X009E-X040E-X087D-X259P, X009E-X040E-X118R-X124I, X009E-X040E-X118R-X128S, X009E-X040E-X118R-X129P, X009E-X040E-X118R-X130S, X009E-X040E-X118R-X145R, X009E-X040E-X118R-X166Q, X009E-X040E-X118R-X185Q, X009E-X040E-X118R-X210I, X009E-X040E-X118R-X217L, X009E-X040E-X118R-X218S, X009E-X040E-X118R-X248D, X009E-X040E-X118R-X259P, X009E-X040E-X124I-X128S, X009E-X040E-X124I-X129P, X009E-X040E-X124I-X130S, X009E-X040E-X124I-X145R, X009E-X040E-X124I-X166Q, X009E-X040E-X124I-X185Q, X009E-X040E-X124I-X210I, X009E-X040E-X124I-X217L, X009E-X040E-X124I-X218S, X009E-X040E-X124I-X248D, X009E-X040E-X124I-X259P, X009E-X040E-X128 S-X129P, X009E-X040E-X128 S-X130S, X009E-X040E-X128 S-X145R, X009E-X040E-X128 S-X166Q, X009E-X040E-X128 S-X185Q, X009E-X040E-X128 S-X210I, X009E-X040E-X128 S-X217L, X009E-X040E-X128 S-X218S, X009E-X040E-X128 S-X248D, X009E-X040E-X128S-X259P, X009E-X040E-X129P-X130S, X009E-X040E-X129P-X145R, X009E-X040E-X129P-X166Q, X009E-X040E-X129P-X185Q, X009E-X040E-X129P-X210I, X009E-X040E-X129P-X217L, X009E-X040E-X129P-X218S, X009E-X040E-X129P-X248D, X009E-X040E-X129P-X259P, X009E-X040E-X130S-X145R, X009E-X040E-X130S-X166Q, X009E-X040E-X130S-X185Q, X009E-X040E-X130S-X210I, X009E-X040E-X130S-X217L, X009E-X040E-X130S-X218S, X009E-X040E-X130S-X248D, X009E-X040E-X130S-X259P, X009E-X040E-X145R-X166Q, X009E-X040E-X145R-X185Q, X009E-X040E-X145R-X210I, X009E-X040E-X145R-X217L, X009E-X040E-X145R-X218S, X009E-X040E-X145R-X248D, X009E-X040E-X145R-X259P, X009E-X040E-X166Q-X185Q, X009E-X040E-X166Q-X210I, X009E-X040E-X166Q-X217L, X009E-X040E-X166Q-X218S, X009E-X040E-X166Q-X248D, X009E-X040E-X166Q-X259P, X009E-X040E-X185Q-X210I, X009E-X040E-X185Q-X217L, X009E-X040E-X185Q-X218S, X009E-X040E-X185Q-X248D, X009E-X040E-X185Q-X259P, X009E-X040E-X210I-X217L, X009E-X040E-X210I-X218S, X009E-X040E-X210I-X248D, X009E-X040E-X210I-X259P, X009E-X040E-X217L-X218S, X009E-X040E-X217L-X248D, X009E-X040E-X217L-X259P, X009E-X040E-X218 S-X248D, X009E-X040E-X218 S-X259P, X009E-X040E-X248D-X259P, X009E-X069S-X076D-X078N, X009E-X069S-X076D-X079I, X009E-X069S-X076D-X087D, X009E-X069S-X076D-X118R, X009E-X069S-X076D-X124I, X009E-X069S-X076D-X128S, X009E-X069S-X076D-X129P, X009E-X069S-X076D-X130S, X009E-X069S-X076D-X145R, X009E-X069S-X076D-X166Q, X009E-X069S-X076D-X185Q, X009E-X069S-X076D-X210I, X009E-X069S-X076D-X217L, X009E-X069S-X076D-X218S, X009E-X069S-X076D-X248D, X009E-X069S-X076D-X259P, X009E-X069S-X078N-X079I, X009E-X069S-X078N-X087D, X009E-X069S-X078N-X118R, X009E-X069S-X078N-X124I, X009E-X069S-X078N-X128S, X009E-X069S-X078N-X129P, X009E-X069S-X078N-X130S, X009E-X069S-X078N-X145R, X009E-X069S-X078N-X166Q, X009E-X069S-X078N-X185Q, X009E-X069S-X078N-X210I, X009E-X069S-X078N-X217L, X009E-X069S-X078N-X218S, X009E-X069S-X078N-X248D, X009E-X069S-X078N-X259P, X009E-X069S-X079I-X087D, X009E-X069S-X079I-X118R, X009E-X069S-X079I-X124I, X009E-X069S-X079I-X128S, X009E-X069S-X079I-X129P, X009E-X069S-X079I-X130S, X009E-X069S-X079I-X145R, X009E-X069S-X079I-X166Q, X009E-X069S-X079I-X185Q, X009E-X069S-X079I-X210I, X009E-X069S-X079I-X217L, X009E-X069S-X079I-X218S, X009E-X069S-X079I-X248D, X009E-X069S-X079I-X259P, X009E-X069S-X087D-X118R, X009E-X069S-X087D-X124I, X009E-X069S-X087D-X128S, X009E-X069S-X087D-X129P, X009E-X069S-X087D-X130S, X009E-X069S-X087D-X145R, X009E-X069S-X087D-X166Q, X009E-X069S-X087D-X185Q, X009E-X069S-X087D-X210I, X009E-X069S-X087D-X217L, X009E-X069S-X087D-X218S, X009E-X069S-X087D-X248D, X009E-X069S-X087D-X259P, X009E-X069S-X118R-X124I, X009E-X069S-X118R-X128S, X009E-X069S-X118R-X129P, X009E-X069S-X118R-X130S, X009E-X069S-X118R-

X145R, X009E-X069S-X118R-X166Q, X009E-X069S-X118R-X185Q, X009E-X069S-X118R-X210I, X009E-X069S-X118R-X217L, X009E-X069S-X118R-X218S, X009E-X069S-X118R-X248D, X009E-X069S-X118R-X259P, X009E-X069S-X124I-X128S, X009E-X069S-X124I-X129P, X009E-X069S-X124I-X130S, X009E-X069S-X124I-X145R, X009E-X069S-X124I-X166Q, X009E-X069S-X124I-X185Q, X009E-X069S-X124I-X210I, X009E-X069S-X124I-X217L, X009E-X069S-X124I-X218S, X009E-X069S-X124I-X248D, X009E-X069S-X124I-X259P, X009E-X069S-X128S-X129P, X009E-X069S-X128S-X130S, X009E-X069S-X128S-X145R, X009E-X069S-X128S-X166Q, X009E-X069S-X128S-X185Q, X009E-X069S-X128S-X210I, X009E-X069S-X128S-X217L, X009E-X069S-X128S-X218S, X009E-X069S-X128S-X248D, X009E-X069S-X128S-X259P, X009E-X069S-X129P-X130S, X009E-X069S-X129P-X145R, X009E-X069S-X129P-X166Q, X009E-X069S-X129P-X185Q, X009E-X069S-X129P-X210I, X009E-X069S-X129P-X217L, X009E-X069S-X129P-X218S, X009E-X069S-X129P-X248D, X009E-X069S-X129P-X259P, X009E-X069S-X130S-X145R, X009E-X069S-X130S-X166Q, X009E-X069S-X130S-X185Q, X009E-X069S-X130S-X210I, X009E-X069S-X130S-X217L, X009E-X069S-X130S-X218S, X009E-X069S-X130S-X248D, X009E-X069S-X130S-X259P, X009E-X069S-X145R-X166Q, X009E-X069S-X145R-X185Q, X009E-X069S-X145R-X210I, X009E-X069S-X145R-X217L, X009E-X069S-X145R-X218S, X009E-X069S-X145R-X248D, X009E-X069S-X145R-X259P, X009E-X069S-X166Q-X185Q, X009E-X069S-X166Q-X210I, X009E-X069S-X166Q-X217L, X009E-X069S-X166Q-X218S, X009E-X069S-X166Q-X248D, X009E-X069S-X166Q-X259P, X009E-X069S-X185Q-X210I, X009E-X069S-X185Q-X217L, X009E-X069S-X185Q-X218S, X009E-X069S-X185Q-X248D, X009E-X069S-X185Q-X259P, X009E-X069S-X210I-X217L, X009E-X069S-X210I-X218S, X009E-X069S-X210I-X248D, X009E-X069S-X210I-X259P, X009E-X069S-X217L-X218S, X009E-X069S-X217L-X248D, X009E-X069S-X217L-X259P, X009E-X069S-X218S-X248D, X009E-X069S-X218S-X259P, X009E-X069S-X248D-X259P, X009E-X076D-X078N-X079I, X009E-X076D-X078N-X087D, X009E-X076D-X078N-X118R, X009E-X076D-X078N-X124I, X009E-X076D-X078N-X128S, X009E-X076D-X078N-X129P, X009E-X076D-X078N-X130S, X009E-X076D-X078N-X145R, X009E-X076D-X078N-X166Q, X009E-X076D-X078N-X185Q, X009E-X076D-X078N-X210I, X009E-X076D-X078N-X217L, X009E-X076D-X078N-X218S, X009E-X076D-X078N-X248D, X009E-X076D-X078N-X259P, X009E-X076D-X079I-X087D, X009E-X076D-X079I-X118R, X009E-X076D-X079I-X124I, X009E-X076D-X079I-X128S, X009E-X076D-X079I-X129P, X009E-X076D-X079I-X130S, X009E-X076D-X079I-X145R, X009E-X076D-X079I-X166Q, X009E-X076D-X079I-X185Q, X009E-X076D-X079I-X210I, X009E-X076D-X079I-X217L, X009E-X076D-X079I-X218S, X009E-X076D-X079I-X248D, X009E-X076D-X079I-X259P, X009E-X076D-X087D-X118R, X009E-X076D-X087D-X124I, X009E-X076D-X087D-X128S, X009E-X076D-X087D-X129P, X009E-X076D-X087D-X130S, X009E-X076D-X087D-X145R, X009E-X076D-X087D-X166Q, X009E-X076D-X087D-X185Q, X009E-X076D-X087D-X210I, X009E-X076D-X087D-X217L, X009E-X076D-X087D-X218S, X009E-X076D-X087D-X248D, X009E-X076D-X087D-X259P, X009E-X076D-X118R-X124I, X009E-X076D-X118R-X128S, X009E-X076D-X118R-X129P, X009E-X076D-X118R-X130S, X009E-X076D-X118R-X145R, X009E-X076D-X118R-X166Q, X009E-X076D-X118R-X185Q, X009E-X076D-X118R-X210I, X009E-X076D-X118R-X217L, X009E-X076D-X118R-X218S, X009E-X076D-X118R-X248D, X009E-X076D-X118R-X259P, X009E-X076D-X124I-X128S, X009E-X076D-X124I-X129P, X009E-X076D-X124I-X130S, X009E-X076D-X124I-X145R, X009E-X076D-X124I-X166Q, X009E-X076D-X124I-X185Q, X009E-X076D-X124I-X210I, X009E-X076D-X124I-X217L, X009E-X076D-X124I-X218S, X009E-X076D-X124I-X248D, X009E-X076D-X124I-X259P, X009E-X076D-X128S-X129P, X009E-X076D-X128S-X130S, X009E-X076D-X128S-X145R, X009E-X076D-X128S-X166Q, X009E-X076D-X128S-X185Q, X009E-X076D-X128S-X210I, X009E-X076D-X128S-X217L, X009E-X076D-X128S-X218S, X009E-X076D-X128S-X248D, X009E-X076D-X128S-X259P, X009E-X076D-X129P-X130S, X009E-X076D-X129P-X145R, X009E-X076D-X129P-X166Q, X009E-X076D-X129P-X185Q, X009E-X076D-X129P-X210I, X009E-X076D-X129P-X217L, X009E-X076D-X129P-X218S, X009E-X076D-X129P-X248D, X009E-X076D-X129P-X259P, X009E-X076D-X130S-X145R, X009E-X076D-X130S-X166Q, X009E-X076D-X130S-X185Q, X009E-X076D-X130S-X210I, X009E-X076D-X130S-X217L, X009E-X076D-X130S-X218S, X009E-X076D-X130S-X248D, X009E-X076D-X130S-X259P, X009E-X076D-X145R-X166Q, X009E-X076D-X145R-X185Q, X009E-X076D-X145R-X210I, X009E-X076D-X145R-X217L, X009E-X076D-X145R-X218S, X009E-X076D-X145R-X248D, X009E-X076D-X145R-X259P, X009E-X076D-X166Q-X185Q, X009E-X076D-X166Q-X210I, X009E-X076D-X166Q-X217L, X009E-X076D-X166Q-X218S, X009E-X076D-X166Q-X248D, X009E-X076D-X166Q-X259P, X009E-X076D-X185Q-X210I, X009E-X076D-X185Q-X217L, X009E-X076D-X185Q-X218S, X009E-X076D-X185Q-X248D, X009E-X076D-X185Q-X259P, X009E-X076D-X210I-X217L, X009E-X076D-X210I-X218S, X009E-X076D-X210I-X248D, X009E-X076D-X210I-X259P, X009E-X076D-X217L-X218S, X009E-X076D-X217L-X248D, X009E-X076D-X217L-X259P, X009E-X076D-X218S-X248D, X009E-X076D-X218S-X259P, X009E-X076D-X248D-X259P, X009E-X078N-X079I-X087D, X009E-X078N-X079I-X118R, X009E-X078N-X079I-X124I, X009E-X078N-X079I-X128S, X009E-X078N-X079I-X129P, X009E-X078N-X079I-X130S, X009E-X078N-X079I-X145R, X009E-X078N-X079I-X166Q, X009E-X078N-X079I-X185Q, X009E-X078N-X079I-X210I, X009E-X078N-X079I-X217L, X009E-X078N-X079I-X218S, X009E-X078N-X079I-X248D, X009E-X078N-X079I-X259P, X009E-X078N-X087D-X118R, X009E-X078N-X087D-X124I, X009E-X078N-X087D-X128S, X009E-X078N-X087D-X129P, X009E-X078N-X087D-X130S, X009E-X078N-X087D-X145R, X009E-X078N-X087D-X166Q, X009E-X078N-X087D-X185Q, X009E-X078N-X087D-X210I, X009E-X078N-X087D-X217L, X009E-X078N-X087D-X218S, X009E-X078N-X087D-X248D, X009E-X078N-X087D-X259P, X009E-X078N-X118R-X124I, X009E-X078N-X118R-X128S, X009E-X078N-X118R-X129P, X009E-X078N-X118R-X130S, X009E-X078N-X118R-X145R, X009E-X078N-X118R-X166Q, X009E-X078N-X118R-X185Q, X009E-X078N-X118R-X210I, X009E-X078N-X118R-X217L, X009E-X078N-X118R-X218S, X009E-X078N-X118R-X248D, X009E-X078N-X118R-X259P, X009E-X078N-X124I-X128S, X009E-X078N-X124I-X129P, X009E-

X078N-X124I-X130S, X009E-X078N-X124I-X145R, X009E-X078N-X124I-X166Q, X009E-X078N-X124I-X185Q, X009E-X078N-X124I-X210I, X009E-X078N-X124I-X217L, X009E-X078N-X124I-X218S, X009E-X078N-X124I-X248D, X009E-X078N-X124I-X259P, X009E-X078N-X128S-X129P, X009E-X078N-X128S-X130S, X009E-X078N-X128S-X145R, X009E-X078N-X128S-X166Q, X009E-X078N-X128S-X185Q, X009E-X078N-X128S-X210I, X009E-X078N-X128S-X217L, X009E-X078N-X128S-X218S, X009E-X078N-X128S-X248D, X009E-X078N-X128S-X259P, X009E-X078N-X129P-X130S, X009E-X078N-X129P-X145R, X009E-X078N-X129P-X166Q, X009E-X078N-X129P-X185Q, X009E-X078N-X129P-X210I, X009E-X078N-X129P-X217L, X009E-X078N-X129P-X218S, X009E-X078N-X129P-X248D, X009E-X078N-X129P-X259P, X009E-X078N-X130S-X145R, X009E-X078N-X130S-X166Q, X009E-X078N-X130S-X185Q, X009E-X078N-X130S-X210I, X009E-X078N-X130S-X217L, X009E-X078N-X130S-X218S, X009E-X078N-X130S-X248D, X009E-X078N-X130S-X259P, X009E-X078N-X145R-X166Q, X009E-X078N-X145R-X185Q, X009E-X078N-X145R-X210I, X009E-X078N-X145R-X217L, X009E-X078N-X145R-X218S, X009E-X078N-X145R-X248D, X009E-X078N-X145R-X259P, X009E-X078N-X166Q-X185Q, X009E-X078N-X166Q-X210I, X009E-X078N-X166Q-X217L, X009E-X078N-X166Q-X218S, X009E-X078N-X166Q-X248D, X009E-X078N-X166Q-X259P, X009E-X078N-X185Q-X210I, X009E-X078N-X185Q-X217L, X009E-X078N-X185Q-X218S, X009E-X078N-X185Q-X248D, X009E-X078N-X185Q-X259P, X009E-X078N-X210I-X217L, X009E-X078N-X210I-X218S, X009E-X078N-X210I-X248D, X009E-X078N-X210I-X259P, X009E-X078N-X217L-X218S, X009E-X078N-X217L-X248D, X009E-X078N-X217L-X259P, X009E-X078N-X218S-X248D, X009E-X078N-X218S-X259P, X009E-X078N-X248D-X259P, X009E-X079I-X087D-X118R, X009E-X079I-X087D-X124I, X009E-X079I-X087D-X128S, X009E-X079I-X087D-X129P, X009E-X079I-X087D-X130S, X009E-X079I-X087D-X145R, X009E-X079I-X087D-X166Q, X009E-X079I-X087D-X185Q, X009E-X079I-X087D-X210I, X009E-X079I-X087D-X217L, X009E-X079I-X087D-X218S, X009E-X079I-X087D-X248D, X009E-X079I-X087D-X259P, X009E-X079I-X118R-X124I, X009E-X079I-X118R-X128S, X009E-X079I-X118R-X129P, X009E-X079I-X118R-X130S, X009E-X079I-X118R-X145R, X009E-X079I-X118R-X166Q, X009E-X079I-X118R-X185Q, X009E-X079I-X118R-X210I, X009E-X079I-X118R-X217L, X009E-X079I-X118R-X218S, X009E-X079I-X118R-X248D, X009E-X079I-X118R-X259P, X009E-X079I-X124I-X128S, X009E-X079I-X124I-X129P, X009E-X079I-X124I-X130S, X009E-X079I-X124I-X145R, X009E-X079I-X124I-X166Q, X009E-X079I-X124I-X185Q, X009E-X079I-X124I-X210I, X009E-X079I-X124I-X217L, X009E-X079I-X124I-X218S, X009E-X079I-X124I-X248D, X009E-X079I-X124I-X259P, X009E-X079I-X128S-X129P, X009E-X079I-X128S-X130S, X009E-X079I-X128S-X145R, X009E-X079I-X128S-X166Q, X009E-X079I-X128S-X185Q, X009E-X079I-X128S-X210I, X009E-X079I-X128S-X217L, X009E-X079I-X128S-X218S, X009E-X079I-X128S-X248D, X009E-X079I-X128S-X259P, X009E-X079I-X129P-X130S, X009E-X079I-X129P-X145R, X009E-X079I-X129P-X166Q, X009E-X079I-X129P-X185Q, X009E-X079I-X129P-X210I, X009E-X079I-X129P-X217L, X009E-X079I-X129P-X218S, X009E-X079I-X129P-X248D, X009E-X079I-X129P-X259P, X009E-X079I-X130S-X145R, X009E-X079I-X130S-X166Q, X009E-X079I-X130S-X185Q, X009E-X079I-X130S-X210I, X009E-X079I-X130S-X217L, X009E-X079I-X130S-X218S, X009E-X079I-X130S-X248D, X009E-X079I-X130S-X259P, X009E-X079I-X145R-X166Q, X009E-X079I-X145R-X185Q, X009E-X079I-X145R-X210I, X009E-X079I-X145R-X217L, X009E-X079I-X145R-X218S, X009E-X079I-X145R-X248D, X009E-X079I-X145R-X259P, X009E-X079I-X166Q-X185Q, X009E-X079I-X166Q-X210I, X009E-X079I-X166Q-X217L, X009E-X079I-X166Q-X218S, X009E-X079I-X166Q-X248D, X009E-X079I-X166Q-X259P, X009E-X079I-X185Q-X210I, X009E-X079I-X185Q-X217L, X009E-X079I-X185Q-X218S, X009E-X079I-X185Q-X248D, X009E-X079I-X185Q-X259P, X009E-X079I-X210I-X217L, X009E-X079I-X210I-X218S, X009E-X079I-X210I-X248D, X009E-X079I-X210I-X259P, X009E-X079I-X217L-X218S, X009E-X079I-X217L-X248D, X009E-X079I-X217L-X259P, X009E-X079I-X218S-X248D, X009E-X079I-X218S-X259P, X009E-X079I-X248D-X259P, X009E-X087D-X118R-X124I, X009E-X087D-X118R-X128S, X009E-X087D-X118R-X129P, X009E-X087D-X118R-X130S, X009E-X087D-X118R-X145R, X009E-X087D-X118R-X166Q, X009E-X087D-X118R-X185Q, X009E-X087D-X118R-X210I, X009E-X087D-X118R-X217L, X009E-X087D-X118R-X218S, X009E-X087D-X118R-X248D, X009E-X087D-X118R-X259P, X009E-X087D-X124I-X128S, X009E-X087D-X124I-X129P, X009E-X087D-X124I-X130S, X009E-X087D-X124I-X145R, X009E-X087D-X124I-X166Q, X009E-X087D-X124I-X185Q, X009E-X087D-X124I-X210I, X009E-X087D-X124I-X217L, X009E-X087D-X124I-X218S, X009E-X087D-X124I-X248D, X009E-X087D-X124I-X259P, X009E-X087D-X128S-X129P, X009E-X087D-X128S-X130S, X009E-X087D-X128S-X145R, X009E-X087D-X128S-X166Q, X009E-X087D-X128S-X185Q, X009E-X087D-X128S-X210I, X009E-X087D-X128S-X217L, X009E-X087D-X128S-X218S, X009E-X087D-X128S-X248D, X009E-X087D-X128S-X259P, X009E-X087D-X129P-X130S, X009E-X087D-X129P-X145R, X009E-X087D-X129P-X166Q, X009E-X087D-X129P-X185Q, X009E-X087D-X129P-X210I, X009E-X087D-X129P-X217L, X009E-X087D-X129P-X218S, X009E-X087D-X129P-X248D, X009E-X087D-X129P-X259P, X009E-X087D-X130S-X145R, X009E-X087D-X130S-X166Q, X009E-X087D-X130S-X185Q, X009E-X087D-X130S-X210I, X009E-X087D-X130S-X217L, X009E-X087D-X130S-X218S, X009E-X087D-X130S-X248D, X009E-X087D-X130S-X259P, X009E-X087D-X145R-X166Q, X009E-X087D-X145R-X185Q, X009E-X087D-X145R-X210I, X009E-X087D-X145R-X217L, X009E-X087D-X145R-X218S, X009E-X087D-X145R-X248D, X009E-X087D-X145R-X259P, X009E-X087D-X166Q-X185Q, X009E-X087D-X166Q-X210I, X009E-X087D-X166Q-X217L, X009E-X087D-X166Q-X218S, X009E-X087D-X166Q-X248D, X009E-X087D-X166Q-X259P, X009E-X087D-X185Q-X210I, X009E-X087D-X185Q-X217L, X009E-X087D-X185Q-X218S, X009E-X087D-X185Q-X248D, X009E-X087D-X185Q-X259P, X009E-X087D-X210I-X217L, X009E-X087D-X210I-X218S, X009E-X087D-X210I-X248D, X009E-X087D-X210I-X259P, X009E-X087D-X217L-X218S, X009E-X087D-X217L-X248D, X009E-X087D-X217L-X259P, X009E-X087D-X218S-X248D, X009E-X087D-X218S-X259P, X009E-X087D-X248D-X259P, X009E-X118R-X124I-X128S, X009E-X118R-X124I-

X129P, X009E-X118R-X124I-X130S, X009E-X118R-X124I-X145R, X009E-X118R-X124I-X166Q, X009E-X118R-X124I-X185Q, X009E-X118R-X124I-X210I, X009E-X118R-X124I-X217L, X009E-X118R-X124I-X218S, X009E-X118R-X124I-X248D, X009E-X118R-X124I-X259P, X009E-X118R-X128S-X129P, X009E-X118R-X128S-X130S, X009E-X118R-X128S-X145R, X009E-X118R-X128S-X166Q, X009E-X118R-X128S-X185Q, X009E-X118R-X128S-X210I, X009E-X118R-X128S-X217L, X009E-X118R-X128S-X218S, X009E-X118R-X128S-X248D, X009E-X118R-X128S-X259P, X009E-X118R-X129P-X130S, X009E-X118R-X129P-X145R, X009E-X118R-X129P-X166Q, X009E-X118R-X129P-X185Q, X009E-X118R-X129P-X210I, X009E-X118R-X129P-X217L, X009E-X118R-X129P-X218S, X009E-X118R-X129P-X248D, X009E-X118R-X129P-X259P, X009E-X118R-X130S-X145R, X009E-X118R-X130S-X166Q, X009E-X118R-X130S-X185Q, X009E-X118R-X130S-X210I, X009E-X118R-X130S-X217L, X009E-X118R-X130S-X218S, X009E-X118R-X130S-X248D, X009E-X118R-X130S-X259P, X009E-X118R-X145R-X166Q, X009E-X118R-X145R-X185Q, X009E-X118R-X145R-X210I, X009E-X118R-X145R-X217L, X009E-X118R-X145R-X218S, X009E-X118R-X145R-X248D, X009E-X118R-X145R-X259P, X009E-X118R-X166Q-X185Q, X009E-X118R-X166Q-X210I, X009E-X118R-X166Q-X217L, X009E-X118R-X166Q-X218S, X009E-X118R-X166Q-X248D, X009E-X118R-X166Q-X259P, X009E-X118R-X185Q-X210I, X009E-X118R-X185Q-X217L, X009E-X118R-X185Q-X218S, X009E-X118R-X185Q-X248D, X009E-X118R-X185Q-X259P, X009E-X118R-X210I-X217L, X009E-X118R-X210I-X218S, X009E-X118R-X210I-X248D, X009E-X118R-X210I-X259P, X009E-X118R-X217L-X218S, X009E-X118R-X217L-X248D, X009E-X118R-X217L-X259P, X009E-X118R-X218S-X248D, X009E-X118R-X218S-X259P, X009E-X118R-X248D-X259P, X009E-X124I-X128S-X129P, X009E-X124I-X128S-X130S, X009E-X124I-X128S-X145R, X009E-X124I-X128S-X166Q, X009E-X124I-X128S-X185Q, X009E-X124I-X128S-X210I, X009E-X124I-X128S-X217L, X009E-X124I-X128S-X218S, X009E-X124I-X128S-X248D, X009E-X124I-X128S-X259P, X009E-X124I-X129P-X130S, X009E-X124I-X129P-X145R, X009E-X124I-X129P-X166Q, X009E-X124I-X129P-X185Q, X009E-X124I-X129P-X210I, X009E-X124I-X129P-X217L, X009E-X124I-X129P-X218S, X009E-X124I-X129P-X248D, X009E-X124I-X129P-X259P, X009E-X124I-X130S-X145R, X009E-X124I-X130S-X166Q, X009E-X124I-X130S-X185Q, X009E-X124I-X130S-X210I, X009E-X124I-X130S-X217L, X009E-X124I-X130S-X218S, X009E-X124I-X130S-X248D, X009E-X124I-X130S-X259P, X009E-X124I-X145R-X166Q, X009E-X124I-X145R-X185Q, X009E-X124I-X145R-X210I, X009E-X124I-X145R-X217L, X009E-X124I-X145R-X218S, X009E-X124I-X145R-X248D, X009E-X124I-X145R-X259P, X009E-X124I-X166Q-X185Q, X009E-X124I-X166Q-X210I, X009E-X124I-X166Q-X217L, X009E-X124I-X166Q-X218S, X009E-X124I-X166Q-X248D, X009E-X124I-X166Q-X259P, X009E-X124I-X185Q-X210I, X009E-X124I-X185Q-X217L, X009E-X124I-X185Q-X218S, X009E-X124I-X185Q-X248D, X009E-X124I-X185Q-X259P, X009E-X124I-X210I-X217L, X009E-X124I-X210I-X218S, X009E-X124I-X210I-X248D, X009E-X124I-X210I-X259P, X009E-X124I-X217L-X218S, X009E-X124I-X217L-X248D, X009E-X124I-X217L-X259P, X009E-X124I-X218S-X248D, X009E-X124I-X218S-X259P, X009E-X124I-X248D-X259P, X009E-X128S-X129P-X130S, X009E-X128S-X129P-X145R, X009E-X128S-X129P-X166Q, X009E-X128S-X129P-X185Q, X009E-X128S-X129P-X210I, X009E-X128S-X129P-X217L, X009E-X128S-X129P-X218S, X009E-X128S-X129P-X248D, X009E-X128S-X129P-X259P, X009E-X128S-X130S-X145R, X009E-X128S-X130S-X166Q, X009E-X128S-X130S-X185Q, X009E-X128S-X130S-X210I, X009E-X128S-X130S-X217L, X009E-X128S-X130S-X218S, X009E-X128S-X130S-X248D, X009E-X128S-X130S-X259P, X009E-X128S-X145R-X166Q, X009E-X128S-X145R-X185Q, X009E-X128S-X145R-X210I, X009E-X128S-X145R-X217L, X009E-X128S-X145R-X218S, X009E-X128S-X145R-X248D, X009E-X128S-X145R-X259P, X009E-X128S-X166Q-X185Q, X009E-X128S-X166Q-X210I, X009E-X128S-X166Q-X217L, X009E-X128S-X166Q-X218S, X009E-X128S-X166Q-X248D, X009E-X128S-X166Q-X259P, X009E-X128S-X185Q-X210I, X009E-X128S-X185Q-X217L, X009E-X128S-X185Q-X218S, X009E-X128S-X185Q-X248D, X009E-X128S-X185Q-X259P, X009E-X128S-X210I-X217L, X009E-X128S-X210I-X218S, X009E-X128S-X210I-X248D, X009E-X128S-X210I-X259P, X009E-X128S-X217L-X218S, X009E-X128S-X217L-X248D, X009E-X128S-X217L-X259P, X009E-X128S-X218S-X248D, X009E-X128S-X218S-X259P, X009E-X128S-X248D-X259P, X009E-X129P-X130S-X145R, X009E-X129P-X130S-X166Q, X009E-X129P-X130S-X185Q, X009E-X129P-X130S-X210I, X009E-X129P-X130S-X217L, X009E-X129P-X130S-X218S, X009E-X129P-X130S-X248D, X009E-X129P-X130S-X259P, X009E-X129P-X145R-X166Q, X009E-X129P-X145R-X185Q, X009E-X129P-X145R-X210I, X009E-X129P-X145R-X217L, X009E-X129P-X145R-X218S, X009E-X129P-X145R-X248D, X009E-X129P-X145R-X259P, X009E-X129P-X166Q-X185Q, X009E-X129P-X166Q-X210I, X009E-X129P-X166Q-X217L, X009E-X129P-X166Q-X218S, X009E-X129P-X166Q-X248D, X009E-X129P-X166Q-X259P, X009E-X129P-X185Q-X210I, X009E-X129P-X185Q-X217L, X009E-X129P-X185Q-X218S, X009E-X129P-X185Q-X248D, X009E-X129P-X185Q-X259P, X009E-X129P-X210I-X217L, X009E-X129P-X210I-X218S, X009E-X129P-X210I-X248D, X009E-X129P-X210I-X259P, X009E-X129P-X217L-X218S, X009E-X129P-X217L-X248D, X009E-X129P-X217L-X259P, X009E-X129P-X218S-X248D, X009E-X129P-X218S-X259P, X009E-X129P-X248D-X259P, X009E-X130S-X145R-X166Q, X009E-X130S-X145R-X185Q, X009E-X130S-X145R-X210I, X009E-X130S-X145R-X217L, X009E-X130S-X145R-X218S, X009E-X130S-X145R-X248D, X009E-X130S-X145R-X259P, X009E-X130S-X166Q-X185Q, X009E-X130S-X166Q-X210I, X009E-X130S-X166Q-X217L, X009E-X130S-X166Q-X218S, X009E-X130S-X166Q-X248D, X009E-X130S-X166Q-X259P, X009E-X130S-X185Q-X210I, X009E-X130S-X185Q-X217L, X009E-X130S-X185Q-X218S, X009E-X130S-X185Q-X248D, X009E-X130S-X185Q-X259P, X009E-X130S-X210I-X217L, X009E-X130S-X210I-X218S, X009E-X130S-X210I-X248D, X009E-X130S-X210I-X259P, X009E-X130S-X217L-X218S, X009E-X130S-X217L-X248D, X009E-X130S-X217L-X259P, X009E-X130S-X218S-X248D, X009E-X130S-X218S-X259P, X009E-X130S-X248D-X259P, X009E-X145R-X166Q-X185Q, X009E-X145R-X166Q-X210I, X009E-X145R-X166Q-X217L, X009E-X145R-X166Q-X218S, X009E-X145R-X166Q-X248D, X009E-X145R-X166Q-X259P, X009E-

X145R-X185Q-X210I, X009E-X145R-X185Q-X217L, X009E-X145R-X185Q-X218S, X009E-X145R-X185Q-X248D, X009E-X145R-X185Q-X259P, X009E-X145R-X210I-X217L, X009E-X145R-X210I-X218S, X009E-X145R-X210I-X248D, X009E-X145R-X210I-X259P, X009E-X145R-X217L-X218S, X009E-X145R-X217L-X248D, X009E-X145R-X217L-X259P, X009E-X145R-X218S-X248D, X009E-X145R-X218S-X259P, X009E-X145R-X248D-X259P, X009E-X166Q-X185Q-X210I, X009E-X166Q-X185Q-X217L, X009E-X166Q-X185Q-X218S, X009E-X166Q-X185Q-X248D, X009E-X166Q-X185Q-X259P, X009E-X166Q-X210I-X217L, X009E-X166Q-X210I-X218S, X009E-X166Q-X210I-X248D, X009E-X166Q-X210I-X259P, X009E-X166Q-X217L-X218S, X009E-X166Q-X217L-X248D, X009E-X166Q-X217L-X259P, X009E-X166Q-X218S-X248D, X009E-X166Q-X218S-X259P, X009E-X166Q-X248D-X259P, X009E-X185Q-X210I-X217L, X009E-X185Q-X210I-X218S, X009E-X185Q-X210I-X248D, X009E-X185Q-X210I-X259P, X009E-X185Q-X217L-X218S, X009E-X185Q-X217L-X248D, X009E-X185Q-X217L-X259P, X009E-X185Q-X218S-X248D, X009E-X185Q-X218S-X259P, X009E-X185Q-X248D-X259P, X009E-X210I-X217L-X218S, X009E-X210I-X217L-X248D, X009E-X210I-X217L-X259P, X009E-X210I-X218S-X248D, X009E-X210I-X218S-X259P, X009E-X210I-X248D-X259P, X009E-X217L-X218S-X248D, X009E-X217L-X218S-X259P, X009E-X217L-X248D-X259P, X009E-X218S-X248D-X259P, X024Q-X040E-X069S-X076D, X024Q-X040E-X069S-X078N, X024Q-X040E-X069S-X079I, X024Q-X040E-X069S-X087D, X024Q-X040E-X069S-X118R, X024Q-X040E-X069S-X124I, X024Q-X040E-X069S-X128S, X024Q-X040E-X069S-X129P, X024Q-X040E-X069S-X130S, X024Q-X040E-X069S-X145R, X024Q-X040E-X069S-X166Q, X024Q-X040E-X069S-X185Q, X024Q-X040E-X069S-X210I, X024Q-X040E-X069S-X217L, X024Q-X040E-X069S-X218S, X024Q-X040E-X069S-X248D, X024Q-X040E-X069S-X259P, X024Q-X040E-X076D-X078N, X024Q-X040E-X076D-X079I, X024Q-X040E-X076D-X087D, X024Q-X040E-X076D-X118R, X024Q-X040E-X076D-X124I, X024Q-X040E-X076D-X128S, X024Q-X040E-X076D-X129P, X024Q-X040E-X076D-X130S, X024Q-X040E-X076D-X145R, X024Q-X040E-X076D-X166Q, X024Q-X040E-X076D-X185Q, X024Q-X040E-X076D-X210I, X024Q-X040E-X076D-X217L, X024Q-X040E-X076D-X218S, X024Q-X040E-X076D-X248D, X024Q-X040E-X076D-X259P, X024Q-X040E-X078N-X079I, X024Q-X040E-X078N-X087D, X024Q-X040E-X078N-X118R, X024Q-X040E-X078N-X124I, X024Q-X040E-X078N-X128S, X024Q-X040E-X078N-X129P, X024Q-X040E-X078N-X130S, X024Q-X040E-X078N-X145R, X024Q-X040E-X078N-X166Q, X024Q-X040E-X078N-X185Q, X024Q-X040E-X078N-X210I, X024Q-X040E-X078N-X217L, X024Q-X040E-X078N-X218S, X024Q-X040E-X078N-X248D, X024Q-X040E-X078N-X259P, X024Q-X040E-X079I-X087D, X024Q-X040E-X079I-X118R, X024Q-X040E-X079I-X124I, X024Q-X040E-X079I-X128S, X024Q-X040E-X079I-X129P, X024Q-X040E-X079I-X130S, X024Q-X040E-X079I-X145R, X024Q-X040E-X079I-X166Q, X024Q-X040E-X079I-X185Q, X024Q-X040E-X079I-X210I, X024Q-X040E-X079I-X217L, X024Q-X040E-X079I-X218S, X024Q-X040E-X079I-X248D, X024Q-X040E-X079I-X259P, X024Q-X040E-X087D-X118R, X024Q-X040E-X087D-X124I, X024Q-X040E-X087D-X128S, X024Q-X040E-X087D-X129P, X024Q-X040E-X087D-X130S, X024Q-X040E-X087D-X145R, X024Q-X040E-X087D-X166Q, X024Q-X040E-X087D-X185Q, X024Q-X040E-X087D-X210I, X024Q-X040E-X087D-X217L, X024Q-X040E-X087D-X218S, X024Q-X040E-X087D-X248D, X024Q-X040E-X087D-X259P, X024Q-X040E-X118R-X124I, X024Q-X040E-X118R-X128S, X024Q-X040E-X118R-X129P, X024Q-X040E-X118R-X130S, X024Q-X040E-X118R-X145R, X024Q-X040E-X118R-X166Q, X024Q-X040E-X118R-X185Q, X024Q-X040E-X118R-X210I, X024Q-X040E-X118R-X217L, X024Q-X040E-X118R-X218S, X024Q-X040E-X118R-X248D, X024Q-X040E-X118R-X259P, X024Q-X040E-X124I-X128S, X024Q-X040E-X124I-X129P, X024Q-X040E-X124I-X130S, X024Q-X040E-X124I-X145R, X024Q-X040E-X124I-X166Q, X024Q-X040E-X124I-X185Q, X024Q-X040E-X124I-X210I, X024Q-X040E-X124I-X217L, X024Q-X040E-X124I-X218S, X024Q-X040E-X124I-X248D, X024Q-X040E-X124I-X259P, X024Q-X040E-X128S-X129P, X024Q-X040E-X128S-X130S, X024Q-X040E-X128S-X145R, X024Q-X040E-X128S-X166Q, X024Q-X040E-X128S-X185Q, X024Q-X040E-X128S-X210I, X024Q-X040E-X128S-X217L, X024Q-X040E-X128S-X218S, X024Q-X040E-X128S-X248D, X024Q-X040E-X128S-X259P, X024Q-X040E-X129P-X130S, X024Q-X040E-X129P-X145R, X024Q-X040E-X129P-X166Q, X024Q-X040E-X129P-X185Q, X024Q-X040E-X129P-X210I, X024Q-X040E-X129P-X217L, X024Q-X040E-X129P-X218S, X024Q-X040E-X129P-X248D, X024Q-X040E-X129P-X259P, X024Q-X040E-X130S-X145R, X024Q-X040E-X130S-X166Q, X024Q-X040E-X130S-X185Q, X024Q-X040E-X130S-X210I, X024Q-X040E-X130S-X217L, X024Q-X040E-X130S-X218S, X024Q-X040E-X130S-X248D, X024Q-X040E-X130S-X259P, X024Q-X040E-X145R-X166Q, X024Q-X040E-X145R-X185Q, X024Q-X040E-X145R-X210I, X024Q-X040E-X145R-X217L, X024Q-X040E-X145R-X218S, X024Q-X040E-X145R-X248D, X024Q-X040E-X145R-X259P, X024Q-X040E-X166Q-X185Q, X024Q-X040E-X166Q-X210I, X024Q-X040E-X166Q-X217L, X024Q-X040E-X166Q-X218S, X024Q-X040E-X166Q-X248D, X024Q-X040E-X166Q-X259P, X024Q-X040E-X185Q-X210I, X024Q-X040E-X185Q-X217L, X024Q-X040E-X185Q-X218S, X024Q-X040E-X185Q-X248D, X024Q-X040E-X185Q-X259P, X024Q-X040E-X210I-X217L, X024Q-X040E-X210I-X218S, X024Q-X040E-X210I-X248D, X024Q-X040E-X210I-X259P, X024Q-X040E-X217L-X218S, X024Q-X040E-X217L-X248D, X024Q-X040E-X217L-X259P, X024Q-X040E-X218S-X248D, X024Q-X040E-X218S-X259P, X024Q-X040E-X248D-X259P, X024Q-X069S-X076D-X078N, X024Q-X069S-X076D-X079I, X024Q-X069S-X076D-X087D, X024Q-X069S-X076D-X118R, X024Q-X069S-X076D-X124I, X024Q-X069S-X076D-X128S, X024Q-X069S-X076D-X129P, X024Q-X069S-X076D-X130S, X024Q-X069S-X076D-X145R, X024Q-X069S-X076D-X166Q, X024Q-X069S-X076D-X185Q, X024Q-X069S-X076D-X210I, X024Q-X069S-X076D-X217L, X024Q-X069S-X076D-X218S, X024Q-X069S-X076D-X248D, X024Q-X069S-X076D-X259P, X024Q-X069S-X078N-X079I, X024Q-X069S-X078N-X087D, X024Q-X069S-X078N-X118R, X024Q-X069S-X078N-X124I, X024Q-X069S-X078N-X128S, X024Q-X069S-X078N-X129P, X024Q-X069S-X078N-X130S, X024Q-X069S-X078N-X145R, X024Q-X069S-X078N-X166Q, X024Q-X069S-X078N-X185Q, X024Q-X069S-X078N-X210I, X024Q-X069S-X078N-X217L, X024Q-X069S-X078N-X218S, X024Q-X069S-X078N-X248D, X024Q-X069S-X078N-X259P, X024Q-X069S-X079I-

X087D, X024Q-X069S-X079I-X118R, X024Q-X069S-X079I-X124I, X024Q-X069S-X079I-X128S, X024Q-X069S-X079I-X129P, X024Q-X069S-X079I-X130S, X024Q-X069S-X079I-X145R, X024Q-X069S-X079I-X166Q, X024Q-X069S-X079I-X185Q, X024Q-X069S-X079I-X210I, X024Q-X069S-X079I-X217L, X024Q-X069S-X079I-X218S, X024Q-X069S-X079I-X248D, X024Q-X069S-X079I-X259P, X024Q-X069S-X087D-X118R, X024Q-X069S-X087D-X124I, X024Q-X069S-X087D-X128S, X024Q-X069S-X087D-X129P, X024Q-X069S-X087D-X130S, X024Q-X069S-X087D-X145R, X024Q-X069S-X087D-X166Q, X024Q-X069S-X087D-X185Q, X024Q-X069S-X087D-X210I, X024Q-X069S-X087D-X217L, X024Q-X069S-X087D-X218S, X024Q-X069S-X087D-X248D, X024Q-X069S-X087D-X259P, X024Q-X069S-X118R-X124I, X024Q-X069S-X118R-X128S, X024Q-X069S-X118R-X129P, X024Q-X069S-X118R-X130S, X024Q-X069S-X118R-X145R, X024Q-X069S-X118R-X166Q, X024Q-X069S-X118R-X185Q, X024Q-X069S-X118R-X210I, X024Q-X069S-X118R-X217L, X024Q-X069S-X118R-X218S, X024Q-X069S-X118R-X248D, X024Q-X069S-X118R-X259P, X024Q-X069S-X124I-X128S, X024Q-X069S-X124I-X129P, X024Q-X069S-X124I-X130S, X024Q-X069S-X124I-X145R, X024Q-X069S-X124I-X166Q, X024Q-X069S-X124I-X185Q, X024Q-X069S-X124I-X210I, X024Q-X069S-X124I-X217L, X024Q-X069S-X124I-X218S, X024Q-X069S-X124I-X248D, X024Q-X069S-X124I-X259P, X024Q-X069S-X128S-X129P, X024Q-X069S-X128S-X130S, X024Q-X069S-X128S-X145R, X024Q-X069S-X128S-X166Q, X024Q-X069S-X128S-X185Q, X024Q-X069S-X128S-X210I, X024Q-X069S-X128S-X217L, X024Q-X069S-X128S-X218S, X024Q-X069S-X128S-X248D, X024Q-X069S-X128S-X259P, X024Q-X069S-X129P-X130S, X024Q-X069S-X129P-X145R, X024Q-X069S-X129P-X166Q, X024Q-X069S-X129P-X185Q, X024Q-X069S-X129P-X210I, X024Q-X069S-X129P-X217L, X024Q-X069S-X129P-X218S, X024Q-X069S-X129P-X248D, X024Q-X069S-X129P-X259P, X024Q-X069S-X130S-X145R, X024Q-X069S-X130S-X166Q, X024Q-X069S-X130S-X185Q, X024Q-X069S-X130S-X210I, X024Q-X069S-X130S-X217L, X024Q-X069S-X130S-X218S, X024Q-X069S-X130S-X248D, X024Q-X069S-X130S-X259P, X024Q-X069S-X145R-X166Q, X024Q-X069S-X145R-X185Q, X024Q-X069S-X145R-X210I, X024Q-X069S-X145R-X217L, X024Q-X069S-X145R-X218S, X024Q-X069S-X145R-X248D, X024Q-X069S-X145R-X259P, X024Q-X069S-X166Q-X185Q, X024Q-X069S-X166Q-X210I, X024Q-X069S-X166Q-X217L, X024Q-X069S-X166Q-X218S, X024Q-X069S-X166Q-X248D, X024Q-X069S-X166Q-X259P, X024Q-X069S-X185Q-X210I, X024Q-X069S-X185Q-X217L, X024Q-X069S-X185Q-X218S, X024Q-X069S-X185Q-X248D, X024Q-X069S-X185Q-X259P, X024Q-X069S-X210I-X217L, X024Q-X069S-X210I-X218S, X024Q-X069S-X210I-X248D, X024Q-X069S-X210I-X259P, X024Q-X069S-X217L-X218S, X024Q-X069S-X217L-X248D, X024Q-X069S-X217L-X259P, X024Q-X069S-X218S-X248D, X024Q-X069S-X218S-X259P, X024Q-X069S-X248D-X259P, X024Q-X076D-X078N-X079I, X024Q-X076D-X078N-X087D, X024Q-X076D-X078N-X118R, X024Q-X076D-X078N-X124I, X024Q-X076D-X078N-X128S, X024Q-X076D-X078N-X129P, X024Q-X076D-X078N-X130S, X024Q-X076D-X078N-X145R, X024Q-X076D-X078N-X166Q, X024Q-X076D-X078N-X185Q, X024Q-X076D-X078N-X210I, X024Q-X076D-X078N-X217L, X024Q-X076D-X078N-X218S, X024Q-X076D-X078N-X248D, X024Q-X076D-X078N-X259P, X024Q-X076D-X079I-X087D, X024Q-X076D-X079I-X118R, X024Q-X076D-X079I-X124I, X024Q-X076D-X079I-X128S, X024Q-X076D-X079I-X129P, X024Q-X076D-X079I-X130S, X024Q-X076D-X079I-X145R, X024Q-X076D-X079I-X166Q, X024Q-X076D-X079I-X185Q, X024Q-X076D-X079I-X210I, X024Q-X076D-X079I-X217L, X024Q-X076D-X079I-X218S, X024Q-X076D-X079I-X248D, X024Q-X076D-X079I-X259P, X024Q-X076D-X087D-X118R, X024Q-X076D-X087D-X124I, X024Q-X076D-X087D-X128S, X024Q-X076D-X087D-X129P, X024Q-X076D-X087D-X130S, X024Q-X076D-X087D-X145R, X024Q-X076D-X087D-X166Q, X024Q-X076D-X087D-X185Q, X024Q-X076D-X087D-X210I, X024Q-X076D-X087D-X217L, X024Q-X076D-X087D-X218S, X024Q-X076D-X087D-X248D, X024Q-X076D-X087D-X259P, X024Q-X076D-X118R-X124I, X024Q-X076D-X118R-X128S, X024Q-X076D-X118R-X129P, X024Q-X076D-X118R-X130S, X024Q-X076D-X118R-X145R, X024Q-X076D-X118R-X166Q, X024Q-X076D-X118R-X185Q, X024Q-X076D-X118R-X210I, X024Q-X076D-X118R-X217L, X024Q-X076D-X118R-X218S, X024Q-X076D-X118R-X248D, X024Q-X076D-X118R-X259P, X024Q-X076D-X124I-X128S, X024Q-X076D-X124I-X129P, X024Q-X076D-X124I-X130S, X024Q-X076D-X124I-X145R, X024Q-X076D-X124I-X166Q, X024Q-X076D-X124I-X185Q, X024Q-X076D-X124I-X210I, X024Q-X076D-X124I-X217L, X024Q-X076D-X124I-X218S, X024Q-X076D-X124I-X248D, X024Q-X076D-X124I-X259P, X024Q-X076D-X128S-X129P, X024Q-X076D-X128S-X130S, X024Q-X076D-X128S-X145R, X024Q-X076D-X128S-X166Q, X024Q-X076D-X128S-X185Q, X024Q-X076D-X128S-X210I, X024Q-X076D-X128S-X217L, X024Q-X076D-X128S-X218S, X024Q-X076D-X128S-X248D, X024Q-X076D-X128S-X259P, X024Q-X076D-X129P-X130S, X024Q-X076D-X129P-X145R, X024Q-X076D-X129P-X166Q, X024Q-X076D-X129P-X185Q, X024Q-X076D-X129P-X210I, X024Q-X076D-X129P-X217L, X024Q-X076D-X129P-X218S, X024Q-X076D-X129P-X248D, X024Q-X076D-X129P-X259P, X024Q-X076D-X130S-X145R, X024Q-X076D-X130S-X166Q, X024Q-X076D-X130S-X185Q, X024Q-X076D-X130S-X210I, X024Q-X076D-X130S-X217L, X024Q-X076D-X130S-X218S, X024Q-X076D-X130S-X248D, X024Q-X076D-X130S-X259P, X024Q-X076D-X145R-X166Q, X024Q-X076D-X145R-X185Q, X024Q-X076D-X145R-X210I, X024Q-X076D-X145R-X217L, X024Q-X076D-X145R-X218S, X024Q-X076D-X145R-X248D, X024Q-X076D-X145R-X259P, X024Q-X076D-X166Q-X185Q, X024Q-X076D-X166Q-X210I, X024Q-X076D-X166Q-X217L, X024Q-X076D-X166Q-X218S, X024Q-X076D-X166Q-X248D, X024Q-X076D-X166Q-X259P, X024Q-X076D-X185Q-X210I, X024Q-X076D-X185Q-X217L, X024Q-X076D-X185Q-X218S, X024Q-X076D-X185Q-X248D, X024Q-X076D-X185Q-X259P, X024Q-X076D-X210I-X217L, X024Q-X076D-X210I-X218S, X024Q-X076D-X210I-X248D, X024Q-X076D-X210I-X259P, X024Q-X076D-X217L-X218S, X024Q-X076D-X217L-X248D, X024Q-X076D-X217L-X259P, X024Q-X076D-X218S-X248D, X024Q-X076D-X218S-X259P, X024Q-X076D-X248D-X259P, X024Q-X078N-X079I-X087D, X024Q-X078N-X079I-X118R, X024Q-X078N-X079I-X124I, X024Q-X078N-X079I-X128S, X024Q-X078N-X079I-X129P, X024Q-X078N-X079I-X130S, X024Q-X078N-X079I-X145R, X024Q-X078N-X079I-X166Q, X024Q-X078N-X079I-X185Q, X024Q-X078N-X079I-X210I, X024Q-

X078N-X079I-X217L, X024Q-X078N-X079I-X218S, X024Q-X078N-X079I-X248D, X024Q-X078N-X079I-X259P, X024Q-X078N-X087D-X118R, X024Q-X078N-X087D-X124I, X024Q-X078N-X087D-X128S, X024Q-X078N-X087D-X129P, X024Q-X078N-X087D-X130S, X024Q-X078N-X087D-X145R, X024Q-X078N-X087D-X166Q, X024Q-X078N-X087D-X185Q, X024Q-X078N-X087D-X210I, X024Q-X078N-X087D-X217L, X024Q-X078N-X087D-X218S, X024Q-X078N-X087D-X248D, X024Q-X078N-X087D-X259P, X024Q-X078N-X118R-X124I, X024Q-X078N-X118R-X128S, X024Q-X078N-X118R-X129P, X024Q-X078N-X118R-X130S, X024Q-X078N-X118R-X145R, X024Q-X078N-X118R-X166Q, X024Q-X078N-X118R-X185Q, X024Q-X078N-X118R-X210I, X024Q-X078N-X118R-X217L, X024Q-X078N-X118R-X218S, X024Q-X078N-X118R-X248D, X024Q-X078N-X118R-X259P, X024Q-X078N-X124I-X128S, X024Q-X078N-X124I-X129P, X024Q-X078N-X124I-X130S, X024Q-X078N-X124I-X145R, X024Q-X078N-X124I-X166Q, X024Q-X078N-X124I-X185Q, X024Q-X078N-X124I-X210I, X024Q-X078N-X124I-X217L, X024Q-X078N-X124I-X218S, X024Q-X078N-X124I-X248D, X024Q-X078N-X124I-X259P, X024Q-X078N-X128S-X129P, X024Q-X078N-X128S-X130S, X024Q-X078N-X128S-X145R, X024Q-X078N-X128S-X166Q, X024Q-X078N-X128S-X185Q, X024Q-X078N-X128S-X210I, X024Q-X078N-X128S-X217L, X024Q-X078N-X128S-X218S, X024Q-X078N-X128S-X248D, X024Q-X078N-X128S-X259P, X024Q-X078N-X129P-X130S, X024Q-X078N-X129P-X145R, X024Q-X078N-X129P-X166Q, X024Q-X078N-X129P-X185Q, X024Q-X078N-X129P-X210I, X024Q-X078N-X129P-X217L, X024Q-X078N-X129P-X218S, X024Q-X078N-X129P-X248D, X024Q-X078N-X129P-X259P, X024Q-X078N-X130S-X145R, X024Q-X078N-X130S-X166Q, X024Q-X078N-X130S-X185Q, X024Q-X078N-X130S-X210I, X024Q-X078N-X130S-X217L, X024Q-X078N-X130S-X218S, X024Q-X078N-X130S-X248D, X024Q-X078N-X130S-X259P, X024Q-X078N-X145R-X166Q, X024Q-X078N-X145R-X185Q, X024Q-X078N-X145R-X210I, X024Q-X078N-X145R-X217L, X024Q-X078N-X145R-X218S, X024Q-X078N-X145R-X248D, X024Q-X078N-X145R-X259P, X024Q-X078N-X166Q-X185Q, X024Q-X078N-X166Q-X210I, X024Q-X078N-X166Q-X217L, X024Q-X078N-X166Q-X218S, X024Q-X078N-X166Q-X248D, X024Q-X078N-X166Q-X259P, X024Q-X078N-X185Q-X210I, X024Q-X078N-X185Q-X217L, X024Q-X078N-X185Q-X218S, X024Q-X078N-X185Q-X248D, X024Q-X078N-X185Q-X259P, X024Q-X078N-X210I-X217L, X024Q-X078N-X210I-X218S, X024Q-X078N-X210I-X248D, X024Q-X078N-X210I-X259P, X024Q-X078N-X217L-X218S, X024Q-X078N-X217L-X248D, X024Q-X078N-X217L-X259P, X024Q-X078N-X218S-X248D, X024Q-X078N-X218S-X259P, X024Q-X078N-X248D-X259P, X024Q-X079I-X087D-X118R, X024Q-X079I-X087D-X124I, X024Q-X079I-X087D-X128S, X024Q-X079I-X087D-X129P, X024Q-X079I-X087D-X130S, X024Q-X079I-X087D-X145R, X024Q-X079I-X087D-X166Q, X024Q-X079I-X087D-X185Q, X024Q-X079I-X087D-X210I, X024Q-X079I-X087D-X217L, X024Q-X079I-X087D-X218S, X024Q-X079I-X087D-X248D, X024Q-X079I-X087D-X259P, X024Q-X079I-X118R-X124I, X024Q-X079I-X118R-X128S, X024Q-X079I-X118R-X129P, X024Q-X079I-X118R-X130S, X024Q-X079I-X118R-X145R, X024Q-X079I-X118R-X166Q, X024Q-X079I-X118R-X185Q, X024Q-X079I-X118R-X210I, X024Q-X079I-X118R-X217L, X024Q-X079I-X118R-X218S, X024Q-X079I-X118R-X248D, X024Q-X079I-X118R-X259P, X024Q-X079I-X124I-X128S, X024Q-X079I-X124I-X129P, X024Q-X079I-X124I-X130S, X024Q-X079I-X124I-X145R, X024Q-X079I-X124I-X166Q, X024Q-X079I-X124I-X185Q, X024Q-X079I-X124I-X210I, X024Q-X079I-X124I-X217L, X024Q-X079I-X124I-X218S, X024Q-X079I-X124I-X248D, X024Q-X079I-X124I-X259P, X024Q-X079I-X128S-X129P, X024Q-X079I-X128S-X130S, X024Q-X079I-X128S-X145R, X024Q-X079I-X128S-X166Q, X024Q-X079I-X128S-X185Q, X024Q-X079I-X128S-X210I, X024Q-X079I-X128S-X217L, X024Q-X079I-X128S-X218S, X024Q-X079I-X128S-X248D, X024Q-X079I-X128S-X259P, X024Q-X079I-X129P-X130S, X024Q-X079I-X129P-X145R, X024Q-X079I-X129P-X166Q, X024Q-X079I-X129P-X185Q, X024Q-X079I-X129P-X210I, X024Q-X079I-X129P-X217L, X024Q-X079I-X129P-X218S, X024Q-X079I-X129P-X248D, X024Q-X079I-X129P-X259P, X024Q-X079I-X130S-X145R, X024Q-X079I-X130S-X166Q, X024Q-X079I-X130S-X185Q, X024Q-X079I-X130S-X210I, X024Q-X079I-X130S-X217L, X024Q-X079I-X130S-X218S, X024Q-X079I-X130S-X248D, X024Q-X079I-X130S-X259P, X024Q-X079I-X145R-X166Q, X024Q-X079I-X145R-X185Q, X024Q-X079I-X145R-X210I, X024Q-X079I-X145R-X217L, X024Q-X079I-X145R-X218S, X024Q-X079I-X145R-X248D, X024Q-X079I-X145R-X259P, X024Q-X079I-X166Q-X185Q, X024Q-X079I-X166Q-X210I, X024Q-X079I-X166Q-X217L, X024Q-X079I-X166Q-X218S, X024Q-X079I-X166Q-X248D, X024Q-X079I-X166Q-X259P, X024Q-X079I-X185Q-X210I, X024Q-X079I-X185Q-X217L, X024Q-X079I-X185Q-X218S, X024Q-X079I-X185Q-X248D, X024Q-X079I-X185Q-X259P, X024Q-X079I-X210I-X217L, X024Q-X079I-X210I-X218S, X024Q-X079I-X210I-X248D, X024Q-X079I-X210I-X259P, X024Q-X079I-X217L-X218S, X024Q-X079I-X217L-X248D, X024Q-X079I-X217L-X259P, X024Q-X079I-X218S-X248D, X024Q-X079I-X218S-X259P, X024Q-X079I-X248D-X259P, X024Q-X087D-X118R-X124I, X024Q-X087D-X118R-X128S, X024Q-X087D-X118R-X129P, X024Q-X087D-X118R-X130S, X024Q-X087D-X118R-X145R, X024Q-X087D-X118R-X166Q, X024Q-X087D-X118R-X185Q, X024Q-X087D-X118R-X210I, X024Q-X087D-X118R-X217L, X024Q-X087D-X118R-X218S, X024Q-X087D-X118R-X248D, X024Q-X087D-X118R-X259P, X024Q-X087D-X124I-X128S, X024Q-X087D-X124I-X129P, X024Q-X087D-X124I-X130S, X024Q-X087D-X124I-X145R, X024Q-X087D-X124I-X166Q, X024Q-X087D-X124I-X185Q, X024Q-X087D-X124I-X210I, X024Q-X087D-X124I-X217L, X024Q-X087D-X124I-X218S, X024Q-X087D-X124I-X248D, X024Q-X087D-X124I-X259P, X024Q-X087D-X128S-X129P, X024Q-X087D-X128S-X130S, X024Q-X087D-X128S-X145R, X024Q-X087D-X128S-X166Q, X024Q-X087D-X128S-X185Q, X024Q-X087D-X128S-X210I, X024Q-X087D-X128S-X217L, X024Q-X087D-X128S-X218S, X024Q-X087D-X128S-X248D, X024Q-X087D-X128S-X259P, X024Q-X087D-X129P-X130S, X024Q-X087D-X129P-X145R, X024Q-X087D-X129P-X166Q, X024Q-X087D-X129P-X185Q, X024Q-X087D-X129P-X210I, X024Q-X087D-X129P-X217L, X024Q-X087D-X129P-X218S, X024Q-X087D-X129P-X248D, X024Q-X087D-X129P-X259P, X024Q-X087D-X130S-X145R, X024Q-X087D-X130S-X166Q, X024Q-X087D-X130S-X185Q, X024Q-X087D-X130S-X210I, X024Q-X087D-X130S-X217L, X024Q-X087D-X130S-X218S, X024Q-X087D-X130S-

X248D, X024Q-X087D-X130S-X259P, X024Q-X087D-X145R-X166Q, X024Q-X087D-X145R-X185Q, X024Q-X087D-X145R-X210I, X024Q-X087D-X145R-X217L, X024Q-X087D-X145R-X218S, X024Q-X087D-X145R-X248D, X024Q-X087D-X145R-X259P, X024Q-X087D-X166Q-X185Q, X024Q-X087D-X166Q-X210I, X024Q-X087D-X166Q-X217L, X024Q-X087D-X166Q-X218S, X024Q-X087D-X166Q-X248D, X024Q-X087D-X166Q-X259P, X024Q-X087D-X185Q-X210I, X024Q-X087D-X185Q-X217L, X024Q-X087D-X185Q-X218S, X024Q-X087D-X185Q-X248D, X024Q-X087D-X185Q-X259P, X024Q-X087D-X210I-X217L, X024Q-X087D-X210I-X218S, X024Q-X087D-X210I-X248D, X024Q-X087D-X210I-X259P, X024Q-X087D-X217L-X218S, X024Q-X087D-X217L-X248D, X024Q-X087D-X217L-X259P, X024Q-X087D-X218S-X248D, X024Q-X087D-X218S-X259P, X024Q-X087D-X248D-X259P, X024Q-X118R-X124I-X128S, X024Q-X118R-X124I-X129P, X024Q-X118R-X124I-X130S, X024Q-X118R-X124I-X145R, X024Q-X118R-X124I-X166Q, X024Q-X118R-X124I-X185Q, X024Q-X118R-X124I-X210I, X024Q-X118R-X124I-X217L, X024Q-X118R-X124I-X218S, X024Q-X118R-X124I-X248D, X024Q-X118R-X124I-X259P, X024Q-X118R-X128S-X129P, X024Q-X118R-X128S-X130S, X024Q-X118R-X128S-X145R, X024Q-X118R-X128S-X166Q, X024Q-X118R-X128S-X185Q, X024Q-X118R-X128S-X210I, X024Q-X118R-X128S-X217L, X024Q-X118R-X128S-X218S, X024Q-X118R-X128S-X248D, X024Q-X118R-X128S-X259P, X024Q-X118R-X129P-X130S, X024Q-X118R-X129P-X145R, X024Q-X118R-X129P-X166Q, X024Q-X118R-X129P-X185Q, X024Q-X118R-X129P-X210I, X024Q-X118R-X129P-X217L, X024Q-X118R-X129P-X218S, X024Q-X118R-X129P-X248D, X024Q-X118R-X129P-X259P, X024Q-X118R-X130S-X145R, X024Q-X118R-X130S-X166Q, X024Q-X118R-X130S-X185Q, X024Q-X118R-X130S-X210I, X024Q-X118R-X130S-X217L, X024Q-X118R-X130S-X218S, X024Q-X118R-X130S-X248D, X024Q-X118R-X130S-X259P, X024Q-X118R-X145R-X166Q, X024Q-X118R-X145R-X185Q, X024Q-X118R-X145R-X210I, X024Q-X118R-X145R-X217L, X024Q-X118R-X145R-X218S, X024Q-X118R-X145R-X248D, X024Q-X118R-X145R-X259P, X024Q-X118R-X166Q-X185Q, X024Q-X118R-X166Q-X210I, X024Q-X118R-X166Q-X217L, X024Q-X118R-X166Q-X218S, X024Q-X118R-X166Q-X248D, X024Q-X118R-X166Q-X259P, X024Q-X118R-X185Q-X210I, X024Q-X118R-X185Q-X217L, X024Q-X118R-X185Q-X218S, X024Q-X118R-X185Q-X248D, X024Q-X118R-X185Q-X259P, X024Q-X118R-X210I-X217L, X024Q-X118R-X210I-X218S, X024Q-X118R-X210I-X248D, X024Q-X118R-X210I-X259P, X024Q-X118R-X217L-X218S, X024Q-X118R-X217L-X248D, X024Q-X118R-X217L-X259P, X024Q-X118R-X218S-X248D, X024Q-X118R-X218S-X259P, X024Q-X118R-X248D-X259P, X024Q-X124I-X128S-X129P, X024Q-X124I-X128S-X130S, X024Q-X124I-X128S-X145R, X024Q-X124I-X128S-X166Q, X024Q-X124I-X128S-X185Q, X024Q-X124I-X128S-X210I, X024Q-X124I-X128S-X217L, X024Q-X124I-X128S-X218S, X024Q-X124I-X128S-X248D, X024Q-X124I-X128S-X259P, X024Q-X124I-X129P-X130S, X024Q-X124I-X129P-X145R, X024Q-X124I-X129P-X166Q, X024Q-X124I-X129P-X185Q, X024Q-X124I-X129P-X210I, X024Q-X124I-X129P-X217L, X024Q-X124I-X129P-X218S, X024Q-X124I-X129P-X248D, X024Q-X124I-X129P-X259P, X024Q-X124I-X130S-X145R, X024Q-X124I-X130S-X166Q, X024Q-X124I-X130S-X185Q, X024Q-X124I-X130S-X210I, X024Q-X124I-X130S-X217L, X024Q-X124I-X130S-X218S, X024Q-X124I-X130S-X248D, X024Q-X124I-X130S-X259P, X024Q-X124I-X145R-X166Q, X024Q-X124I-X145R-X185Q, X024Q-X124I-X145R-X210I, X024Q-X124I-X145R-X217L, X024Q-X124I-X145R-X218S, X024Q-X124I-X145R-X248D, X024Q-X124I-X145R-X259P, X024Q-X124I-X166Q-X185Q, X024Q-X124I-X166Q-X210I, X024Q-X124I-X166Q-X217L, X024Q-X124I-X166Q-X218S, X024Q-X124I-X166Q-X248D, X024Q-X124I-X166Q-X259P, X024Q-X124I-X185Q-X210I, X024Q-X124I-X185Q-X217L, X024Q-X124I-X185Q-X218S, X024Q-X124I-X185Q-X248D, X024Q-X124I-X185Q-X259P, X024Q-X124I-X210I-X217L, X024Q-X124I-X210I-X218S, X024Q-X124I-X210I-X248D, X024Q-X124I-X210I-X259P, X024Q-X124I-X217L-X218S, X024Q-X124I-X217L-X248D, X024Q-X124I-X217L-X259P, X024Q-X124I-X218S-X248D, X024Q-X124I-X218S-X259P, X024Q-X124I-X248D-X259P, X024Q-X128S-X129P-X130S, X024Q-X128S-X129P-X145R, X024Q-X128S-X129P-X166Q, X024Q-X128S-X129P-X185Q, X024Q-X128S-X129P-X210I, X024Q-X128S-X129P-X217L, X024Q-X128S-X129P-X218S, X024Q-X128S-X129P-X248D, X024Q-X128S-X129P-X259P, X024Q-X128S-X130S-X145R, X024Q-X128S-X130S-X166Q, X024Q-X128S-X130S-X185Q, X024Q-X128S-X130S-X210I, X024Q-X128S-X130S-X217L, X024Q-X128S-X130S-X218S, X024Q-X128S-X130S-X248D, X024Q-X128S-X130S-X259P, X024Q-X128S-X145R-X166Q, X024Q-X128S-X145R-X185Q, X024Q-X128S-X145R-X210I, X024Q-X128S-X145R-X217L, X024Q-X128S-X145R-X218S, X024Q-X128S-X145R-X248D, X024Q-X128S-X145R-X259P, X024Q-X128S-X166Q-X185Q, X024Q-X128S-X166Q-X210I, X024Q-X128S-X166Q-X217L, X024Q-X128S-X166Q-X218S, X024Q-X128S-X166Q-X248D, X024Q-X128S-X166Q-X259P, X024Q-X128S-X185Q-X210I, X024Q-X128S-X185Q-X217L, X024Q-X128S-X185Q-X218S, X024Q-X128S-X185Q-X248D, X024Q-X128S-X185Q-X259P, X024Q-X128S-X210I-X217L, X024Q-X128S-X210I-X218S, X024Q-X128S-X210I-X248D, X024Q-X128S-X210I-X259P, X024Q-X128S-X217L-X218S, X024Q-X128S-X217L-X248D, X024Q-X128S-X217L-X259P, X024Q-X128S-X218S-X248D, X024Q-X128S-X218S-X259P, X024Q-X128S-X248D-X259P, X024Q-X129P-X130S-X145R, X024Q-X129P-X130S-X166Q, X024Q-X129P-X130S-X185Q, X024Q-X129P-X130S-X210I, X024Q-X129P-X130S-X217L, X024Q-X129P-X130S-X218S, X024Q-X129P-X130S-X248D, X024Q-X129P-X130S-X259P, X024Q-X129P-X145R-X166Q, X024Q-X129P-X145R-X185Q, X024Q-X129P-X145R-X210I, X024Q-X129P-X145R-X217L, X024Q-X129P-X145R-X218S, X024Q-X129P-X145R-X248D, X024Q-X129P-X145R-X259P, X024Q-X129P-X166Q-X185Q, X024Q-X129P-X166Q-X210I, X024Q-X129P-X166Q-X217L, X024Q-X129P-X166Q-X218S, X024Q-X129P-X166Q-X248D, X024Q-X129P-X166Q-X259P, X024Q-X129P-X185Q-X210I, X024Q-X129P-X185Q-X217L, X024Q-X129P-X185Q-X218S, X024Q-X129P-X185Q-X248D, X024Q-X129P-X185Q-X259P, X024Q-X129P-X210I-X217L, X024Q-X129P-X210I-X218S, X024Q-X129P-X210I-X248D, X024Q-X129P-X210I-X259P, X024Q-X129P-X217L-X218S, X024Q-X129P-X217L-X248D, X024Q-X129P-X217L-X259P, X024Q-X129P-X218S-X248D, X024Q-X129P-X218S-X259P, X024Q-X129P-X248D-X259P, X024Q-X130S-X145R-X166Q, X024Q-X130S-X145R-X185Q, X024Q-X130S-X145R-X210I, X024Q-

X130S-X145R-X217L, X024Q-X130S-X145R-X218S, X024Q-X130S-X145R-X248D, X024Q-X130S-X145R-X259P, X024Q-X130S-X166Q-X185Q, X024Q-X130S-X166Q-X210I, X024Q-X130S-X166Q-X217L, X024Q-X130S-X166Q-X218S, X024Q-X130S-X166Q-X248D, X024Q-X130S-X166Q-X259P, X024Q-X130S-X185Q-X210I, X024Q-X130S-X185Q-X217L, X024Q-X130S-X185Q-X218S, X024Q-X130S-X185Q-X248D, X024Q-X130S-X185Q-X259P, X024Q-X130S-X210I-X217L, X024Q-X130S-X210I-X218S, X024Q-X130S-X210I-X248D, X024Q-X130S-X210I-X259P, X024Q-X130S-X217L-X218S, X024Q-X130S-X217L-X248D, X024Q-X130S-X217L-X259P, X024Q-X130S-X218S-X248D, X024Q-X130S-X218S-X259P, X024Q-X130S-X248D-X259P, X024Q-X145R-X166Q-X185Q, X024Q-X145R-X166Q-X210I, X024Q-X145R-X166Q-X217L, X024Q-X145R-X166Q-X218S, X024Q-X145R-X166Q-X248D, X024Q-X145R-X166Q-X259P, X024Q-X145R-X185Q-X210I, X024Q-X145R-X185Q-X217L, X024Q-X145R-X185Q-X218S, X024Q-X145R-X185Q-X248D, X024Q-X145R-X185Q-X259P, X024Q-X145R-X210I-X217L, X024Q-X145R-X210I-X218S, X024Q-X145R-X210I-X248D, X024Q-X145R-X210I-X259P, X024Q-X145R-X217L-X218S, X024Q-X145R-X217L-X248D, X024Q-X145R-X217L-X259P, X024Q-X145R-X218S-X248D, X024Q-X145R-X218S-X259P, X024Q-X145R-X248D-X259P, X024Q-X166Q-X185Q-X210I, X024Q-X166Q-X185Q-X217L, X024Q-X166Q-X185Q-X218S, X024Q-X166Q-X185Q-X248D, X024Q-X166Q-X185Q-X259P, X024Q-X166Q-X210I-X217L, X024Q-X166Q-X210I-X218S, X024Q-X166Q-X210I-X248D, X024Q-X166Q-X210I-X259P, X024Q-X166Q-X217L-X218S, X024Q-X166Q-X217L-X248D, X024Q-X166Q-X217L-X259P, X024Q-X166Q-X218S-X248D, X024Q-X166Q-X218S-X259P, X024Q-X166Q-X248D-X259P, X024Q-X185Q-X210I-X217L, X024Q-X185Q-X210I-X218S, X024Q-X185Q-X210I-X248D, X024Q-X185Q-X210I-X259P, X024Q-X185Q-X217L-X218S, X024Q-X185Q-X217L-X248D, X024Q-X185Q-X217L-X259P, X024Q-X185Q-X218S-X248D, X024Q-X185Q-X218S-X259P, X024Q-X185Q-X248D-X259P, X024Q-X210I-X217L-X218S, X024Q-X210I-X217L-X248D, X024Q-X210I-X217L-X259P, X024Q-X210I-X218S-X248D, X024Q-X210I-X218S-X259P, X024Q-X210I-X248D-X259P, X024Q-X217L-X218S-X248D, X024Q-X217L-X218S-X259P, X024Q-X217L-X248D-X259P, X024Q-X218S-X248D-X259P, X040E-X069S-X076D-X078N, X040E-X069S-X076D-X079I, X040E-X069S-X076D-X087D, X040E-X069S-X076D-X118R, X040E-X069S-X076D-X124I, X040E-X069S-X076D-X128S, X040E-X069S-X076D-X129P, X040E-X069S-X076D-X130S, X040E-X069S-X076D-X145R, X040E-X069S-X076D-X166Q, X040E-X069S-X076D-X185Q, X040E-X069S-X076D-X210I, X040E-X069S-X076D-X217L, X040E-X069S-X076D-X218S, X040E-X069S-X076D-X248D, X040E-X069S-X076D-X259P, X040E-X069S-X078N-X079I, X040E-X069S-X078N-X087D, X040E-X069S-X078N-X118R, X040E-X069S-X078N-X124I, X040E-X069S-X078N-X128S, X040E-X069S-X078N-X129P, X040E-X069S-X078N-X130S, X040E-X069S-X078N-X145R, X040E-X069S-X078N-X166Q, X040E-X069S-X078N-X185Q, X040E-X069S-X078N-X210I, X040E-X069S-X078N-X217L, X040E-X069S-X078N-X218S, X040E-X069S-X078N-X248D, X040E-X069S-X078N-X259P, X040E-X069S-X079I-X087D, X040E-X069S-X079I-X118R, X040E-X069S-X079I-X124I, X040E-X069S-X079I-X128S, X040E-X069S-X079I-X129P, X040E-X069S-X079I-X130S, X040E-X069S-X079I-X145R, X040E-X069S-X079I-X166Q, X040E-X069S-X079I-X185Q, X040E-X069S-X079I-X210I, X040E-X069S-X079I-X217L, X040E-X069S-X079I-X218S, X040E-X069S-X079I-X248D, X040E-X069S-X079I-X259P, X040E-X069S-X087D-X118R, X040E-X069S-X087D-X124I, X040E-X069S-X087D-X128S, X040E-X069S-X087D-X129P, X040E-X069S-X087D-X130S, X040E-X069S-X087D-X145R, X040E-X069S-X087D-X166Q, X040E-X069S-X087D-X185Q, X040E-X069S-X087D-X210I, X040E-X069S-X087D-X217L, X040E-X069S-X087D-X218S, X040E-X069S-X087D-X248D, X040E-X069S-X087D-X259P, X040E-X069S-X118R-X124I, X040E-X069S-X118R-X128S, X040E-X069S-X118R-X129P, X040E-X069S-X118R-X130S, X040E-X069S-X118R-X145R, X040E-X069S-X118R-X166Q, X040E-X069S-X118R-X185Q, X040E-X069S-X118R-X210I, X040E-X069S-X118R-X217L, X040E-X069S-X118R-X218S, X040E-X069S-X118R-X248D, X040E-X069S-X118R-X259P, X040E-X069S-X124I-X128S, X040E-X069S-X124I-X129P, X040E-X069S-X124I-X130S, X040E-X069S-X124I-X145R, X040E-X069S-X124I-X166Q, X040E-X069S-X124I-X185Q, X040E-X069S-X124I-X210I, X040E-X069S-X124I-X217L, X040E-X069S-X124I-X218S, X040E-X069S-X124I-X248D, X040E-X069S-X124I-X259P, X040E-X069S-X128S-X129P, X040E-X069S-X128S-X130S, X040E-X069S-X128S-X145R, X040E-X069S-X128S-X166Q, X040E-X069S-X128S-X185Q, X040E-X069S-X128S-X210I, X040E-X069S-X128S-X217L, X040E-X069S-X128S-X218S, X040E-X069S-X128S-X248D, X040E-X069S-X128S-X259P, X040E-X069S-X129P-X130S, X040E-X069S-X129P-X145R, X040E-X069S-X129P-X166Q, X040E-X069S-X129P-X185Q, X040E-X069S-X129P-X210I, X040E-X069S-X129P-X217L, X040E-X069S-X129P-X218S, X040E-X069S-X129P-X248D, X040E-X069S-X129P-X259P, X040E-X069S-X130S-X145R, X040E-X069S-X130S-X166Q, X040E-X069S-X130S-X185Q, X040E-X069S-X130S-X210I, X040E-X069S-X130S-X217L, X040E-X069S-X130S-X218S, X040E-X069S-X130S-X248D, X040E-X069S-X130S-X259P, X040E-X069S-X145R-X166Q, X040E-X069S-X145R-X185Q, X040E-X069S-X145R-X210I, X040E-X069S-X145R-X217L, X040E-X069S-X145R-X218S, X040E-X069S-X145R-X248D, X040E-X069S-X145R-X259P, X040E-X069S-X166Q-X185Q, X040E-X069S-X166Q-X210I, X040E-X069S-X166Q-X217L, X040E-X069S-X166Q-X218S, X040E-X069S-X166Q-X248D, X040E-X069S-X166Q-X259P, X040E-X069S-X185Q-X210I, X040E-X069S-X185Q-X217L, X040E-X069S-X185Q-X218S, X040E-X069S-X185Q-X248D, X040E-X069S-X185Q-X259P, X040E-X069S-X210I-X217L, X040E-X069S-X210I-X218S, X040E-X069S-X210I-X248D, X040E-X069S-X210I-X259P, X040E-X069S-X217L-X218S, X040E-X069S-X217L-X248D, X040E-X069S-X217L-X259P, X040E-X069S-X218S-X248D, X040E-X069S-X218S-X259P, X040E-X069S-X248D-X259P, X040E-X076D-X078N-X079I, X040E-X076D-X078N-X087D, X040E-X076D-X078N-X118R, X040E-X076D-X078N-X124I, X040E-X076D-X078N-X128S, X040E-X076D-X078N-X129P, X040E-X076D-X078N-X130S, X040E-X076D-X078N-X145R, X040E-X076D-X078N-X166Q, X040E-X076D-X078N-X185Q, X040E-X076D-X078N-X210I, X040E-X076D-X078N-X217L, X040E-X076D-X078N-X218S, X040E-X076D-X078N-X248D, X040E-X076D-X078N-X259P, X040E-X076D-X079I-X087D, X040E-X076D-X079I-X118R, X040E-X076D-X079I-

X124I, X040E-X076D-X079I-X128S, X040E-X076D-X079I-X129P, X040E-X076D-X079I-X130S, X040E-X076D-X079I-X145R, X040E-X076D-X079I-X166Q, X040E-X076D-X079I-X185Q, X040E-X076D-X079I-X210I, X040E-X076D-X079I-X217L, X040E-X076D-X079I-X218S, X040E-X076D-X079I-X248D, X040E-X076D-X079I-X259P, X040E-X076D-X087D-X118R, X040E-X076D-X087D-X124I, X040E-X076D-X087D-X128S, X040E-X076D-X087D-X129P, X040E-X076D-X087D-X130S, X040E-X076D-X087D-X145R, X040E-X076D-X087D-X166Q, X040E-X076D-X087D-X185Q, X040E-X076D-X087D-X210I, X040E-X076D-X087D-X217L, X040E-X076D-X087D-X218S, X040E-X076D-X087D-X248D, X040E-X076D-X087D-X259P, X040E-X076D-X118R-X124I, X040E-X076D-X118R-X128S, X040E-X076D-X118R-X129P, X040E-X076D-X118R-X130S, X040E-X076D-X118R-X145R, X040E-X076D-X118R-X166Q, X040E-X076D-X118R-X185Q, X040E-X076D-X118R-X210I, X040E-X076D-X118R-X217L, X040E-X076D-X118R-X218S, X040E-X076D-X118R-X248D, X040E-X076D-X118R-X259P, X040E-X076D-X124I-X128S, X040E-X076D-X124I-X129P, X040E-X076D-X124I-X130S, X040E-X076D-X124I-X145R, X040E-X076D-X124I-X166Q, X040E-X076D-X124I-X185Q, X040E-X076D-X124I-X210I, X040E-X076D-X124I-X217L, X040E-X076D-X124I-X218S, X040E-X076D-X124I-X248D, X040E-X076D-X124I-X259P, X040E-X076D-X128S-X129P, X040E-X076D-X128S-X130S, X040E-X076D-X128S-X145R, X040E-X076D-X128S-X166Q, X040E-X076D-X128S-X185Q, X040E-X076D-X128S-X210I, X040E-X076D-X128S-X217L, X040E-X076D-X128S-X218S, X040E-X076D-X128S-X248D, X040E-X076D-X128S-X259P, X040E-X076D-X129P-X130S, X040E-X076D-X129P-X145R, X040E-X076D-X129P-X166Q, X040E-X076D-X129P-X185Q, X040E-X076D-X129P-X210I, X040E-X076D-X129P-X217L, X040E-X076D-X129P-X218S, X040E-X076D-X129P-X248D, X040E-X076D-X129P-X259P, X040E-X076D-X130S-X145R, X040E-X076D-X130S-X166Q, X040E-X076D-X130S-X185Q, X040E-X076D-X130S-X210I, X040E-X076D-X130S-X217L, X040E-X076D-X130S-X218S, X040E-X076D-X130S-X248D, X040E-X076D-X130S-X259P, X040E-X076D-X145R-X166Q, X040E-X076D-X145R-X185Q, X040E-X076D-X145R-X210I, X040E-X076D-X145R-X217L, X040E-X076D-X145R-X218S, X040E-X076D-X145R-X248D, X040E-X076D-X145R-X259P, X040E-X076D-X166Q-X185Q, X040E-X076D-X166Q-X210I, X040E-X076D-X166Q-X217L, X040E-X076D-X166Q-X218S, X040E-X076D-X166Q-X248D, X040E-X076D-X166Q-X259P, X040E-X076D-X185Q-X210I, X040E-X076D-X185Q-X217L, X040E-X076D-X185Q-X218S, X040E-X076D-X185Q-X248D, X040E-X076D-X185Q-X259P, X040E-X076D-X210I-X217L, X040E-X076D-X210I-X218S, X040E-X076D-X210I-X248D, X040E-X076D-X210I-X259P, X040E-X076D-X217L-X218S, X040E-X076D-X217L-X248D, X040E-X076D-X217L-X259P, X040E-X076D-X218S-X248D, X040E-X076D-X218S-X259P, X040E-X076D-X248D-X259P, X040E-X078N-X079I-X087D, X040E-X078N-X079I-X118R, X040E-X078N-X079I-X124I, X040E-X078N-X079I-X128S, X040E-X078N-X079I-X129P, X040E-X078N-X079I-X130S, X040E-X078N-X079I-X145R, X040E-X078N-X079I-X166Q, X040E-X078N-X079I-X185Q, X040E-X078N-X079I-X210I, X040E-X078N-X079I-X217L, X040E-X078N-X079I-X218S, X040E-X078N-X079I-X248D, X040E-X078N-X079I-X259P, X040E-X078N-X087D-X118R, X040E-X078N-X087D-X124I, X040E-X078N-X087D-X128S, X040E-X078N-X087D-X129P, X040E-X078N-X087D-X130S, X040E-X078N-X087D-X145R, X040E-X078N-X087D-X166Q, X040E-X078N-X087D-X185Q, X040E-X078N-X087D-X210I, X040E-X078N-X087D-X217L, X040E-X078N-X087D-X218S, X040E-X078N-X087D-X248D, X040E-X078N-X087D-X259P, X040E-X078N-X118R-X124I, X040E-X078N-X118R-X128S, X040E-X078N-X118R-X129P, X040E-X078N-X118R-X130S, X040E-X078N-X118R-X145R, X040E-X078N-X118R-X166Q, X040E-X078N-X118R-X185Q, X040E-X078N-X118R-X210I, X040E-X078N-X118R-X217L, X040E-X078N-X118R-X218S, X040E-X078N-X118R-X248D, X040E-X078N-X118R-X259P, X040E-X078N-X124I-X128S, X040E-X078N-X124I-X129P, X040E-X078N-X124I-X130S, X040E-X078N-X124I-X145R, X040E-X078N-X124I-X166Q, X040E-X078N-X124I-X185Q, X040E-X078N-X124I-X210I, X040E-X078N-X124I-X217L, X040E-X078N-X124I-X218S, X040E-X078N-X124I-X248D, X040E-X078N-X124I-X259P, X040E-X078N-X128S-X129P, X040E-X078N-X128S-X130S, X040E-X078N-X128S-X145R, X040E-X078N-X128S-X166Q, X040E-X078N-X128S-X185Q, X040E-X078N-X128S-X210I, X040E-X078N-X128S-X217L, X040E-X078N-X128S-X218S, X040E-X078N-X128S-X248D, X040E-X078N-X128S-X259P, X040E-X078N-X129P-X130S, X040E-X078N-X129P-X145R, X040E-X078N-X129P-X166Q, X040E-X078N-X129P-X185Q, X040E-X078N-X129P-X210I, X040E-X078N-X129P-X217L, X040E-X078N-X129P-X218S, X040E-X078N-X129P-X248D, X040E-X078N-X129P-X259P, X040E-X078N-X130S-X145R, X040E-X078N-X130S-X166Q, X040E-X078N-X130S-X185Q, X040E-X078N-X130S-X210I, X040E-X078N-X130S-X217L, X040E-X078N-X130S-X218S, X040E-X078N-X130S-X248D, X040E-X078N-X130S-X259P, X040E-X078N-X145R-X166Q, X040E-X078N-X145R-X185Q, X040E-X078N-X145R-X210I, X040E-X078N-X145R-X217L, X040E-X078N-X145R-X218S, X040E-X078N-X145R-X248D, X040E-X078N-X145R-X259P, X040E-X078N-X166Q-X185Q, X040E-X078N-X166Q-X210I, X040E-X078N-X166Q-X217L, X040E-X078N-X166Q-X218S, X040E-X078N-X166Q-X248D, X040E-X078N-X166Q-X259P, X040E-X078N-X185Q-X210I, X040E-X078N-X185Q-X217L, X040E-X078N-X185Q-X218S, X040E-X078N-X185Q-X248D, X040E-X078N-X185Q-X259P, X040E-X078N-X210I-X217L, X040E-X078N-X210I-X218S, X040E-X078N-X210I-X248D, X040E-X078N-X210I-X259P, X040E-X078N-X217L-X218S, X040E-X078N-X217L-X248D, X040E-X078N-X217L-X259P, X040E-X078N-X218S-X248D, X040E-X078N-X218S-X259P, X040E-X078N-X248D-X259P, X040E-X079I-X087D-X118R, X040E-X079I-X087D-X124I, X040E-X079I-X087D-X128S, X040E-X079I-X087D-X129P, X040E-X079I-X087D-X130S, X040E-X079I-X087D-X145R, X040E-X079I-X087D-X166Q, X040E-X079I-X087D-X185Q, X040E-X079I-X087D-X210I, X040E-X079I-X087D-X217L, X040E-X079I-X087D-X218S, X040E-X079I-X087D-X248D, X040E-X079I-X087D-X259P, X040E-X079I-X118R-X124I, X040E-X079I-X118R-X128S, X040E-X079I-X118R-X129P, X040E-X079I-X118R-X130S, X040E-X079I-X118R-X145R, X040E-X079I-X118R-X166Q, X040E-X079I-X118R-X185Q, X040E-X079I-X118R-X210I, X040E-X079I-X118R-X217L, X040E-X079I-X118R-X218S, X040E-X079I-X118R-X248D, X040E-X079I-X118R-X259P, X040E-X079I-X124I-X128S, X040E-X079I-X124I-X129P, X040E-

X079I-X124I-X130S, X040E-X079I-X124I-X145R, X040E-X079I-X124I-X166Q, X040E-X079I-X124I-X185Q, X040E-X079I-X124I-X210I, X040E-X079I-X124I-X217L, X040E-X079I-X124I-X218S, X040E-X079I-X124I-X248D, X040E-X079I-X124I-X259P, X040E-X079I-X128S-X129P, X040E-X079I-X128S-X130S, X040E-X079I-X128S-X145R, X040E-X079I-X128S-X166Q, X040E-X079I-X128S-X185Q, X040E-X079I-X128S-X210I, X040E-X079I-X128S-X217L, X040E-X079I-X128S-X218S, X040E-X079I-X128S-X248D, X040E-X079I-X128S-X259P, X040E-X079I-X129P-X130S, X040E-X079I-X129P-X145R, X040E-X079I-X129P-X166Q, X040E-X079I-X129P-X185Q, X040E-X079I-X129P-X210I, X040E-X079I-X129P-X217L, X040E-X079I-X129P-X218S, X040E-X079I-X129P-X248D, X040E-X079I-X129P-X259P, X040E-X079I-X130S-X145R, X040E-X079I-X130S-X166Q, X040E-X079I-X130S-X185Q, X040E-X079I-X130S-X210I, X040E-X079I-X130S-X217L, X040E-X079I-X130S-X218S, X040E-X079I-X130S-X248D, X040E-X079I-X130S-X259P, X040E-X079I-X145R-X166Q, X040E-X079I-X145R-X185Q, X040E-X079I-X145R-X210I, X040E-X079I-X145R-X217L, X040E-X079I-X145R-X218S, X040E-X079I-X145R-X248D, X040E-X079I-X145R-X259P, X040E-X079I-X166Q-X185Q, X040E-X079I-X166Q-X210I, X040E-X079I-X166Q-X217L, X040E-X079I-X166Q-X218S, X040E-X079I-X166Q-X248D, X040E-X079I-X166Q-X259P, X040E-X079I-X185Q-X210I, X040E-X079I-X185Q-X217L, X040E-X079I-X185Q-X218S, X040E-X079I-X185Q-X248D, X040E-X079I-X185Q-X259P, X040E-X079I-X210I-X217L, X040E-X079I-X210I-X218S, X040E-X079I-X210I-X248D, X040E-X079I-X210I-X259P, X040E-X079I-X217L-X218S, X040E-X079I-X217L-X248D, X040E-X079I-X217L-X259P, X040E-X079I-X218S-X248D, X040E-X079I-X218S-X259P, X040E-X079I-X248D-X259P, X040E-X087D-X118R-X124I, X040E-X087D-X118R-X128S, X040E-X087D-X118R-X129P, X040E-X087D-X118R-X130S, X040E-X087D-X118R-X145R, X040E-X087D-X118R-X166Q, X040E-X087D-X118R-X185Q, X040E-X087D-X118R-X210I, X040E-X087D-X118R-X217L, X040E-X087D-X118R-X218S, X040E-X087D-X118R-X248D, X040E-X087D-X118R-X259P, X040E-X087D-X124I-X128S, X040E-X087D-X124I-X129P, X040E-X087D-X124I-X130S, X040E-X087D-X124I-X145R, X040E-X087D-X124I-X166Q, X040E-X087D-X124I-X185Q, X040E-X087D-X124I-X210I, X040E-X087D-X124I-X217L, X040E-X087D-X124I-X218S, X040E-X087D-X124I-X248D, X040E-X087D-X124I-X259P, X040E-X087D-X128S-X129P, X040E-X087D-X128S-X130S, X040E-X087D-X128S-X145R, X040E-X087D-X128S-X166Q, X040E-X087D-X128S-X185Q, X040E-X087D-X128S-X210I, X040E-X087D-X128S-X217L, X040E-X087D-X128S-X218S, X040E-X087D-X128S-X248D, X040E-X087D-X128S-X259P, X040E-X087D-X129P-X130S, X040E-X087D-X129P-X145R, X040E-X087D-X129P-X166Q, X040E-X087D-X129P-X185Q, X040E-X087D-X129P-X210I, X040E-X087D-X129P-X217L, X040E-X087D-X129P-X218S, X040E-X087D-X129P-X248D, X040E-X087D-X129P-X259P, X040E-X087D-X130S-X145R, X040E-X087D-X130S-X166Q, X040E-X087D-X130S-X185Q, X040E-X087D-X130S-X210I, X040E-X087D-X130S-X217L, X040E-X087D-X130S-X218S, X040E-X087D-X130S-X248D, X040E-X087D-X130S-X259P, X040E-X040E-X087D-X145R-X166Q, X040E-X087D-X145R-X185Q, X040E-X087D-X145R-X210I, X040E-X087D-X145R-X217L, X040E-X087D-X145R-X218S, X040E-X087D-X145R-X248D, X040E-X087D-X145R-X259P, X040E-X087D-X166Q-X185Q, X040E-X087D-X166Q-X210I, X040E-X087D-X166Q-X217L, X040E-X087D-X166Q-X218S, X040E-X087D-X166Q-X248D, X040E-X087D-X166Q-X259P, X040E-X087D-X185Q-X210I, X040E-X087D-X185Q-X217L, X040E-X087D-X185Q-X218S, X040E-X087D-X185Q-X248D, X040E-X087D-X185Q-X259P, X040E-X087D-X210I-X217L, X040E-X087D-X210I-X218S, X040E-X087D-X210I-X248D, X040E-X087D-X210I-X259P, X040E-X087D-X217L-X218S, X040E-X087D-X217L-X248D, X040E-X087D-X217L-X259P, X040E-X087D-X218S-X248D, X040E-X087D-X218S-X259P, X040E-X087D-X248D-X259P, X040E-X118R-X124I-X128S, X040E-X118R-X124I-X129P, X040E-X118R-X124I-X130S, X040E-X118R-X124I-X145R, X040E-X118R-X124I-X166Q, X040E-X118R-X124I-X185Q, X040E-X118R-X124I-X210I, X040E-X118R-X124I-X217L, X040E-X118R-X124I-X218S, X040E-X118R-X124I-X248D, X040E-X118R-X124I-X259P, X040E-X118R-X128S-X129P, X040E-X118R-X128S-X130S, X040E-X118R-X128S-X145R, X040E-X118R-X128S-X166Q, X040E-X118R-X128S-X185Q, X040E-X118R-X128S-X210I, X040E-X118R-X128S-X217L, X040E-X118R-X128S-X218S, X040E-X118R-X128S-X248D, X040E-X118R-X128S-X259P, X040E-X118R-X129P-X130S, X040E-X118R-X129P-X145R, X040E-X118R-X129P-X166Q, X040E-X118R-X129P-X185Q, X040E-X118R-X129P-X210I, X040E-X118R-X129P-X217L, X040E-X118R-X129P-X218S, X040E-X118R-X129P-X248D, X040E-X118R-X129P-X259P, X040E-X118R-X130S-X145R, X040E-X118R-X130S-X166Q, X040E-X118R-X130S-X185Q, X040E-X118R-X130S-X210I, X040E-X118R-X130S-X217L, X040E-X118R-X130S-X218S, X040E-X118R-X130S-X248D, X040E-X118R-X130S-X259P, X040E-X118R-X145R-X166Q, X040E-X118R-X145R-X185Q, X040E-X118R-X145R-X210I, X040E-X118R-X145R-X217L, X040E-X118R-X145R-X218S, X040E-X118R-X145R-X248D, X040E-X118R-X145R-X259P, X040E-X118R-X166Q-X185Q, X040E-X118R-X166Q-X210I, X040E-X118R-X166Q-X217L, X040E-X118R-X166Q-X218S, X040E-X118R-X166Q-X248D, X040E-X118R-X166Q-X259P, X040E-X118R-X185Q-X210I, X040E-X118R-X185Q-X217L, X040E-X118R-X185Q-X218S, X040E-X118R-X185Q-X248D, X040E-X118R-X185Q-X259P, X040E-X118R-X210I-X217L, X040E-X118R-X210I-X218S, X040E-X118R-X210I-X248D, X040E-X118R-X210I-X259P, X040E-X118R-X217L-X218S, X040E-X118R-X217L-X248D, X040E-X118R-X217L-X259P, X040E-X118R-X218S-X248D, X040E-X118R-X218S-X259P, X040E-X118R-X248D-X259P, X040E-X124I-X128S-X129P, X040E-X124I-X128S-X130S, X040E-X124I-X128S-X145R, X040E-X124I-X128S-X166Q, X040E-X124I-X128S-X185Q, X040E-X124I-X128S-X210I, X040E-X124I-X128S-X217L, X040E-X124I-X128S-X218S, X040E-X124I-X128S-X248D, X040E-X124I-X128S-X259P, X040E-X124I-X129P-X130S, X040E-X124I-X129P-X145R, X040E-X124I-X129P-X166Q, X040E-X124I-X129P-X185Q, X040E-X124I-X129P-X210I, X040E-X124I-X129P-X217L, X040E-X124I-X129P-X218S, X040E-X124I-X129P-X248D, X040E-X124I-X129P-X259P, X040E-X124I-X130S-X145R, X040E-X124I-X130S-X166Q, X040E-X124I-X130S-X185Q, X040E-X124I-X130S-X210I, X040E-X124I-X130S-X217L, X040E-X124I-X130S-X218S, X040E-X124I-X130S-X248D, X040E-X124I-X130S-

X259P, X040E-X124I-X145R-X166Q, X040E-X124I-X145R-X185Q, X040E-X124I-X145R-X210I, X040E-X124I-X145R-X217L, X040E-X124I-X145R-X218S, X040E-X124I-X145R-X248D, X040E-X124I-X145R-X259P, X040E-X124I-X166Q-X185Q, X040E-X124I-X166Q-X210I, X040E-X124I-X166Q-X217L, X040E-X124I-X166Q-X218S, X040E-X124I-X166Q-X248D, X040E-X124I-X166Q-X259P, X040E-X124I-X185Q-X210I, X040E-X124I-X185Q-X217L, X040E-X124I-X185Q-X218S, X040E-X124I-X185Q-X248D, X040E-X124I-X185Q-X259P, X040E-X124I-X210I-X217L, X040E-X124I-X210I-X218S, X040E-X124I-X210I-X248D, X040E-X124I-X210I-X259P, X040E-X124I-X217L-X218S, X040E-X124I-X217L-X248D, X040E-X124I-X217L-X259P, X040E-X124I-X218S-X248D, X040E-X124I-X218S-X259P, X040E-X124I-X248D-X259P, X040E-X128S-X129P-X130S, X040E-X128S-X129P-X145R, X040E-X128S-X129P-X166Q, X040E-X128S-X129P-X185Q, X040E-X128S-X129P-X210I, X040E-X128S-X129P-X217L, X040E-X128S-X129P-X218S, X040E-X128S-X129P-X248D, X040E-X128S-X129P-X259P, X040E-X128S-X130S-X145R, X040E-X128S-X130S-X166Q, X040E-X128S-X130S-X185Q, X040E-X128S-X130S-X210I, X040E-X128S-X130S-X217L, X040E-X128S-X130S-X218S, X040E-X128S-X130S-X248D, X040E-X128S-X130S-X259P, X040E-X128S-X145R-X166Q, X040E-X128S-X145R-X185Q, X040E-X128S-X145R-X210I, X040E-X128S-X145R-X217L, X040E-X128S-X145R-X218S, X040E-X128S-X145R-X248D, X040E-X128S-X145R-X259P, X040E-X128S-X166Q-X185Q, X040E-X128S-X166Q-X210I, X040E-X128S-X166Q-X217L, X040E-X128S-X166Q-X218S, X040E-X128S-X166Q-X248D, X040E-X128S-X166Q-X259P, X040E-X128S-X185Q-X210I, X040E-X128S-X185Q-X217L, X040E-X128S-X185Q-X218S, X040E-X128S-X185Q-X248D, X040E-X128S-X185Q-X259P, X040E-X128S-X210I-X217L, X040E-X128S-X210I-X218S, X040E-X128S-X210I-X248D, X040E-X128S-X210I-X259P, X040E-X128S-X217L-X218S, X040E-X128S-X217L-X248D, X040E-X128S-X217L-X259P, X040E-X128S-X218S-X248D, X040E-X128S-X218S-X259P, X040E-X128S-X248D-X259P, X040E-X129P-X130S-X145R, X040E-X129P-X130S-X166Q, X040E-X129P-X130S-X185Q, X040E-X129P-X130S-X210I, X040E-X129P-X130S-X217L, X040E-X129P-X130S-X218S, X040E-X129P-X130S-X248D, X040E-X129P-X130S-X259P, X040E-X129P-X145R-X166Q, X040E-X129P-X145R-X185Q, X040E-X129P-X145R-X210I, X040E-X129P-X145R-X217L, X040E-X129P-X145R-X218S, X040E-X129P-X145R-X248D, X040E-X129P-X145R-X259P, X040E-X129P-X166Q-X185Q, X040E-X129P-X166Q-X210I, X040E-X129P-X166Q-X217L, X040E-X129P-X166Q-X218S, X040E-X129P-X166Q-X248D, X040E-X129P-X166Q-X259P, X040E-X129P-X185Q-X210I, X040E-X129P-X185Q-X217L, X040E-X129P-X185Q-X218S, X040E-X129P-X185Q-X248D, X040E-X129P-X185Q-X259P, X040E-X129P-X210I-X217L, X040E-X129P-X210I-X218S, X040E-X129P-X210I-X248D, X040E-X129P-X210I-X259P, X040E-X129P-X217L-X218S, X040E-X129P-X217L-X248D, X040E-X129P-X217L-X259P, X040E-X129P-X218S-X248D, X040E-X129P-X218S-X259P, X040E-X129P-X248D-X259P, X040E-X130S-X145R-X166Q, X040E-X130S-X145R-X185Q, X040E-X130S-X145R-X210I, X040E-X130S-X145R-X217L, X040E-X130S-X145R-X218S, X040E-X130S-X145R-X248D, X040E-X130S-X145R-X259P, X040E-X130S-X166Q-X185Q, X040E-X130S-X166Q-X210I, X040E-X130S-X166Q-X217L, X040E-X130S-X166Q-X218S, X040E-X130S-X166Q-X248D, X040E-X130S-X166Q-X259P, X040E-X130S-X185Q-X210I, X040E-X130S-X185Q-X217L, X040E-X130S-X185Q-X218S, X040E-X130S-X185Q-X248D, X040E-X130S-X185Q-X259P, X040E-X130S-X210I-X217L, X040E-X130S-X210I-X218S, X040E-X130S-X210I-X248D, X040E-X130S-X210I-X259P, X040E-X130S-X217L-X218S, X040E-X130S-X217L-X248D, X040E-X130S-X217L-X259P, X040E-X130S-X218S-X248D, X040E-X130S-X218S-X259P, X040E-X130S-X248D-X259P, X040E-X145R-X166Q-X185Q, X040E-X145R-X166Q-X210I, X040E-X145R-X166Q-X217L, X040E-X145R-X166Q-X218S, X040E-X145R-X166Q-X248D, X040E-X145R-X166Q-X259P, X040E-X145R-X185Q-X210I, X040E-X145R-X185Q-X217L, X040E-X145R-X185Q-X218S, X040E-X145R-X185Q-X248D, X040E-X145R-X185Q-X259P, X040E-X145R-X210I-X217L, X040E-X145R-X210I-X218S, X040E-X145R-X210I-X248D, X040E-X145R-X210I-X259P, X040E-X145R-X217L-X218S, X040E-X145R-X217L-X248D, X040E-X145R-X217L-X259P, X040E-X145R-X218S-X248D, X040E-X145R-X218S-X259P, X040E-X145R-X248D-X259P, X040E-X166Q-X185Q-X210I, X040E-X166Q-X185Q-X217L, X040E-X166Q-X185Q-X218S, X040E-X166Q-X185Q-X248D, X040E-X166Q-X185Q-X259P, X040E-X166Q-X210I-X217L, X040E-X166Q-X210I-X218S, X040E-X166Q-X210I-X248D, X040E-X166Q-X210I-X259P, X040E-X166Q-X217L-X218S, X040E-X166Q-X217L-X248D, X040E-X166Q-X217L-X259P, X040E-X166Q-X218S-X248D, X040E-X166Q-X218S-X259P, X040E-X166Q-X248D-X259P, X040E-X185Q-X210I-X217L, X040E-X185Q-X210I-X218S, X040E-X185Q-X210I-X248D, X040E-X185Q-X210I-X259P, X040E-X185Q-X217L-X218S, X040E-X185Q-X217L-X248D, X040E-X185Q-X217L-X259P, X040E-X185Q-X218S-X248D, X040E-X185Q-X218S-X259P, X040E-X185Q-X248D-X259P, X040E-X210I-X217L-X218S, X040E-X210I-X217L-X248D, X040E-X210I-X217L-X259P, X040E-X210I-X218S-X248D, X040E-X210I-X218S-X259P, X040E-X210I-X248D-X259P, X040E-X217L-X218S-X248D, X040E-X217L-X218S-X259P, X040E-X217L-X248D-X259P, X040E-X218S-X248D-X259P, X069S-X076D-X078N-X079I, X069S-X076D-X078N-X087D, X069S-X076D-X078N-X118R, X069S-X076D-X078N-X124I, X069S-X076D-X078N-X128S, X069S-X076D-X078N-X129P, X069S-X076D-X078N-X130S, X069S-X076D-X078N-X145R, X069S-X076D-X078N-X166Q, X069S-X076D-X078N-X185Q, X069S-X076D-X078N-X210I, X069S-X076D-X078N-X217L, X069S-X076D-X078N-X218S, X069S-X076D-X078N-X248D, X069S-X076D-X078N-X259P, X069S-X076D-X079I-X087D, X069S-X076D-X079I-X118R, X069S-X076D-X079I-X124I, X069S-X076D-X079I-X128S, X069S-X076D-X079I-X129P, X069S-X076D-X079I-X130S, X069S-X076D-X079I-X145R, X069S-X076D-X079I-X166Q, X069S-X076D-X079I-X185Q, X069S-X076D-X079I-X210I, X069S-X076D-X079I-X217L, X069S-X076D-X079I-X218S, X069S-X076D-X079I-X248D, X069S-X076D-X079I-X259P, X069S-X076D-X087D-X118R, X069S-X076D-X087D-X124I, X069S-X076D-X087D-X128S, X069S-X076D-X087D-X129P, X069S-X076D-X087D-X130S, X069S-X076D-X087D-X145R, X069S-X076D-X087D-X166Q, X069S-X076D-X087D-X185Q, X069S-X076D-X087D-X210I, X069S-X076D-X087D-X217L, X069S-X076D-X087D-X218S, X069S-X076D-X087D-X248D, X069S-

X076D-X087D-X259P, X069S-X076D-X118R-X124I, X069S-X076D-X118R-X128S, X069S-X076D-X118R-X129P, X069S-X076D-X118R-X130S, X069S-X076D-X118R-X145R, X069S-X076D-X118R-X166Q, X069S-X076D-X118R-X185Q, X069S-X076D-X118R-X210I, X069S-X076D-X118R-X217L, X069S-X076D-X118R-X218S, X069S-X076D-X118R-X248D, X069S-X076D-X118R-X259P, X069S-X076D-X124I-X128S, X069S-X076D-X124I-X129P, X069S-X076D-X124I-X130S, X069S-X076D-X124I-X145R, X069S-X076D-X124I-X166Q, X069S-X076D-X124I-X185Q, X069S-X076D-X124I-X210I, X069S-X076D-X124I-X217L, X069S-X076D-X124I-X218S, X069S-X076D-X124I-X248D, X069S-X076D-X124I-X259P, X069S-X076D-X128S-X129P, X069S-X076D-X128S-X130S, X069S-X076D-X128S-X145R, X069S-X076D-X128S-X166Q, X069S-X076D-X128S-X185Q, X069S-X076D-X128S-X210I, X069S-X076D-X128S-X217L, X069S-X076D-X128S-X218S, X069S-X076D-X128S-X248D, X069S-X076D-X128S-X259P, X069S-X076D-X129P-X130S, X069S-X076D-X129P-X145R, X069S-X076D-X129P-X166Q, X069S-X076D-X129P-X185Q, X069S-X076D-X129P-X210I, X069S-X076D-X129P-X217L, X069S-X076D-X129P-X218S, X069S-X076D-X129P-X248D, X069S-X076D-X129P-X259P, X069S-X076D-X130S-X145R, X069S-X076D-X130S-X166Q, X069S-X076D-X130S-X185Q, X069S-X076D-X130S-X210I, X069S-X076D-X130S-X217L, X069S-X076D-X130S-X218S, X069S-X076D-X130S-X248D, X069S-X076D-X130S-X259P, X069S-X076D-X145R-X166Q, X069S-X076D-X145R-X185Q, X069S-X076D-X145R-X210I, X069S-X076D-X145R-X217L, X069S-X076D-X145R-X218S, X069S-X076D-X145R-X248D, X069S-X076D-X145R-X259P, X069S-X076D-X166Q-X185Q, X069S-X076D-X166Q-X210I, X069S-X076D-X166Q-X217L, X069S-X076D-X166Q-X218S, X069S-X076D-X166Q-X248D, X069S-X076D-X166Q-X259P, X069S-X076D-X185Q-X210I, X069S-X076D-X185Q-X217L, X069S-X076D-X185Q-X218S, X069S-X076D-X185Q-X248D, X069S-X076D-X185Q-X259P, X069S-X076D-X210I-X217L, X069S-X076D-X210I-X218S, X069S-X076D-X210I-X248D, X069S-X076D-X210I-X259P, X069S-X076D-X217L-X218S, X069S-X076D-X217L-X248D, X069S-X076D-X217L-X259P, X069S-X076D-X218S-X248D, X069S-X076D-X218S-X259P, X069S-X076D-X248D-X259P, X069S-X078N-X079I-X087D, X069S-X078N-X079I-X118R, X069S-X078N-X079I-X124I, X069S-X078N-X079I-X128S, X069S-X078N-X079I-X129P, X069S-X078N-X079I-X130S, X069S-X078N-X079I-X145R, X069S-X078N-X079I-X166Q, X069S-X078N-X079I-X185Q, X069S-X078N-X079I-X210I, X069S-X078N-X079I-X217L, X069S-X078N-X079I-X218S, X069S-X078N-X079I-X248D, X069S-X078N-X079I-X259P, X069S-X078N-X087D-X118R, X069S-X078N-X087D-X124I, X069S-X078N-X087D-X128S, X069S-X078N-X087D-X129P, X069S-X078N-X087D-X130S, X069S-X078N-X087D-X145R, X069S-X078N-X087D-X166Q, X069S-X078N-X087D-X185Q, X069S-X078N-X087D-X210I, X069S-X078N-X087D-X217L, X069S-X078N-X087D-X218S, X069S-X078N-X087D-X248D, X069S-X078N-X087D-X259P, X069S-X078N-X118R-X124I, X069S-X078N-X118R-X128S, X069S-X078N-X118R-X129P, X069S-X078N-X118R-X130S, X069S-X078N-X118R-X145R, X069S-X078N-X118R-X166Q, X069S-X078N-X118R-X185Q, X069S-X078N-X118R-X210I, X069S-X078N-X118R-X217L, X069S-X078N-X118R-X218S, X069S-X078N-X118R-X248D, X069S-X078N-X118R-X259P, X069S-X078N-X124I-X128S, X069S-X078N-X124I-X129P, X069S-X078N-X124I-X130S, X069S-X078N-X124I-X145R, X069S-X078N-X124I-X166Q, X069S-X078N-X124I-X185Q, X069S-X078N-X124I-X210I, X069S-X078N-X124I-X217L, X069S-X078N-X124I-X218S, X069S-X078N-X124I-X248D, X069S-X078N-X124I-X259P, X069S-X078N-X128S-X129P, X069S-X078N-X128S-X130S, X069S-X078N-X128S-X145R, X069S-X078N-X128S-X166Q, X069S-X078N-X128S-X185Q, X069S-X078N-X128S-X210I, X069S-X078N-X128S-X217L, X069S-X078N-X128S-X218S, X069S-X078N-X128S-X248D, X069S-X078N-X128S-X259P, X069S-X078N-X129P-X130S, X069S-X078N-X129P-X145R, X069S-X078N-X129P-X166Q, X069S-X078N-X129P-X185Q, X069S-X078N-X129P-X210I, X069S-X078N-X129P-X217L, X069S-X078N-X129P-X218S, X069S-X078N-X129P-X248D, X069S-X078N-X129P-X259P, X069S-X078N-X130S-X145R, X069S-X078N-X130S-X166Q, X069S-X078N-X130S-X185Q, X069S-X078N-X130S-X210I, X069S-X078N-X130S-X217L, X069S-X078N-X130S-X218S, X069S-X078N-X130S-X248D, X069S-X078N-X130S-X259P, X069S-X078N-X145R-X166Q, X069S-X078N-X145R-X185Q, X069S-X078N-X145R-X210I, X069S-X078N-X145R-X217L, X069S-X078N-X145R-X218S, X069S-X078N-X145R-X248D, X069S-X078N-X145R-X259P, X069S-X078N-X166Q-X185Q, X069S-X078N-X166Q-X210I, X069S-X078N-X166Q-X217L, X069S-X078N-X166Q-X218S, X069S-X078N-X166Q-X248D, X069S-X078N-X166Q-X259P, X069S-X078N-X185Q-X210I, X069S-X078N-X185Q-X217L, X069S-X078N-X185Q-X218S, X069S-X078N-X185Q-X248D, X069S-X078N-X185Q-X259P, X069S-X078N-X210I-X217L, X069S-X078N-X210I-X218S, X069S-X078N-X210I-X248D, X069S-X078N-X210I-X259P, X069S-X078N-X217L-X218S, X069S-X078N-X217L-X248D, X069S-X078N-X217L-X259P, X069S-X078N-X218S-X248D, X069S-X078N-X218S-X259P, X069S-X078N-X248D-X259P, X069S-X079I-X087D-X118R, X069S-X079I-X087D-X124I, X069S-X079I-X087D-X128S, X069S-X079I-X087D-X129P, X069S-X079I-X087D-X130S, X069S-X079I-X087D-X145R, X069S-X079I-X087D-X166Q, X069S-X079I-X087D-X185Q, X069S-X079I-X087D-X210I, X069S-X079I-X087D-X217L, X069S-X079I-X087D-X218S, X069S-X079I-X087D-X248D, X069S-X079I-X087D-X259P, X069S-X079I-X118R-X124I, X069S-X079I-X118R-X128S, X069S-X079I-X118R-X129P, X069S-X079I-X118R-X130S, X069S-X079I-X118R-X145R, X069S-X079I-X118R-X166Q, X069S-X079I-X118R-X185Q, X069S-X079I-X118R-X210I, X069S-X079I-X118R-X217L, X069S-X079I-X118R-X218S, X069S-X079I-X118R-X248D, X069S-X079I-X118R-X259P, X069S-X079I-X124I-X128S, X069S-X079I-X124I-X129P, X069S-X079I-X124I-X130S, X069S-X079I-X124I-X145R, X069S-X079I-X124I-X166Q, X069S-X079I-X124I-X185Q, X069S-X079I-X124I-X210I, X069S-X079I-X124I-X217L, X069S-X079I-X124I-X218S, X069S-X079I-X124I-X248D, X069S-X079I-X124I-X259P, X069S-X079I-X128S-X129P, X069S-X079I-X128S-X130S, X069S-X079I-X128S-X145R, X069S-X079I-X128S-X166Q, X069S-X079I-X128S-X185Q, X069S-X079I-X128S-X210I, X069S-X079I-X128S-X217L, X069S-X079I-X128S-X218S, X069S-X079I-X128S-X248D, X069S-X079I-X128S-X259P, X069S-X079I-X129P-X130S, X069S-X079I-X129P-X145R, X069S-X079I-X129P-X166Q, X069S-X079I-X129P-X185Q, X069S-X079I-X129P-

X210I, X069S-X079I-X129P-X217L, X069S-X079I-X129P-X218S, X069S-X079I-X129P-X248D, X069S-X079I-X129P-X259P, X069S-X079I-X130S-X145R, X069S-X079I-X130S-X166Q, X069S-X079I-X130S-X185Q, X069S-X079I-X130S-X210I, X069S-X079I-X130S-X217L, X069S-X079I-X130S-X218S, X069S-X079I-X130S-X248D, X069S-X079I-X130S-X259P, X069S-X079I-X145R-X166Q, X069S-X079I-X145R-X185Q, X069S-X079I-X145R-X210I, X069S-X079I-X145R-X217L, X069S-X079I-X145R-X218S, X069S-X079I-X145R-X248D, X069S-X079I-X145R-X259P, X069S-X079I-X166Q-X185Q, X069S-X079I-X166Q-X210I, X069S-X079I-X166Q-X217L, X069S-X079I-X166Q-X218S, X069S-X079I-X166Q-X248D, X069S-X079I-X166Q-X259P, X069S-X079I-X185Q-X210I, X069S-X079I-X185Q-X217L, X069S-X079I-X185Q-X218S, X069S-X079I-X185Q-X248D, X069S-X079I-X185Q-X259P, X069S-X079I-X210I-X217L, X069S-X079I-X210I-X218S, X069S-X079I-X210I-X248D, X069S-X079I-X210I-X259P, X069S-X079I-X217L-X218S, X069S-X079I-X217L-X248D, X069S-X079I-X217L-X259P, X069S-X079I-X218S-X248D, X069S-X079I-X218S-X259P, X069S-X079I-X248D-X259P, X069S-X087D-X118R-X124I, X069S-X087D-X118R-X128S, X069S-X087D-X118R-X129P, X069S-X087D-X118R-X130S, X069S-X087D-X118R-X145R, X069S-X087D-X118R-X166Q, X069S-X087D-X118R-X185Q, X069S-X087D-X118R-X210I, X069S-X087D-X118R-X217L, X069S-X087D-X118R-X218S, X069S-X087D-X118R-X248D, X069S-X087D-X118R-X259P, X069S-X087D-X124I-X128S, X069S-X087D-X124I-X129P, X069S-X087D-X124I-X130S, X069S-X087D-X124I-X145R, X069S-X087D-X124I-X166Q, X069S-X087D-X124I-X185Q, X069S-X087D-X124I-X210I, X069S-X087D-X124I-X217L, X069S-X087D-X124I-X218S, X069S-X087D-X124I-X248D, X069S-X087D-X124I-X259P, X069S-X087D-X128S-X129P, X069S-X087D-X128S-X130S, X069S-X087D-X128S-X145R, X069S-X087D-X128S-X166Q, X069S-X087D-X128S-X185Q, X069S-X087D-X128S-X210I, X069S-X087D-X128S-X217L, X069S-X087D-X128S-X218S, X069S-X087D-X128S-X248D, X069S-X087D-X128S-X259P, X069S-X087D-X129P-X130S, X069S-X087D-X129P-X145R, X069S-X087D-X129P-X166Q, X069S-X087D-X129P-X185Q, X069S-X087D-X129P-X210I, X069S-X087D-X129P-X217L, X069S-X087D-X129P-X218S, X069S-X087D-X129P-X248D, X069S-X087D-X129P-X259P, X069S-X087D-X130S-X145R, X069S-X087D-X130S-X166Q, X069S-X087D-X130S-X185Q, X069S-X087D-X130S-X210I, X069S-X087D-X130S-X217L, X069S-X087D-X130S-X218S, X069S-X087D-X130S-X248D, X069S-X087D-X130S-X259P, X069S-X087D-X145R-X166Q, X069S-X087D-X145R-X185Q, X069S-X087D-X145R-X210I, X069S-X087D-X145R-X217L, X069S-X087D-X145R-X218S, X069S-X087D-X145R-X248D, X069S-X087D-X145R-X259P, X069S-X087D-X166Q-X185Q, X069S-X087D-X166Q-X210I, X069S-X087D-X166Q-X217L, X069S-X087D-X166Q-X218S, X069S-X087D-X166Q-X248D, X069S-X087D-X166Q-X259P, X069S-X087D-X185Q-X210I, X069S-X087D-X185Q-X217L, X069S-X087D-X185Q-X218S, X069S-X087D-X185Q-X248D, X069S-X087D-X185Q-X259P, X069S-X087D-X210I-X217L, X069S-X087D-X210I-X218S, X069S-X087D-X210I-X248D, X069S-X087D-X210I-X259P, X069S-X087D-X217L-X218S, X069S-X087D-X217L-X248D, X069S-X087D-X217L-X259P, X069S-X087D-X218S-X248D, X069S-X087D-X218S-X259P, X069S-X087D-X248D-X259P, X069S-X118R-X124I-X128S, X069S-X118R-X124I-X129P, X069S-X118R-X124I-X130S, X069S-X118R-X124I-X145R, X069S-X118R-X124I-X166Q, X069S-X118R-X124I-X185Q, X069S-X118R-X124I-X210I, X069S-X118R-X124I-X217L, X069S-X118R-X124I-X218S, X069S-X118R-X124I-X248D, X069S-X118R-X124I-X259P, X069S-X118R-X128S-X129P, X069S-X118R-X128S-X130S, X069S-X118R-X128S-X145R, X069S-X118R-X128S-X166Q, X069S-X118R-X128S-X185Q, X069S-X118R-X128S-X210I, X069S-X118R-X128S-X217L, X069S-X118R-X128S-X218S, X069S-X118R-X128S-X248D, X069S-X118R-X128S-X259P, X069S-X118R-X129P-X130S, X069S-X118R-X129P-X145R, X069S-X118R-X129P-X166Q, X069S-X118R-X129P-X185Q, X069S-X118R-X129P-X210I, X069S-X118R-X129P-X217L, X069S-X118R-X129P-X218S, X069S-X118R-X129P-X248D, X069S-X118R-X129P-X259P, X069S-X118R-X130S-X145R, X069S-X118R-X130S-X166Q, X069S-X118R-X130S-X185Q, X069S-X118R-X130S-X210I, X069S-X118R-X130S-X217L, X069S-X118R-X130S-X218S, X069S-X118R-X130S-X248D, X069S-X118R-X130S-X259P, X069S-X118R-X145R-X166Q, X069S-X118R-X145R-X185Q, X069S-X118R-X145R-X210I, X069S-X118R-X145R-X217L, X069S-X118R-X145R-X218S, X069S-X118R-X145R-X248D, X069S-X118R-X145R-X259P, X069S-X118R-X166Q-X185Q, X069S-X118R-X166Q-X210I, X069S-X118R-X166Q-X217L, X069S-X118R-X166Q-X218S, X069S-X118R-X166Q-X248D, X069S-X118R-X166Q-X259P, X069S-X118R-X185Q-X210I, X069S-X118R-X185Q-X217L, X069S-X118R-X185Q-X218S, X069S-X118R-X185Q-X248D, X069S-X118R-X185Q-X259P, X069S-X118R-X210I-X217L, X069S-X118R-X210I-X218S, X069S-X118R-X210I-X248D, X069S-X118R-X210I-X259P, X069S-X118R-X217L-X218S, X069S-X118R-X217L-X248D, X069S-X118R-X217L-X259P, X069S-X118R-X218S-X248D, X069S-X118R-X218S-X259P, X069S-X118R-X248D-X259P, X069S-X124I-X128S-X129P, X069S-X124I-X128S-X130S, X069S-X124I-X128S-X145R, X069S-X124I-X128S-X166Q, X069S-X124I-X128S-X185Q, X069S-X124I-X128S-X210I, X069S-X124I-X128S-X217L, X069S-X124I-X128S-X218S, X069S-X124I-X128S-X248D, X069S-X124I-X128S-X259P, X069S-X124I-X129P-X130S, X069S-X124I-X129P-X145R, X069S-X124I-X129P-X166Q, X069S-X124I-X129P-X185Q, X069S-X124I-X129P-X210I, X069S-X124I-X129P-X217L, X069S-X124I-X129P-X218S, X069S-X124I-X129P-X248D, X069S-X124I-X129P-X259P, X069S-X124I-X130S-X145R, X069S-X124I-X130S-X166Q, X069S-X124I-X130S-X185Q, X069S-X124I-X130S-X210I, X069S-X124I-X130S-X217L, X069S-X124I-X130S-X218S, X069S-X124I-X130S-X248D, X069S-X124I-X130S-X259P, X069S-X124I-X145R-X166Q, X069S-X124I-X145R-X185Q, X069S-X124I-X145R-X210I, X069S-X124I-X145R-X217L, X069S-X124I-X145R-X218S, X069S-X124I-X145R-X248D, X069S-X124I-X145R-X259P, X069S-X124I-X166Q-X185Q, X069S-X124I-X166Q-X210I, X069S-X124I-X166Q-X217L, X069S-X124I-X166Q-X218S, X069S-X124I-X166Q-X248D, X069S-X124I-X166Q-X259P, X069S-X124I-X185Q-X210I, X069S-X124I-X185Q-X217L, X069S-X124I-X185Q-X218S, X069S-X124I-X185Q-X248D, X069S-X124I-X185Q-X259P, X069S-X124I-X210I-X217L, X069S-X124I-X210I-X218S, X069S-X124I-X210I-X248D, X069S-X124I-X210I-X259P, X069S-X124I-X217L-X218S, X069S-

X124I-X217L-X248D, X069S-X124I-X217L-X259P, X069S-X124I-X218S-X248D, X069S-X124I-X218S-X259P, X069S-X124I-X248D-X259P, X069S-X128S-X129P-X130S, X069S-X128S-X129P-X145R, X069S-X128S-X129P-X166Q, X069S-X128S-X129P-X185Q, X069S-X128S-X129P-X210I, X069S-X128S-X129P-X217L, X069S-X128S-X129P-X218S, X069S-X128S-X129P-X248D, X069S-X128S-X129P-X259P, X069S-X128S-X130S-X145R, X069S-X128S-X130S-X166Q, X069S-X128S-X130S-X185Q, X069S-X128S-X130S-X210I, X069S-X128S-X130S-X217L, X069S-X128S-X130S-X218S, X069S-X128S-X130S-X248D, X069S-X128S-X130S-X259P, X069S-X128S-X145R-X166Q, X069S-X128S-X145R-X185Q, X069S-X128S-X145R-X210I, X069S-X128S-X145R-X217L, X069S-X128S-X145R-X218S, X069S-X128S-X145R-X248D, X069S-X128S-X145R-X259P, X069S-X128S-X166Q-X185Q, X069S-X128S-X166Q-X210I, X069S-X128S-X166Q-X217L, X069S-X128S-X166Q-X218S, X069S-X128S-X166Q-X248D, X069S-X128S-X166Q-X259P, X069S-X128S-X185Q-X210I, X069S-X128S-X185Q-X217L, X069S-X128S-X185Q-X218S, X069S-X128S-X185Q-X248D, X069S-X128S-X185Q-X259P, X069S-X128S-X210I-X217L, X069S-X128S-X210I-X218S, X069S-X128S-X210I-X248D, X069S-X128S-X210I-X259P, X069S-X128S-X217L-X218S, X069S-X128S-X217L-X248D, X069S-X128S-X217L-X259P, X069S-X128S-X218S-X248D, X069S-X128S-X218S-X259P, X069S-X128S-X248D-X259P, X069S-X129P-X130S-X145R, X069S-X129P-X130S-X166Q, X069S-X129P-X130S-X185Q, X069S-X129P-X130S-X210I, X069S-X129P-X130S-X217L, X069S-X129P-X130S-X218S, X069S-X129P-X130S-X248D, X069S-X129P-X130S-X259P, X069S-X129P-X145R-X166Q, X069S-X129P-X145R-X185Q, X069S-X129P-X145R-X210I, X069S-X129P-X145R-X217L, X069S-X129P-X145R-X218S, X069S-X129P-X145R-X248D, X069S-X129P-X145R-X259P, X069S-X129P-X166Q-X185Q, X069S-X129P-X166Q-X210I, X069S-X129P-X166Q-X217L, X069S-X129P-X166Q-X218S, X069S-X129P-X166Q-X248D, X069S-X129P-X166Q-X259P, X069S-X129P-X185Q-X210I, X069S-X129P-X185Q-X217L, X069S-X129P-X185Q-X218S, X069S-X129P-X185Q-X248D, X069S-X129P-X185Q-X259P, X069S-X129P-X210I-X217L, X069S-X129P-X210I-X218S, X069S-X129P-X210I-X248D, X069S-X129P-X210I-X259P, X069S-X129P-X217L-X218S, X069S-X129P-X217L-X248D, X069S-X129P-X217L-X259P, X069S-X129P-X218S-X248D, X069S-X129P-X218S-X259P, X069S-X129P-X248D-X259P, X069S-X130S-X145R-X166Q, X069S-X130S-X145R-X185Q, X069S-X130S-X145R-X210I, X069S-X130S-X145R-X217L, X069S-X130S-X145R-X218S, X069S-X130S-X145R-X248D, X069S-X130S-X145R-X259P, X069S-X130S-X166Q-X185Q, X069S-X130S-X166Q-X210I, X069S-X130S-X166Q-X217L, X069S-X130S-X166Q-X218S, X069S-X130S-X166Q-X248D, X069S-X130S-X166Q-X259P, X069S-X130S-X185Q-X210I, X069S-X130S-X185Q-X217L, X069S-X130S-X185Q-X218S, X069S-X130S-X185Q-X248D, X069S-X130S-X185Q-X259P, X069S-X130S-X210I-X217L, X069S-X130S-X210I-X218S, X069S-X130S-X210I-X248D, X069S-X130S-X210I-X259P, X069S-X130S-X217L-X218S, X069S-X130S-X217L-X248D, X069S-X130S-X217L-X259P, X069S-X130S-X218S-X248D, X069S-X130S-X218S-X259P, X069S-X130S-X248D-X259P, X069S-X145R-X166Q-X185Q, X069S-X145R-X166Q-X210I, X069S-X145R-X166Q-X217L, X069S-X145R-X166Q-X218S, X069S-X145R-X166Q-X248D, X069S-X145R-X166Q-X259P, X069S-X145R-X185Q-X210I, X069S-X145R-X185Q-X217L, X069S-X145R-X185Q-X218S, X069S-X145R-X185Q-X248D, X069S-X145R-X185Q-X259P, X069S-X145R-X210I-X217L, X069S-X145R-X210I-X218S, X069S-X145R-X210I-X248D, X069S-X145R-X210I-X259P, X069S-X145R-X217L-X218S, X069S-X145R-X217L-X248D, X069S-X145R-X217L-X259P, X069S-X145R-X218S-X248D, X069S-X145R-X218S-X259P, X069S-X145R-X248D-X259P, X069S-X166Q-X185Q-X210I, X069S-X166Q-X185Q-X217L, X069S-X166Q-X185Q-X218S, X069S-X166Q-X185Q-X248D, X069S-X166Q-X185Q-X259P, X069S-X166Q-X210I-X217L, X069S-X166Q-X210I-X218S, X069S-X166Q-X210I-X248D, X069S-X166Q-X210I-X259P, X069S-X166Q-X217L-X218S, X069S-X166Q-X217L-X248D, X069S-X166Q-X217L-X259P, X069S-X166Q-X218S-X248D, X069S-X166Q-X218S-X259P, X069S-X166Q-X248D-X259P, X069S-X185Q-X210I-X217L, X069S-X185Q-X210I-X218S, X069S-X185Q-X210I-X248D, X069S-X185Q-X210I-X259P, X069S-X185Q-X217L-X218S, X069S-X185Q-X217L-X248D, X069S-X185Q-X217L-X259P, X069S-X185Q-X218S-X248D, X069S-X185Q-X218S-X259P, X069S-X185Q-X248D-X259P, X069S-X210I-X217L-X218S, X069S-X210I-X217L-X248D, X069S-X210I-X217L-X259P, X069S-X210I-X218S-X248D, X069S-X210I-X218S-X259P, X069S-X210I-X248D-X259P, X069S-X217L-X218S-X248D, X069S-X217L-X218S-X259P, X069S-X217L-X248D-X259P, X069S-X218S-X248D-X259P, X076D-X078N-X079I-X087D, X076D-X078N-X079I-X118R, X076D-X078N-X079I-X124I, X076D-X078N-X079I-X128S, X076D-X078N-X079I-X129P, X076D-X078N-X079I-X130S, X076D-X078N-X079I-X145R, X076D-X078N-X079I-X166Q, X076D-X078N-X079I-X185Q, X076D-X078N-X079I-X210I, X076D-X078N-X079I-X217L, X076D-X078N-X079I-X218S, X076D-X078N-X079I-X248D, X076D-X078N-X079I-X259P, X076D-X078N-X087D-X118R, X076D-X078N-X087D-X124I, X076D-X078N-X087D-X128S, X076D-X078N-X087D-X129P, X076D-X078N-X087D-X130S, X076D-X078N-X087D-X145R, X076D-X078N-X087D-X166Q, X076D-X078N-X087D-X185Q, X076D-X078N-X087D-X210I, X076D-X078N-X087D-X217L, X076D-X078N-X087D-X218S, X076D-X078N-X087D-X248D, X076D-X078N-X087D-X259P, X076D-X078N-X118R-X124I, X076D-X078N-X118R-X128S, X076D-X078N-X118R-X129P, X076D-X078N-X118R-X130S, X076D-X078N-X118R-X145R, X076D-X078N-X118R-X166Q, X076D-X078N-X118R-X185Q, X076D-X078N-X118R-X210I, X076D-X078N-X118R-X217L, X076D-X078N-X118R-X218S, X076D-X078N-X118R-X248D, X076D-X078N-X118R-X259P, X076D-X078N-X124I-X128S, X076D-X078N-X124I-X129P, X076D-X078N-X124I-X130S, X076D-X078N-X124I-X145R, X076D-X078N-X124I-X166Q, X076D-X078N-X124I-X185Q, X076D-X078N-X124I-X210I, X076D-X078N-X124I-X217L, X076D-X078N-X124I-X218S, X076D-X078N-X124I-X248D, X076D-X078N-X124I-X259P, X076D-X078N-X128S-X129P, X076D-X078N-X128S-X130S, X076D-X078N-X128S-X145R, X076D-X078N-X128S-X166Q, X076D-X078N-X128S-X185Q, X076D-X078N-X128S-X210I, X076D-X078N-X128S-X217L, X076D-X078N-X128S-X218S, X076D-X078N-X128S-X248D, X076D-X078N-X128S-X259P, X076D-X078N-X129P-X130S, X076D-X078N-X129P-X145R, X076D-X078N-X129P-X166Q, X076D-X078N-X129P-X185Q, X076D-X078N-X129P-

X210I, X076D-X078N-X129P-X217L, X076D-X078N-X129P-X218S, X076D-X078N-X129P-X248D, X076D-X078N-X129P-X259P, X076D-X078N-X130S-X145R, X076D-X078N-X130S-X166Q, X076D-X078N-X130S-X185Q, X076D-X078N-X130S-X210I, X076D-X078N-X130S-X217L, X076D-X078N-X130S-X218S, X076D-X078N-X130S-X248D, X076D-X078N-X130S-X259P, X076D-X078N-X145R-X166Q, X076D-X078N-X145R-X185Q, X076D-X078N-X145R-X210I, X076D-X078N-X145R-X217L, X076D-X078N-X145R-X218S, X076D-X078N-X145R-X248D, X076D-X078N-X145R-X259P, X076D-X078N-X166Q-X185Q, X076D-X078N-X166Q-X210I, X076D-X078N-X166Q-X217L, X076D-X078N-X166Q-X218S, X076D-X078N-X166Q-X248D, X076D-X078N-X166Q-X259P, X076D-X078N-X185Q-X210I, X076D-X078N-X185Q-X217L, X076D-X078N-X185Q-X218S, X076D-X078N-X185Q-X248D, X076D-X078N-X185Q-X259P, X076D-X078N-X210I-X217L, X076D-X078N-X210I-X218S, X076D-X078N-X210I-X248D, X076D-X078N-X210I-X259P, X076D-X078N-X217L-X218S, X076D-X078N-X217L-X248D, X076D-X078N-X217L-X259P, X076D-X078N-X218S-X248D, X076D-X078N-X218S-X259P, X076D-X078N-X248D-X259P, X076D-X079I-X087D-X118R, X076D-X079I-X087D-X124I, X076D-X079I-X087D-X128S, X076D-X079I-X087D-X129P, X076D-X079I-X087D-X130S, X076D-X079I-X087D-X145R, X076D-X079I-X087D-X166Q, X076D-X079I-X087D-X185Q, X076D-X079I-X087D-X210I, X076D-X079I-X087D-X217L, X076D-X079I-X087D-X218S, X076D-X079I-X087D-X248D, X076D-X079I-X087D-X259P, X076D-X079I-X118R-X124I, X076D-X079I-X118R-X128S, X076D-X079I-X118R-X129P, X076D-X079I-X118R-X130S, X076D-X079I-X118R-X145R, X076D-X079I-X118R-X166Q, X076D-X079I-X118R-X185Q, X076D-X079I-X118R-X210I, X076D-X079I-X118R-X217L, X076D-X079I-X118R-X218S, X076D-X079I-X118R-X248D, X076D-X079I-X118R-X259P, X076D-X079I-X124I-X128S, X076D-X079I-X124I-X129P, X076D-X079I-X124I-X130S, X076D-X079I-X124I-X145R, X076D-X079I-X124I-X166Q, X076D-X079I-X124I-X185Q, X076D-X079I-X124I-X210I, X076D-X079I-X124I-X217L, X076D-X079I-X124I-X218S, X076D-X079I-X124I-X248D, X076D-X079I-X124I-X259P, X076D-X079I-X128S-X129P, X076D-X079I-X128S-X130S, X076D-X079I-X128S-X145R, X076D-X079I-X128S-X166Q, X076D-X079I-X128S-X185Q, X076D-X079I-X128S-X210I, X076D-X079I-X128S-X217L, X076D-X079I-X128S-X218S, X076D-X079I-X128S-X248D, X076D-X079I-X128S-X259P, X076D-X079I-X129P-X130S, X076D-X079I-X129P-X145R, X076D-X079I-X129P-X166Q, X076D-X079I-X129P-X185Q, X076D-X079I-X129P-X210I, X076D-X079I-X129P-X217L, X076D-X079I-X129P-X218S, X076D-X079I-X129P-X248D, X076D-X079I-X129P-X259P, X076D-X079I-X130S-X145R, X076D-X079I-X130S-X166Q, X076D-X079I-X130S-X185Q, X076D-X079I-X130S-X210I, X076D-X079I-X130S-X217L, X076D-X079I-X130S-X218S, X076D-X079I-X130S-X248D, X076D-X079I-X130S-X259P, X076D-X079I-X145R-X166Q, X076D-X079I-X145R-X185Q, X076D-X079I-X145R-X210I, X076D-X079I-X145R-X217L, X076D-X079I-X145R-X218S, X076D-X079I-X145R-X248D, X076D-X079I-X145R-X259P, X076D-X079I-X166Q-X185Q, X076D-X079I-X166Q-X210I, X076D-X079I-X166Q-X217L, X076D-X079I-X166Q-X218S, X076D-X079I-X166Q-X248D, X076D-X079I-X166Q-X259P, X076D-X079I-X185Q-X210I, X076D-X079I-X185Q-X217L, X076D-X079I-X185Q-X218S, X076D-X079I-X185Q-X248D, X076D-X079I-X185Q-X259P, X076D-X079I-X210I-X217L, X076D-X079I-X210I-X218S, X076D-X079I-X210I-X248D, X076D-X079I-X210I-X259P, X076D-X079I-X217L-X218S, X076D-X079I-X217L-X248D, X076D-X079I-X217L-X259P, X076D-X079I-X218S-X248D, X076D-X079I-X218S-X259P, X076D-X079I-X248D-X259P, X076D-X087D-X118R-X124I, X076D-X087D-X118R-X128S, X076D-X087D-X118R-X129P, X076D-X087D-X118R-X130S, X076D-X087D-X118R-X145R, X076D-X087D-X118R-X166Q, X076D-X087D-X118R-X185Q, X076D-X087D-X118R-X210I, X076D-X087D-X118R-X217L, X076D-X087D-X118R-X218S, X076D-X087D-X118R-X248D, X076D-X087D-X118R-X259P, X076D-X087D-X124I-X128S, X076D-X087D-X124I-X129P, X076D-X087D-X124I-X130S, X076D-X087D-X124I-X145R, X076D-X087D-X124I-X166Q, X076D-X087D-X124I-X185Q, X076D-X087D-X124I-X210I, X076D-X087D-X124I-X217L, X076D-X087D-X124I-X218S, X076D-X087D-X124I-X248D, X076D-X087D-X124I-X259P, X076D-X087D-X128S-X129P, X076D-X087D-X128S-X130S, X076D-X087D-X128S-X145R, X076D-X087D-X128S-X166Q, X076D-X087D-X128S-X185Q, X076D-X087D-X128S-X210I, X076D-X087D-X128S-X217L, X076D-X087D-X128S-X218S, X076D-X087D-X128S-X248D, X076D-X087D-X128S-X259P, X076D-X087D-X129P-X130S, X076D-X087D-X129P-X145R, X076D-X087D-X129P-X166Q, X076D-X087D-X129P-X185Q, X076D-X087D-X129P-X210I, X076D-X087D-X129P-X217L, X076D-X087D-X129P-X218S, X076D-X087D-X129P-X248D, X076D-X087D-X129P-X259P, X076D-X087D-X130S-X145R, X076D-X087D-X130S-X166Q, X076D-X087D-X130S-X185Q, X076D-X087D-X130S-X210I, X076D-X087D-X130S-X217L, X076D-X087D-X130S-X218S, X076D-X087D-X130S-X248D, X076D-X087D-X130S-X259P, X076D-X087D-X145R-X166Q, X076D-X087D-X145R-X185Q, X076D-X087D-X145R-X210I, X076D-X087D-X145R-X217L, X076D-X087D-X145R-X218S, X076D-X087D-X145R-X248D, X076D-X087D-X145R-X259P, X076D-X087D-X166Q-X185Q, X076D-X087D-X166Q-X210I, X076D-X087D-X166Q-X217L, X076D-X087D-X166Q-X218S, X076D-X087D-X166Q-X248D, X076D-X087D-X166Q-X259P, X076D-X087D-X185Q-X210I, X076D-X087D-X185Q-X217L, X076D-X087D-X185Q-X218S, X076D-X087D-X185Q-X248D, X076D-X087D-X185Q-X259P, X076D-X087D-X210I-X217L, X076D-X087D-X210I-X218S, X076D-X087D-X210I-X248D, X076D-X087D-X210I-X259P, X076D-X087D-X217L-X218S, X076D-X087D-X217L-X248D, X076D-X087D-X217L-X259P, X076D-X087D-X218S-X248D, X076D-X087D-X218S-X259P, X076D-X087D-X248D-X259P, X076D-X118R-X124I-X128S, X076D-X118R-X124I-X129P, X076D-X118R-X124I-X130S, X076D-X118R-X124I-X145R, X076D-X118R-X124I-X166Q, X076D-X118R-X124I-X185Q, X076D-X118R-X124I-X210I, X076D-X118R-X124I-X217L, X076D-X118R-X124I-X218S, X076D-X118R-X124I-X248D, X076D-X118R-X124I-X259P, X076D-X118R-X128S-X129P, X076D-X118R-X128S-X130S, X076D-X118R-X128S-X145R, X076D-X118R-X128S-X166Q, X076D-X118R-X128S-X185Q, X076D-X118R-X128S-X210I, X076D-X118R-X128S-X217L, X076D-X118R-X128S-X218S, X076D-X118R-X128S-X248D, X076D-X118R-X128S-X259P, X076D-X118R-X129P-X130S, X076D-X118R-X129P-X145R, X076D-X118R-X129P-X166Q, X076D-X118R-X129P-X185Q, X076D-

X118R-X129P-X210I, X076D-X118R-X129P-X217L, X076D-X118R-X129P-X218S, X076D-X118R-X129P-X248D, X076D-X118R-X129P-X259P, X076D-X118R-X130S-X145R, X076D-X118R-X130S-X166Q, X076D-X118R-X130S-X185Q, X076D-X118R-X130S-X210I, X076D-X118R-X130S-X217L, X076D-X118R-X130S-X218S, X076D-X118R-X130S-X248D, X076D-X118R-X130S-X259P, X076D-X118R-X145R-X166Q, X076D-X118R-X145R-X185Q, X076D-X118R-X145R-X210I, X076D-X118R-X145R-X217L, X076D-X118R-X145R-X218S, X076D-X118R-X145R-X248D, X076D-X118R-X145R-X259P, X076D-X118R-X166Q-X185Q, X076D-X118R-X166Q-X210I, X076D-X118R-X166Q-X217L, X076D-X118R-X166Q-X218S, X076D-X118R-X166Q-X248D, X076D-X118R-X166Q-X259P, X076D-X118R-X185Q-X210I, X076D-X118R-X185Q-X217L, X076D-X118R-X185Q-X218S, X076D-X118R-X185Q-X248D, X076D-X118R-X185Q-X259P, X076D-X118R-X210I-X217L, X076D-X118R-X210I-X218S, X076D-X118R-X210I-X248D, X076D-X118R-X210I-X259P, X076D-X118R-X217L-X218S, X076D-X118R-X217L-X248D, X076D-X118R-X217L-X259P, X076D-X118R-X218S-X248D, X076D-X118R-X218S-X259P, X076D-X118R-X248D-X259P, X076D-X124I-X128S-X129P, X076D-X124I-X128S-X130S, X076D-X124I-X128S-X145R, X076D-X124I-X128S-X166Q, X076D-X124I-X128S-X185Q, X076D-X124I-X128S-X210I, X076D-X124I-X128S-X217L, X076D-X124I-X128S-X218S, X076D-X124I-X128S-X248D, X076D-X124I-X128S-X259P, X076D-X124I-X129P-X130S, X076D-X124I-X129P-X145R, X076D-X124I-X129P-X166Q, X076D-X124I-X129P-X185Q, X076D-X124I-X129P-X210I, X076D-X124I-X129P-X217L, X076D-X124I-X129P-X218S, X076D-X124I-X129P-X248D, X076D-X124I-X129P-X259P, X076D-X124I-X130S-X145R, X076D-X124I-X130S-X166Q, X076D-X124I-X130S-X185Q, X076D-X124I-X130S-X210I, X076D-X124I-X130S-X217L, X076D-X124I-X130S-X218S, X076D-X124I-X130S-X248D, X076D-X124I-X130S-X259P, X076D-X124I-X145R-X166Q, X076D-X124I-X145R-X185Q, X076D-X124I-X145R-X210I, X076D-X124I-X145R-X217L, X076D-X124I-X145R-X218S, X076D-X124I-X145R-X248D, X076D-X124I-X145R-X259P, X076D-X124I-X166Q-X185Q, X076D-X124I-X166Q-X210I, X076D-X124I-X166Q-X217L, X076D-X124I-X166Q-X218S, X076D-X124I-X166Q-X248D, X076D-X124I-X166Q-X259P, X076D-X124I-X185Q-X210I, X076D-X124I-X185Q-X217L, X076D-X124I-X185Q-X218S, X076D-X124I-X185Q-X248D, X076D-X124I-X185Q-X259P, X076D-X124I-X210I-X217L, X076D-X124I-X210I-X218S, X076D-X124I-X210I-X248D, X076D-X124I-X210I-X259P, X076D-X124I-X217L-X218S, X076D-X124I-X217L-X248D, X076D-X124I-X217L-X259P, X076D-X124I-X218S-X248D, X076D-X124I-X218S-X259P, X076D-X124I-X248D-X259P, X076D-X128S-X129P-X130S, X076D-X128S-X129P-X145R, X076D-X128S-X129P-X166Q, X076D-X128S-X129P-X185Q, X076D-X128S-X129P-X210I, X076D-X128S-X129P-X217L, X076D-X128S-X129P-X218S, X076D-X128S-X129P-X248D, X076D-X128S-X129P-X259P, X076D-X128S-X130S-X145R, X076D-X128S-X130S-X166Q, X076D-X128S-X130S-X185Q, X076D-X128S-X130S-X210I, X076D-X128S-X130S-X217L, X076D-X128S-X130S-X218S, X076D-X128S-X130S-X248D, X076D-X128S-X130S-X259P, X076D-X128S-X145R-X166Q, X076D-X128S-X145R-X185Q, X076D-X128S-X145R-X210I, X076D-X128S-X145R-X217L, X076D-X128S-X145R-X218S, X076D-X128S-X145R-X248D, X076D-X128S-X145R-X259P, X076D-X128S-X166Q-X185Q, X076D-X128S-X166Q-X210I, X076D-X128S-X166Q-X217L, X076D-X128S-X166Q-X218S, X076D-X128S-X166Q-X248D, X076D-X128S-X166Q-X259P, X076D-X128S-X185Q-X210I, X076D-X128S-X185Q-X217L, X076D-X128S-X185Q-X218S, X076D-X128S-X185Q-X248D, X076D-X128S-X185Q-X259P, X076D-X128S-X210I-X217L, X076D-X128S-X210I-X218S, X076D-X128S-X210I-X248D, X076D-X128S-X210I-X259P, X076D-X128S-X217L-X218S, X076D-X128S-X217L-X248D, X076D-X128S-X217L-X259P, X076D-X128S-X218S-X248D, X076D-X128S-X218S-X259P, X076D-X128S-X248D-X259P, X076D-X129P-X130S-X145R, X076D-X129P-X130S-X166Q, X076D-X129P-X130S-X185Q, X076D-X129P-X130S-X210I, X076D-X129P-X130S-X217L, X076D-X129P-X130S-X218S, X076D-X129P-X130S-X248D, X076D-X129P-X130S-X259P, X076D-X129P-X145R-X166Q, X076D-X129P-X145R-X185Q, X076D-X129P-X145R-X210I, X076D-X129P-X145R-X217L, X076D-X129P-X145R-X218S, X076D-X129P-X145R-X248D, X076D-X129P-X145R-X259P, X076D-X129P-X166Q-X185Q, X076D-X129P-X166Q-X210I, X076D-X129P-X166Q-X217L, X076D-X129P-X166Q-X218S, X076D-X129P-X166Q-X248D, X076D-X129P-X166Q-X259P, X076D-X129P-X185Q-X210I, X076D-X129P-X185Q-X217L, X076D-X129P-X185Q-X218S, X076D-X129P-X185Q-X248D, X076D-X129P-X185Q-X259P, X076D-X129P-X210I-X217L, X076D-X129P-X210I-X218S, X076D-X129P-X210I-X248D, X076D-X129P-X210I-X259P, X076D-X129P-X217L-X218S, X076D-X129P-X217L-X248D, X076D-X129P-X217L-X259P, X076D-X129P-X218S-X248D, X076D-X129P-X218S-X259P, X076D-X129P-X248D-X259P, X076D-X130S-X145R-X166Q, X076D-X130S-X145R-X185Q, X076D-X130S-X145R-X210I, X076D-X130S-X145R-X217L, X076D-X130S-X145R-X218S, X076D-X130S-X145R-X248D, X076D-X130S-X145R-X259P, X076D-X130S-X166Q-X185Q, X076D-X130S-X166Q-X210I, X076D-X130S-X166Q-X217L, X076D-X130S-X166Q-X218S, X076D-X130S-X166Q-X248D, X076D-X130S-X166Q-X259P, X076D-X130S-X185Q-X210I, X076D-X130S-X185Q-X217L, X076D-X130S-X185Q-X218S, X076D-X130S-X185Q-X248D, X076D-X130S-X185Q-X259P, X076D-X130S-X210I-X217L, X076D-X130S-X210I-X218S, X076D-X130S-X210I-X248D, X076D-X130S-X210I-X259P, X076D-X130S-X217L-X218S, X076D-X130S-X217L-X248D, X076D-X130S-X217L-X259P, X076D-X130S-X218S-X248D, X076D-X130S-X218S-X259P, X076D-X130S-X248D-X259P, X076D-X145R-X166Q-X185Q, X076D-X145R-X166Q-X210I, X076D-X145R-X166Q-X217L, X076D-X145R-X166Q-X218S, X076D-X145R-X166Q-X248D, X076D-X145R-X166Q-X259P, X076D-X145R-X185Q-X210I, X076D-X145R-X185Q-X217L, X076D-X145R-X185Q-X218S, X076D-X145R-X185Q-X248D, X076D-X145R-X185Q-X259P, X076D-X145R-X210I-X217L, X076D-X145R-X210I-X218S, X076D-X145R-X210I-X248D, X076D-X145R-X210I-X259P, X076D-X145R-X217L-X218S, X076D-X145R-X217L-X248D, X076D-X145R-X217L-X259P, X076D-X145R-X218S-X248D, X076D-X145R-X218S-X259P, X076D-X145R-X248D-X259P, X076D-X166Q-X185Q-X210I, X076D-X166Q-X185Q-X217L, X076D-X166Q-X185Q-X218S, X076D-X166Q-X185Q-X248D, X076D-X166Q-X185Q-X259P, X076D-X166Q-X210I-X217L, X076D-X166Q-X210I-X218S, X076D-X166Q-X210I-X248D, X076D-X166Q-X210I-

X259P, X076D-X166Q-X217L-X218S, X076D-X166Q-X217L-X248D, X076D-X166Q-X217L-X259P, X076D-X166Q-X218S-X248D, X076D-X166Q-X218S-X259P, X076D-X166Q-X248D-X259P, X076D-X185Q-X210I-X217L, X076D-X185Q-X210I-X218S, X076D-X185Q-X210I-X248D, X076D-X185Q-X210I-X259P, X076D-X185Q-X217L-X218S, X076D-X185Q-X217L-X248D, X076D-X185Q-X217L-X259P, X076D-X185Q-X218S-X248D, X076D-X185Q-X218S-X259P, X076D-X185Q-X248D-X259P, X076D-X210I-X217L-X218S, X076D-X210I-X217L-X248D, X076D-X210I-X217L-X259P, X076D-X210I-X218S-X248D, X076D-X210I-X218S-X259P, X076D-X210I-X248D-X259P, X076D-X217L-X218S-X248D, X076D-X217L-X218S-X259P, X076D-X217L-X248D-X259P, X076D-X218S-X248D-X259P, X078N-X079I-X087D-X118R, X078N-X079I-X087D-X124I, X078N-X079I-X087D-X128S, X078N-X079I-X087D-X129P, X078N-X079I-X087D-X130S, X078N-X079I-X087D-X145R, X078N-X079I-X087D-X166Q, X078N-X079I-X087D-X185Q, X078N-X079I-X087D-X210I, X078N-X079I-X087D-X217L, X078N-X079I-X087D-X218S, X078N-X079I-X087D-X248D, X078N-X079I-X087D-X259P, X078N-X079I-X118R-X124I, X078N-X079I-X118R-X128S, X078N-X079I-X118R-X129P, X078N-X079I-X118R-X130S, X078N-X079I-X118R-X145R, X078N-X079I-X118R-X166Q, X078N-X079I-X118R-X185Q, X078N-X079I-X118R-X210I, X078N-X079I-X118R-X217L, X078N-X079I-X118R-X218S, X078N-X079I-X118R-X248D, X078N-X079I-X118R-X259P, X078N-X079I-X124I-X128S, X078N-X079I-X124I-X129P, X078N-X079I-X124I-X130S, X078N-X079I-X124I-X145R, X078N-X079I-X124I-X166Q, X078N-X079I-X124I-X185Q, X078N-X079I-X124I-X210I, X078N-X079I-X124I-X217L, X078N-X079I-X124I-X218S, X078N-X079I-X124I-X248D, X078N-X079I-X124I-X259P, X078N-X079I-X128S-X129P, X078N-X079I-X128S-X130S, X078N-X079I-X128S-X145R, X078N-X079I-X128S-X166Q, X078N-X079I-X128S-X185Q, X078N-X079I-X128S-X210I, X078N-X079I-X128S-X217L, X078N-X079I-X128S-X218S, X078N-X079I-X128S-X248D, X078N-X079I-X128S-X259P, X078N-X079I-X129P-X130S, X078N-X079I-X129P-X145R, X078N-X079I-X129P-X166Q, X078N-X079I-X129P-X185Q, X078N-X079I-X129P-X210I, X078N-X079I-X129P-X217L, X078N-X079I-X129P-X218S, X078N-X079I-X129P-X248D, X078N-X079I-X129P-X259P, X078N-X079I-X130S-X145R, X078N-X079I-X130S-X166Q, X078N-X079I-X130S-X185Q, X078N-X079I-X130S-X210I, X078N-X079I-X130S-X217L, X078N-X079I-X130S-X218S, X078N-X079I-X130S-X248D, X078N-X079I-X130S-X259P, X078N-X079I-X145R-X166Q, X078N-X079I-X145R-X185Q, X078N-X079I-X145R-X210I, X078N-X079I-X145R-X217L, X078N-X079I-X145R-X218S, X078N-X079I-X145R-X248D, X078N-X079I-X145R-X259P, X078N-X079I-X166Q-X185Q, X078N-X079I-X166Q-X210I, X078N-X079I-X166Q-X217L, X078N-X079I-X166Q-X218S, X078N-X079I-X166Q-X248D, X078N-X079I-X166Q-X259P, X078N-X079I-X185Q-X210I, X078N-X079I-X185Q-X217L, X078N-X079I-X185Q-X218S, X078N-X079I-X185Q-X248D, X078N-X079I-X185Q-X259P, X078N-X079I-X210I-X217L, X078N-X079I-X210I-X218S, X078N-X079I-X210I-X248D, X078N-X079I-X210I-X259P, X078N-X079I-X217L-X218S, X078N-X079I-X217L-X248D, X078N-X079I-X217L-X259P, X078N-X079I-X218S-X248D, X078N-X079I-X218S-X259P, X078N-X079I-X248D-X259P, X078N-X087D-X118R-X124I, X078N-X087D-X118R-X128S, X078N-X087D-X118R-X129P, X078N-X087D-X118R-X130S, X078N-X087D-X118R-X145R, X078N-X087D-X118R-X166Q, X078N-X087D-X118R-X185Q, X078N-X087D-X118R-X210I, X078N-X087D-X118R-X217L, X078N-X087D-X118R-X218S, X078N-X087D-X118R-X248D, X078N-X087D-X118R-X259P, X078N-X087D-X124I-X128S, X078N-X087D-X124I-X129P, X078N-X087D-X124I-X130S, X078N-X087D-X124I-X145R, X078N-X087D-X124I-X166Q, X078N-X087D-X124I-X185Q, X078N-X087D-X124I-X210I, X078N-X087D-X124I-X217L, X078N-X087D-X124I-X218S, X078N-X087D-X124I-X248D, X078N-X087D-X124I-X259P, X078N-X087D-X128S-X129P, X078N-X087D-X128S-X130S, X078N-X087D-X128S-X145R, X078N-X087D-X128S-X166Q, X078N-X087D-X128S-X185Q, X078N-X087D-X128S-X210I, X078N-X087D-X128S-X217L, X078N-X087D-X128S-X218S, X078N-X087D-X128S-X248D, X078N-X087D-X128S-X259P, X078N-X087D-X129P-X130S, X078N-X087D-X129P-X145R, X078N-X087D-X129P-X166Q, X078N-X087D-X129P-X185Q, X078N-X087D-X129P-X210I, X078N-X087D-X129P-X217L, X078N-X087D-X129P-X218S, X078N-X087D-X129P-X248D, X078N-X087D-X129P-X259P, X078N-X087D-X130S-X145R, X078N-X087D-X130S-X166Q, X078N-X087D-X130S-X185Q, X078N-X087D-X130S-X210I, X078N-X087D-X130S-X217L, X078N-X087D-X130S-X218S, X078N-X087D-X130S-X248D, X078N-X087D-X130S-X259P, X078N-X087D-X145R-X166Q, X078N-X087D-X145R-X185Q, X078N-X087D-X145R-X210I, X078N-X087D-X145R-X217L, X078N-X087D-X145R-X218S, X078N-X087D-X145R-X248D, X078N-X087D-X145R-X259P, X078N-X087D-X166Q-X185Q, X078N-X087D-X166Q-X210I, X078N-X087D-X166Q-X217L, X078N-X087D-X166Q-X218S, X078N-X087D-X166Q-X248D, X078N-X087D-X166Q-X259P, X078N-X087D-X185Q-X210I, X078N-X087D-X185Q-X217L, X078N-X087D-X185Q-X218S, X078N-X087D-X185Q-X248D, X078N-X087D-X185Q-X259P, X078N-X087D-X210I-X217L, X078N-X087D-X210I-X218S, X078N-X087D-X210I-X248D, X078N-X087D-X210I-X259P, X078N-X087D-X217L-X218S, X078N-X087D-X217L-X248D, X078N-X087D-X217L-X259P, X078N-X087D-X218S-X248D, X078N-X087D-X218S-X259P, X078N-X087D-X248D-X259P, X078N-X118R-X124I-X128S, X078N-X118R-X124I-X129P, X078N-X118R-X124I-X130S, X078N-X118R-X124I-X145R, X078N-X118R-X124I-X166Q, X078N-X118R-X124I-X185Q, X078N-X118R-X124I-X210I, X078N-X118R-X124I-X217L, X078N-X118R-X124I-X218S, X078N-X118R-X124I-X248D, X078N-X118R-X124I-X259P, X078N-X118R-X128S-X129P, X078N-X118R-X128S-X130S, X078N-X118R-X128S-X145R, X078N-X118R-X128S-X166Q, X078N-X118R-X128S-X185Q, X078N-X118R-X128S-X210I, X078N-X118R-X128S-X217L, X078N-X118R-X128S-X218S, X078N-X118R-X128S-X248D, X078N-X118R-X128S-X259P, X078N-X118R-X129P-X130S, X078N-X118R-X129P-X145R, X078N-X118R-X129P-X166Q, X078N-X118R-X129P-X185Q, X078N-X118R-X129P-X210I, X078N-X118R-X129P-X217L, X078N-X118R-X129P-X218S, X078N-X118R-X129P-X248D, X078N-X118R-X129P-X259P, X078N-X118R-X130S-X145R, X078N-X118R-X130S-X166Q, X078N-X118R-X130S-X185Q, X078N-X118R-X130S-X210I, X078N-X118R-X130S-X217L, X078N-X118R-X130S-X218S, X078N-X118R-X130S-X248D, X078N-X118R-X130S-X259P, X078N-X118R-X145R-X166Q, X078N-

X118R-X145R-X185Q, X078N-X118R-X145R-X210I, X078N-X118R-X145R-X217L, X078N-X118R-X145R-X218S, X078N-X118R-X145R-X248D, X078N-X118R-X145R-X259P, X078N-X118R-X166Q-X185Q, X078N-X118R-X166Q-X210I, X078N-X118R-X166Q-X217L, X078N-X118R-X166Q-X218S, X078N-X118R-X166Q-X248D, X078N-X118R-X166Q-X259P, X078N-X118R-X185Q-X210I, X078N-X118R-X185Q-X217L, X078N-X118R-X185Q-X218S, X078N-X118R-X185Q-X248D, X078N-X118R-X185Q-X259P, X078N-X118R-X210I-X217L, X078N-X118R-X210I-X218S, X078N-X118R-X210I-X248D, X078N-X118R-X210I-X259P, X078N-X118R-X217L-X218S, X078N-X118R-X217L-X248D, X078N-X118R-X217L-X259P, X078N-X118R-X218S-X248D, X078N-X118R-X218S-X259P, X078N-X118R-X248D-X259P, X078N-X124I-X128S-X129P, X078N-X124I-X128S-X130S, X078N-X124I-X128S-X145R, X078N-X124I-X128S-X166Q, X078N-X124I-X128S-X185Q, X078N-X124I-X128S-X210I, X078N-X124I-X128S-X217L, X078N-X124I-X128S-X218S, X078N-X124I-X128S-X248D, X078N-X124I-X128S-X259P, X078N-X124I-X129P-X130S, X078N-X124I-X129P-X145R, X078N-X124I-X129P-X166Q, X078N-X124I-X129P-X185Q, X078N-X124I-X129P-X210I, X078N-X124I-X129P-X217L, X078N-X124I-X129P-X218S, X078N-X124I-X129P-X248D, X078N-X124I-X129P-X259P, X078N-X124I-X130S-X145R, X078N-X124I-X130S-X166Q, X078N-X124I-X130S-X185Q, X078N-X124I-X130S-X210I, X078N-X124I-X130S-X217L, X078N-X124I-X130S-X218S, X078N-X124I-X130S-X248D, X078N-X124I-X130S-X259P, X078N-X124I-X145R-X166Q, X078N-X124I-X145R-X185Q, X078N-X124I-X145R-X210I, X078N-X124I-X145R-X217L, X078N-X124I-X145R-X218S, X078N-X124I-X145R-X248D, X078N-X124I-X145R-X259P, X078N-X124I-X166Q-X185Q, X078N-X124I-X166Q-X210I, X078N-X124I-X166Q-X217L, X078N-X124I-X166Q-X218S, X078N-X124I-X166Q-X248D, X078N-X124I-X166Q-X259P, X078N-X124I-X185Q-X210I, X078N-X124I-X185Q-X217L, X078N-X124I-X185Q-X218S, X078N-X124I-X185Q-X248D, X078N-X124I-X185Q-X259P, X078N-X124I-X210I-X217L, X078N-X124I-X210I-X218S, X078N-X124I-X210I-X248D, X078N-X124I-X210I-X259P, X078N-X124I-X217L-X218S, X078N-X124I-X217L-X248D, X078N-X124I-X217L-X259P, X078N-X124I-X218S-X248D, X078N-X124I-X218S-X259P, X078N-X124I-X248D-X259P, X078N-X128S-X129P-X130S, X078N-X128S-X129P-X145R, X078N-X128S-X129P-X166Q, X078N-X128S-X129P-X185Q, X078N-X128S-X129P-X210I, X078N-X128S-X129P-X217L, X078N-X128S-X129P-X218S, X078N-X128S-X129P-X248D, X078N-X128S-X129P-X259P, X078N-X128S-X130S-X145R, X078N-X128S-X130S-X166Q, X078N-X128S-X130S-X185Q, X078N-X128S-X130S-X210I, X078N-X128S-X130S-X217L, X078N-X128S-X130S-X218S, X078N-X128S-X130S-X248D, X078N-X128S-X130S-X259P, X078N-X128S-X145R-X166Q, X078N-X128S-X145R-X185Q, X078N-X128S-X145R-X210I, X078N-X128S-X145R-X217L, X078N-X128S-X145R-X218S, X078N-X128S-X145R-X248D, X078N-X128S-X145R-X259P, X078N-X128S-X166Q-X185Q, X078N-X128S-X166Q-X210I, X078N-X128S-X166Q-X217L, X078N-X128S-X166Q-X218S, X078N-X128S-X166Q-X248D, X078N-X128S-X166Q-X259P, X078N-X128S-X185Q-X210I, X078N-X128S-X185Q-X217L, X078N-X128S-X185Q-X218S, X078N-X128S-X185Q-X248D, X078N-X128S-X185Q-X259P, X078N-X128S-X210I-X217L, X078N-X128S-X210I-X218S, X078N-X128S-X210I-X248D, X078N-X128S-X210I-X259P, X078N-X128S-X217L-X218S, X078N-X128S-X217L-X248D, X078N-X128S-X217L-X259P, X078N-X128S-X218S-X248D, X078N-X128S-X218S-X259P, X078N-X128S-X248D-X259P, X078N-X129P-X130S-X145R, X078N-X129P-X130S-X166Q, X078N-X129P-X130S-X185Q, X078N-X129P-X130S-X210I, X078N-X129P-X130S-X217L, X078N-X129P-X130S-X218S, X078N-X129P-X130S-X248D, X078N-X129P-X130S-X259P, X078N-X129P-X145R-X166Q, X078N-X129P-X145R-X185Q, X078N-X129P-X145R-X210I, X078N-X129P-X145R-X217L, X078N-X129P-X145R-X218S, X078N-X129P-X145R-X248D, X078N-X129P-X145R-X259P, X078N-X129P-X166Q-X185Q, X078N-X129P-X166Q-X210I, X078N-X129P-X166Q-X217L, X078N-X129P-X166Q-X218S, X078N-X129P-X166Q-X248D, X078N-X129P-X166Q-X259P, X078N-X129P-X185Q-X210I, X078N-X129P-X185Q-X217L, X078N-X129P-X185Q-X218S, X078N-X129P-X185Q-X248D, X078N-X129P-X185Q-X259P, X078N-X129P-X210I-X217L, X078N-X129P-X210I-X218S, X078N-X129P-X210I-X248D, X078N-X129P-X210I-X259P, X078N-X129P-X217L-X218S, X078N-X129P-X217L-X248D, X078N-X129P-X217L-X259P, X078N-X129P-X218S-X248D, X078N-X129P-X218S-X259P, X078N-X129P-X248D-X259P, X078N-X130S-X145R-X166Q, X078N-X130S-X145R-X185Q, X078N-X130S-X145R-X210I, X078N-X130S-X145R-X217L, X078N-X130S-X145R-X218S, X078N-X130S-X145R-X248D, X078N-X130S-X145R-X259P, X078N-X130S-X166Q-X185Q, X078N-X130S-X166Q-X210I, X078N-X130S-X166Q-X217L, X078N-X130S-X166Q-X218S, X078N-X130S-X166Q-X248D, X078N-X130S-X166Q-X259P, X078N-X130S-X185Q-X210I, X078N-X130S-X185Q-X217L, X078N-X130S-X185Q-X218S, X078N-X130S-X185Q-X248D, X078N-X130S-X185Q-X259P, X078N-X130S-X210I-X217L, X078N-X130S-X210I-X218S, X078N-X130S-X210I-X248D, X078N-X130S-X210I-X259P, X078N-X130S-X217L-X218S, X078N-X130S-X217L-X248D, X078N-X130S-X217L-X259P, X078N-X130S-X218S-X248D, X078N-X130S-X218S-X259P, X078N-X130S-X248D-X259P, X078N-X145R-X166Q-X185Q, X078N-X145R-X166Q-X210I, X078N-X145R-X166Q-X217L, X078N-X145R-X166Q-X218S, X078N-X145R-X166Q-X248D, X078N-X145R-X166Q-X259P, X078N-X145R-X185Q-X210I, X078N-X145R-X185Q-X217L, X078N-X145R-X185Q-X218S, X078N-X145R-X185Q-X248D, X078N-X145R-X185Q-X259P, X078N-X145R-X210I-X217L, X078N-X145R-X210I-X218S, X078N-X145R-X210I-X248D, X078N-X145R-X210I-X259P, X078N-X145R-X217L-X218S, X078N-X145R-X217L-X248D, X078N-X145R-X217L-X259P, X078N-X145R-X218S-X248D, X078N-X145R-X218S-X259P, X078N-X145R-X248D-X259P, X078N-X166Q-X185Q-X210I, X078N-X166Q-X185Q-X217L, X078N-X166Q-X185Q-X218S, X078N-X166Q-X185Q-X248D, X078N-X166Q-X185Q-X259P, X078N-X166Q-X210I-X217L, X078N-X166Q-X210I-X218S, X078N-X166Q-X210I-X248D, X078N-X166Q-X210I-X259P, X078N-X166Q-X217L-X218S, X078N-X166Q-X217L-X248D, X078N-X166Q-X217L-X259P, X078N-X166Q-X218S-X248D, X078N-X166Q-X218S-X259P, X078N-X166Q-X248D-X259P, X078N-X185Q-X210I-X217L, X078N-X185Q-X210I-X218S, X078N-X185Q-X210I-X248D, X078N-X185Q-X210I-X259P, X078N-X185Q-X217L-X218S, X078N-X185Q-X217L-X248D, X078N-X185Q-X217L-X259P, X078N-X185Q-X218S-

X248D, X078N-X185Q-X218S-X259P, X078N-X185Q-X248D-X259P, X078N-X210I-X217L-X218S, X078N-X210I-X217L-X248D, X078N-X210I-X217L-X259P, X078N-X210I-X218S-X248D, X078N-X210I-X218S-X259P, X078N-X210I-X248D-X259P, X078N-X217L-X218S-X248D, X078N-X217L-X218S-X259P, X078N-X217L-X248D-X259P, X078N-X218S-X248D-X259P, X079I-X087D-X118R-X124I, X079I-X087D-X118R-X128S, X079I-X087D-X118R-X129P, X079I-X087D-X118R-X130S, X079I-X087D-X118R-X145R, X079I-X087D-X118R-X166Q, X079I-X087D-X118R-X185Q, X079I-X087D-X118R-X210I, X079I-X087D-X118R-X217L, X079I-X087D-X118R-X218S, X079I-X087D-X118R-X248D, X079I-X087D-X118R-X259P, X079I-X087D-X124I-X128S, X079I-X087D-X124I-X129P, X079I-X087D-X124I-X130S, X079I-X087D-X124I-X145R, X079I-X087D-X124I-X166Q, X079I-X087D-X124I-X185Q, X079I-X087D-X124I-X210I, X079I-X087D-X124I-X217L, X079I-X087D-X124I-X218S, X079I-X087D-X124I-X248D, X079I-X087D-X124I-X259P, X079I-X087D-X128S-X129P, X079I-X087D-X128S-X130S, X079I-X087D-X128S-X145R, X079I-X087D-X128S-X166Q, X079I-X087D-X128S-X185Q, X079I-X087D-X128S-X210I, X079I-X087D-X128S-X217L, X079I-X087D-X128S-X218S, X079I-X087D-X128S-X248D, X079I-X087D-X128S-X259P, X079I-X087D-X129P-X130S, X079I-X087D-X129P-X145R, X079I-X087D-X129P-X166Q, X079I-X087D-X129P-X185Q, X079I-X087D-X129P-X210I, X079I-X087D-X129P-X217L, X079I-X087D-X129P-X218S, X079I-X087D-X129P-X248D, X079I-X087D-X129P-X259P, X079I-X087D-X130S-X145R, X079I-X087D-X130S-X166Q, X079I-X087D-X130S-X185Q, X079I-X087D-X130S-X210I, X079I-X087D-X130S-X217L, X079I-X087D-X130S-X218S, X079I-X087D-X130S-X248D, X079I-X087D-X130S-X259P, X079I-X087D-X145R-X166Q, X079I-X087D-X145R-X185Q, X079I-X087D-X145R-X210I, X079I-X087D-X145R-X217L, X079I-X087D-X145R-X218S, X079I-X087D-X145R-X248D, X079I-X087D-X145R-X259P, X079I-X087D-X166Q-X185Q, X079I-X087D-X166Q-X210I, X079I-X087D-X166Q-X217L, X079I-X087D-X166Q-X218S, X079I-X087D-X166Q-X248D, X079I-X087D-X166Q-X259P, X079I-X087D-X185Q-X210I, X079I-X087D-X185Q-X217L, X079I-X087D-X185Q-X218S, X079I-X087D-X185Q-X248D, X079I-X087D-X185Q-X259P, X079I-X087D-X210I-X217L, X079I-X087D-X210I-X218S, X079I-X087D-X210I-X248D, X079I-X087D-X210I-X259P, X079I-X087D-X217L-X218S, X079I-X087D-X217L-X248D, X079I-X087D-X217L-X259P, X079I-X087D-X218S-X248D, X079I-X087D-X218S-X259P, X079I-X087D-X248D-X259P, X079I-X118R-X124I-X128S, X079I-X118R-X124I-X129P, X079I-X118R-X124I-X130S, X079I-X118R-X124I-X145R, X079I-X118R-X124I-X166Q, X079I-X118R-X124I-X185Q, X079I-X118R-X124I-X210I, X079I-X118R-X124I-X217L, X079I-X118R-X124I-X218S, X079I-X118R-X124I-X248D, X079I-X118R-X124I-X259P, X079I-X118R-X128S-X129P, X079I-X118R-X128S-X130S, X079I-X118R-X128S-X145R, X079I-X118R-X128S-X166Q, X079I-X118R-X128S-X185Q, X079I-X118R-X128S-X210I, X079I-X118R-X128S-X217L, X079I-X118R-X128S-X218S, X079I-X118R-X128S-X248D, X079I-X118R-X128S-X259P, X079I-X118R-X129P-X130S, X079I-X118R-X129P-X145R, X079I-X118R-X129P-X166Q, X079I-X118R-X129P-X185Q, X079I-X118R-X129P-X210I, X079I-X118R-X129P-X217L, X079I-X118R-X129P-X218S, X079I-X118R-X129P-X248D, X079I-X118R-X129P-X259P, X079I-X118R-X130S-X145R, X079I-X118R-X130S-X166Q, X079I-X118R-X130S-X185Q, X079I-X118R-X130S-X210I, X079I-X118R-X130S-X217L, X079I-X118R-X130S-X218S, X079I-X118R-X130S-X248D, X079I-X118R-X130S-X259P, X079I-X118R-X145R-X166Q, X079I-X118R-X145R-X185Q, X079I-X118R-X145R-X210I, X079I-X118R-X145R-X217L, X079I-X118R-X145R-X218S, X079I-X118R-X145R-X248D, X079I-X118R-X145R-X259P, X079I-X118R-X166Q-X185Q, X079I-X118R-X166Q-X210I, X079I-X118R-X166Q-X217L, X079I-X118R-X166Q-X218S, X079I-X118R-X166Q-X248D, X079I-X118R-X166Q-X259P, X079I-X118R-X185Q-X210I, X079I-X118R-X185Q-X217L, X079I-X118R-X185Q-X218S, X079I-X118R-X185Q-X248D, X079I-X118R-X185Q-X259P, X079I-X118R-X210I-X217L, X079I-X118R-X210I-X218S, X079I-X118R-X210I-X248D, X079I-X118R-X210I-X259P, X079I-X118R-X217L-X218S, X079I-X118R-X217L-X248D, X079I-X118R-X217L-X259P, X079I-X118R-X218S-X248D, X079I-X118R-X218S-X259P, X079I-X118R-X248D-X259P, X079I-X124I-X128S-X129P, X079I-X124I-X128S-X130S, X079I-X124I-X128S-X145R, X079I-X124I-X128S-X166Q, X079I-X124I-X128S-X185Q, X079I-X124I-X128S-X210I, X079I-X124I-X128S-X217L, X079I-X124I-X128S-X218S, X079I-X124I-X128S-X248D, X079I-X124I-X128S-X259P, X079I-X124I-X129P-X130S, X079I-X124I-X129P-X145R, X079I-X124I-X129P-X166Q, X079I-X124I-X129P-X185Q, X079I-X124I-X129P-X210I, X079I-X124I-X129P-X217L, X079I-X124I-X129P-X218S, X079I-X124I-X129P-X248D, X079I-X124I-X129P-X259P, X079I-X124I-X130S-X145R, X079I-X124I-X130S-X166Q, X079I-X124I-X130S-X185Q, X079I-X124I-X130S-X210I, X079I-X124I-X130S-X217L, X079I-X124I-X130S-X218S, X079I-X124I-X130S-X248D, X079I-X124I-X130S-X259P, X079I-X124I-X145R-X166Q, X079I-X124I-X145R-X185Q, X079I-X124I-X145R-X210I, X079I-X124I-X145R-X217L, X079I-X124I-X145R-X218S, X079I-X124I-X145R-X248D, X079I-X124I-X145R-X259P, X079I-X124I-X166Q-X185Q, X079I-X124I-X166Q-X210I, X079I-X124I-X166Q-X217L, X079I-X124I-X166Q-X218S, X079I-X124I-X166Q-X248D, X079I-X124I-X166Q-X259P, X079I-X124I-X185Q-X210I, X079I-X124I-X185Q-X217L, X079I-X124I-X185Q-X218S, X079I-X124I-X185Q-X248D, X079I-X124I-X185Q-X259P, X079I-X124I-X210I-X217L, X079I-X124I-X210I-X218S, X079I-X124I-X210I-X248D, X079I-X124I-X210I-X259P, X079I-X124I-X217L-X218S, X079I-X124I-X217L-X248D, X079I-X124I-X217L-X259P, X079I-X124I-X218S-X248D, X079I-X124I-X218S-X259P, X079I-X124I-X248D-X259P, X079I-X128S-X129P-X130S, X079I-X128S-X129P-X145R, X079I-X128S-X129P-X166Q, X079I-X128S-X129P-X185Q, X079I-X128S-X129P-X210I, X079I-X128S-X129P-X217L, X079I-X128S-X129P-X218S, X079I-X128S-X129P-X248D, X079I-X128S-X129P-X259P, X079I-X128S-X130S-X145R, X079I-X128S-X130S-X166Q, X079I-X128S-X130S-X185Q, X079I-X128S-X130S-X210I, X079I-X128S-X130S-X217L, X079I-X128S-X130S-X218S, X079I-X128S-X130S-X248D, X079I-X128S-X130S-X259P, X079I-X128S-X145R-X166Q, X079I-X128S-X145R-X185Q, X079I-X128S-X145R-X210I, X079I-X128S-X145R-X217L, X079I-X128S-X145R-X218S, X079I-X128S-X145R-X248D, X079I-X128S-X145R-

X259P, X079I-X128S-X166Q-X185Q, X079I-X128S-X166Q-X210I, X079I-X128S-X166Q-X217L, X079I-X128S-X166Q-X218S, X079I-X128S-X166Q-X248D, X079I-X128S-X166Q-X259P, X079I-X128S-X185Q-X210I, X079I-X128S-X185Q-X217L, X079I-X128S-X185Q-X218S, X079I-X128S-X185Q-X248D, X079I-X128S-X185Q-X259P, X079I-X128S-X210I-X217L, X079I-X128S-X210I-X218S, X079I-X128S-X210I-X248D, X079I-X128S-X210I-X259P, X079I-X128S-X217L-X218S, X079I-X128S-X217L-X248D, X079I-X128S-X217L-X259P, X079I-X128S-X218S-X248D, X079I-X128S-X218S-X259P, X079I-X128S-X248D-X259P, X079I-X129P-X130S-X145R, X079I-X129P-X130S-X166Q, X079I-X129P-X130S-X185Q, X079I-X129P-X130S-X210I, X079I-X129P-X130S-X217L, X079I-X129P-X130S-X218S, X079I-X129P-X130S-X248D, X079I-X129P-X130S-X259P, X079I-X129P-X145R-X166Q, X079I-X129P-X145R-X185Q, X079I-X129P-X145R-X210I, X079I-X129P-X145R-X217L, X079I-X129P-X145R-X218S, X079I-X129P-X145R-X248D, X079I-X129P-X145R-X259P, X079I-X129P-X166Q-X185Q, X079I-X129P-X166Q-X210I, X079I-X129P-X166Q-X217L, X079I-X129P-X166Q-X218S, X079I-X129P-X166Q-X248D, X079I-X129P-X166Q-X259P, X079I-X129P-X185Q-X210I, X079I-X129P-X185Q-X217L, X079I-X129P-X185Q-X218S, X079I-X129P-X185Q-X248D, X079I-X129P-X185Q-X259P, X079I-X129P-X210I-X217L, X079I-X129P-X210I-X218S, X079I-X129P-X210I-X248D, X079I-X129P-X210I-X259P, X079I-X129P-X217L-X218S, X079I-X129P-X217L-X248D, X079I-X129P-X217L-X259P, X079I-X129P-X218S-X248D, X079I-X129P-X218S-X259P, X079I-X129P-X248D-X259P, X079I-X130S-X145R-X166Q, X079I-X130S-X145R-X185Q, X079I-X130S-X145R-X210I, X079I-X130S-X145R-X217L, X079I-X130S-X145R-X218S, X079I-X130S-X145R-X248D, X079I-X130S-X145R-X259P, X079I-X130S-X166Q-X185Q, X079I-X130S-X166Q-X210I, X079I-X130S-X166Q-X217L, X079I-X130S-X166Q-X218S, X079I-X130S-X166Q-X248D, X079I-X130S-X166Q-X259P, X079I-X130S-X185Q-X210I, X079I-X130S-X185Q-X217L, X079I-X130S-X185Q-X218S, X079I-X130S-X185Q-X248D, X079I-X130S-X185Q-X259P, X079I-X130S-X210I-X217L, X079I-X130S-X210I-X218S, X079I-X130S-X210I-X248D, X079I-X130S-X210I-X259P, X079I-X130S-X217L-X218S, X079I-X130S-X217L-X248D, X079I-X130S-X217L-X259P, X079I-X130S-X218S-X248D, X079I-X130S-X218S-X259P, X079I-X130S-X248D-X259P, X079I-X145R-X166Q-X185Q, X079I-X145R-X166Q-X210I, X079I-X145R-X166Q-X217L, X079I-X145R-X166Q-X218S, X079I-X145R-X166Q-X248D, X079I-X145R-X166Q-X259P, X079I-X145R-X185Q-X210I, X079I-X145R-X185Q-X217L, X079I-X145R-X185Q-X218S, X079I-X145R-X185Q-X248D, X079I-X145R-X185Q-X259P, X079I-X145R-X210I-X217L, X079I-X145R-X210I-X218S, X079I-X145R-X210I-X248D, X079I-X145R-X210I-X259P, X079I-X145R-X217L-X218S, X079I-X145R-X217L-X248D, X079I-X145R-X217L-X259P, X079I-X145R-X218S-X248D, X079I-X145R-X218S-X259P, X079I-X145R-X248D-X259P, X079I-X166Q-X185Q-X210I, X079I-X166Q-X185Q-X217L, X079I-X166Q-X185Q-X218S, X079I-X166Q-X185Q-X248D, X079I-X166Q-X185Q-X259P, X079I-X166Q-X210I-X217L, X079I-X166Q-X210I-X218S, X079I-X166Q-X210I-X248D, X079I-X166Q-X210I-X259P, X079I-X166Q-X217L-X218S, X079I-X166Q-X217L-X248D, X079I-X166Q-X217L-X259P, X079I-X166Q-X218S-X248D, X079I-X166Q-X218S-X259P, X079I-X166Q-X248D-X259P, X079I-X185Q-X210I-X217L, X079I-X185Q-X210I-X218S, X079I-X185Q-X210I-X248D, X079I-X185Q-X210I-X259P, X079I-X185Q-X217L-X218S, X079I-X185Q-X217L-X248D, X079I-X185Q-X217L-X259P, X079I-X185Q-X218S-X248D, X079I-X185Q-X218S-X259P, X079I-X185Q-X248D-X259P, X079I-X210I-X217L-X218S, X079I-X210I-X217L-X248D, X079I-X210I-X217L-X259P, X079I-X210I-X218S-X248D, X079I-X210I-X218S-X259P, X079I-X210I-X248D-X259P, X079I-X217L-X218S-X248D, X079I-X217L-X218S-X259P, X079I-X217L-X248D-X259P, X079I-X218S-X248D-X259P, X087D-X118R-X124I-X128S, X087D-X118R-X124I-X129P, X087D-X118R-X124I-X130S, X087D-X118R-X124I-X145R, X087D-X118R-X124I-X166Q, X087D-X118R-X124I-X185Q, X087D-X118R-X124I-X210I, X087D-X118R-X124I-X217L, X087D-X118R-X124I-X218S, X087D-X118R-X124I-X248D, X087D-X118R-X124I-X259P, X087D-X118R-X128S-X129P, X087D-X118R-X128S-X130S, X087D-X118R-X128S-X145R, X087D-X118R-X128S-X166Q, X087D-X118R-X128S-X185Q, X087D-X118R-X128S-X210I, X087D-X118R-X128S-X217L, X087D-X118R-X128S-X218S, X087D-X118R-X128S-X248D, X087D-X118R-X128S-X259P, X087D-X118R-X129P-X130S, X087D-X118R-X129P-X145R, X087D-X118R-X129P-X166Q, X087D-X118R-X129P-X185Q, X087D-X118R-X129P-X210I, X087D-X118R-X129P-X217L, X087D-X118R-X129P-X218S, X087D-X118R-X129P-X248D, X087D-X118R-X129P-X259P, X087D-X118R-X130S-X145R, X087D-X118R-X130S-X166Q, X087D-X118R-X130S-X185Q, X087D-X118R-X130S-X210I, X087D-X118R-X130S-X217L, X087D-X118R-X130S-X218S, X087D-X118R-X130S-X248D, X087D-X118R-X130S-X259P, X087D-X118R-X145R-X166Q, X087D-X118R-X145R-X185Q, X087D-X118R-X145R-X210I, X087D-X118R-X145R-X217L, X087D-X118R-X145R-X218S, X087D-X118R-X145R-X248D, X087D-X118R-X145R-X259P, X087D-X118R-X166Q-X185Q, X087D-X118R-X166Q-X210I, X087D-X118R-X166Q-X217L, X087D-X118R-X166Q-X218S, X087D-X118R-X166Q-X248D, X087D-X118R-X166Q-X259P, X087D-X118R-X185Q-X210I, X087D-X118R-X185Q-X217L, X087D-X118R-X185Q-X218S, X087D-X118R-X185Q-X248D, X087D-X118R-X185Q-X259P, X087D-X118R-X210I-X217L, X087D-X118R-X210I-X218S, X087D-X118R-X210I-X248D, X087D-X118R-X210I-X259P, X087D-X118R-X217L-X218S, X087D-X118R-X217L-X248D, X087D-X118R-X217L-X259P, X087D-X118R-X218S-X248D, X087D-X118R-X218S-X259P, X087D-X118R-X248D-X259P, X087D-X124I-X128S-X129P, X087D-X124I-X128S-X130S, X087D-X124I-X128S-X145R, X087D-X124I-X128S-X166Q, X087D-X124I-X128S-X185Q, X087D-X124I-X128S-X210I, X087D-X124I-X128S-X217L, X087D-X124I-X128S-X218S, X087D-X124I-X128S-X248D, X087D-X124I-X128S-X259P, X087D-X124I-X129P-X130S, X087D-X124I-X129P-X145R, X087D-X124I-X129P-X166Q, X087D-X124I-X129P-X185Q, X087D-X124I-X129P-X210I, X087D-X124I-X129P-X217L, X087D-X124I-X129P-X218S, X087D-X124I-X129P-X248D, X087D-X124I-X129P-X259P, X087D-X124I-X130S-X145R, X087D-X124I-X130S-X166Q, X087D-X124I-X130S-X185Q, X087D-X124I-X130S-X210I, X087D-X124I-X130S-X217L, X087D-X124I-X130S-X218S, X087D-X124I-X130S-X248D, X087D-X124I-X130S-X259P, X087D-

X124I-X145R-X166Q, X087D-X124I-X145R-X185Q, X087D-X124I-X145R-X210I, X087D-X124I-X145R-X217L, X087D-X124I-X145R-X218S, X087D-X124I-X145R-X248D, X087D-X124I-X145R-X259P, X087D-X124I-X166Q-X185Q, X087D-X124I-X166Q-X210I, X087D-X124I-X166Q-X217L, X087D-X124I-X166Q-X218S, X087D-X124I-X166Q-X248D, X087D-X124I-X166Q-X259P, X087D-X124I-X185Q-X210I, X087D-X124I-X185Q-X217L, X087D-X124I-X185Q-X218S, X087D-X124I-X185Q-X248D, X087D-X124I-X185Q-X259P, X087D-X124I-X210I-X217L, X087D-X124I-X210I-X218S, X087D-X124I-X210I-X248D, X087D-X124I-X210I-X259P, X087D-X124I-X217L-X218S, X087D-X124I-X217L-X248D, X087D-X124I-X217L-X259P, X087D-X124I-X218S-X248D, X087D-X124I-X218S-X259P, X087D-X124I-X248D-X259P, X087D-X128S-X129P-X130S, X087D-X128S-X129P-X145R, X087D-X128S-X129P-X166Q, X087D-X128S-X129P-X185Q, X087D-X128S-X129P-X210I, X087D-X128S-X129P-X217L, X087D-X128S-X129P-X218S, X087D-X128S-X129P-X248D, X087D-X128S-X129P-X259P, X087D-X128S-X130S-X145R, X087D-X128S-X130S-X166Q, X087D-X128S-X130S-X185Q, X087D-X128S-X130S-X210I, X087D-X128S-X130S-X217L, X087D-X128S-X130S-X218S, X087D-X128S-X130S-X248D, X087D-X128S-X130S-X259P, X087D-X128S-X145R-X166Q, X087D-X128S-X145R-X185Q, X087D-X128S-X145R-X210I, X087D-X128S-X145R-X217L, X087D-X128S-X145R-X218S, X087D-X128S-X145R-X248D, X087D-X128S-X145R-X259P, X087D-X128S-X166Q-X185Q, X087D-X128S-X166Q-X210I, X087D-X128S-X166Q-X217L, X087D-X128S-X166Q-X218S, X087D-X128S-X166Q-X248D, X087D-X128S-X166Q-X259P, X087D-X128S-X185Q-X210I, X087D-X128S-X185Q-X217L, X087D-X128S-X185Q-X218S, X087D-X128S-X185Q-X248D, X087D-X128S-X185Q-X259P, X087D-X128S-X210I-X217L, X087D-X128S-X210I-X218S, X087D-X128S-X210I-X248D, X087D-X128S-X210I-X259P, X087D-X128S-X217L-X218S, X087D-X128S-X217L-X248D, X087D-X128S-X217L-X259P, X087D-X128S-X218S-X248D, X087D-X128S-X218S-X259P, X087D-X128S-X248D-X259P, X087D-X129P-X130S-X145R, X087D-X129P-X130S-X166Q, X087D-X129P-X130S-X185Q, X087D-X129P-X130S-X210I, X087D-X129P-X130S-X217L, X087D-X129P-X130S-X218S, X087D-X129P-X130S-X248D, X087D-X129P-X130S-X259P, X087D-X129P-X145R-X166Q, X087D-X129P-X145R-X185Q, X087D-X129P-X145R-X210I, X087D-X129P-X145R-X217L, X087D-X129P-X145R-X218S, X087D-X129P-X145R-X248D, X087D-X129P-X145R-X259P, X087D-X129P-X166Q-X185Q, X087D-X129P-X166Q-X210I, X087D-X129P-X166Q-X217L, X087D-X129P-X166Q-X218S, X087D-X129P-X166Q-X248D, X087D-X129P-X166Q-X259P, X087D-X129P-X185Q-X210I, X087D-X129P-X185Q-X217L, X087D-X129P-X185Q-X218S, X087D-X129P-X185Q-X248D, X087D-X129P-X185Q-X259P, X087D-X129P-X210I-X217L, X087D-X129P-X210I-X218S, X087D-X129P-X210I-X248D, X087D-X129P-X210I-X259P, X087D-X129P-X217L-X218S, X087D-X129P-X217L-X248D, X087D-X129P-X217L-X259P, X087D-X129P-X218S-X248D, X087D-X129P-X218S-X259P, X087D-X129P-X248D-X259P, X087D-X130S-X145R-X166Q, X087D-X130S-X145R-X185Q, X087D-X130S-X145R-X210I, X087D-X130S-X145R-X217L, X087D-X130S-X145R-X218S, X087D-X130S-X145R-X248D, X087D-X130S-X145R-X259P, X087D-X130S-X166Q-X185Q, X087D-X130S-X166Q-X210I, X087D-X130S-X166Q-X217L, X087D-X130S-X166Q-X218S, X087D-X130S-X166Q-X248D, X087D-X130S-X166Q-X259P, X087D-X130S-X185Q-X210I, X087D-X130S-X185Q-X217L, X087D-X130S-X185Q-X218S, X087D-X130S-X185Q-X248D, X087D-X130S-X185Q-X259P, X087D-X130S-X210I-X217L, X087D-X130S-X210I-X218S, X087D-X130S-X210I-X248D, X087D-X130S-X210I-X259P, X087D-X130S-X217L-X218S, X087D-X130S-X217L-X248D, X087D-X130S-X217L-X259P, X087D-X130S-X218S-X248D, X087D-X130S-X218S-X259P, X087D-X130S-X248D-X259P, X087D-X145R-X166Q-X185Q, X087D-X145R-X166Q-X210I, X087D-X145R-X166Q-X217L, X087D-X145R-X166Q-X218S, X087D-X145R-X166Q-X248D, X087D-X145R-X166Q-X259P, X087D-X145R-X185Q-X210I, X087D-X145R-X185Q-X217L, X087D-X145R-X185Q-X218S, X087D-X145R-X185Q-X248D, X087D-X145R-X185Q-X259P, X087D-X145R-X210I-X217L, X087D-X145R-X210I-X218S, X087D-X145R-X210I-X248D, X087D-X145R-X210I-X259P, X087D-X145R-X217L-X218S, X087D-X145R-X217L-X248D, X087D-X145R-X217L-X259P, X087D-X145R-X218S-X248D, X087D-X145R-X218S-X259P, X087D-X145R-X248D-X259P, X087D-X166Q-X185Q-X210I, X087D-X166Q-X185Q-X217L, X087D-X166Q-X185Q-X218S, X087D-X166Q-X185Q-X248D, X087D-X166Q-X185Q-X259P, X087D-X166Q-X210I-X217L, X087D-X166Q-X210I-X218S, X087D-X166Q-X210I-X248D, X087D-X166Q-X210I-X259P, X087D-X166Q-X217L-X218S, X087D-X166Q-X217L-X248D, X087D-X166Q-X217L-X259P, X087D-X166Q-X218S-X248D, X087D-X166Q-X218S-X259P, X087D-X166Q-X248D-X259P, X087D-X185Q-X210I-X217L, X087D-X185Q-X210I-X218S, X087D-X185Q-X210I-X248D, X087D-X185Q-X210I-X259P, X087D-X185Q-X217L-X218S, X087D-X185Q-X217L-X248D, X087D-X185Q-X217L-X259P, X087D-X185Q-X218S-X248D, X087D-X185Q-X218S-X259P, X087D-X185Q-X248D-X259P, X087D-X210I-X217L-X218S, X087D-X210I-X217L-X248D, X087D-X210I-X217L-X259P, X087D-X210I-X218S-X248D, X087D-X210I-X218S-X259P, X087D-X210I-X248D-X259P, X087D-X217L-X218S-X248D, X087D-X217L-X218S-X259P, X087D-X217L-X248D-X259P, X087D-X218S-X248D-X259P, X118R-X124I-X128S-X129P, X118R-X124I-X128S-X130S, X118R-X124I-X128S-X145R, X118R-X124I-X128S-X166Q, X118R-X124I-X128S-X185Q, X118R-X124I-X128S-X210I, X118R-X124I-X128S-X217L, X118R-X124I-X128S-X218S, X118R-X124I-X128S-X248D, X118R-X124I-X128S-X259P, X118R-X124I-X129P-X130S, X118R-X124I-X129P-X145R, X118R-X124I-X129P-X166Q, X118R-X124I-X129P-X185Q, X118R-X124I-X129P-X210I, X118R-X124I-X129P-X217L, X118R-X124I-X129P-X218S, X118R-X124I-X129P-X248D, X118R-X124I-X129P-X259P, X118R-X124I-X130S-X145R, X118R-X124I-X130S-X166Q, X118R-X124I-X130S-X185Q, X118R-X124I-X130S-X210I, X118R-X124I-X130S-X217L, X118R-X124I-X130S-X218S, X118R-X124I-X130S-X248D, X118R-X124I-X130S-X259P, X118R-X124I-X145R-X166Q, X118R-X124I-X145R-X185Q, X118R-X124I-X145R-X210I, X118R-X124I-X145R-X217L, X118R-X124I-X145R-X218S, X118R-X124I-X145R-X248D, X118R-X124I-X145R-X259P, X118R-X124I-X166Q-X185Q, X118R-X124I-X166Q-X210I, X118R-X124I-X166Q-X217L, X118R-X124I-X166Q-X218S, X118R-X124I-X166Q-X248D, X118R-X124I-X166Q-X259P, X118R-X124I-X185Q-X210I, X118R-X124I-X185Q-

X217L, X118R-X124I-X185Q-X218S, X118R-X124I-X185Q-X248D, X118R-X124I-X185Q-X259P, X118R-X124I-X210I-X217L, X118R-X124I-X210I-X218S, X118R-X124I-X210I-X248D, X118R-X124I-X210I-X259P, X118R-X124I-X217L-X218S, X118R-X124I-X217L-X248D, X118R-X124I-X217L-X259P, X118R-X124I-X218S-X248D, X118R-X124I-X218S-X259P, X118R-X124I-X248D-X259P, X118R-X128S-X129P-X130S, X118R-X128S-X129P-X145R, X118R-X128S-X129P-X166Q, X118R-X128S-X129P-X185Q, X118R-X128S-X129P-X210I, X118R-X128S-X129P-X217L, X118R-X128S-X129P-X218S, X118R-X128S-X129P-X248D, X118R-X128S-X129P-X259P, X118R-X128S-X130S-X145R, X118R-X128S-X130S-X166Q, X118R-X128S-X130S-X185Q, X118R-X128S-X130S-X210I, X118R-X128S-X130S-X217L, X118R-X128S-X130S-X218S, X118R-X128S-X130S-X248D, X118R-X128S-X130S-X259P, X118R-X128S-X145R-X166Q, X118R-X128S-X145R-X185Q, X118R-X128S-X145R-X210I, X118R-X128S-X145R-X217L, X118R-X128S-X145R-X218S, X118R-X128S-X145R-X248D, X118R-X128S-X145R-X259P, X118R-X128S-X166Q-X185Q, X118R-X128S-X166Q-X210I, X118R-X128S-X166Q-X217L, X118R-X128S-X166Q-X218S, X118R-X128S-X166Q-X248D, X118R-X128S-X166Q-X259P, X118R-X128S-X185Q-X210I, X118R-X128S-X185Q-X217L, X118R-X128S-X185Q-X218S, X118R-X128S-X185Q-X248D, X118R-X128S-X185Q-X259P, X118R-X128S-X210I-X217L, X118R-X128S-X210I-X218S, X118R-X128S-X210I-X248D, X118R-X128S-X210I-X259P, X118R-X128S-X217L-X218S, X118R-X128S-X217L-X248D, X118R-X128S-X217L-X259P, X118R-X128S-X218S-X248D, X118R-X128S-X218S-X259P, X118R-X128S-X248D-X259P, X118R-X129P-X130S-X145R, X118R-X129P-X130S-X166Q, X118R-X129P-X130S-X185Q, X118R-X129P-X130S-X210I, X118R-X129P-X130S-X217L, X118R-X129P-X130S-X218S, X118R-X129P-X130S-X248D, X118R-X129P-X130S-X259P, X118R-X129P-X145R-X166Q, X118R-X129P-X145R-X185Q, X118R-X129P-X145R-X210I, X118R-X129P-X145R-X217L, X118R-X129P-X145R-X218S, X118R-X129P-X145R-X248D, X118R-X129P-X145R-X259P, X118R-X129P-X166Q-X185Q, X118R-X129P-X166Q-X210I, X118R-X129P-X166Q-X217L, X118R-X129P-X166Q-X218S, X118R-X129P-X166Q-X248D, X118R-X129P-X166Q-X259P, X118R-X129P-X185Q-X210I, X118R-X129P-X185Q-X217L, X118R-X129P-X185Q-X218S, X118R-X129P-X185Q-X248D, X118R-X129P-X185Q-X259P, X118R-X129P-X210I-X217L, X118R-X129P-X210I-X218S, X118R-X129P-X210I-X248D, X118R-X129P-X210I-X259P, X118R-X129P-X217L-X218S, X118R-X129P-X217L-X248D, X118R-X129P-X217L-X259P, X118R-X129P-X218S-X248D, X118R-X129P-X218S-X259P, X118R-X129P-X248D-X259P, X118R-X130S-X145R-X166Q, X118R-X130S-X145R-X185Q, X118R-X130S-X145R-X210I, X118R-X130S-X145R-X217L, X118R-X130S-X145R-X218S, X118R-X130S-X145R-X248D, X118R-X130S-X145R-X259P, X118R-X130S-X166Q-X185Q, X118R-X130S-X166Q-X210I, X118R-X130S-X166Q-X217L, X118R-X130S-X166Q-X218S, X118R-X130S-X166Q-X248D, X118R-X130S-X166Q-X259P, X118R-X130S-X185Q-X210I, X118R-X130S-X185Q-X217L, X118R-X130S-X185Q-X218S, X118R-X130S-X185Q-X248D, X118R-X130S-X185Q-X259P, X118R-X130S-X210I-X217L, X118R-X130S-X210I-X218S, X118R-X130S-X210I-X248D, X118R-X130S-X210I-X259P, X118R-X130S-X217L-X218S, X118R-X130S-X217L-X248D, X118R-X130S-X217L-X259P, X118R-X130S-X218S-X248D, X118R-X130S-X218S-X259P, X118R-X130S-X248D-X259P, X118R-X145R-X166Q-X185Q, X118R-X145R-X166Q-X210I, X118R-X145R-X166Q-X217L, X118R-X145R-X166Q-X218S, X118R-X145R-X166Q-X248D, X118R-X145R-X166Q-X259P, X118R-X145R-X185Q-X210I, X118R-X145R-X185Q-X217L, X118R-X145R-X185Q-X218S, X118R-X145R-X185Q-X248D, X118R-X145R-X185Q-X259P, X118R-X145R-X210I-X217L, X118R-X145R-X210I-X218S, X118R-X145R-X210I-X248D, X118R-X145R-X210I-X259P, X118R-X145R-X217L-X218S, X118R-X145R-X217L-X248D, X118R-X145R-X217L-X259P, X118R-X145R-X218S-X248D, X118R-X145R-X218S-X259P, X118R-X145R-X248D-X259P, X118R-X166Q-X185Q-X210I, X118R-X166Q-X185Q-X217L, X118R-X166Q-X185Q-X218S, X118R-X166Q-X185Q-X248D, X118R-X166Q-X185Q-X259P, X118R-X166Q-X210I-X217L, X118R-X166Q-X210I-X218S, X118R-X166Q-X210I-X248D, X118R-X166Q-X210I-X259P, X118R-X166Q-X217L-X218S, X118R-X166Q-X217L-X248D, X118R-X166Q-X217L-X259P, X118R-X166Q-X218S-X248D, X118R-X166Q-X218S-X259P, X118R-X166Q-X248D-X259P, X118R-X185Q-X210I-X217L, X118R-X185Q-X210I-X218S, X118R-X185Q-X210I-X248D, X118R-X185Q-X210I-X259P, X118R-X185Q-X217L-X218S, X118R-X185Q-X217L-X248D, X118R-X185Q-X217L-X259P, X118R-X185Q-X218S-X248D, X118R-X185Q-X218S-X259P, X118R-X185Q-X248D-X259P, X118R-X210I-X217L-X218S, X118R-X210I-X217L-X248D, X118R-X210I-X217L-X259P, X118R-X210I-X218S-X248D, X118R-X210I-X218S-X259P, X118R-X210I-X248D-X259P, X118R-X217L-X218S-X248D, X118R-X217L-X218S-X259P, X118R-X217L-X248D-X259P, X118R-X218S-X248D-X259P, X124I-X128S-X129P-X130S, X124I-X128S-X129P-X145R, X124I-X128S-X129P-X166Q, X124I-X128S-X129P-X185Q, X124I-X128S-X129P-X210I, X124I-X128S-X129P-X217L, X124I-X128S-X129P-X218S, X124I-X128S-X129P-X248D, X124I-X128S-X129P-X259P, X124I-X128S-X130S-X145R, X124I-X128S-X130S-X166Q, X124I-X128S-X130S-X185Q, X124I-X128S-X130S-X210I, X124I-X128S-X130S-X217L, X124I-X128S-X130S-X218S, X124I-X128S-X130S-X248D, X124I-X128S-X130S-X259P, X124I-X128S-X145R-X166Q, X124I-X128S-X145R-X185Q, X124I-X128S-X145R-X210I, X124I-X128S-X145R-X217L, X124I-X128S-X145R-X218S, X124I-X128S-X145R-X248D, X124I-X128S-X145R-X259P, X124I-X128S-X166Q-X185Q, X124I-X128S-X166Q-X210I, X124I-X128S-X166Q-X217L, X124I-X128S-X166Q-X218S, X124I-X128S-X166Q-X248D, X124I-X128S-X166Q-X259P, X124I-X128S-X185Q-X210I, X124I-X128S-X185Q-X217L, X124I-X128S-X185Q-X218S, X124I-X128S-X185Q-X248D, X124I-X128S-X185Q-X259P, X124I-X128S-X210I-X217L, X124I-X128S-X210I-X218S, X124I-X128S-X210I-X248D, X124I-X128S-X210I-X259P, X124I-X128S-X217L-X218S, X124I-X128S-X217L-X248D, X124I-X128S-X217L-X259P, X124I-X128S-X218S-X248D, X124I-X128S-X218S-X259P, X124I-X128S-X248D-X259P, X124I-X129P-X130S-X145R, X124I-X129P-X130S-X166Q, X124I-X129P-X130S-X185Q, X124I-X129P-X130S-X210I, X124I-X129P-X130S-X217L, X124I-X129P-X130S-X218S, X124I-X129P-X130S-X248D, X124I-X129P-X130S-X259P, X124I-X129P-X145R-X166Q, X124I-X129P-X145R-X185Q, X124I-X129P-X145R-X210I, X124I-

X129P-X145R-X217L, X124I-X129P-X145R-X218S, X124I-X129P-X145R-X248D, X124I-X129P-X145R-X259P, X124I-X129P-X166Q-X185Q, X124I-X129P-X166Q-X210I, X124I-X129P-X166Q-X217L, X124I-X129P-X166Q-X218S, X124I-X129P-X166Q-X248D, X124I-X129P-X166Q-X259P, X124I-X129P-X185Q-X210I, X124I-X129P-X185Q-X217L, X124I-X129P-X185Q-X218S, X124I-X129P-X185Q-X248D, X124I-X129P-X185Q-X259P, X124I-X129P-X210I-X217L, X124I-X129P-X210I-X218S, X124I-X129P-X210I-X248D, X124I-X129P-X210I-X259P, X124I-X129P-X217L-X218S, X124I-X129P-X217L-X248D, X124I-X129P-X217L-X259P, X124I-X129P-X218S-X248D, X124I-X129P-X218S-X259P, X124I-X129P-X248D-X259P, X124I-X130S-X145R-X166Q, X124I-X130S-X145R-X185Q, X124I-X130S-X145R-X210I, X124I-X130S-X145R-X217L, X124I-X130S-X145R-X218S, X124I-X130S-X145R-X248D, X124I-X130S-X145R-X259P, X124I-X130S-X166Q-X185Q, X124I-X130S-X166Q-X210I, X124I-X130S-X166Q-X217L, X124I-X130S-X166Q-X218S, X124I-X130S-X166Q-X248D, X124I-X130S-X166Q-X259P, X124I-X130S-X185Q-X210I, X124I-X130S-X185Q-X217L, X124I-X130S-X185Q-X218S, X124I-X130S-X185Q-X248D, X124I-X130S-X185Q-X259P, X124I-X130S-X210I-X217L, X124I-X130S-X210I-X218S, X124I-X130S-X210I-X248D, X124I-X130S-X210I-X259P, X124I-X130S-X217L-X218S, X124I-X130S-X217L-X248D, X124I-X130S-X217L-X259P, X124I-X130S-X218S-X248D, X124I-X130S-X218S-X259P, X124I-X130S-X248D-X259P, X124I-X145R-X166Q-X185Q, X124I-X145R-X166Q-X210I, X124I-X145R-X166Q-X217L, X124I-X145R-X166Q-X218S, X124I-X145R-X166Q-X248D, X124I-X145R-X166Q-X259P, X124I-X145R-X185Q-X210I, X124I-X145R-X185Q-X217L, X124I-X145R-X185Q-X218S, X124I-X145R-X185Q-X248D, X124I-X145R-X185Q-X259P, X124I-X145R-X210I-X217L, X124I-X145R-X210I-X218S, X124I-X145R-X210I-X248D, X124I-X145R-X210I-X259P, X124I-X145R-X217L-X218S, X124I-X145R-X217L-X248D, X124I-X145R-X217L-X259P, X124I-X145R-X218S-X248D, X124I-X145R-X218S-X259P, X124I-X145R-X248D-X259P, X124I-X166Q-X185Q-X210I, X124I-X166Q-X185Q-X217L, X124I-X166Q-X185Q-X218S, X124I-X166Q-X185Q-X248D, X124I-X166Q-X185Q-X259P, X124I-X166Q-X210I-X217L, X124I-X166Q-X210I-X218S, X124I-X166Q-X210I-X248D, X124I-X166Q-X210I-X259P, X124I-X166Q-X217L-X218S, X124I-X166Q-X217L-X248D, X124I-X166Q-X217L-X259P, X124I-X166Q-X218S-X248D, X124I-X166Q-X218S-X259P, X124I-X166Q-X248D-X259P, X124I-X185Q-X210I-X217L, X124I-X185Q-X210I-X218S, X124I-X185Q-X210I-X248D, X124I-X185Q-X210I-X259P, X124I-X185Q-X217L-X218S, X124I-X185Q-X217L-X248D, X124I-X185Q-X217L-X259P, X124I-X185Q-X218S-X248D, X124I-X185Q-X218S-X259P, X124I-X185Q-X248D-X259P, X124I-X210I-X217L-X218S, X124I-X210I-X217L-X248D, X124I-X210I-X217L-X259P, X124I-X210I-X218S-X248D, X124I-X210I-X218S-X259P, X124I-X210I-X248D-X259P, X124I-X217L-X218S-X248D, X124I-X217L-X218S-X259P, X124I-X217L-X248D-X259P, X124I-X218S-X248D-X259P, X128S-X129P-X130S-X145R, X128S-X129P-X130S-X166Q, X128S-X129P-X130S-X185Q, X128S-X129P-X130S-X210I, X128S-X129P-X130S-X217L, X128S-X129P-X130S-X218S, X128S-X129P-X130S-X248D, X128S-X129P-X130S-X259P, X128S-X129P-X145R-X166Q, X128S-X129P-X145R-X185Q, X128S-X129P-X145R-X210I, X128S-X129P-X145R-X217L, X128S-X129P-X145R-X218S, X128S-X129P-X145R-X248D, X128S-X129P-X145R-X259P, X128S-X129P-X166Q-X185Q, X128S-X129P-X166Q-X210I, X128S-X129P-X166Q-X217L, X128S-X129P-X166Q-X218S, X128S-X129P-X166Q-X248D, X128S-X129P-X166Q-X259P, X128S-X129P-X185Q-X210I, X128S-X129P-X185Q-X217L, X128S-X129P-X185Q-X218S, X128S-X129P-X185Q-X248D, X128S-X129P-X185Q-X259P, X128S-X129P-X210I-X217L, X128S-X129P-X210I-X218S, X128S-X129P-X210I-X248D, X128S-X129P-X210I-X259P, X128S-X129P-X217L-X218S, X128S-X129P-X217L-X248D, X128S-X129P-X217L-X259P, X128S-X129P-X218S-X248D, X128S-X129P-X218S-X259P, X128S-X129P-X248D-X259P, X128S-X130S-X145R-X166Q, X128S-X130S-X145R-X185Q, X128S-X130S-X145R-X210I, X128S-X130S-X145R-X217L, X128S-X130S-X145R-X218S, X128S-X130S-X145R-X248D, X128S-X130S-X145R-X259P, X128S-X130S-X166Q-X185Q, X128S-X130S-X166Q-X210I, X128S-X130S-X166Q-X217L, X128S-X130S-X166Q-X218S, X128S-X130S-X166Q-X248D, X128S-X130S-X166Q-X259P, X128S-X130S-X185Q-X210I, X128S-X130S-X185Q-X217L, X128S-X130S-X185Q-X218S, X128S-X130S-X185Q-X248D, X128S-X130S-X185Q-X259P, X128S-X130S-X210I-X217L, X128S-X130S-X210I-X218S, X128S-X130S-X210I-X248D, X128S-X130S-X210I-X259P, X128S-X130S-X217L-X218S, X128S-X130S-X217L-X248D, X128S-X130S-X217L-X259P, X128S-X130S-X218S-X248D, X128S-X130S-X218S-X259P, X128S-X130S-X248D-X259P, X128S-X145R-X166Q-X185Q, X128S-X145R-X166Q-X210I, X128S-X145R-X166Q-X217L, X128S-X145R-X166Q-X218S, X128S-X145R-X166Q-X248D, X128S-X145R-X166Q-X259P, X128S-X145R-X185Q-X210I, X128S-X145R-X185Q-X217L, X128S-X145R-X185Q-X218S, X128S-X145R-X185Q-X248D, X128S-X145R-X185Q-X259P, X128S-X145R-X210I-X217L, X128S-X145R-X210I-X218S, X128S-X145R-X210I-X248D, X128S-X145R-X210I-X259P, X128S-X145R-X217L-X218S, X128S-X145R-X217L-X248D, X128S-X145R-X217L-X259P, X128S-X145R-X218S-X248D, X128S-X145R-X218S-X259P, X128S-X145R-X248D-X259P, X128S-X166Q-X185Q-X210I, X128S-X166Q-X185Q-X217L, X128S-X166Q-X185Q-X218S, X128S-X166Q-X185Q-X248D, X128S-X166Q-X185Q-X259P, X128S-X166Q-X210I-X217L, X128S-X166Q-X210I-X218S, X128S-X166Q-X210I-X248D, X128S-X166Q-X210I-X259P, X128S-X166Q-X217L-X218S, X128S-X166Q-X217L-X248D, X128S-X166Q-X217L-X259P, X128S-X166Q-X218S-X248D, X128S-X166Q-X218S-X259P, X128S-X166Q-X248D-X259P, X128S-X185Q-X210I-X217L, X128S-X185Q-X210I-X218S, X128S-X185Q-X210I-X248D, X128S-X185Q-X210I-X259P, X128S-X185Q-X217L-X218S, X128S-X185Q-X217L-X248D, X128S-X185Q-X217L-X259P, X128S-X185Q-X218S-X248D, X128S-X185Q-X218S-X259P, X128S-X185Q-X248D-X259P, X128S-X210I-X217L-X218S, X128S-X210I-X217L-X248D, X128S-X210I-X217L-X259P, X128S-X210I-X218S-X248D, X128S-X210I-X218S-X259P, X128S-X210I-X248D-X259P, X128S-X217L-X218S-X248D, X128S-X217L-X218S-X259P, X128S-X217L-X248D-X259P, X128S-X218S-X248D-X259P, X129P-X130S-X145R-X166Q, X129P-X130S-X145R-X185Q, X129P-X130S-X145R-X210I, X129P-X130S-X145R-X217L, X129P-X130S-X145R-X218S, X129P-X130S-X145R-

X248D, X129P-X130S-X145R-X259P, X129P-X130S-X166Q-X185Q, X129P-X130S-X166Q-X210I, X129P-X130S-X166Q-X217L, X129P-X130S-X166Q-X218S, X129P-X130S-X166Q-X248D, X129P-X130S-X166Q-X259P, X129P-X130S-X185Q-X210I, X129P-X130S-X185Q-X217L, X129P-X130S-X185Q-X218S, X129P-X130S-X185Q-X248D, X129P-X130S-X185Q-X259P, X129P-X130S-X210I-X217L, X129P-X130S-X210I-X218S, X129P-X130S-X210I-X248D, X129P-X130S-X210I-X259P, X129P-X130S-X217L-X218S, X129P-X130S-X217L-X248D, X129P-X130S-X217L-X259P, X129P-X130S-X218S-X248D, X129P-X130S-X218S-X259P, X129P-X130S-X248D-X259P, X129P-X145R-X166Q-X185Q, X129P-X145R-X166Q-X210I, X129P-X145R-X166Q-X217L, X129P-X145R-X166Q-X218S, X129P-X145R-X166Q-X248D, X129P-X145R-X166Q-X259P, X129P-X145R-X185Q-X210I, X129P-X145R-X185Q-X217L, X129P-X145R-X185Q-X218S, X129P-X145R-X185Q-X248D, X129P-X145R-X185Q-X259P, X129P-X145R-X210I-X217L, X129P-X145R-X210I-X218S, X129P-X145R-X210I-X248D, X129P-X145R-X210I-X259P, X129P-X145R-X217L-X218S, X129P-X145R-X217L-X248D, X129P-X145R-X217L-X259P, X129P-X145R-X218S-X248D, X129P-X145R-X218S-X259P, X129P-X145R-X248D-X259P, X129P-X166Q-X185Q-X210I, X129P-X166Q-X185Q-X217L, X129P-X166Q-X185Q-X218S, X129P-X166Q-X185Q-X248D, X129P-X166Q-X185Q-X259P, X129P-X166Q-X210I-X217L, X129P-X166Q-X210I-X218S, X129P-X166Q-X210I-X248D, X129P-X166Q-X210I-X259P, X129P-X166Q-X217L-X218S, X129P-X166Q-X217L-X248D, X129P-X166Q-X217L-X259P, X129P-X166Q-X218S-X248D, X129P-X166Q-X218S-X259P, X129P-X166Q-X248D-X259P, X129P-X185Q-X210I-X217L, X129P-X185Q-X210I-X218S, X129P-X185Q-X210I-X248D, X129P-X185Q-X210I-X259P, X129P-X185Q-X217L-X218S, X129P-X185Q-X217L-X248D, X129P-X185Q-X217L-X259P, X129P-X185Q-X218S-X248D, X129P-X185Q-X218S-X259P, X129P-X185Q-X248D-X259P, X129P-X210I-X217L-X218S, X129P-X210I-X217L-X248D, X129P-X210I-X217L-X259P, X129P-X210I-X218S-X248D, X129P-X210I-X218S-X259P, X129P-X210I-X248D-X259P, X129P-X217L-X218S-X248D, X129P-X217L-X218S-X259P, X129P-X217L-X248D-X259P, X129P-X218S-X248D-X259P, X130S-X145R-X166Q-X185Q, X130S-X145R-X166Q-X210I, X130S-X145R-X166Q-X217L, X130S-X145R-X166Q-X218S, X130S-X145R-X166Q-X248D, X130S-X145R-X166Q-X259P, X130S-X145R-X185Q-X210I, X130S-X145R-X185Q-X217L, X130S-X145R-X185Q-X218S, X130S-X145R-X185Q-X248D, X130S-X145R-X185Q-X259P, X130S-X145R-X210I-X217L, X130S-X145R-X210I-X218S, X130S-X145R-X210I-X248D, X130S-X145R-X210I-X259P, X130S-X145R-X217L-X218S, X130S-X145R-X217L-X248D, X130S-X145R-X217L-X259P, X130S-X145R-X218S-X248D, X130S-X145R-X218S-X259P, X130S-X145R-X248D-X259P, X130S-X166Q-X185Q-X210I, X130S-X166Q-X185Q-X217L, X130S-X166Q-X185Q-X218S, X130S-X166Q-X185Q-X248D, X130S-X166Q-X185Q-X259P, X130S-X166Q-X210I-X217L, X130S-X166Q-X210I-X218S, X130S-X166Q-X210I-X248D, X130S-X166Q-X210I-X259P, X130S-X166Q-X217L-X218S, X130S-X166Q-X217L-X248D, X130S-X166Q-X217L-X259P, X130S-X166Q-X218S-X248D, X130S-X166Q-X218S-X259P, X130S-X166Q-X248D-X259P, X130S-X185Q-X210I-X217L, X130S-X185Q-X210I-X218S, X130S-X185Q-X210I-X248D, X130S-X185Q-X210I-X259P, X130S-X185Q-X217L-X218S, X130S-X185Q-X217L-X248D, X130S-X185Q-X217L-X259P, X130S-X185Q-X218S-X248D, X130S-X185Q-X218S-X259P, X130S-X185Q-X248D-X259P, X130S-X210I-X217L-X218S, X130S-X210I-X217L-X248D, X130S-X210I-X217L-X259P, X130S-X210I-X218S-X248D, X130S-X210I-X218S-X259P, X130S-X210I-X248D-X259P, X130S-X217L-X218S-X248D, X130S-X217L-X218S-X259P, X130S-X217L-X248D-X259P, X130S-X218S-X248D-X259P, X145R-X166Q-X185Q-X210I, X145R-X166Q-X185Q-X217L, X145R-X166Q-X185Q-X218S, X145R-X166Q-X185Q-X248D, X145R-X166Q-X185Q-X259P, X145R-X166Q-X210I-X217L, X145R-X166Q-X210I-X218S, X145R-X166Q-X210I-X248D, X145R-X166Q-X210I-X259P, X145R-X166Q-X217L-X218S, X145R-X166Q-X217L-X248D, X145R-X166Q-X217L-X259P, X145R-X166Q-X218S-X248D, X145R-X166Q-X218S-X259P, X145R-X166Q-X248D-X259P, X145R-X185Q-X210I-X217L, X145R-X185Q-X210I-X218S, X145R-X185Q-X210I-X248D, X145R-X185Q-X210I-X259P, X145R-X185Q-X217L-X218S, X145R-X185Q-X217L-X248D, X145R-X185Q-X217L-X259P, X145R-X185Q-X218S-X248D, X145R-X185Q-X218S-X259P, X145R-X185Q-X248D-X259P, X145R-X210I-X217L-X218S, X145R-X210I-X217L-X248D, X145R-X210I-X217L-X259P, X145R-X210I-X218S-X248D, X145R-X210I-X218S-X259P, X145R-X210I-X248D-X259P, X145R-X217L-X218S-X248D, X145R-X217L-X218S-X259P, X145R-X217L-X248D-X259P, X145R-X218S-X248D-X259P, X166Q-X185Q-X210I-X217L, X166Q-X185Q-X210I-X218S, X166Q-X185Q-X210I-X248D, X166Q-X185Q-X210I-X259P, X166Q-X185Q-X217L-X218S, X166Q-X185Q-X217L-X248D, X166Q-X185Q-X217L-X259P, X166Q-X185Q-X218S-X248D, X166Q-X185Q-X218S-X259P, X166Q-X185Q-X248D-X259P, X166Q-X210I-X217L-X218S, X166Q-X210I-X217L-X248D, X166Q-X210I-X217L-X259P, X166Q-X210I-X218S-X248D, X166Q-X210I-X218S-X259P, X166Q-X210I-X248D-X259P, X166Q-X217L-X218S-X248D, X166Q-X217L-X218S-X259P, X166Q-X217L-X248D-X259P, X166Q-X218S-X248D-X259P, X185Q-X210I-X217L-X218S, X185Q-X210I-X217L-X248D, X185Q-X210I-X217L-X259P, X185Q-X210I-X218S-X248D, X185Q-X210I-X218S-X259P, X185Q-X210I-X248D-X259P, X185Q-X217L-X218S-X248D, X185Q-X217L-X218S-X259P, X185Q-X217L-X248D-X259P, X185Q-X218S-X248D-X259P, X210I-X217L-X218S-X248D, X210I-X217L-X218S-X259P, X210I-X217L-X248D-X259P, X210I-X218S-X248D-X259P, X217L-X218S-X248D-X259P, where the positions are numbered by correspondence with the amino acid sequence of SEQ ID NO:1 (BPN').

In other embodiments, the subtilisin variants disclosed herein contain a combination of four or more features with respect to SEQ ID NO: 1, where the combination of four or more features are selected from the group consisting of X003V-X009E-X040E-X076D, X003V-X009E-X040E-X166Q, X003V-X009E-X040E-X185Q, X003V-X009E-X069S-X078N, X003V-X009E-X069S-X166Q, X003V-X009E-X069S-X185Q, X003V-X009E-X076D-X166Q, X003V-X009E-X076D-X218S, X003V-X009E-X166Q-X185Q, X003V-X009E-X166Q-X259P, X003V-X009E-X218S-X259P, X003V-X040E-X069S-X076D, X003V-X040E-X069S-X166Q, X003V-X040E-X076D-X078N, X003V-X040E-X076D-X129P, X003V-X040E-X076D-X185Q, X003V-X040E-X076D-X218S, X003V-X040E-X078N-X124I, X003V-X040E-X124I-X218S, X003V-

X040E-X166Q-X185Q, X003V-X040E-X166Q-X259P, X003V-X069S-X076D-X078N, X003V-X069S-X076D-X128S, X003V-X069S-X076D-X185Q, X003V-X069S-X076D-X218S, X003V-X069S-X076D-X259P, X003V-X069S-X078N-X128S, X003V-X069S-X078N-X129P, X003V-X069S-X078N-X166Q, X003V-X069S-X078N-X185Q, X003V-X069S-X078N-X218S, X003V-X069S-X078N-X259P, X003V-X069S-X124I-X218S, X003V-X069S-X128S-X166Q, X003V-X069S-X128S-X185Q, X003V-X069S-X128S-X259P, X003V-X069S-X129P-X185Q, X003V-X069S-X129P-X218S, X003V-X069S-X129P-X259P, X003V-X069S-X166Q-X185Q, X003V-X069S-X166Q-X218S, X003V-X069S-X185Q-X218S, X003V-X069S-X185Q-X259P, X003V-X069S-X218S-X259P, X003V-X076D-X078N-X128S, X003V-X076D-X078N-X166Q, X003V-X076D-X078N-X259P, X003V-X076D-X124I-X166Q, X003V-X076D-X128S-X259P, X003V-X076D-X129P-X166Q, X003V-X076D-X129P-X185Q, X003V-X076D-X129P-X259P, X003V-X076D-X166Q-X185Q, X003V-X076D-X166Q-X259P, X003V-X076D-X185Q-X259P, X003V-X076D-X218S-X259P, X003V-X078N-X124I-X166Q, X003V-X078N-X128S-X185Q, X003V-X078N-X128S-X218S, X003V-X078N-X129P-X185Q, X003V-X078N-X129P-X259P, X003V-X078N-X166Q-X259P, X003V-X078N-X185Q-X218S, X003V-X078N-X185Q-X259P, X003V-X078N-X218S-X259P, X003V-X124I-X128S-X166Q, X003V-X124I-X128S-X218S, X003V-X124I-X128S-X259P, X003V-X124I-X166Q-X259P, X003V-X124I-X185Q-X259P, X003V-X128S-X129P-X185Q, X003V-X128S-X166Q-X218S, X003V-X128S-X185Q-X218S, X003V-X128S-X185Q-X259P, X003V-X128S-X218S-X259P, X003V-X129P-X185Q-X218S, X003V-X166Q-X185Q-X218S, X003V-X166Q-X185Q-X259P, X003V-X166Q-X218S-X259P, X003V-X185Q-X218S-X259P, X009E-X040E-X069S-X076D, X009E-X040E-X069S-X078N, X009E-X040E-X069S-X185Q, X009E-X040E-X069S-X218S, X009E-X040E-X069S-X259P, X009E-X040E-X076D-X078N, X009E-X040E-X076D-X185Q, X009E-X040E-X078N-X185Q, X009E-X040E-X078N-X259P, X009E-X040E-X166Q-X218S, X009E-X040E-X166Q-X259P, X009E-X040E-X185Q-X218S, X009E-X040E-X185Q-X259P, X009E-X040E-X218S-X259P, X009E-X069S-X076D-X078N, X009E-X069S-X076D-X166Q, X009E-X069S-X076D-X185Q, X009E-X069S-X076D-X218S, X009E-X069S-X076D-X259P, X009E-X069S-X078N-X166Q, X009E-X069S-X078N-X218S, X009E-X069S-X166Q-X185Q, X009E-X069S-X166Q-X218S, X009E-X069S-X166Q-X259P, X009E-X069S-X185Q-X218S, X009E-X069S-X218S-X259P, X009E-X076D-X078N-X166Q, X009E-X076D-X078N-X185Q, X009E-X076D-X078N-X259P, X009E-X076D-X166Q-X185Q, X009E-X076D-X166Q-X218S, X009E-X076D-X166Q-X259P, X009E-X076D-X185Q-X218S, X009E-X076D-X185Q-X259P, X009E-X076D-X218S-X259P, X009E-X078N-X166Q-X185Q, X009E-X078N-X166Q-X218S, X009E-X078N-X185Q-X218S, X009E-X078N-X185Q-X259P, X009E-X078N-X218S-X259P, X009E-X166Q-X185Q-X218S, X009E-X166Q-X185Q-X259P, X009E-X166Q-X218S-X259P, X009E-X185Q-X218S-X259P, X040E-X069S-X076D-X078N, X040E-X069S-X076D-X185Q, X040E-X069S-X078N-X166Q, X040E-X069S-X078N-X218S, X040E-X069S-X078N-X259P, X040E-X069S-X129P-X218S, X040E-X069S-X166Q-X218S, X040E-X069S-X166Q-X259P, X040E-X069S-X185Q-X218S, X040E-X069S-X185Q-X259P, X040E-X069S-X218S-X259P, X040E-X076D-X078N-X166Q, X040E-X076D-X078N-X185Q, X040E-X076D-X078N-X218S, X040E-X076D-X124I-X218S, X040E-X076D-X166Q-X185Q, X040E-X076D-X166Q-X218S, X040E-X076D-X166Q-X259P, X040E-X076D-X185Q-X218S, X040E-X076D-X185Q-X259P, X040E-X076D-X218S-X259P, X040E-X078N-X166Q-X218S, X040E-X078N-X185Q-X259P, X040E-X078N-X218S-X259P, X040E-X124I-X218S-X259P, X040E-X166Q-X185Q-X218S, X040E-X185Q-X218S-X259P, X069S-X076D-X078N-X128S, X069S-X076D-X078N-X185Q, X069S-X076D-X078N-X218S, X069S-X076D-X078N-X259P, X069S-X076D-X124I-X128S, X069S-X076D-X129P-X166Q, X069S-X076D-X129P-X259P, X069S-X076D-X166Q-X185Q, X069S-X076D-X166Q-X218S, X069S-X076D-X166Q-X259P, X069S-X076D-X185Q-X218S, X069S-X076D-X185Q-X259P, X069S-X076D-X218S-X259P, X069S-X078N-X128S-X218S, X069S-X078N-X129P-X185Q, X069S-X078N-X166Q-X185Q, X069S-X078N-X166Q-X218S, X069S-X078N-X185Q-X218S, X069S-X078N-X185Q-X259P, X069S-X078N-X218S-X259P, X069S-X124I-X128S-X185Q, X069S-X124I-X128S-X218S, X069S-X124I-X129P-X259P, X069S-X124I-X185Q-X218S, X069S-X128S-X166Q-X218S, X069S-X128S-X218S-X259P, X069S-X129P-X166Q-X185Q, X069S-X129P-X166Q-X218S, X069S-X129P-X166Q-X259P, X069S-X129P-X185Q-X218S, X069S-X166Q-X185Q-X218S, X069S-X166Q-X185Q-X259P, X069S-X166Q-X218S-X259P, X069S-X185Q-X218S-X259P, X076D-X078N-X124I-X218S, X076D-X078N-X128S-X259P, X076D-X078N-X129P-X185Q, X076D-X078N-X166Q-X185Q, X076D-X078N-X166Q-X218S, X076D-X078N-X166Q-X259P, X076D-X078N-X185Q-X218S, X076D-X078N-X185Q-X259P, X076D-X078N-X218S-X259P, X076D-X124I-X128S-X166Q, X076D-X124I-X128S-X259P, X076D-X128S-X166Q-X218S, X076D-X129P-X166Q-X259P, X076D-X129P-X185Q-X218S, X076D-X166Q-X185Q-X218S, X076D-X166Q-X185Q-X259P, X076D-X166Q-X218S-X259P, X076D-X185Q-X218S-X259P, X078N-X124I-X128S-X218S, X078N-X124I-X128S-X259P, X078N-X124I-X166Q-X259P, X078N-X128S-X166Q-X218S, X078N-X128S-X218S-X259P, X078N-X129P-X166Q-X259P, X078N-X129P-X185Q-X218S, X078N-X129P-X185Q-X259P, X078N-X166Q-X185Q-X218S, X078N-X166Q-X185Q-X259P, X078N-X166Q-X218S-X259P, X078N-X185Q-X218S-X259P, X124I-X128S-X166Q-X259P, X124I-X129P-X166Q-X259P, X124I-X166Q-X218S-X259P, X124I-X185Q-X218S-X259P, X128S-X129P-X166Q-X259P, X128S-X166Q-X185Q-X218S, X128S-X166Q-X185Q-X259P, X129P-X166Q-X185Q-X259P, X129P-X166Q-X218S-X259P, X129P-X185Q-X218S-X259P, and X166Q-X185Q-X218S-X259P, where the positions are numbered by correspondence with the amino acid sequence of SEQ ID NO:1 (BPN').

In yet another embodiment, the disclosure provides a subtilisin variant having at least two or more features selected from the group consisting of X003V-X009E, X003V-X040E, X003V-X069S, X003V-X076D, X003V-X078N, X003V-X166Q, X003V-X185Q, X003V-X218S, X003V-X259P, X009E-X040E, X009E-X069S, X009E-X076D, X009E-X078N, X009E-X166Q, X009E-X185Q, X009E-X218S, X009E-X259P, X040E-X069S, X040E-X076D, X040E-X078N, X040E-X166Q, X040E-X185Q, X040E-X218S, X040E-X259P, X069S-X076D, X069S-X078N, X069S-X166Q, X069S-X185Q, X069S-X218S, X069S-X259P, X076D-X078N, X076D-X166Q, X076D-X185Q, X076D-X218S, X076D-X259P, X078N-X166Q, X078N-X185Q, X078N-X218S, X078N-X259P, X166Q-X185Q, X166Q-X218S, X166Q-X259P, X185Q-X218S, X185Q-X259P, and X218S-X259P.

In yet another embodiment, the disclosure provides a subtilisin variant having at least three or more features selected from the group consisting of X003V-X009E-X040E, X003V-X009E-X069S, X003V-X009E-X076D, X003V-X009E-X078N, X003V-X009E-X166Q, X003V-X009E-X185Q, X003V-X009E-X218S, X003V-X009E-X259P, X003V-X040E-X069S, X003V-X040E-X076D, X003V-X040E-X078N, X003V-X040E-X166Q, X003V-X040E-X185Q, X003V-X040E-X218S, X003V-X040E-X259P, X003V-X069S-X076D, X003V-X069S-X078N, X003V-X069S-X166Q, X003V-X069S-X185Q, X003V-X069S-X218S, X003V-X069S-X259P, X003V-X076D-X078N, X003V-X076D-X166Q, X003V-X076D-X185Q, X003V-X076D-X218S, X003V-X076D-X259P, X003V-X078N-X166Q, X003V-X078N-X185Q, X003V-X078N-X218S, X003V-X078N-X259P, X003V-X166Q-X185Q, X003V-X166Q-X218S, X003V-X166Q-X259P, X003V-X185Q-X218S, X003V-X185Q-X259P, X003V-X218S-X259P, X009E-X040E-X069S, X009E-X040E-X076D, X009E-X040E-X078N, X009E-X040E-X166Q, X009E-X040E-X185Q, X009E-X040E-X218S, X009E-X040E-X259P, X009E-X069S-X076D, X009E-X069S-X078N, X009E-X069S-X166Q, X009E-X069S-X185Q, X009E-X069S-X218S, X009E-X069S-X259P, X009E-X076D-X078N, X009E-X076D-X166Q, X009E-X076D-X185Q, X009E-X076D-X218S, X009E-X076D-X259P, X009E-X078N-X166Q, X009E-X078N-X185Q, X009E-X078N-X218S, X009E-X078N-X259P, X009E-X166Q-X185Q, X009E-X166Q-X218S, X009E-X166Q-X259P, X009E-X185Q-X218S, X009E-X185Q-X259P, X009E-X218S-X259P, X040E-X069S-X076D, X040E-X069S-X078N, X040E-X069S-X166Q, X040E-X069S-X185Q, X040E-X069S-X218S, X040E-X069S-X259P, X040E-X076D-X078N, X040E-X076D-X166Q, X040E-X076D-X185Q, X040E-X076D-X218S, X040E-X076D-X259P, X040E-X078N-X166Q, X040E-X078N-X185Q, X040E-X078N-X218S, X040E-X078N-X259P, X040E-X166Q-X185Q, X040E-X166Q-X218S, X040E-X166Q-X259P, X040E-X185Q-X218S, X040E-X185Q-X259P, X040E-X218S-X259P, X069S-X076D-X078N, X069S-X076D-X166Q, X069S-X076D-X185Q, X069S-X076D-X218S, X069S-X076D-X259P, X069S-X078N-X166Q, X069S-X078N-X185Q, X069S-X078N-X218S, X069S-X078N-X259P, X069S-X166Q-X185Q, X069S-X166Q-X218S, X069S-X166Q-X259P, X069S-X185Q-X218S, X069S-X185Q-X259P, X069S-X218S-X259P, X076D-X078N-X166Q, X076D-X078N-X185Q, X076D-X078N-X218S, X076D-X078N-X259P, X076D-X166Q-X185Q, X076D-X166Q-X218S, X076D-X166Q-X259P, X076D-X185Q-X218S, X076D-X185Q-X259P, X076D-X218S-X259P, X078N-X166Q-X185Q, X078N-X166Q-X218S, X078N-X166Q-X259P, X078N-X185Q-X218S, X078N-X185Q-X259P, X078N-X218S-X259P, X166Q-X185Q-X218S, X166Q-X185Q-X259P, X166Q-X218S-X259P, and X185Q-X218S-X259P, where the positions are numbered by correspondence with the amino acid sequence of SEQ ID NO:1 (BPN').

In yet another embodiment, the disclosure provides subtilisin variants with one or more mutations at E003, Q003, S003, T003, P009, S009, T009, A024, N024, S024, A040, P040, S040, A069, N076, D078, S078, T078, E079, L079, T079, V079, E087, N087, Q087, S087, G118, M118, N118, L124, M124, G128, I128, T128, A129, D129, S129, A130, M130, Q130, T130, V130, E145, Q145, S145, G166, S166, Q182, S182, N185, R185, S185, V185, L210, P210, F217, M217, Y217, N218, P218, T218, A248, N248, Q248, S248, D259, G259, and N259, where the positions are numbered by correspondence with the amino acid sequence of SEQ ID NO:1 (BPN'). In yet another embodiment, the disclosure provides variants of subtilisin AprE with one or more mutations at S003, S009, S024, P040, A069, N076, S078, S087, N118, M124, G128, T130, S145, G166, S182, P210, Y217, N218, and N259, where the positions are numbered by correspondence with the amino acid sequence of SEQ ID NO:1 (BPN').

In yet another embodiment, the disclosure provides variants of subtilisin AprE from the group consisting of 5003V, N076D, S078N, G166Q, Y217L, N218S, N259P, S009E, P040E, S003V-N259P, S003V-P040E, S003V-M124I, S003V-S078N, S003V-N076D, S003V-G166Q, S003V-G128S, A069S-N076D, A069S-N218S, A069S-G166Q, A069S-N259P, A069S-S078N, A069S-G128S, A069S-M124I, N076D-G128S, N076D-S078N, N076D-N218S, N076D-G166Q, N076D-M124I, S078T-M124I, S078N-G128S, S078N-N259P, S078N-N218S, S078N-G166Q, M124I-G166Q, M124I-N259P, M124I-G128S, M124I-N218S, G128S-N259P, G128S-N218S, G128S-G166Q, G166Q-N259P, G166Q-N218S, N218S-N259P, S003V-S009E, S003V-A069S, S003V-N218S, S009E-P040E, S009E-A069S, S009E-N076D, S009E-S078N, S009E-G166Q, S009E-N218S, S009E-N259P, P040E-A069S, P040E-N076D, P040E-S078N, P040E-G166Q, P040E-N218S, P040E-N259P, N076D-N259P, S003V-N076D-S078N, S003V-S078N-N218S, S003V-M124I-N259P, S003V-G128S-G166Q, S003V-G166Q-N218S, S003V-N218S-N259P, P040E-N076D-S078N, G128S-G166Q-N259P, S003V-S009E-P040E, S003V-S009E-A069S, S003V-S009E-N076D, S003V-S009E-S078N, S003V-S009E-G166Q, S003V-S009E-N218S, S003V-S009E-N259P, S003V-P040E-A069S, S003V-P040E-N076D, S003V-P040E-N218S, S003V-P040E-N259P, S003V-A069S-N076D, S003V-A069S-S078N, S003V-A069S-G166Q, S003V-A069S-N218S, S003V-A069S-N259P, S003V-N076D-G166Q, S003V-N076D-N218S, S003V-N076D-N259P, S003V-S078N-N259P, S003V-G166Q-N259P, S009E-P040E-A069S, S009E-P040E-N076D, S009E-P040E-S078N, S009E-P040E-G166Q, S009E-P040E-N218S, S009E-P040E-N259P, S009E-A069S-N076D, S009E-A069S-S078N, S009E-A069S-G166Q, S009E-A069S-N218S, S009E-A069S-N259P, S009E-N076D-S078N, S009E-N076D-G166Q, S009E-N076D-N218S, S009E-N076D-N259P, S009E-S078N-G166Q, S009E-S078N-N218S, S009E-S078N-N259P, S009E-G166Q-N218S, S009E-G166Q-N259P, S009E-N218S-N259P, P040E-A069S-S078N, P040E-A069S-G166Q, P040E-A069S-N218S, P040E-A069S-N259P, P040E-N076D-G166Q, P040E-N076D-N218S, P040E-N076D-N259P, P040E-S078N-G166Q, P040E-S078N-N218S, P040E-S078N-N259P, P040E-G166Q-N218S, P040E-G166Q-N259P, P040E-N218S-N259P, A069S-N076D-S078N, A069S-N076D-G166Q, A069S-N076D-N218S, A069S-N076D-N259P, A069S-S078N-G166Q, A069S-S078N-N218S, A069S-S078N-N259P, A069S-G166Q-N218S, A069S-G166Q-N259P, A069S-N218S-N259P, N076D-S078N-G166Q, N076D-S078N-N218S, N076D-S078N-N259P, N076D-G166Q-N218S, N076D-G166Q-N259P, N076D-N218S-N259P, S078N-G166Q-N218S, S078N-G166Q-N259P, S078N-N218S-N259P, G166Q-N218S-N259P, S003V-P040E-N076D-S078N, S003V-P040E-S078N-M124I, S003V-P040E-M124I-N218S, S003V-N076D-S078N-G128S, S003V-N076D-M124I-

G166Q, S003V-N076D-G128S-N259P, S003V-N076D-G166Q-N259P, S003V-N076D-N218S-N259P, S003V-M124I-G128S-N218S, S003V-G128S-G166Q-N218S, P040E-N076D-S078N-G166Q, P040E-N076D-M124I-N218S, P040E-N076D-G166Q-N218S, P040E-N076D-G166Q-N259P, N076D-S078N-M124I-N218S, N076D-S078N-G128S-N259P, N076D-S078N-G166Q-N259P, N076D-M124I-G128S-G166Q, N076D-M124I-G128S-N259P, N076D-G128S-G166Q-N218S, S078N-G128S-G166Q-N218S, S078N-G128S-N218S-N259P, M124I-G166Q-N218S-N259P, S003V-P040E-A069S-G166Q, S003V-P040E-N076D-N218S, S003V-A069S-G166Q-N218S, S009E-P040E-A069S-N076D, S009E-P040E-A069S-N259P, S009E-P040E-S078N-N259P, S009E-P040E-G166Q-N218S, S009E-P040E-G166Q-N259P, S009E-P040E-N218S-N259P, S009E-A069S-S078N-G166Q, S009E-S078N-N218S-N259P, S009E-G166Q-N218S-N259P, P040E-A069S-N076D-S078N, P040E-A069S-S078N-G166Q, P040E-A069S-S078N-N259P, P040E-A069S-G166Q-N218S, N076D-S078N-G166Q-N218S, and N076D-G166Q-N218S-N259P, where the positions are numbered by correspondence with the amino acid sequence of SEQ ID NO:1 (BPN'). In yet another embodiment, the disclosure provides variants of subtilisin Bad02409 with one or more mutations at T003, P009, S024, A069, N076, S078, V079, N087, G118, M124, G128, S129, M130, S145, G166, S182, N185, P210, Y217, N218, N248, and D259, where the positions are numbered by correspondence with the amino acid sequence of SEQ ID NO:1 (BPN').

In yet another embodiment, the disclosure provides variants of subtilisin Bad02409 from the group consisting of N076D, S078N, G128S, S182E, T003V-N218S, T003V-A069S, T003V-D259P, T003V-M124I, T003V-N076D, T003V-N185Q, T003V-G166Q, T003V-S078N, T003V-S129P, A069S-S129P, A069S-G166Q, A069S-N076D, A069S-S078N, N076D-S129P, S078N-N185Q, M124I-S129P, S129P-D259P, S129P-G166Q, G166Q-N218S, T003V-A069S-G166Q, T003V-N076D-D259P, T003V-S078N-N185Q, T003V-S129P-N185Q, T003V-G166Q-D259P, T003V-N185Q-D259P, A069S-N076D-G166Q, N076D-G166Q-N185Q, T003V-A069S-S078N-S129P, T003V-N076D-N185Q-D259P, T003V-S078N-S129P-N185Q, T003V-S078N-G166Q-D259P, T003V-G166Q-N185Q-D259P, A069S-N076D-S129P-D259P, A069S-S078N-S129P-N185Q, A069S-S129P-G166Q-N185Q, N076D-S078N-S129P-N185Q, N076D-S129P-G166Q-D259P, and N076D-G166Q-N185Q-D259P, where the positions are numbered by correspondence with the amino acid sequence of SEQ ID NO:1 (BPN').

In yet another embodiment, the disclosure provides variants of subtilisin Bba02069 with one or more mutations at Q003, T009, N024, P040, A069, N076, Q087, G118, M124, G128, S129, G166, S182, V185, P210, Y217, N218, Q248, and S259, where the positions are numbered by correspondence with the amino acid sequence of SEQ ID NO:1 (BPN').

In yet another embodiment, the disclosure provides variants of subtilisin Bba02069 from the group consisting of S129P, G118R, Q087D, N076D, M124I, Q248D, A069S, G128S, N024Q, Q003V, P040E, T009E, N218S, G166Q, S259P, Q003V-A069S, Q003V-V185Q, Q003V-S129P, Q003V-M124I, Q003V-G166Q, Q003V-G128S, Q003V-S259P, Q003V-N076D, P040E-V185Q, P040E-G166Q, A069S-G128S, A069S-S259P, A069S-M124I, A069S-G166Q, A069S-N076D, N076D-G128S, N076D-G166Q, N076D-M124I, N076D-S259P, N076D-S129P, M124I-G128S, M124I-V185Q, M124I-S129P, M124I-S259P, M124I-G166Q, M124I-N218S, G128S-S129P, G128S-G166Q, G128S-S259P, G128S-V185Q, S129P-G166Q, S129P-V185Q, S129P-S259P, G166Q-S259P, G166Q-V185Q, V185Q-S259P, V185Q-N218S, N218S-S259P, Q003V-T009E, Q003V-P040E, Q003V-N218S, T009E-P040E, T009E-A069S, T009E-N076D, T009E-G166Q, T009E-V185Q, T009E-N218S, T009E-S259P, P040E-A069S, P040E-N076D, P040E-N218S, P040E-S259P, A069S-V185Q, A069S-N218S, N076D-V185Q, N076D-N218S, G166Q-N218S, Q003V-P040E-G166Q, Q003V-G166Q-S259P, A069S-S129P-G166Q, A069S-S129P-V185Q, G128S-S129P-N218S, G128S-V185Q-N218S, Q003V-T009E-P040E, Q003V-T009E-A069S, Q003V-T009E-N076D, Q003V-T009E-G166Q, Q003V-T009E-V185Q, Q003V-T009E-N218S, Q003V-T009E-S259P, Q003V-P040E-A069S, Q003V-P040E-N076D, Q003V-P040E-V185Q, Q003V-P040E-N218S, Q003V-P040E-S259P, Q003V-A069S-N076D, Q003V-A069S-G166Q, Q003V-A069S-N218S, Q003V-A069S-S259P, Q003V-N076D-G166Q, Q003V-N076D-V185Q, Q003V-N076D-N218S, Q003V-N076D-S259P, Q003V-G166Q-V185Q, Q003V-G166Q-N218S, Q003V-V185Q-S259P, Q003V-N218S-S259P, T009E-P040E-A069S, T009E-P040E-N076D, T009E-P040E-G166Q, T009E-P040E-V185Q, T009E-P040E-N218S, T009E-P040E-S259P, T009E-A069S-N076D, T009E-A069S-G166Q, T009E-A069S-V185Q, T009E-A069S-N218S, T009E-A069S-S259P, T009E-N076D-G166Q, T009E-N076D-V185Q, T009E-N076D-N218S, T009E-N076D-S259P, T009E-G166Q-V185Q, T009E-G166Q-N218S, T009E-G166Q-S259P, T009E-V185Q-N218S, T009E-V185Q-S259P, T009E-N218S-S259P, P040E-A069S-N076D, P040E-A069S-G166Q, P040E-A069S-V185Q, P040E-A069S-N218S, P040E-A069S-S259P, P040E-N076D-G166Q, P040E-N076D-V185Q, P040E-N076D-N218S, P040E-N076D-S259P, P040E-G166Q-V185Q, P040E-G166Q-N218S, P040E-G166Q-S259P, P040E-V185Q-N218S, P040E-V185Q-S259P, P040E-N218S-S259P, A069S-N076D-G166Q, A069S-N076D-V185Q, A069S-N076D-N218S, A069S-N076D-S259P, A069S-G166Q-V185Q, A069S-G166Q-N218S, A069S-G166Q-S259P, A069S-V185Q-N218S, A069S-V185Q-S259P, A069S-N218S-S259P, N076D-G166Q-V185Q, N076D-G166Q-N218S, N076D-G166Q-S259P, N076D-V185Q-N218S, N076D-V185Q-S259P, N076D-N218S-S259P, G166Q-V185Q-N218S, G166Q-V185Q-S259P, G166Q-N218S-S259P, V185Q-N218S-S259P, Q003V-A069S-S129P-S259P, Q003V-M124I-G128S-G166Q, Q003V-G128S-S129P-V185Q, P040E-A069S-S129P-N218S, P040E-M124I-N218S-S259P, A069S-N076D-S129P-G166Q, A069S-M124I-S129P-S259P, A069S-M124I-V185Q-N218S, G128S-G166Q-V185Q-N218S, S129P-G166Q-V185Q-S259P, Q003V-T009E-P040E-G166Q, Q003V-T009E-P040E-V185Q, Q003V-T009E-N076D-N218S, Q003V-T009E-G166Q-V185Q, Q003V-P040E-N076D-V185Q, T009E-P040E-A069S-V185Q, T009E-P040E-A069S-N218S, T009E-P040E-N076D-V185Q, T009E-A069S-N076D-N218S, T009E-A069S-G166Q-V185Q, T009E-A069S-G166Q-N218S, T009E-A069S-V185Q-N218S, T009E-N076D-V185Q-S259P, T009E-V185Q-N218S-S259P, P040E-A069S-N076D-V185Q, P040E-A069S-G166Q-N218S, P040E-A069S-V185Q-N218S, P040E-A069S-V185Q-S259P, P040E-A069S-N218S-S259P, P040E-N076D-G166Q-V185Q, P040E-N076D-V185Q-N218S, P040E-N076D-V185Q-S259P, P040E-G166Q-V185Q-N218S, P040E-V185Q-N218S-S259P, A069S-N076D-

G166Q-V185Q, A069S-N076D-G166Q-N218S, A069S-N076D-G166Q-S259P, A069S-N076D-V185Q-N218S, A069S-N076D-N218S-S259P, A069S-G166Q-V185Q-N218S, N076D-G166Q-V185Q-S259P, N076D-G166Q-N218S-S259P, and G166Q-V185Q-N218S-S259P, where the positions are numbered by correspondence with the amino acid sequence of SEQ ID NO:1 (BPN').

In yet another embodiment, the disclosure provides variants of subtilisin Bpan01744 with one or more mutations at S003, S009, S024, A069, N076, S078, N087, G118, M124, T128, S129, A130, G166, Q182, N185, P210, N218, N248, and N259, where the positions are numbered by correspondence with the amino acid sequence of SEQ ID NO:1 (BPN').

In yet another embodiment, the disclosure provides variants of subtilisin Bpan01744 from the group consisting of S003V, S078N, S009E, N076D, N185Q, N218S, N259P, S003V-N185Q, S003V-N076D, S003V-A069S, S003V-S078N, S003V-N218S, S003V-N259P, A069S-N076D, A069S-G166Q, A069S-N185Q, A069S-S078N, A069S-N218S, N076D-S078N, N076D-S129P, S078N-G166Q, S078N-M124I, S078N-S129P, M124I-N218S, M124I-S129P, M124I-N185Q, S129P-N259P, S129P-N185Q, S129P-N218S, S129P-G166Q, G166Q-N259P, G166Q-N218S, G166Q-N185Q, N185Q-N218S, N185Q-N259P, N218S-N259P, S003V-S009E, S003V-G166Q, S009E-N076D, S009E-S078N, S009E-G166Q, S009E-N185Q, S009E-N218S, S009E-N259P, N076D-G166Q, N076D-N185Q, N076D-N218S, N076D-N259P, S078N-N185Q, S078N-N218S, S078N-N259P, S003V-A069S-N076D, S003V-A069S-S129P, S003V-A069S-N185Q, S003V-N076D-S129P, S003V-N076D-N185Q, S003V-S078N-G166Q, S003V-S129P-N259P, S003V-G166Q-N218S, A069S-N076D-N185Q, A069S-G166Q-N185Q, N076D-S078N-G166Q, N076D-S129P-N218S, S078N-S129P-N259P, S078N-N185Q-N259P, S003V-S009E-A069S, S003V-S009E-N076D, S003V-S009E-S078N, S003V-S009E-N185Q, S003V-S009E-N218S, S003V-S009E-N259P, S003V-A069S-S078N, S003V-A069S-N218S, S003V-N076D-S078N, S003V-N076D-G166Q, S003V-N076D-N218S, S003V-S078N-N185Q, S003V-S078N-N218S, S003V-S078N-N259P, S003V-N185Q-N218S, S003V-N185Q-N259P, S003V-N218S-N259P, S009E-A069S-N076D, S009E-A069S-S078N, S009E-A069S-G166Q, S009E-A069S-N259P, S009E-N076D-S078N, S009E-N076D-G166Q, S009E-N076D-N185Q, S009E-N076D-N218S, S009E-N076D-N259P, S009E-S078N-N185Q, S009E-S078N-N218S, S009E-S078N-N259P, S009E-G166Q-N185Q, S009E-G166Q-N218S, S009E-N185Q-N218S, S009E-N185Q-N259P, S009E-N218S-N259P, A069S-N076D-S078N, A069S-N076D-G166Q, A069S-N076D-N218S, A069S-N076D-N259P, A069S-S078N-N185Q, A069S-S078N-N218S, A069S-S078N-N259P, A069S-G166Q-N218S, A069S-N185Q-N218S, A069S-N218S-N259P, N076D-S078N-N185Q, N076D-S078N-N218S, N076D-S078N-N259P, N076D-G166Q-N218S, N076D-N185Q-N218S, N076D-N185Q-N259P, S078N-G166Q-N218S, S078N-N185Q-N218S, S078N-N218S-N259P, G166Q-N185Q-N218S, N185Q-N218S-N259P, S003V-A069S-N076D-S078N, S003V-A069S-N076D-N185Q, S003V-A069S-N076D-N259P, S003V-A069S-S078N-S129P, S003V-A069S-S078N-N185Q, S003V-A069S-S129P-N218S, S003V-A069S-N185Q-N259P, S003V-N076D-S129P-G166Q, S003V-N076D-S129P-N185Q, S003V-N076D-S129P-N259P, S003V-S078N-N185Q-N218S, S003V-S078N-N185Q-N259P, S003V-G166Q-N185Q-N259P, S003V-N185Q-N218S-N259P, A069S-N076D-S078N-N218S, A069S-N076D-N185Q-N259P, A069S-S078N-N185Q-N218S, A069S-S129P-G166Q-N218S, A069S-S129P-N185Q-N218S, A069S-G166Q-N218S-N259P, A069S-N185Q-N218S-N259P, N076D-S078N-S129P-N185Q, N076D-S078N-N185Q-N218S, N076D-S129P-N185Q-N218S, N076D-G166Q-N185Q-N259P, S078N-S129P-G166Q-N259P, S078N-S129P-N185Q-N259P, S078N-G166Q-N218S-N259P, S129P-G166Q-N218S-N259P, S129P-N185Q-N218S-N259P, S003V-S009E-A069S-N185Q, S003V-S009E-N218S-N259P, S003V-A069S-N076D-N218S, S003V-A069S-N185Q-N218S, S003V-A069S-N218S-N259P, S003V-N076D-N218S-N259P, S003V-G166Q-N185Q-N218S, S009E-A069S-N076D-S078N, S009E-A069S-S078N-G166Q, S009E-A069S-S078N-N218S, S009E-A069S-G166Q-N218S, S009E-A069S-N218S-N259P, S009E-N076D-S078N-G166Q, S009E-N076D-S078N-N185Q, S009E-N076D-N218S-N259P, S009E-S078N-N185Q-N218S, S009E-S078N-N218S-N259P, S009E-G166Q-N185Q-N218S, A069S-N076D-S078N-N259P, A069S-S078N-G166Q-N218S, A069S-S078N-N185Q-N259P, A069S-S078N-N218S-N259P, N076D-S078N-G166Q-N185Q, N076D-S078N-G166Q-N218S, N076D-S078N-N218S-N259P, N076D-G166Q-N185Q-N218S, N076D-G166Q-N218S-N259P, N076D-N185Q-N218S-N259P, S078N-G166Q-N185Q-N218S, and S078N-G166Q-N185Q-N259P, where the positions are numbered by correspondence with the amino acid sequence of SEQ ID NO:1 (BPN').

In yet another embodiment, the disclosure provides variants of subtilisin BspAI02518 with one or more mutations at T003, S009, A069, N076, S078, S087, G118, M124, G128, T130, S166, S182, N185, P210, N218, Q248, and N259, where the positions are numbered by correspondence with the amino acid sequence of SEQ ID NO:1 (BPN').

In yet another embodiment, the disclosure provides variants of subtilisin BspAI02518 from the group consisting of S003V, S009E, N076D, S078N, M124I, S182E, N185Q, N218S, N259P, S166Q, S003V-N259P, S003V-N218S, S003V-A069S, S003V-N185Q, S003V-G128S, S003V-M124I, S003V-N076D, S003V-S166Q, A069S-N218S, A069S-N076D, A069S-S078N, A069S-N185Q, A069S-S166Q, N076D-N218S, N076D-N259P, N076D-G128S, N076D-M124I, N076D-N185Q, N076D-S078N, S078N-M124I, S078N-N218S, S078N-N259P, S078N-G128S, S078N-N185Q, M124I-G128S, M124I-S166Q, M124I-N185Q, S166Q-N218S, S166Q-N259P, N185Q-N259P, N218S-N259P, S003V-S009E, S003V-S078N, S009E-A069S, S009E-N076D, S009E-S078N, S009E-S166Q, S009E-N185Q, S009E-N218S, S009E-N259P, A069S-N259P, N076D-S166Q, S078N-S166Q, S166Q-N185Q, N185Q-N218S, S003V-A069S-N185Q, S003V-S078N-G128S, S003V-N185Q-N259P, A069S-N076D-G128S, A069S-N076D-N218S, A069S-S078N-M124I, N076D-S078N-N185Q, N076D-S078N-N218S, N076D-G128S-S166Q, M124I-G128S-N185Q, G128S-S166Q-N185Q, S003V-S009E-A069S, S003V-S009E-N076D, S003V-S009E-S078N, S003V-S009E-S166Q, S003V-S009E-N185Q, S003V-S009E-N218S, S003V-S009E-N259P, S003V-A069S-N076D, S003V-A069S-S078N, S003V-A069S-N218S, S003V-N076D-S078N, S003V-N076D-S166Q, S003V-N076D-N185Q, S003V-N076D-N218S, S003V-N076D-N259P, S003V-S078N-S166Q, S003V-S078N-N185Q, S003V-S078N-N218S, S003V-S078N-N259P, S003V-S166Q-N185Q, S003V-S166Q-N259P, S003V-N185Q-N218S, S003V-N218S-N259P, S009E-A069S-N076D, S009E-A069S-N185Q, S009E-A069S-

N218S, S009E-N076D-S078N, S009E-N076D-S166Q, S009E-N076D-N185Q, S009E-N076D-N218S, S009E-N076D-N259P, S009E-S078N-S166Q, S009E-S078N-N185Q, S009E-S078N-N218S, S009E-S078N-N259P, S009E-S166Q-N185Q, S009E-S166Q-N218S, S009E-S166Q-N259P, S009E-N185Q-N218S, S009E-N185Q-N259P, S009E-N218S-N259P, A069S-N076D-S078N, A069S-N076D-S166Q, A069S-N076D-N185Q, A069S-N076D-N259P, A069S-S078N-S166Q, A069S-S078N-N218S, A069S-S166Q-N185Q, A069S-S166Q-N218S, A069S-S166Q-N259P, A069S-N185Q-N218S, A069S-N218S-N259P, N076D-S078N-5166Q, N076D-S078N-N259P, N076D-5166Q-N185Q, N076D-5166Q-N218S, N076D-5166Q-N259P, N076D-N185Q-N218S, N076D-N185Q-N259P, N076D-N218S-N259P, S078N-S166Q-N185Q, S078N-S166Q-N218S, S078N-S166Q-N259P, S078N-N185Q-N218S, S078N-N185Q-N259P, S078N-N218S-N259P, S166Q-N185Q-N218S, S166Q-N185Q-N259P, S166Q-N218S-N259P, S003V-A069S-N076D-G128S, S003V-A069S-S078N-G128S, S003V-A069S-S078N-S166Q, S003V-A069S-M124I-N218S, S003V-A069S-G128S-S166Q, S003V-A069S-G128S-N259P, S003V-N076D-S166Q-N185Q, S003V-S078N-M124I-S166Q, S003V-S078N-G128S-N185Q, S003V-S078N-G128S-N218S, S003V-M124I-S166Q-N259P, S003V-M124I-N185Q-N259P, S003V-G128S-N185Q-N218S, S003V-G128S-N218S-N259P, S003V-S166Q-N218S-N259P, A069S-N076D-S078N-G128S, A069S-N076D-M124I-G128S, A069S-N076D-S166Q-N218S, A069S-N076D-N185Q-N259P, A069S-N076D-N218S-N259P, A069S-S078N-G128S-N218S, A069S-S078N-N185Q-N259P, A069S-M124I-G128S-N185Q, A069S-M124I-G128S-N218S, A069S-G128S-S166Q-N218S, A069S-G128S-N218S-N259P, N076D-S166Q-N185Q-N259P, S078N-M124I-G128S-N218S, S078N-N185Q-N218S-N259P, M124I-G128S-S166Q-N259P, M124I-S166Q-N218S-N259P, G128S-S166Q-N185Q-N259P, S003V-S009E-N076D-S166Q, S003V-A069S-S078N-N259P, S003V-A069S-S166Q-N218S, S003V-N076D-S078N-S166Q, S003V-N076D-S078N-N259P, S003V-N076D-S166Q-N259P, S003V-S166Q-N185Q-N259P, S009E-A069S-N076D-S166Q, S009E-A069S-N076D-N218S, S009E-A069S-N076D-N259P, S009E-A069S-S078N-S166Q, S009E-A069S-S078N-N218S, S009E-A069S-S166Q-N259P, S009E-N076D-S078N-N259P, S009E-N076D-S166Q-N185Q, S009E-N076D-S166Q-N259P, S009E-N076D-N185Q-N218S, S009E-N076D-N185Q-N259P, S009E-S078N-S166Q-N218S, S009E-S078N-N185Q-N259P, S009E-S078N-N218S-N259P, A069S-N076D-S078N-N218S, A069S-N076D-S166Q-N185Q, A069S-N076D-N185Q-N218S, A069S-S078N-S166Q-N218S, A069S-S078N-N185Q-N218S, A069S-S078N-N218S-N259P, A069S-S166Q-N185Q-N218S, A069S-S166Q-N185Q-N259P, N076D-S078N-S166Q-N218S, N076D-S078N-N185Q-N218S, N076D-S078N-N185Q-N259P, N076D-S078N-N218S-N259P, N076D-S166Q-N185Q-N218S, N076D-S166Q-N218S-N259P, N076D-N185Q-N218S-N259P, S078N-S166Q-N185Q-N218S, S078N-S166Q-N185Q-N259P, and S166Q-N185Q-N218S-N259P, where the positions are numbered by correspondence with the amino acid sequence of SEQ ID NO:1 (BPN').

In yet another embodiment, the disclosure provides variants of subtilisin BspAK01305 with one or more mutations at S003, S024, S040, A069, D078, E079, E087, N118, L124, S145, G166, Q182, S185, P210, S248, and D259, where the positions are numbered by correspondence with the amino acid sequence of SEQ ID NO:1 (BPN').

In yet another embodiment, the disclosure provides variants of subtilisin BspAK01305 from the group consisting of S003V, S040E, G166Q, S185Q, P210I, S003V-S185Q, S003V-G166Q, S003V-R262L, S003V-S040E, S040E-G166Q, S040E-S185Q, and G166Q-S185Q, where the positions are numbered by correspondence with the amino acid sequence of SEQ ID NO:1 (BPN').

In yet another embodiment, the disclosure provides variants of subtilisin BspZ00056 with one or more mutations at T003, P009, A024, A069, D078, L079, Q087, G118, M124, G128, S129, Q130, E145, G166, Q182, N185, P210, F217, N218, N248, and G259, where the positions are numbered by correspondence with the amino acid sequence of SEQ ID NO:1 (BPN').

In yet another embodiment, the disclosure provides variants of subtilisin BspZ00056 from the group consisting of Q182E, G128S, E145R, M124I, N218S, S129P, T003V, P009E, A069S, G166Q, N185Q, G259P, G128S-S129P, G128S-N218S, A069S-N185Q, A069S-D078N, D078N-G166Q, G166Q-N185Q, T003V-M124I, G128S-N185Q, A069S-G128S, M124I-N185Q, G166Q-G259P, A069S-G259P, S129P-G166Q, T003V-G259P, T003V-N185Q, D078N-G259P, M124I-N218S, G128S-G166Q, A069S-M124I, S129P-N185Q, G128S-G259P, T003V-G166Q, T003V-G128S, T003V-A069S, M124I-G166Q, M124I-S129P, N218S-G259P, N185Q-G259P, D078N-S129P, M124I-G128S, T003V-N218S, A069S-G166Q, P009E-G166Q, P009E-G259P, A069S-N218S, G166Q-N218S, N185Q-N218S, T003V-S129P-G166Q, T003V-S129P-N185Q, T003V-S129P-G259P, T003V-N185Q-N218S, A069S-G128S-N185Q, A069S-S129P-G259P, A069S-G166Q-N185Q, A069S-G166Q-N218S, M124I-S129P-N185Q, M124I-S129P-G259P, M124I-N185Q-G259P, M124I-N218S-G259P, G128S-G166Q-G259P, G128S-N185Q-G259P, G166Q-N218S-G259P, T003V-P009E-G166Q, T003V-A069S-G166Q, T003V-A069S-G259P, T003V-G166Q-N185Q, T003V-G166Q-N218S, T003V-G166Q-G259P, T003V-N185Q-G259P, T003V-N218S-G259P, P009E-A069S-G166Q, P009E-A069S-G259P, P009E-G166Q-N185Q, P009E-G166Q-N218S, P009E-G166Q-G259P, P009E-N218S-G259P, A069S-G166Q-G259P, A069S-N185Q-G259P, A069S-N218S-G259P, G166Q-N185Q-G259P, N185Q-N218S-G259P, T003V-A069S-G128S-N185Q, T003V-A069S-N185Q-G259P, T003V-A069S-N218S-G259P, T003V-M124I-G166Q-G259P, T003V-N185Q-N218S-G259P, A069S-S129P-G166Q-G259P, M124I-S129P-G166Q-G259P, M124I-G166Q-N218S-G259P, M124I-N185Q-N218S-G259P, G128S-S129P-G166Q-G259P, S129P-G166Q-N185Q-G259P, T003V-P009E-A069S-G166Q, T003V-P009E-G166Q-G259P, T003V-A069S-G166Q-N185Q, T003V-G166Q-N218S-G259P, P009E-A069S-G166Q-N218S, P009E-G166Q-N185Q-N218S, P009E-G166Q-N185Q-G259P, P009E-G166Q-N218S-G259P, P009E-N185Q-N218S-G259P, A069S-G166Q-N185Q-N218S, A069S-G166Q-N185Q-G259P, A069S-G166Q-N218S-G259P, and G166Q-N185Q-N218S-G259P, where the positions are numbered by correspondence with the amino acid sequence of SEQ ID NO:1 (BPN').

In yet another embodiment, the disclosure provides variants of subtilisin BspZ00258 with one or more mutations at E003, N024, A069, D078, L079, N118, M124, G128, A129, V130, Q145, G166, S182, N185, L210, N218, A248, and D259, where the positions are numbered by correspondence with the amino acid sequence of SEQ ID NO:1 (BPN').

In yet another embodiment, the disclosure provides variants of subtilisin BspZ00258 from the group consisting of E003V, G166Q, D259P, A069S-N185Q, A069S-N218S, A129P-D259P, G166Q-N185Q, G166Q-D259P, E003V-A069S-G128S, E003V-G128S-D259P, E003V-A129P-N185Q, A069S-A129P-G166Q, E003V-A069S-G128S-N185Q, E003V-A069S-A129P-N185Q, E003V-G128S-N185Q-D259P, and E003V-A129P-N185Q-N218S, where the positions are numbered by correspondence with the amino acid sequence of SEQ ID NO:1 (BPN').

In yet another embodiment, the disclosure provides variants of subtilisin Chemgen_164A with one or more mutations at T003, T009, S024, P040, A069, N076, T078, N087, N118, M124, G128, S129, 5145, G166, S182, N185, P210, Y217, N218, and D259, where the positions are numbered by correspondence with the amino acid sequence of SEQ ID NO:1 (BPN').

In yet another embodiment, the disclosure provides variants of subtilisin Chemgen_164A from the group consisting of T003V, A069S, N087D, N118R, S129P, G166Q, S182E, N218S, P040E, N076D, T078N, N185Q, T003V-N076D, T003V-N185Q, T003V-G128S, T003V-S129P, T003V-G166Q, T003V-T078N, T003V-A069S, T003V-M124I, T003V-N218S, P040E-M124I, A069S-G128S, A069S-G166Q, A069S-T078N, A069S-D259P, A069S-S129P, A069S-N076D, A069S-N218S, A069S-N185Q, N076D-G166Q, N076D-N218S, N076D-M124I, N076D-T078N, N076D-D259P, N076D-S129P, N076D-G128S, T078N-G128S, T078N-N185Q, T078N-N218S, T078N-D259P, T078N-S129P, T078N-M124I, T078N-G166Q, G128S-N218S, G128S-D259P, G128S-N185Q, S129P-N185Q, S129P-G166Q, S129P-N218S, G166Q-D259P, G166Q-N185Q, G166Q-N218S, N185Q-N218S, N185Q-D259P, N218S-D259P, T003V-T009E, T003V-P040E, T003V-D259P, T009E-A069S, T009E-N076D, T009E-T078N, T009E-G166Q, T009E-N185Q, T009E-D259P, P040E-T078N, P040E-G166Q, P040E-N185Q, P040E-N218S, N076D-N185Q, T003V-T009E-P040E, T003V-T009E-A069S, T003V-T009E-N185Q, T003V-P040E-N076D, T003V-P040E-G166Q, T003V-P040E-N185Q, T003V-P040E-D259P, T003V-A069S-N076D, T003V-A069S-T078N, T003V-A069S-G166Q, T003V-A069S-N185Q, T003V-A069S-N218S, T003V-A069S-D259P, T003V-N076D-T078N, T003V-N076D-G166Q, T003V-N076D-N185Q, T003V-N076D-N218S, T003V-N076D-D259P, T003V-T078N-G166Q, T003V-T078N-N185Q, T003V-T078N-D259P, T003V-G166Q-N185Q, T003V-G166Q-D259P, T003V-N185Q-N218S, T003V-N185Q-D259P, T003V-N218S-D259P, T009E-P040E-A069S, T009E-P040E-N076D, T009E-P040E-T078N, T009E-P040E-G166Q, T009E-P040E-N218S, T009E-P040E-D259P, T009E-A069S-N076D, T009E-A069S-T078N, T009E-A069S-G166Q, T009E-A069S-N218S, T009E-A069S-D259P, T009E-N076D-T078N, T009E-N076D-G166Q, T009E-N076D-N185Q, T009E-N076D-N218S, T009E-N076D-D259P, T009E-T078N-G166Q, T009E-T078N-N185Q, T009E-T078N-N218S, T009E-T078N-D259P, T009E-G166Q-N218S, T009E-G166Q-D259P, T009E-N185Q-N218S, T009E-N185Q-D259P, P040E-A069S-N076D, P040E-A069S-T078N, P040E-A069S-G166Q, P040E-A069S-D259P, P040E-N076D-T078N, P040E-N076D-G166Q, P040E-N076D-N185Q, P040E-N076D-N218S, P040E-T078N-N185Q, P040E-T078N-D259P, P040E-G166Q-N185Q, P040E-G166Q-N218S, P040E-G166Q-D259P, P040E-N185Q-N218S, P040E-N185Q-D259P, P040E-N218S-D259P, A069S-N076D-T078N, A069S-N076D-G166Q, A069S-N076D-N185Q, A069S-N076D-N218S, A069S-N076D-D259P, A069S-T078N-G166Q, A069S-T078N-N185Q, A069S-T078N-N218S, A069S-T078N-D259P, A069S-G166Q-N218S, A069S-G166Q-D259P, A069S-N185Q-N218S, A069S-N185Q-D259P, A069S-N218S-D259P, N076D-T078N-G166Q, N076D-T078N-N218S, N076D-T078N-D259P, N076D-G166Q-N218S, N076D-G166Q-D259P, N076D-N185Q-N218S, N076D-N218S-D259P, T078N-G166Q-N185Q, T078N-G166Q-N218S, T078N-N185Q-D259P, T078N-N218S-D259P, G166Q-N185Q-N218S, G166Q-N185Q-D259P, G166Q-N218S-D259P, N185Q-N218S-D259P, T003V-T009E-P040E-N185Q, T003V-T009E-A069S-T078N, T003V-P040E-G166Q-D259P, T003V-N076D-T078N-D259P, T003V-N185Q-N218S-D259P, T009E-P040E-A069S-T078N, T009E-P040E-A069S-N185Q, T009E-P040E-A069S-D259P, T009E-P040E-N076D-T078N, T009E-P040E-T078N-N185Q, T009E-P040E-N185Q-N218S, T009E-P040E-N185Q-D259P, T009E-A069S-N076D-G166Q, T009E-A069S-N076D-N185Q, T009E-N076D-G166Q-N218S, T009E-T078N-G166Q-N185Q, P040E-A069S-T078N-N218S, P040E-A069S-G166Q-N218S, P040E-A069S-G166Q-D259P, P040E-N076D-T078N-N185Q, P040E-N076D-T078N-N218S, P040E-N076D-G166Q-D259P, P040E-T078N-N185Q-D259P, P040E-T078N-N218S-D259P, A069S-N076D-T078N-N185Q, A069S-N076D-T078N-D259P, A069S-N076D-G166Q-D259P, A069S-T078N-G166Q-N185Q, A069S-T078N-N185Q-D259P, N076D-T078N-G166Q-N218S, N076D-T078N-G166Q-D259P, N076D-T078N-N218S-D259P, and T078N-N185Q-N218S-D259P, where the positions are numbered by correspondence with the amino acid sequence of SEQ ID NO:1 (BPN').

In yet another embodiment, the disclosure provides variants of subtilisin CP474 with one or more mutations at T003, P009, S024, A040, A069, T078, T079, 5087, G118, L124, 5166, Q182, N185, P210, N218, N248, and D259, where the positions are numbered by correspondence with the amino acid sequence of SEQ ID NO:1 (BPN').

In yet another embodiment, the disclosure provides variants of subtilisin CP474 from the group consisting of T003V, A040E, A069S, T078N, T079I, S166Q, N185Q, T003V-5166Q, T003V-N185Q, T003V-N218S, T003V-A040E, T003V-D259P, T003V-A069S, T003V-T078N, T003V-T079I, T003V-L124I, A040E-S166Q, A040E-N185Q, A040E-N218S, A040E-D259P, A040E-A069S, A040E-T078N, A040E-T079I, A040E-L124I, A069S-N185Q, A069S-T078N, A069S-T079I, A069S-S166Q, T078N-D259P, T078N-T079I, T078N-S166Q, T078N-N185Q, T078N-N218S, T079I-L124I, T079I-S166Q, T079I-N185Q, T079I-N218S, T079I-D259P, S166Q-N218S, N185Q-D259P, N185Q-N218S, and N218S-D259P, where the positions are numbered by correspondence with the amino acid sequence of SEQ ID NO:1 (BPN').

In yet another embodiment, the disclosure provides variants of subtilisin DSM14391 with one or more mutations at T003, T009, S024, S040, A069, N076, S078, S087, N118, M124, D129, A130, G166, Q182, R185, L210, M217, P218, N248, and N259, where the positions are numbered by correspondence with the amino acid sequence of SEQ ID NO:1 (BPN').

In yet another embodiment, the disclosure provides variants of subtilisin DSM14391 from the group consisting of T003V, T009E, S024Q, S040E, A069S, N076D, S078N, A130S, G166Q, Q182E, R185Q, P218S, N248D, N259P, T003V-R185Q, T003V-A069S, T003V-G166Q, T003V-N259P, T003V-N076D, T003V-S078N, T003V-P218S, S040E-S078N, A069S-S078N, A069S-N259P, A069S-

R185Q, A069S-P218S, A069S-N076D, N076D-S078N, N076D-P218S, N076D-D129P, S078N-D129P, S078N-N259P, S078N-M124I, S078N-P218S, S078N-R185Q, M124I-G166Q, M124I-P218S, M124I-N259K, D129P-P218S, D129P-G166Q, D129P-R185Q, D129P-N259P, G166Q-R185Q, G166Q-N259P, R185Q-P218S, R185Q-N259P, T003V-T009E, T003V-S040E, T009E-S040E, T009E-A069S, T009E-N076D, T009E-S078N, T009E-R185Q, T009E-P218S, T009E-N259P, S040E-A069S, S040E-N076D, S040E-R185Q, S040E-P218S, S040E-N259P, N076D-R185Q, N076D-N259P, G166Q-P218S, P218S-N259P, T003V-S040E-P218S, T003V-G166Q-P218S, T003V-G166Q-N259P, S040E-N076D-G166Q, S040E-N076D-R185Q, S040E-S078N-D129P, S040E-R185Q-P218S, S040E-R185Q-N259P, A069S-S078N-N259P, A069S-D129P-P218S, A069S-P218S-N259P, N076D-R185Q-P218S, N076D-P218S-N259P, S078N-R185Q-P218S, S078N-P218S-N259P, T003V-T009E-S040E, T003V-T009E-A069S, T003V-T009E-N076D, T003V-T009E-S078N, T003V-T009E-R185Q, T003V-T009E-P218S, T003V-T009E-N259P, T003V-S040E-A069S, T003V-S040E-N076D, T003V-S040E-S078N, T003V-S040E-R185Q, T003V-S040E-N259P, T003V-A069S-N076D, T003V-A069S-R185Q, T003V-A069S-P218S, T003V-N076D-S078N, T003V-N076D-R185Q, T003V-N076D-P218S, T003V-N076D-N259P, T003V-S078N-R185Q, T003V-S078N-P218S, T003V-S078N-N259P, T003V-R185Q-P218S, T003V-R185Q-N259P, T003V-P218S-N259P, T009E-S040E-N076D, T009E-S040E-S078N, T009E-S040E-R185Q, T009E-S040E-P218S, T009E-S040E-N259P, T009E-A069S-S078N, T009E-A069S-P218S, T009E-A069S-N259P, T009E-N076D-S078N, T009E-N076D-R185Q, T009E-N076D-P218S, T009E-N076D-N259P, T009E-S078N-R185Q, T009E-S078N-P218S, T009E-S078N-N259P, T009E-G166Q-P218S, T009E-R185Q-P218S, T009E-R185Q-N259P, T009E-P218S-N259P, S040E-A069S-N076D, S040E-A069S-R185Q, S040E-A069S-P218S, S040E-A069S-N259P, S040E-N076D-S078N, S040E-N076D-P218S, S040E-N076D-N259P, S040E-S078N-R185Q, S040E-S078N-P218S, S040E-S078N-N259P, S040E-G166Q-P218S, S040E-P218S-N259P, A069S-N076D-S078N, A069S-N076D-R185Q, A069S-N076D-P218S, A069S-N076D-N259P, A069S-S078N-R185Q, A069S-S078N-P218S, A069S-G166Q-P218S, A069S-R185Q-P218S, A069S-R185Q-N259P, N076D-S078N-R185Q, N076D-S078N-P218S, N076D-S078N-N259P, N076D-G166Q-P218S, S078N-G166Q-P218S, S078N-R185Q-N259P, G166Q-R185Q-P218S, G166Q-P218S-N259P, R185Q-P218S-N259P, T003V-S040E-A069S-N076D, T003V-S040E-N076D-S078N, T003V-S040E-N076D-D129P, T003V-S040E-G166Q-R185Q, T003V-S040E-G166Q-N259P, T003V-A069S-R185Q-N259P, T003V-N076D-S078N-N259P, T003V-N076D-R185Q-N259P, T003V-S078N-D129P-N259P, T003V-S078N-P218S-N259P, S040E-N076D-S078N-R185Q, S040E-N076D-P218S-N259P, S040E-S078N-G166Q-P218S, S040E-R185Q-P218S-N259P, A069S-D129P-R185Q-P218S, A069S-R185Q-P218S-N259P, S078N-D129P-R185Q-P218S, D129P-R185Q-P218S-N259P, T003V-T009E-S040E-N076D, T003V-A069S-S078N-P218S, T003V-G166Q-R185Q-P218S, T003V-R185Q-P218S-N259P, T009E-S040E-A069S-P218S, T009E-A069S-N076D-R185Q, T009E-N076D-S078N-R185Q, T009E-N076D-G166Q-P218S, T009E-S078N-R185Q-P218S, S040E-A069S-S078N-P218S, S040E-A069S-G166Q-P218S, S040E-N076D-G166Q-R185Q, S040E-N076D-G166Q-P218S, A069S-N076D-S078N-N259P, A069S-S078N-R185Q-P218S, N076D-S078N-G166Q-R185Q, S078N-G166Q-P218S-N259P, and S078N-R185Q-P218S-N259P, where the positions are numbered by correspondence with the amino acid sequence of SEQ ID NO:1 (BPN').

In yet another embodiment, the disclosure provides variants of subtilisin WP_082194748 with one or more mutations at T003, P009, A024, P040, A069, T078, S087, N118, M124, G128, G166, S182, V185, P210, Y217, T218, Q248, and S259, where the positions are numbered by correspondence with the amino acid sequence of SEQ ID NO:1 (BPN').

In yet another embodiment, the disclosure provides variants of subtilisin WP_082194748 from the group consisting of Y217L, S087D, T078N, G128S, G166Q, S182E, G128S-V185Q, A069S-G128S, T078N-V185Q, V185Q-S259P, G166Q-V185Q, T078N-S259P, T003V-G128S, T078N-G128S, G128S-S259P, G166Q-S259P, A069S-M124I, T003V-M124I, M124I-S259P, M124I-V185Q, T003V-S259P, A069S-S259P, M124I-G128S, A069S-G166Q, T078N-M124I, M124I-G166Q, T078N-G166Q, T003V-G166Q, T003V-T078N-G166Q, T003V-T078N-S259P, T003V-M124I-G128S, T003V-G128S-G166Q, T003V-G128S-S259P, T003V-G166Q-S259P, T078N-M124I-G166Q, T078N-G128S-G166Q, T078N-G166Q-S259P, M124I-G128S-G166Q, M124I-G166Q-S259P, T003V-T078N-M124I-G166Q, T003V-T078N-G166Q-S259P, T003V-M124I-G128S-S259P, T003V-M124I-G166Q-S259P, T078N-M124I-G128S-S259P, and T078N-M124I-G166Q-S259P, where the positions are numbered by correspondence with the amino acid sequence of SEQ ID NO:1 (BPN').

In yet another embodiment, the disclosure provides variants of subtilisin ZP-00454 with one or more mutations at P009, S024, A040, A069, N076, T078, T079, N087, M118, M124, I128, S129, T130, S145, G166, S182, N185, P210, F217, N218, N248, and D259, where the positions are numbered by correspondence with the amino acid sequence of SEQ ID NO:1 (BPN').

In yet another embodiment, the disclosure provides variants of subtilisin ZP-00454 from the group consisting of A040E, A069S, N076D, T078N, T079I, I128S, A040E-M124I, A040E-I128S, A040E-S129P, A040E-G166Q, A040E-A069S, A040E-N185Q, A040E-N076D, A040E-N218S, A040E-T078N, A040E-D259P, A069S-N076D, A069S-N218S, A069S-T078N, A069S-T079I, A069S-1128S, A069S-S129P, A069S-N185Q, N076D-N185Q, N076D-N218S, N076D-T078N, N076D-D259P, N076D-T079I, N076D-M124I, N076D-I128S, N076D-S129P, N076D-G166Q, T078N-N185Q, T078N-D259P, T078N-T079I, T078N-I128S, T078N-S129P, T078N-G166Q, T079I-N218S, T079I-D259P, T079I-M124I, T07914128S, T079I-S129P, T079I-G166Q, T079I-N185Q, 1128S-S129P, and S129P-G166Q, where the positions are numbered by correspondence with the amino acid sequence of SEQ ID NO:1 (BPN').

The subtilisin variants having at least one, two, three, four, or more features selected from the group consisting of: X003T, X003V, X009E, X024Q, X040E, X069S, X076D, X078N, X079I, X087D, X118R, X124I, X128R, X128S, X129P, X130S, X145R, X166Q, X182E, X185Q, X210I, X211P, X217L, X218S, X248D, and X259P, where the amino acid positions are numbered by correspondence with SEQ ID NO: 1, include variants derived from subtilisin polypeptides of AprE (e.g. WP_003233171); WP_082194748 (formerly WP_008359041); Chemgen_164A (SEQ ID NO: 2 in U.S. Pat. No. 5,275,945);

CP474 (e.g. SEQ ID NO: 3 in WO2015038792); ZP-00454 (e.g. variant of WP_010192403, SEQ ID NO:7 in WO2015/038792); DSM14391 (SEQ ID NO: 13 in WO2018118917); WP_010192403 (formerly ZP 07707657 (SEQ ID NO: 7 in WO2015038792)); BspZ00056 (SEQ ID NO:9 in WO 2016069544); Bba02069 (SEQ ID NO: 3 in WO2016061438); Bad02409 (SEQ ID NO: 13 in WO201069557); BspAK01305 (SEQ ID NO: 6 in WO2016069569); BspZ00258 (SEQ ID NO: 9 in WO2016069552); BspAI02518 (SEQ ID NO: 3 in WO2015089441); and Bpan01744 (SEQ ID NO: 3 in WO2016069563). Other subtilisin polypeptides in which the disclosed substitutions find use include, but are not limited to, SEQ ID NO:7 in WO2016/001449; SEQ ID NO: 1 in WO2012/139964; SEQ ID NO: 7 in WO2012/163855; SEQ ID NO: 9 in WO2016/001449; SEQ ID NO: 5 in WO2016/001449; SEQ ID NO: 6 in WO2016/001449; SEQ ID NO: 6 in WO2014/177430; SEQ ID NO: 4 in WO2011/036263; SEQ ID NO: 4 in WO2016/174234; SEQ ID NO: 7 in WO2015144932; SEQ ID NO: 119 in U.S. Pat. No. 7,981,659; SEQ ID NO: 4 in WO2016/001449; SEQ ID NO: 2 in JP2004313043; SEQ ID NO: 2 in US2015/275148; SEQ ID NO: 12 in WO 201600144; SEQ ID NO: 2 in WO 2016000970; SEQ ID NO:19 in U.S. Pat. No. 8,530,218; SEQ ID NO: 8 in WO 2016000973; SEQ ID NO: 8 in WO2016001449; SEQ ID NO 21 or 22 in WO2016203064 and SEQ ID NO: 21 in U.S. Pat. No. 8,530,218. That is, in some embodiments, the substitutions provided herein can be used in any subtilisin having at least about 80% sequence identity to SEQ ID NO: 8, 9, 10, 11, 12, 13, 14, 15, 16, 17, 18, 19, or 22. For example, subtilisins, such as SEQ ID NO 21 or 22 in WO2016203064 can be engineered to include one, two, three or more additional features with respect to SEQ ID NO: 1 selected from a T, or V at position 3; an E at position 9; a Q at position 24; an E at position 40; an S at position 69; a D at position 76; a N at position 78; an I at position 79; a D at position 87; an Rat position 118; an I at position 124; an R, or S at position 128; a P at position 129; an S at position 130; an Rat position 145; a Q at position 166; an E at position 182; a Q at position 185; an I at position 210; a P at position 211; an L at position 217; an S at position 218; a D at position 248; and a P at position 259. In one such embodiment, subtilisins, such as SEQ ID NO 21 or 22 in WO2016203064 can be engineered to include one, two, three, four, or more, substitutions with respect to SEQ ID NO: 1 selected from a T, or V at position 3; an E at position 9; a Q at position 24; an E at position 40; an S at position 69; a D at position 76; a N at position 78; an I at position 79; a D at position 87; an Rat position 118; an I at position 124; an R, or S at position 128; a P at position 129; an S at position 130; an R at position 145; a Q at position 166; an E at position 182; a Q at position 185; an I at position 210; a P at position 211; an L at position 217; an S at position 218; a D at position 248; and a P at position 259.

Still other subtilisin polypeptides in which the disclosed substitutions find use include, but are not limited to, those disclosed in WO_2012_175708_2; WO_2012_175708_4; U.S. Pat. No. 7,951,573 B22; U.S. Pat. No. 7,951,573 B24; U.S. Pat. No. 7,951,573 B26; U.S. Pat. No. 7,951,573 B237; US7727756-0001; US9365844-0001; US7262042-0002; US20090275493-0002; US7811076-0004; US8455424-0003; WO03054184-CAE48421/SEQ ID NO: 25 in WO2015089447; WO2007131657-CA591385/SEQ ID NO:24 in WO2015089447; WO2008086916-CAV33594/SEQ ID NO:26 in WO2015089447; WO2017089162-0001; WO2017089162-0002; WO2017089162-0003; WO2017089162-0004; WO2017089162-0005; WO2017089162-0006; WO2017089162-0007; WO2017089162-0008, and WO2019180111.

In an even still further embodiment, one or more subtilisin variants described herein has improved stability, for example, improved stability in a detergent composition. In another embodiment, parent subtilisin comprises an amino acid sequence of SEQ ID NO: 8, 9, 10, 11, 12, 13, 14, 15, 16, 17, 18, 19, or 22, or has 50%, 55%, 60%, 65%, 70%, 75%, 80%, 85%, 86%, 87%, 88%, 89%, 90%, 91%, 92%, 93%, 94%, 95%, 96%, 97%, 98%, or 99% amino acid sequence identity to the amino acid sequence of SEQ ID NO: 8, 9, 10, 11, 12, 13, 14, 15, 16, 17, 18, 19, or 22. In still yet another embodiment, the stability of the one or more subtilisin variants in detergent is measured in accordance with the stability assays of Example 2.

In other embodiments, one or more subtilisin variants are more stable than a reference, or parent subtilisin lacking the one, two, three or more features. In some embodiments, such variants having increased stability are characterized by having a Performance Index (PI) greater than about 1.1 with respect to a parent, or reference, protease after 20 minutes incubation in 10% liquid detergent at 30-70 degrees Celsius. In some embodiments, the reference subtilisin refers to a subtilisin having the highest identity to the variant subtilisin, but not containing the recited features.

One or more subtilisin variants described herein can be subject to various changes, such as one or more amino acid insertion, deletion, and/or substitution, either conservative or non-conservative, including where such changes do not substantially alter the enzymatic activity of the variant. Similarly, a polynucleotide encoding the subtilisin variant of the invention can also be subject to various changes, such as one or more substitution of one or more nucleotide in one or more codon such that a particular codon encodes the same or a different amino acid, resulting in either a silent variation (e.g., when the encoded amino acid is not altered by the nucleotide mutation) or non-silent variation; one or more deletion of one or more nucleotides (or codon) in the sequence; one or more addition or insertion of one or more nucleotides (or codon) in the sequence; and/or cleavage of, or one or more truncation, of one or more nucleotides (or codon) in the sequence. Many such changes in the nucleic acid sequence may not substantially alter the enzymatic activity of the resulting encoded polypeptide enzyme compared to the polypeptide enzyme encoded by the original nucleic acid sequence. A nucleic acid sequence described herein can also be modified to include one or more codon that provides for optimum expression in an expression system (e.g., bacterial expression system), while, if desired, said one or more codon still encodes the same amino acid(s).

Described herein is one or more isolated, non-naturally occurring, or recombinant polynucleotide comprising a nucleic acid sequence that encodes one or more subtilisin variants described herein, or recombinant polypeptide or active fragment thereof. One or more nucleic acid sequence described herein is useful in recombinant production (e.g., expression) of one or more subtilisin variants described herein, for example, through expression of a plasmid expression vector comprising a sequence encoding the one or more subtilisin variants described herein or fragment thereof. One embodiment provides nucleic acids encoding one or more subtilisin variants described herein, wherein the variant is a mature form having proteolytic activity. In some embodiments, one or more subtilisin variants described herein is expressed recombinantly with a homologous pro-peptide sequence. In other embodiments, one or more subtilisin variants described herein is expressed recombinantly with a heterologous pro-peptide sequence (e.g., pro-peptide sequence from *B. lentus*).

One or more nucleic acid sequence described herein can be generated by using any suitable synthesis, manipulation, and/or isolation techniques, or combinations thereof. For example, one or more polynucleotide described herein may be produced using standard nucleic acid synthesis techniques, such as solid-phase synthesis techniques that are well-known to those skilled in the art. In such techniques, fragments of up to 50 or more nucleotide bases are typically synthesized, then joined (e.g., by enzymatic or chemical ligation methods) to form essentially any desired continuous nucleic acid sequence. The synthesis of the one or more polynucleotide described herein can be also facilitated by any suitable method known in the art, including but not limited to chemical synthesis using the classical phosphoramidite method (See e.g., Beaucage et al. *Tetrahedron Letters* 22:1859-69 (1981)), or the method described in Matthes et al., *EMBO J.* 3:801-805 (1984) as is typically practiced in automated synthetic methods. One or more polynucleotide described herein can also be produced by using an automatic DNA synthesizer. Customized nucleic acids can be ordered from a variety of commercial sources (e.g., ATUM (DNA 2.0), Newark, CA, USA; Life Tech (GeneArt), Carlsbad, CA, USA; GenScript, Ontario, Canada; Base Clear B. V., Leiden, Netherlands; Integrated DNA Technologies, Skokie, IL, USA; Ginkgo Bioworks (Gen9), Boston, MA, USA; and Twist Bioscience, San Francisco, CA, USA). Other techniques for synthesizing nucleic acids and related principles are described by, for example, Itakura et al., *Ann. Rev. Biochem.* 53:323 (1984) and Itakura et al., Science 198:1056 (1984).

Recombinant DNA techniques useful in modification of nucleic acids are well known in the art, such as, for example, restriction endonuclease digestion, ligation, reverse transcription and cDNA production, and polymerase chain reaction (e.g., PCR). One or more polynucleotide described herein may also be obtained by screening cDNA libraries using one or more oligonucleotide probes that can hybridize to or PCR-amplify polynucleotides which encode one or more subtilisin variant described herein, or recombinant polypeptide or active fragment thereof. Procedures for screening and isolating cDNA clones and PCR amplification procedures are well known to those of skill in the art and described in standard references known to those skilled in the art. One or more polynucleotide described herein can be obtained by altering a naturally occurring polynucleotide backbone (e.g., that encodes one or more subtilisin variant described herein or reference subtilisin) by, for example, a known mutagenesis procedure (e.g., site-directed mutagenesis, site saturation mutagenesis, and in vitro recombination). A variety of methods are known in the art that are suitable for generating modified polynucleotides described herein that encode one or more subtilisin variant described herein, including, but not limited to, for example, site-saturation mutagenesis, scanning mutagenesis, insertional mutagenesis, deletion mutagenesis, random mutagenesis, site-directed mutagenesis, and directed-evolution, as well as various other recombinatorial approaches.

A further embodiment is directed to one or more vector comprising one or more subtilisin variant described herein (e.g., a polynucleotide encoding one or more subtilisin variant described herein); expression vectors or expression cassettes comprising one or more nucleic acid or polynucleotide sequence described herein; isolated, substantially pure, or recombinant DNA constructs comprising one or more nucleic acid or polynucleotide sequence described herein; isolated or recombinant cells comprising one or more polynucleotide sequence described herein; and compositions comprising one or more such vector, nucleic acid, expression vector, expression cassette, DNA construct, cell, cell culture, or any combination or mixtures thereof.

Some embodiments are directed to one or more recombinant cell comprising one or more vector (e.g., expression vector or DNA construct) described herein which comprises one or more nucleic acid or polynucleotide sequence described herein. Some such recombinant cells are transformed or transfected with such at least one vector, although other methods are available and known in the art. Such cells are typically referred to as host cells. Some such cells comprise bacterial cells, including, but not limited to *Bacillus* sp. cells, such as *B. subtilis* cells. Other embodiments are directed to recombinant cells (e.g., recombinant host cells) comprising one or more subtilisin described herein.

In some embodiments, one or more vector described herein is an expression vector or expression cassette comprising one or more polynucleotide sequence described herein operably linked to one or more additional nucleic acid segments required for efficient gene expression (e.g., a promoter operably linked to one or more polynucleotide sequence described herein). A vector may include a transcription terminator and/or a selection gene (e.g., an antibiotic resistance gene) that enables continuous cultural maintenance of plasmid-infected host cells by growth in antimicrobial-containing media.

An expression vector may be derived from plasmid or viral DNA, or in alternative embodiments, contains elements of both. Exemplary vectors include, but are not limited to pC194, pJH101, pE194, pHP13 (See, Harwood and Cutting [eds.], Chapter 3, Molecular Biological Methods for *Bacillus*, John Wiley & Sons (1990); suitable replicating plasmids for *B. subtilis* include those listed on p. 92). (See also, Perego, "Integrational Vectors for Genetic Manipulations in *Bacillus subtilis*"; Sonenshein et al., [eds.]; "*Bacillus subtilis* and Other Gram-Positive Bacteria: Biochemistry, Physiology and Molecular Genetics", American Society for Microbiology, Washington, D.C. (1993), pp. 615-624); and p2JM103BBI).

For expression and production of a protein of interest (e.g., one or more subtilisin variant described herein) in a cell, one or more expression vector comprising one or more copy of a polynucleotide encoding one or more subtilisin variant described herein, and in some instances comprising multiple copies, is transformed into the cell under conditions suitable for expression of the variant. In some embodiments, a polynucleotide sequence encoding one or more subtilisin variant described herein (as well as other sequences included in the vector) is integrated into the genome of the host cell, while in other embodiments, a plasmid vector comprising a polynucleotide sequence encoding one or more subtilisin variant described herein remains as autonomous extra-chromosomal element within the cell. Some embodiments provide both extrachromosomal nucleic acid elements as well as incoming nucleotide sequences that are integrated into the host cell genome. The vectors described herein are useful for production of the one or more subtilisin variant described herein. In some embodiments, a polynucleotide construct encoding one or more subtilisin variant described herein is present on an integrating vector that enables the integration and optionally the amplification of the polynucleotide encoding the variant into the host chromosome. Examples of sites for integration are well known to those skilled in the art. In some embodiments, transcription of a polynucleotide encoding one or more subtilisin variant described herein is effectuated by a promoter that is the wildtype promoter for the parent subtilisin. In some other embodiments, the promoter is heterologous to the one or more subtilisin variant described herein, but is functional in the host cell. Exemplary promoters for use in bacterial host cells include, but are not limited to the amyE, amyQ, amyL, pstS, sacB, pSPAC, pAprE, pVeg, pHpaII promoters; the promoter of the *B. stearothermophilus* maltogenic amylase gene; the *B. amyloliquefaciens* (BAN) amylase gene; the *B. subtilis* alkaline protease gene; the *B. clausii* alkaline protease gene; the *B. pumilis* xylosidase gene; the *B. thuringiensis* cryIIIA; and the *B. licheniformis* alpha-amylase gene. Additional promoters include, but are not limited to the A4 promoter, as well as phage Lambda PR or PL promoters and the *E. coli* lac, trp or tac promoters.

One or more subtilisin variant described herein can be produced in host cells of any suitable microorganism, including bacteria and fungi. In some embodiments, one or more subtilisin variant described herein can be produced in Gram-positive bacteria. In some embodiments, the host cells are *Bacillus* spp., *Streptomyces* spp., *Escherichia* spp., *Aspergillus* spp., *Trichoderma* spp., *Pseudomonas* spp., *Corynebacterium* spp., *Saccharomyces* spp., or *Pichia* spp. In some embodiments, one or more subtilisin variant described herein is produced by *Bacillus* sp. host cells. Examples of *Bacillus* sp. host cells that find use in the production of the one or more subtilisin variant described herein include, but are not limited to *B. licheniformis, B. lentus, B. subtilis, B. amyloliquefaciens, B. brevis, B. stearothermophilus, B. alkalophilus, B. coagulans, B. circulans, B. pumilis, B. thuringiensis, B. clausii*, and *B. megaterium*, as well as other organisms within the genus *Bacillus*. In some embodiments, *B. subtilis* host cells are used to produce the variants described herein. U.S. Pat. Nos. 5,264,366 and 4,760,025 (RE 34,606) describe various *Bacillus* host strains that can be used to produce one or more subtilisin variant described herein, although other suitable strains can be used.

Several bacterial strains that can be used to produce one or more subtilisin variant described herein include non-recombinant (i.e., wildtype) *Bacillus* sp. strains, as well as variants of naturally-occurring strains and/or recombinant strains. In some embodiments, the host strain is a recombinant strain, wherein a polynucleotide encoding one or more subtilisin variant described herein has been introduced into the host. In some embodiments, the host strain is a *B. subtilis* host strain and particularly a recombinant *B. subtilis* host strain. Numerous *B. subtilis* strains are known, including, but not limited to for example, 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211strain (See e.g., Hoch et al., *Genetics* 73:215-228 (1973); See also, U.S. Pat. Nos. 4,450,235; 4,302,544; and EP 0134048). The use of *B. subtilis* as an expression host cell is well known in the art (See e.g., Palva et al., *Gene* 19:81-87 (1982); Fahnestock and Fischer, *J. Bacteriol.,* 165:796-804 (1986); and Wang et al., *Gene* 69:39-47 (1988)).

In some embodiments, the *Bacillus* host cell is a *Bacillus* sp. that includes a mutation or deletion in at least one of the following genes: degU, degS, degR and degQ. In some embodiments, the mutation is in a degU gene, and in some embodiments the mutation is degU(Hy)32 (See e.g., Msadek et al., *J. Bacteriol.* 172:824-834 (1990); and Olmos et al., *Mol. Gen. Genet.* 253:562-567 (1997)). In some embodiments, the *Bacillus* host comprises a mutation or deletion in scoC4 (See e.g., Caldwell et al., *J. Bacteriol.* 183:7329-7340 (2001)); spoIIE (See e.g., Arigoni et al., *Mol. Microbiol.* 31:1407-1415 (1999)); and/or oppA or other genes of the opp operon (See e.g., Perego et al., Mol. Microbiol. 5:173-185 (1991)). Indeed, it is contemplated that any mutation in the opp operon that causes the same phenotype as a mutation in the oppA gene will find use in some embodiments of the altered *Bacillus* strain described herein. In some embodiments, these mutations occur alone, while in other embodiments, combinations of mutations are present. In some embodiments, an altered *Bacillus* host cell strain that can be used to produce one or more subtilisin variant described herein is a *Bacillus* host strain that already includes a mutation in one or more of the above-mentioned genes. In addition, *Bacillus* sp. host cells that comprise mutation(s) and/or deletion(s) of endogenous protease genes find use. In some embodiments, the *Bacillus* host cell comprises a deletion of the aprE and the nprE genes. In other embodiments, the *Bacillus* sp. host cell comprises a deletion of 5 protease genes, while in other embodiments the *Bacillus* sp. host cell comprises a deletion of 9 protease genes (See e.g., US 2005/0202535).

Host cells are transformed with one or more nucleic acid sequence encoding one or more subtilisin variant described herein using any suitable method known in the art. Methods for introducing a nucleic acid (e.g., DNA) into *Bacillus* cells or *E. coli* cells utilizing plasmid DNA constructs or vectors and transforming such plasmid DNA constructs or vectors into such cells are well known. In some embodiments, the plasmids are subsequently isolated from *E. coli* cells and transformed into *Bacillus* cells. However, it is not essential to use intervening microorganisms such as *E. coli*, and in some embodiments, a DNA construct or vector is directly introduced into a *Bacillus* host.

Exemplary methods for introducing one or more nucleic acid sequence described herein into *Bacillus* cells are described in, for example, Ferrari et al., "Genetics," in Harwood et al. [eds.], *Bacillus*, Plenum Publishing Corp. (1989), pp. 57-72; Saunders et al., *J. Bacteriol.* 157:718-726 (1984); Hoch et al., *J. Bacteriol.* 93:1925-1937 (1967); Mann et al., *Current Microbiol.* 13:131-135 (1986); Holubova, *Folia Microbiol.* 30:97 (1985); Chang et al., *Mol. Gen. Genet.* 168:11-115 (1979); Vorobjeva et al., *FEMS Microbiol. Lett.* 7:261-263 (1980); Smith et al., *Appl. Env. Microbiol.* 51:634 (1986); Fisher et al., *Arch. Microbiol.* 139:213-217 (1981); and McDonald, *J. Gen. Microbiol.* 130:203 (1984)). Indeed, such methods as transformation, including protoplast transformation and transfection, transduction, and protoplast fusion are well known and suited for use herein. Methods known in the art to transform *Bacillus* cells include such methods as plasmid marker rescue transformation, which involves the uptake of a donor plasmid by competent cells carrying a partially homologous resident plasmid (See, Contente et al., *Plasmid* 2:555-571 (1979); Haima et al., *Mol. Gen. Genet.* 223:185-191 (1990); Weinrauch et al., *J. Bacteriol.* 154:1077-1087 (1983); and Weinrauch et al., *J. Bacteriol.* 169:1205-1211 (1987)). In this method, the incoming donor plasmid recombines with the homologous region of the resident "helper" plasmid in a process that mimics chromosomal transformation.

In addition to commonly used methods, in some embodiments, host cells are directly transformed with a DNA construct or vector comprising a nucleic acid encoding one or more subtilisin variant described herein (i.e., an intermediate cell is not used to amplify, or otherwise process, the DNA construct or vector prior to introduction into the host cell). Introduction of a DNA construct or vector described herein into the host cell includes those physical and chemical methods known in the art to introduce a nucleic acid sequence (e.g., DNA sequence) into a host cell without insertion into the host genome. Such methods include, but are not limited to calcium chloride precipitation, electroporation, naked DNA, and liposomes. In additional embodiments, DNA constructs or vector are co-transformed with a plasmid, without being inserted into the plasmid. In further embodiments, a selective marker is deleted from the altered *Bacillus* strain by methods known in the art (See, Stahl et al., *J. Bacteriol.* 158:411-418 (1984); and Palmeros et al., *Gene* 247:255-264 (2000)).

In some embodiments, the transformed cells are cultured in conventional nutrient media. The suitable specific culture conditions, such as temperature, pH and the like are known to those skilled in the art and are well described in the scientific literature. Some embodiments provide a culture (e.g., cell culture) comprising one or more subtilisin variant or nucleic acid sequence described herein.

In some embodiments, host cells transformed with one or more polynucleotide sequence encoding one or more subtilisin variant described herein are cultured in a suitable nutrient medium under conditions permitting the expression of the variant, after which the resulting variant is recovered from the culture. In some embodiments, the variant produced by the cells is recovered from the culture medium by conventional procedures, including, but not limited to, for example, separating the host cells from the medium by centrifugation or filtration, precipitating the proteinaceous components of the supernatant or filtrate by means of a salt (e.g., ammonium sulfate), and chromatographic purification (e.g., ion exchange, gel filtration, affinity, etc.).

In some embodiments, one or more subtilisin variant produced by a recombinant host cell is secreted into the culture medium. A nucleic acid sequence that encodes a purification facilitating domain may be used to facilitate purification of the variant. A vector or DNA construct comprising a polynucleotide sequence encoding one or more subtilisin variant described herein may further comprise a nucleic acid sequence encoding a purification facilitating domain to facilitate purification of the variant (See e.g., Kroll et al., *DNA Cell Biol.* 12:441-53 (1993)). Such purification facilitating domains include, but are not limited to, for example, metal chelating peptides such as histidine-tryptophan modules that allow purification on immobilized metals (See, Porath, *Protein Expr. Purif.* 3:263-281 [1992]), protein A domains that allow purification on immobilized immunoglobulin, and the domain utilized in the FLAGS extension/affinity purification system. The inclusion of a cleavable linker sequence such as Factor XA or enterokinase (e.g., sequences available from Invitrogen, San Diego, CA) between the purification domain and the heterologous protein also find use to facilitate purification.

A variety of methods can be used to determine the level of production of one or more mature subtilisin variant described herein in a host cell. Such methods include, but are not limited to, for example, methods that utilize either polyclonal or monoclonal antibodies specific for the protease. Exemplary methods include, but are not limited to enzyme-linked immunosorbent assays (ELISA), radioimmunoassays (MA), fluorescent immunoassays (FIA), and fluorescent activated cell sorting (FACS). These and other assays are well known in the art (See e.g., Maddox et al., *J. Exp. Med.* 158:1211 (1983)).

Some other embodiments provide methods for making or producing one or more mature subtilisin variant described herein. A mature subtilisin variant does not include a signal peptide or a propeptide sequence. Some methods comprise making or producing one or more subtilisin variant described herein in a recombinant bacterial host cell, such as for example, a *Bacillus* sp. cell (e.g., a *B. subtilis* cell). Other embodiments provide a method of producing one or more subtilisin variant described herein, wherein the method comprises cultivating a recombinant host cell comprising a recombinant expression vector comprising a nucleic acid sequence encoding one or more subtilisin variant described herein under conditions conducive to the production of the variant. Some such methods further comprise recovering the variant from the culture.

Further embodiments provide methods of producing one or more subtilisin variant described herein, wherein the methods comprise: (a) introducing a recombinant expression vector comprising a nucleic acid encoding the variant into a population of cells (e.g., bacterial cells, such as *B. subtilis* cells); and (b) culturing the cells in a culture medium under conditions conducive to produce the variant encoded by the expression vector. Some such methods further comprise: (c) isolating the variant from the cells or from the culture medium.

Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated. Compositions described herein include cleaning compositions, such as detergent compositions. In the exemplified detergent compositions, the enzyme levels are expressed by pure enzyme by weight of the total composition and unless otherwise specified, the detergent ingredients are expressed by weight of the total compositions.

The subtilisin variants provided herein may be used in the production of various compositions, such as enzyme compositions and cleaning or detergent compositions. An enzyme composition comprises a subtilisin variant as provided herein. The enzyme composition can be in any form, such as granule, liquid formulations, or enzyme slurries.

Enzyme granules may be made by, e.g., rotary atomization, wet granulation, dry granulation, spray drying, disc granulation, extrusion, pan coating, spheronization, drum granulation, fluid-bed agglomeration, high-shear granulation, fluid-bed spray coating, crystallization, precipitation, emulsion gelation, spinning disc atomization and other casting approaches, and prilling processes. The core of the granule may be the granule itself or the inner nucleus of a layered granule.

The core may comprise one or more water soluble or dispersible agent(s), including but not limited to, sodium sulfate, sodium chloride, magnesium sulfate, zinc sulfate, and ammonium sulfate), citric acid, sugars (e.g., sucrose, lactose, glucose, granulated sucrose, maltodextrin and fructose), plasticizers (e.g., polyols, urea, dibutyl phthalate, and dimethyl phthalate), fibrous material (e.g., cellulose and cellulose derivatives such as hydroxyl-propyl-methyl cellulose, carboxy-methyl cellulose, and hydroxyl-ethyl cellulose), phosphate, calcium, a protease inhibitor and combinations thereof. Suitable dispersible agents include, but are not limited to, clays, nonpareils (combinations of sugar and starch; e.g., starch-sucrose non-pareils-ASNP), talc, silicates, carboxymethyl cellulose, starch, and combinations thereof.

In some embodiments, the core comprises mainly sodium sulfate. In some embodiments, the core consists essentially of sodium sulfate. In a particular embodiment, the core consists of only sodium sulfate.

In some embodiments, the core comprises a subtilisin variant as provided herein. In other embodiments, the core comprises one or more enzymes in addition to protease. In other embodiments, the core is inert and does not comprise enzymes.

In some embodiments, the core is an enzyme powder, including UFC containing an enzyme. The enzyme powder may be spray dried and may optionally be admixed with any of the water soluble or dispersible agents listed, herein. The enzyme may be, or may include, the protease to be stabilized, in which case the enzyme power should further include a stabilizer.

In some embodiments the core is coated with at least one coating layer. In a particular embodiment, the core is coated with at least two coating layers. In another particular embodiment the core is coated with at least three coating layers. The materials used in the coating layer(s) can be suitable for use in cleaning and/or detergent compositions.

In some embodiments, a coating layer comprises one of more of the following materials: an inorganic salt (e.g., sodium sulfate, sodium chloride, magnesium sulfate, zinc sulfate, and ammonium sulfate), citric acid, a sugar (e.g., sucrose, lactose, glucose, and fructose), a plasticizer (e.g., polyols, urea, dibutyl phthalate, and dimethyl phthalate), fibrous material (e.g., cellulose and cellulose derivatives such as hydroxyl-propyl-methyl cellulose, carboxy-methyl cellulose, and hydroxyl-ethyl cellulose), clay, nonpareil (a combination of sugar and starch), silicate, carboxymethyl cellulose, phosphate, starch (e.g., corn starch), fats, oils (e.g., rapeseed oil, and paraffin oil), lipids, vinyl polymers, vinyl copolymers, polyvinyl alcohol (PVA), plasticizers (e.g., polyols, urea, dibutyl phthalate, dimethyl phthalate, and water), anti-agglomeration agents (e.g., talc, clays, amorphous silica, and titanium dioxide), anti-foam agents (such as FOAMBLAST 882® and EROL 6000K®), and talc. US20100124586, WO9932595, and U.S. Pat. No. 5,324,649 detail suitable components for the coating layers.

In some embodiments, the coating layer comprises sugars (e.g., sucrose, lactose, glucose, granulated sucrose, maltodextrin and fructose). In some embodiments, the coating layer comprises a polymer such as polyvinyl alcohol (PVA). Suitable PVA for incorporation in the coating layer(s) of the multi-layered granule include partially hydrolyzed, fully hydrolyzed and intermediately hydrolyzed having low to high degrees of viscosity. In some embodiments, the coating layer comprises an inorganic salt, such as sodium sulfate.

In some embodiments, at least one coating layer is an enzyme coating layer. In some embodiments the core is coated with at least two enzyme layers. In another embodiment the core is coated with at least three or more enzyme layers.

In some embodiments, the enzymes are protease in combination with one or more additional enzymes selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, nucleases (e.g. DNases and/or RNases), oxidases, oxidoreductases, pectate lyases, pectin acetyl esterases, pectinases, pentosanases, perhydrolases, peroxidases, phenoloxidases, phosphatases, phospholipases, phytases, polygalacturonases, polyesterases, additional proteases, pullulanases, reductases, rhamnogalacturonases, beta-glucanases, tannases, transglutaminases, xylan acetylesterases, xylanases, xyloglucanases, xylosidases, and any combination or mixture thereof. Generally, at least one enzyme coating layer comprises at least one protease.

The above enzyme lists are examples only and are not meant to be exclusive. Any enzyme can be used in the granules described herein, including wild type, recombinant and variant enzymes of bacterial, fungal, yeast sources, and acid, neutral or alkaline enzymes.

In one embodiment, one or more subtilisin variant described herein is useful in cleaning applications, such as, for example, but not limited to, cleaning dishware or tableware items, fabrics, medical instruments and items having hard surfaces (e.g., the hard surface of a table, table top, wall, furniture item, floor, and ceiling). In other embodiments, one or more subtilisin variant described herein is useful in disinfecting applications, such as, for example, but not limited to, disinfecting an automatic dishwashing or laundry machine. In other embodiments, one or more subtilisin variant described herein and compositions comprising such variant are useful in applications to remove or prevent malodor, such as, for example, but not limited to, on laundry, hard surfaces, automatic dishwashing or laundry machines.

Another embodiment is directed to a composition comprising one or more subtilisin variant described herein. In some embodiments, the composition is a cleaning composition. In other embodiments, the composition is a detergent composition. In yet other embodiments, the composition is selected from a laundry detergent composition, an automatic dishwashing (ADW) composition, a hand (manual) dishwashing detergent composition, a hard surface cleaning composition, an eyeglass cleaning composition, a medical instrument cleaning composition, a disinfectant (e.g., malodor or microbial) composition, and a personal care cleaning composition. In still other embodiments, the composition is a laundry detergent composition, an ADW composition, or a hand (manual) dishwashing detergent composition. Even still further embodiments are directed to fabric cleaning compositions, while other embodiments are directed to non-fabric cleaning compositions. In some embodiments, the cleaning composition is boron-free. In other embodiments, the cleaning composition is phosphate-free. In still other embodiments, the composition comprises one or more subtilisin variant described herein and one or more of an excipient, adjunct material, and/or additional enzyme.

In yet still a further embodiment, the composition described herein contains phosphate, is phosphate-free, contains boron, is boron-free, or combinations thereof. In other embodiments, the composition is a boron-free composition. In some embodiments, a boron-free composition is a composition to which a borate stabilizer has not been added. In another embodiment, a boron-free composition is a composition that contains less than 5.5% boron. In a still further embodiment, a boron-free composition is a composition that contains less than 4.5% boron. In yet still another embodiment, a boron-free composition is a composition that contains less than 3.5% boron. In yet still a further embodiment, a boron-free composition is a composition that contains less than 2.5% boron. In even further embodiments, a boron-free composition is a composition that contains less than 1.5% boron. In another embodiment, a boron-free composition is a composition that contains less than 1.0% boron. In still further embodiments, a boron-free composition is a composition that contains less than 0.5% boron. In still further embodiments, a boron-free composition is a composition substantially free of boron. In other embodiments, the composition is a composition free or substantially free of enzyme stabilizers or peptide inhibitors.

In another embodiment, one or more composition described herein is in a form selected from gel, tablet, powder, granular, solid, liquid, unit dose, and combinations thereof. In yet another embodiment, one or more composition described herein is in a form selected from a low water compact formula, low water HDL or Unit Dose (UD), or high water formula or HDL. In some embodiments, the cleaning composition described herein is in a unit dose form. In other embodiments, the unit dose form is selected from pills, tablets, capsules, gelcaps, sachets, pouches, multi-compartment pouches, and pre-measured powders or liquids. In some embodiments, the unit dose format is designed to provide controlled release of the ingredients within a multi-compartment pouch (or other unit dose format). Suitable unit dose and controlled release formats are described, for example, in EP 2100949; WO 02/102955; U.S. Pat. Nos. 4,765,916; 4,972,017; and WO 04/111178. In some embodiments, the unit dose form is a tablet or powder contained in a water-soluble film or pouch.

Exemplary laundry detergent compositions include, but are not limited to, for example, liquid and powder laundry detergent compositions. Exemplary hard surface cleaning compositions include, but are not limited to, for example, compositions used to clean the hard surface of a non-dishware item, non-tableware item, table, table top, furniture item, wall, floor, and ceiling. Exemplary hard surface cleaning compositions are described, for example, in U.S. Pat. Nos. 6,610,642, 6,376,450, and 6,376,450. Exemplary personal care compositions include, but are not limited to, compositions used to clean dentures, teeth, hair, contact lenses, and skin. Exemplary components of such oral care composition include those described in, for example, U.S. Pat. No. 6,376,450.

In some embodiments, one or more subtilisin variant described herein cleans at low temperatures. In other embodiments, one or more composition described herein cleans at low temperatures. In other embodiments, one or more composition described herein comprises an effective amount of one or more subtilisin variant described herein as useful or effective for cleaning a surface in need of proteinaceous stain removal.

In some embodiments, adjunct materials are incorporated, for example, to assist or enhance cleaning performance; for treatment of the substrate to be cleaned; or to modify the aesthetics of the cleaning composition as is the case with perfumes, colorants, dyes or the like. One embodiment is directed to a composition comprising one or more adjunct material and one or more subtilisin variant described herein. Another embodiment is directed to a composition comprising one or more adjunct material and one or more subtilisin variant described herein, wherein the adjunct material is selected from a bleach catalyst, an additional enzyme, an enzyme stabilizer (including, for example, an enzyme stabilizing system), a chelant, an optical brightener, a soil release polymer, a dye transfer agent, a dispersant, a suds suppressor, a dye, a perfume, a colorant, a filler, a photoactivator, a fluorescer, a fabric conditioner, a hydrolyzable surfactant, a preservative, an anti-oxidant, an anti-shrinkage agent, an anti-wrinkle agent, a germicide, a fungicide, a color speckle, a silvercare agent, an anti-tarnish agent, an anti-corrosion agent, an alkalinity source, a solubilizing agent, a carrier, a processing aid, a pigment, a pH control agent, a surfactant, a builder, a chelating agent, a dye transfer inhibiting agent, a deposition aid, a catalytic material, a bleach activator, a bleach booster, a hydrogen peroxide, a source of hydrogen peroxide, a preformed peracid, a polymeric dispersing agent, a clay soil removal/anti-redeposition agent, a structure elasticizing agent, a fabric softener, a carrier, a hydrotrope, a processing aid, a pigment, and combinations thereof. Exemplary adjunct materials and levels of use are found in U.S. Pat. Nos. 5,576,282; 6,306,812; 6,326,348; 6,610,642; 6,605,458; 5,705,464; 5,710,115; 5,698,504; 5,695,679; 5,686,014 and 5,646,101. In embodiments in which one or more cleaning adjunct material is not compatible with one or more subtilisin variant described herein, methods are employed to keep the adjunct material and variant(s) separated (i.e., not in contact with each other) until combination of the two components is appropriate. Such separation methods include any suitable method known in the art (e.g., gelcaps, encapsulation, tablets, physical separation, etc.).

Some embodiments are directed to cleaning additive products comprising one or more subtilisin variant described herein. In some embodiments, the additive is packaged in a dosage form for addition to a cleaning process. In some embodiments, the additive is packaged in a dosage form for addition to a cleaning process where a source of peroxygen is employed and increased bleaching effectiveness is desired.

Exemplary fillers or carriers for granular compositions include, but are not limited to, for example, various salts of sulfate, carbonate and silicate; talc; and clay. Exemplary fillers or carriers for liquid compositions include, but are not limited to, for example, water or low molecular weight primary and secondary alcohols including polyols and diols (e.g., methanol, ethanol, propanol and isopropanol). In some embodiments, the compositions contain from about 5% to about 90% of such filler or carrier. Acidic fillers may be included in such compositions to reduce the pH of the resulting solution in the cleaning method or application.

In one embodiment, one or more cleaning composition described herein comprises an effective amount of one or more subtilisin variant described herein, alone or in combination with one or more additional enzyme. Typically, a cleaning composition comprises at least about 0.0001 to about 20 wt %, from about 0.0001 to about 10 wt %, from about 0.0001 to about 1 wt %, from about 0.001 to about 1 wt %, or from about 0.01 to about 0.1 wt % of one or more protease. In another embodiment, one or more cleaning composition described herein comprises from about 0.01 to about 10 mg, about 0.01 to about 5 mg, about 0.01 to about 2 mg, about 0.01 to about 1 mg, about 0.05 to about 1 mg, about 0.5 to about 10 mg, about 0.5 to about 5 mg, about 0.5 to about 4 mg, about 0.5 to about 3 mg, about 0.5 to about 2 mg, about 0.5 to about 1 mg, about 0.1 to about 10 mg, about 0.1 to about 5 mg, about 0.1 to about 4 mg, about 0.1 to about 3 mg, about 0.1 to about 2 mg, about 0.1 to about 1 mg, or about 0.1 to about 0.5 mg of one or more protease per gram of composition.

The cleaning compositions described herein are typically formulated such that during use in aqueous cleaning operations, the wash water will have a pH of from about 4.0 to about 11.5, or even from about 5.0 to about 11.5, or even from about 5.0 to about 8.0, or even from about 7.5 to about 10.5. Liquid product formulations are typically formulated to have a pH from about 3.0 to about 9.0 or even from about 3 to about 5. Granular laundry products are typically formulated to have a pH from about 8 to about 11. In some embodiments, the cleaning compositions of the present invention can be formulated to have an alkaline pH under wash conditions, such as a pH of from about 8.0 to about 12.0, or from about 8.5 to about 11.0, or from about 9.0 to about 11.0. In some embodiments, the cleaning compositions of the present invention can be formulated to have a neutral pH under wash conditions, such as a pH of from about 5.0 to about 8.0, or from about 5.5 to about 8.0, or from about 6.0 to about 8.0, or from about 6.0 to about 7.5. In some embodiments, the neutral pH conditions can be measured when the cleaning composition is dissolved 1:100 (wt:wt) in de-ionised water at 20° C., measured using a conventional pH meter. Techniques for controlling pH at recommended usage levels include the use of buffers, alkalis, acids, etc., and are well known to those skilled in the art.

In some embodiments, one or more subtilisin variant described herein is encapsulated to protect it during storage from the other components in the composition and/or control the availability of the variant during cleaning. In some embodiments, encapsulation enhances the performance of the variant and/or additional enzyme. In some embodiments, the encapsulating material typically encapsulates at least part of the subtilisin variant described herein. Typically, the encapsulating material is water-soluble and/or water-dispersible. In some embodiments, the encapsulating material has a glass transition temperature (Tg) of 0° C. or higher. Exemplary encapsulating materials include, but are not limited to, carbohydrates, natural or synthetic gums, chitin, chitosan, cellulose and cellulose derivatives, silicates, phosphates, borates, polyvinyl alcohol, polyethylene glycol, paraffin waxes, and combinations thereof. When the encapsulating material is a carbohydrate, it is typically selected from monosaccharides, oligosaccharides, polysaccharides, and combinations thereof. In some embodiments, the encapsulating material is a starch (See e.g., EP0922499, U.S. Pat. Nos. 4,977,252, 5,354,559, and 5,935,826). In some embodiments, the encapsulating material is a microsphere made from plastic such as thermoplastics, acrylonitrile, methacrylonitrile, polyacrylonitrile, polymethacrylonitrile and mixtures thereof. Exemplary commercial microspheres include, but are not limited to EXPANCEL® (Stockviksverken, Sweden); and PM 6545, PM 6550, PM 7220, PM 7228, EXTENDOSPHERES®, LUXSIL®, Q-CEL®, and SPHERICEL® (PQ Corp., Valley Forge, PA).

There are a variety of wash conditions including varying detergent formulations, wash water volumes, wash water temperatures, and lengths of wash time to which one or more subtilisin variant described herein may be exposed. A low detergent concentration system is directed to wash water containing less than about 800 ppm detergent components. A medium detergent concentration system is directed to wash containing between about 800 ppm and about 2000 ppm detergent components. A high detergent concentration system is directed to wash water containing greater than about 2000 ppm detergent components. In some embodiments, the "cold water washing" of the present invention utilizes "cold water detergent" suitable for washing at temperatures from about 10° C. to about 40° C., from about 20° C. to about 30° C., or from about 15° C. to about 25° C., as well as all other combinations within the range of about 15° C. to about 35° C. or 10° C. to 40° C.

Different geographies have different water hardness. Hardness is a measure of the amount of calcium ($Ca^{2+}$) and magnesium ($Mg^{2+}$) in the water. Water hardness is usually described in terms of the grains per gallon (gpg) mixed $Ca^{2+}/Mg^{2+}$. Most water in the United States is hard, but the degree of hardness varies. Moderately hard (60-120 ppm) to hard (121-181 ppm) water has 60 to 181 ppm (ppm can be converted to grains per U.S. gallon by dividing ppm by 17.1) of hardness minerals.

| Water | Grains per gallon | Parts per million |
|---|---|---|
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

Other embodiments are directed to one or more cleaning composition comprising from about 0.00001% to about 10% by weight composition of one or more subtilisin variant described herein and from about 99.999% to about 90.0% by weight composition of one or more adjunct material. In another embodiment, the cleaning composition comprises from about 0.0001% to about 10%, about 0.001% to about 5%, about 0.001% to about 2%, or about 0.005% to about 0.5% by weight composition of one or more subtilisin variant and from about 99.9999% to about 90.0%, about 99.999% to about 98%, about 99.995% to about 99.5% by weight composition of one or more adjunct material.

In other embodiments, the composition described herein comprises one or more subtilisin variant described herein and one or more additional enzyme. The one or more additional enzyme is selected from acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, metalloproteases, nucleases (e.g. DNases and RNases), oxidases, oxidoreductases, pectate lyases, pectin acetyl esterases, pectinases, pentosanases, perhydrolases, peroxidases, phenoloxidases, phosphatases, phospholipases, phytases, polygalacturonases, polyesterases, additional proteases, pullulanases, reductases, rhamnogalacturonases, beta-glucanases, tannases, transglutaminases, xylan acetyl-esterases, xylanases, xyloglucanases, xylosidases, and any combination or mixture thereof. Some embodiments are directed to a combination of enzymes (i.e., a "cocktail") comprising conventional enzymes like amylase, lipase, cutinase, mannanase and/or cellulase in conjunction with one or more subtilisin variant described herein and/or one or more additional protease.

In another embodiment, one or more composition described herein comprises one or more subtilisin variant described herein and one or more additional protease. In one embodiment, the additional protease is a serine protease. In another embodiment, the additional protease is an alkaline microbial protease or a trypsin-like protease. Suitable additional proteases include those of animal, plant or microbial origin. In some embodiments, the additional protease is a microbial protease. In other embodiments, the additional protease is a chemically or genetically modified mutant. In another embodiment, the additional protease is a metalloprotease, a fungal subtilisin, an alkaline microbial protease or a trypsin-like protease. Exemplary alkaline proteases include subtilisins derived from, for example, *Bacillus* (e.g., *subtilis, lentus, amyloliquefaciens, licheniformis, gibsonii, clausii, alkalophilus*, subtilisin 309, subtilisin 147 and subtilisin 168). Exemplary additional proteases include but are not limited to those described in WO92/21760, WO95/

23221, WO2008/010925, WO09/149200, WO09/149144, WO09/149145, WO 10/056640, WO10/056653, WO2010/0566356, WO11/072099, WO2011/13022, WO11/140364, WO 12/151534, WO2015/038792, WO2015/089447, WO2015/089441, WO2019180111, US Publ. No. 2008/0090747, U.S. Pat. Nos. 5,801,039, 5,340,735, 5,500,364, 5,855,625, RE 34,606, U.S. Pat. Nos. 5,955,340, 5,700,676 6,312,936, 6,482,628, 8,530,219, U.S. Provisional Appl Nos. 62/180,673 and 62/161,077, and PCT Appl Nos. PCT/US2015/021813, PCT/US2015/055900, PCT/US2015/057497, PCT/US2015/057492, PCT/US2015/057512, PCT/US2015/057526, PCT/US2015/057520, PCT/US2015/057502, PCT/US2016/022282, and PCT/US16/32514, as well as metalloproteases described in WO1999014341, WO1999033960, WO1999014342, WO1999034003, WO2007044993, WO2009058303, WO 2009058661, WO2014071410, WO2014194032, WO2014194034, WO 2014194054, and WO 2014/194117. Exemplary additional proteases include, but are not limited to trypsin (e.g., of porcine or bovine origin) and the *Fusarium* protease described in WO89/06270. Exemplary commercial proteases include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™ PREFERENZ™ proteases (e.g. P100, P110, P280, P300), EFFECTENZ™ proteases (e.g. P1000, P1050, P2000), EXCELLENZ™ proteases (e.g. P1000), ULTIMASE®, and PURAFAST™ (DuPont); ALCALASE®, BLAZE®, and BLAZE® variants, BLAZE® EVITY® 16L, CORONASE®, SAVINASE®, SAVINASE® ULTRA, SAVINASE® EVITY®, SAVINASE® EVERTS®, PRIMASE®, DURAZYM™, POLARZYME®, OVOZYME®, KANNASE®, LIQUANASE®, LIQUANASE EVERTS®, NEUTRASE®, RELASE® PROGRESS®, EASYZYME®, and ESPERASE® (Novozymes); BLAP™ and BLAP™ variants (Henkel); KAP (*B. alkalophilus* subtilisin (Kao)); and BIOTOUCH® (AB Enzymes). Exemplary metalloproteases include nprE, the recombinant form of neutral metalloprotease expressed in *B. subtilis* (See e.g., WO 07/044993), and PMN, the purified neutral metalloprotease from *B. amyloliquefaciens.*

Another embodiment is directed to a composition comprising one or more subtilisin variant described herein and one or more lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. An exemplary lipase can be a chemically or genetically modified mutant. Exemplary lipases include, but are not limited to, e.g., those of bacterial or fungal origin, such as, e.g., *H. lanuginosa* lipase (see, e.g., EP 258068 and EP 305216), *T. lanuginosus* lipase (see, e.g., WO 2014/059360 and WO2015/010009), *Rhizomucor miehei* lipase (see, e.g., EP 238023), *Candida* lipase, such as *C. antarctica* lipase (e.g., *C. antarctica* lipase A or B) (see, e.g., EP 214761), *Pseudomonas* lipases such as *P. alcaligenes* and *P. pseudoalcaligenes* lipase (see, e.g., EP 218272), *P. cepacia* lipase (see, e.g., EP 331376), *P. stutzeri* lipase (see, e.g., GB 1,372,034), *P. fluorescens* lipase, *Bacillus* lipase (e.g., *B. subtilis* lipase (Dartois et al., *Biochem. Biophys. Acta* 1131: 253-260 (1993)), *B. stearothermophilus* lipase (see, e.g., JP 64/744992), and *B. pumilus* lipase (see, e.g., WO 91/16422)). Exemplary cloned lipases include, but not limited to *Penicillium camembertii* lipase (See, Yamaguchi et al., *Gene* 103:61-67 (1991)), *Geotricum candidum* lipase (See, Schimada et al., *J. Biochem.*, 106:383-388 (1989)), and various *Rhizopus* lipases, such as, *R. delemar* lipase (See, Hass et al., *Gene* 109:117-113 (1991)), *R. niveus* lipase (Kugimiya et al., *Biosci. Biotech. Biochem.* 56:716-719 (1992)) and *R. oryzae* lipase. Other lipolytic enzymes, such as cutinases, may also find use in one or more composition described herein, including, but not limited to, e.g., cutinase derived from *Pseudomonas mendocina* (see, WO 88/09367) and/or *Fusarium solani pisi* (see, WO90/09446). Exemplary commercial lipases include, but are not limited to M1 LIPASE™, LUMA FAST™, and LIPOMAX™ (DuPont); LIPEX®, LIPOCLEAN®, LIPOLASE® and LIPOLASE® ULTRA (Novozymes); and LIPASE P™ (Amano Pharmaceutical Co. Ltd).

A still further embodiment is directed to a composition comprising one or more subtilisin variant described herein and one or more amylase. In one embodiment, the composition comprises from about 0.00001% to about 10%, about 0.0001% to about 10%, about 0.001% to about 5%, about 0.001% to about 2%, or about 0.005% to about 0.5% amylase by weight composition. Any amylase (e.g., alpha and/or beta) suitable for use in alkaline solutions may be useful to include in such composition. An exemplary amylase can be a chemically or genetically modified mutant. Exemplary amylases include, but are not limited to those of bacterial or fungal origin, such as, for example, amylases described in GB 1,296,839, WO9100353, WO9402597, WO94183314, WO9510603, WO9526397, WO9535382, WO9605295, WO9623873, WO9623874, WO 9630481, WO9710342, WO9741213, WO9743424, WO9813481, WO 9826078, WO9902702, WO 9909183, WO9919467, WO9923211, WO9929876, WO9942567, WO 9943793, WO9943794, WO 9946399, WO0029560, WO0060058, WO0060059, WO0060060, WO 0114532, WO0134784, WO 0164852, WO0166712, WO0188107, WO0196537, WO02092797, WO 0210355, WO0231124, WO 2004055178, WO2004113551, WO2005001064, WO2005003311, WO 2005018336, WO2005019443, WO2005066338, WO2006002643, WO2006012899, WO2006012902, WO2006031554, WO 2006063594, WO2006066594, WO2006066596, WO2006136161, WO 2008000825, WO2008088493, WO2008092919, WO2008101894, WO2008/112459, WO2009061380, WO2009061381, WO 2009100102, WO2009140504, WO2009149419, WO 2010/059413, WO 2010088447, WO2010091221, WO2010104675, WO2010115021, WO10115028, WO2010117511, WO 2011076123, WO2011076897, WO2011080352, WO2011080353, WO 2011080354, WO2011082425, WO2011082429, WO 2011087836, WO2011098531, WO2013063460, WO2013184577, WO 2014099523, WO2014164777, and WO2015077126. Exemplary commercial amylases include, but are not limited to AMPLIFY®, DURAMYL®, TERMAMYL®, FUNGAMYL®, STAINZYME®, STAINZYME PLUS®, STAINZYME ULTRA® EVITY®, and BAN™ (Novozymes); EFFECTENZ™ S 1000, POWERASE™, PREFERENZ™ S 100, PREFERENZ™ S 110, PREFERENZ™ S 210, EXCELLENZ™ S 2000, RAPIDASE® and MAXAMYL® P (DuPont). In some embodiments, the subtilisin variants provided herein may be combined with one or more amylases selected from the group consisting of AA707, AA560, AAI10, BspAmy24, and CspAmyl, and variants thereof, and combinations thereof.

Yet a still further embodiment is directed to a composition comprising one or more subtilisin variant described herein and one or more cellulase. In one embodiment, the composition comprises from about 0.00001% to about 10%, 0.0001% to about 10%, about 0.001% to about 5%, about 0.001% to about 2%, or about 0.005% to about 0.5% cellulase by weight of composition. Any suitable cellulase may find use in a composition described herein. An exemplary cellulase can be a chemically or genetically modified mutant. Exemplary cellulases include, but are not limited to, those of bacterial or fungal origin, such as, for example, those described in WO2005054475, WO2005056787, U.S. Pat. Nos. 7,449,318, 7,833,773, 4,435,307; EP 0495257; and U.S. Provisional Appl. No. 62/296,678. Exemplary commercial cellulases include, but are not limited to, CELLUCLEAN®, CELLUZYME®, CAREZYME®, ENDOLASE®, RENOZYME®, and CAREZYME® PREMIUM (Novozymes); REVITALENZ™ 100, REVITALENZ™ 200/220, and REVITALENZ® 2000 (DuPont); and KAC-500(B)™ (Kao Corporation). In some embodiments, cellulases are incorporated as portions or fragments of mature wildtype or variant cellulases, wherein a portion of the N-terminus is deleted (see, e.g., U.S. Pat. No. 5,874,276).

An even still further embodiment is directed to a composition comprising one or more subtilisin variant described herein and one or more mannanase. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, those described in WO 2016/007929; U.S. Pat. Nos. 6,566,114; 6,602,842; and 6,440,991: and U.S. Provisional Appl. Nos. 62/251,516, 62/278,383, and 62/278,387. Exemplary commercial mannanases include, but are not limited to MANNAWAY® (Novozymes) and EFFECTENZ™ M 1000, PREFERENZ® M 100, MANNASTAR®, and PURABRITE™ (DuPont).

A yet even still further embodiment is directed to a composition comprising one or more subtilisin variant described herein and one or more peroxidase and/or oxidase enzyme. In one embodiment, the composition comprises from about 0.00001% to about 10%, about 0.0001% to about 10%, about 0.001% to about 5%, about 0.001% to about 2%, or about 0.005% to about 0.5% peroxidase or oxidase by weight composition. A peroxidase may be used in combination with hydrogen peroxide or a source thereof (e.g., a percarbonate, perborate or persulfate) and an oxidase may be used in combination with oxygen. Peroxidases and oxidases are used for "solution bleaching" (i.e., to prevent transfer of a textile dye from a dyed fabric to another fabric when the fabrics are washed together in a wash liquor), alone or in combination with an enhancing agent (see, e.g., WO94/12621 and WO95/01426). An exemplary peroxidase and/or oxidase can be a chemically or genetically modified mutant. Exemplary peroxidases/oxidases include, but are not limited to those of plant, bacterial, or fungal origin.

Another embodiment is directed to a composition comprising one or more subtilisin variant described herein, and one or more perhydrolase, such as, for example, those described in WO2005/056782, WO2007/106293, WO 2008/063400, WO2008/106214, and WO2008/106215.

Another embodiment is directed to a composition comprising one or more subtilisin variant described herein, and one or more pectate lyase, such as, for example, XPect®.

In yet another embodiment, the one or more subtilisin variant described herein and one or more additional enzyme contained in one or more composition described herein may each independently range to about 10%, wherein the balance of the cleaning composition is one or more adjunct material.

In some embodiments, one or more composition described herein finds use as a detergent additive, wherein said additive is in a solid or liquid form. Such additive products are intended to supplement and/or boost the performance of conventional detergent compositions and can be added at any stage of the cleaning process. In some embodiments, the density of the laundry detergent composition ranges from about 400 to about 1200 g/liter, while in other embodiments it ranges from about 500 to about 950 g/liter of composition measured at 20° C.

Some embodiments are directed to a laundry detergent composition comprising one or more subtilisin variant described herein and one or more adjunct material selected from surfactants, enzyme stabilizers, builder compounds, polymeric compounds, bleaching agents, additional enzymes, suds suppressors, dispersants, lime-soap dispersants, soil suspension agents, anti-redeposition agents, corrosion inhibitors, and combinations thereof. In some embodiments, the laundry compositions also contain softening agents.

Further embodiments are directed to manual dishwashing composition comprising one or more subtilisin variant described herein and one or more adjunct material selected from surfactants, organic polymeric compounds, suds enhancing agents, group II metal ions, solvents, hydrotropes, and additional enzymes.

Other embodiments are directed to one or more composition described herein, wherein said composition is a compact granular fabric cleaning composition that finds use in laundering colored fabrics or provides softening through the wash capacity, or is a heavy duty liquid (HDL) fabric cleaning composition. Exemplary fabric cleaning compositions and/or processes for making such compositions are described in USPNs 6,610,642 and 6,376,450. Other exemplary cleaning compositions are described, for example, in U.S. Pat. Nos. 6,605,458; 6,294,514; 5,929,022; 5,879,584; 5,691,297; 5,565,145; 5,574,005; 5,569,645; 5,565,422; 5,516,448; 5,489,392; and 5,486,303; 4,968,451; 4,597,898; 4,561,998; 4,550,862; 4,537,706; 4,515,707; and 4,515,705.

In some embodiments, the cleaning compositions comprise an acidifying particle or an amino carboxylic builder. Examples of an amino carboxylic builder include aminocarboxylic acids, salts and derivatives thereof. In some embodiment, the amino carboxylic builder is an aminopolycarboxylic builder, such as glycine-N,N-diacetic acid or derivative of general formula MOOC—CHR-N($CH_2COOM$)$_2$ where R is $C_{1-12}$alkyl and M is alkali metal. In some embodiments, the amino carboxylic builder can be methylglycine diacetic acid (MGDA), GLDA (glutamic-N,N-diacetic acid), iminodisuccinic acid (IDS), carboxymethyl inulin and salts and derivatives thereof, aspartic acid-N-monoacetic acid (ASMA), aspartic acid-N,N-diacetic acid (ASDA), aspartic acid-N-monopropionic acid (ASMP), N-(2-sulfomethyl) aspartic acid (SMAS), N-(2-sulfoethyl)aspartic acid (SEAS), N-(2-sulfomethyl)glutamic acid (SMGL), N-(2-sulfoethyl) glutamic acid (SEGL), IDA (iminodiacetic acid) and salts and derivatives thereof such as N-methyliminodiacetic acid (MIDA), alpha-alanine-N,N-diacetic acid (alpha-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts and derivative thereof. In some embodiments, the acidifying particle has a weight geometric mean particle size of from about 400 microns to about 1200 microns and a bulk density of at least 550 g/L. In some embodiments, the acidifying particle comprises at least about 5% of the builder.

In some embodiments, the acidifying particle can comprise any acid, including organic acids and mineral acids. Organic acids can have one or two carboxyls and in some instances up to 15 carbons, especially up to 10 carbons, such as formic, acetic, propionic, capric, oxalic, succinic, adipic, maleic, fumaric, sebacic, malic, lactic, glycolic, tartaric and glyoxylic acids. In some embodiments, the acid is citric acid. Mineral acids include hydrochloric and sulfuric acid. In some instances, the acidifying particle is a highly active particle comprising a high level of amino carboxylic builder. Sulfuric acid has also been found to further contribute to the stability of the final particle.

Additional embodiments are directed to a cleaning composition comprising one or more subtilisin variant and one or more surfactant and/or surfactant system, wherein the surfactant is selected from nonionic surfactants, anionic surfactants, cationic surfactants, ampholytic surfactants, zwitterionic surfactants, semi-polar nonionic surfactants, and mixtures thereof. In some embodiments, the surfactant is present at a level of from about 0.1 to about 60%, while in alternative embodiments the level is from about 1 to about 50%, while in still further embodiments the level is from about 5 to about 40%, by weight of the cleaning composition.

In some embodiments, one or more composition described herein comprises one or more detergent builders or builder systems. In one embodiment, the composition comprises from about 1% or greater, from about 0.1% to about 80%, from about 3% to about 60%, from about 5% to about 40%, or from about 10% to about 50% builder by weight composition. Exemplary builders include, but are not limited to alkali metal; ammonium and alkanolammonium salts of polyphosphates; alkali metal silicates; alkaline earth and alkali metal carbonates; aluminosilicates; polycarboxylate compounds; ether hydroxypolycarboxylates; copolymers of maleic anhydride with ethylene or vinyl methyl ether, 1, 3, 5-trihydroxy benzene-2, 4, 6-trisulphonic acid, and carboxymethyloxysuccinic acid; ammonium and substituted ammonium salts of polyacetic acids such as ethylenediamine tetraacetic acid and nitrilotriacetic acid; polycarboxylates such as mellitic acid, succinic acid, citric acid, oxydisuccinic acid, polymaleic acid, benzene 1,3,5-tricarboxylic acid, carboxymethyloxysuccinic acid; and soluble salts thereof. In some such compositions, the builders form water-soluble hardness ion complexes (e.g., sequestering builders), such as citrates and polyphosphates, e.g., sodium tripolyphosphate, sodium tripolyphospate hexahydrate, potassium tripolyphosphate, and mixed sodium and potassium tripolyphosphate. Exemplary builders are described in, e.g., EP 2100949. In some embodiments, the builders include phosphate builders and non-phosphate builders. In some embodiments, the builder is a phosphate builder. In some embodiments, the builder is a non-phosphate builder. In some embodiments, the builder comprises a mixture of phosphate and non-phosphate builders. Exemplary phosphate builders include, but are not limited to mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above-mentioned compounds include the ammonium and/or alkali metal salts, i.e. the lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

In some embodiments, one or more composition described herein comprises one or more chelating agent. In one embodiment, the composition comprises from about 0.1% to about 15% or about 3% to about 10% chelating agent by weight composition. Exemplary chelating agents include, but are not limited to, e.g., copper, iron, manganese, and mixtures thereof.

In some embodiments, one or more composition described herein comprises one or more deposition aid. Exemplary deposition aids include, but are not limited to, e.g., polyethylene glycol; polypropylene glycol; polycarboxylate; soil release polymers, such as, e.g., polyterephthalic acid; clays such as, e.g., kaolinite, montmorillonite, attapulgite, illite, bentonite, and halloysite; and mixtures thereof.

In other embodiments, one or more composition described herein comprises one or more anti-redeposition agent or non-ionic surfactant (which can prevent the re-deposition of soils) (see, e.g., EP 2100949). For example, in ADW compositions, non-ionic surfactants find use for surface modification purposes, in particular for sheeting, to avoid filming and spotting and to improve shine. These non-ionic surfactants also find use in preventing the re-deposition of soils. In some embodiments, the non-ionic surfactant can be ethoxylated nonionic surfactants, epoxy-capped poly(oxyalkylated) alcohols and amine oxides surfactants.

In some embodiments, one or more composition described herein comprises one or more dye transfer inhibiting agent. Exemplary polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, polyvinylimidazoles, and mixtures thereof. In one embodiment, the composition comprises from about 0.0001% to about 10%, about 0.01% to about 5%, or about 0.1% to about 3% dye transfer inhibiting agent by weight composition.

In some embodiments, one or more composition described herein comprises one or more silicate. Exemplary silicates include, but are not limited to, sodium silicates, e.g., sodium disilicate, sodium metasilicate, and crystalline phyllosilicates. In some embodiments, silicates are present at a level of from about 1% to about 20% or about 5% to about 15% by weight of the composition.

In some still additional embodiments, one or more composition described herein comprises one or more dispersant. Exemplary water-soluble organic materials include, but are not limited to, e.g., homo- or co-polymeric acids or their salts, in which the polycarboxylic acid comprises at least two carboxyl radicals separated from each other by not more than two carbon atoms.

In some further embodiments, one or more composition described herein comprises one or more inorganic enzyme stabilizer. In some embodiments, the enzyme stabilizer is water-soluble sources of calcium and/or magnesium ions. In some embodiments, the enzyme stabilizers include oligosaccharides, polysaccharides, and inorganic divalent metal salts, including alkaline earth metals, such as calcium salts. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (III), tin (II), cobalt (II), copper (II), nickel (II), and oxovanadium (IV)). Chlorides and sulfates also find use in some embodiments. Exemplary oligosaccharides and polysaccharides (e.g., dextrins) are described, for example, in WO 07/145964. In some embodiments, reversible protease inhibitors also find use, such as boron-containing compounds (e.g., borate, 4-formyl phenyl boronic acid, and phenyl-boronic acid derivatives (such for example, those described in WO96/41859) and/or a peptide aldehyde, such as, for example, is further described in WO2009/118375 and WO2013004636.

Peptidic inhibitors can be naturally derived or synthetically produced oligopeptides able to bind to protease and inhibit its proteolytic activity, and thus used as protease stabilizers in liquid laundry formulations. Peptide aldehydes are peptidic inhibitors and may be used as protease stabilizers in detergent formulations as previously described (WO199813458, WO2011036153, US20140228274). Examples of peptide aldehyde stabilizers are peptide aldehydes, ketones, or halomethyl ketones and might be 'N-capped' with for instance a ureido, a carbamate, or a urea moiety, or 'doubly N-capped' with for instance a carbonyl, a ureido, an oxiamide, a thioureido, a dithiooxamide, or a thiooxamide moiety(EP2358857B1). The molar ratio of these inhibitors to the protease may be 0.1:1 to 100:1, e.g. 0.5:1-50:1, 1:1-25:1 or 2:1-10:1. Other examples of protease stabilizers are benzophenone or benzoic acid anilide derivatives, which might contain carboxyl groups (U.S. Pat. No. 7,968,508 B2). The molar ratio of these stabilizers to protease is preferably in the range of 1:1 to 1000:1 in particular 1:1 to 500:1 especially preferably from 1:1 to 100:1, most especially preferably from 1:1 to 20:1.

In other embodiments, the one or more compositions provided herein does not contain an enzyme stabilizer, or peptidic inhibitors, or contains a reduced amount of an enzyme stabilizer and peptide inhibitors, such as peptide aldehydes. That is, the subtilisin variants provided herein have an increased stability with respect to a reference subtilisin in compositions that lack an enzyme stabilizer or peptide inhibitors, or contain a reduced amount of an enzyme stabilizer or peptide inhibitor.

In some embodiments, one or more composition described herein comprises one or more bleach, bleach activator, and/or bleach catalyst. In some embodiments, one or more composition described herein comprises one or more inorganic and/or organic bleaching compound. Exemplary inorganic bleaches include, but are not limited to perhydrate salts, e.g., perborate, percarbonate, perphosphate, persulfate, and persilicate salts. In some embodiments, inorganic perhydrate salts are alkali metal salts. In some embodiments, inorganic perhydrate salts are included as the crystalline solid, without additional protection, although in some other embodiments, the salt is coated. Bleach activators are typically organic peracid precursors that enhance the bleaching action in the course of cleaning at temperatures of 60° C. and below. Exemplary bleach activators include compounds which, under perhydrolysis conditions, give aliphatic peroxoycarboxylic acids having from about 1 to about 10 carbon atoms or about 2 to about 4 carbon atoms, and/or optionally substituted perbenzoic acid. Exemplary bleach activators ae described, for example, in EP 2100949. Exemplary bleach catalysts include, but are not limited to, manganese triazacyclononane and related complexes, as well as cobalt, copper, manganese, and iron complexes. Additional exemplary bleach catalysts are described, for example, in U.S. Pat. Nos. 4,246,612; 5,227,084; 4,810,410; WO 99/06521; and EP 2100949.

In some embodiments, one or more composition described herein comprises one or more catalytic metal complexes. In some embodiments, a metal-containing bleach catalyst finds use. In some embodiments, the metal bleach catalyst comprises a catalyst system comprising a transition metal cation of defined bleach catalytic activity (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof (see, e.g., U.S. Pat. No. 4,430,243). In some embodiments, one or more composition described herein is catalyzed by means of a manganese compound. Such compounds and levels of use are described, for example, in U.S. Pat. No. 5,576,282. In additional embodiments, cobalt bleach catalysts find use and are included in one or more composition described herein. Various cobalt bleach catalysts are described, for example, in U.S. Pat. Nos. 5,597,936 and 5,595,967.

In some additional embodiments, one or more composition described herein includes a transition metal complex of a macropolycyclic rigid ligand (MRL). As a practical matter, and not by way of limitation, in some embodiments, the compositions and cleaning processes described herein are adjusted to provide on the order of at least one part per hundred million, from about 0.005 ppm to about 25 ppm, about 0.05 ppm to about 10 ppm, or about 0.1 ppm to about 5 ppm of active MRL in the wash liquor. Exemplary MRLs include, but are not limited to special ultra-rigid ligands that are cross-bridged, such as, e.g., 5,12-diethyl-1,5,8,12-tetraazabicyclo(6.6.2)hexadecane. Exemplary metal MRLs are described, for example, in WO 2000/32601 and U.S. Pat. No. 6,225,464.

In another embodiment, one or more composition described herein comprises one or more metal care agent. In some embodiments, the composition comprises from about 0.1% to about 5% metal care agent by weight composition. Exemplary metal care agents include, for example, aluminum, stainless steel, and non-ferrous metals (e.g., silver and copper). Additional exemplary metal care agents are described, for example, in EP 2100949, WO 94/26860, and WO 94/26859. In some compositions, the metal care agent is a zinc salt.

In some embodiments, the cleaning composition is a high density liquid (HDL) composition comprising one or more subtilisin variant described herein. The HDL liquid laundry detergent can comprise a detersive surfactant (10-40%) comprising anionic detersive surfactant selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof; and optionally non-ionic surfactant selected from a group of linear or branched or random chain, substituted or unsubstituted alkyl alkoxylated alcohol, for example, a $C_8$-$C_{18}$alkyl ethoxylated alcohol and/or $C_6$-$C_{12}$alkyl phenol alkoxylates, optionally wherein the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from alkyl pyridinium compounds, alkyl quarternary ammonium compounds, alkyl quarternary phosphonium compounds, alkyl ternary sulphonium compounds, and/or mixtures thereof); zwitterionic and/or amphoteric detersive surfactants (selected from alkanolamine sulpho-betaines); ampholytic surfactants; semi-polar non-ionic surfactants; and mixtures thereof.

In another embodiment, the cleaning composition is a liquid or gel detergent, which is not unit dosed, that may be aqueous, typically containing at least 20% and up to 95% water by weight, such as up to about 70% water by weight, up to about 65% water by weight, up to about 55% water by weight, up to about 45% water by weight, or up to about 35% water by weight. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

The composition can comprise optionally, a surfactancy boosting polymer consisting of amphiphilic alkoxylated grease cleaning polymers selected from a group of alkoxylated polymers having branched hydrophilic and hydrophobic properties, such as alkoxylated polyalkylen imines in the range of 0.05 wt %-10 wt % and/or random graft polymers typically comprising a hydrophilic backbone comprising monomers selected from the group consisting of: unsaturated $C_1$-$C_6$carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: $C_4$-$C_{25}$alkyl group, polypropylene, polybutylene, vinyl ester of a saturated $C_2$-$C_6$mono-carboxylic acid, $C_1$-$C_6$alkyl ester of acrylic or methacrylic acid, and mixtures thereof.

The composition can comprise additional polymers such as soil release polymers including, for example, anionically end-capped polyesters, for example SRP1; polymers comprising at least one monomer unit selected from saccharide, dicarboxylic acid, polyol and combinations thereof, in random or block configuration; ethylene terephthalate-based polymers and co-polymers thereof in random or block configuration, for example, Repel-o-tex SF, SF-2 and SRP6, Texcare SRA100, SRA300, SRN100, SRN170, SRN240, SRN300 and SRN325, Marloquest SL; anti-redeposition polymers (0.1 wt % to 10 wt %, including, for example, carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof; vinylpyrrolidone homopolymer; and/or polyethylene glycol with a molecular weight in the range of from 500 to 100,000 Da); cellulosic polymer (including, for example, alkyl cellulose; alkyl alkoxyalkyl cellulose; carboxyalkyl cellulose; alkyl carboxyalkyl cellulose, examples of which include carboxymethyl cellulose, methyl cellulose, methyl hydroxyethyl cellulose, methyl carboxymethyl cellulose; and mixtures thereof); and polymeric carboxylate (such as, for example, maleate/acrylate random copolymer or polyacrylate homopolymer).

The composition can further comprise saturated or unsaturated fatty acid, preferably saturated or unsaturated $C_{12}$-$C_{24}$fatty acid (0-10 wt %); deposition aids (including, for example, polysaccharides, cellulosic polymers, polydiallyl dimethyl ammonium halides (DADMAC), and copolymers of DADMAC with vinyl pyrrolidone, acrylamides, imidazoles, imidazolinium halides, and mixtures thereof, in random or block configuration; cationic guar gum; cationic cellulose such as cationic hydroxyethyl cellulose; cationic starch; cationic polyacylamides; and mixtures thereof.

The composition can further comprise dye transfer inhibiting agents examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP); hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetracetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethylethylenediaminetri-acetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

The composition can further comprise silicone or fatty-acid based suds suppressors; an enzyme stabilizer; hueing dyes, calcium and magnesium cations, visual signaling ingredients, anti-foam (0.001 to about 4.0 wt %), and/or structurant/thickener (0.01-5 wt %) selected from the group consisting of diglycerides, triglycerides, ethylene glycol distearate, microcrystalline cellulose, cellulose based materials, microfiber cellulose, biopolymers, xanthan gum, gellan gum, and mixtures thereof.

In some embodiments, the cleaning composition is a high density powder (HDD) composition comprising one or more subtilisin variant described herein. The HDD powder laundry detergent can comprise a detersive surfactant including anionic detersive surfactants (selected from linear or branched or random chain, substituted or unsubstituted alkyl sulphates, alkyl sulphonates, alkyl alkoxylated sulphate, alkyl phosphates, alkyl phosphonates, alkyl carboxylates and/or mixtures thereof), non-ionic detersive surfactant (selected from 1 linear or branched or random chain, substituted or unsubstituted $C_8$-$C_{18}$ alkyl ethoxylates, and/or $C_6$-$C_{12}$ alkyl phenol alkoxylates), cationic detersive surfactants (selected from alkyl pyridinium compounds, alkyl quaternary ammonium compounds, alkyl quaternary phosphonium compounds, alkyl ternary sulphonium compounds, and mixtures thereof); zwitterionic and/or amphoteric detersive surfactants (selected from alkanolamine sulpho-betaines); ampholytic surfactants; semi-polar non-ionic surfactants and mixtures thereof; builders (phosphate free builders, e.g., zeolite builders examples of which include zeolite A, zeolite X, zeolite P and zeolite MAP in the range of 0 to less than 10 wt %); phosphate builders, e.g., sodium tripolyphosphate in the range of 0 to less than 10 wt %; citric acid, citrate salts and nitrilotriacetic acid or salt thereof in the range of less than 15 wt %; silicate salt (sodium or potassium silicate or sodium meta-silicate in the range of 0 to less than 10 wt % or layered silicate (SKS-6)); carbonate salt (sodium carbonate and/or sodium bicarbonate in the range of 0 to less than 10 wt %); and bleaching agents (photobleaches, e.g., sulfonated zinc phthalocyanines, sulfonated aluminum phthalocyanines, xanthenes dyes, and mixtures thereof); hydrophobic or hydrophilic bleach activators (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, and nonanoyloxybenzene sulfonate-NOBS, nitrile quats, and mixtures thereof); hydrogen peroxide; sources of hydrogen peroxide (inorganic perhydrate salts, e.g., mono or tetra hydrate sodium salt of perborate, percarbonate, persulfate, perphosphate, or persilicate); preformed hydrophilic and/or hydrophobic peracids (selected from percarboxylic acids and salts, percarbonic acids and salts, perimidic acids and salts, peroxymonosulfuric acids and salts, and mixtures thereof); and/or bleach catalyst (e.g., imine bleach boosters, such as iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof), metal-containing bleach catalyst (e.g., copper, iron, titanium, ruthenium, tungsten, molybdenum, or manganese cations along with an auxiliary metal cations such as zinc or aluminum and a sequestrate such as ethylenediaminetetraacetic acid, ethylenediaminetetra(methylenephosphonic acid) and water-soluble salts thereof).

The composition can further comprise additional detergent ingredients including perfume microcapsules, starch encapsulated perfume accord, an enzyme stabilizer, hueing agents, additional polymers including fabric integrity and cationic polymers, dye lock ingredients, fabric-softening agents, brighteners (for example C.I. Fluorescent brighteners), flocculating agents, chelating agents, alkoxylated polyamines, fabric deposition aids, and/or cyclodextrin.

In some embodiments, the cleaning composition is an automatic (auto) dish washing (ADW) detergent composition comprising one or more subtilisin variant described herein. The ADW detergent composition can comprise two or more non-ionic surfactants selected from ethoxylated non-ionic surfactants, alcohol alkoxylated surfactants, epoxy-capped poly(oxyalkylated) alcohols, and amine oxide surfactants present in amounts from 0-10% by wt; builders in the range of 5-60% by wt. comprising either phosphate (mono-phosphates, di-phosphates, tri-polyphosphates or oligomeric-polyphosphates), sodium tripolyphosphate-STPP or phosphate-free builders (amino acid based compounds, e.g., MGDA (methyl-glycine-diacetic acid) and salts and derivatives thereof, GLDA (glutamic-N,Ndiacetic acid) and salts and derivatives thereof, IDS (iminodisuccinic acid) and salts and derivatives thereof, carboxy methyl inulin and salts and derivatives thereof and mixtures thereof, nitrilotriacetic acid (NTA), diethylene triamine penta acetic acid (DTPA), and B-alaninediacetic acid (B-ADA) and their salts), homopolymers and copolymers of poly-carboxylic acids and their partially or completely neutralized salts, monomeric polycarboxylic acids and hydroxycarboxylic acids and their salts in the range of 0.5-50% by wt; sulfonated/carboxylated polymers (provide dimensional stability to the product) in the range of about 0.1 to about 50% by wt; drying aids in the range of about 0.1 to about 10% by wt (selected from polyesters, especially anionic polyesters optionally together with further monomers with 3-6 functionalities which are conducive to polycondensation, specifically acid, alcohol or ester functionalities, polycarbonate-, polyurethane- and/or polyurea-polyorganosiloxane compounds or precursor compounds thereof of the reactive cyclic carbonate and urea type); silicates in the range from about 1 to about 20% by wt (sodium or potassium silicates, e.g., sodium disilicate, sodium meta-silicate and crystalline phyllosilicates); bleach-inorganic (e.g., perhydrate salts such as perborate, percarbonate, perphosphate, persulfate and persilicate salts) and organic (e.g., organic peroxyacids including diacyl and tetraacylperoxides, especially diperoxydodecanedioic acid, diperoxytetradecanedioic acid, and diperoxyhexadecanedioic acid); bleach activator-organic peracid precursors in the range from about 0.1 to about 10% by wt; bleach catalysts (selected from manganese triazacyclononane and related complexes, Co, Cu, Mn and Fe bispyridylamine and related complexes, and pentamine acetate cobalt(III) and related complexes); metal care agents in the range from about 0.1-5% by wt (selected from benzatriazoles, metal salts and complexes, and silicates); enzymes in the range from about 0.01-5.0 mg of active enzyme per gram of ADW detergent composition (acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, mannanases, oxidases, oxidoreductases, pectate lyases, pectin acetyl esterases, pectinases, pentosanases, peroxidases, phenoloxidases, phosphatases, phospholipases, phytases, polyestersases, polygalacturonases, proteases, pullulanases, reductases, rhamnogalacturonases, beta-glucanases, tannases, transglutaminases, xylan acetyl-esterases, xylanases, xyloglucanases, xylosidases, and mixtures thereof); and enzyme stabilizer components (selected from oligosaccharides, polysaccharides and inorganic divalent metal salts).

More embodiments are directed to compositions and methods of treating fabrics (e.g., to desize a textile) using one or more subtilisin variant described herein. Fabric-treating methods are well known in the art (see, e.g., U.S. Pat. No. 6,077,316). For example, the feel and appearance of a fabric can be improved by a method comprising contacting the fabric with a variant described herein in a solution. The fabric can be treated with the solution under pressure.

One or more subtilisin variant described herein can be applied during or after weaving a textile, during the desizing stage, or one or more additional fabric processing steps. During the weaving of textiles, the threads are exposed to considerable mechanical strain. Prior to weaving on mechanical looms, warp yarns are often coated with sizing starch or starch derivatives to increase their tensile strength and to prevent breaking. One or more subtilisin variant described herein can be used alone or with other desizing chemical reagents and/or desizing enzymes to desize fabrics, including cotton-containing fabrics, as detergent additives, e.g., in aqueous compositions. An amylase also can be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of proteolytic enzymes to provide softness to the fabric and make the cotton more accessible to the subsequent enzymatic finishing steps. One or more subtilisin variant described herein can be used in methods of finishing denim garments (e.g., a “bio-stoning process”), enzymatic desizing and providing softness to fabrics, and/or finishing process.

One or more subtilisin variant described herein finds further use in the enzyme aided bleaching of paper pulps such as chemical pulps, semi-chemical pulps, kraft pulps, mechanical pulps or pulps prepared by the sulfite method. In general terms, paper pulps are incubated with one or more subtilisin variant described herein under conditions suitable for bleaching the paper pulp.

In some embodiments, the pulps are chlorine free pulps bleached with oxygen, ozone, peroxide or peroxyacids. In some embodiments, one or more subtilisin variant described herein is used in enzyme aided bleaching of pulps produced by modified or continuous pulping methods that exhibit low lignin contents. In some other embodiments, one or more subtilisin variant described herein is applied alone or preferably in combination with xylanase and/or endoglucanase and/or alpha-galactosidase and/or cellobiohydrolase enzymes.

The following examples are provided to demonstrate and illustrate certain preferred embodiments and aspects of the present disclosure and should not be construed as limiting.

Example 1

Construction and Expression of Subtilisin Protease Variants

Variants of a series of subtilisins of bacterial origin having one, two or more substitutions in each of the parental backbones (Table 1) were generated using molecular biology techniques known in the art. Libraries of genes were generated that have various combinations of the following amino acid features: X003T, X003V, X009E, X024Q, X040E, X069S, X076D, X078N, X079I, X087D, X118R, X124I, X128R, X128S, X129P, X130S, X145R, X166Q, X182E, X185Q, X210I, X211P, X217L, X218S, X248D, X259P, listed in BPN' (SEQ ID NO:1) numbering. Libraries of constructs for each subtilisin protease (parent and variants) were transformed into a suitable *Bacillus subtilis* strain using methods known in the art. The transformation mixtures were plated on LA containing skim milk and the appropriate antibiotic resistance selection. Single colonies were picked and grown on Luria broth with the appropriate antibiotic resistance selection. The DNA was extracted and the sequence of each gene of interest was confirmed by PacBio sequencing method.

For recombinant protein expression experiments, transformed cells were grown in 96-well microtiter plates (MTPs) in cultivation medium (enriched semi-defined media based on MOPs buffer, with urea as major nitrogen source, glucose as the main carbon source, supplemented with 1% soytone for robust cell growth, containing antibiotic selection) for 3 days at 32° C., 300 rpm, with 80% humidity in shaking incubator. After centrifugation and filtration, clarified culture supernatants containing the proteases of interest were used for assays.

Table 1 below provides the names and sequences for the subtilisin parental backbones (parent) used in this study. All subtilisins, with the exception of DSM14391 and CP474, were cloned and expressed using their own (wildtype) propeptide sequences. For expression of DSM14391 and CP474, the *B. lentus* subtilisin propeptide (SEQ ID NO: 40) was used instead, but the naturally occurring propeptide sequences for these protease are listed on Table 1. Prior references and accession numbers for the various subtilisin parent backbones of this study are provided on Table 1. The DNA sequence encoding the expression cassette for the pro-mature polypeptide for each parental backbone is listed on Table 1, along with the pro-peptide and predicted mature protein sequences for each protease.

TABLE 1

List of subtilisin backbones used for evaluation of variants with improved stability. Prior patent references and sequence ID NOs, or accession numbers are provided.

| | | SEQ ID Nos | | |
|---|---|---|---|---|
| Subtilisin | Prior patent references or accession number | DNA sequence | pro-peptide AA sequence | mature protein AA sequence |
| AprE (subtilisin E) | WP_003233171 | 24 | 41 | 8 |
| WP_082194748 | WP_082194748 [formerly listed as WP_008359041] | 25 | 42 | 9 |
| Chemgen_164A | SEQ ID NO: 2 in U.S. Pat. No. 5,275,945 | 26 | 43 | 10 |
| CP474 | A variant of LG12 SprC protease (SprC is SEQ ID NO: 3 in WO2015/038792) | 27 | 40 | 11 |
| ZP-00454 | A variant of WP_010192403 (previously ZP_07707657) (ZP_07707657 is SEQ ID NO: 7 in WO2015/038792) | 28 | 44 | 12 |
| Bpan01744 | SEQ ID NO: 3 in WO2016069563 | 29 | 45 | 13 |
| DSM14391 | SEQ ID NO: 13 in WO2018/118917 | 30 | 46 | 14 |
| BspAK01305 | SEQ ID NO: 6 in WO2016/069569 | 31 | 47 | 15 |
| BspAI02518 | SEQ ID NO: 3 in WO2015/089441 | 32 | 48 | 16 |
| BspZ00056 | SEQ ID NO: 9 in WO 2016/069544 | 33 | 49 | 17 |
| Bad02409 | SEQ ID NO: 13 in WO2010/69557 | 34 | 23 | 18 |
| Bba02069 | SEQ ID NO: 3 in WO2016/061438 | 35 | 39 | 19 |
| BspZ00258 | SEQ ID NO: 9 in WO 2016/069552 | 38 | 36 | 22 |

Example 2

Enzyme Assays

Protein Determination Assay: Culture supernatants were diluted into 10 mM NaCl, 0.1 mM $CaCl_2$), 0.005% Tween® 80 to a concentration that fits within the linear range of the standard curve for loading onto column. For high resolution concentration determinations, high performance liquid chromatography (HPLC) method was performed on protein samples. An Agilent 1100 HPLC equipped with an Agilent 300SB-C8 column was used for protein quantitation. Samples were eluted from the column using a gradient of 0.1% trifluoroacetic acid (TFA) in water and 0.1% TFA in acetonitrile. Absorbance was measured at 220 nm, and peaks were integrated using CHEMSTATION software (Agilent Technologies, USA). The protein concentrations of the samples were calculated based on a standard curve of a purified protease.

Alternatively, the concentration of the sample proteases in culture supernatant was determined by UHPLC using a ZORBAX 300 SB-C3 column and linear gradient of 0.1% Trifluoroacetic acid (Buffer A) and 0.07% Trifluoroacetic acid in Acetonitrile (Buffer B) with absorbance detection at 220 nm. The protein concentration of the samples was calculated using a standard curve of the purified protease.

Protease Activity: The protease activity of parent and variants thereof was tested by measuring the hydrolysis of N-suc-AAPF-pNA substrate. For the AAPF assay, the reagent solutions used were: 100 mM Tris pH 8.6, 10 mM CalCl2, 0.005% Tween®-80 (Tris/Ca buffer) and 160 mM suc-AAPF-pNA in DMSO (suc-AAPF-pNA stock solution) (Sigma: S-7388). To prepare a working solution, 1 mL suc-AAPF-pNA stock solution was added to 100 mL Tris/Ca buffer and mixed. An enzyme sample was added to a microtiter plate (MTP) containing 1 mg/mL suc-AAPF-pNA working solution and assayed for activity at 405 nm over 3-5 min using a SPECTRAMAX plate reader in kinetic mode at room temperature (RT). The protease activity was expressed as mOD/min.

Cleaning performance assays: Detergents used in these studies include: Persil Small & Mighty Non-Bio Liquid Detergent "Persil Non-Bio" (PNB, Unilever) heavy duty liquid laundry (HDL) purchased in 2014 from local supermarket; GSM-B Phosphate-free automatic dishwashing (ADW) formula purchased without enzymes from WFK Testgewebe GmbH, Brüggen, Deutschland (www.testgewebe.de), composition listed on Table 2; and ECE2 heavy duty powder detergent (HDD) from WFK Testgewebe GmbH, Brüggen, Deutschland (www.testgewebe.de), composition listed on Table 3. Table 4 lists the conditions used for the cleaning performance assays. Persil Non-Bio Small & Mighty (Persil Non-Bio, PNB), is considered boron-free since it contains≤5 mg/Kg of boron, when tested for elemental boron content.

TABLE 2

Composition of GSM-B Phosphate-Free Detergent (GSM-B, pH 10.5)

| Component | wt % |
|---|---|
| Sodium citrate dehydrate | 30 |
| Maleic acid/acrylic acid copolymer sodium Salt (SOKALAN ® CP5, BASF) | 12 |
| Sodium perborate monohydrate | 5 |
| TAED | 2 |
| Sodium disilicate: Protil A (Cognis) | 25 |
| Linear fatty alcohol ethoxylate | 2 |
| Sodium carbonate anhydrous | add to 100 |

TABLE 3

Composition of ECE-2 powder detergent (HDD)

| Component | Weight % |
|---|---|
| Linear sodium alkyl benzene sulfonate | 9.7 |
| Ethoxylated fatty alcohol C12-18 (7 EO) | 5.2 |
| Sodium soap | 3.6 |
| Antifoam DC2-4248S | 4.5 |
| Sodium aluminum silicate zeolite 4A | 32.5 |
| Sodium carbonate | 11.8 |
| Sodium salt of a copolymer from acrylic and maleic acid (Sokalan CP5) | 5.2 |
| Sodium silicate (SiO2:Na2O = 3.3:1) | 3.4 |
| Carboxymethylcellulose | 1.3 |
| Diethylene triamine penta (methylene phosphonic acid) | 0.8 |
| Sodium sulfate | 9.8 |
| Water | 12.2 |

TABLE 4

Conditions for subtilisin cleaning performance evaluations

| Detergent | Type | Final Wash Conc, (g/L) | Hardness Conc. (ppm) | Buffer | pH |
|---|---|---|---|---|---|
| Persil Non-Bio (PNB) | HDL | 2.7 | 250 | 5 mM HEPES | 8.2 |
| GSM-B | ADW | 3.0 | 374 | not buffered | 10.5 |
| ECE-2 | HDD | 6.5 | 374 | not buffered | 10 |

Subtilisin variants were tested for cleaning performance relative to each parent backbone on BMI (EMPA-116, blood/milk/ink on cotton) for laundry-based HDL and HDD applications, and on egg yolk (PAS-38, egg yolk on polyacryl fabric, aged and colored with carbon black dye) for dish-based applications in 96 well (MTP) microtiter plates. PAS-38 swatches and pre-rinsed EMPA116 were purchased from Center for Testmaterials B.V., Vlaardingen. For all stains, pre-punched swatches in MTP plates (Costar 9017 or Greiner 655101) were prepared. These microswatch-containing plates were filled with detergent solution (listed on Table 4) prior to enzyme addition. Aliquots of enzyme were added to detergent-filled MTPs containing microswatches to reach a final volume of 180 microliters for laundry and ADW assays. Laundry cleaning assays with HDL and HDD formulas were carried out at 25° C. for 20 min, while ADW assays were carried out at 40° C. for 30 min. Following incubation, 100-150 microliters of supernatant was transferred to a fresh MTP and absorbance was read at 405 nm using a SPECTRAMAX plate reader. Absorbance results were obtained by subtracting the value for a blank control (no enzyme) from each sample value. For each condition and subtilisin variant in Example 3, a cleaning performance index (PI) was calculated by dividing the blank subtracted absorbance of the variant by that of the respective parent protease at the same concentration. The blank subtracted absorbance value for the parent protease at the corresponding concentration of the variant was determined using a standard curve of the parent protease, which was included in the test and was generated using a Langmuir fit or Hill Sigmoidal fit, as appropriate. Results for each subtilisin variant sample were compared to the results for the parent molecule in each assay plate to generate a normalized PI and mitigate plate to plate variation.

Detergent Stability Assay: Subtilisin enzymes were tested for stability in 10% PNB detergent (10-fold dilution of commercial detergent) at temperatures specified on Table 5 to determine the residual activity following incubation at elevated temperature. The elevated temperature was set to enable discrimination of residual activity of the stressed sample compared to the unstressed sample during an incubation period of 20 minutes in a range appropriate to discern differences of variant enzymes versus their parent. A diluted enzyme sample was mixed in appropriate detergent and the protease activity on AAPF substrate was measured immediately, to serve as the unstressed value. The samples were subsequently placed in a PCR plate, sealed and incubated at elevated temperature for 20 min using a thermocycler, then assayed for AAPF activity to obtain the stressed value. Assays were carried out in 384 well MTPs. The residual activity was calculated by dividing the stressed activity by the unstressed activity for each enzyme. In some instances, the relative stability of the variant enzymes is reported at a performance index (PI), and in other instances it is reported at a percent residual activity (% RA). The stability Performance Index (PI) for each variant under each assay condition was obtained by dividing the residual activity of the variant by the residual activity of the parent wild type. The percent residual activity for each variant under each assay condition was obtained by dividing the AAPF activity absorbance for stressed sample by the AAPF activity absorbance for unstressed sample and multiplying by 100.

TABLE 5

Stress Conditions for Stability Tests in 10% PNB detergent

| Subtilisin Backbone | 20 min incubation at Temperature (° C.) |
|---|---|
| AprE | 41-42 |
| WP_082194748 | 46 |
| Chemgen_164A | 51-56 |
| CP474 | 37 |
| ZP-00454 | 42 |
| Bpan01744 | 44-46 |
| DSM14391 | 30-36 |
| BspAI02518 | 30-36 |
| BspZ00056 | 63-64 |
| Bad02409 | 67 |
| Bba02069 | 39-40 |
| BspAK01305 | 47 |
| BspZ00258 | 62 |

Example 3

AprE & WP_082194748 Subtilisin Variants with Improved Stability in Detergent Variants of AprE (Subtilisin E, SEQ ID NO: 8) and WP_082194748 (SEQ ID NO: 9) subtilisins were evaluated for stability and cleaning performance using methods described in Example 2, and performance index for each variant was calculated versus the respective parent molecule. The AprE (Subtilisin E) and WP_082194748 subtilisin are more closely related in sequence to BPN' subtilisin than to other known subtilisins (86.5% and 76.4% amino acid sequence identity, respectively).

Detergent stability results are reported as either performance index (PI) or % residual activity (% RA). Tables 6A and 6B show the stability results for AprE (Subtilisin E), and Table 8 for WP_082194748 variants having stability PI values 1.1 and greater, where the cleaning performance index was at least 0.5 or greater (relative to parent) in at least one cleaning assay. Tables 7 and 9 show the cleaning assays results for AprE variants in Table 6A and WP_082194748 variants in Table 8 respectively, having cleaning performance PI values 1.0 or greater for at least one condition when compared to the respective parent subtilisin, and also displaying stability PI values 1.1 or greater.

TABLE 6A

AprE subtilisin variants with improved stability in liquid detergent at 41° C. (PI values ≥ 1.1) compared to AprE parent

| AprE Variant Sample ID | Substitutions in AprE numbering | Substitutions in BPN' numbering | Stability PI |
|---|---|---|---|
| AprE-00772 | S003V | S003V | 1.8 |
| AprE-00795 | N076D | N076D | 2.0 |
| AprE-00488 | S078N | S078N | 1.6 |
| AprE-00944 | G166Q | G166Q | 1.9 |
| AprE-00511 | Y217L | Y217L | 1.5 |
| AprE-00924 | N218S | N218S | 1.7 |
| AprE-00447 | N259P | N259P | 1.7 |
| AprE-00370 | S003V-N259P | S003V-N259P | 2.0 |
| AprE-00380 | S003V-P040E | S003V-P040E | 1.5 |
| AprE-00413 | S003V-M124I | S003V-M124I | 1.8 |
| AprE-00515 | S003V-S078N | S003V-S078N | 1.8 |
| AprE-00729 | S003V-N076D | S003V-N076D | 2.0 |
| AprE-00841 | S003V-G166Q | S003V-G166Q | 2.2 |
| AprE-00907 | S003V-G128S | S003V-G128S | 1.8 |
| AprE-00498 | A069S-N076D | A069S-N076D | 1.9 |
| AprE-00594 | A069S-N218S | A069S-N218S | 1.6 |
| AprE-00666 | A069S-G166Q | A069S-G166Q | 1.8 |
| AprE-00758 | A069S-N259P | A069S-N259P | 1.5 |
| AprE-00788 | A069S-S078N | A069S-S078N | 1.4 |
| AprE-00943 | A069S-G128S | A069S-G128S | 1.4 |
| AprE-00966 | A069S-M124I | A069S-M124I | 1.2 |
| AprE-00416 | N076D-G128S | N076D-G128S | 2.5 |
| AprE-00774 | N076D-S078N | N076D-S078N | 2.1 |
| AprE-00912 | N076D-N218S | N076D-N218S | 2.3 |
| AprE-00920 | N076D-G166Q | N076D-G166Q | 2.5 |
| AprE-00946 | N076D-M124I | N076D-M124I | 2.3 |
| AprE-00365 | S078T-M124I | S078T-M124I | 1.9 |
| AprE-00655 | S078N-G128S | S078N-G128S | 2.0 |
| AprE-00891 | S078N-N259P | S078N-N259P | 2.0 |
| AprE-00904 | S078N-N218S | S078N-N218S | 2.0 |
| AprE-00974 | S078N-G166Q | S078N-G166Q | 2.1 |
| AprE-00442 | M124I-G166Q | M124I-G166Q | 1.9 |
| AprE-00653 | M124I-N259P | M124I-N259P | 1.5 |
| AprE-00770 | M124I-G128S | M124I-G128S | 1.5 |
| AprE-00861 | M124I-N218S | M124I-N218S | 1.7 |
| AprE-00732 | G128S-N259P | G128S-N259P | 1.6 |
| AprE-00757 | G128S-N218S | G128S-N218S | 1.7 |
| AprE-00824 | G128S-G166Q | G128S-G166Q | 2.0 |
| AprE-00694 | G166Q-N259P | G166Q-N259P | 2.0 |
| AprE-00698 | G166Q-N218S | G166Q-N218S | 2.1 |
| AprE-00646 | N218S-N259P | N218S-N259P | 2.0 |

TABLE 6B

Additional AprE subtilisin variants with improved stability in liquid detergent at 42° C., reported as percent residual activity (% RA) compared to AprE parent

| AprE Variant Sample ID | Substitutions in AprE numbering | Substitutions in BPN' numbering | % RA |
|---|---|---|---|
| AprE | — | — | 27 |
| AprE-01081 | S009E | S009E | 80 |
| AprE-01080 | P040E | P040E | 100 |
| AprE-01089 | S003V-S009E | S003V-S009E | 88 |
| AprE-01078 | S003V-A069S | S003V-A069S | 42 |
| AprE-01842 | S003V-N218S | S003V-N218S | 58 |
| AprE-01082 | S009E-P040E | S009E-P040E | 82 |
| AprE-01083 | S009E-A069S | S009E-A069S | 70 |
| AprE-01025 | S009E-N076D | S009E-N076D | 96 |
| AprE-01850 | S009E-S078N | S009E-S078N | 75 |
| AprE-01959 | S009E-G166Q | S009E-G166Q | 90 |
| AprE-01111 | S009E-N218S | S009E-N218S | 83 |
| AprE-01096 | S009E-N259P | S009E-N259P | 84 |
| AprE-01951 | P040E-A069S | P040E-A069S | 33 |

TABLE 6B-continued

| Additional AprE subtilisin variants with improved stability in liquid detergent at 42° C., reported as percent residual activity (% RA) compared to AprE parent | | | |
|---|---|---|---|
| AprE Variant Sample ID | Substitutions in AprE numbering | Substitutions in BPN' numbering | % RA |
| AprE-01108 | P040E-N076D | P040E-N076D | 72 |
| AprE-01844 | P040E-S078N | P040E-S078N | 43 |
| AprE-01107 | P040E-G166Q | P040E-G166Q | 75 |
| AprE-01054 | P040E-N218S | P040E-N218S | 65 |
| AprE-01105 | P040E-N259P | P040E-N259P | 48 |
| AprE-01836 | N076D-N259P | N076D-N259P | 70 |

TABLE 7

AprE variants with cleaning performance on par or improved compared to AprE parent

| | Cleaning performance, PI | |
|---|---|---|
| AprE Variant Sample ID | BMI stain in PNB detergent | PAS-38 stain n GSM-B detergent |
| AprE-00772 | 1.2 | 1.2 |
| AprE-00795 | 1.0 | 1.1 |
| AprE-00488 | 1.0 | 1.1 |
| AprE-00944 | 1.0 | 1.1 |
| AprE-00511 | 1.1 | 1.3 |
| AprE-00924 | 0.9 | 1.0 |
| AprE-00447 | 0.9 | 1.1 |
| AprE-00370 | 1.0 | 1.0 |
| AprE-00380 | 1.0 | 1.0 |
| AprE-00413 | 1.0 | 1.0 |
| AprE-00515 | 1.0 | 1.2 |
| AprE-00729 | 1.0 | 1.1 |
| AprE-00841 | 1.1 | 1.1 |
| AprE-00907 | 1.0 | 1.1 |
| AprE-00498 | 1.0 | 1.1 |
| AprE-00594 | 1.0 | 1.1 |
| AprE-00666 | 0.9 | 1.1 |
| AprE-00758 | 1.1 | 1.1 |
| AprE-00788 | 1.1 | 1.2 |
| AprE-00943 | 0.9 | 1.0 |
| AprE-00966 | 1.0 | 1.1 |
| AprE-00416 | 1.1 | 1.0 |
| AprE-00774 | 1.0 | 1.1 |
| AprE-00912 | 0.9 | 1.0 |
| AprE-00920 | 1.1 | 1.1 |
| AprE-00946 | 1.1 | 1.0 |
| AprE-00365 | 1.0 | 1.1 |
| AprE-00655 | 1.1 | 1.1 |
| AprE-00891 | 0.9 | 1.1 |
| AprE-00904 | 1.0 | 1.1 |
| AprE-00974 | 0.9 | 1.1 |
| AprE-00442 | 1.1 | 1.1 |
| AprE-00653 | 1.1 | 1.1 |
| AprE-00770 | 1.3 | 0.9 |
| AprE-00861 | 1.1 | 1.1 |
| AprE-00732 | 1.1 | 1.0 |
| AprE-00757 | 1.1 | 1.0 |
| AprE-00824 | 1.0 | 1.1 |
| AprE-00694 | 1.0 | 1.0 |
| AprE-00698 | 0.9 | 1.0 |
| AprE-00646 | 1.1 | 1.1 |

TABLE 8

WP_082194748 subtilisin variants with improved stability in liquid detergent at 46° C. (PI values > 1.1) compared to WP082194748 parent

| WP_082194748 Variant Sample ID | Substitutions in WP_082194748 numbering | Substitutions in BPN' numbering | Stability PI |
|---|---|---|---|
| WP_082194748-00179 | Y217L | Y217L | 1.2 |
| WP_082194748-00103 | S087D | S087D | 1.2 |
| WP_082194748-00040 | T078N | T078N | 1.4 |
| WP_082194748-00446 | G128S | G128S | 1.4 |
| WP_082194748-00466 | G166Q | G166Q | 2.1 |
| WP_082194748-00047 | S182E | S182E | 2.5 |
| WP_082194748-00571 | G128S-V185Q | G128S-V185Q | 1.1 |
| WP_082194748-00612 | A069S-G128S | A069S-G128S | 1.1 |
| WP_082194748-00380 | T078N-V185Q | T078N-V185Q | 1.3 |
| WP_082194748-00025 | V185Q-S259P | V185Q-S259P | 1.5 |
| WP_082194748-00461 | G166Q-V185Q | G166Q-V185Q | 1.6 |
| WP_082194748-00441 | T078N-S259P | T078N-S259P | 1.6 |
| WP_082194748-00099 | T003V-G128S | T003V-G128S | 1.7 |
| WP_082194748-00306 | T078N-G128S | T078N-G128S | 1.7 |
| WP_082194748-00582 | G128S-S259P | G128S-S259P | 1.8 |
| WP_082194748-00486 | G166Q-S259P | G166Q-S259P | 1.9 |
| WP_082194748-00242 | A069S-M124I | A069S-M124I | 1.9 |
| WP_082194748-00458 | T003V-M124I | T003V-M124I | 1.9 |
| WP_082194748-00546 | M124I-S259P | M124I-S259P | 1.9 |
| WP_082194748-00275 | M124I-V185Q | M124I-V185Q | 2.0 |
| WP_082194748-00299 | T003V-S259P | T003V-S259P | 2.1 |
| WP_082194748-00066 | A069S-S259P | A069S-S259P | 2.1 |
| WP_082194748-00415 | M124I-G128S | M124I-G128S | 2.1 |
| WP_082194748-00340 | A069S-G166Q | A069S-G166Q | 2.1 |
| WP_082194748-00038 | T078N-M124I | T078N-M124I | 2.2 |
| WP_082194748-00060 | M124I-G166Q | M124I-G166Q | 2.5 |
| WP_082194748-00259 | T078N-G166Q | T078N-G166Q | 2.5 |
| WP_082194748-00297 | T003V-G166Q | T003V-G166Q | 2.8 |

TABLE 9

WP_082194748 variants with cleaning performance on par or improved compared to WP_082194748 parent

| | Cleaning performance, PI | |
|---|---|---|
| WP_082194748 Variant Sample ID | BMI stain in PNB detergent | PAS-38 stain in GSM-B detergent |
| WP_082194748-00179 | 1.0 | 1.0 |
| WP_082194748-00103 | 1.1 | 1.0 |
| WP_082194748-00040 | 1.0 | 1.0 |
| WP_082194748-00446 | 1.0 | 0.9 |
| WP_082194748-00466 | 1.0 | 1.0 |
| WP_082194748-00047 | 1.1 | 0.9 |
| WP_082194748-00571 | 1.1 | 0.9 |
| WP_082194748-00612 | 1.1 | 0.9 |
| WP_082194748-00380 | 1.0 | 1.1 |
| WP_082194748-00025 | 1.0 | 1.0 |
| WP_082194748-00461 | 1.0 | 1.0 |
| WP_082194748-00441 | 1.0 | 1.0 |
| WP_082194748-00099 | 0.8 | 1.0 |
| WP_082194748-00306 | 1.0 | 1.0 |
| WP_082194748-00582 | 1.1 | 0.9 |
| WP_082194748-00486 | 1.1 | 1.0 |
| WP_082194748-00242 | 1.1 | 0.9 |
| WP_082194748-00458 | 1.1 | 1.0 |
| WP_082194748-00546 | 0.9 | 1.0 |
| WP_082194748-00275 | 1.2 | 1.0 |
| WP_082194748-00299 | 0.8 | 1.0 |
| WP_082194748-00066 | 1.0 | 1.0 |
| WP_082194748-00340 | 1.0 | 1.0 |
| WP_082194748-00038 | 1.2 | 1.1 |
| WP_082194748-00060 | 1.0 | 1.0 |
| WP_082194748-00259 | 1.0 | 1.0 |
| WP_082194748-00297 | 0.9 | 1.0 |

Example 4

Chemgen_164A, CP474, & ZP-00454 Subtilisin Variants with Improved Stability in Detergent Variants of Chemgen_164A (Chemgen, SEQ ID NO: 10), CP474 (SEQ ID NO: 11) and ZP-00454 (SEQ ID NO: 12) subtilisins were evaluated for stability and cleaning performance using methods described in Example 2, and performance index for each variant was calculated versus the respective parent molecule. The Chemgen_164A, CP474, and ZP-00454 subtilisins share high sequence homology with the LG12 (SprC) protease (described in WO2015/038792), having amino acid sequence identities of 81.8%, 79.6% and 90.2%, respectively.

Detergent stability results are reported as either performance index (PI) or residual activity (% RA). Tables 10A and 10B, show the stability results for Chemgen_164A, Table 11 for CP474, and Table 12 for ZP-00454 variants having stability PI values 1.1 and greater, where the cleaning performance index was at least 0.5 or greater (relative to parent) in at least one cleaning assay. Tables 13, and 14 show the cleaning assay results for CP474 variants, and ZP-00454 variants respectively, having cleaning performance PI values 1.0 or greater when compared to the respective parent subtilisin, and also displaying stability PI values 1.1 or greater. Due to conditions of the assay, in some instances the PI values calculated were very large (due to parent subtilisin activity being at level of detection), therefore PI values greater than 4.0 are shown as ≥4.0.

TABLE 10A

Chemgen_164A subtilisin variants with improved stability in liquid detergent at 56° C. (PI values ≥ 1.1) compared to Chemgen_164A wildtype (parent)

| Chemgen_164A variant Sample ID | Substitutions in Chemgen_164A numbering | Substitutions in BPN' numbering | Stability PI |
|---|---|---|---|
| Chemgen-00272 | T003V | T003V | 3.1 |
| Chemgen-00032 | A069S | A069S | 1.5 |
| Chemgen-00626 | N087D | N087D | 3.2 |
| Chemgen-00300 | N118R | N118R | 1.1 |
| Chemgen-00173 | S129P | S129P | 1.8 |
| Chemgen-00404 | G166Q | G166Q | 2.2 |
| Chemgen-00591 | S182E | S182E | 2.0 |
| Chemgen-00547 | N218S | N218S | 2.4 |
| Chemgen-00076 | T003V-N076D | T003V-N076D | 3.1 |
| Chemgen-00108 | T003V-N185Q | T003V-N185Q | 3.1 |
| Chemgen-00196 | T003V-G128S | T003V-G128S | 2.9 |
| Chemgen-00329 | T003V-S129P | T003V-S129P | 3.2 |
| Chemgen-00378 | T003V-G166Q | T003V-G166Q | 3.2 |
| Chemgen-00443 | T003V-T078N | T003V-T078N | 3.2 |
| Chemgen-00481 | T003V-A069S | T003V-A069S | 3.2 |
| Chemgen-00513 | T003V-M124I | T003V-M124I | 2.0 |
| Chemgen-00634 | T003V-N218S | T003V-N218S | 3.2 |
| Chemgen-00289 | P040E-M124I | P040E-M124I | 2.5 |
| Chemgen-00262 | A069S-G128S | A069S-G128S | 1.2 |
| Chemgen-00394 | A069S-G166Q | A069S-G166Q | 2.9 |
| Chemgen-00436 | A069S-T078N | A069S-T078N | 3.2 |
| Chemgen-00444 | A069S-D259P | A069S-D259P | 3.0 |
| Chemgen-00525 | A069S-S129P | A069S-S129P | 2.0 |
| Chemgen-00527 | A069S-N076D | A069S-N076D | 3.2 |
| Chemgen-00569 | A069S-N218S | A069S-N218S | 2.6 |
| Chemgen-00617 | A069S-N185Q | A069S-N185Q | 1.9 |
| Chemgen-00132 | N076D-G166Q | N076D-G166Q | 3.1 |
| Chemgen-00367 | N076D-N218S | N076D-N218S | 3.2 |
| Chemgen-00369 | N076D-M124I | N076D-M124I | 3.2 |
| Chemgen-00459 | N076D-T078N | N076D-T078N | 3.2 |
| Chemgen-00546 | N076D-D259P | N076D-D259P | 3.2 |
| Chemgen-00619 | N076D-S129P | N076D-S129P | 3.2 |
| Chemgen-00621 | N076D-G128S | N076D-G128S | 3.2 |

TABLE 10A-continued

Chemgen_164A subtilisin variants with improved stability in liquid detergent at 56° C. (PI values ≥ 1.1) compared to Chemgen_164A wildtype (parent)

| Chemgen_164A variant Sample ID | Substitutions in Chemgen_164A numbering | Substitutions in BPN' numbering | Stability PI |
|---|---|---|---|
| Chemgen-00212 | T078N-G128S | T078N-G128S | 2.5 |
| Chemgen-00224 | T078N-N185Q | T078N-N185Q | 3.1 |
| Chemgen-00313 | T078N-N218S | T078N-N218S | 3.1 |
| Chemgen-00350 | T078N-D259P | T078N-D259P | 3.2 |
| Chemgen-00351 | T078N-S129P | T078N-S129P | 3.2 |
| Chemgen-00413 | T078N-M124I | T078N-M124I | 1.5 |
| Chemgen-00560 | T078N-G166Q | T078N-G166Q | 3.2 |
| Chemgen-00115 | G128S-N218S | G128S-N218S | 2.1 |
| Chemgen-00448 | G128S-D259P | G128S-D259P | 2.2 |
| Chemgen-00517 | G128S-N185Q | G128S-N185Q | 1.1 |
| Chemgen-00105 | S129P-N185Q | S129P-N185Q | 1.9 |
| Chemgen-00375 | S129P-G166Q | S129P-G166Q | 3.2 |
| Chemgen-00616 | S129P-N218S | S129P-N218S | 2.9 |
| Chemgen-00010 | G166Q-D259P | G166Q-D259P | 3.1 |
| Chemgen-00122 | G166Q-N185Q | G166Q-N185Q | 2.9 |
| Chemgen-00335 | G166Q-N218S | G166Q-N218S | 3.2 |
| Chemgen-00198 | N185Q-N218S | N185Q-N218S | 2.1 |
| Chemgen-00359 | N185Q-D259P | N185Q-D259P | 2.3 |
| Chemgen-00309 | N218S-D259P | N218S-D259P | 3.1 |

TABLE 10B

Chemgen_164A subtilisin variants with improved stability in liquid detergent at 51° C. (reported as percent residual activity, % RA) compared to Chemgen_164A wildtype (parent)

| Chemgen_164A variant Sample ID | Substitutions in Chemgen_164A numbering | Substitutions in BPN' numbering | % RA |
|---|---|---|---|
| Chemgen_164A | — | — | 31 |
| Chemgen-00815 | P040E | P040E | 63 |
| Chemgen-00718 | N076D | N076D | 60 |
| Chemgen-00720 | T078N | T078N | 65 |
| Chemgen-00723 | N185Q | N185Q | 34 |
| Chemgen-00795 | T003V-T009E | T003V-T009E | 66 |
| Chemgen-00794 | T003V-P040E | T003V-P040E | 100 |
| Chemgen-00650 | T003V-D259P | T003V-D259P | 100 |
| Chemgen-00788 | T009E-A069S | T009E-A069S | 36 |
| Chemgen-00712 | T009E-N076D | T009E-N076D | 73 |
| Chemgen-00714 | T009E-T078N | T009E-T078N | 57 |
| Chemgen-00797 | T009E-G166Q | T009E-G166Q | 58 |
| Chemgen-00798 | T009E-N185Q | T009E-N185Q | 36 |
| Chemgen-00741 | T009E-D259P | T009E-D259P | 37 |
| Chemgen-00715 | P040E-T078N | P040E-T078N | 84 |
| Chemgen-01467 | P040E-G166Q | P040E-G166Q | 63 |
| Chemgen-00716 | P040E-N185Q | P040E-N185Q | 100 |
| Chemgen-01219 | P040E-N218S | P040E-N218S | 49 |
| Chemgen-00804 | N076D-N185Q | N076D-N185Q | 94 |

TABLE 11

CP474 subtilisin variants with improved stability in liquid detergent at 37° C. (PI values ≥ 1.1) compared to CP474 parent

| CP474 Variant Sample ID | Substitutions in CP474 numbering | Substitutions in BPN' numbering | Stability PI |
|---|---|---|---|
| CP474-00571 | T003V | T003V | 1.8 |
| CP474-00581 | A040E | A040E | ≥4.0 |
| CP474-00591 | A069S | A069S | 1.3 |
| CP474-00601 | T078N | T078N | 1.8 |
| CP474-00611 | T079I | T079I | ≥4.0 |
| CP474-00631 | S162Q | S166Q | 1.2 |
| CP474-00562 | N181Q | N185Q | 1.4 |
| CP474-00563 | T003V-S162Q | T003V-S166Q | 2.5 |

TABLE 11-continued

CP474 subtilisin variants with improved stability in liquid detergent at 37° C. (PI values ≥ 1.1) compared to CP474 parent

| CP474 Variant Sample ID | Substitutions in CP474 numbering | Substitutions in BPN' numbering | Stability PI |
|---|---|---|---|
| CP474-00573 | T003V-N181Q | T003V-N185Q | 2.1 |
| CP474-00583 | T003V-N214S | T003V-N218S | 1.6 |
| CP474-00592 | T003V-A040E | T003V-A040E | ≥4.0 |
| CP474-00593 | T003V-D255P | T003V-D259P | 1.7 |
| CP474-00602 | T003V-A069S | T003V-A069S | 2.3 |
| CP474-00612 | T003V-T078N | T003V-T078N | 2.5 |
| CP474-00622 | T003V-T079I | T003V-T079I | ≥4.0 |
| CP474-00632 | T003V-L124I | T003V-L124I | 1.5 |
| CP474-00564 | A040E-S162Q | A040E-S166Q | ≥4.0 |
| CP474-00574 | A040E-N181Q | A040E-N185Q | ≥4.0 |
| CP474-00584 | A040E-N214S | A040E-N218S | ≥4.0 |
| CP474-00594 | A040E-D255P | A040E-D259P | ≥4.0 |
| CP474-00603 | A040E-A069S | A040E-A069S | ≥4.0 |
| CP474-00613 | A040E-T078N | A040E-T078N | ≥4.0 |
| CP474-00623 | A040E-T079I | A040E-T079I | ≥4.0 |
| CP474-00633 | A040E-L124I | A040E-L124I | ≥4.0 |
| CP474-00565 | A069S-N181Q | A069S-N185Q | 1.4 |
| CP474-00604 | A069S-T078N | A069S-T078N | 1.5 |
| CP474-00614 | A069S-T079I | A069S-T079I | ≥4.0 |
| CP474-00634 | A069S-S162Q | A069S-S166Q | 1.5 |
| CP474-00566 | T078N-D255P | T078N-D259P | 1.6 |
| CP474-00595 | T078N-T079I | T078N-T079I | ≥4.0 |
| CP474-00615 | T078N-S162Q | T078N-S166Q | 2.2 |
| CP474-00625 | T078N-N181Q | T078N-N185Q | 2.0 |
| CP474-00635 | T078N-N214S | T078N-N218S | 1.5 |
| CP474-00576 | T079I-L124I | T079I-L124I | ≥4.0 |
| CP474-00586 | T079I-S162Q | T079I-S166Q | ≥4.0 |
| CP474-00596 | T079I-N181Q | T079I-N185Q | ≥4.0 |
| CP474-00606 | T079I-N214S | T079I-N218S | ≥4.0 |
| CP474-00616 | T079I-D255P | T079I-D259P | ≥4.0 |
| CP474-00597 | S162Q-N214S | S166Q-N218S | 1.4 |
| CP474-00579 | N181Q-D255P | N185Q-D259P | 1.4 |
| CP474-00617 | N181Q-N214S | N185Q-N218S | 1.3 |
| CP474-00627 | N214S-D255P | N218S-D259P | 1.1 |

TABLE 12

ZP-00454 subtilisin variants with improved stability in liquid detergent at 42° C. (PI values ≥ 1.1) compared to ZP-00454 parent

| ZP-00454 Variant Sample ID | Substitutions in ZP-00454 numbering | Substitutions in BPN' numbering | Stability PI |
|---|---|---|---|
| ZP-00454-00011 | A040E | A040E | 2.1 |
| ZP-00454-00021 | A069S | A069S | 1.1 |
| ZP-00454-00031 | N076D | N076D | 1.7 |
| ZP-00454-00041 | T078N | T078N | 1.5 |
| ZP-00454-00051 | T079I | T079I | 2.1 |
| ZP-00454-00071 | I128S | I128S | 1.2 |
| ZP-00454-00013 | A040E-M124I | A040E-M124I | 2.0 |
| ZP-00454-00023 | A040E-I128S | A040E-I128S | 1.7 |
| ZP-00454-00033 | A040E-S129P | A040E-S129P | 2.1 |
| ZP-00454-00043 | A040E-G166Q | A040E-G166Q | 2.1 |
| ZP-00454-00052 | A040E-A069S | A040E-A069S | 2.2 |
| ZP-00454-00053 | A040E-N185Q | A040E-N185Q | 2.3 |
| ZP-00454-00062 | A040E-N076D | A040E-N076D | 2.2 |
| ZP-00454-00063 | A040E-N218S | A040E-N218S | 2.1 |
| ZP-00454-00072 | A040E-T078N | A040E-T078N | 2.1 |
| ZP-00454-00073 | A040E-D259P | A040E-D259P | 2.0 |
| ZP-00454-00004 | A069S-N076D | A069S-N076D | 1.7 |
| ZP-00454-00005 | A069S-N218S | A069S-N218S | 1.2 |
| ZP-00454-00014 | A069S-T078N | A069S-T078N | 1.7 |
| ZP-00454-00024 | A069S-T079I | A069S-T079I | 2.0 |
| ZP-00454-00044 | A069S-I128S | A069S-I128S | 1.2 |
| ZP-00454-00054 | A069S-S129P | A069S-S129P | 1.2 |
| ZP-00454-00074 | A069S-N185Q | A069S-N185Q | 1.2 |
| ZP-00454-00006 | N076D-N185Q | N076D-N185Q | 1.6 |
| ZP-00454-00016 | N076D-N218S | N076D-N218S | 1.6 |
| ZP-00454-00025 | N076D-T078N | N076D-T078N | 1.8 |

TABLE 12-continued

ZP-00454 subtilisin variants with improved stability in liquid detergent at 42° C. (PI values ≥ 1.1) compared to ZP-00454 parent

| ZP-00454 Variant Sample ID | Substitutions in ZP-00454 numbering | Substitutions in BPN' numbering | Stability PI |
|---|---|---|---|
| ZP-00454-00026 | N076D-D259P | N076D-D259P | 1.5 |
| ZP-00454-00035 | N076D-T079I | N076D-T079I | 2.1 |
| ZP-00454-00045 | N076D-M124I | N076D-M124I | 1.3 |
| ZP-00454-00055 | N076D-I128S | N076D-I128S | 1.8 |
| ZP-00454-00065 | N076D-S129P | N076D-S129P | 1.6 |
| ZP-00454-00075 | N076D-G166Q | N076D-G166Q | 1.8 |
| ZP-00454-00007 | T078N-N185Q | T078N-N185Q | 1.5 |
| ZP-00454-00027 | T078N-D259P | T078N-D259P | 1.4 |
| ZP-00454-00036 | T078N-T079I | T078N-T079I | 2.0 |
| ZP-00454-00056 | T078N-I128S | T078N-I128S | 1.7 |
| ZP-00454-00066 | T078N-S129P | T078N-S129P | 1.5 |
| ZP-00454-00076 | T078N-G166Q | T078N-G166Q | 1.6 |
| ZP-00454-00008 | T079I-N218S | T079I-N218S | 2.1 |
| ZP-00454-00018 | T079I-D259P | T079I-D259P | 1.9 |
| ZP-00454-00037 | T079I-M124I | T079I-M124I | 2.4 |
| ZP-00454-00047 | T079I-I128S | T079I-I128S | 2.1 |
| ZP-00454-00057 | T079I-S129P | T079I-S129P | 2.0 |
| ZP-00454-00067 | T079I-G166Q | T079I-G166Q | 2.0 |
| ZP-00454-00077 | T079I-N185Q | T079I-N185Q | 2.0 |
| ZP-00454-00009 | I128S-S129P | I128S-S129P | 1.1 |
| ZP-00454-00059 | S129P-G166Q | S129P-G166Q | 1.1 |

TABLE 13

CP474 variants with cleaning performance on par or improved compared to CP474 parent

| CP474 Variant Sample ID | Cleaning Performance PI, BMI stain PNB detergent |
|---|---|
| CP474-00591 | 1.1 |
| CP474-00601 | 1.0 |
| CP474-00611 | 1.1 |
| CP474-00562 | 1.0 |
| CP474-00573 | 1.2 |
| CP474-00583 | 1.1 |
| CP474-00592 | 1.0 |
| CP474-00593 | 1.1 |
| CP474-00602 | 1.2 |
| CP474-00612 | 1.2 |
| CP474-00622 | 1.2 |
| CP474-00574 | 1.2 |
| CP474-00584 | 1.1 |
| CP474-00594 | 1.1 |
| CP474-00603 | 1.2 |
| CP474-00613 | 1.1 |
| CP474-00623 | 1.2 |
| CP474-00565 | 1.2 |
| CP474-00604 | 1.3 |
| CP474-00614 | 1.4 |
| CP474-00634 | 1.0 |
| CP474-00595 | 1.3 |
| CP474-00625 | 1.2 |
| CP474-00635 | 1.1 |
| CP474-00586 | 1.2 |
| CP474-00596 | 1.2 |
| CP474-00606 | 1.2 |
| CP474-00616 | 1.1 |
| CP474-00597 | 1.1 |
| CP474-00617 | 1.3 |
| CP474-00627 | 1.0 |

TABLE 14

| ZP-00454 variants with cleaning performance on par or improved compared to ZP-00454 parent | |
|---|---|
| ZP-00454 Variant Sample ID | Cleaning Performance PI, BMI stain PNB detergent |
| ZP-00454-00031 | 1.0 |
| ZP-00454-00041 | 1.1 |
| ZP-00454-00051 | 2.1 |
| ZP-00454-00033 | 1.0 |
| ZP-00454-00043 | 1.0 |
| ZP-00454-00052 | 1.1 |
| ZP-00454-00053 | 1.0 |
| ZP-00454-00024 | 1.1 |
| ZP-00454-00044 | 1.0 |
| ZP-00454-00054 | 1.1 |
| ZP-00454-00074 | 1.0 |
| ZP-00454-00006 | 1.0 |
| ZP-00454-00016 | 1.1 |
| ZP-00454-00025 | 1.1 |
| ZP-00454-00026 | 1.0 |
| ZP-00454-00035 | 1.8 |
| ZP-00454-00055 | 1.0 |
| ZP-00454-00065 | 1.0 |
| ZP-00454-00075 | 1.0 |
| ZP-00454-00027 | 1.0 |
| ZP-00454-00036 | 1.0 |
| ZP-00454-00056 | 1.0 |
| ZP-00454-00076 | 1.0 |
| ZP-00454-00018 | 1.5 |
| ZP-00454-00037 | 1.0 |
| ZP-00454-00057 | 1.7 |
| ZP-00454-00067 | 2.2 |
| ZP-00454-00077 | 1.4 |
| ZP-00454-00059 | 1.0 |

Example 5

Bpan01744 Subtilisin Variants with Improved Stability in Detergent

Variants of Bpan01744 (SEQ ID NO: 13) subtilisin were evaluated for stability and cleaning performance using methods described in Example 2, and performance index for each variant was calculated versus the parent molecule. The Bpan01744 wildtype subtilisin was described as SEQ ID NO: 3 in patent application WO2016069563.

Detergent stability results are reported as either performance index (PI) or % residual activity (% RA). Tables 15A and 15B show the stability results for Bpan01744 variants having stability PI values 1.1 and greater, where the cleaning performance index was at least 0.5 or greater (relative to parent) in at least one cleaning assay. Table 16 shows the cleaning assays results for Bpan01744 variants from Table 15A having cleaning performance PI values 1.0 or greater for at least one condition when compared to the parent subtilisin, and also displaying stability PI values 1.1 or greater. Due to conditions of the assay, in some instances the PI values calculated were very large (due to parent subtilisin activity being at level of detection), therefore PI values greater than 4.0 are shown as ≥4.0.

TABLE 15A

| Bpan01744 subtilisin variants with improved stability in liquid detergent at 46° C. (PI values ≥ 1.1) compared to Bpan01744 parent | | | |
|---|---|---|---|
| Bpan01744 Variant Sample ID | Substitutions in Bpan01744 numbering | Substitutions in BPN' numbering | Stability PI |
| Bpan01744-00498 | S003V | S003V | 1.8 |
| Bpan01744-00574 | S076N | S078N | 2.4 |
| Bpan01744-00152 | S003V-N179Q | S003V-N185Q | 3.1 |
| Bpan01744-00166 | S003V-N074D | S003V-N076D | ≥4.0 |
| Bpan01744-00167 | S003V-A067S | S003V-A069S | 1.9 |
| Bpan01744-00304 | S003V-S076N | S003V-S078N | 3.5 |
| Bpan01744-00417 | S003V-N212S | S003V-N218S | ≥4.0 |
| Bpan01744-00544 | S003V-N253P | S003V-N259P | 2.0 |
| Bpan01744-00088 | A067S-N074D | A069S-N076D | ≥4.0 |
| Bpan01744-00153 | A067S-G160Q | A069S-G166Q | 3.8 |
| Bpan01744-00414 | A067S-N179Q | A069S-N185Q | 1.7 |
| Bpan01744-00423 | A067S-S076N | A069S-S078N | 2.6 |
| Bpan01744-00488 | A067S-N212S | A069S-N218S | 3.6 |
| Bpan01744-00337 | N074D-S076N | N076D-S078N | ≥4.0 |
| Bpan01744-00554 | N074D-S127P | N076D-S129P | ≥4.0 |
| Bpan01744-00158 | S076N-G160Q | S078N-G166Q | ≥4.0 |
| Bpan01744-00179 | S076N-M122I | S078N-M124I | 2.1 |
| Bpan01744-00258 | S076N-S127P | S078N-S129P | 3.8 |
| Bpan01744-00121 | M122I-N212S | M124I-N218S | ≥4.0 |
| Bpan01744-00362 | M122I-S127P | M124I-S129P | ≥4.0 |
| Bpan01744-00550 | M122I-N179Q | M124I-N185Q | 1.6 |
| Bpan01744-00238 | S127P-N253P | S129P-N259P | 1.9 |
| Bpan01744-00251 | S127P-N179Q | S129P-N185Q | 2.4 |
| Bpan01744-00282 | S127P-N212S | S129P-N218S | ≥4.0 |
| Bpan01744-00545 | S127P-G160Q | S129P-G166Q | 3.3 |
| Bpan01744-00048 | G160Q-N253P | G166Q-N259P | 3.1 |
| Bpan01744-00172 | G160Q-N212S | G166Q-N218S | ≥4.0 |
| Bpan01744-00369 | G160Q-N179Q | G166Q-N185Q | 3.1 |
| Bpan01744-00094 | N179Q-N212S | N185Q-N218S | ≥4.0 |
| Bpan01744-00339 | N179Q-N253P | N185Q-N259P | 1.6 |
| Bpan01744-00126 | N212S-N253P | N218S-N259P | 3.5 |

TABLE 15B

| Bpan01744 subtilisin variants with improved stability in liquid detergent at 44° C. (reported as percent residual activity, % RA) compared to Bpan01744 parent | | | |
|---|---|---|---|
| Bpan01744 Variant Sample ID | Substitutions in Bpan01744 numbering | Substitutions in BPN' numbering | % RA |
| Bpan01744 | — | — | 19 |
| Bpan01744-02141 | S009E | S009E | 36 |
| Bpan01744-01310 | N074D | N076D | 75 |
| Bpan01744-00717 | N179Q | N185Q | 23 |
| Bpan01744-00892 | N212S | N218S | 47 |
| Bpan01744-01737 | N253P | N259P | 27 |
| Bpan01744-00830 | S003V-S009E | S003V-S009E | 58 |
| Bpan01744-01145 | S003V-G160Q | S003V-G166Q | 77 |
| Bpan01744-01257 | S009E-N074D | S009E-N076D | 83 |
| Bpan01744-02075 | S009E-S076N | S009E-S078N | 57 |
| Bpan01744-01122 | S009E-G160Q | S009E-G166Q | 62 |
| Bpan01744-01123 | S009E-N179Q | S009E-N185Q | 33 |
| Bpan01744-00795 | S009E-N212S | S009E-N218S | 69 |
| Bpan01744-01124 | S009E-N253P | S009E-N259P | 29 |
| Bpan01744-01035 | N074D-G160Q | N076D-G166Q | 74 |
| Bpan01744-01133 | N074D-N179Q | N076D-N185Q | 76 |
| Bpan01744-01135 | N074D-N212S | N076D-N218S | 92 |
| Bpan01744-01148 | N074D-N253P | N076D-N259P | 81 |
| Bpan01744-01629 | S076N-N179Q | S078N-N185Q | 37 |
| Bpan01744-00991 | S076N-N212S | S078N-N218S | 71 |
| Bpan01744-01151 | S076N-N253P | S078N-N259P | 37 |

TABLE 16

Bpan01744 variants with cleaning performance on par or improved compared to Bpan01744 parent

| BpaN01744 Variant Sample ID | Cleaning Performance PI BMI stain PNB detergent | PAS-38 stain GSM-B detergent | BMI stain ECE-2 detergent |
|---|---|---|---|
| Bpan01744-00498 | 1.0 | 1.0 | 0.9 |
| Bpan01744-00574 | 0.9 | 1.1 | 1.0 |
| Bpan01744-00166 | 1.0 | 0.9 | 0.9 |
| Bpan01744-00167 | 1.0 | 1.0 | 0.9 |
| Bpan01744-00304 | 1.0 | 1.0 | 1.0 |
| Bpan01744-00417 | 1.0 | 0.9 | 0.7 |
| Bpan01744-00544 | 0.9 | 1.1 | 0.9 |
| Bpan01744-00088 | 1.0 | 0.9 | 0.9 |
| Bpan01744-00414 | 0.9 | 1.0 | 0.9 |
| Bpan01744-00423 | 1.0 | 0.9 | 1.0 |
| Bpan01744-00488 | 0.9 | 1.0 | 0.8 |
| Bpan01744-00337 | 1.0 | 1.0 | 0.9 |
| Bpan01744-00179 | 1.0 | 0.9 | 0.7 |
| Bpan01744-00258 | 1.0 | 0.9 | 0.9 |
| Bpan01744-00550 | 1.0 | 0.9 | 0.7 |
| Bpan01744-00238 | 1.0 | 0.9 | 0.9 |
| Bpan01744-00251 | 1.0 | 1.0 | 0.9 |
| Bpan01744-00339 | 1.0 | 1.1 | 1.0 |
| Bpan01744-00126 | 0.9 | 1.0 | 0.8 |

Example 6

DSM14391 Subtilisin Variants with Improved Stability in Detergent

Variants of DSM14391 (SEQ ID NO: 14) subtilisin were evaluated for stability using methods described in Example 2, and performance index for each variant was calculated versus the parent molecule. The *B. gibsonii* subtilisin DSM14391 (previously described in SEQ ID NO:13 of patent application WO2018118917) shares high sequence homology with *B. gibsonii* subtilisin Bgi02446 (described previously as SEQ ID NO:11 of patent application WO2018118917) with 90% amino acid sequence identity.

Detergent stability results are reported as either performance index (PI) or % residual activity (% RA). Tables 17A and 17B show the stability results for DSM14391 variants having stability PI values 1.1 and greater, where the cleaning performance index was at least 0.5 or greater (relative to parent) in at least one cleaning assay. Due to conditions of the assay, in some instances the PI values calculated were very large (due to parent subtilisin activity being at level of detection), therefore PI values greater than 4.0 are shown as ≥4.0.

TABLE 17A

DSM14391 subtilisin variants with improved stability in liquid detergent at 36° C. (PI values ≥ 1.1) compared to DSM14391 parent

| DSM14391 Variant Sample ID | Substitutions in DSM14391 numbering | Substitutions in BPN' numbering | Stability PI |
|---|---|---|---|
| DSM14391-00436 | T003V | T003V | 1.2 |
| DSM14391-00091 | T009E | T009E | ≥4.0 |
| DSM14391-00382 | S024Q | S024Q | 1.2 |
| DSM14391-00475 | S039E | S040E | ≥4.0 |
| DSM14391-00098 | A067S | A069S | 1.5 |
| DSM14391-00189 | N074D | N076D | ≥4.0 |
| DSM14391-00257 | S076N | S078N | 2.6 |
| DSM14391-00286 | A128S | A130S | 1.4 |
| DSM14391-00409 | G160Q | G166Q | ≥4.0 |
| DSM14391-00289 | Q176E | Q182E | 3.3 |
| DSM14391-00248 | R179Q | R185Q | ≥4.0 |
| DSM14391-00202 | P212S | P218S | ≥4.0 |
| DSM14391-00058 | N242D | N248D | 1.2 |
| DSM14391-00504 | N253P | N259P | 1.5 |
| DSM14391-00016 | T003V-R179Q | T003V-R185Q | ≥4.0 |
| DSM14391-00025 | T003V-A067S | T003V-A069S | 2.2 |
| DSM14391-00028 | T003V-G160Q | T003V-G166Q | ≥4.0 |
| DSM14391-00063 | T003V-N253P | T003V-N259P | 2.1 |
| DSM14391-00340 | T003V-N074D | T003V-N076D | ≥4.0 |
| DSM14391-00373 | T003V-S076N | T003V-S078N | 3.0 |
| DSM14391-00492 | T003V-P212S | T003V-P218S | ≥4.0 |
| DSM14391-00217 | S039E-S076N | S040E-S078N | ≥4.0 |
| DSM14391-00005 | A067S-S076N | A069S-S078N | 3.4 |
| DSM14391-00096 | A067S-N253P | A069S-N259P | 2.5 |
| DSM14391-00136 | A067S-R179Q | A069S-R185Q | ≥4.0 |
| DSM14391-00432 | A067S-P212S | A069S-P218S | ≥4.0 |
| DSM14391-00494 | A067S-N074D | A069S-N076D | ≥4.0 |
| DSM14391-00007 | N074D-S076N | N076D-S078N | ≥4.0 |
| DSM14391-00168 | N074D-P212S | N076D-P218S | ≥4.0 |
| DSM14391-00230 | N074D-D127P | N076D-D129P | ≥4.0 |
| DSM14391-00104 | S076N-D127P | S078N-D129P | 3.0 |
| DSM14391-00113 | S076N-N253P | S078N-N259P | 3.7 |
| DSM14391-00147 | S076N-M122I | S078N-M124I | ≥4.0 |
| DSM14391-00252 | S076N-P212S | S078N-P218S | ≥4.0 |
| DSM14391-00302 | S076N-R179Q | S078N-R185Q | ≥4.0 |
| DSM14391-00335 | M122I-G160Q | M124I-G166Q | ≥4.0 |
| DSM14391-00355 | M122I-P212S | M124I-P218S | ≥4.0 |
| DSM14391-00507 | M122I-N253K | M124I-N259K | ≥4.0 |
| DSM14391-00021 | D127P-P212S | D129P-P218S | ≥4.0 |
| DSM14391-00122 | D127P-G160Q | D129P-G166Q | ≥4.0 |
| DSM14391-00367 | D127P-R179Q | D129P-R185Q | 1.3 |
| DSM14391-00438 | D127P-N253P | D129P-N259P | 2.3 |
| DSM14391-00171 | G160Q-R179Q | G166Q-R185Q | ≥4.0 |
| DSM14391-00430 | G160Q-N253P | G166Q-N259P | ≥4.0 |
| DSM14391-00161 | R179Q-P212S | R185Q-P218S | ≥4.0 |
| DSM14391-00203 | R179Q-N253P | R185Q-N259P | ≥4.0 |

TABLE 17B

DSM14391 subtilisin variants with improved stability in liquid detergent at 30° C. (reported as percent residual activity, % RA) compared to DSM14391 parent

| DSM14391 Variant Sample ID | Substitutions in DSM14391 numbering | Substitutions in BPN' numbering | % RA |
|---|---|---|---|
| DSM14391 | — | — | 40 |
| DSM14391-00986 | T003V-T009E | T003V-T009E | 80 |
| DSM14391-00987 | T003V-S039E | T003V-S040E | 74 |
| DSM14391-00863 | T009E-S039E | T009E-S040E | 98 |
| DSM14391-00864 | T009E-A067S | T009E-A069S | 86 |
| DSM14391-00839 | T009E-N074D | T009E-N076D | 91 |
| DSM14391-00962 | T009E-S076N | T009E-S078N | 84 |
| DSM14391-01005 | T009E-R179Q | T009E-R185Q | 94 |
| DSM14391-00971 | T009E-P212S | T009E-P218S | 99 |
| DSM14391-00867 | T009E-N253P | T009E-N259P | 76 |
| DSM14391-00968 | S039E-A067S | S040E-A069S | 71 |
| DSM14391-00969 | S039E-N074D | S040E-N076D | 83 |
| DSM14391-00985 | S039E-R179Q | S040E-R185Q | 96 |
| DSM14391-00977 | S039E-P212S | S040E-P218S | 95 |
| DSM14391-00849 | S039E-N253P | S040E-N259P | 72 |
| DSM14391-00974 | N074D-R179Q | N076D-R185Q | 100 |
| DSM14391-00976 | N074D-N253P | N076D-N259P | 84 |
| DSM14391-00828 | G160Q-P212S | G166Q-P218S | 96 |
| DSM14391-00844 | P212S-N253P | P218S-N259P | 96 |

Example 7

BspAI02518 Subtilisin Variants with Improved Stability in Detergent

Variants of BspAI02518 (SEQ ID NO: 16) subtilisin were evaluated for stability and cleaning performance using methods described in Example 2, and performance index for each variant was calculated versus the parent molecule. The BspAI02518 subtilisin was previously described as SEQ ID NO: 3 in WO2015089441 patent application, and is a member of the *B. akibai/clarkii* clade of subtilisins.

Detergent stability results are reported as either performance index (PI) or residual activity (% RA). Tables 18A and 18B show the stability results for BspAI02518 variants having stability PI values 1.1 and greater, where the cleaning performance index was at least 0.5 or greater (relative to parent) in at least one cleaning assay. Table 19 shows the cleaning assays results for BspAI02518 variants from Table 18A having cleaning performance PI values 1.0 or greater for at least one condition when compared to the parent subtilisin, and also displaying stability PI values 1.1 or greater. Due to conditions of the assay, in some instances the PI values calculated were very large (due to parent subtilisin activity being at level of detection), therefore PI values greater than 4.0 are shown as ≥4.0.

TABLE 18A

BspAI02518 subtilisin variants with improved stability in liquid detergent at 36° C. (PI values ≥ 1.1) compared to BspAI02518 parent

| BspAI02518 Variant Sample ID | Substitutions in BspAI02518 numbering | Substitutions in BPN' numbering | Stability PI |
|---|---|---|---|
| BspAI02518-00709 | S003V | S003V | 2.7 |
| BspAI02518-00637 | S009E | S009E | 2.3 |
| BspAI02518-00689 | N074D | N076D | ≥4.0 |
| BspAI02518-00585 | S076N | S078N | 2.8 |
| BspAI02518-00621 | M122I | M124I | 1.3 |
| BspAI02518-00941 | S176E | S182E | 2.2 |
| BspAI02518-00764 | N179Q | N185Q | 1.6 |
| BspAI02518-00819 | N212S | N218S | 3.5 |
| BspAI02518-00838 | N253P | N259P | 1.3 |
| BspAI02518-00506 | S003V-N253P | S003V-N259P | 2.6 |
| BspAI02518-00564 | S003V-N212S | S003V-N218S | ≥4.0 |
| BspAI02518-00599 | S003V-A067S | S003V-A069S | 1.9 |
| BspAI02518-00624 | S003V-N179Q | S003V-N185Q | 3.3 |
| BspAI02518-00664 | S003V-G126S | S003V-G128S | 2.2 |
| BspAI02518-00784 | S003V-M122I | S003V-M124I | 2.7 |
| BspAI02518-00897 | S003V-N074D | S003V-N076D | ≥4.0 |
| BspAI02518-00959 | S003V-S160Q | S003V-S166Q | ≥4.0 |
| BspAI02518-00405 | A067S-N212S | A069S-N218S | 3.1 |
| BspAI02518-00412 | A067S-N074D | A069S-N076D | ≥4.0 |
| BspAI02518-00590 | A067S-S076N | A069S-S078N | 2.2 |
| BspAI02518-00646 | A067S-N179Q | A069S-N185Q | 1.3 |
| BspAI02518-01025 | A067S-S160Q | A069S-S166Q | 2.7 |
| BspAI02518-00535 | N074D-N212S | N076D-N218S | ≥4.0 |
| BspAI02518-00695 | N074D-N253P | N076D-N259P | ≥4.0 |
| BspAI02518-00732 | N074D-G126S | N076D-G128S | ≥4.0 |
| BspAI02518-00772 | N074D-M122I | N076D-M124I | ≥4.0 |
| BspAI02518-00802 | N074D-N179Q | N076D-N185Q | ≥4.0 |
| BspAI02518-00814 | N074D-S076N | N076D-S078N | ≥4.0 |
| BspAI02518-00625 | S076N-M122I | S078N-M124I | 2.8 |
| BspAI02518-00800 | S076N-N212S | S078N-N218S | ≥4.0 |
| BspAI02518-00937 | S076N-N253P | S078N-N259P | 2.6 |
| BspAI02518-01001 | S076N-G126S | S078N-G128S | 2.7 |
| BspAI02518-01032 | S076N-N179Q | S078N-N185Q | 3.4 |
| BspAI02518-00594 | M122I-G126S | M124I-G128S | 1.9 |
| BspAI02518-00749 | M122I-S160Q | M124I-S166Q | 3.1 |
| BspAI02518-00758 | M122I-N179Q | M124I-N185Q | 1.5 |
| BspAI02518-01002 | S160Q-N212S | S166Q-N218S | ≥4.0 |

TABLE 18A-continued

BspAI02518 subtilisin variants with improved stability in liquid detergent at 36° C. (PI values ≥ 1.1) compared to BspAI02518 parent

| BspAI02518 Variant Sample ID | Substitutions in BspAI02518 numbering | Substitutions in BPN' numbering | Stability PI |
|---|---|---|---|
| BspAI02518-01006 | S160Q-N253P | S166Q-N259P | 3.3 |
| BspAI02518-00439 | N179Q-N253P | N185Q-N259P | 1.7 |
| BspAI02518-00548 | N212S-N253P | N218S-N259P | 4.0 |

TABLE 18B

BspAI02518 subtilisin variants with improved stability in liquid detergent at 30° C. (reported as percent residual activity, % RA) compared to BspAI02518 parent

| BspAI02518 Variant Sample ID | Substitutions in BspAI02518 numbering | Substitutions in BPN' numbering | % RA |
|---|---|---|---|
| BspAI02518 | — | — | 32 |
| BspAI02518-01177 | S160Q | S166Q | 59 |
| BspAI02518-01175 | S003V-S009E | S003V-S009E | 70 |
| BspAI02518-01179 | S003V-S076N | S003V-S078N | 62 |
| BspAI02518-01676 | S009E-A067S | S009E-A069S | 45 |
| BspAI02518-01178 | S009E-N074D | S009E-N076D | 82 |
| BspAI02518-01186 | S009E-S076N | S009E-S078N | 68 |
| BspAI02518-01991 | S009E-S160Q | S009E-S166Q | 78 |
| BspAI02518-01187 | S009E-N179Q | S009E-N185Q | 60 |
| BspAI02518-01811 | S009E-N212S | S009E-N218S | 84 |
| BspAI02518-02004 | S009E-N253P | S009E-N259P | 56 |
| BspAI02518-01920 | A067S-N253P | A069S-N259P | 34 |
| BspAI02518-01184 | N074D-S160Q | N076D-S166Q | 86 |
| BspAI02518-01190 | S076N-S160Q | S078N-S166Q | 67 |
| BspAI02518-02195 | S160Q-N179Q | S166Q-N185Q | 64 |
| BspAI02518-01094 | N179Q-N212S | N185Q-N218S | 73 |

TABLE 19

BspAI02518 variants with cleaning performance on par or improved compared to BspAI02518 parent

| BspAI02518 Variant Sample ID | Cleaning performance PIs: BMI stain in PNB detergent | PAS-38 stain in GSM-B detergent | BMI stain in ECE-2 detergent |
|---|---|---|---|
| BspAI02518-00709 | 1.1 | 1.0 | 1.0 |
| BspAI02518-00637 | 1.4 | 2.5 | 1.4 |
| BspAI02518-00689 | 1.0 | 1.0 | 0.8 |
| BspAI02518-00585 | 1.1 | 1.2 | 1.1 |
| BspAI02518-00621 | 1.0 | 1.2 | 1.1 |
| BspAI02518-00941 | 0.9 | 1.0 | 0.8 |
| BspAI02518-00764 | 0.9 | 1.2 | 1.1 |
| BspAI02518-00819 | 1.0 | 1.0 | 0.9 |
| BspAI02518-00838 | 1.1 | 1.0 | 1.0 |
| BspAI02518-00506 | 1.0 | 1.0 | 0.8 |
| BspAI02518-00564 | 1.0 | 0.9 | 1.0 |
| BspAI02518-00599 | 1.4 | 2.4 | 1.3 |
| BspAI02518-00624 | 1.1 | 1.6 | 1.1 |
| BspAI02518-00664 | 1.1 | 1.0 | 0.9 |
| BspAI02518-00784 | 1.0 | 1.0 | 0.9 |
| BspAI02518-00897 | 1.1 | 1.0 | 0.8 |
| BspAI02518-00959 | 1.0 | 1.3 | 1.3 |
| BspAI02518-00405 | 0.9 | 1.0 | 0.8 |
| BspAI02518-00412 | 1.1 | 2.5 | 1.4 |
| BspAI02518-00590 | 1.2 | 2.8 | 1.3 |
| BspAI02518-00646 | 1.0 | 2.0 | 1.0 |
| BspAI02518-01025 | 1.4 | 2.8 | 2.4 |
| BspAI02518-00695 | 1.0 | 1.0 | 0.8 |
| BspAI02518-00732 | 1.4 | 3.0 | 1.6 |
| BspAI02518-00772 | 1.0 | 1.0 | 0.9 |
| BspAI02518-00802 | 1.3 | 6.1 | 2.4 |

TABLE 19-continued

BspAI02518 variants with cleaning performance on par or improved compared to BspAI02518 parent

| BspAI02518 Variant Sample ID | Cleaning performance PIs<br>BMI stain in PNB detergent | PAS-38 stain in GSM-B detergent | BMI stain in ECE-2 detergent |
|---|---|---|---|
| BspAI02518-00814 | 1.1 | 1.1 | 1.0 |
| BspAI02518-00625 | 1.0 | 1.0 | 0.9 |
| BspAI02518-00800 | 0.9 | 1.0 | 0.9 |
| BspAI02518-01001 | 1.3 | 1.4 | 1.4 |
| BspAI02518-01032 | 1.3 | 1.7 | 1.3 |
| BspAI02518-00594 | 1.0 | 1.0 | 0.6 |
| BspAI02518-00749 | 1.0 | 1.0 | 0.8 |
| BspAI02518-00758 | 1.2 | 1.4 | 1.2 |
| BspAI02518-01002 | 1.1 | 1.0 | 1.0 |
| BspAI02518-00439 | 1.0 | 1.0 | 0.9 |

Example 8

Bad02409 Subtilisin Variants with Improved Stability in Detergent

Variants of Bad02409 (SEQ ID NO: 18) subtilisin were evaluated for stability and cleaning performance using methods described in Example 2, and performance index for each variant was calculated versus the parent molecule.

Table 20 shows the stability results for Bad02409 variants having stability PI values 1.1 and greater, where the cleaning performance index was at least 0.5 or greater (relative to parent) in at least one cleaning assay. Table 21 shows the cleaning assays results for Bad02409 variants having cleaning performance PI values 1.0 or greater for at least one condition when compared to the parent subtilisin, and also displaying stability PI values 1.1 or greater.

TABLE 20

Bad02409 subtilisin variants with improved stability in liquid detergent at 67° C. (PI values ≥ 1.1) compared to Bad02409 parent

| Bad02409 Variant Sample ID | Substitutions in Bad02409 numbering | Substitutions in BPN' numbering | Stability PI |
|---|---|---|---|
| Bad02409-00124 | N078D | N076D | 2.2 |
| Bad02409-00592 | S080N | S078N | 1.5 |
| Bad02409-00355 | G130S | G128S | 1.2 |
| Bad02409-00369 | S185E | S182E | 1.5 |
| Bad02409-00046 | T003V-N221S | T003V-N218S | 1.9 |
| Bad02409-00328 | T003V-A071S | T003V-A069S | 1.8 |
| Bad02409-00360 | T003V-D262P | T003V-D259P | 2.3 |
| Bad02409-00398 | T003V-M126I | T003V-M124I | 2.4 |
| Bad02409-00449 | T003V-N078D | T003V-N076D | 2.8 |
| Bad02409-00462 | T003V-N188Q | T003V-N185Q | 1.4 |
| Bad02409-00543 | T003V-G169Q | T003V-G166Q | 2.0 |
| Bad02409-00583 | T003V-S080N | T003V-S078N | 2.0 |
| Bad02409-00634 | T003V-S131P | T003V-S129P | 1.7 |
| Bad02409-00262 | A071S-S131P | A069S-S129P | 1.1 |
| Bad02409-00388 | A071S-G169Q | A069S-G166Q | 2.1 |
| Bad02409-00394 | A071S-N078D | A069S-N076D | 2.4 |
| Bad02409-00574 | A071S-S080N | A069S-S078N | 1.9 |
| Bad02409-00077 | N078D-S131P | N076D-S129P | 3.0 |
| Bad02409-00566 | S080N-N188Q | S078N-N185Q | 2.0 |
| Bad02409-00564 | M126I-S131P | M124I-S129P | 1.2 |
| Bad02409-00458 | S131P-D262P | S129P-D259P | 1.6 |
| Bad02409-00567 | S131P-G169Q | S129P-G166Q | 1.7 |
| Bad02409-00156 | G169Q-N221S | G166Q-N218S | 1.2 |

TABLE 21

Bad02409 variants with cleaning performance on par or improved compared to Bad02409 parent

| Bad02409 Variant Sample ID | Cleaning performance PI<br>BMI stain in PNB detergent | PAS-38 stain In GSM-B detergent |
|---|---|---|
| Bad02409-00124 | 1.2 | 1.1 |
| Bad02409-00592 | 1.1 | 1.0 |
| Bad02409-00355 | 1.3 | 1.0 |
| Bad02409-00369 | 1.0 | 1.0 |
| Bad02409-00046 | 1.0 | 1.0 |
| Bad02409-00328 | 1.0 | 1.0 |
| Bad02409-00360 | 1.2 | 1.1 |
| Bad02409-00398 | 1.2 | 1.0 |
| Bad02409-00449 | 0.9 | 1.1 |
| Bad02409-00462 | 1.1 | 1.1 |
| Bad02409-00543 | 1.5 | 0.9 |
| Bad02409-00583 | 1.0 | 1.0 |
| Bad02409-00634 | 0.9 | 1.2 |
| Bad02409-00262 | 1.1 | 1.1 |
| Bad02409-00388 | 1.2 | 1.0 |
| Bad02409-00394 | 1.0 | 1.0 |
| Bad02409-00574 | 1.0 | 1.0 |
| Bad02409-00077 | 1.0 | 0.8 |
| Bad02409-00566 | 0.9 | 1.1 |
| Bad02409-00564 | 1.1 | 0.9 |
| Bad02409-00458 | 0.8 | 1.2 |
| Bad02409-00567 | 0.8 | 1.0 |
| Bad02409-00156 | 1.6 | 1.0 |

Example 9

Bba02069 Subtilisin Variants with Improved Stability in Detergent

Variants of Bba02069 (SEQ ID NO: 19) subtilisin were evaluated for stability and cleaning performance using methods described in Example 2, and performance index for each variant was calculated versus the parent molecule. The Bba02069 subtilisin was previously described as SEQ ID NO:3 in WO 2016/061438 patent application, and is a member of the *B. agaradhaerens* clade of subtilisins.

Detergent stability results are reported as either performance index (PI) or residual activity (% RA). Tables 22A and 22B show the stability results for Bba02069 variants having stability PI values 1.1 and greater, where the cleaning performance index was at least 0.5 or greater (relative to parent) in at least one cleaning assay. The stability data shown on Table 22 was collected in two separate experiments, and PI values for certain variants evaluated on both occasions showed varying degree of improvements, as can be expected due to assay to assay fluctuations. Table 23 shows the cleaning assays results for Bba02069 variants from Table 22A having cleaning performance PI values 1.0 or greater for at least one condition when compared to the parent subtilisin, and also displaying stability PI values 1.1 or greater.

TABLE 22A

Bba02069 subtilisin variants with improved stability in liquid detergent at 40° C. (PI values ≥ 1.1) compared to Bba02069 parent

| Bba02069 Variant Sample ID | Substitutions in Bba02069 numbering | Substitutions in BPN' numbering | Stability PI |
|---|---|---|---|
| Bba02069-00641 | S129P | S129P | 1.3 |
| Bba02069-00642 | G118R | G118R | 1.5 |

TABLE 22A-continued

Bba02069 subtilisin variants with improved stability in liquid detergent at 40° C. (PI values ≥ 1.1) compared to Bba02069 parent

| Bba02069 Variant Sample ID | Substitutions in Bba02069 numbering | Substitutions in BPN' numbering | Stability PI |
|---|---|---|---|
| Bba02069-00643 | Q087D | Q087D | 1.5 |
| Bba02069-00644 | N076D | N076D | 3.2 |
| Bba02069-00646 | M124I | M124I | 2.6 |
| Bba02069-00647 | Q249D | Q248D | 1.4 |
| Bba02069-00648 | A069S | A069S | 1.9 |
| Bba02069-00649 | G128S | G128S | 1.5 |
| Bba02069-00650 | N024Q | N024Q | 1.1 |
| Bba02069-00652 | Q003V | Q003V | 2.0 |
| Bba02069-00653 | P040E | P040E | 1.3 |
| Bba02069-00654 | T009E | T009E | 2.3 |
| Bba02069-00655 | N219S | N218S | 3.1 |
| Bba02069-00111 | G167Q | G166Q | 2.0 |
| Bba02069-00217 | S260P | S259P | 1.7 |
| Bba02069-00030 | Q003V-A069S | Q003V-A069S | 2.0 |
| Bba02069-00121 | Q003V-V186Q | Q003V-V185Q | 2.0 |
| Bba02069-00203 | Q003V-S129P | Q003V-S129P | 2.0 |
| Bba02069-00291 | Q003V-M124I | Q003V-M124I | 2.8 |
| Bba02069-00347 | Q003V-G167Q | Q003V-G166Q | 3.9 |
| Bba02069-00400 | Q003V-G128S | Q003V-G128S | 2.4 |
| Bba02069-00477 | Q003V-S260P | Q003V-S259P | 3.2 |
| Bba02069-00564 | Q003V-N076D | Q003V-N076D | 2.4 |
| Bba02069-00377 | P040E-V186Q | P040E-V185Q | 1.8 |
| Bba02069-00499 | P040E-G167Q | P040E-G166Q | 3.1 |
| Bba02069-00007 | A069S-G128S | A069S-G128S | 1.8 |
| Bba02069-00114 | A069S-S260P | A069S-S259P | 2.1 |
| Bba02069-00116 | A069S-M124I | A069S-M124I | 2.2 |
| Bba02069-00505 | A069S-G167Q | A069S-G166Q | 2.5 |
| Bba02069-00518 | A069S-N076D | A069S-N076D | 3.0 |
| Bba02069-00118 | N076D-G128S | N076D-G128S | 2.4 |
| Bba02069-00247 | N076D-G167Q | N076D-G166Q | 3.0 |
| Bba02069-00281 | N076D-M124I | N076D-M124I | 3.1 |
| Bba02069-00423 | N076D-S260P | N076D-S259P | 2.5 |
| Bba02069-00473 | N076D-S129P | N076D-S129P | 3.2 |
| Bba02069-00037 | M124I-G128S | M124I-G128S | 1.9 |
| Bba02069-00254 | M124I-V186Q | M124I-V185Q | 1.8 |
| Bba02069-00390 | M124I-S129P | M124I-S129P | 2.3 |
| Bba02069-00461 | M124I-S260P | M124I-S259P | 3.2 |
| Bba02069-00465 | M124I-G167Q | M124I-G166Q | 2.7 |
| Bba02069-00568 | M124I-N219S | M124I-N218S | 3.3 |
| Bba02069-00223 | G128S-S129P | G128S-S129P | 1.5 |
| Bba02069-00399 | G128S-G167Q | G128S-G166Q | 2.6 |
| Bba02069-00429 | G128S-S260P | G128S-S259P | 2.4 |
| Bba02069-00483 | G128S-V186Q | G128S-V185Q | 1.6 |
| Bba02069-00008 | S129P-G167Q | S129P-G166Q | 2.1 |
| Bba02069-00133 | S129P-V186Q | S129P-V185Q | 1.4 |
| Bba02069-00274 | S129P-S260P | S129P-S259P | 1.8 |
| Bba02069-00043 | G167Q-S260P | G166Q-S259P | 2.6 |
| Bba02069-00190 | G167Q-V186Q | G166Q-V185Q | 2.1 |
| Bba02069-00005 | V186Q-S260P | V185Q-S259P | 2.1 |
| Bba02069-00493 | V186Q-N219S | V185Q-N218S | 1.6 |
| Bba02069-00051 | N219S-S260P | N218S-S259P | 1.9 |

TABLE 22B

Bba02069 subtilisin variants with improved stability in liquid detergent at 39° C. (reported as percent residual activity, % RA) compared to Bba02069 parent

| Bba02069 Variant Sample ID | Substitutions in Bba02069 numbering | Substitutions in BPN' numbering | % RA |
|---|---|---|---|
| Bba02069 | — | — | 23 |
| Bba02069-00854 | Q003V-T009E | Q003V-T009E | 87 |
| Bba02069-00855 | Q003V-P040E | Q003V-P040E | 56 |
| Bba02069-00856 | Q003V-N219S | Q003V-N218S | 74 |
| Bba02069-00755 | T009E-P040E | T009E-P040E | 72 |
| Bba02069-00756 | T009E-A069S | T009E-A069S | 70 |
| Bba02069-00757 | T009E-N076D | T009E-N076D | 100 |
| Bba02069-00871 | T009E-G167Q | T009E-G166Q | 76 |

TABLE 22B-continued

Bba02069 subtilisin variants with improved stability in liquid detergent at 39° C. (reported as percent residual activity, % RA) compared to Bba02069 parent

| Bba02069 Variant Sample ID | Substitutions in Bba02069 numbering | Substitutions in BPN' numbering | % RA |
|---|---|---|---|
| Bba02069-00866 | T009E-V186Q | T009E-V185Q | 67 |
| Bba02069-00865 | T009E-N219S | T009E-N218S | 84 |
| Bba02069-00758 | T009E-S260P | T009E-S259P | 90 |
| Bba02069-00863 | P040E-A069S | P040E-A069S | 41 |
| Bba02069-00824 | P040E-N076D | P040E-N076D | 77 |
| Bba02069-01952 | P040E-N219S | P040E-N218S | 59 |
| Bba02069-00845 | P040E-S260P | P040E-S259P | 64 |
| Bba02069-00844 | A069S-V186Q | A069S-V185Q | 31 |
| Bba02069-00736 | A069S-N219S | A069S-N218S | 61 |
| Bba02069-00822 | N076D-V186Q | N076D-V185Q | 74 |
| Bba02069-00815 | N076D-N219S | N076D-N218S | 80 |
| Bba02069-00817 | G167Q-N219S | G166Q-N218S | 68 |

TABLE 23

Bba02069 variants with cleaning performance on par or improved compared to Bba02069 parent

| Bba02069 Variant Sample ID | Cleaning performance PI | | |
|---|---|---|---|
| | BMI in PNB detergent | PAS-38 in GSM-B detergent | BMI in ECE-2 detergent |
| Bba02069-00111 | 0.8 | 1.0 | 0.9 |
| Bba02069-00217 | 1.0 | 0.9 | 0.9 |
| Bba02069-00121 | 0.8 | 1.0 | 1.0 |
| Bba02069-00203 | 1.1 | 1.1 | 1.0 |
| Bba02069-00291 | 0.7 | 1.4 | 0.8 |
| Bba02069-00400 | 0.7 | 1.0 | 0.8 |
| Bba02069-00377 | 1.2 | 1.0 | 0.8 |
| Bba02069-00499 | 1.0 | 0.9 | 0.8 |
| Bba02069-00114 | 1.1 | 0.9 | 1.1 |
| Bba02069-00116 | 0.9 | 1.3 | 0.9 |
| Bba02069-00505 | 1.0 | 0.8 | 0.9 |
| Bba02069-00518 | 1.1 | 0.9 | 0.8 |
| Bba02069-00118 | 1.1 | 1.0 | 1.0 |
| Bba02069-00247 | 1.1 | 0.9 | 0.8 |
| Bba02069-00281 | 1.5 | 1.1 | 0.7 |
| Bba02069-00423 | 1.1 | 0.8 | 1.1 |
| Bba02069-00473 | 1.2 | 0.9 | 1.2 |
| Bba02069-00037 | 1.3 | 1.2 | 0.8 |
| Bba02069-00254 | 1.1 | 1.2 | 0.7 |
| Bba02069-00390 | 0.7 | 1.2 | 0.8 |
| Bba02069-00461 | 0.9 | 1.1 | 0.9 |
| Bba02069-00465 | 1.0 | 1.0 | 0.7 |
| Bba02069-00568 | 0.9 | 1.1 | 0.6 |
| Bba02069-00223 | 1.0 | 1.0 | 1.0 |
| Bba02069-00399 | 1.0 | 0.9 | 0.8 |
| Bba02069-00429 | 0.7 | 1.0 | 0.8 |
| Bba02069-00483 | 0.9 | 0.9 | 1.0 |
| Bba02069-00133 | 1.1 | 0.9 | 1.0 |
| Bba02069-00274 | 1.2 | 1.0 | 1.2 |
| Bba02069-00043 | 1.0 | 0.8 | 0.9 |
| Bba02069-00190 | 0.8 | 1.0 | 0.9 |

Example 10

BspZ00056 Subtilisin Variants with Improved Stability in Detergent

Variants of BspZ00056 (SEQ ID NO: 17) subtilisin were evaluated for stability and cleaning performance using methods described in Example 2, and performance index for each variant was calculated versus the parent molecule. The BspZ00056 subtilisin was previously described as SEQ ID NO: 9 in WO 2016/069544 patent application, and is a member of the BspAP02013 clade of subtilisins.

Detergent stability results are reported as either performance index (PI) or residual activity (% RA). Tables 24A and 24B show the stability results for BspZ00056 variants having stability PI values 1.1 and greater, where the cleaning performance index was at least 0.5 or greater (relative to parent) in at least one cleaning assay. Table 25 shows the cleaning assays results for BspZ00056 variants from Table 24A having cleaning performance PI values 1.0 or greater for at least one condition when compared to the parent subtilisin, and also displaying stability PI values 1.1 or greater. PI values of less than 0.5 are denoted as <0.5.

TABLE 24A

BspZ00056 subtilisin variants with improved stability in liquid detergent at 63° C. (PI values > 1.1) compared to BspZ00056 parent

| BspZ00056 Variant Sample ID | Substitutions in BspZ00056 numbering | Substitutions in BPN' numbering | Stability PI |
|---|---|---|---|
| BspZ00056-00354 | Q187E | Q182E | 1.2 |
| BspZ00056-00177 | G132S | G128S | 1.7 |
| BspZ00056-00408 | E149R | E145R | 1.5 |
| BspZ00056-00191 | M128I | M124I | 1.7 |
| BspZ00056-00248 | N223S | N218S | 1.1 |
| BspZ00056-00380 | S133P | S129P | 1.5 |
| BspZ00056-00022 | G132S-S133P | G128S-S129P | 1.5 |
| BspZ00056-00005 | G132S-N223S | G128S-N218S | 1.9 |
| BspZ00056-00042 | A073S-N190Q | A069S-N185Q | 1.1 |
| BspZ00056-00490 | A073S-D082N | A069S-D078N | 1.2 |
| BspZ00056-00297 | D082N-G171Q | D078N-G166Q | 1.5 |
| BspZ00056-00257 | G171Q-N190Q | G166Q-N185Q | 2.0 |
| BspZ00056-00357 | T003V-M128I | T003V-M124I | 2.1 |
| BspZ00056-00294 | G132S-N190Q | G128S-N185Q | 1.5 |
| BspZ00056-00492 | A073S-G132S | A069S-G128S | 2.0 |
| BspZ00056-00259 | M128I-N190Q | M124I-N185Q | 1.8 |
| BspZ00056-00133 | G171Q-G264P | G166Q-G259P | 2.1 |
| BspZ00056-00151 | A073S-G264P | A069S-G259P | 1.9 |
| BspZ00056-00288 | S133P-G171Q | S129P-G166Q | 2.1 |
| BspZ00056-00384 | T003V-G264P | T003V-G259P | 2.1 |
| BspZ00056-00116 | T003V-N190Q | T003V-N185Q | 1.1 |
| BspZ00056-00088 | D082N-G264P | D078N-G259P | 1.7 |
| BspZ00056-00092 | M128I-N223S | M124I-N218S | 1.8 |
| BspZ00056-00451 | G132S-G171Q | G128S-G166Q | 2.1 |
| BspZ00056-00324 | A073S-M128I | A069S-M124I | 2.2 |
| BspZ00056-00207 | S133P-N190Q | S129P-N185Q | 1.4 |
| BspZ00056-00135 | G132S-G264P | G128S-G259P | 2.2 |
| BspZ00056-00221 | T003V-G171Q | T003V-G166Q | 2.1 |
| BspZ00056-00359 | T003V-G132S | T003V-G128S | 1.8 |
| BspZ00056-00094 | T003V-A073S | T003V-A069S | 1.2 |
| BspZ00056-00422 | M128I-G171Q | M124I-G166Q | 2.2 |
| BspZ00056-00429 | M128I-S133P | M124I-S129P | 2.0 |
| BspZ00056-00491 | N223S-G264P | N218S-G259P | 1.9 |
| BspZ00056-00377 | N190Q-G264P | N185Q-G259P | 1.9 |
| BspZ00056-00399 | D082N-S133P | D078N-S129P | 1.1 |
| BspZ00056-00201 | M128I-G132S | M124I-G128S | 1.7 |
| BspZ00056-00368 | T003V-N223S | T003V-N218S | 1.4 |
| BspZ00056-00389 | A073S-G171Q | A069S-G166Q | 2.2 |

TABLE 24B

BspZ00056 subtilisin variants with improved stability in liquid detergent at 64° C. (reported as percent residual activity, % RA) compared to BspZ00056 parent

| BspZ00056 Variant Sample ID | Substitutions in BspZ00056 numbering | Substitutions in BPN' numbering | % RA |
|---|---|---|---|
| BspZ00056 | — | — | 30 |
| BspZ00056-00876 | T003V | T003V | 35 |
| BspZ00056-01485 | P009E | P009E | 33 |
| BspZ00056-00863 | A073S | A069S | 42 |

TABLE 24B-continued

BspZ00056 subtilisin variants with improved stability in liquid detergent at 64° C. (reported as percent residual activity, % RA) compared to BspZ00056 parent

| BspZ00056 Variant Sample ID | Substitutions in BspZ00056 numbering | Substitutions in BPN' numbering | % RA |
|---|---|---|---|
| BspZ00056-00864 | G171Q | G166Q | 69 |
| BspZ00056-00663 | N190Q | N185Q | 38 |
| BspZ00056-00819 | G264P | G259P | 80 |
| BspZ00056-01478 | P009E-G171Q | P009E-G166Q | 69 |
| BspZ00056-00875 | P009E-G264P | P009E-G259P | 83 |
| BspZ00056-00873 | A073S-N223S | A069S-N218S | 44 |
| BspZ00056-00837 | G171Q-N223S | G166Q-N218S | 80 |
| BspZ00056-01030 | N190Q-N223S | N185Q-N218S | 35 |

TABLE 25

BspZ00056 variants with performance on par or improved compared to BspZ00056 parent

| BspZ00056 Variant Sample ID | Cleaning performance PI | |
|---|---|---|
| | BMI stain in PNB detergent | PAS-38 stain in GSM-B detergent |
| BspZ00056-00354 | 1.1 | 0.8 |
| BspZ00056-00022 | 1.2 | 0.9 |
| BspZ00056-00005 | 1.2 | 0.9 |
| BspZ00056-00042 | 1.1 | 0.7 |
| BspZ00056-00490 | 1.1 | 0.9 |
| BspZ00056-00297 | 1.0 | 1.4 |
| BspZ00056-00257 | 1.0 | 1.3 |
| BspZ00056-00357 | 1.0 | <0.5 |
| BspZ00056-00294 | 1.0 | 0.9 |
| BspZ00056-00492 | 1.0 | 0.5 |
| BspZ00056-00133 | 1.0 | 1.4 |
| BspZ00056-00288 | 0.9 | 1.2 |
| BspZ00056-00088 | 0.9 | 1.0 |
| BspZ00056-00451 | 0.8 | 1.2 |
| BspZ00056-00207 | 0.9 | 1.1 |
| BspZ00056-00221 | 0.9 | 1.4 |
| BspZ00056-00389 | 0.6 | 1.0 |

Example 11

BspAK01305 Subtilisin Variants with Improved Stability in Detergent

Variants of BspAK01305 (SEQ ID NO: 15) subtilisin were evaluated for stability and cleaning performance using methods described in Example 2, and performance index for each variant was calculated versus the parent molecule. The BspAK01305 subtilisin was previously described as SEQ ID NO:6 in WO 2016/069569 patent application, and is a member of the BspAL03279 clade of subtilisins.

Table 26 shows the stability results for BspAK01305 variants having stability PI values 1.1 and greater, where the cleaning performance index was at least 0.5 or greater (relative to parent) in at least one cleaning assay. Table 27 shows the cleaning assays results for BspAK01305 variants having cleaning performance PI values 1.0 or greater for at least one condition when compared to the parent subtilisin, and also displaying stability PI values 1.1 or greater.

TABLE 26

| BspAK01305 subtilisin variants with improved stability in liquid detergent at 47° C. (PI values ≥ 1.1) compared to BspAK01305 parent | | | |
|---|---|---|---|
| BspAK01305 Variant Sample ID | Substitutions in BspAK01305 numbering | Substitutions in BPN' numbering | Stability PI |
| BspAK01305-00530 | S003V | S003V | 1.5 |
| BspAK01305-00444 | S039E | S040E | 1.5 |
| BspAK01305-00325 | G160Q | G166Q | 1.7 |
| BspAK01305-00495 | S179Q | S185Q | 1.4 |
| BspAK01305-00060 | P204I | P210I | 1.9 |
| BspAK01305-00509 | S003V-S179Q | S003V-S185Q | 1.9 |
| BspAK01305-00514 | S003V-G160Q | S003V-G166Q | 1.7 |
| BspAK01305-00538 | S003V-R256L | S003V-R262L | 1.5 |
| BspAK01305-00564 | S003V-S039E | S003V-S040E | 1.7 |
| BspAK01305-00027 | S039E-G160Q | S040E-G166Q | 2.3 |
| BspAK01305-00264 | S039E-S179Q | S040E-S185Q | 1.8 |
| BspAK01305-00316 | G160Q-S179Q | G166Q-S185Q | 2.2 |

TABLE 27

| BspAK01305 variants with performance on par or improved compared to BspAK01305 parent | | |
|---|---|---|
| | Cleaning performance PI | |
| BspAK01305 Variant Sample ID | BMI stain in PNB detergent | PAS-38 stain in GSM-B detergent |
| BspAK01305-00530 | 0.9 | 1.1 |
| BspAK01305-00444 | 0.9 | 1.5 |
| BspAK01305-00325 | 1.1 | 2.2 |
| BspAK01305-00060 | 1.1 | 1.1 |
| BspAK01305-00514 | 0.9 | 1.8 |
| BspAK01305-00564 | 1.3 | 1.2 |
| BspAK01305-00027 | 0.6 | 1.0 |
| BspAK01305-00264 | 1.0 | 0.9 |
| BspAK01305-00316 | 0.6 | 1.2 |

Example 12

Sequence Comparison and Structural Features of Subtilisin Sites Providing Enhanced Stability A multiple sequence alignment of the mature (in some cases predicted) polypeptide regions of the subtilisin backbones evaluated in this study, as well as other subtilisins was generated using the following sequences: AprE (subtilisin E, SEQ ID NO:8); WP_082194748 (SEQ ID NO: 9); Chemgen_164A (SEQ ID NO:10); CP474 (SEQ ID NO:11); ZP-00454 (SEQ ID NO:12); Bpan01744 (SEQ ID NO:13); DSM14391 (SEQ ID NO:14); BspAK01305 (SEQ ID NO:15); BspAI02518 (SEQ ID NO:16); BspZ00056 (SEQ ID NO:17); Bad02409 (SEQ ID NO:18); Bba02069 (SEQ ID NO:19); BspZ00258 (SEQ ID NO:22); BPN' (SEQ ID NO:1); *B. licheniformis* AprL (SEQ ID NO:2); *B. lentus* GG36 (SEQ ID NO:3); *B. gibsonii* Bgi02446 (SEQ ID NO:4); and *Bacillus* sp LG12 (SEQ ID NO:6). The multiple protein sequence alignments, shown in Table 28, were generated using structural (main chain) alignments from available protein crystal structures and amino acid sequence homology to guide positioning of loops in the sequences, and using BPN' numbering (as assigned to all variants in this application, and used in the Examples above). Positions where insertions would occur using BPN' sequence as a reference are numbered according to BPN' and a suffix (example: position 42, 42a, 42b). The alignments shown correspond to residues 1-275 of BPN', and additional C-terminal residues in some subtilisin backbones are not shown. An empty cell corresponds to a position where no amino acid can be assigned for that particular subtilisin sequence. The subtilisins on Table 28 with an asterisk (*) denote backbones not evaluated in this study, and shown here for reference.

TABLE 28

| Structure-based multiple sequence alignment of various subtilisins. | | | | | | | | | |
|---|---|---|---|---|---|---|---|---|---|
| BPN' numbering | *BPN' | AprE | WP_082194748 | *AprL | *LG12 | Chemgen_164A | CP474 | ZP-00454 | *GG36 |
| 1 | A | A | A | A | A | A | A | A | A |
| 2 | Q | Q | Q | Q | Q | Q | Q | Q | Q |
| 3 | S | S | T | T | T | T | T | V | S |
| 4 | V | V | V | V | V | T | V | V | V |
| 5 | P | P | P | P | P | P | P | P | P |
| 6 | Y | Y | Y | Y | W | W | W | W | W |
| 7 | G | G | G | G | G | G | G | G | G |
| 8 | V | I | I | I | I | I | I | I | I |
| 9 | S | S | P | P | P | T | P | P | S |
| 10 | Q | Q | Q | L | H | H | H | H | R |
| 11 | I | I | I | I | I | I | I | I | V |
| 12 | K | K | K | K | K | N | K | K | Q |
| 13 | A | A | A | A | A | A | A | A | A |
| 14 | P | P | P | D | D | H | D | D | P |

TABLE 28-continued

| Structure-based multiple sequence alignment of various subtilisins. | | | | | | | | | |
|---|---|---|---|---|---|---|---|---|---|
| 15 | A | A | A | K | K | K | K | K | A |
| 16 | L | L | V | V | A | A | A | A | A |
| 17 | H | H | H | Q | H | H | H | H | H |
| 17a | | | | | | | | | |
| 18 | S | S | A | A | A | S | A | A | N |
| 19 | Q | Q | Q | Q | A | S | A | S | R |
| 20 | G | G | G | G | G | S | G | G | G |
| 21 | Y | Y | Y | F | V | V | V | V | L |
| 22 | T | T | K | K | T | T | T | T | T |
| 23 | G | G | G | G | G | G | G | G | G |
| 24 | S | S | A | A | S | S | S | S | S |
| 25 | N | N | N | N | G | G | G | G | G |
| 26 | V | V | V | V | V | V | V | V | V |
| 27 | K | K | K | K | K | K | K | K | K |
| 28 | V | V | V | V | V | V | V | V | V |
| 29 | A | A | A | A | A | A | A | A | A |
| 30 | V | V | V | V | I | V | I | V | V |
| 31 | L | L | L | L | L | L | L | L | L |
| 32 | D | D | D | D | D | D | D | D | D |
| 33 | S | S | T | T | T | T | T | T | T |
| 34 | G | G | G | G | G | G | G | G | G |
| 35 | I | I | I | I | I | I | I | I | I |
| 36 | D | D | H | Q | D | D | D | D | S |
| 37 | S | S | A | A | A | A | A | A | |
| 38 | S | S | A | S | N | S | N | N | T |
| 39 | H | H | H | H | H | H | H | H | H |
| 40 | P | P | P | P | A | P | A | A | P |
| 41 | D | D | D | D | D | D | D | D | D |
| 42 | L | L | L | L | L | L | L | L | L |
| 42a | | | | | | | | | |
| 42b | | | | | | | | | |
| 43 | K | N | N | N | N | N | N | N | N |
| 44 | V | V | V | V | V | V | V | V | I |
| 45 | A | R | A | V | K | K | K | K | R |
| 46 | G | G | G | G | G | G | G | G | G |
| 47 | G | G | G | G | G | G | G | G | G |
| 48 | A | A | A | A | A | A | A | A | A |
| 49 | S | S | S | S | S | S | S | S | S |
| 50 | M | F | F | F | F | F | F | F | F |

TABLE 28-continued

Structure-based multiple sequence alignment of various subtilisins.

| | | | | | | | | | |
|---|---|---|---|---|---|---|---|---|---|
| 51 | V | V | V | V | V | I | V | V | V |
| 52 | P | P | P | A | S | S | A | S | P |
| 53 | S | S | S | G | G | G | G | G | G |
| 54 | E | E | E | E | E | E | E | E | E |
| 55 | T | T | P | | P | P | P | P | P |
| 56 | N | N | N | A | N | N | N | N | S |
| 56a | | | | | | | | | |
| 56b | | | | | | | | | |
| 57 | P | P | A | Y | A | A | A | A | |
| 58 | F | Y | T | N | L | L | L | L | T |
| 59 | Q | Q | Q | T | Q | V | Q | Q | Q |
| 60 | D | D | D | D | D | D | D | D | D |
| 61 | N | G | F | G | G | T | G | G | G |
| 62 | N | S | Q | N | N | N | N | N | N |
| 63 | S | S | S | G | G | G | G | G | G |
| 64 | H | H | H | H | H | H | H | H | H |
| 65 | G | G | G | G | G | G | G | G | G |
| 66 | T | T | T | T | T | T | T | T | T |
| 67 | H | H | H | H | H | H | H | H | H |
| 68 | V | V | V | V | V | V | V | V | V |
| 69 | A | A | A | A | A | A | A | A | A |
| 70 | G | G | G | G | G | G | G | G | G |
| 71 | T | T | T | T | T | T | T | T | T |
| 72 | V | I | I | V | V | V | V | V | I |
| 73 | A | A | A | A | A | A | A | A | A |
| 74 | A | A | A | A | A | A | A | A | A |
| 75 | L | L | L | L | L | L | L | L | L |
| 76 | N | N | D | D | N | N | D | N | N |
| 77 | N | N | N | N | N | N | N | N | N |
| 78 | S | S | T | T | T | T | T | T | S |
| 79 | I | I | I | T | T | I | T | T | I |
| 80 | G | G | G | G | G | G | G | G | G |
| 81 | V | V | V | V | V | V | V | V | V |
| 82 | L | L | L | L | L | V | L | L | L |
| 83 | G | G | G | G | G | G | G | G | G |
| 84 | V | V | V | V | V | V | V | V | V |
| 85 | A | A | A | A | A | A | A | A | A |
| 86 | P | P | P | P | Y | Y | P | Y | P |
| 87 | S | S | S | S | N | N | S | N | S |

TABLE 28-continued

| Structure-based multiple sequence alignment of various subtilisins. | | | | | | | | | |
|---|---|---|---|---|---|---|---|---|---|
| 88 | A | A | A | V | A | A | V | A | A |
| 89 | S | S | S | S | D | D | S | F | E |
| 90 | L | L | L | L | L | L | L | L | L |
| 91 | Y | Y | Y | Y | Y | Y | Y | Y | Y |
| 92 | A | A | A | A | A | A | A | A | A |
| 93 | V | V | V | V | V | V | V | V | V |
| 94 | K | K | K | K | K | K | K | K | K |
| 95 | V | V | V | V | V | V | V | V | V |
| 96 | L | L | L | L | L | L | L | L | L |
| 97 | G | D | D | N | S | S | G | G | G |
| 98 | A | S | R | S | A | A | A | A | A |
| 99 | D | T | N | S | S | S | S | S | S |
| 100 | G | G | G | G | G | G | G | G | G |
| 101 | S | S | D | S | S | S | S | S | S |
| 102 | G | G | G | G | G | G | G | G | G |
| 103 | Q | Q | Q | S | T | T | S | T | S |
| 104 | Y | Y | Y | Y | L | L | V | L | V |
| 105 | S | S | S | S | S | S | S | S | S |
| 106 | W | W | W | G | G | G | S | G | S |
| 107 | I | I | I | I | I | I | I | I | I |
| 108 | I | I | I | V | A | A | A | A | A |
| 109 | N | N | S | S | Q | Q | Q | Q | Q |
| 110 | G | G | G | G | G | G | G | G | G |
| 111 | I | I | I | I | I | V | L | I | L |
| 112 | E | E | E | E | E | E | E | E | E |
| 113 | W | W | W | W | W | W | W | W | W |
| 114 | A | A | A | A | S | A | A | S | A |
| 115 | I | I | V | T | I | I | G | I | G |
| 116 | A | S | A | T | S | A | N | A | N |
| 117 | N | N | N | N | N | N | N | N | N |
| 118 | N | N | N | G | G | N | G | D | G |
| 119 | M | M | M | M | M | M | M | M | M |
| 120 | D | D | D | D | N | D | H | D | H |
| 121 | V | V | V | V | V | V | V | V | V |
| 122 | I | I | I | I | I | I | A | I | A |
| 123 | N | N | N | N | N | N | N | N | N |
| 124 | M | M | M | M | M | M | L | M | L |
| 125 | S | S | S | S | S | S | S | S | S |
| 126 | L | L | L | L | L | L | L | L | L |

TABLE 28-continued

Structure-based multiple sequence alignment of various subtilisins.

| | | | | | | | | | |
|---|---|---|---|---|---|---|---|---|---|
| 127 | G | G | G | G | G | G | G | G | G |
| 128 | G | G | G | G | G | G | S | I | S |
| 129 | P | P | P | A | S | S | P | S | P |
| 130 | S | T | S | S | S | S | S | T | S |
| 131 | G | G | G | G | G | G | P | G | P |
| 132 | S | S | S | S | S | S | S | S | S |
| 133 | A | T | T | T | T | T | A | T | A |
| 134 | A | A | A | A | A | A | T | A | T |
| 135 | L | L | L | M | L | L | L | L | L |
| 136 | K | K | K | K | Q | K | E | Q | E |
| 137 | A | T | N | Q | Q | Q | Q | Q | Q |
| 138 | A | V | A | A | A | A | A | A | A |
| 139 | V | V | V | V | C | V | V | C | V |
| 140 | D | D | D | D | N | D | N | N | N |
| 141 | K | K | T | N | N | N | S | N | S |
| 142 | A | A | A | A | A | A | A | A | A |
| 143 | V | V | N | Y | Y | Y | T | Y | T |
| 144 | A | S | N | A | N | A | S | A | S |
| 145 | S | S | R | R | R | S | R | S | R |
| 146 | G | G | G | G | G | G | G | G | G |
| 147 | V | I | V | V | I | I | V | I | V |
| 148 | V | V | V | V | V | V | L | V | L |
| 149 | V | V | V | V | V | V | V | V | V |
| 150 | V | A | V | V | I | V | V | V | V |
| 151 | A | A | A | A | S | A | A | A | A |
| 152 | A | A | A | A | S | A | A | A | A |
| 153 | A | A | A | A | A | A | S | A | S |
| 154 | G | G | G | G | G | G | G | G | G |
| 155 | N | N | N | N | N | N | N | N | N |
| 156 | E | E | S | S | S | S | S | S | S |
| 157 | G | G | G | G | G | G | G | G | G |
| 158 | T | S | S | S | S | T | A | S | A |
| 158a | | | | | | | | | |
| 159 | S | S | S | S | S | R | | N | |
| 160 | G | G | G | G | G | G | G | G | G |
| 161 | S | S | S | N | N | R | | K | |
| 162 | S | T | T | T | R | Q | | R | |
| 163 | S | S | S | N | N | N | | N | |
| 164 | T | T | T | T | T | T | S | T | S |

TABLE 28-continued

Structure-based multiple sequence alignment of various subtilisins.

| | | | | | | | | | |
|---|---|---|---|---|---|---|---|---|---|
| 165 | V | V | V | I | M | M | I | M | I |
| 166 | G | G | G | G | G | G | S | G | S |
| 167 | Y | Y | Y | Y | Y | Y | Y | Y | Y |
| 168 | P | P | P | P | P | P | P | P | P |
| 169 | A | A | A | A | A | A | A | A | A |
| 170 | K | K | K | K | R | R | R | R | R |
| 171 | Y | Y | Y | Y | Y | Y | Y | Y | Y |
| 172 | P | P | D | D | S | S | A | S | A |
| 173 | S | S | S | S | S | S | N | S | N |
| 174 | V | T | T | V | V | V | A | V | A |
| 175 | I | I | I | I | I | I | M | I | M |
| 176 | A | A | A | A | A | A | A | A | A |
| 177 | V | V | V | V | V | V | V | V | V |
| 178 | G | G | A | G | G | G | G | G | G |
| 179 | A | A | N | A | A | A | A | A | A |
| 180 | V | V | V | V | V | V | T | V | T |
| 181 | D | N | N | D | S | D | D | D | D |
| 182 | S | S | S | S | S | S | Q | S | Q |
| 183 | S | S | N | N | N | N | N | S | N |
| 184 | N | N | N | S | N | N | N | N | N |
| 185 | Q | Q | V | N | T | N | N | N | N |
| 186 | R | R | R | R | R | R | R | R | R |
| 187 | A | A | N | A | A | A | A | A | A |
| 188 | S | S | S | S | S | S | S | S | S |
| 189 | F | F | S | F | F | F | F | F | F |
| 190 | S | S | S | S | S | S | S | S | S |
| 191 | S | S | S | S | S | S | Q | S | Q |
| 192 | V | A | A | V | V | V | Y | V | Y |
| 193 | G | G | G | G | G | G | G | G | G |
| 194 | P | S | P | A | S | A | A | S | A |
| 195 | E | E | E | E | E | E | G | E | G |
| 196 | L | L | L | L | L | L | L | L | L |
| 197 | D | D | D | E | E | E | D | E | D |
| 198 | V | V | V | V | V | V | I | V | I |
| 199 | M | M | S | M | M | M | V | M | V |
| 200 | A | A | A | A | A | A | A | A | A |
| 201 | P | P | P | P | P | P | P | P | P |
| 202 | G | G | G | G | G | G | G | G | G |
| 203 | V | V | T | A | V | V | V | V | V |

TABLE 28-continued

Structure-based multiple sequence alignment of various subtilisins.

| | | | | | | | | | |
|---|---|---|---|---|---|---|---|---|---|
| 204 | S | S | S | G | N | S | N | S | N |
| 205 | I | I | I | V | I | V | I | I | V |
| 206 | Q | Q | L | Y | L | L | L | L | Q |
| 207 | S | S | S | S | S | S | S | S | S |
| 208 | T | T | T | T | T | T | T | T | T |
| 209 | L | L | V | Y | T | V | T | T | Y |
| 210 | P | P | P | P | P | P | P | P | P |
| 211 | G | G | S | T | G | G | G | G | G |
| 212 | N | G | S | N | N | G | N | N | S |
| 213 | K | T | G | T | N | G | N | N | T |
| 214 | Y | Y | Y | Y | Y | Y | Y | Y | Y |
| 215 | G | G | A | A | A | A | A | E | A |
| 216 | A | A | S | T | S | S | S | S | S |
| 217 | Y | Y | Y | L | F | Y | L | F | L |
| 218 | N | N | T | N | N | N | N | N | N |
| 219 | G | G | G | G | G | G | G | G | G |
| 220 | T | T | T | T | T | T | T | T | T |
| 221 | S | S | S | S | S | S | S | S | S |
| 222 | M | M | M | M | M | M | M | M | M |
| 223 | A | A | A | A | A | A | A | A | A |
| 224 | S | T | S | S | A | S | A | S | T |
| 225 | P | P | P | P | P | P | P | P | P |
| 226 | H | H | H | H | H | H | H | H | H |
| 227 | V | V | V | V | V | V | V | V | V |
| 228 | A | A | A | A | A | A | A | A | A |
| 229 | G | G | G | G | G | G | G | G | G |
| 230 | A | A | A | A | A | A | A | A | A |
| 231 | A | A | A | A | A | A | A | A | A |
| 232 | A | A | A | A | A | A | A | A | A |
| 233 | L | L | L | L | L | L | L | L | L |
| 234 | I | I | I | I | I | I | I | I | V |
| 235 | L | L | L | L | K | K | K | K | K |
| 236 | S | S | S | S | A | A | A | A | Q |
| 237 | K | K | K | K | K | K | K | K | K |
| 238 | H | H | H | H | Y | Y | Y | Y | N |
| 239 | P | P | P | P | P | P | P | P | P |
| 240 | N | T | N | N | S | S | S | S | S |
| 241 | W | W | L | L | M | L | M | M | W |
| 242 | T | T | T | S | T | S | T | T | S |

TABLE 28-continued

| Structure-based multiple sequence alignment of various subtilisins. | | | | | | | | | |
|---|---|---|---|---|---|---|---|---|---|
| 243 | N | N | N | A | N | A | N | N | N |
| 244 | T | A | T | S | V | S | V | V | V |
| 245 | Q | Q | Q | Q | Q | Q | Q | Q | Q |
| 246 | V | V | V | V | I | I | I | I | I |
| 247 | R | R | R | R | R | R | R | R | R |
| 248 | S | D | Q | N | E | D | N | N | N |
| 249 | S | R | R | R | R | R | R | K | H |
| 250 | L | L | L | L | L | L | L | L | L |
| 251 | E | E | E | S | K | R | K | K | K |
| 252 | N | S | N | S | N | N | N | N | N |
| 253 | T | T | T | T | T | T | T | T | T |
| 254 | T | A | A | A | A | A | A | A | A |
| 255 | T | T | T | T | T | T | T | T | T |
| 256 | K | Y | P | Y | N | Y | N | N | S |
| 257 | L | L | L | L | L | L | L | L | L |
| 258 | G | G | G | G | G | G | G | G | G |
| 259 | D | N | S | S | D | D | D | D | S |
| 260 | S | S | S | S | P | P | P | A | T |
| 261 | F | F | F | F | F | F | F | F | N |
| 262 | Y | Y | Y | Y | F | Y | F | Y | L |
| 263 | Y | Y | Y | Y | Y | Y | Y | Y | Y |
| 264 | G | G | G | G | G | G | G | G | G |
| 265 | K | K | K | K | K | N | K | H | S |
| 266 | G | G | G | G | G | G | G | G | G |
| 267 | L | L | L | L | V | V | V | V | L |
| 268 | I | I | I | I | I | I | I | I | V |
| 269 | N | N | N | N | N | N | N | N | N |
| 270 | V | V | V | V | V | V | V | V | A |
| 271 | Q | Q | Q | E | E | E | E | E | E |
| 272 | A | A | A | A | S | R | S | K | A |
| 273 | A | A | A | A | A | A | A | A | A |
| 274 | A | A | A | A | L | L | L | L | T |
| 275 | Q | Q | N | Q | Q | Q | Q | Q | R |

| BPN' numbering | Bpan01744 | *Bgi02446 | DSM14391 | BspAK01305 | BspZ00258 | BspAI02518 | BspZ00056 | Bad02409 | Bba02069 |
|---|---|---|---|---|---|---|---|---|---|
| 1 | A | Q | Q | A | A | A | G | A | Q |
| 2 | Q | Q | Q | Q | Q | Q | Q | Q | Q |
| 3 | S | T | T | S | E | S | T | T | Q |
| 4 | V | V | V | I | V | T | V | V | T |
| 5 | P | P | P | P | P | P | P | P | P |

TABLE 28-continued

Structure-based multiple sequence alignment of various subtilisins.

| | | | | | | | | | |
|---|---|---|---|---|---|---|---|---|---|
| 6 | W | W | W | W | Y | W | W | W | W |
| 7 | G | G | G | G | G | G | G | G | G |
| 8 | I | I | I | I | I | I | I | V | I |
| 9 | S | T | T | E | E | S | P | P | T |
| 10 | R | R | R | R | Q | R | H | H | R |
| 11 | V | V | V | I | I | I | V | V | V |
| 12 | Q | Q | Q | G | G | N | Q | Q | Q |
| 13 | A | A | A | T | A | A | G | G | G |
| 14 | Q | P | P | P | I | P | T | T | I |
| 15 | S | A | T | A | D | A | A | D | A |
| 16 | A | V | V | A | V | V | A | A | A |
| 17 | H | H | H | H | Q | H | Q | H | Q |
| 17a | | | | | V | | | | |
| 18 | N | N | N | A | N | S | D | A | S |
| 19 | R | R | R | S | D | T | A | A | Q |
| 20 | G | G | G | G | G | G | G | G | G |
| 21 | I | I | I | F | N | N | Y | H | Y |
| 22 | T | T | T | T | T | F | T | T | T |
| 23 | G | G | G | G | G | G | G | G | G |
| 24 | S | S | S | S | N | Q | A | S | N |
| 25 | G | G | G | G | G | G | G | G | N |
| 26 | V | V | V | V | V | V | L | V | V |
| 27 | K | R | K | S | S | R | K | K | K |
| 28 | V | V | V | V | V | V | V | V | V |
| 29 | A | A | A | A | A | A | A | A | A |
| 30 | V | I | I | V | V | V | I | I | V |
| 31 | L | L | L | L | L | L | L | L | L |
| 32 | D | D | D | D | D | D | D | D | D |
| 33 | T | S | T | T | T | S | T | T | S |
| 34 | G | G | G | G | G | G | G | G | G |
| 35 | I | I | I | I | I | V | I | I | I |
| 36 | S | S | A | D | A | A | D | D | D |
| 37 | | | | | | | R | R | R |
| 38 | T | A | Q | P | A | S | N | N | S |
| 39 | H | H | H | H | H | H | H | H | H |
| 40 | E | S | S | S | E | E | E | E | P |
| 41 | D | D | D | D | D | D | D | D | D |
| 42 | L | L | L | L | L | L | L | L | L |
| 42a | | | | | | | F | | S |

TABLE 28-continued

Structure-based multiple sequence alignment of various subtilisins.

| | | | | | | | | | |
|---|---|---|---|---|---|---|---|---|---|
| 42b | | | | | | | A | | A |
| 43 | N | N | T | N | N | R | N | N | N |
| 44 | V | I | I | V | V | I | V | V | V |
| 45 | R | R | R | Q | V | A | K | R | R |
| 46 | G | G | G | G | D | G | G | G | G |
| 47 | G | G | G | G | G | G | G | G | G |
| 48 | A | A | A | V | A | V | H | H | Y |
| 49 | S | S | S | S | S | S | S | S | S |
| 50 | F | F | F | F | F | F | V | V | V |
| 51 | V | V | V | V | I | V | F | F | F |
| 52 | A | P | P | P | A | A | T | T | G |
| 53 | G | G | G | G | G | S | D | D | D |
| 54 | E | E | E | E | E | E | S | S | S |
| 55 | P | P | S | S | P | P | A | A | P |
| 56 | G | T | T | G | D | S | N | N | |
| 56a | | | | | | | S | R | |
| 56b | | | | | | | D | D | |
| 57 | | | | | | | P | P | |
| 58 | Y | T | T | A | Y | Y | F | Y | Y |
| 59 | Q | A | A | D | E | Q | Y | Y | N |
| 60 | D | D | D | D | D | D | D | D | D |
| 61 | G | L | L | G | Y | Y | A | G | G |
| 62 | N | N | N | N | N | N | D | S | N |
| 63 | G | G | G | G | G | G | G | G | G |
| 64 | H | H | H | H | H | H | H | H | H |
| 65 | G | G | G | G | G | G | G | G | G |
| 66 | T | T | T | T | T | T | T | T | T |
| 67 | H | H | H | H | H | H | H | H | H |
| 68 | V | V | V | V | V | V | V | V | V |
| 69 | A | A | A | A | A | A | A | A | A |
| 70 | G | G | G | G | G | G | G | G | G |
| 71 | T | T | T | T | T | T | T | T | T |
| 72 | I | V | V | I | V | I | V | V | V |
| 73 | A | A | A | A | A | A | A | A | G |
| 74 | A | A | A | A | A | G | A | A | A |
| 75 | L | L | L | L | L | L | V | L | V |
| 76 | N | N | N | D | D | N | D | N | N |
| 77 | N | N | N | N | N | N | N | N | N |
| 78 | S | S | S | D | D | S | D | S | N |

TABLE 28-continued

Structure-based multiple sequence alignment of various subtilisins.

| | | | | | | | | | |
|---|---|---|---|---|---|---|---|---|---|
| 79 | I | I | I | E | L | V | L | V | I |
| 80 | G | G | G | G | D | G | G | G | G |
| 81 | V | V | V | V | V | V | V | V | V |
| 82 | L | I | I | L | L | L | V | L | I |
| 83 | G | G | G | G | G | G | G | G | G |
| 84 | V | V | V | V | V | V | V | V | V |
| 85 | A | A | A | A | S | A | A | A | A |
| 86 | P | P | P | P | P | P | S | Y | P |
| 87 | N | N | S | E | D | S | Q | N | Q |
| 88 | A | A | A | V | V | V | A | A | A |
| 89 | E | E | D | D | D | Q | E | E | D |
| 90 | L | L | L | L | L | L | L | L | V |
| 91 | L | Y | Y | F | Y | Y | Y | Y | Y |
| 92 | A | A | A | A | A | A | A | A | A |
| 93 | V | V | V | V | V | V | V | V | V |
| 94 | K | K | K | K | K | K | K | K | K |
| 95 | V | V | V | V | V | V | V | V | V |
| 96 | L | L | L | L | L | L | L | L | L |
| 97 | G | G | G | S | G | D | N | N | N |
| 98 | A | A | A | A | A | R | N | N | N |
| 99 | S | N | N | S | D | N | S | S | S |
| 100 | G | G | G | G | G | G | G | G | G |
| 101 | S | S | R | S | G | G | S | S | S |
| 102 | G | G | G | G | G | G | G | G | G |
| 103 | S | S | S | S | S | N | S | S | S |
| 104 | I | V | V | I | H | H | Y | Y | Y |
| 105 | S | S | S | S | A | S | A | A | A |
| 106 | G | G | G | S | S | D | G | G | G |
| 107 | I | I | I | I | I | I | I | I | I |
| 108 | A | A | A | A | A | A | A | A | A |
| 109 | Q | Q | Q | Q | Q | R | E | E | Q |
| 110 | G | G | G | G | G | G | G | G | G |
| 111 | L | L | L | L | I | I | I | I | I |
| 112 | Q | E | E | E | E | E | E | E | E |
| 113 | W | W | W | W | Y | W | W | W | W |
| 114 | A | A | A | T | A | S | S | A | S |
| 115 | G | A | A | A | V | V | I | V | I |
| 116 | N | T | T | E | D | N | N | N | N |
| 117 | N | N | N | N | N | N | N | N | N |

TABLE 28-continued

Structure-based multiple sequence alignment of various subtilisins.

| | | | | | | | | | |
|---|---|---|---|---|---|---|---|---|---|
| 118 | G | N | N | N | N | G | G | G | G |
| 119 | M | M | M | I | I | M | M | M | M |
| 120 | H | H | H | D | D | H | D | D | D |
| 121 | I | I | I | V | V | V | I | I | I |
| 122 | A | A | A | A | V | V | I | I | I |
| 123 | N | N | N | N | N | N | N | N | N |
| 124 | M | M | M | L | M | M | M | M | M |
| 125 | S | S | S | S | S | S | S | S | S |
| 126 | L | L | L | L | L | L | L | L | L |
| 127 | G | G | G | G | G | G | G | G | G |
| 128 | T | S | S | S | G | G | G | G | G |
| 129 | S | D | D | P | A | P | S | S | S |
| 130 | A | F | A | S | V | T | Q | M | S |
| 131 | P | P | P | P | G | G | S | S | S |
| 132 | S | S | S | S | S | S | S | S | S |
| 133 | A | S | T | Q | T | T | S | S | S |
| 134 | T | T | T | T | T | T | I | I | I |
| 135 | L | L | L | L | L | L | L | L | L |
| 136 | E | E | E | E | E | Q | K | E | E |
| 137 | Q | R | R | Q | Q | R | Q | E | Q |
| 138 | A | A | A | A | A | A | F | W | Y |
| 139 | V | V | V | V | V | A | S | C | C |
| 140 | N | N | N | N | N | D | D | N | N |
| 141 | A | Y | Y | D | Y | N | L | I | L |
| 142 | A | A | A | A | A | A | A | A | A |
| 143 | T | T | T | T | H | Y | Y | Y | Y |
| 144 | S | S | S | D | S | N | E | N | N |
| 145 | R | R | R | S | Q | R | E | S | R |
| 146 | G | D | G | G | G | G | G | G | G |
| 147 | V | V | V | V | V | V | L | V | L |
| 148 | L | L | L | L | T | L | L | L | L |
| 149 | V | V | V | V | L | L | V | V | V |
| 150 | I | I | I | V | I | I | V | V | V |
| 151 | A | A | A | A | A | A | A | A | A |
| 152 | A | A | A | A | A | A | A | A | A |
| 153 | S | T | T | A | A | A | A | A | A |
| 154 | G | G | G | G | G | G | G | G | G |
| 155 | N | N | N | N | N | N | N | N | N |
| 156 | S | N | N | S | E | T | S | S | S |

TABLE 28-continued

Structure-based multiple sequence alignment of various subtilisins.

| | | | | | | | | | |
|---|---|---|---|---|---|---|---|---|---|
| 157 | G | G | G | G | G | G | G | G | G |
| 158 | A | S | T | T | S | T | N | R | T |
| 158a | | | | | L | | R | T | A |
| 159 | | | | S | I | S | G | N | A |
| 160 | G | G | G | | P | | G | G | G |
| 161 | | | | | G | | N | R | N |
| 162 | | | | | L | | N | G | T |
| 163 | | | | | N | | D | D | N |
| 164 | S | S | S | S | T | G | T | T | T |
| 165 | V | V | I | L | I | V | V | V | V |
| 166 | G | G | G | G | G | S | G | G | G |
| 167 | Y | Y | Y | Y | Y | F | Y | Y | Y |
| 168 | P | P | P | P | P | P | P | P | P |
| 169 | A | A | A | A | A | A | A | A | A |
| 170 | R | R | R | R | K | R | K | K | R |
| 171 | Y | Y | Y | Y | Y | Y | Y | Y | Y |
| 172 | A | A | A | D | D | S | D | D | N |
| 173 | N | N | N | N | N | S | S | S | S |
| 174 | A | A | A | A | V | V | V | V | V |
| 175 | M | M | M | M | I | M | I | I | I |
| 176 | A | A | A | A | A | A | A | A | A |
| 177 | V | V | V | V | V | V | V | V | V |
| 178 | G | G | G | G | G | A | A | A | A |
| 179 | A | A | A | A | A | A | A | A | A |
| 180 | T | T | T | T | V | T | V | V | T |
| 181 | D | D | D | D | D | D | D | D | N |
| 182 | Q | Q | Q | Q | S | S | Q | S | S |
| 183 | N | N | N | S | N | N | N | S | N |
| 184 | N | N | N | D | N | N | N | N | N |
| 185 | N | R | R | S | N | N | N | N | V |
| 186 | R | R | R | L | R | R | R | R | R |
| 187 | A | A | A | A | A | A | A | A | G |
| 188 | S | N | S | S | S | S | T | S | N |
| 189 | F | F | F | F | F | F | F | F | F |
| 190 | S | S | S | S | S | S | S | S | S |
| 191 | Q | Q | Q | Q | S | T | S | S | S |
| 192 | Y | Y | Y | Y | V | Y | T | T | T |
| 193 | G | G | G | G | G | G | G | G | G |
| 194 | A | T | T | E | N | S | P | P | P |

TABLE 28-continued

Structure-based multiple sequence alignment of various subtilisins.

| | | | | | | | | | |
|---|---|---|---|---|---|---|---|---|---|
| 195 | G | G | G | G | E | Q | A | A | T |
| 196 | L | I | I | L | L | I | V | V | V |
| 197 | D | D | D | D | D | E | E | E | E |
| 198 | I | I | I | L | V | I | I | I | L |
| 199 | V | V | V | V | V | S | S | A | S |
| 200 | A | A | A | A | A | A | A | A | A |
| 201 | P | P | P | P | P | P | P | P | P |
| 202 | G | G | G | G | G | G | G | G | G |
| 203 | V | V | V | V | V | V | V | V | V |
| 204 | G | N | G | G | S | G | S | N | S |
| 205 | V | V | I | V | I | I | I | I | V |
| 206 | Q | Q | Q | E | L | N | L | L | L |
| 207 | S | S | S | S | S | S | S | S | S |
| 208 | T | T | T | T | T | T | T | T | T |
| 209 | Y | Y | Y | Y | Y | Y | T | T | T |
| 210 | P | P | L | P | L | P | P | P | P |
| 211 | G | G | N | G | G | T | G | G | G |
| 212 | N | N | N | G | N | N | N | N | G |
| 213 | R | R | S | G | D | G | N | S | N |
| 214 | Y | Y | Y | Y | Y | Y | Y | Y | Y |
| 215 | A | V | A | D | A | S | A | A | A |
| 216 | S | S | S | S | A | S | A | S | S |
| 217 | L | M | M | L | L | L | F | Y | Y |
| 218 | N | N | N | P | S | N | N | N | N |
| 219 | G | G | G | G | G | G | G | G | G |
| 220 | T | T | T | T | T | T | T | T | T |
| 221 | S | S | S | S | S | S | S | S | S |
| 222 | M | M | M | M | M | M | M | M | M |
| 223 | A | A | A | A | A | A | A | A | A |
| 224 | T | T | T | A | S | S | S | S | S |
| 225 | P | P | P | P | P | P | P | P | P |
| 226 | H | H | H | H | H | H | H | H | H |
| 227 | V | V | V | V | V | V | V | V | V |
| 228 | A | A | A | A | A | A | A | A | A |
| 229 | G | G | G | G | G | G | G | G | G |
| 230 | V | A | V | A | A | V | V | V | V |
| 231 | A | A | A | A | A | A | A | A | A |
| 232 | A | A | A | A | A | A | A | A | A |
| 233 | L | L | L | L | L | L | Q | L | Q |

TABLE 28-continued

Structure-based multiple sequence alignment of various subtilisins.

| | | | | | | | | | |
|---|---|---|---|---|---|---|---|---|---|
| 234 | V | V | V | V | L | V | V | V | V |
| 235 | K | K | K | K | L | K | W | L | W |
| 236 | Q | Q | Q | Q | A | A | Q | A | Q |
| 237 | K | R | K | K | E | R | A | A | A |
| 238 | N | Y | N | N | N | Y | K | N | R |
| 239 | P | P | P | P | P | P | P | P | P |
| 240 | S | S | S | G | G | S | E | N | N |
| 241 | W | W | W | W | L | A | L | L | L |
| 242 | S | N | N | T | T | T | S | S | S |
| 243 | N | A | A | N | N | N | N | N | N |
| 244 | V | T | T | E | D | A | V | V | A |
| 245 | Q | Q | Q | Q | Q | Q | E | E | Q |
| 246 | V | I | I | I | V | I | L | L | L |
| 247 | R | R | R | R | R | R | R | R | R |
| 248 | N | N | N | S | A | Q | N | N | Q |
| 249 | H | H | H | H | V | H | L | R | I |
| 250 | L | L | L | L | F | L | L | L | L |
| 251 | K | K | K | N | N | R | N | N | N |
| 252 | N | N | N | D | E | S | E | D | A |
| 253 | T | T | T | T | T | T | T | T | S |
| 254 | A | A | A | A | A | S | A | A | A |
| 255 | T | T | T | N | V | T | V | Q | Q |
| 256 | N | N | N | D | P | Y | N | N | N |
| 257 | L | L | L | L | L | L | L | L | L |
| 258 | G | G | G | G | G | G | G | G | G |
| 259 | N | N | N | D | D | N | G | D | S |
| 260 | T | S | S | S | H | S | S | A | S |
| 261 | N | S | S | F | F | T | N | N | Y |
| 262 | L | Q | Q | R | Y | Y | Q | H | Q |
| 263 | Y | F | F | F | Y | Y | F | F | Y |
| 264 | G | G | G | G | G | G | G | G | G |
| 265 | S | S | S | S | N | S | H | N | N |
| 266 | G | G | G | G | G | G | G | G | G |
| 267 | L | L | L | L | L | L | L | L | L |
| 268 | V | V | V | L | I | V | V | V | V |
| 269 | N | N | N | N | D | D | Q | R | R |
| 270 | A | A | A | A | V | A | S | A | S |
| 271 | E | E | D | E | R | Q | L | V | L |
| 272 | A | A | A | N | A | R | D | D | N |

TABLE 28-continued

Structure-based multiple sequence alignment of various subtilisins.

| | | | | | | | | | |
|---|---|---|---|---|---|---|---|---|---|
| 273 | A | A | A | A | A | A | A | A | A |
| 274 | T | T | T | V | I | T | I | I | I |
| 275 | R | R | R | Q | D | N | Q | N | Q |

The percent identity for the mature (in some cases predicted) amino acid sequences of the subtilisins (corresponding to residues 1-275 of BPN') was calculated based on the alignment shown on Table 28, using the MUSCLE (Geneious version 10.2.6) software, and results are shown on Table 29.

TABLE 29

Percent identity over the mature amino acid sequence of multiple subtilisins.

| | BPN' | AprE | WP_082194748 | AprL | LG12 | Chemgen'164A | CP474 | ZP-00454 | GG36 | Bpan01744 |
|---|---|---|---|---|---|---|---|---|---|---|
| BPN' | 100 | 86.5 | 76.4 | 69.5 | 65.1 | 68 | 60.7 | 68 | 60 | 58.2 |
| AprE | 86.5 | 100 | 77.5 | 69.8 | 65.8 | 66.5 | 58.9 | 66.5 | 60.4 | 59.3 |
| WP_082194748 | 76.4 | 77.5 | 100 | 73.8 | 65.8 | 66.2 | 61.5 | 64.7 | 58.5 | 55.3 |
| AprL | 69.5 | 69.8 | 73.8 | 100 | 70.9 | 72 | 66.5 | 70.2 | 61.1 | 60.4 |
| LG12 | 65.1 | 65.8 | 65.8 | 70.9 | 100 | 81.8 | 79.6 | 90.2 | 63.3 | 64.4 |
| Chemgen_164A | 68 | 66.5 | 66.2 | 72 | 81.8 | 100 | 69.8 | 82.9 | 62.5 | 62.2 |
| CP474 | 60.7 | 58.9 | 61.5 | 66.5 | 79.6 | 69.8 | 100 | 76 | 81.2 | 76.8 |
| ZP-00454 | 68 | 66.5 | 64.7 | 70.2 | 90.2 | 82.9 | 76 | 100 | 63.3 | 64.4 |
| GG36 | 60 | 60.4 | 58.5 | 61.1 | 63.3 | 62.5 | 81.2 | 63.3 | 100 | 89.6 |
| Bpan01744 | 58.2 | 59.3 | 55.3 | 60.4 | 64.4 | 62.2 | 76.8 | 64.4 | 89.6 | 100 |
| Bgi02446 | 56 | 56 | 54.2 | 54.9 | 60 | 58.5 | 69.7 | 58.9 | 79.9 | 80.3 |
| DSM14391 | 55.6 | 54.9 | 54.5 | 55.6 | 58.9 | 57.8 | 69.4 | 57.5 | 78.4 | 79.2 |
| BspAK01305 | 56.7 | 56 | 54.2 | 57.1 | 59.3 | 60 | 69.5 | 60 | 72.2 | 69.3 |
| BspZ00258 | 60.6 | 59.2 | 60.6 | 64.6 | 61 | 61.7 | 61 | 62.1 | 58.2 | 59.6 |
| BspAI02518 | 57.1 | 58.5 | 58.5 | 57.1 | 58.9 | 58.2 | 58.8 | 58.5 | 63.3 | 63.3 |
| BspZ00056 | 53.6 | 52.1 | 53.6 | 57.1 | 60 | 57.5 | 56.1 | 60 | 53.2 | 56.1 |
| Bad02409 | 57.6 | 56.5 | 56.8 | 58.6 | 64.7 | 61.5 | 60.4 | 65.1 | 58.6 | 62.2 |
| Bba02069 | 55.4 | 56.1 | 56.5 | 57.9 | 60.1 | 61.5 | 53.6 | 58.6 | 57 | 58.5 |

| | Bgi02446 | DSM14391 | BspAK01305 | BspZ00258 | BspAI02518 | BspZ00056 | Bad02409 | Bba02069 |
|---|---|---|---|---|---|---|---|---|
| BPN' | 56 | 55.6 | 56.7 | 60.6 | 57.1 | 53.6 | 57.6 | 55.4 |
| AprE | 56 | 54.9 | 56 | 59.2 | 58.5 | 52.1 | 56.5 | 56.1 |
| WP_082194748 | 54.2 | 54.5 | 54.2 | 60.6 | 58.5 | 53.6 | 56.8 | 56.5 |
| AprL | 54.9 | 55.6 | 57.1 | 64.6 | 57.1 | 57.1 | 58.6 | 57.9 |
| LG12 | 60 | 58.9 | 59.3 | 61 | 58.9 | 60 | 64.7 | 60.1 |
| Chemgen_164A | 58.5 | 57.8 | 60 | 61.7 | 58.2 | 57.5 | 61.5 | 61.5 |
| CP474 | 69.7 | 69.4 | 69.5 | 61 | 58.8 | 56.1 | 60.4 | 53.6 |
| ZP-00454 | 58.9 | 57.5 | 60 | 62.1 | 58.5 | 60 | 65.1 | 58.6 |
| GG36 | 79.9 | 78.4 | 72.2 | 58.2 | 63.3 | 53.2 | 58.6 | 57 |
| Bpan01744 | 80.3 | 79.2 | 69.3 | 59.6 | 63.3 | 56.1 | 62.2 | 58.5 |
| Bgi02446 | 100 | 90 | 65.6 | 55.6 | 61.1 | 52.5 | 56.1 | 56 |
| DSM14391 | 90 | 100 | 65.9 | 57.1 | 61.1 | 51.4 | 55.8 | 53.8 |
| BspAK01305 | 65.6 | 65.9 | 100 | 58.9 | 57.2 | 49.3 | 53.6 | 53.1 |
| BspZ00258 | 55.6 | 57.1 | 58.9 | 100 | 57.1 | 53.2 | 56.2 | 52.7 |
| BspAI02518 | 61.1 | 61.1 | 57.2 | 57.1 | 100 | 49.3 | 54 | 54.2 |
| BspZ00056 | 52.5 | 51.4 | 49.3 | 53.2 | 49.3 | 100 | 77.2 | 72.2 |
| Bad02409 | 56.1 | 55.8 | 53.6 | 56.2 | 54 | 77.2 | 100 | 69 |
| Bba02069 | 56 | 53.8 | 53.1 | 52.7 | 54.2 | 72.2 | 69 | 100 |

An analysis of available crystal structures and homology models of several of the subtilisin proteases evaluated in this study or their close homologs was performed. The three-dimensional structures or homology models of six subtilisins: the *B. subtilis* (strain 168) subtilisin E (AprE) Protein Data Bank (PDB) entry 1SCJ; the *Bacillus* sp. subtilisin LG12 SprC (LG12) homology model described in WO2015038792; the *B. amyloliquefaciens* (BPN') PDB entry 2ST1; the *B. licheniformis* (AprL) PDB entry 1CSE; *B. lentus* (GG36) PDB entry 1JEA; and the *B. gibsonii* DSM14391 subtilisin homology model (based on *B. gibsonii*-clade BSP-00801 structure described in WO2016205755) were used to examine sites where globally beneficial substitutions were evaluated and identified. The superposition of the main chain fold of these subtilisins (image not shown) indicates that the structures overlap along the bulk of the sequences, having a common catalytic triad, corresponding to residues Asp 32, His 64, Ser 221 (numbered with respect to subtilisin BPN' sequence, SEQ ID NO:1) and minor differences, mostly in loops and surface exposed regions.

Figure 2:
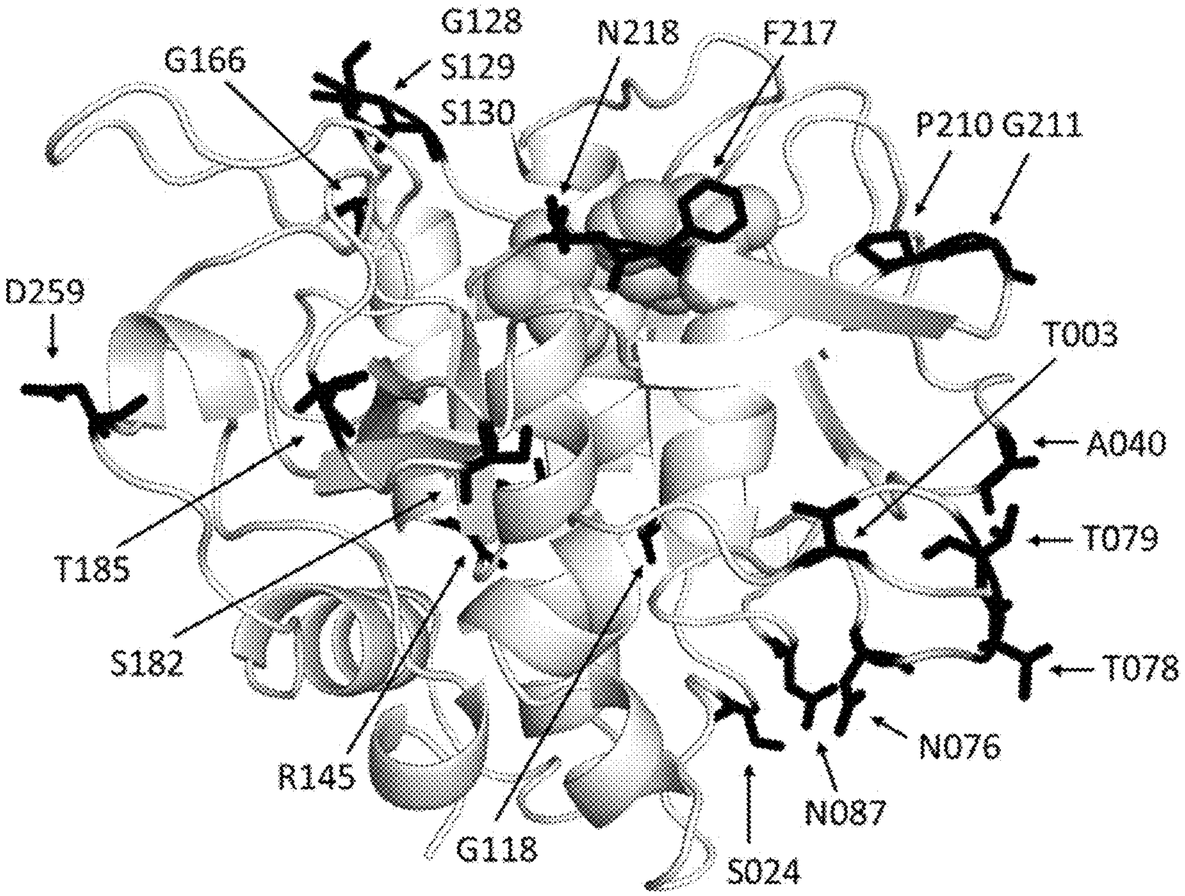
FIG. 2 depicts the locations on a structural homology model of *Bacillus* sp LG12 SprC subtilisin (described in WO2015038792) for a subset of sites where certain amino acid residues evaluated in this study show benefit in increasing stability. The main chain fold of LG12 is schematically represented in light gray, the catalytic triad is shown as gray spheres, and the sites evaluated for stability improvement are shown as black stick figures (numbered with respect to BPN' subtilisin sequence). The subtilisins Chemgen_164A, CP474, and ZP-00454 evaluated in this study are close homologs of LG12 (with amino acid sequence identity of 81.8%, 79.6% and 90.2%, respectively) and would be expected to adopt a similar fold.
Figure 3:
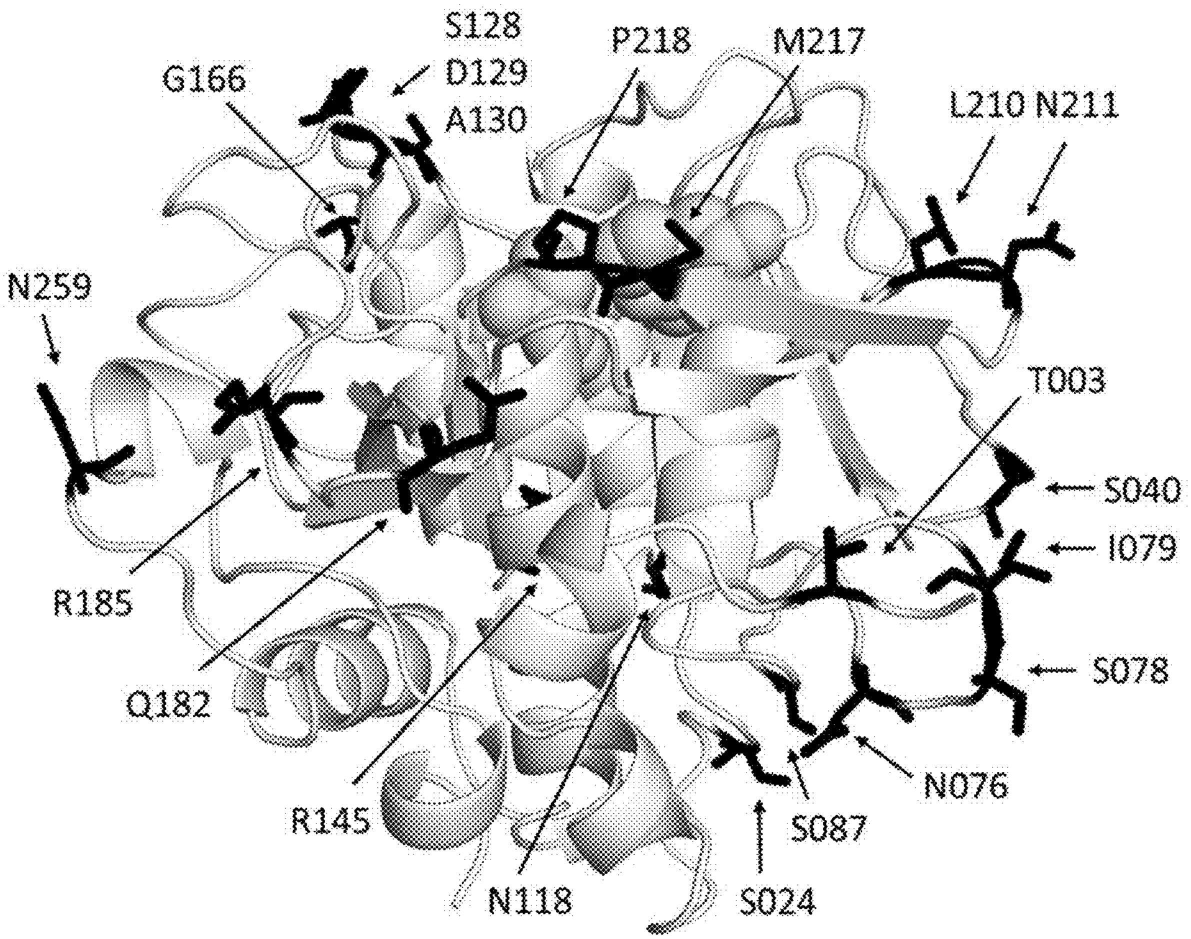
FIG. 3 depicts the locations on a structural homology model of *B. gibsonii* DSM14391 subtilisin for a subset of sites where certain amino acid residues evaluated in this study show benefit in increasing stability. The homology model was built based on the structure of BSP-00801 (described in WO2016205755), which is a variant of the Bgi02446 subtilisin from *B. gibsonii* clade. The DSM14391 subtilisin, evaluated in this study is a close homolog of the Bgi02446 subtilisin and of the BSP-00801 variant subtilisin (with amino acid sequence identity of 90% and 89.6%, respectively). The main chain fold of DSM14391 is schematically represented in light gray, the catalytic triad is shown as gray spheres, and the sites evaluated for stability improvement are shown as black stick figures (numbered with respect to BPN' subtilisin sequence).
Figure 4:
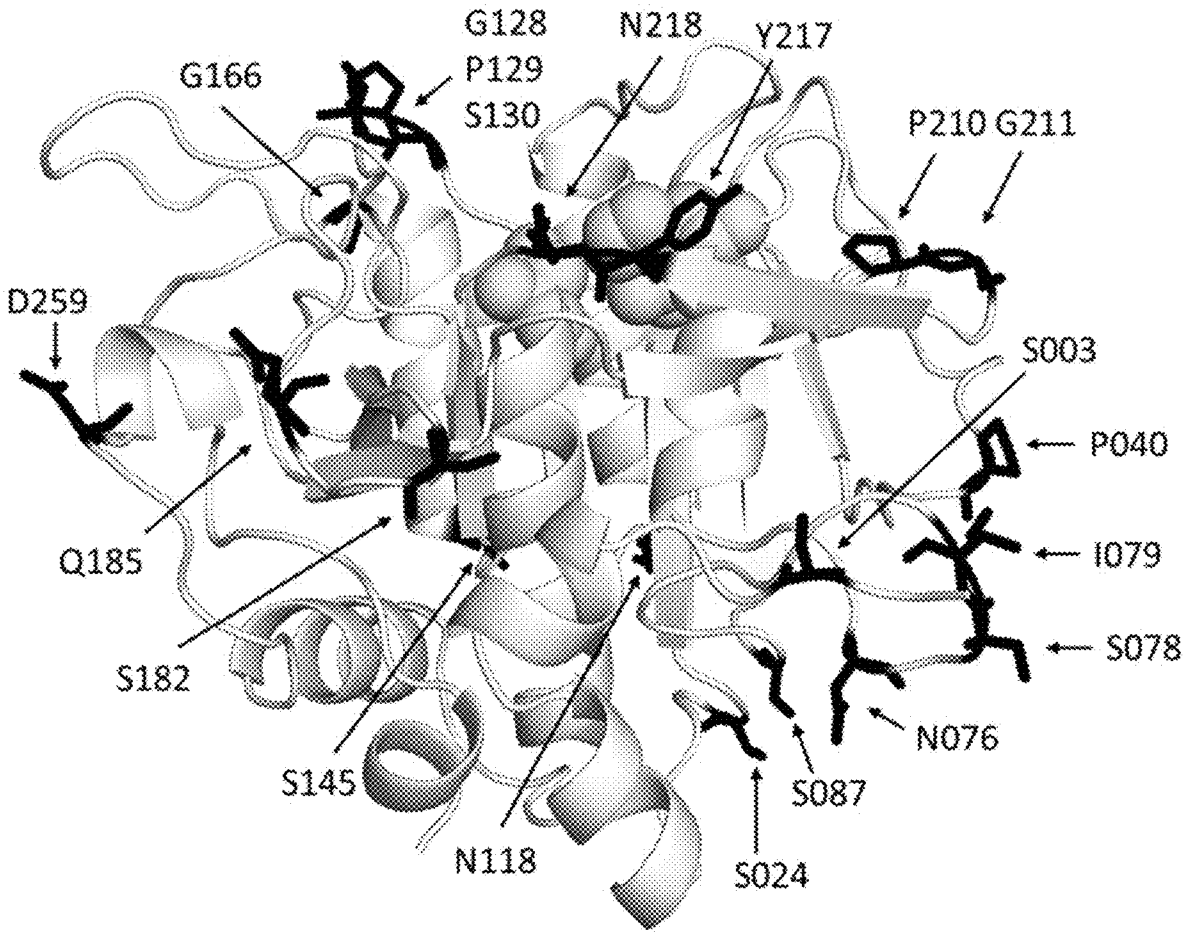
FIG. 4 depicts the locations on the structure of BPN' subtilisin from *B. amyloliquefaciens* (PDB entry 2ST1) for a subset of sites where certain amino acid residues evaluated in this study show benefit in increasing stability at corresponding positions in other subtilisins. The main chain fold of BPN' is schematically represented in light gray, the catalytic triad is shown as gray spheres, and the sites evaluated for stability improvement are shown as black stick figures (numbered with respect to BPN' subtilisin sequence).
Figure 5:
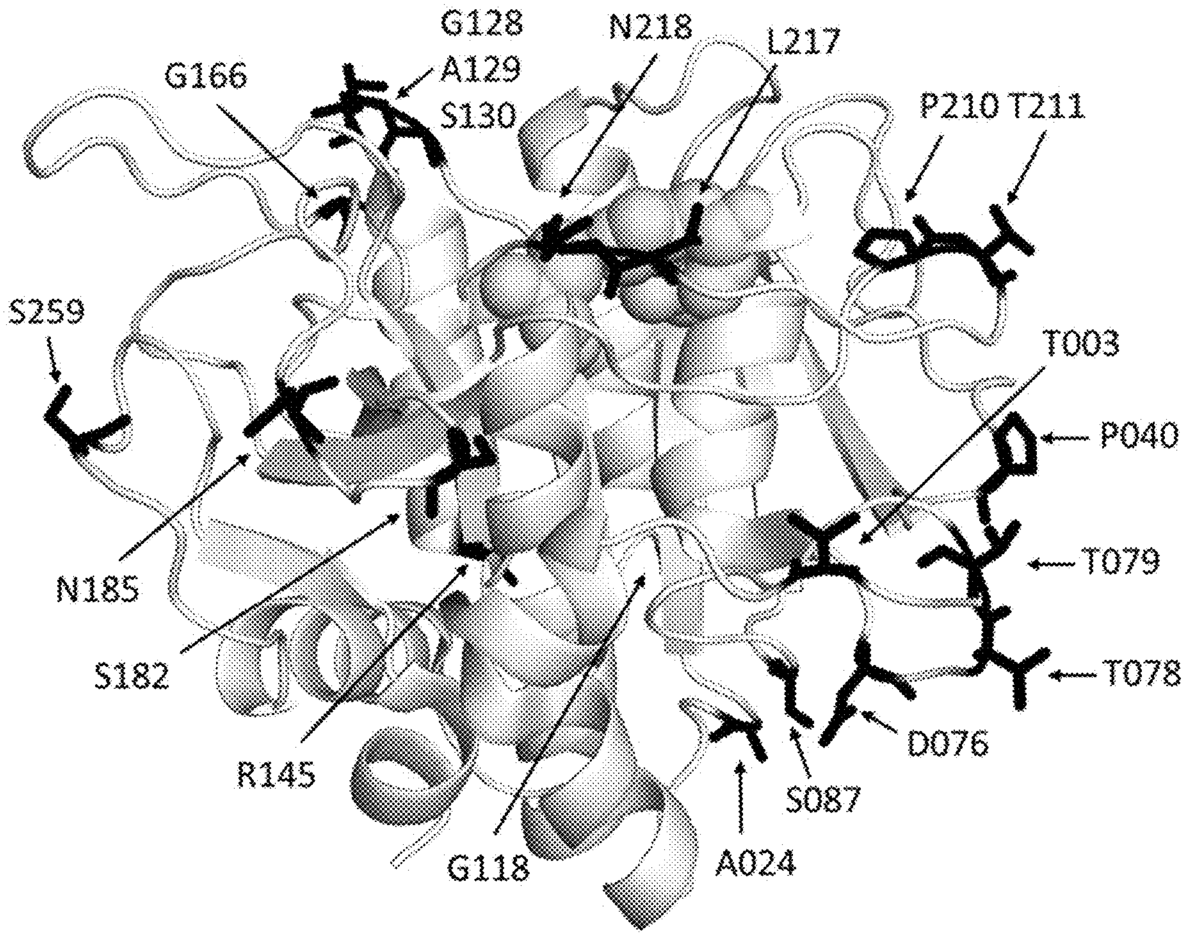
FIG. 5 depicts the locations on the structure of AprL (subtilisin Carlsberg) from *B. licheniformis* (PDB entry 1CSE) for a subset of sites where certain amino acid residues evaluated in this study show benefit in increasing stability at corresponding positions in other subtilisins. The main chain fold of AprL is schematically represented in light gray, the catalytic triad is shown as gray spheres, and the sites evaluated for stability improvement are shown as black stick figures (numbered with respect to BPN' subtilisin sequence).
Figure 6:
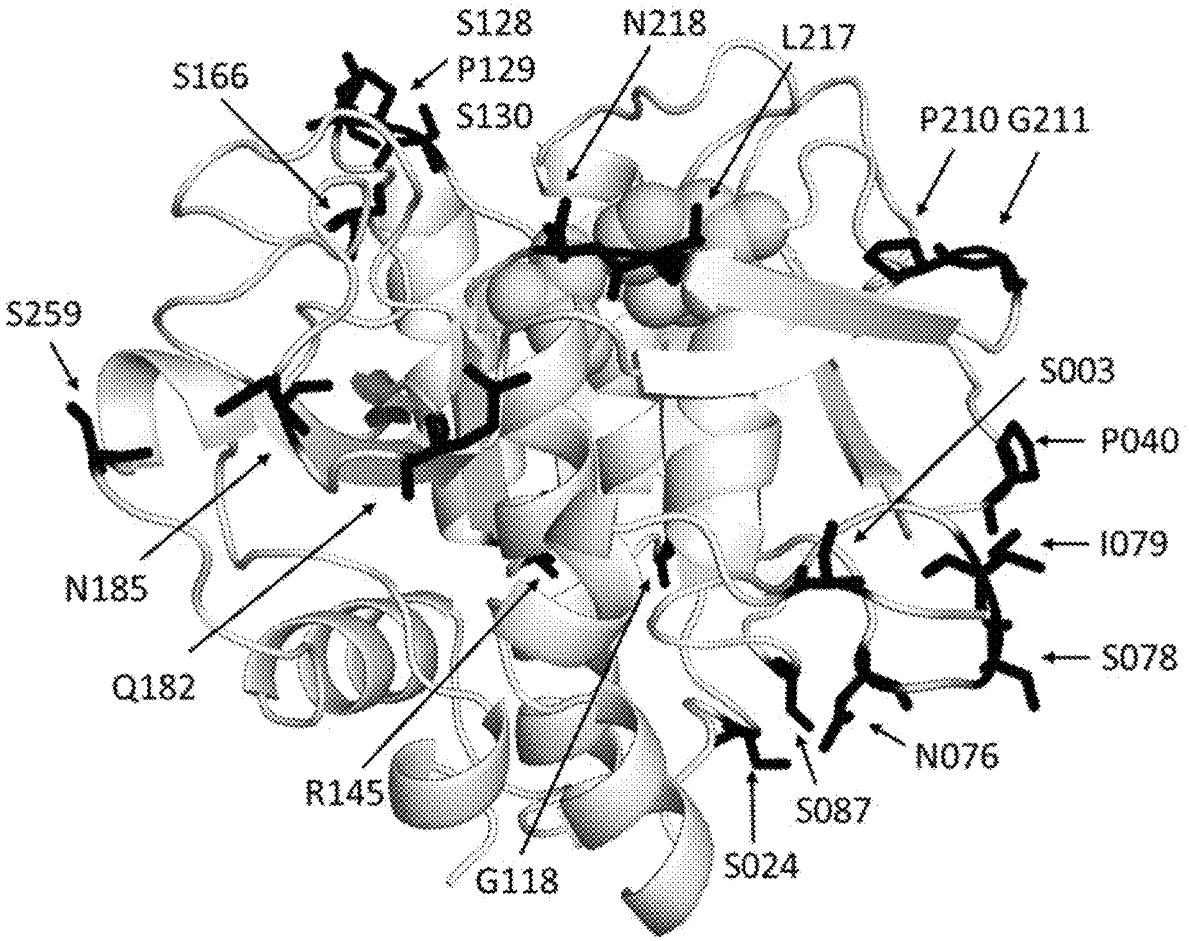
FIG. 6 depicts the locations on the structure of *B. lentus* GG36 subtilisin (PDB entry 1JEA) for a subset of sites where certain amino acid residues evaluated in this study show benefit in increasing stability at corresponding positions in other subtilisins, including Bpan01744 (with amino acid sequence identity of 89.6%). The main chain fold of GG36 is schematically represented in light gray, the catalytic triad is shown as gray spheres, and the sites evaluated for stability improvement are shown as black stick figures (numbered with respect to BPN' subtilisin sequence).

FIGS. 1-6 illustrate the spatial positions of a subset of the beneficial sites evaluated in this study, wherein the residues are numbered according to the BPN' sequence (as shown in Table 28 above). FIG. 1 shows *B. subtilis* (strain 168) subtilisin E (AprE) PDB entry 1SCJ (mature subtilisin region only, excluding the propeptide segment); FIG. 2 shows *Bacillus* sp. subtilisin LG12 SprC (LG12) homology model described in WO2015038792; FIG. 3 shows *B. gibsonii* DSM14391 subtilisin homology model (prepared based on the BSP-00801 *B. gibsonii*-clade subtilisin structure described in WO2016205755); FIG. 4 shows *B. amyloliquefaciens* subtilisin BPN' PDB entry 2ST1; FIG. 5 shows *B. licheniformis* subtilisin Carlsberg (AprL) PDB entry 1CSE; and FIG. 6 shows *B. lentus* subtilisin GG36 PDB entry 1JEA. In each figure, the main chain fold of each subtilisin is schematically represented in light gray and the following sites are depicted as black sticks: 3, 24, 40, 76, 78, 79, 87, 118, 128, 129, 130, 145, 166, 182, 185, 210, 211, 217, 218, 259 (BPN' numbering). These sites are all surface exposed and are situated in loops, outside of secondary structure motifs.

Furthermore, a subset of the sites highlighted in FIGS. 1-6 were observed to be distributed among the loops that together form an extended surface. In particular, sites 76, 78 and 79 (which are part of the same loop) are situated in spatial proximity to sites 3 and 40, which are located on distinct loops. Moreover, site 76 is also situated in spatial proximity to site 24, which, in turn, is spatially close to site 87 (belonging to a different loop). Site 40 resides on a loop that is located in spatial proximity to sites 210 and 211. Thus, sites 3, 24, 40, 76, 78, 79, 87, 210 and 211 (BPN' numbering) are situated along a surface formed by a series of loops in which these sites reside. Sites 128, 129 and 130 (BPN' numbering) are in spatial proximity to site 166, as the loop containing sites 128, 129 and 130 comes close to the loop where site 166 is situated. Sites 182 and 185 are also located in spatial proximity to each other—these sites form part of a turn in a loop where they reside. While site 259 is located on a different loop, it appears to form part of the same surface as the loop containing sites 182 and 185.

Together, the surface exposed sites 3, 9, 24, 40, 76, 78, 79, 87, 118, 128, 129, 130, 145, 166, 182, 185, 210, 211, 217, 218, 248 and 259 (BPN' numbering) account for twenty-two of the twenty-four sites evaluated in this study, and the substitutions explored were: X003T, X003V, X009E, X024Q, X040E, X069S, X076D, X078N, X079I, X087D, X118R, X124I, X128R, X128S, X129P, X130S, X145R, X166Q, X182E, X185Q, X210I, X211P, X217L, X218S, X248D, X259P. The location of these sites on the surface of the molecules, and mostly in loop regions outside of secondary structure motifs, suggests an underlying structural commonality for the improvements in protein stability provided by the amino acid substitutions evaluated in this study.

Example 13

Additional AprE & WP_082194748 Subtilisin Variants with Improved Stability in Detergent Variants of AprE (Subtilisin E, SEQ ID NO: 8) and WP_082194748 (SEQ ID NO: 9) subtilisins containing three or four amino acid substitutions at positions of interest to increase enzyme stability, were generated using methods similar to the ones described in Example 1. These variant samples were evaluated for detergent stability (% residual activity) and cleaning performance (PI) using methods described in Example 2. Results for AprE (Subtilisin E) variants are shown on Tables 30A and 30B, and results for WP_082194748 variants are shown on Table 31.

TABLE 30A

AprE subtilisin variants with improved stability in liquid detergent at 41° C. (reported as percent residual activity, % RA) compared to AprE parent

| AprE Variant Sample ID | Substitutions in AprE numbering | Substitutions in BPN' numbering | % RA | Cleaning performance, PI: BMI stain in PNB detergent | Cleaning performance, PI: PAS-38 stain in GSM-B detergent |
|---|---|---|---|---|---|
| AprE | — | — | 40 | 1.0 | 1.0 |
| AprE-00685 | S003V-N076D-S078N | S003V-N076D-S078N | 81 | 1.1 | 1.1 |
| AprE-00353 | S003V-S078N-N218S | S003V-S078N-N218S | 87 | 1.1 | 1.1 |
| AprE-00806 | S003V-M124I-N259P | S003V-M124I-N259P | 71 | 1.1 | 1.2 |
| AprE-00696 | S003V-G128S-G166Q | S003V-G128S-G166Q | 79 | 1.1 | 1.0 |
| AprE-00773 | S003V-G166Q-N218S | S003V-G166Q-N218S | 91 | 1.2 | 1.1 |
| AprE-00753 | S003V-N218S-N259P | S003V-N218S-N259P | 84 | 1.0 | 1.1 |
| AprE-00540 | P040E-N076D-S078N | P040E-N076D-S078N | 86 | 1.1 | 1.0 |
| AprE-00635 | G128S-G166Q-N259P | G128S-G166Q-N259P | 83 | 1.1 | 1.0 |
| AprE-00452 | S003V-P040E-N076D-S078N | S003V-P040E-N076D-S078N | 83 | 1.1 | 0.9 |
| AprE-00850 | S003V-P040E-S078N-M124I | S003V-P040E-S078N-M124I | 80 | 1.3 | 1.1 |
| AprE-00756 | S003V-P040E-M124I-N218S | S003V-P040E-M124I-N218S | 85 | 1.2 | 1.1 |
| AprE-00613 | S003V-N076D-S078N-G128S | S003V-N076D-S078N-G128S | 100 | 1.2 | 1.0 |
| AprE-00462 | S003V-N076D-M124I-G166Q | S003V-N076D-M124I-G166Q | 100 | 1.0 | 0.9 |
| AprE-00665 | S003V-N076D-G128S-N259P | S003V-N076D-G128S-N259P | 100 | 1.2 | 1.0 |
| AprE-00705 | S003V-N076D-G166Q-N259P | S003V-N076D-G166Q-N259P | 91 | 1.1 | 1.1 |
| AprE-00796 | S003V-N076D-N218S-N259P | S003V-N076D-N218S-N259P | 96 | 1.1 | 1.1 |
| AprE-00551 | S003V-M124I-G128S-N218S | S003V-M124I-G128S-N218S | 81 | 1.1 | 0.9 |
| AprE-00617 | S003V-G128S-G166Q-N218S | S003V-G128S-G166Q-N218S | 99 | 1.3 | 1.0 |

TABLE 30A-continued

AprE subtilisin variants with improved stability in liquid detergent at 41° C. (reported as percent residual activity, % RA) compared to AprE parent

| AprE Variant Sample ID | Substitutions in AprE numbering | Substitutions in BPN' numbering | % RA | Cleaning performance, PI: BMI stain in PNB detergent | Cleaning performance, PI: PAS-38 stain in GSM-B detergent |
|---|---|---|---|---|---|
| AprE-00510 | P040E-N076D-S078N-G166Q | P040E-N076D-S078N-G166Q | 100 | 1.1 | 1.0 |
| AprE-00403 | P040E-N076D-M124I-N218S | P040E-N076D-M124I-N218S | 93 | 1.2 | 1.0 |
| AprE-00764 | P040E-N076D-G166Q-N218S | P040E-N076D-G166Q-N218S | 98 | 1.2 | 1.0 |
| AprE-00547 | P040E-N076D-G166Q-N259P | P040E-N076D-G166Q-N259P | 98 | 1.1 | 1.0 |
| AprE-00769 | N076D-S078N-M124I-N218S | N076D-S078N-M124I-N218S | 89 | 1.3 | 1.1 |
| AprE-00684 | N076D-S078N-G128S-N259P | N076D-S078N-G128S-N259P | 94 | 1.2 | 0.9 |
| AprE-00507 | N076D-S078N-G166Q-N259P | N076D-S078N-G166Q-N259P | 97 | 1.0 | 1.0 |
| AprE-00591 | N076D-M124I-G128S-G166Q | N076D-M124I-G128S-G166Q | 100 | 1.1 | 0.8 |
| AprE-00583 | N076D-M124I-G128S-N259P | N076D-M124I-G128S-N259P | 100 | 1.3 | 0.8 |
| AprE-00709 | N076D-G128S-G166Q-N218S | N076D-G128S-G166Q-N218S | 95 | 1.2 | 0.9 |
| AprE-00518 | S078N-G128S-G166Q-N218S | S078N-G128S-G166Q-N218S | 100 | 1.2 | 0.9 |
| AprE-00589 | S078N-G128S-N218S-N259P | S078N-G128S-N218S-N259P | 96 | 1.1 | 1.0 |
| AprE-00366 | M124I-G166Q-N218S-N259P | M124I-G166Q-N218S-N259P | 90 | 1.1 | 1.0 |

TABLE 30B

AprE subtilisin variants with improved stability in liquid detergent at 42° C. (reported as percent residual activity, % RA) compared to AprE parent

| AprE Variant Sample ID | Substitutions in AprE numbering | Substitutions in BPN' numbering | % RA |
|---|---|---|---|
| AprE | — | — | 27 |
| AprE-01102 | S003V-S009E-P040E | S003V-S009E-P040E | 85 |
| AprE-01101 | S003V-S009E-A069S | S003V-S009E-A069S | 89 |
| AprE-01051 | S003V-S009E-N076D | S003V-S009E-N076D | 94 |
| AprE-01099 | S003V-S009E-S078N | S003V-S009E-S078N | 90 |
| AprE-01045 | S003V-S009E-G166Q | S003V-S009E-G166Q | 95 |
| AprE-01077 | S003V-S009E-N218S | S003V-S009E-N218S | 91 |
| AprE-01047 | S003V-S009E-N259P | S003V-S009E-N259P | 86 |
| AprE-01009 | S003V-P040E-A069S | S003V-P040E-A069S | 61 |
| AprE-01048 | S003V-P040E-N076D | S003V-P040E-N076D | 69 |
| AprE-01915 | S003V-P040E-N218S | S003V-P040E-N218S | 77 |
| AprE-01039 | S003V-P040E-N259P | S003V-P040E-N259P | 67 |
| AprE-01864 | S003V-A069S-N076D | S003V-A069S-N076D | 54 |
| AprE-01056 | S003V-A069S-S078N | S003V-A069S-S078N | 48 |
| AprE-00991 | S003V-A069S-G166Q | S003V-A069S-G166Q | 75 |
| AprE-01060 | S003V-A069S-N218S | S003V-A069S-N218S | 70 |
| AprE-01064 | S003V-A069S-N259P | S003V-A069S-N259P | 48 |
| AprE-01340 | S003V-N076D-G166Q | S003V-N076D-G166Q | 100 |
| AprE-01867 | S003V-N076D-N218S | S003V-N076D-N218S | 82 |
| AprE-01062 | S003V-N076D-N259P | S003V-N076D-N259P | 84 |
| AprE-01068 | S003V-S078N-N259P | S003V-S078N-N259P | 73 |
| AprE-01855 | S003V-G166Q-N259P | S003V-G166Q-N259P | 68 |
| AprE-01674 | S009E-P040E-A069S | S009E-P040E-A069S | 73 |
| AprE-01069 | S009E-P040E-N076D | S009E-P040E-N076D | 94 |
| AprE-01997 | S009E-P040E-S078N | S009E-P040E-S078N | 82 |
| AprE-01984 | S009E-P040E-G166Q | S009E-P040E-G166Q | 88 |
| AprE-01529 | S009E-P040E-N218S | S009E-P040E-N218S | 97 |
| AprE-01125 | S009E-P040E-N259P | S009E-P040E-N259P | 88 |
| AprE-01071 | S009E-A069S-N076D | S009E-A069S-N076D | 91 |
| AprE-01091 | S009E-A069S-S078N | S009E-A069S-S078N | 84 |

TABLE 30B-continued

AprE subtilisin variants with improved stability in liquid detergent at 42° C. (reported as percent residual activity, % RA) compared to AprE parent

| AprE Variant Sample ID | Substitutions in AprE numbering | Substitutions in BPN' numbering | % RA |
|---|---|---|---|
| AprE-01871 | S009E-A069S-G166Q | S009E-A069S-G166Q | 83 |
| AprE-01087 | S009E-A069S-N218S | S009E-A069S-N218S | 87 |
| AprE-01857 | S009E-A069S-N259P | S009E-A069S-N259P | 73 |
| AprE-01892 | S009E-N076D-S078N | S009E-N076D-S078N | 92 |
| AprE-01093 | S009E-N076D-G166Q | S009E-N076D-G166Q | 100 |
| AprE-01052 | S009E-N076D-N218S | S009E-N076D-N218S | 98 |
| AprE-01860 | S009E-N076D-N259P | S009E-N076D-N259P | 100 |
| AprE-01095 | S009E-S078N-G166Q | S009E-S078N-G166Q | 94 |
| AprE-01019 | S009E-S078N-N218S | S009E-S078N-N218S | 97 |
| AprE-01014 | S009E-S078N-N259P | S009E-S078N-N259P | 88 |
| AprE-01029 | S009E-G166Q-N218S | S009E-G166Q-N218S | 94 |
| AprE-01028 | S009E-G166Q-N259P | S009E-G166Q-N259P | 97 |
| AprE-01026 | S009E-N218S-N259P | S009E-N218S-N259P | 94 |
| AprE-01024 | P040E-A069S-S078N | P040E-A069S-S078N | 44 |
| AprE-01865 | P040E-A069S-G166Q | P040E-A069S-G166Q | 56 |
| AprE-01823 | P040E-A069S-N218S | P040E-A069S-N218S | 61 |
| AprE-01036 | P040E-A069S-N259P | P040E-A069S-N259P | 48 |
| AprE-01032 | P040E-N076D-G166Q | P040E-N076D-G166Q | 96 |
| AprE-01824 | P040E-N076D-N218S | P040E-N076D-N218S | 78 |
| AprE-01031 | P040E-N076D-N259P | P040E-N076D-N259P | 81 |
| AprE-01825 | P040E-S078N-G166Q | P040E-S078N-G166Q | 81 |
| AprE-01030 | P040E-S078N-N218S | P040E-S078N-N218S | 82 |
| AprE-01035 | P040E-S078N-N259P | P040E-S078N-N259P | 59 |
| AprE-01820 | P040E-G166Q-N218S | P040E-G166Q-N218S | 80 |
| AprE-01831 | P040E-G166Q-N259P | P040E-G166Q-N259P | 71 |
| AprE-01826 | P040E-N218S-N259P | P040E-N218S-N259P | 67 |
| AprE-01810 | A069S-N076D-S078N | A069S-N076D-S078N | 58 |
| AprE-01812 | A069S-N076D-G166Q | A069S-N076D-G166Q | 86 |
| AprE-01403 | A069S-N076D-N218S | A069S-N076D-N218S | 81 |
| AprE-01829 | A069S-N076D-N259P | A069S-N076D-N259P | 73 |
| AprE-01830 | A069S-S078N-G166Q | A069S-S078N-G166Q | 69 |
| AprE-01693 | A069S-S078N-N218S | A069S-S078N-N218S | 59 |
| AprE-01873 | A069S-S078N-N259P | A069S-S078N-N259P | 47 |
| AprE-00996 | A069S-G166Q-N218S | A069S-G166Q-N218S | 68 |
| AprE-01117 | A069S-G166Q-N259P | A069S-G166Q-N259P | 54 |
| AprE-01807 | A069S-N218S-N259P | A069S-N218S-N259P | 48 |
| AprE-01805 | N076D-S078N-G166Q | N076D-S078N-G166Q | 85 |
| AprE-01407 | N076D-S078N-N218S | N076D-S078N-N218S | 85 |
| AprE-01118 | N076D-S078N-N259P | N076D-S078N-N259P | 96 |
| AprE-01802 | N076D-G166Q-N218S | N076D-G166Q-N218S | 100 |
| AprE-01819 | N076D-G166Q-N259P | N076D-G166Q-N259P | 92 |
| AprE-01817 | N076D-N218S-N259P | N076D-N218S-N259P | 87 |
| AprE-01722 | S078N-G166Q-N218S | S078N-G166Q-N218S | 83 |
| AprE-01816 | S078N-G166Q-N259P | S078N-G166Q-N259P | 69 |
| AprE-01112 | S078N-N218S-N259P | S078N-N218S-N259P | 70 |
| AprE-01815 | G166Q-N218S-N259P | G166Q-N218S-N259P | 67 |
| AprE-02047 | S003V-P040E-A069S-G166Q | S003V-P040E-A069S-G166Q | 76 |
| AprE-01188 | S003V-P040E-N076D-N218S | S003V-P040E-N076D-N218S | 81 |
| AprE-02059 | S003V-A069S-G166Q-N218S | S003V-A069S-G166Q-N218S | 87 |
| AprE-01547 | S009E-P040E-A069S-N076D | S009E-P040E-A069S-N076D | 84 |
| AprE-01712 | S009E-P040E-A069S-N259P | S009E-P040E-A069S-N259P | 71 |
| AprE-01975 | S009E-P040E-S078N-N259P | S009E-P040E-S078N-N259P | 84 |
| AprE-01553 | S009E-P040E-G166Q-N218S | S009E-P040E-G166Q-N218S | 93 |
| AprE-01917 | S009E-P040E-G166Q-N259P | S009E-P040E-G166Q-N259P | 88 |
| AprE-01772 | S009E-P040E-N218S-N259P | S009E-P040E-N218S-N259P | 93 |
| AprE-01551 | S009E-A069S-S078N-G166Q | S009E-A069S-S078N-G166Q | 88 |
| AprE-02023 | S009E-S078N-N218S-N259P | S009E-S078N-N218S-N259P | 94 |
| AprE-01666 | S009E-G166Q-N218S-N259P | S009E-G166Q-N218S-N259P | 94 |
| AprE-00988 | P040E-A069S-N076D-S078N | P040E-A069S-N076D-S078N | 50 |
| AprE-01794 | P040E-A069S-S078N-G166Q | P040E-A069S-S078N-G166Q | 75 |
| AprE-01879 | P040E-A069S-S078N-N259P | P040E-A069S-S078N-N259P | 56 |
| AprE-01953 | P040E-A069S-G166Q-N218S | P040E-A069S-G166Q-N218S | 83 |
| AprE-01990 | N076D-S078N-G166Q-N218S | N076D-S078N-G166Q-N218S | 93 |
| AprE-01979 | N076D-G166Q-N218S-N259P | N076D-G166Q-N218S-N259P | 91 |

TABLE 31

WP_082194748 subtilisin variants with improved stability in liquid detergent at 46° C. (reported as percent residual activity, % RA) compared to WP_082194748 parent

| WP_082194748 Variant Sample ID | Substitutions in WP_082194748 numbering | Substitutions in BPN' numbering | % RA | Cleaning performance, PI: BMI stain in PNB detergent | Cleaning performance, PI: PAS-38 stain in GSM-B detergent |
|---|---|---|---|---|---|
| WP_082194748 | — | — | 36 | 1.0 | 1.0 |
| WP_082194748-00562 | T003V-T078N-G166Q | T003V-T078N-G166Q | 93 | 1.2 | 1.5 |
| WP_082194748-00205 | T003V-T078N-S259P | T003V-T078N-S259P | 70 | 1.4 | 1.3 |
| WP_082194748-00037 | T003V-M124I-G128S | T003V-M124I-G128S | 88 | 1.3 | 0.4 |
| WP_082194748-00219 | T003V-G128S-G166Q | T003V-G128S-G166Q | 100 | 1.4 | 1.2 |
| WP_082194748-00101 | T003V-G128S-S259P | T003V-G128S-S259P | 93 | 1.2 | 1.1 |
| WP_082194748-00511 | T003V-G166Q-S259P | T003V-G166Q-S259P | 98 | 1.3 | 1.3 |
| WP_082194748-00185 | T078N-M124I-G166Q | T078N-M124I-G166Q | 80 | 1.4 | 1.3 |
| WP_082194748-00433 | T078N-G128S-G166Q | T078N-G128S-G166Q | 98 | 1.4 | 1.2 |
| WP_082194748-00339 | T078N-G166Q-S259P | T078N-G166Q-S259P | 100 | 1.3 | 1.3 |
| WP_082194748-00127 | M124I-G128S-G166Q | M124I-G128S-G166Q | 90 | 1.3 | 0.8 |
| WP_082194748-00218 | M124I-G166Q-S259P | M124I-G166Q-S259P | 99 | 1.3 | 1.3 |
| WP_082194748-00547 | T003V-T078N-M124I-G166Q | T003V-T078N-M124I-G166Q | 100 | 0.9 | 1.3 |
| WP_082194748-00442 | T003V-T078N-G166Q-S259P | T003V-T078N-G166Q-S259P | 73 | 1.1 | 1.2 |
| WP_082194748-00555 | T003V-M124I-G128S-S259P | T003V-M124I-G128S-S259P | 100 | 1.5 | 0.5 |
| WP_082194748-00465 | T003V-M124I-G166Q-S259P | T003V-M124I-G166Q-S259P | 100 | 1.1 | 1.2 |
| WP_082194748-00149 | T078N-M124I-G128S-S259P | T078N-M124I-G128S-S259P | 100 | 1.2 | 1.0 |
| WP_082194748-00448 | T078N-M124I-G166Q-S259P | T078N-M124I-G166Q-S259P | 100 | 1.1 | 1.2 |

Example 14

Chemgen_164A Subtilisin Variants with Improved Stability in Detergent

Variants of Chemgen_164A (Chemgen, SEQ ID NO: 10) subtilisin containing three or four amino acid substitutions at positions of interest to increase enzyme stability were generated using methods similar to the ones described in Example 1. These variant samples were evaluated for detergent stability (% residual activity) using methods described in Example 2. Table 32 shows the detergent stability results (% RA) for Chemgen_164A variants.

TABLE 32

Chemgen_164A subtilisin variants with improved stability in liquid detergent at 51° C. (reported as percent residual activity, % RA) compared to Chemgen_164A parent

| Chemgen_164A Variant Sample ID | Substitutions in Chemgen_164A numbering | Substitutions in BPN' numbering | % RA |
|---|---|---|---|
| Chemgen_164A | — | — | 31 |
| Chemgen-00801 | T003V-T009E-P040E | T003V-T009E-P040E | 89 |
| Chemgen-01562 | T003V-T009E-A069S | T003V-T009E-A069S | 66 |
| Chemgen-00792 | T003V-T009E-N185Q | T003V-T009E-N185Q | 70 |
| Chemgen-01640 | T003V-P040E-N076D | T003V-P040E-N076D | 100 |
| Chemgen-00793 | T003V-P040E-G166Q | T003V-P040E-G166Q | 100 |
| Chemgen-01651 | T003V-P040E-N185Q | T003V-P040E-N185Q | 100 |
| Chemgen-00724 | T003V-P040E-D259P | T003V-P040E-D259P | 100 |
| Chemgen-00816 | T003V-A069S-N076D | T003V-A069S-N076D | 100 |
| Chemgen-00808 | T003V-A069S-T078N | T003V-A069S-T078N | 100 |
| Chemgen-00807 | T003V-A069S-G166Q | T003V-A069S-G166Q | 100 |
| Chemgen-01642 | T003V-A069S-N185Q | T003V-A069S-N185Q | 94 |

TABLE 32-continued

Chemgen_164A subtilisin variants with improved stability in liquid detergent at 51° C. (reported as percent residual activity, % RA) compared to Chemgen_164A parent

| Chemgen_164A Variant Sample ID | Substitutions in Chemgen_164A numbering | Substitutions in BPN' numbering | % RA |
|---|---|---|---|
| Chemgen-00727 | T003V-A069S-N218S | T003V-A069S-N218S | 100 |
| Chemgen-01658 | T003V-A069S-D259P | T003V-A069S-D259P | 100 |
| Chemgen-00729 | T003V-N076D-T078N | T003V-N076D-T078N | 100 |
| Chemgen-00694 | T003V-N076D-G166Q | T003V-N076D-G166Q | 100 |
| Chemgen-00776 | T003V-N076D-N185Q | T003V-N076D-N185Q | 100 |
| Chemgen-00775 | T003V-N076D-N218S | T003V-N076D-N218S | 100 |
| Chemgen-00832 | T003V-N076D-D259P | T003V-N076D-D259P | 100 |
| Chemgen-00774 | T003V-T078N-G166Q | T003V-T078N-G166Q | 100 |
| Chemgen-00696 | T003V-T078N-N185Q | T003V-T078N-N185Q | 100 |
| Chemgen-00834 | T003V-T078N-D259P | T003V-T078N-D259P | 100 |
| Chemgen-00738 | T003V-G166Q-N185Q | T003V-G166Q-N185Q | 100 |
| Chemgen-00739 | T003V-G166Q-D259P | T003V-G166Q-D259P | 79 |
| Chemgen-00785 | T003V-N185Q-N218S | T003V-N185Q-N218S | 91 |
| Chemgen-00698 | T003V-N185Q-D259P | T003V-N185Q-D259P | 100 |
| Chemgen-00780 | T003V-N218S-D259P | T003V-N218S-D259P | 100 |
| Chemgen-01553 | T009E-P040E-A069S | T009E-P040E-A069S | 53 |
| Chemgen-00703 | T009E-P040E-N076D | T009E-P040E-N076D | 93 |
| Chemgen-00683 | T009E-P040E-T078N | T009E-P040E-T078N | 81 |
| Chemgen-00702 | T009E-P040E-G166Q | T009E-P040E-G166Q | 78 |
| Chemgen-00822 | T009E-P040E-N218S | T009E-P040E-N218S | 62 |
| Chemgen-01604 | T009E-P040E-D259P | T009E-P040E-D259P | 68 |
| Chemgen-00684 | T009E-A069S-N076D | T009E-A069S-N076D | 79 |
| Chemgen-00700 | T009E-A069S-T078N | T009E-A069S-T078N | 71 |
| Chemgen-00823 | T009E-A069S-G166Q | T009E-A069S-G166Q | 66 |
| Chemgen-00681 | T009E-A069S-N218S | T009E-A069S-N218S | 86 |
| Chemgen-00829 | T009E-A069S-D259P | T009E-A069S-D259P | 46 |
| Chemgen-00825 | T009E-N076D-T078N | T009E-N076D-T078N | 87 |
| Chemgen-01315 | T009E-N076D-G166Q | T009E-N076D-G166Q | 100 |
| Chemgen-00737 | T009E-N076D-N185Q | T009E-N076D-N185Q | 78 |
| Chemgen-00690 | T009E-N076D-N218S | T009E-N076D-N218S | 88 |
| Chemgen-01420 | T009E-N076D-D259P | T009E-N076D-D259P | 74 |
| Chemgen-00826 | T009E-T078N-G166Q | T009E-T078N-G166Q | 86 |
| Chemgen-01162 | T009E-T078N-N185Q | T009E-T078N-N185Q | 60 |
| Chemgen-00688 | T009E-T078N-N218S | T009E-T078N-N218S | 79 |
| Chemgen-00818 | T009E-T078N-D259P | T009E-T078N-D259P | 80 |
| Chemgen-00687 | T009E-G166Q-N218S | T009E-G166Q-N218S | 95 |
| Chemgen-00686 | T009E-G166Q-D259P | T009E-G166Q-D259P | 100 |
| Chemgen-00705 | T009E-N185Q-N218S | T009E-N185Q-N218S | 60 |
| Chemgen-00685 | T009E-N185Q-D259P | T009E-N185Q-D259P | 51 |
| Chemgen-00878 | P040E-A069S-N076D | P040E-A069S-N076D | 85 |
| Chemgen-00876 | P040E-A069S-T078N | P040E-A069S-T078N | 83 |
| Chemgen-00868 | P040E-A069S-G166Q | P040E-A069S-G166Q | 63 |
| Chemgen-01310 | P040E-A069S-D259P | P040E-A069S-D259P | 64 |
| Chemgen-00761 | P040E-N076D-T078N | P040E-N076D-T078N | 100 |
| Chemgen-00642 | P040E-N076D-G166Q | P040E-N076D-G166Q | 100 |
| Chemgen-00660 | P040E-N076D-N185Q | P040E-N076D-N185Q | 100 |
| Chemgen-00641 | P040E-N076D-N218S | P040E-N076D-N218S | 95 |
| Chemgen-01465 | P040E-T078N-N185Q | P040E-T078N-N185Q | 90 |
| Chemgen-00758 | P040E-T078N-D259P | P040E-T078N-D259P | 100 |
| Chemgen-00872 | P040E-G166Q-N185Q | P040E-G166Q-N185Q | 88 |
| Chemgen-00873 | P040E-G166Q-N218S | P040E-G166Q-N218S | 79 |
| Chemgen-00752 | P040E-G166Q-D259P | P040E-G166Q-D259P | 84 |
| Chemgen-00750 | P040E-N185Q-N218S | P040E-N185Q-N218S | 66 |
| Chemgen-00851 | P040E-N185Q-D259P | P040E-N185Q-D259P | 87 |
| Chemgen-00845 | P040E-N218S-D259P | P040E-N218S-D259P | 83 |
| Chemgen-00844 | A069S-N076D-T078N | A069S-N076D-T078N | 100 |
| Chemgen-00746 | A069S-N076D-G166Q | A069S-N076D-G166Q | 100 |
| Chemgen-00748 | A069S-N076D-N185Q | A069S-N076D-N185Q | 79 |
| Chemgen-01054 | A069S-N076D-N218S | A069S-N076D-N218S | 94 |
| Chemgen-00744 | A069S-N076D-D259P | A069S-N076D-D259P | 100 |
| Chemgen-00861 | A069S-T078N-G166Q | A069S-T078N-G166Q | 100 |
| Chemgen-00860 | A069S-T078N-N185Q | A069S-T078N-N185Q | 78 |
| Chemgen-00859 | A069S-T078N-N218S | A069S-T078N-N218S | 86 |
| Chemgen-00756 | A069S-T078N-D259P | A069S-T078N-D259P | 78 |
| Chemgen-00862 | A069S-G166Q-N218S | A069S-G166Q-N218S | 100 |
| Chemgen-00753 | A069S-G166Q-D259P | A069S-G166Q-D259P | 91 |
| Chemgen-00659 | A069S-N185Q-N218S | A069S-N185Q-N218S | 60 |
| Chemgen-00863 | A069S-N185Q-D259P | A069S-N185Q-D259P | 58 |
| Chemgen-00864 | A069S-N218S-D259P | A069S-N218S-D259P | 79 |
| Chemgen-00645 | N076D-T078N-G166Q | N076D-T078N-G166Q | 100 |
| Chemgen-00865 | N076D-T078N-N218S | N076D-T078N-N218S | 90 |
| Chemgen-00866 | N076D-T078N-D259P | N076D-T078N-D259P | 89 |
| Chemgen-00770 | N076D-G166Q-N218S | N076D-G166Q-N218S | 100 |

TABLE 32-continued

Chemgen_164A subtilisin variants with improved stability in liquid detergent at 51° C. (reported as percent residual activity, % RA) compared to Chemgen_164A parent

| Chemgen_164A Variant Sample ID | Substitutions in Chemgen_164A numbering | Substitutions in BPN' numbering | % RA |
|---|---|---|---|
| Chemgen-01542 | N076D-G166Q-D259P | N076D-G166Q-D259P | 100 |
| Chemgen-00771 | N076D-N185Q-N218S | N076D-N185Q-N218S | 95 |
| Chemgen-00846 | N076D-N218S-D259P | N076D-N218S-D259P | 100 |
| Chemgen-00847 | T078N-G166Q-N185Q | T078N-G166Q-N185Q | 91 |
| Chemgen-00763 | T078N-G166Q-N218S | T078N-G166Q-N218S | 100 |
| Chemgen-00849 | T078N-N185Q-D259P | T078N-N185Q-D259P | 100 |
| Chemgen-00768 | T078N-N218S-D259P | T078N-N218S-D259P | 100 |
| Chemgen-00765 | G166Q-N185Q-N218S | G166Q-N185Q-N218S | 87 |
| Chemgen-00870 | G166Q-N185Q-D259P | G166Q-N185Q-D259P | 94 |
| Chemgen-00880 | G166Q-N218S-D259P | G166Q-N218S-D259P | 100 |
| Chemgen-00767 | N185Q-N218S-D259P | N185Q-N218S-D259P | 86 |
| Chemgen-01489 | T003V-T009E-P040E-N185Q | T003V-T009E-P040E-N185Q | 65 |
| Chemgen-01037 | T003V-T009E-A069S-T078N | T003V-T009E-A069S-T078N | 98 |
| Chemgen-01217 | T003V-P040E-G166Q-D259P | T003V-P040E-G166Q-D259P | 100 |
| Chemgen-01076 | T003V-N076D-T078N-D259P | T003V-N076D-T078N-D259P | 100 |
| Chemgen-01516 | T003V-N185Q-N218S-D259P | T003V-N185Q-N218S-D259P | 100 |
| Chemgen-01083 | T009E-P040E-A069S-T078N | T009E-P040E-A069S-T078N | 79 |
| Chemgen-01336 | T009E-P040E-A069S-N185Q | T009E-P040E-A069S-N185Q | 61 |
| Chemgen-00796 | T009E-P040E-A069S-D259P | T009E-P040E-A069S-D259P | 61 |
| Chemgen-01279 | T009E-P040E-N076D-T078N | T009E-P040E-N076D-T078N | 91 |
| Chemgen-01153 | T009E-P040E-T078N-N185Q | T009E-P040E-T078N-N185Q | 77 |
| Chemgen-01326 | T009E-P040E-N185Q-N218S | T009E-P040E-N185Q-N218S | 68 |
| Chemgen-01040 | T009E-P040E-N185Q-D259P | T009E-P040E-N185Q-D259P | 73 |
| Chemgen-01521 | T009E-A069S-N076D-G166Q | T009E-A069S-N076D-G166Q | 100 |
| Chemgen-01261 | T009E-A069S-N076D-N185Q | T009E-A069S-N076D-N185Q | 76 |
| Chemgen-01074 | T009E-N076D-G166Q-N218S | T009E-N076D-G166Q-N218S | 98 |
| Chemgen-01290 | T009E-T078N-G166Q-N185Q | T009E-T078N-G166Q-N185Q | 100 |
| Chemgen-01624 | P040E-A069S-T078N-N218S | P040E-A069S-T078N-N218S | 100 |
| Chemgen-01317 | P040E-A069S-G166Q-N218S | P040E-A069S-G166Q-N218S | 88 |
| Chemgen-01466 | P040E-A069S-G166Q-D259P | P040E-A069S-G166Q-D259P | 89 |
| Chemgen-01147 | P040E-N076D-T078N-N185Q | P040E-N076D-T078N-N185Q | 100 |
| Chemgen-01000 | P040E-N076D-T078N-N218S | P040E-N076D-T078N-N218S | 100 |
| Chemgen-01238 | P040E-N076D-G166Q-D259P | P040E-N076D-G166Q-D259P | 100 |
| Chemgen-01578 | P040E-T078N-N185Q-D259P | P040E-T078N-N185Q-D259P | 96 |
| Chemgen-01527 | P040E-T078N-N218S-D259P | P040E-T078N-N218S-D259P | 79 |
| Chemgen-01548 | A069S-N076D-T078N-N185Q | A069S-N076D-T078N-N185Q | 75 |
| Chemgen-01080 | A069S-N076D-T078N-D259P | A069S-N076D-T078N-D259P | 100 |
| Chemgen-01510 | A069S-N076D-G166Q-D259P | A069S-N076D-G166Q-D259P | 100 |
| Chemgen-01158 | A069S-T078N-G166Q-N185Q | A069S-T078N-G166Q-N185Q | 100 |
| Chemgen-01278 | A069S-T078N-N185Q-D259P | A069S-T078N-N185Q-D259P | 80 |
| Chemgen-01073 | N076D-T078N-G166Q-N218S | N076D-T078N-G166Q-N218S | 100 |
| Chemgen-01184 | N076D-T078N-G166Q-D259P | N076D-T078N-G166Q-D259P | 100 |
| Chemgen-01273 | N076D-T078N-N218S-D259P | N076D-T078N-N218S-D259P | 100 |
| Chemgen-01595 | T078N-N185Q-N218S-D259P | T078N-N185Q-N218S-D259P | 100 |

Example 15

Bpan01744 Subtilisin Variants with Improved Stability in Detergent

Variants of Bpan01744 (SEQ ID NO: 13) subtilisin containing three or four amino acid substitutions at positions of interest to increase enzyme stability were generated using methods similar to the ones described in Example 1. These variant samples were evaluated for detergent stability and cleaning performance using methods described in Example 2. Tables 33A and 33B show the results for Bpan01744 variants.

TABLE 33A

Bpan01744 subtilisin variants with improved stability in liquid detergent at 46° C. (reported as percent residual activity, % RA) compared to Bpan01744 parent

| | | | | Cleaning performance, PI | | |
|---|---|---|---|---|---|---|
| Bpan01744 Variant Sample ID | Substitutions in Bpan01744 numbering | Substitutions in BPN' numbering | % RA | BMI stain in PNB detergent | PAS-38 stain in GSM-B detergent | BMI stain in ECE-2 detergent |
| Bpan01744 | — | — | 11 | 1.0 | 1.0 | 1.0 |
| Bpan01744-00169 | S003V-A067S-N074D | S003V-A069S-N076D | 72 | 1.4 | 1.2 | 1.2 |
| Bpan01744-00248 | S003V-A067S-S127P | S003V-A069S-S129P | 48 | 1.2 | 1.4 | 1.1 |

TABLE 33A-continued

Bpan01744 subtilisin variants with improved stability in liquid detergent at 46° C. (reported as percent residual activity, % RA) compared to Bpan01744 parent

| Bpan01744 Variant Sample ID | Substitutions in Bpan01744 numbering | Substitutions in BPN' numbering | % RA | Cleaning performance, PI BMI stain in PNB detergent | PAS-38 stain in GSM-B detergent | BMI stain in ECE-2 detergent |
|---|---|---|---|---|---|---|
| Bpan01744-00150 | S003V-A067S-N179Q | S003V-A069S-N185Q | 29 | 1.2 | 1.2 | 1.2 |
| Bpan01744-00270 | S003V-N074D-S127P | S003V-N076D-S129P | 81 | 1.3 | 1.3 | 1.0 |
| Bpan01744-00170 | S003V-N074D-N179Q | S003V-N076D-N185Q | 74 | 1.5 | 1.2 | 1.2 |
| Bpan01744-00059 | S003V-S076N-G160Q | S003V-S078N-G166Q | 66 | 1.0 | 1.1 | 1.0 |
| Bpan01744-00518 | S003V-S127P-N253P | S003V-S129P-N259P | 40 | 1.2 | 1.1 | 1.3 |
| Bpan01744-00547 | S003V-G160Q-N212S | S003V-G166Q-N218S | 85 | 1.1 | 1.0 | 1.0 |
| Bpan01744-00291 | A067S-N074D-N179Q | A069S-N076D-N185Q | 73 | 1.2 | 1.5 | 1.2 |
| Bpan01744-00174 | A067S-G160Q-N179Q | A069S-G166Q-N185Q | 53 | 1.1 | 1.1 | 0.8 |
| Bpan01744-00228 | N074D-S076N-G160Q | N076D-S078N-G166Q | 100 | 1.2 | 1.1 | 0.8 |
| Bpan01744-00478 | N074D-S127P-N212S | N076D-S129P-N218S | 77 | 1.2 | 1.2 | 0.9 |
| Bpan01744-00040 | S076N-S127P-N253P | S078N-S129P-N259P | 43 | 1.3 | 1.1 | 1.2 |
| Bpan01744-00034 | S076N-N179Q-N253P | S078N-N185Q-N259P | 37 | 1.5 | 1.2 | 1.3 |
| Bpan01744-00224 | S003V-A067S-N074D-S076N | S003V-A069S-N076D-S078N | 79 | 1.2 | 1.1 | 1.0 |
| Bpan01744-00437 | S003V-A067S-N074D-N179Q | S003V-A069S-N076D-N185Q | 73 | 1.5 | 1.5 | 0.9 |
| Bpan01744-00104 | S003V-A067S-N074D-N253P | S003V-A069S-N076D-N259P | 75 | 1.2 | 1.2 | 1.3 |
| Bpan01744-00130 | S003V-A067S-S076N-S127P | S003V-A069S-S078N-S129P | 51 | 1.2 | 1.1 | 1.1 |
| Bpan01744-00468 | S003V-A067S-S076N-N179Q | S003V-A069S-S078N-N185Q | 50 | 1.2 | 1.2 | 1.0 |
| Bpan01744-00456 | S003V-A067S-S127P-N212S | S003V-A069S-S129P-N218S | 67 | 1.1 | 1.1 | 0.8 |
| Bpan01744-00474 | S003V-A067S-N179Q-N253P | S003V-A069S-N185Q-N259P | 32 | 1.1 | 0.2 | 1.1 |
| Bpan01744-00010 | S003V-N074D-S127P-G160Q | S003V-N076D-S129P-G166Q | 93 | 1.1 | 1.1 | 0.9 |
| Bpan01744-00155 | S003V-N074D-S127P-N179Q | S003V-N076D-S129P-N185Q | 84 | 1.3 | 1.1 | 1.2 |
| Bpan01744-00470 | S003V-N074D-S127P-N253P | S003V-N076D-S129P-N259P | 81 | 1.3 | 1.3 | 0.9 |
| Bpan01744-00562 | S003V-S076N-N179Q-N212S | S003V-S078N-N185Q-N218S | 78 | 2.2 | 1.4 | 1.4 |
| Bpan01744-00164 | S003V-S076N-N179Q-N253P | S003V-S078N-N185Q-N259P | 56 | 1.3 | 1.3 | 1.5 |
| Bpan01744-00435 | S003V-G160Q-N179Q-N253P | S003V-G166Q-N185Q-N259P | 57 | 1.1 | 1.3 | 1.0 |
| Bpan01744-00269 | S003V-N179Q-N212S-N253P | S003V-N185Q-N218S-N259P | 60 | 1.2 | 1.5 | 1.0 |
| Bpan01744-00259 | A067S-N074D-S076N-N212S | A069S-N076D-S078N-N218S | 84 | 1.3 | 1.2 | 0.9 |
| Bpan01744-00515 | A067S-N074D-N179Q-N253P | A069S-N076D-N185Q-N259P | 76 | 1.2 | 1.1 | 1.1 |
| Bpan01744-00272 | A067S-S076N-N179Q-N212S | A069S-S078N-N185Q-N218S | 74 | 1.2 | 0.3 | 0.8 |
| Bpan01744-00301 | A067S-S127P-G160Q-N212S | A069S-S129P-G166Q-N218S | 88 | 0.9 | 1.2 | 0.9 |
| Bpan01744-00573 | A067S-S127P-N179Q-N212S | A069S-S129P-N185Q-N218S | 57 | 1.6 | 1.3 | 1.4 |
| Bpan01744-00035 | A067S-G160Q-N212S-N253P | A069S-G166Q-N218S-N259P | 80 | 1.1 | 1.0 | 0.9 |
| Bpan01744-00479 | A067S-N179Q-N212S-N253P | A069S-N185Q-N218S-N259P | 50 | 1.3 | 1.3 | 0.9 |
| Bpan01744-00415 | N074D-S076N-S127P-N179Q | N076D-S078N-S129P-N185Q | 87 | 1.2 | 1.3 | 1.0 |
| Bpan01744-00452 | N074D-S076N-N179Q-N212S | N076D-S078N-N185Q-N218S | 85 | 1.2 | 1.4 | 1.0 |

TABLE 33A-continued

Bpan01744 subtilisin variants with improved stability in liquid detergent at 46° C. (reported as percent residual activity, % RA) compared to Bpan01744 parent

| Bpan01744 Variant Sample ID | Substitutions in Bpan01744 numbering | Substitutions in BPN' numbering | % RA | Cleaning performance, PI: BMI stain in PNB detergent | Cleaning performance, PI: PAS-38 stain in GSM-B detergent | Cleaning performance, PI: BMI stain in ECE-2 detergent |
|---|---|---|---|---|---|---|
| Bpan01744-00183 | N074D-S127P-N179Q-N212S | N076D-S129P-N185Q-N218S | 83 | 1.3 | 1.1 | 1.1 |
| Bpan01744-00261 | N074D-G160Q-N179Q-N253P | N076D-G166Q-N185Q-N259P | 100 | 1.1 | 1.3 | 0.9 |
| Bpan01744-00143 | S076N-S127P-G160Q-N253P | S078N-S129P-G166Q-N259P | 70 | 1.0 | 1.1 | 1.1 |
| Bpan01744-00246 | S076N-S127P-N179Q-N253P | S078N-S129P-N185Q-N259P | 50 | 1.3 | 1.3 | 1.1 |
| Bpan01744-00432 | S076N-G160Q-N212S-N253P | S078N-G166Q-N218S-N259P | 83 | 1.1 | 1.2 | 1.0 |
| Bpan01744-00300 | S127P-G160Q-N212S-N253P | S129P-G166Q-N218S-N259P | 77 | 1.1 | 1.1 | 0.8 |
| Bpan01744-00292 | S127P-N179Q-N212S-N253P | S129P-N185Q-N218S-N259P | 53 | 1.2 | 1.3 | 1.1 |

TABLE 33B

Bpan01744 subtilisin variants with improved stability in liquid detergent at 44° C. (reported as percent residual activity, % RA) compared to Bpan01744 parent

| Bpan01744 Variant Sample ID | Substitutions in Bpan01744 numbering | Substitutions in BPN' numbering | % RA |
|---|---|---|---|
| Bpan01744 | — | — | 19 |
| Bpan01744-01709 | S003V-S009E-A067S | S003V-S009E-A069S | 52 |
| Bpan01744-01195 | S003V-S009E-N074D | S003V-S009E-N076D | 91 |
| Bpan01744-01267 | S003V-S009E-S076N | S003V-S009E-S078N | 67 |
| Bpan01744-01140 | S003V-S009E-N179Q | S003V-S009E-N185Q | 62 |
| Bpan01744-01141 | S003V-S009E-N212S | S003V-S009E-N218S | 86 |
| Bpan01744-01315 | S003V-S009E-N253P | S003V-S009E-N259P | 59 |
| Bpan01744-01142 | S003V-A067S-S076N | S003V-A069S-S078N | 50 |
| Bpan01744-00677 | S003V-A067S-N212S | S003V-A069S-N218S | 62 |
| Bpan01744-01265 | S003V-N074D-S076N | S003V-N076D-S078N | 81 |
| Bpan01744-01585 | S003V-N074D-G160Q | S003V-N076D-G166Q | 100 |
| Bpan01744-01252 | S003V-N074D-N212S | S003V-N076D-N218S | 98 |
| Bpan01744-01253 | S003V-S076N-N179Q | S003V-S078N-N185Q | 52 |
| Bpan01744-01254 | S003V-S076N-N212S | S003V-S078N-N218S | 78 |
| Bpan01744-01260 | S003V-S076N-N253P | S003V-S078N-N259P | 49 |
| Bpan01744-01274 | S003V-N179Q-N212S | S003V-N185Q-N218S | 67 |
| Bpan01744-00685 | S003V-N179Q-N253P | S003V-N185Q-N259P | 39 |
| Bpan01744-01275 | S003V-N212S-N253P | S003V-N218S-N259P | 60 |
| Bpan01744-00693 | S009E-A067S-N074D | S009E-A069S-N076D | 77 |
| Bpan01744-00777 | S009E-A067S-S076N | S009E-A069S-S078N | 44 |
| Bpan01744-00898 | S009E-A067S-G160Q | S009E-A069S-G166Q | 100 |
| Bpan01744-01231 | S009E-A067S-N253P | S009E-A069S-N259P | 33 |
| Bpan01744-01236 | S009E-N074D-S076N | S009E-N076D-S078N | 92 |
| Bpan01744-01237 | S009E-N074D-G160Q | S009E-N076D-G166Q | 65 |
| Bpan01744-01238 | S009E-N074D-N179Q | S009E-N076D-N185Q | 90 |
| Bpan01744-01196 | S009E-N074D-N212S | S009E-N076D-N218S | 99 |
| Bpan01744-01307 | S009E-N074D-N253P | S009E-N076D-N259P | 73 |
| Bpan01744-01248 | S009E-S076N-N179Q | S009E-S078N-N185Q | 59 |
| Bpan01744-01241 | S009E-S076N-N212S | S009E-S078N-N218S | 85 |
| Bpan01744-01242 | S009E-S076N-N253P | S009E-S078N-N259P | 50 |
| Bpan01744-01165 | S009E-G160Q-N179Q | S009E-G166Q-N185Q | 65 |
| Bpan01744-01244 | S009E-G160Q-N212S | S009E-G166Q-N218S | 99 |
| Bpan01744-00976 | S009E-N179Q-N212S | S009E-N185Q-N218S | 78 |
| Bpan01744-01351 | S009E-N179Q-N253P | S009E-N185Q-N259P | 31 |
| Bpan01744-01157 | S009E-N212S-N253P | S009E-N218S-N259P | 68 |
| Bpan01744-00810 | A067S-N074D-S076N | A069S-N076D-S078N | 91 |
| Bpan01744-01159 | A067S-N074D-G160Q | A069S-N076D-G166Q | 74 |
| Bpan01744-00736 | A067S-N074D-N212S | A069S-N076D-N218S | 85 |
| Bpan01744-00888 | A067S-N074D-N253P | A069S-N076D-N259P | 71 |
| Bpan01744-01154 | A067S-S076N-N179Q | A069S-S078N-N185Q | 40 |
| Bpan01744-01162 | A067S-S076N-N212S | A069S-S078N-N218S | 70 |
| Bpan01744-01779 | A067S-S076N-N253P | A069S-S078N-N259P | 38 |
| Bpan01744-01885 | A067S-G160Q-N212S | A069S-G166Q-N218S | 100 |
| Bpan01744-00963 | A067S-N179Q-N212S | A069S-N185Q-N218S | 50 |

TABLE 33B-continued

Bpan01744 subtilisin variants with improved stability in liquid detergent at 44° C. (reported as percent residual activity, % RA) compared to Bpan01744 parent

| Bpan01744 Variant Sample ID | Substitutions in Bpan01744 numbering | Substitutions in BPN' numbering | % RA |
|---|---|---|---|
| Bpan01744-01174 | A067S-N212S-N253P | A069S-N218S-N259P | 44 |
| Bpan01744-01182 | N074D-S076N-N179Q | N076D-S078N-N185Q | 86 |
| Bpan01744-01173 | N074D-S076N-N212S | N076D-S078N-N218S | 95 |
| Bpan01744-01957 | N074D-S076N-N253P | N076D-S078N-N259P | 75 |
| Bpan01744-01170 | N074D-G160Q-N212S | N076D-G166Q-N218S | 100 |
| Bpan01744-01292 | N074D-N179Q-N212S | N076D-N185Q-N218S | 95 |
| Bpan01744-01289 | N074D-N179Q-N253P | N076D-N185Q-N259P | 76 |
| Bpan01744-01294 | S076N-G160Q-N212S | S078N-G166Q-N218S | 86 |
| Bpan01744-01717 | S076N-N179Q-N212S | S078N-N185Q-N218S | 73 |
| Bpan01744-01952 | S076N-N212S-N253P | S078N-N218S-N259P | 61 |
| Bpan01744-00899 | G160Q-N179Q-N212S | G166Q-N185Q-N218S | 96 |
| Bpan01744-01867 | N179Q-N212S-N253P | N185Q-N218S-N259P | 48 |
| Bpan01744-00749 | S003V-S009E-A067S-N179Q | S003V-S009E-A069S-N185Q | 58 |
| Bpan01744-02012 | S003V-S009E-N212S-N253P | S003V-S009E-N218S-N259P | 77 |
| Bpan01744-00879 | S003V-A067S-N074D-N212S | S003V-A069S-N076D-N218S | 94 |
| Bpan01744-02146 | S003V-A067S-N179Q-N212S | S003V-A069S-N185Q-N218S | 71 |
| Bpan01744-01874 | S003V-A067S-N212S-N253P | S003V-A069S-N218S-N259P | 59 |
| Bpan01744-01995 | S003V-N074D-N212S-N253P | S003V-N076D-N218S-N259P | 84 |
| Bpan01744-01812 | S003V-G160Q-N179Q-N212S | S003V-G166Q-N185Q-N218S | 87 |
| Bpan01744-00832 | S009E-A067S-N074D-S076N | S009E-A069S-N076D-S078N | 95 |
| Bpan01744-01838 | S009E-A067S-S076N-G160Q | S009E-A069S-S078N-G166Q | 44 |
| Bpan01744-01675 | S009E-A067S-S076N-N212S | S009E-A069S-S078N-N218S | 87 |
| Bpan01744-01985 | S009E-A067S-G160Q-N212S | S009E-A069S-G166Q-N218S | 59 |
| Bpan01744-00765 | S009E-A067S-N212S-N253P | S009E-A069S-N218S-N259P | 67 |
| Bpan01744-01907 | S009E-N074D-S076N-G160Q | S009E-N076D-S078N-G166Q | 77 |
| Bpan01744-02114 | S009E-N074D-S076N-N179Q | S009E-N076D-S078N-N185Q | 90 |
| Bpan01744-00845 | S009E-N074D-N212S-N253P | S009E-N076D-N218S-N259P | 89 |
| Bpan01744-01813 | S009E-S076N-N179Q-N212S | S009E-S078N-N185Q-N218S | 87 |
| Bpan01744-01847 | S009E-S076N-N212S-N253P | S009E-S078N-N218S-N259P | 80 |
| Bpan01744-00974 | S009E-G160Q-N179Q-N212S | S009E-G166Q-N185Q-N218S | 100 |
| Bpan01744-01036 | A067S-N074D-S076N-N253P | A069S-N076D-S078N-N259P | 81 |
| Bpan01744-00791 | A067S-S076N-G160Q-N212S | A069S-S078N-G166Q-N218S | 83 |
| Bpan01744-01856 | A067S-S076N-N179Q-N253P | A069S-S078N-N185Q-N259P | 36 |
| Bpan01744-00743 | A067S-S076N-N212S-N253P | A069S-S078N-N218S-N259P | 67 |
| Bpan01744-01873 | N074D-S076N-G160Q-N179Q | N076D-S078N-G166Q-N185Q | 100 |
| Bpan01744-00813 | N074D-S076N-G160Q-N212S | N076D-S078N-G166Q-N218S | 95 |
| Bpan01744-02034 | N074D-S076N-N212S-N253P | N076D-S078N-N218S-N259P | 86 |
| Bpan01744-02019 | N074D-G160Q-N179Q-N212S | N076D-G166Q-N185Q-N218S | 100 |
| Bpan01744-01690 | N074D-G160Q-N212S-N253P | N076D-G166Q-N218S-N259P | 86 |
| Bpan01744-00970 | N074D-N179Q-N212S-N253P | N076D-N185Q-N218S-N259P | 97 |
| Bpan01744-00912 | S076N-G160Q-N179Q-N212S | S078N-G166Q-N185Q-N218S | 95 |
| Bpan01744-01078 | S076N-G160Q-N179Q-N253P | S078N-G166Q-N185Q-N259P | 100 |

Example 16

DSM14391 Subtilisin Variants with Improved Stability in Detergent

Variants of DSM14391 (SEQ ID NO: 14) subtilisin containing three or four amino acid substitutions at positions of interest to increase enzyme stability, were generated using methods similar to the ones described in Example 1. These variant samples were evaluated for detergent stability and cleaning performance using methods described in Example 2. Tables 34A and 34B show the results for DSM14391 variants.

TABLE 34A

DSM14391 subtilisin variants with improved stability in liquid detergent at 36° C. (reported as percent residual activity, % RA) compared to DSM14391 parent

| DSM14391 Variant Sample ID | Substitutions in DSM14391 numbering | Substitutions in BPN' numbering | % RA | BMI stain in PNB detergent | PAS-38 stain in GSM-B detergent |
|---|---|---|---|---|---|
| DSM14391 | — | — | 11 | 1.0 | 1.0 |
| DSM14391-00421 | T003V-S039E-P212S | T003V-S040E-P218S | 93 | 1.2 | 1.1 |
| DSM14391-00214 | T003V-G160Q-P212S | T003V-G166Q-P218S | 100 | 0.9 | 1.1 |
| DSM14391-00359 | T003V-G160Q-N253P | T003V-G166Q-N259P | 75 | 1.0 | 1.2 |
| DSM14391-00272 | S039E-N074D-G160Q | S040E-N076D-G166Q | 100 | 1.3 | 1.2 |
| DSM14391-00469 | S039E-N074D-R179Q | S040E-N076D-R185Q | 96 | 1.5 | 1.3 |
| DSM14391-00251 | S039E-S076N-D127P | S040E-S078N-D129P | 59 | 1.0 | 1.1 |
| DSM14391-00281 | S039E-R179Q-P212S | S040E-R185Q-P218S | 100 | 1.4 | 1.1 |
| DSM14391-00293 | S039E-R179Q-N253P | S040E-R185Q-N259P | 100 | 1.6 | 1.2 |
| DSM14391-00474 | A067S-S076N-N253P | A069S-S078N-N259P | 32 | 1.1 | 1.2 |

TABLE 34A-continued

DSM14391 subtilisin variants with improved stability in liquid detergent at 36° C. (reported as percent residual activity, % RA) compared to DSM14391 parent

| DSM14391 Variant Sample ID | Substitutions in DSM14391 numbering | Substitutions in BPN' numbering | % RA | BMI stain in PNB detergent | PAS-38 stain in GSM-B detergent |
|---|---|---|---|---|---|
| DSM14391-00357 | A067S-D127P-P212S | A069S-D129P-P218S | 91 | 1.0 | 0.8 |
| DSM14391-00264 | A067S-P212S-N253P | A069S-P218S-N259P | 100 | 1.1 | 0.9 |
| DSM14391-00473 | N074D-R179Q-P212S | N076D-R185Q-P218S | 95 | 1.5 | 1.1 |
| DSM14391-00162 | N074D-P212S-N253P | N076D-P218S-N259P | 100 | 1.0 | 1.1 |
| DSM14391-00170 | S076N-R179Q-P212S | S078N-R185Q-P218S | 100 | 1.7 | 1.0 |
| DSM14391-00263 | S076N-P212S-N253P | S078N-P218S-N259P | 100 | 1.0 | 1.0 |
| DSM14391-00169 | T003V-S039E-A067S-N074D | T003V-S040E-A069S-N076D | 61 | 1.6 | 1.3 |
| DSM14391-00292 | T003V-S039E-N074D-S076N | T003V-S040E-N076D-S078N | 79 | 1.4 | 1.3 |
| DSM14391-00463 | T003V-S039E-N074D-D127P | T003V-S040E-N076D-D129P | 61 | 1.0 | 1.1 |
| DSM14391-00221 | T003V-S039E-G160Q-R179Q | T003V-S040E-G166Q-R185Q | 100 | 1.3 | 1.3 |
| DSM14391-00457 | T003V-S039E-G160Q-N253P | T003V-S040E-G166Q-N259P | 93 | 1.0 | 1.2 |
| DSM14391-00454 | T003V-A067S-R179Q-N253P | T003V-A069S-R185Q-N259P | 49 | 1.6 | 1.2 |
| DSM14391-00386 | T003V-N074D-S076N-N253P | T003V-N076D-S078N-N259P | 66 | 1.3 | 1.3 |
| DSM14391-00328 | T003V-N074D-R179Q-N253P | T003V-N076D-R185Q-N259P | 92 | 1.5 | 1.3 |
| DSM14391-00179 | T003V-S076N-D127P-N253P | T003V-S078N-D129P-N259P | 37 | 0.9 | 1.0 |
| DSM14391-00273 | T003V-S076N-P212S-N253P | T003V-S078N-P218S-N259P | 100 | 1.1 | 1.0 |
| DSM14391-00306 | S039E-N074D-S076N-R179Q | S040E-N076D-S078N-R185Q | 100 | 1.6 | 1.2 |
| DSM14391-00178 | S039E-N074D-P212S-N253P | S040E-N076D-P218S-N259P | 100 | 1.3 | 1.1 |
| DSM14391-00405 | S039E-S076N-G160Q-P212S | S040E-S078N-G166Q-P218S | 100 | 1.2 | 1.1 |
| DSM14391-00402 | S039E-R179Q-P212S-N253P | S040E-R185Q-P218S-N259P | 100 | 1.4 | 1.1 |
| DSM14391-00226 | A067S-D127P-R179Q-P212S | A069S-D129P-R185Q-P218S | 100 | 1.0 | 0.9 |
| DSM14391-00267 | A067S-R179Q-P212S-N253P | A069S-R185Q-P218S-N259P | 100 | 1.2 | 0.9 |
| DSM14391-00345 | S076N-D127P-R179Q-P212S | S078N-D129P-R185Q-P218S | 100 | 1.1 | 1.0 |
| DSM14391-00439 | D127P-R179Q-P212S-N253P | D129P-R185Q-P218S-N259P | 100 | 1.0 | 0.9 |

TABLE 34B

DSM14391 subtilisin variants with improved stability in liquid detergent at 30° C. (reported as percent residual activity, % RA) compared to DSM14391 parent

| DSM14391 Variant Sample ID | Substitutions in DSM14391 numbering | Substitutions in BPN' numbering | % RA |
|---|---|---|---|
| DSM14391 | — | — | 40 |
| DSM14391-00824 | T003V-T009E-S039E | T003V-T009E-S040E | 98 |
| DSM14391-00996 | T003V-T009E-A067S | T003V-T009E-A069S | 89 |
| DSM14391-00995 | T003V-T009E-N074D | T003V-T009E-N076D | 98 |
| DSM14391-00823 | T003V-T009E-S076N | T003V-T009E-S078N | 100 |
| DSM14391-00868 | T003V-T009E-R179Q | T003V-T009E-R185Q | 82 |
| DSM14391-00822 | T003V-T009E-P212S | T003V-T009E-P218S | 100 |
| DSM14391-00817 | T003V-T009E-N253P | T003V-T009E-N259P | 86 |
| DSM14391-00836 | T003V-S039E-A067S | T003V-S040E-A069S | 77 |
| DSM14391-00819 | T003V-S039E-N074D | T003V-S040E-N076D | 88 |
| DSM14391-00837 | T003V-S039E-S076N | T003V-S040E-S078N | 76 |
| DSM14391-01004 | T003V-S039E-R179Q | T003V-S040E-R185Q | 94 |
| DSM14391-00829 | T003V-S039E-N253P | T003V-S040E-N259P | 70 |
| DSM14391-00831 | T003V-A067S-N074D | T003V-A069S-N076D | 100 |
| DSM14391-00858 | T003V-A067S-R179Q | T003V-A069S-R185Q | 76 |
| DSM14391-00992 | T003V-A067S-P212S | T003V-A069S-P218S | 97 |
| DSM14391-00833 | T003V-N074D-S076N | T003V-N076D-S078N | 86 |
| DSM14391-01080 | T003V-N074D-R179Q | T003V-N076D-R185Q | 92 |
| DSM14391-01084 | T003V-N074D-P212S | T003V-N076D-P218S | 98 |
| DSM14391-01058 | T003V-N074D-N253P | T003V-N076D-N259P | 87 |

TABLE 34B-continued

DSM14391 subtilisin variants with improved stability in liquid detergent at 30° C. (reported as percent residual activity, % RA) compared to DSM14391 parent

| DSM14391 Variant Sample ID | Substitutions in DSM14391 numbering | Substitutions in BPN' numbering | % RA |
|---|---|---|---|
| DSM14391-00922 | T003V-S076N-R179Q | T003V-S078N-R185Q | 90 |
| DSM14391-01083 | T003V-S076N-P212S | T003V-S078N-P218S | 91 |
| DSM14391-01054 | T003V-S076N-N253P | T003V-S078N-N259P | 68 |
| DSM14391-00929 | T003V-R179Q-P212S | T003V-R185Q-P218S | 98 |
| DSM14391-01078 | T003V-R179Q-N253P | T003V-R185Q-N259P | 79 |
| DSM14391-00919 | T003V-P212S-N253P | T003V-P218S-N259P | 97 |
| DSM14391-00931 | T009E-S039E-N074D | T009E-S040E-N076D | 100 |
| DSM14391-00928 | T009E-S039E-S076N | T009E-S040E-S078N | 85 |
| DSM14391-01025 | T009E-S039E-R179Q | T009E-S040E-R185Q | 91 |
| DSM14391-01034 | T009E-S039E-P212S | T009E-S040E-P218S | 97 |
| DSM14391-00899 | T009E-S039E-N253P | T009E-S040E-N259P | 93 |
| DSM14391-01035 | T009E-A067S-S076N | T009E-A069S-S078N | 92 |
| DSM14391-01030 | T009E-A067S-P212S | T009E-A069S-P218S | 88 |
| DSM14391-01042 | T009E-A067S-N253P | T009E-A069S-N259P | 89 |
| DSM14391-01040 | T009E-N074D-S076N | T009E-N076D-S078N | 89 |
| DSM14391-00908 | T009E-N074D-R179Q | T009E-N076D-R185Q | 95 |
| DSM14391-01038 | T009E-N074D-P212S | T009E-N076D-P218S | 95 |
| DSM14391-01049 | T009E-N074D-N253P | T009E-N076D-N259P | 82 |
| DSM14391-00915 | T009E-S076N-R179Q | T009E-S078N-R185Q | 99 |
| DSM14391-01047 | T009E-S076N-P212S | T009E-S078N-P218S | 97 |
| DSM14391-01053 | T009E-S076N-N253P | T009E-S078N-N259P | 98 |
| DSM14391-01043 | T009E-G160Q-P212S | T009E-G166Q-P218S | 100 |
| DSM14391-00911 | T009E-R179Q-P212S | T009E-R185Q-P218S | 92 |
| DSM14391-00912 | T009E-R179Q-N253P | T009E-R185Q-N259P | 99 |
| DSM14391-01045 | T009E-P212S-N253P | T009E-P218S-N259P | 98 |
| DSM14391-01074 | S039E-A067S-N074D | S040E-A069S-N076D | 86 |
| DSM14391-00689 | S039E-A067S-R179Q | S040E-A069S-R185Q | 88 |
| DSM14391-01032 | S039E-A067S-P212S | S040E-A069S-P218S | 97 |
| DSM14391-01033 | S039E-A067S-N253P | S040E-A069S-N259P | 88 |
| DSM14391-01352 | S039E-N074D-S076N | S040E-N076D-S078N | 84 |
| DSM14391-00953 | S039E-N074D-P212S | S040E-N076D-P218S | 95 |
| DSM14391-00686 | S039E-N074D-N253P | S040E-N076D-N259P | 91 |
| DSM14391-01066 | S039E-S076N-R179Q | S040E-S078N-R185Q | 89 |
| DSM14391-01065 | S039E-S076N-P212S | S040E-S078N-P218S | 97 |
| DSM14391-00659 | S039E-S076N-N253P | S040E-S078N-N259P | 79 |
| DSM14391-00947 | S039E-G160Q-P212S | S040E-G166Q-P218S | 85 |
| DSM14391-00960 | S039E-P212S-N253P | S040E-P218S-N259P | 97 |
| DSM14391-00945 | A067S-N074D-S076N | A069S-N076D-S078N | 81 |
| DSM14391-01016 | A067S-N074D-R179Q | A069S-N076D-R185Q | 91 |
| DSM14391-01013 | A067S-N074D-P212S | A069S-N076D-P218S | 100 |
| DSM14391-01012 | A067S-N074D-N253P | A069S-N076D-N259P | 98 |
| DSM14391-00883 | A067S-S076N-R179Q | A069S-S078N-R185Q | 89 |
| DSM14391-01014 | A067S-S076N-P212S | A069S-S078N-P218S | 96 |
| DSM14391-01007 | A067S-G160Q-P212S | A069S-G166Q-P218S | 98 |
| DSM14391-01105 | A067S-R179Q-P212S | A069S-R185Q-P218S | 88 |
| DSM14391-00882 | A067S-R179Q-N253P | A069S-R185Q-N259P | 98 |
| DSM14391-01018 | N074D-S076N-R179Q | N076D-S078N-R185Q | 91 |
| DSM14391-01021 | N074D-S076N-P212S | N076D-S078N-P218S | 100 |
| DSM14391-01019 | N074D-S076N-N253P | N076D-S078N-N259P | 89 |
| DSM14391-01100 | N074D-G160Q-P212S | N076D-G166Q-P218S | 74 |
| DSM14391-01090 | S076N-G160Q-P212S | S078N-G166Q-P218S | 76 |
| DSM14391-01086 | S076N-R179Q-N253P | S078N-R185Q-N259P | 89 |
| DSM14391-00893 | G160Q-R179Q-P212S | G166Q-R185Q-P218S | 100 |
| DSM14391-01445 | G160Q-P212S-N253P | G166Q-P218S-N259P | 100 |
| DSM14391-00872 | R179Q-P212S-N253P | R185Q-P218S-N259P | 100 |
| DSM14391-01556 | T003V-T009E-S039E-N074D | T003V-T009E-S040E-N076D | 99 |
| DSM14391-01330 | T003V-A067S-S076N-P212S | T003V-A069S-S078N-P218S | 96 |
| DSM14391-01481 | T003V-G160Q-R179Q-P212S | T003V-G166Q-R185Q-P218S | 100 |
| DSM14391-01588 | T003V-R179Q-P212S-N253P | T003V-R185Q-P218S-N259P | 99 |
| DSM14391-01843 | T009E-S039E-A067S-P212S | T009E-S040E-A069S-P218S | 100 |
| DSM14391-01801 | T009E-A067S-N074D-R179Q | T009E-A069S-N076D-R185Q | 100 |
| DSM14391-01467 | T009E-N074D-S076N-R179Q | T009E-N076D-S078N-R185Q | 93 |
| DSM14391-01565 | T009E-N074D-G160Q-P212S | T009E-N076D-G166Q-P218S | 97 |
| DSM14391-01293 | T009E-S076N-R179Q-P212S | T009E-S078N-R185Q-P218S | 100 |
| DSM14391-01322 | S039E-A067S-S076N-P212S | S040E-A069S-S078N-P218S | 100 |
| DSM14391-01634 | S039E-A067S-G160Q-P212S | S040E-A069S-G166Q-P218S | 92 |
| DSM14391-01764 | S039E-N074D-G160Q-R179Q | S040E-N076D-G166Q-R185Q | 100 |
| DSM14391-01881 | S039E-N074D-G160Q-P212S | S040E-N076D-G166Q-P218S | 100 |
| DSM14391-01649 | A067S-N074D-S076N-N253P | A069S-N076D-S078N-N259P | 88 |
| DSM14391-01617 | A067S-S076N-R179Q-P212S | A069S-S078N-R185Q-P218S | 100 |
| DSM14391-01888 | N074D-S076N-G160Q-R179Q | N076D-S078N-G166Q-R185Q | 81 |
| DSM14391-01490 | S076N-G160Q-P212S-N253P | S078N-G166Q-P218S-N259P | 83 |
| DSM14391-01092 | S076N-R179Q-P212S-N253P | S078N-R185Q-P218S-N259P | 94 |

Example 17

BspAI02518 Subtilisin Variants with Improved Stability in Detergent

Variants of BspAI02518 (SEQ ID NO: 16) subtilisin containing three or four amino acid substitutions at positions of interest to increase enzyme stability, were generated using methods similar to the ones described in Example 1. These variant samples were evaluated for detergent stability and cleaning performance using methods described in Example 2. Table 35A and 35B show the results for BspAI02518 variants.

TABLE 35A

BspAI02518 subtilisin variants with improved stability in liquid detergent at 36° C. (reported as percent residual activity, % RA) compared to BspAI02518 parent

| | | | | Cleaning performance, PI | | |
|---|---|---|---|---|---|---|
| BspAI02518 Variant Sample ID | Substitutions in BspAI02518 numbering | Substitutions in BPN' numbering | % RA | BMI stain in PNB detergent | PAS-38 stain in GSM-B detergent | BMI stain in ECE-2 detergent |
| BspAI02518 | — | — | 12 | 1.0 | 1.0 | 1.0 |
| BspAI02518-00534 | S003V-A067S-N179Q | S003V-A069S-N185Q | 29 | 1.1 | 1.9 | 1.2 |
| BspAI02518-00467 | S003V-S076N-G126S | S003V-S078N-G128S | 38 | 1.1 | 1.2 | 1.0 |
| BspAI02518-00539 | S003V-N179Q-N253P | S003V-N185Q-N259P | 40 | 0.8 | 1.0 | 0.8 |
| BspAI02518-00442 | A067S-N074D-G126S | A069S-N076D-G128S | 57 | 1.6 | 5.4 | 1.9 |
| BspAI02518-00870 | A067S-N074D-N212S | A069S-N076D-N218S | 73 | 1.2 | 1.2 | 0.8 |
| BspAI02518-00868 | A067S-S076N-M122I | A069S-S078N-M124I | 23 | 1.1 | 1.3 | 0.9 |
| BspAI02518-00999 | N074D-S076N-N179Q | N076D-S078N-N185Q | 77 | 1.1 | 2.1 | 1.5 |
| BspAI02518-00507 | N074D-S076N-N212S | N076D-S078N-N218S | 86 | 1.0 | 1.0 | 0.9 |
| BspAI02518-00939 | N074D-G126S-S160Q | N076D-G128S-S166Q | 69 | 1.5 | 2.8 | 1.5 |
| BspAI02518-00708 | M122I-G126S-N179Q | M124I-G128S-N185Q | 21 | 1.2 | 1.1 | 0.6 |
| BspAI02518-00607 | G126S-S160Q-N179Q | G128S-S166Q-N185Q | 40 | 1.3 | 1.8 | 1.0 |
| BspAI02518-01017 | S003V-A067S-N074D-G126S | S003V-A069S-N076D-G128S | 62 | 1.5 | 4.8 | 1.8 |
| BspAI02518-00435 | S003V-A067S-S076N-G126S | S003V-A069S-S078N-G128S | 32 | 1.1 | 1.7 | 1.2 |
| BspAI02518-00768 | S003V-A067S-S076N-S160Q | S003V-A069S-S078N-S166Q | 60 | 0.9 | 1.9 | 1.4 |
| BspAI02518-00518 | S003V-A067S-M122I-N212S | S003V-A069S-M124I-N218S | 56 | 1.0 | 1.0 | 1.0 |
| BspAI02518-00555 | S003V-A067S-G126S-S160Q | S003V-A069S-G128S-S166Q | 47 | 1.4 | 2.3 | 1.8 |
| BspAI02518-00887 | S003V-A067S-G126S-N253P | S003V-A069S-G128S-N259P | 18 | 1.3 | 1.0 | 0.8 |
| BspAI02518-00658 | S003V-N074D-S160Q-N179Q | S003V-N076D-S166Q-N185Q | 88 | 1.2 | 1.6 | 1.0 |
| BspAI02518-01005 | S003V-S076N-M122I-S160Q | S003V-S078N-M124I-S166Q | 70 | 1.0 | 1.0 | 0.8 |
| BspAI02518-00556 | S003V-S076N-G126S-N179Q | S003V-S078N-G128S-N185Q | 50 | 1.0 | 1.1 | 1.0 |
| BspAI02518-00509 | S003V-S076N-G126S-N212S | S003V-S078N-G128S-N218S | 75 | 1.0 | 1.0 | 0.9 |
| BspAI02518-00648 | S003V-M122I-S160Q-N253P | S003V-M124I-S166Q-N259P | 60 | 0.9 | 1.2 | 0.8 |
| BspAI02518-00840 | S003V-M122I-N179Q-N253P | S003V-M124I-N185Q-N259P | 36 | 1.1 | 1.2 | 0.8 |
| BspAI02518-00877 | S003V-G126S-N179Q-N212S | S003V-G128S-N185Q-N218S | 60 | 1.2 | 1.1 | 0.8 |
| BspAI02518-00567 | S003V-G126S-N212S-N253P | S003V-G128S-N218S-N259P | 60 | 1.0 | 1.0 | 0.7 |
| BspAI02518-00615 | S003V-S160Q-N212S-N253P | S003V-S166Q-N218S-N259P | 83 | 0.8 | 1.0 | 0.8 |
| BspAI02518-00738 | A067S-N074D-S076N-G126S | A069S-N076D-S078N-G128S | 66 | 1.7 | 10.9 | 2.8 |
| BspAI02518-00888 | A067S-N074D-M122I-G126S | A069S-N076D-M124I-G128S | 70 | 1.5 | 2.6 | 0.8 |
| BspAI02518-00581 | A067S-N074D-S160Q-N212S | A069S-N076D-S166Q-N218S | 89 | 1.2 | 2.4 | 1.8 |
| BspAI02518-00919 | A067S-N074D-N179Q-N253P | A069S-N076D-N185Q-N259P | 57 | 1.4 | 2.2 | 1.4 |

TABLE 35A-continued

BspAI02518 subtilisin variants with improved stability in liquid detergent at 36° C. (reported as percent residual activity, % RA) compared to BspAI02518 parent

| BspAI02518 Variant Sample ID | Substitutions in BspAI02518 numbering | Substitutions in BPN' numbering | % RA | Cleaning performance, PI | | |
|---|---|---|---|---|---|---|
| | | | | BMI stain in PNB detergent | PAS-38 stain in GSM-B detergent | BMI stain in ECE-2 detergent |
| BspAI02518-00530 | A067S-N074D-N212S-N253P | A069S-N076D-N218S-N259P | 76 | 1.3 | 1.3 | 1.1 |
| BspAI02518-00745 | A067S-S076N-G126S-N212S | A069S-S078N-G128S-N218S | 57 | 0.9 | 1.0 | 0.9 |
| BspAI02518-00978 | A067S-S076N-N179Q-N253P | A069S-S078N-N185Q-N259P | 34 | 0.9 | 1.3 | 1.1 |
| BspAI02518-00508 | A067S-M122I-G126S-N179Q | A069S-M124I-G128S-N185Q | 39 | 1.1 | 1.2 | 0.3 |
| BspAI02518-00921 | A067S-M122I-G126S-N212S | A069S-M124I-G128S-N218S | 36 | 1.2 | 1.1 | 0.7 |
| BspAI02518-00699 | A067S-G126S-S160Q-N212S | A069S-G128S-S166Q-N218S | 71 | 1.4 | 1.6 | 1.2 |
| BspAI02518-01013 | A067S-G126S-N212S-N253P | A069S-G128S-N218S-N259P | 43 | 1.0 | 0.8 | 0.7 |
| BspAI02518-00815 | N074D-S160Q-N179Q-N253P | N076D-S166Q-N185Q-N259P | 78 | 0.9 | 1.2 | 0.7 |
| BspAI02518-00867 | S076N-M122I-G126S-N212S | S078N-M124I-G128S-N218S | 56 | 1.1 | 1.1 | 0.5 |
| BspAI02518-00702 | S076N-N179Q-N212S-N253P | S078N-N185Q-N218S-N259P | 75 | 1.1 | 1.2 | 1.0 |
| BspAI02518-00866 | M122I-G126S-S160Q-N253P | M124I-G128S-S166Q-N259P | 43 | 1.0 | 1.1 | 0.4 |
| BspAI02518-00885 | M122I-S160Q-N212S-N253P | M124I-S166Q-N218S-N259P | 78 | 1.0 | 1.0 | 0.8 |
| BspAI02518-00504 | G126S-S160Q-N179Q-N253P | G128S-S166Q-N185Q-N259P | 38 | 1.2 | 1.1 | 0.9 |

TABLE 35B

BspAI02518 subtilisin variants with improved stability in liquid detergent at 30° C. (reported as percent residual activity, % RA) compared to BspAI02518 parent

| BspAI02518 Variant Sample ID | Substitutions in BspAI02518 numbering | Substitutions in BPN' numbering | % RA |
|---|---|---|---|
| BspAI02518 | — | — | 32 |
| BspAI02518-01092 | S003V-S009E-A067S | S003V-S009E-A069S | 68 |
| BspAI02518-01095 | S003V-S009E-N074D | S003V-S009E-N076D | 93 |
| BspAI02518-01270 | S003V-S009E-S076N | S003V-S009E-S078N | 74 |
| BspAI02518-01096 | S003V-S009E-S160Q | S003V-S009E-S166Q | 87 |
| BspAI02518-01276 | S003V-S009E-N179Q | S003V-S009E-N185Q | 75 |
| BspAI02518-01097 | S003V-S009E-N212S | S003V-S009E-N218S | 90 |
| BspAI02518-01282 | S003V-S009E-N253P | S003V-S009E-N259P | 100 |
| BspAI02518-01085 | S003V-A067S-N074D | S003V-A069S-N076D | 84 |
| BspAI02518-01086 | S003V-A067S-S076N | S003V-A069S-S078N | 61 |
| BspAI02518-01087 | S003V-A067S-N212S | S003V-A069S-N218S | 71 |
| BspAI02518-01088 | S003V-N074D-S076N | S003V-N076D-S078N | 83 |
| BspAI02518-01250 | S003V-N074D-S160Q | S003V-N076D-S166Q | 88 |
| BspAI02518-01084 | S003V-N074D-N179Q | S003V-N076D-N185Q | 89 |
| BspAI02518-01220 | S003V-N074D-N212S | S003V-N076D-N218S | 83 |
| BspAI02518-01230 | S003V-N074D-N253P | S003V-N076D-N259P | 73 |
| BspAI02518-01222 | S003V-S076N-S160Q | S003V-S078N-S166Q | 80 |
| BspAI02518-01895 | S003V-S076N-N179Q | S003V-S078N-N185Q | 68 |
| BspAI02518-01231 | S003V-S076N-N212S | S003V-S078N-N218S | 83 |
| BspAI02518-01992 | S003V-S076N-N253P | S003V-S078N-N259P | 65 |
| BspAI02518-01110 | S003V-S160Q-N179Q | S003V-S166Q-N185Q | 70 |
| BspAI02518-02118 | S003V-S160Q-N253P | S003V-S166Q-N259P | 76 |
| BspAI02518-01099 | S003V-N179Q-N212S | S003V-N185Q-N218S | 83 |
| BspAI02518-01960 | S003V-N212S-N253P | S003V-N218S-N259P | 74 |
| BspAI02518-01238 | S009E-A067S-N074D | S009E-A069S-N076D | 81 |
| BspAI02518-01102 | S009E-A067S-N179Q | S009E-A069S-N185Q | 70 |
| BspAI02518-01165 | S009E-A067S-N212S | S009E-A069S-N218S | 83 |
| BspAI02518-01105 | S009E-N074D-S076N | S009E-N076D-S078N | 89 |
| BspAI02518-01235 | S009E-N074D-S160Q | S009E-N076D-S166Q | 94 |
| BspAI02518-01153 | S009E-N074D-N179Q | S009E-N076D-N185Q | 87 |
| BspAI02518-02121 | S009E-N074D-N212S | S009E-N076D-N218S | 99 |
| BspAI02518-01107 | S009E-N074D-N253P | S009E-N076D-N259P | 80 |
| BspAI02518-02083 | S009E-S076N-S160Q | S009E-S078N-S166Q | 80 |

TABLE 35B-continued

BspAI02518 subtilisin variants with improved stability in liquid detergent at 30° C. (reported as percent residual activity, % RA) compared to BspAI02518 parent

| BspAI02518 Variant Sample ID | Substitutions in BspAI02518 numbering | Substitutions in BPN' numbering | % RA |
|---|---|---|---|
| BspAI02518-01268 | S009E-S076N-N179Q | S009E-S078N-N185Q | 67 |
| BspAI02518-01140 | S009E-S076N-N212S | S009E-S078N-N218S | 88 |
| BspAI02518-01142 | S009E-S076N-N253P | S009E-S078N-N259P | 72 |
| BspAI02518-01167 | S009E-S160Q-N179Q | S009E-S166Q-N185Q | 81 |
| BspAI02518-01138 | S009E-S160Q-N212S | S009E-S166Q-N218S | 90 |
| BspAI02518-01226 | S009E-S160Q-N253P | S009E-S166Q-N259P | 82 |
| BspAI02518-01227 | S009E-N179Q-N212S | S009E-N185Q-N218S | 80 |
| BspAI02518-01148 | S009E-N179Q-N253P | S009E-N185Q-N259P | 56 |
| BspAI02518-01251 | S009E-N212S-N253P | S009E-N218S-N259P | 87 |
| BspAI02518-01243 | A067S-N074D-S076N | A069S-N076D-S078N | 86 |
| BspAI02518-01245 | A067S-N074D-S160Q | A069S-N076D-S166Q | 86 |
| BspAI02518-01139 | A067S-N074D-N179Q | A069S-N076D-N185Q | 75 |
| BspAI02518-01219 | A067S-N074D-N253P | A069S-N076D-N259P | 70 |
| BspAI02518-01205 | A067S-S076N-S160Q | A069S-S078N-S166Q | 74 |
| BspAI02518-01207 | A067S-S076N-N212S | A069S-S078N-N218S | 80 |
| BspAI02518-01166 | A067S-S160Q-N179Q | A069S-S166Q-N185Q | 66 |
| BspAI02518-01201 | A067S-S160Q-N212S | A069S-S166Q-N218S | 84 |
| BspAI02518-01151 | A067S-S160Q-N253P | A069S-S166Q-N259P | 64 |
| BspAI02518-01215 | A067S-N179Q-N212S | A069S-N185Q-N218S | 73 |
| BspAI02518-01202 | A067S-N212S-N253P | A069S-N218S-N259P | 69 |
| BspAI02518-01199 | N074D-S076N-S160Q | N076D-S078N-S166Q | 93 |
| BspAI02518-01218 | N074D-S076N-N253P | N076D-S078N-N259P | 76 |
| BspAI02518-01210 | N074D-S160Q-N179Q | N076D-S166Q-N185Q | 85 |
| BspAI02518-01211 | N074D-S160Q-N212S | N076D-S166Q-N218S | 96 |
| BspAI02518-01212 | N074D-S160Q-N253P | N076D-S166Q-N259P | 91 |
| BspAI02518-01124 | N074D-N179Q-N212S | N076D-N185Q-N218S | 92 |
| BspAI02518-01132 | N074D-N179Q-N253P | N076D-N185Q-N259P | 80 |
| BspAI02518-01122 | N074D-N212S-N253P | N076D-N218S-N259P | 88 |
| BspAI02518-02142 | S076N-S160Q-N179Q | S078N-S166Q-N185Q | 89 |
| BspAI02518-01128 | S076N-S160Q-N212S | S078N-S166Q-N218S | 89 |
| BspAI02518-01119 | S076N-S160Q-N253P | S078N-S166Q-N259P | 67 |
| BspAI02518-01114 | S076N-N179Q-N212S | S078N-N185Q-N218S | 83 |
| BspAI02518-01263 | S076N-N179Q-N253P | S078N-N185Q-N259P | 62 |
| BspAI02518-01115 | S076N-N212S-N253P | S078N-N218S-N259P | 79 |
| BspAI02518-01265 | S160Q-N179Q-N212S | S166Q-N185Q-N218S | 86 |
| BspAI02518-01117 | S160Q-N179Q-N253P | S166Q-N185Q-N259P | 65 |
| BspAI02518-01116 | S160Q-N212S-N253P | S166Q-N218S-N259P | 84 |
| BspAI02518-01621 | S003V-S009E-N074D-S160Q | S003V-S009E-N076D-S166Q | 100 |
| BspAI02518-02172 | S003V-A067S-S076N-N253P | S003V-A069S-S078N-N259P | 64 |
| BspAI02518-02095 | S003V-A067S-S160Q-N212S | S003V-A069S-S166Q-N218S | 93 |
| BspAI02518-01687 | S003V-N074D-S076N-S160Q | S003V-N076D-S078N-S166Q | 96 |
| BspAI02518-01786 | S003V-N074D-S076N-N253P | S003V-N076D-S078N-N259P | 82 |
| BspAI02518-01818 | S003V-N074D-S160Q-N253P | S003V-N076D-S166Q-N259P | 95 |
| BspAI02518-01782 | S003V-S160Q-N179Q-N253P | S003V-S166Q-N185Q-N259P | 82 |
| BspAI02518-02090 | S009E-A067S-N074D-S160Q | S009E-A069S-N076D-S166Q | 85 |
| BspAI02518-01666 | S009E-A067S-N074D-N212S | S009E-A069S-N076D-N218S | 87 |
| BspAI02518-01743 | S009E-A067S-N074D-N253P | S009E-A069S-N076D-N259P | 86 |
| BspAI02518-01859 | S009E-A067S-S076N-S160Q | S009E-A069S-S078N-S166Q | 84 |
| BspAI02518-01646 | S009E-A067S-S076N-N212S | S009E-A069S-S078N-N218S | 81 |
| BspAI02518-01924 | S009E-A067S-S160Q-N253P | S009E-A069S-S166Q-N259P | 88 |
| BspAI02518-01696 | S009E-N074D-S076N-N253P | S009E-N076D-S078N-N259P | 92 |
| BspAI02518-02000 | S009E-N074D-S160Q-N179Q | S009E-N076D-S166Q-N185Q | 89 |
| BspAI02518-01753 | S009E-N074D-S160Q-N253P | S009E-N076D-S166Q-N259P | 94 |
| BspAI02518-01299 | S009E-N074D-N179Q-N212S | S009E-N076D-N185Q-N218S | 93 |
| BspAI02518-01620 | S009E-N074D-N179Q-N253P | S009E-N076D-N185Q-N259P | 75 |
| BspAI02518-01959 | S009E-S076N-S160Q-N212S | S009E-S078N-S166Q-N218S | 96 |
| BspAI02518-01703 | S009E-S076N-N179Q-N253P | S009E-S078N-N185Q-N259P | 77 |
| BspAI02518-01628 | S009E-S076N-N212S-N253P | S009E-S078N-N218S-N259P | 94 |
| BspAI02518-01708 | A067S-N074D-S076N-N212S | A069S-N076D-S078N-N218S | 97 |
| BspAI02518-01144 | A067S-N074D-S160Q-N179Q | A069S-N076D-S166Q-N185Q | 93 |
| BspAI02518-01638 | A067S-N074D-N179Q-N212S | A069S-N076D-N185Q-N218S | 85 |
| BspAI02518-01256 | A067S-S076N-S160Q-N212S | A069S-S078N-S166Q-N218S | 94 |
| BspAI02518-01627 | A067S-S076N-N179Q-N212S | A069S-S078N-N185Q-N218S | 86 |
| BspAI02518-01693 | A067S-S076N-N212S-N253P | A069S-S078N-N218S-N259P | 87 |
| BspAI02518-01677 | A067S-S160Q-N179Q-N212S | A069S-S166Q-N185Q-N218S | 81 |
| BspAI02518-01730 | A067S-S160Q-N179Q-N253P | A069S-S166Q-N185Q-N259P | 60 |
| BspAI02518-01887 | N074D-S076N-S160Q-N212S | N076D-S078N-S166Q-N218S | 100 |
| BspAI02518-01778 | N074D-S076N-N179Q-N212S | N076D-S078N-N185Q-N218S | 98 |
| BspAI02518-01581 | N074D-S076N-N179Q-N253P | N076D-S078N-N185Q-N259P | 76 |
| BspAI02518-01720 | N074D-S076N-N212S-N253P | N076D-S078N-N218S-N259P | 96 |
| BspAI02518-01842 | N074D-S160Q-N179Q-N212S | N076D-S166Q-N185Q-N218S | 100 |
| BspAI02518-02079 | N074D-S160Q-N212S-N253P | N076D-S166Q-N218S-N259P | 86 |
| BspAI02518-02016 | N074D-N179Q-N212S-N253P | N076D-N185Q-N218S-N259P | 93 |
| BspAI02518-01792 | S076N-S160Q-N179Q-N212S | S078N-S166Q-N185Q-N218S | 93 |

TABLE 35B-continued

BspAI02518 subtilisin variants with improved stability in liquid detergent at 30° C. (reported as percent residual activity, % RA) compared to BspAI02518 parent

| BspAI02518 Variant Sample ID | Substitutions in BspAI02518 numbering | Substitutions in BPN' numbering | % RA |
|---|---|---|---|
| BspAI02518-02157 | S076N-S160Q-N179Q-N253P | S078N-S166Q-N185Q-N259P | 93 |
| BspAI02518-01716 | S160Q-N179Q-N212S-N253P | S166Q-N185Q-N218S-N259P | 88 |

Example 18

Bad02409 Subtilisin Variants with Improved Stability in Detergent

Variants of Bad02409 (SEQ ID NO: 18) subtilisin containing three or four amino acid substitutions at positions of interest to increase enzyme stability, were generated using methods similar to the ones described in Example 1. These variant samples were evaluated for detergent stability and cleaning performance using methods described in Example 2. Table 36 shows the results for Bad02409 variants.

TABLE 36

Bad02409 subtilisin variants with improved stability in liquid detergent at 67° C. (reported as percent residual activity, % RA) compared to Bad02409 parent

| | | | | Cleaning performance, PI | |
|---|---|---|---|---|---|
| Bad02409 Variant Sample ID | Substitutions in Bad02409 numbering | Substitutions in BPN' numbering | % RA | BMI stain in PNB detergent | PAS-38 stain in GSM-B detergent |
| Bad02409 | — | — | 21 | 1.0 | 1.0 |
| Bad02409-00464 | T003V-A071S-G169Q | T003V-A069S-G166Q | 47 | 1.4 | 1.1 |
| Bad02409-00516 | T003V-N078D-D262P | T003V-N076D-D259P | 76 | 1.1 | 0.9 |
| Bad02409-00380 | T003V-S080N-N188Q | T003V-S078N-N185Q | 51 | 1.0 | 1.2 |
| Bad02409-00327 | T003V-S131P-N188Q | T003V-S129P-N185Q | 40 | 1.0 | 1.2 |
| Bad02409-00323 | T003V-G169Q-D262P | T003V-G166Q-D259P | 43 | 1.2 | 1.1 |
| Bad02409-00167 | T003V-N188Q-D262P | T003V-N185Q-D259P | 45 | 0.9 | 1.1 |
| Bad02409-00548 | A071S-N078D-G169Q | A069S-N076D-G166Q | 73 | 1.1 | 0.9 |
| Bad02409-00344 | N078D-G169Q-N188Q | N076D-G166Q-N185Q | 64 | 1.4 | 1.1 |
| Bad02409-00417 | T003V-A071S-S080N-S131P | T003V-A069S-S078N-S129P | 55 | 1.0 | 1.0 |
| Bad02409-00014 | T003V-N078D-N188Q-D262P | T003V-N076D-N185Q-D259P | 55 | 1.0 | 1.2 |
| Bad02409-00195 | T003V-S080N-S131P-N188Q | T003V-S078N-S129P-N185Q | 52 | 1.4 | 1.2 |
| Bad02409-00098 | T003V-S080N-G169Q-D262P | T003V-S078N-G166Q-D259P | 77 | 1.3 | 1.1 |
| Bad02409-00455 | T003V-G169Q-N188Q-D262P | T003V-G166Q-N185Q-D259P | 46 | 1.2 | 1.2 |
| Bad02409-00209 | A071S-N078D-S131P-D262P | A069S-N076D-S129P-D259P | 82 | 0.9 | 1.1 |
| Bad02409-00465 | A071S-S080N-S131P-N188Q | A069S-S078N-S129P-N185Q | 47 | 1.3 | 1.0 |
| Bad02409-00130 | A071S-S131P-G169Q-N188Q | A069S-S129P-G166Q-N185Q | 38 | 1.5 | 1.0 |
| Bad02409-00349 | N078D-S080N-S131P-N188Q | N076D-S078N-S129P-N185Q | 71 | 0.9 | 1.0 |
| Bad02409-00469 | N078D-S131P-G169Q-D262P | N076D-S129P-G166Q-D259P | 80 | 1.0 | 1.0 |
| Bad02409-00444 | N078D-G169Q-N188Q-D262P | N076D-G166Q-N185Q-D259P | 66 | 1.3 | 1.2 |

Example 19

Bba02069 Subtilisin Variants with Improved Stability in Detergent

Variants of Bba02069 (SEQ ID NO: 19) subtilisin containing three or four amino acid substitutions at positions of interest to increase enzyme stability, were generated using methods similar to the ones described in Example 1. These variant samples were evaluated for detergent stability and cleaning performance using methods described in Example 2. Table 37A and 37B show the results for Bba02069 variants.

TABLE 37A

Bba02069 subtilisin variants with improved stability in liquid detergent at 40° C. (reported as percent residual activity, % RA) compared to Bba02069 parent

| Bba02069 Variant Sample ID | Substitutions in Bba02069 numbering | Substitutions in BPN' numbering | % RA | Cleaning performance, PI: BMI stain in PNB detergent | Cleaning performance, PI: PAS-38 stain in GSM-B detergent | Cleaning performance, PI: BMI stain in ECE-2 detergent |
|---|---|---|---|---|---|---|
| Bba02069 | — | — | 30 | 1.0 | 1.0 | 1.0 |
| Bba02069-00013 | Q003V-P040E-G167Q | Q003V-P040E-G166Q | 85 | 0.9 | 1.2 | 0.9 |
| Bba02069-00471 | Q003V-G167Q-S260P | Q003V-G166Q-S259P | 84 | 0.8 | 1.0 | 1.2 |
| Bba02069-00211 | A069S-S129P-G167Q | A069S-S129P-G166Q | 68 | 0.9 | 1.0 | 0.9 |
| Bba02069-00305 | A069S-S129P-V186Q | A069S-S129P-V185Q | 59 | 1.0 | 0.5 | 0.7 |
| Bba02069-00443 | G128S-S129P-N219S | G128S-S129P-N218S | 54 | 0.9 | 1.0 | 0.9 |
| Bba02069-00510 | G128S-V186Q-N219S | G128S-V185Q-N218S | 74 | 0.7 | 1.1 | 0.9 |
| Bba02069-00170 | Q003V-A069S-S129P-S260P | Q003V-A069S-S129P-S259P | 84 | 0.7 | 1.0 | 1.0 |
| Bba02069-00558 | Q003V-M124I-G128S-G167Q | Q003V-M124I-G128S-G166Q | 100 | 0.6 | 1.3 | 0.7 |
| Bba02069-00196 | Q003V-G128S-S129P-V186Q | Q003V-G128S-S129P-V185Q | 73 | 0.8 | 1.2 | 0.9 |
| Bba02069-00183 | P040E-A069S-S129P-N219S | P040E-A069S-S129P-N218S | 82 | 1.1 | 1.0 | 0.9 |
| Bba02069-00248 | P040E-M124I-N219S-S260P | P040E-M124I-N218S-S259P | 87 | 0.9 | 1.2 | 0.6 |
| Bba02069-00543 | A069S-N076D-S129P-G167Q | A069S-N076D-S129P-G166Q | 96 | 1.0 | 1.0 | 1.1 |
| Bba02069-00437 | A069S-M124I-S129P-S260P | A069S-M124I-S129P-S259P | 77 | 0.9 | 1.3 | 0.7 |
| Bba02069-00469 | A069S-M124I-V186Q-N219S | A069S-M124I-V185Q-N218S | 83 | 0.6 | 1.2 | 0.5 |
| Bba02069-00022 | G128S-G167Q-V186Q-N219S | G128S-G166Q-V185Q-N218S | 76 | 0.9 | 0.9 | 1.0 |
| Bba02069-00484 | S129P-G167Q-V186Q-S260P | S129P-G166Q-V185Q-S259P | 62 | 0.8 | 1.2 | 1.1 |

TABLE 37B

Bba02069 subtilisin variants with improved stability in liquid detergent at 39° C. (reported as percent residual activity, % RA) compared to Bba02069 parent

| Bba02069 Variant Sample ID | Substitutions in Bba02069 numbering | Substitutions in BPN' numbering | % RA |
|---|---|---|---|
| Bba02069 | — | — | 23 |
| Bba02069-00812 | Q003V-T009E-P040E | Q003V-T009E-P040E | 88 |
| Bba02069-00811 | Q003V-T009E-A069S | Q003V-T009E-A069S | 77 |
| Bba02069-00809 | Q003V-T009E-N076D | Q003V-T009E-N076D | 100 |
| Bba02069-00744 | Q003V-T009E-G167Q | Q003V-T009E-G166Q | 95 |
| Bba02069-00808 | Q003V-T009E-V186Q | Q003V-T009E-V185Q | 83 |
| Bba02069-00829 | Q003V-T009E-N219S | Q003V-T009E-N218S | 98 |
| Bba02069-00843 | Q003V-T009E-S260P | Q003V-T009E-S259P | 86 |
| Bba02069-00747 | Q003V-P040E-A069S | Q003V-P040E-A069S | 89 |
| Bba02069-00833 | Q003V-P040E-N076D | Q003V-P040E-N076D | 88 |
| Bba02069-00664 | Q003V-P040E-V186Q | Q003V-P040E-V185Q | 74 |
| Bba02069-00781 | Q003V-P040E-N219S | Q003V-P040E-N218S | 74 |
| Bba02069-00834 | Q003V-P040E-S260P | Q003V-P040E-S259P | 84 |
| Bba02069-00779 | Q003V-A069S-N076D | Q003V-A069S-N076D | 78 |
| Bba02069-00778 | Q003V-A069S-G167Q | Q003V-A069S-G166Q | 95 |
| Bba02069-00679 | Q003V-A069S-N219S | Q003V-A069S-N218S | 81 |
| Bba02069-00776 | Q003V-A069S-S260P | Q003V-A069S-S259P | 81 |
| Bba02069-00836 | Q003V-N076D-G167Q | Q003V-N076D-G166Q | 89 |
| Bba02069-00827 | Q003V-N076D-V186Q | Q003V-N076D-V185Q | 86 |
| Bba02069-00825 | Q003V-N076D-N219S | Q003V-N076D-N218S | 91 |
| Bba02069-00842 | Q003V-N076D-S260P | Q003V-N076D-S259P | 91 |
| Bba02069-00760 | Q003V-G167Q-V186Q | Q003V-G166Q-V185Q | 82 |
| Bba02069-00840 | Q003V-G167Q-N219S | Q003V-G166Q-N218S | 98 |
| Bba02069-00838 | Q003V-V186Q-S260P | Q003V-V185Q-S259P | 73 |
| Bba02069-00764 | Q003V-N219S-S260P | Q003V-N218S-S259P | 88 |
| Bba02069-00846 | T009E-P040E-A069S | T009E-P040E-A069S | 64 |

TABLE 37B-continued

Bba02069 subtilisin variants with improved stability in liquid detergent at 39° C. (reported as percent residual activity, % RA) compared to Bba02069 parent

| Bba02069 Variant Sample ID | Substitutions in Bba02069 numbering | Substitutions in BPN' numbering | % RA |
|---|---|---|---|
| Bba02069-00886 | T009E-P040E-N076D | T009E-P040E-N076D | 97 |
| Bba02069-00847 | T009E-P040E-G167Q | T009E-P040E-G166Q | 92 |
| Bba02069-01933 | T009E-P040E-V186Q | T009E-P040E-V185Q | 70 |
| Bba02069-01674 | T009E-P040E-N219S | T009E-P040E-N218S | 94 |
| Bba02069-00763 | T009E-P040E-S260P | T009E-P040E-S259P | 81 |
| Bba02069-00848 | T009E-A069S-N076D | T009E-A069S-N076D | 90 |
| Bba02069-00849 | T009E-A069S-G167Q | T009E-A069S-G166Q | 94 |
| Bba02069-00791 | T009E-A069S-V186Q | T009E-A069S-V185Q | 67 |
| Bba02069-00722 | T009E-A069S-N219S | T009E-A069S-N218S | 87 |
| Bba02069-00795 | T009E-A069S-S260P | T009E-A069S-S259P | 88 |
| Bba02069-00796 | T009E-N076D-G167Q | T009E-N076D-G166Q | 94 |
| Bba02069-00725 | T009E-N076D-V186Q | T009E-N076D-V185Q | 93 |
| Bba02069-01905 | T009E-N076D-N219S | T009E-N076D-N218S | 99 |
| Bba02069-00793 | T009E-N076D-S260P | T009E-N076D-S259P | 98 |
| Bba02069-00794 | T009E-G167Q-V186Q | T009E-G166Q-V185Q | 83 |
| Bba02069-00797 | T009E-G167Q-N219S | T009E-G166Q-N218S | 91 |
| Bba02069-00715 | T009E-G167Q-S260P | T009E-G166Q-S259P | 84 |
| Bba02069-00799 | T009E-V186Q-N219S | T009E-V185Q-N218S | 88 |
| Bba02069-00718 | T009E-V186Q-S260P | T009E-V185Q-S259P | 78 |
| Bba02069-00801 | T009E-N219S-S260P | T009E-N218S-S259P | 87 |
| Bba02069-00720 | P040E-A069S-N076D | P040E-A069S-N076D | 100 |
| Bba02069-00802 | P040E-A069S-G167Q | P040E-A069S-G166Q | 65 |
| Bba02069-01826 | P040E-A069S-V186Q | P040E-A069S-V185Q | 48 |
| Bba02069-00882 | P040E-A069S-N219S | P040E-A069S-N218S | 70 |
| Bba02069-00730 | P040E-A069S-S260P | P040E-A069S-S259P | 66 |
| Bba02069-00693 | P040E-N076D-G167Q | P040E-N076D-G166Q | 98 |
| Bba02069-00729 | P040E-N076D-V186Q | P040E-N076D-V185Q | 79 |
| Bba02069-00695 | P040E-N076D-N219S | P040E-N076D-N218S | 84 |
| Bba02069-00696 | P040E-N076D-S260P | P040E-N076D-S259P | 94 |
| Bba02069-00692 | P040E-G167Q-V186Q | P040E-G166Q-V185Q | 52 |
| Bba02069-00691 | P040E-G167Q-N219S | P040E-G166Q-N218S | 87 |
| Bba02069-00705 | P040E-G167Q-S260P | P040E-G166Q-S259P | 69 |
| Bba02069-00706 | P040E-V186Q-N219S | P040E-V185Q-N218S | 76 |
| Bba02069-00686 | P040E-V186Q-S260P | P040E-V185Q-S259P | 54 |
| Bba02069-00685 | P040E-N219S-S260P | P040E-N218S-S259P | 77 |
| Bba02069-00708 | A069S-N076D-G167Q | A069S-N076D-G166Q | 92 |
| Bba02069-00883 | A069S-N076D-V186Q | A069S-N076D-V185Q | 75 |
| Bba02069-00684 | A069S-N076D-N219S | A069S-N076D-N218S | 88 |
| Bba02069-00683 | A069S-N076D-S260P | A069S-N076D-S259P | 92 |
| Bba02069-00703 | A069S-G167Q-V186Q | A069S-G166Q-V185Q | 51 |
| Bba02069-01832 | A069S-G167Q-N219S | A069S-G166Q-N218S | 85 |
| Bba02069-00704 | A069S-G167Q-S260P | A069S-G166Q-S259P | 73 |
| Bba02069-01679 | A069S-V186Q-N219S | A069S-V185Q-N218S | 65 |
| Bba02069-00930 | A069S-V186Q-S260P | A069S-V185Q-S259P | 52 |
| Bba02069-00700 | A069S-N219S-S260P | A069S-N218S-S259P | 72 |
| Bba02069-00699 | N076D-G167Q-V186Q | N076D-G166Q-V185Q | 95 |
| Bba02069-00698 | N076D-G167Q-N219S | N076D-G166Q-N218S | 100 |
| Bba02069-01319 | N076D-G167Q-S260P | N076D-G166Q-S259P | 95 |
| Bba02069-01333 | N076D-V186Q-N219S | N076D-V185Q-N218S | 94 |
| Bba02069-01321 | N076D-V186Q-S260P | N076D-V185Q-S259P | 89 |
| Bba02069-01323 | N076D-N219S-S260P | N076D-N218S-S259P | 97 |
| Bba02069-01324 | G167Q-V186Q-N219S | G166Q-V185Q-N218S | 64 |
| Bba02069-01335 | G167Q-V186Q-S260P | G166Q-V185Q-S259P | 52 |
| Bba02069-01328 | G167Q-N219S-S260P | G166Q-N218S-S259P | 73 |
| Bba02069-01329 | V186Q-N219S-S260P | V185Q-N218S-S259P | 60 |
| Bba02069-01318 | Q003V-T009E-P040E-G167Q | Q003V-T009E-P040E-G166Q | 97 |
| Bba02069-01136 | Q003V-T009E-P040E-V186Q | Q003V-T009E-P040E-V185Q | 82 |
| Bba02069-01264 | Q003V-T009E-N076D-N219S | Q003V-T009E-N076D-N218S | 82 |
| Bba02069-01585 | Q003V-T009E-G167Q-V186Q | Q003V-T009E-G166Q-V185Q | 95 |
| Bba02069-01764 | Q003V-P040E-N076D-V186Q | Q003V-P040E-N076D-V185Q | 73 |
| Bba02069-01124 | T009E-P040E-A069S-V186Q | T009E-P040E-A069S-V185Q | 80 |
| Bba02069-01219 | T009E-P040E-A069S-N219S | T009E-P040E-A069S-N218S | 100 |
| Bba02069-01040 | T009E-P040E-N076D-V186Q | T009E-P040E-N076D-V185Q | 99 |
| Bba02069-01182 | T009E-A069S-N076D-N219S | T009E-A069S-N076D-N218S | 98 |
| Bba02069-01203 | T009E-A069S-G167Q-V186Q | T009E-A069S-G166Q-V185Q | 83 |
| Bba02069-01007 | T009E-A069S-G167Q-N219S | T009E-A069S-G166Q-N218S | 100 |
| Bba02069-00924 | T009E-A069S-V186Q-N219S | T009E-A069S-V185Q-N218S | 82 |
| Bba02069-00904 | T009E-N076D-V186Q-S260P | T009E-N076D-V185Q-S259P | 98 |
| Bba02069-00908 | T009E-V186Q-N219S-S260P | T009E-V185Q-N218S-S259P | 83 |
| Bba02069-01165 | P040E-A069S-N076D-V186Q | P040E-A069S-N076D-V185Q | 89 |
| Bba02069-01900 | P040E-A069S-G167Q-N219S | P040E-A069S-G166Q-N218S | 94 |
| Bba02069-01768 | P040E-A069S-V186Q-N219S | P040E-A069S-V185Q-N218S | 67 |
| Bba02069-01072 | P040E-A069S-V186Q-S260P | P040E-A069S-V185Q-S259P | 72 |
| Bba02069-01470 | P040E-A069S-N219S-S260P | P040E-A069S-N218S-S259P | 82 |

TABLE 37B-continued

Bba02069 subtilisin variants with improved stability in liquid detergent at 39° C. (reported as percent residual activity, % RA) compared to Bba02069 parent

| Bba02069 Variant Sample ID | Substitutions in Bba02069 numbering | Substitutions in BPN' numbering | % RA |
|---|---|---|---|
| Bba02069-01003 | P040E-N076D-G167Q-V186Q | P040E-N076D-G166Q-V185Q | 94 |
| Bba02069-00893 | P040E-N076D-V186Q-N219S | P040E-N076D-V185Q-N218S | 86 |
| Bba02069-00996 | P040E-N076D-V186Q-S260P | P040E-N076D-V185Q-S259P | 92 |
| Bba02069-01478 | P040E-G167Q-V186Q-N219S | P040E-G166Q-V185Q-N218S | 79 |
| Bba02069-01856 | P040E-V186Q-N219S-S260P | P040E-V185Q-N218S-S259P | 78 |
| Bba02069-00954 | A069S-N076D-G167Q-V186Q | A069S-N076D-G166Q-V185Q | 95 |
| Bba02069-01024 | A069S-N076D-G167Q-N219S | A069S-N076D-G166Q-N218S | 96 |
| Bba02069-01011 | A069S-N076D-G167Q-S260P | A069S-N076D-G166Q-S259P | 97 |
| Bba02069-01803 | A069S-N076D-V186Q-N219S | A069S-N076D-V185Q-N218S | 94 |
| Bba02069-01919 | A069S-N076D-N219S-S260P | A069S-N076D-N218S-S259P | 93 |
| Bba02069-01842 | A069S-G167Q-V186Q-N219S | A069S-G166Q-V185Q-N218S | 62 |
| Bba02069-01958 | N076D-G167Q-V186Q-S260P | N076D-G166Q-V185Q-S259P | 93 |
| Bba02069-01312 | N076D-G167Q-N219S-S260P | N076D-G166Q-N218S-S259P | 99 |
| Bba02069-01570 | G167Q-V186Q-N219S-S260P | G166Q-V185Q-N218S-S259P | 68 |

Example 20

BspZ00258 Subtilisin Variants with Improved Stability in Detergent

Variants of BspZ00258 (SEQ ID NO: 22) subtilisin containing one, two, three or four amino acid substitutions at positions of interest to increase enzyme stability, were evaluated for detergent stability and cleaning performance using methods described in Example 2. The BspZ00258 subtilisin was previously described as SEQ ID NO:9 in WO 2016069552 patent application, and is a member of the BspM04284-clade of subtilisins. Table 38 shows the results for BspZ00258 variants.

Example 21

BspZ00056 Subtilisin Variants with Improved Stability in Detergent

Variants of BspZ00056 (SEQ ID NO:17) subtilisin containing three or four amino acid substitutions at positions of interest to increase enzyme stability, were generated using methods similar to the ones described in Example 1. These variant samples were evaluated for detergent stability and cleaning performance using methods described in Example 2. Table 39A and 39B show the results for BspZ00056 variants.

TABLE 38

BspZ00258 subtilisin variants with improved stability in liquid detergent at 62° C. (reported as percent residual activity, % RA) compared to BspZ00258 parent

| | | | | Cleaning performance, PI | |
|---|---|---|---|---|---|
| BspZ00258 Variant Sample ID | Substitutions in BspZ00258 numbering | Substitutions in BPN' numbering | % RA | BMI stain in PNB detergent | PAS-38 stain in GSM-B detergent |
| BspZ00258 | — | — | 57 | 1.0 | 1.0 |
| BspZ00258-00124 | E003V | E003V | 84 | 0.6 | 1.1 |
| BspZ00258-00027 | G166Q | G166Q | 78 | 0.5 | 1.1 |
| BspZ00258-00045 | D259P | D259P | 66 | 0.9 | 1.6 |
| BspZ00258-00098 | A068S-N185Q | A069S-N185Q | 67 | 0.8 | 1.3 |
| BspZ00258-00429 | A068S-N218S | A069S-N218S | 61 | 1.0 | 1.6 |
| BspZ00258-00244 | A128P-D259P | A129P-D259P | 76 | 0.9 | 1.4 |
| BspZ00258-00338 | G166Q-N185Q | G166Q-N185Q | 78 | 0.7 | 1.1 |
| BspZ00258-00106 | G166Q-D259P | G166Q-D259P | 72 | 0.8 | 1.3 |
| BspZ00258-00476 | E003V-A068S-G127S | E003V-A069S-G128S | 90 | 0.9 | 1.6 |
| BspZ00258-00565 | E003V-G127S-D259P | E003V-G128S-D259P | 88 | 2.3 | 3.4 |
| BspZ00258-00337 | E003V-A128P-N185Q | E003V-A129P-N185Q | 88 | 0.7 | 1.4 |
| BspZ00258-00538 | A068S-A128P-G166Q | A069S-A129P-G166Q | 79 | 0.8 | 1.2 |
| BspZ00258-00095 | E003V-A068S-G127S-N185Q | E003V-A069S-G128S-N185Q | 90 | 1.2 | 2.6 |
| BspZ00258-00020 | E003V-A068S-A128P-N185Q | E003V-A069S-A129P-N185Q | 88 | 0.8 | 2.0 |
| BspZ00258-00145 | E003V-G127S-N185Q-D259P | E003V-G128S-N185Q-D259P | 93 | 1.5 | 2.7 |
| BspZ00258-00096 | E003V-A128P-N185Q-N218S | E003V-A129P-N185Q-N218S | 86 | 0.7 | 1.6 |

TABLE 39A

BspZ00056 subtilisin variants with improved stability in liquid detergent at 64° C. (reported as percent residual activity, % RA) compared to BspZ00056 parent

| | | | | Cleaning performance, PI | |
|---|---|---|---|---|---|
| BspZ00056 Variant Sample ID | Substitutions in BspZ00056 numbering | Substitutions in BPN' numbering | % RA | BMI stain in PNB detergent | PAS-38 stain in GSM-B detergent |
| BspZ00056 | — | — | 23 | 1.0 | 1.0 |
| BspZ00056-00318 | T003V-S133P-G171Q | T003V-S129P-G166Q | 84 | 1.0 | 0.6 |
| BspZ00056-00428 | T003V-S133P-N190Q | T003V-S129P-N185Q | 61 | 1.2 | 0.7 |
| BspZ00056-00131 | T003V-S133P-G264P | T003V-S129P-G259P | 80 | 1.3 | 0.8 |
| BspZ00056-00223 | T003V-N190Q-N223S | T003V-N185Q-N218S | 46 | 1.3 | 0.2 |
| BspZ00056-00474 | A073S-G132S-N190Q | A069S-G128S-N185Q | 74 | 1.1 | 0.2 |
| BspZ00056-00104 | A073S-S133P-G264P | A069S-S129P-G259P | 86 | 1.3 | 0.4 |
| BspZ00056-00110 | A073S-G171Q-N190Q | A069S-G166Q-N185Q | 80 | 1.3 | 0.7 |
| BspZ00056-00500 | A073S-G171Q-N223S | A069S-G166Q-N218S | 82 | 1.5 | 0.7 |
| BspZ00056-00113 | M128I-S133P-N190Q | M124I-S129P-N185Q | 67 | 1.3 | 0.3 |
| BspZ00056-00198 | M128I-S133P-G264P | M124I-S129P-G259P | 88 | 1.3 | 0.2 |
| BspZ00056-00303 | M128I-N190Q-G264P | M124I-N185Q-G259P | 85 | 1.2 | 0.2 |
| BspZ00056-00264 | M128I-N223S-G264P | M124I-N218S-G259P | 89 | 1.3 | 0.1 |
| BspZ00056-00302 | G132S-G171Q-G264P | G128S-G166Q-G259P | 85 | 1.2 | 0.6 |
| BspZ00056-00483 | G132S-N190Q-G264P | G128S-N185Q-G259P | 100 | 1.4 | 0.6 |
| BspZ00056-00238 | G171Q-N223S-G264P | G166Q-N218S-G259P | 87 | 1.1 | 0.7 |
| BspZ00056-00334 | T003V-A073S-G132S-N190Q | T003V-A069S-G128S-N185Q | 75 | 1.6 | 0.2 |
| BspZ00056-00482 | T003V-A073S-N190Q-G264P | T003V-A069S-N185Q-G259P | 81 | 1.8 | 0.6 |
| BspZ00056-00498 | T003V-A073S-N223S-G264P | T003V-A069S-N218S-G259P | 75 | 1.5 | 0.3 |
| BspZ00056-00021 | T003V-M128I-G171Q-G264P | T003V-M124I-G166Q-G259P | 89 | 1.3 | 0.3 |
| BspZ00056-00041 | T003V-N190Q-N223S-G264P | T003V-N185Q-N218S-G259P | 78 | 1.5 | 0.3 |
| BspZ00056-00376 | A073S-S133P-G171Q-G264P | A069S-S129P-G166Q-G259P | 85 | 1.0 | 0.5 |
| BspZ00056-00308 | M128I-S133P-G171Q-G264P | M124I-S129P-G166Q-G259P | 91 | 1.0 | 0.2 |
| BspZ00056-00158 | M128I-G171Q-N223S-G264P | M124I-G166Q-N218S-G259P | 90 | 1.1 | 0.3 |
| BspZ00056-00409 | M128I-N190Q-N223S-G264P | M124I-N185Q-N218S-G259P | 95 | 1.0 | 0.2 |
| BspZ00056-00155 | G132S-S133P-G171Q-G264P | G128S-S129P-G166Q-G259P | 90 | 1.2 | 0.5 |
| BspZ00056-00012 | S133P-G171Q-N190Q-G264P | S129P-G166Q-N185Q-G259P | 84 | 1.5 | 0.8 |

TABLE 39B

BspZ00056 subtilisin variants with improved stability in liquid detergent at 64° C. (reported as percent residual activity, % RA) compared to BspZ00056 parent

| BspZ00056 Variant Sample ID | Substitutions in Backbone Numbering | Substitutions in BPN' Numbering | % RA |
|---|---|---|---|
| BspZ00056 | — | — | 30 |
| BspZ00056-00909 | T003V-P009E-G171Q | T003V-P009E-G166Q | 74 |
| BspZ00056-00859 | T003V-A073S-G171Q | T003V-A069S-G166Q | 72 |
| BspZ00056-00848 | T003V-A073S-G264P | T003V-A069S-G259P | 92 |
| BspZ00056-00808 | T003V-G171Q-N190Q | T003V-G166Q-N185Q | 68 |
| BspZ00056-00785 | T003V-G171Q-N223S | T003V-G166Q-N218S | 78 |
| BspZ00056-00786 | T003V-G171Q-G264P | T003V-G166Q-G259P | 93 |
| BspZ00056-00891 | T003V-N190Q-G264P | T003V-N185Q-G259P | 75 |
| BspZ00056-00787 | T003V-N223S-G264P | T003V-N218S-G259P | 79 |
| BspZ00056-00810 | P009E-A073S-G171Q | P009E-A069S-G166Q | 67 |
| BspZ00056-01468 | P009E-A073S-G264P | P009E-A069S-G259P | 87 |
| BspZ00056-00783 | P009E-G171Q-N190Q | P009E-G166Q-N185Q | 73 |
| BspZ00056-00913 | P009E-G171Q-N223S | P009E-G166Q-N218S | 75 |
| BspZ00056-01238 | P009E-G171Q-G264P | P009E-G166Q-G259P | 91 |
| BspZ00056-00884 | P009E-N223S-G264P | P009E-N218S-G259P | 82 |
| BspZ00056-00704 | A073S-G171Q-G264P | A069S-G166Q-G259P | 87 |
| BspZ00056-00693 | A073S-N190Q-G264P | A069S-N185Q-G259P | 78 |
| BspZ00056-00705 | A073S-N223S-G264P | A069S-N218S-G259P | 90 |
| BspZ00056-00710 | G171Q-N190Q-G264P | G166Q-N185Q-G259P | 69 |
| BspZ00056-01490 | N190Q-N223S-G264P | N185Q-N218S-G259P | 98 |

TABLE 39B-continued

BspZ00056 subtilisin variants with improved stability in liquid detergent at 64° C. (reported as percent residual activity, % RA) compared to BspZ00056 parent

| BspZ00056 Variant Sample ID | Substitutions in Backbone Numbering | Substitutions in BPN' Numbering | % RA |
|---|---|---|---|
| BspZ00056-01432 | T003V-P009E-A073S-G171Q | T003V-P009E-A069S-G166Q | 86 |
| BspZ00056-01158 | T003V-P009E-G171Q-G264P | T003V-P009E-G166Q-G259P | 100 |
| BspZ00056-01153 | T003V-A073S-G171Q-N190Q | T003V-A069S-G166Q-N185Q | 90 |
| BspZ00056-01078 | T003V-G171Q-N223S-G264P | T003V-G166Q-N218S-G259P | 97 |
| BspZ00056-01084 | P009E-A073S-G171Q-N223S | P009E-A069S-G166Q-N218S | 79 |
| BspZ00056-01115 | P009E-G171Q-N190Q-N223S | P009E-G166Q-N185Q-N218S | 82 |
| BspZ00056-01032 | P009E-G171Q-N190Q-G264P | P009E-G166Q-N185Q-G259P | 100 |
| BspZ00056-01179 | P009E-G171Q-N223S-G264P | P009E-G166Q-N218S-G259P | 87 |
| BspZ00056-01233 | P009E-N190Q-N223S-G264P | P009E-N185Q-N218S-G259P | 79 |
| BspZ00056-01152 | A073S-G171Q-N190Q-N223S | A069S-G166Q-N185Q-N218S | 82 |
| BspZ00056-01379 | A073S-G171Q-N190Q-G264P | A069S-G166Q-N185Q-G259P | 83 |
| BspZ00056-01194 | A073S-G171Q-N223S-G264P | A069S-G166Q-N218S-G259P | 92 |
| BspZ00056-01234 | G171Q-N190Q-N223S-G264P | G166Q-N185Q-N218S-G259P | 100 |

Example 22

Globally Beneficial Stability Mutations in Subtilisins

Analysis of improved detergent stability results across the following backbones: AprE (subtilisin E, SEQ ID NO:8); Chemgen_164A (SEQ ID NO:10); Bpan01744 (SEQ ID NO:13); DSM14391 (SEQ ID NO:14); BspAI02518 (SEQ ID NO:16); BspZ00056 (SEQ ID NO:17); Bba02069 (SEQ ID NO:19); CP474 (SEQ ID NO:11) and ZP-00454 (SEQ ID NO:12) was performed. Variants comprising 1 or 2 substitutions on the wild-type backbone are shown in Table 40. At least half of all possible double combinations of the following features: X003V, X009E, X040E, X069S, X076D, X078N, X166Q, X185Q, X218S, and X259P introduced into the 9 backbones listed above showed increased stability for singly or doubly substituted variants. Variants comprising 3 substitutions on the wild-type backbone are shown on Table 41. At least half of all possible triple combinations of the following features: X003V, X009E, X040E, X069S, X076D, X078N, X166Q, X185Q, X218S, and X259P introduced into the following 7 backbones AprE (subtilisin E, SEQ ID NO:8); Chemgen_164A (SEQ ID NO:10); Bpan01744 (SEQ ID NO:13); DSM14391 (SEQ ID NO:14); BspAI02518 (SEQ ID NO:16); BspZ00056 (SEQ ID NO:17); Bba02069 (SEQ ID NO:19) showed increased stability for triply substituted variants.

In Tables 40 and 41, the term "shared feature" corresponds to amino acid position of interest where a substitution was introduced, or in some cases the amino acid of interest is naturally occurring. Sample IDs on Table 40 are as follows: variants of AprE have an AprE suffix, variants of Chemgen_164A have a Chemgen suffix, variants of DSM14391 have a DSM14391 suffix, variants of BspZ00056 have a BspZ00056 suffix, variants of Bba02069 have a Bba02069 suffix, variants of BspAI02518 have a BspAI02518 suffix, variants of Bpan01744 have a Bpan01744 suffix, variants of CP474 have a CP474 suffix, and variants of ZP-00454 have a ZP-00454 suffix. All substitutions are listed based on corresponding positions in BPN' numbering (SEQ ID NO: 1) according to multiple protein sequence alignment shown in Table 28.

TABLE 40

Variants of AprE, Chemgen, DSM14391, BspZ00056, Bba02069, BspAI02518, Bpan01744, CP474, and ZP-00454 subtilisins with shared features

| Shared feature in BPN' numbering | Variants with shared feature |
|---|---|
| X003V-X009E | AprE-01089, Chemgen-00795, Bpan01744-00830, DSM14391-00986, BspAI02518-01175, Bba02069-00854 |
| X003V-X040E | AprE-00380, Chemgen-00794, CP474-00592, ZP-00454-00011, Bpan01744-00498, DSM14391-00987, BspAI02518-00709, Bba02069-00855, BspZ00056-00876 |
| X003V-X069S | AprE-01078, Chemgen-00481, CP474-00602, ZP-00454-00021, Bpan01744-00167, DSM14391-00025, BspAI02518-00599, Bba02069-00030, BspZ00056-00094 |
| X003V-X076D | AprE-00729, Chemgen-00076, CP474-00571, ZP-00454-00031, Bpan01744-00166, DSM14391-00340, BspAI02518-00897, Bba02069-00564, BspZ00056-00876 |
| X003V-X078N | AprE-00515, Chemgen-00443, CP474-00612, ZP-00454-00041, Bpan01744-00304, DSM14391-00373, BspAI02518-01179, Bba02069-00652 |
| X003V-X166Q | AprE-00841, Chemgen-00378, CP474-00563, Bpan01744-01145, DSM14391-00028, BspAI02518-00959, Bba02069-00347, BspZ00056-00221 |
| X003V-X185Q | AprE-00772, Chemgen-00108, CP474-00573, Bpan01744-00152, DSM14391-00016, BspAI02518-00624, Bba2069-00121, BspZ00056-00116 |
| X003V-X218S | AprE-01842, Chemgen-00634, CP474-00583, Bpan01744-00417, DSM14391-00492, BspAI02518-00564, Bba02069-00856, BspZ00056-00368 |
| X003V-X259P | AprE-00370, Chemgen-00650, CP474-00593, Bpan01744-00544, DSM14391-00063, BspAI02518-00506, Bba02069-00477, BspZ00056-00384 |

TABLE 40-continued

Variants of AprE, Chemgen, DSM14391, BspZ00056, Bba02069, BspAI02518, Bpan01744, CP474, and ZP-00454 subtilisins with shared features

| Shared feature in BPN' numbering | Variants with shared feature |
| --- | --- |
| X009E-X040E | AprE-01082, Bpan01744-02141, DSM14391-00863, BspAI02518-00637, Bba02069-00755, BspZ00056-01485 |
| X009E-X069S | AprE-01083, Chemgen-00788, DSM14391-00864, BspAI02518-01198, Bba02069-00756 |
| X009E-X076D | AprE-01025, Chemgen-00712, Bpan01744-01257, DSM14391-00839, BspAI02518-01178, Bba02069-00757, BspZ00056-01485 |
| X009E-X078N | AprE-01850, Chemgen-00714, Bpan01744-02075, DSM14391-00962, BspAI02518-01186, Bba02069-00654 |
| X009E-X166Q | AprE-01959, Chemgen-00797, Bpan01744-01122, BspAI02518-01991, Bba02069-00871, BspZ00056-01478 |
| X009E-X185Q | AprE-01081, Chemgen-00798, Bpan01744-01123, DSM14391-01005, BspAI02518-01187, Bba02069-00866 |
| X009E-X218S | AprE-01111, Bpan01744-00795, DSM14391-00971, BspAI02518-01811, Bba02069-00865 |
| X009E-X259P | AprE-01096, Chemgen-00741, Bpan01744-01124, DSM14391-00867, BspAI02518-02004, Bba02069-00758, BspZ00056-00875 |
| X040E-X069S | AprE-01951, CP474-00603, ZP-00454-00052, DSM14391-00968, Bba02069-00863, BspZ00056-00863 |
| X040E-X076D | AprE-01108, CP474-00581, ZP-00454-00062, Bpan01744-01310, DSM14391-00969, BspAI02518-00689, Bba02069-00824 |
| X040E-X078N | AprE-01844, Chemgen-00715, CP474-00613, ZP-00454-00072, Bpan01744-00574, DSM14391-00217, BspAI02518-00585, Bba02069-00653 |
| X040E-X166Q | AprE-01107, Chemgen-01467, CP474-00564, ZP-00454-00043, BspAI02518-01177, Bba02069-00499, BspZ00056-00864 |
| X040E-X185Q | AprE-01080, Chemgen-00716, CP474-00574, ZP-00454-00053, Bpan01744-00717, DSM14391-00985, BspAI02518-00764, Bba02069-00377, BspZ00056-00663 |
| X040E-X218S | AprE-01054, Chemgen-01219, CP474-00584, ZP-00454-00063, Bpan01744-00892, DSM14391-00977, BspAI02518-00819, Bba02069-01952, BspZ00056-00248 |
| X040E-X259P | AprE-01105, CP474-00594, ZP-00454-00073, Bpan01744-01737, DSM14391-00849, BspAI02518-00838, Bba02069-00845, BspZ00056-00819 |
| X069S-X076D | AprE-00498, Chemgen-00527, CP474-00591, ZP-00454-00004, Bpan01744-00088, DSM14391-00494, BspAI02518-00412, Bba02069-00518, BspZ00056-00863 |
| X069S-X078N | AprE-00788, Chemgen-00436, CP474-00604, ZP-00454-00014, Bpan01744-00423, DSM14391-00005, BspAI02518-00590, Bba02069-00648, BspZ00056-00490 |
| X069S-X166Q | AprE-00666, Chemgen-00394, CP474-00634, Bpan01744-00153, BspAI02518-01025, Bba02069-00505, BspZ00056-00389 |
| X069S-X185Q | Chemgen-00617, CP474-00565, ZP-00454-00074, Bpan01744-00414, DSM14391-00136, BspAI02518-00646, Bba02069-00844, BspZ00056-00042 |
| X069S-X218S | AprE-00594, Chemgen-00569, ZP-00454-00005, Bpan01744-00488, DSM14391-00432, BspAI02518-00405, Bba02069-00736, BspZ00056-00873 |
| X069S-X259P | AprE-00758, Chemgen-00444, DSM14391-00096, BspAI02518-01920, Bba02069-00114, BspZ00056-00151 |
| X076D-X078N | AprE-00774, Chemgen-00459, CP474-00601, ZP-00454-00025, Bpan01744-00337, DSM14391-00007, BspAI02518-00814, Bba02069-00644 |
| X076D-X166Q | AprE-00920, Chemgen-00132, CP474-00631, ZP-00454-00075, Bpan01744-01035, BspAI02518-01184, Bba02069-00247, BspZ00056-00864 |
| X076D-X185Q | AprE-00795, Chemgen-00804, CP474-00562, ZP-00454-00006, Bpan01744-01133, DSM14391-00974, BspAI02518-00802, Bba02069-00822, BspZ00056-00663 |
| X076D-X218S | AprE-00912, Chemgen-00367, ZP-00454-00016, Bpan01744-01135, DSM14391-00168, BspAI02518-00535, Bba02069-00815, BspZ00056-00248 |
| X076D-X259P | AprE-01836, Chemgen-00546, ZP-00454-00026, Bpan01744-01148, DSM14391-00976, BspAI02518-00695, Bba02069-00423, BspZ00056-00819 |
| X078N-X166Q | AprE-00974, Chemgen-00560, CP474-00615, ZP-00454-00076, Bpan01744-00158, BspAI02518-01190, Bba02069-00111, BspZ00056-00297 |
| X078N-X185Q | AprE-00488, Chemgen-00224, CP474-00625, ZP-00454-00007, Bpan01744-01629, DSM14391-00302, BspAI02518-01032 |
| X078N-X218S | AprE-00904, Chemgen-00313, CP474-00635, Bpan01744-00991, DSM14391-00252, BspAI02518-00800, Bba02069-00655 |
| X078N-X259P | AprE-00891, Chemgen-00350, CP474-00566, ZP-00454-00027, Bpan01744-01151, DSM14391-00113, BspAI02518-00937, Bba02069-00217, BspZ00056-00088 |
| X166Q-X185Q | AprE-00944, Chemgen-00122, Bpan01744-00369, DSM14391-00171, BspAI02518-02195, Bba02069-00190, BspZ00056-00257 |
| X166Q-X218S | AprE-00698, Chemgen-00335, CP474-00597, Bpan01744-00172, DSM14391-00828, BspAI02518-01002, Bba02069-00817, BspZ00056-00837 |
| X166Q-X259P | AprE-00694, Chemgen-00010, Bpan01744-00048, DSM14391-00430, BspAI02518-01006, Bba02069-00043, BspZ00056-00133 |
| X185Q-X218S | AprE-00924, Chemgen-00198, CP474-00617, Bpan01744-00094, DSM14391-00161, BspAI02518-01094, Bba02069-00493, BspZ00056-01030 |

TABLE 40-continued

Variants of AprE, Chemgen, DSM14391, BspZ00056, Bba02069, BspAI02518, Bpan01744, CP474, and ZP-00454 subtilisins with shared features

| Shared feature in BPN' numbering | Variants with shared feature |
|---|---|
| X185Q-X259P | AprE-00447, Chemgen-00359, CP474-00579, Bpan01744-00339, DSM14391-00203, BspAI02518-00439, Bba02069-00005, BspZ00056-00377 |
| X218S-X259P | AprE-00646, Chemgen-00309, CP474-00627, Bpan01744-00126, DSM14391-00844, BspAI02518-00548, Bba02069-00051, BspZ00056-00491 |

TABLE 41

Variants of AprE, Chemgen, DSM14391, BspZ00056, Bba02069, BspAI02518, and Bpan01744 subtilisins with shared features

| Shared feature in BPN' numbering | Variants with shared feature |
|---|---|
| X003V-X009E-X040E | AprE-01102, Chemgen-00801, Bpan01744-00830, DSM14391-00824, BspAI02518-01175, Bba02069-00812 |
| X003V-X009E-X069S | AprE-01101, Chemgen-01562, Bpan01744-01709, DSM14391-00996, BspAI02518-01092, Bba02069-00811 |
| X003V-X009E-X076D | AprE-01051, Bpan01744-01195, DSM14391-00995, BspAI02518-01095, Bba02069-00809 |
| X003V-X009E-X078N | AprE-01099, Bpan01744-01267, DSM14391-00823, BspAI02518-01270, Bba02069-00854 |
| X003V-X009E-X166Q | AprE-01045, BspAI02518-01096, Bba02069-00744, BspZ00056-00909 |
| X003V-X009E-X185Q | AprE-01089, Chemgen-00792, Bpan01744-01140, DSM14391-00868, BspAI02518-01276, Bba02069-00808 |
| X003V-X009E-X218S | AprE-01077, Bpan01744-01141, DSM14391-00822, BspAI02518-01097, Bba02069-00829 |
| X003V-X009E-X259P | AprE-01047, Bpan01744-01315, DSM14391-00817, BspAI02518-01282, Bba02069-00843 |
| X003V-X040E-X069S | AprE-01009, Bpan01744-00167, DSM14391-00836, BspAI02518-00599, Bba02069-00747, BspZ00056-00094 |
| X003V-X040E-X076D | AprE-01048, Chemgen-01640, Bpan01744-00166, DSM14391-00819, BspAI02518-00897, Bba02069-00833 |
| X003V-X040E-X078N | Bpan01744-00304, DSM14391-00837, BspAI02518-01179, Bba02069-00855 |
| X003V-X040E-X166Q | Chemgen-00793, Bpan01744-01145, BspAI02518-00959, Bba02069-00013, BspZ00056-00221 |
| X003V-X040E-X185Q | AprE-00380, Chemgen-01651, Bpan01744-00152, DSM14391-01004, BspAI02518-00624, Bba02069-00664, BspZ00056-00116 |
| X003V-X040E-X218S | AprE-01915, Bpan01744-00417, DSM14391-00421, BspAI02518-00564, Bba02069-00781, BspZ00056-00368 |
| X003V-X040E-X259P | AprE-01039, Chemgen-00724, Bpan01744-00544, DSM14391-00829, BspAI02518-00506, Bba02069-00834, BspZ00056-00384 |
| X003V-X069S-X076D | AprE-01864, Chemgen-00816, Bpan01744-00169, DSM14391-00831, BspAI02518-01085, Bba02069-00779, BspZ00056-00094 |
| X003V-X069S-X078N | AprE-01056, Chemgen-00808, Bpan01744-01142, BspAI02518-01086, Bba02069-00030 |
| X003V-X069S-X166Q | AprE-00991, Chemgen-00807, Bba02069-00778, BspZ00056-00859 |
| X003V-X069S-X185Q | AprE-01078, Chemgen-01642, Bpan01744-00150, DSM14391-00858, BspAI02518-00534 |
| X003V-X069S-X218S | AprE-01060, Chemgen-00727, Bpan01744-00677, DSM14391-00992, BspAI02518-01087, Bba02069-00679 |
| X003V-X069S-X259P | AprE-01064, Chemgen-01658, Bba02069-00776, BspZ00056-00848 |
| X003V-X076D-X078N | AprE-00685, Chemgen-00729, Bpan01744-01265, DSM14391-00833, BspAI02518-01088, Bba02069-00564 |
| X003V-X076D-X166Q | AprE-01340, Chemgen-00694, Bpan01744-01585, BspAI02518-01250, Bba02069-00836, BspZ00056-00221 |
| X003V-X076D-X185Q | AprE-00729, Chemgen-00776, Bpan01744-00170, DSM14391-01080, BspAI02518-01084, Bba02069-00827, BspZ00056-00116 |
| X003V-X076D-X218S | AprE-01867, Chemgen-00775, Bpan01744-01252, DSM14391-01084, BspAI02518-01220, Bba02069-00825, BspZ00056-00368 |
| X003V-X076D-X259P | AprE-01062, Chemgen-00832, DSM14391-01058, BspAI02518-01230, Bba02069-00842, BspZ00056-00384 |
| X003V-X078N-X166Q | Chemgen-00774, Bpan01744-00059, BspAI02518-01222, Bba02069-00347 |
| X003V-X078N-X185Q | AprE-00515, Chemgen-00696, Bpan01744-01253, DSM14391-00922, BspAI02518-01895, Bba02069-00121 |
| X003V-X078N-X218S | AprE-00353, Bpan01744-01254, DSM14391-01083, BspAI02518-01231, Bba02069-00856 |
| X003V-X078N-X259P | AprE-01068, Chemgen-00834, Bpan01744-01260, DSM14391-01054, BspAI02518-01992, Bba02069-00477 |

TABLE 41-continued

Variants of AprE, Chemgen, DSM14391, BspZ00056, Bba02069, BspAI02518, and Bpan01744 subtilisins with shared features

| Shared feature in BPN' numbering | Variants with shared feature |
|---|---|
| X003V-X166Q-X185Q | AprE-00841, Chemgen-00738, BspAI02518-01110, Bba02069-00760, BspZ00056-00808 |
| X003V-X166Q-X218S | AprE-00773, Bpan01744-00547, DSM14391-00214, Bba02069-00840, BspZ00056-00785 |
| X003V-X166Q-X259P | AprE-01855, Chemgen-00739, DSM14391-00359, BspAI02518-02118, Bba02069-00471, BspZ00056-00786 |
| X003V-X185Q-X218S | AprE-01842, Chemgen-00785, Bpan01744-01274, DSM14391-00929, BspAI02518-01099, BspZ00056-00223 |
| X003V-X185Q-X259P | AprE-00370, Chemgen-00698, Bpan01744-00685, DSM14391-01078, BspAI02518-00539, Bba02069-00838, BspZ00056-00891 |
| X003V-X218S-X259P | AprE-00753, Chemgen-00780, Bpan01744-01275, DSM14391-00919, BspAI02518-01960, Bba02069-00764, BspZ00056-00787 |
| X009E-X040E-X069S | AprE-01674, Chemgen-01553, BspAI02518-01198, Bba02069-00846 |
| X009E-X040E-X076D | AprE-01069, Chemgen-00703, Bpan01744-01257, DSM14391-00931, BspAI02518-01178, Bba02069-00886 |
| X009E-X040E-X078N | AprE-01997, Chemgen-00683, Bpan01744-02075, DSM14391-00928, BspAI02518-01186, Bba02069-00755 |
| X009E-X040E-X166Q | AprE-01984, Chemgen-00702, Bpan01744-01122, BspAI02518-01991, Bba02069-00847, BspZ00056-01478 |
| X009E-X040E-X185Q | AprE-01082, Bpan01744-01123, DSM14391-01025, BspAI02518-01187, Bba02069-01933 |
| X009E-X040E-X218S | AprE-01529, Chemgen-00822, Bpan01744-00795, DSM14391-01034, BspAI02518-01811, Bba02069-01674 |
| X009E-X040E-X259P | AprE-01125, Chemgen-01604, Bpan01744-01124, DSM14391-00899, BspAI02518-02004, Bba02069-00763, BspZ00056-00875 |
| X009E-X069S-X076D | AprE-01071, Chemgen-00684, Bpan01744-00693, BspAI02518-01238, Bba02069-00848 |
| X009E-X069S-X078N | AprE-01091, Chemgen-00700, Bpan01744-00777, DSM14391-01035, Bba02069-00756 |
| X009E-X069S-X166Q | AprE-01871, Chemgen-00823, Bpan01744-00898, Bba02069-00849, BspZ00056-00810 |
| X009E-X069S-X185Q | AprE-01083, BspAI02518-01102, Bba02069-00791 |
| X009E-X069S-X218S | AprE-01087, Chemgen-00681, DSM14391-01030, BspAI02518-01165, Bba02069-00722 |
| X009E-X069S-X259P | AprE-01857, Chemgen-00829, Bpan01744-01231, DSM14391-01042, Bba02069-00795, BspZ00056-01468 |
| X009E-X076D-X078N | AprE-01892, Chemgen-00825, Bpan01744-01236, DSM14391-01040, BspAI02518-01105, Bba02069-00757 |
| X009E-X076D-X166Q | AprE-01093, Chemgen-01315, Bpan01744-01237, BspAI02518-01235, Bba02069-00796, BspZ00056-01478 |
| X009E-X076D-X185Q | AprE-01025, Chemgen-00737, Bpan01744-01238, DSM14391-00908, BspAI02518-01153, Bba02069-00725 |
| X009E-X076D-X218S | AprE-01052, Chemgen-00690, Bpan01744-01196, DSM14391-01038, BspAI02518-02121, Bba02069-01905 |
| X009E-X076D-X259P | AprE-01860, Chemgen-01420, Bpan01744-01307, DSM14391-01049, BspAI02518-01107, Bba02069-00793, BspZ00056-00875 |
| X009E-X078N-X166Q | AprE-01095, Chemgen-00826, BspAI02518-02083, Bba02069-00871 |
| X009E-X078N-X185Q | AprE-01850, Chemgen-01162, Bpan01744-01248, DSM14391-00915, BspAI02518-01268, Bba02069-00866 |
| X009E-X078N-X218S | AprE-01019, Chemgen-00688, Bpan01744-01241, DSM14391-01047, BspAI02518-01140, Bba02069-00865 |
| X009E-X078N-X259P | AprE-01014, Chemgen-00818, Bpan01744-01242, DSM14391-01053, BspAI02518-01142, Bba02069-00758 |
| X009E-X166Q-X185Q | AprE-01959, Bpan01744-01165, BspAI02518-01167, Bba02069-00794, BspZ00056-00783 |
| X009E-X166Q-X218S | AprE-01029, Chemgen-00687, Bpan01744-01244, DSM14391-01043, BspAI02518-01138, Bba02069-00797, BspZ00056-00913 |
| X009E-X166Q-X259P | AprE-01028, Chemgen-00686, BspAI02518-01226, Bba02069-00715, BspZ00056-01238 |
| X009E-X185Q-X218S | AprE-01111, Chemgen-00705, Bpan01744-00976, DSM14391-00911, BspAI02518-01227, Bba02069-00799 |
| X009E-X185Q-X259P | AprE-01096, Chemgen-00685, Bpan01744-01351, DSM14391-00912, BspAI02518-01148, Bba02069-00718 |
| X009E-X218S-X259P | AprE-01026, Bpan01744-01157, DSM14391-01045, BspAI02518-01251, Bba02069-00801, BspZ00056-00884 |
| X040E-X069S-X076D | Chemgen-00878, Bpan01744-00088, DSM14391-01074, BspAI02518-00412, Bba02069-00720 |
| X040E-X069S-X078N | AprE-01024, Chemgen-00876, Bpan01744-00423, BspAI02518-00590, Bba02069-00863, BspZ00056-00490 |
| X040E-X069S-X166Q | AprE-01865, Chemgen-00868, Bpan01744-00153, BspAI02518-01025, Bba02069-00802, BspZ00056-00389 |
| X040E-X069S-X185Q | AprE-01951, Bpan01744-00414, DSM14391-00689, BspAI02518-00646, Bba02069-01826, BspZ00056-00042 |

TABLE 41-continued

Variants of AprE, Chemgen, DSM14391, BspZ00056, Bba02069, BspAI02518, and Bpan01744 subtilisins with shared features

| Shared feature in BPN' numbering | Variants with shared feature |
|---|---|
| X040E-X069S-X218S | AprE-01823, Bpan01744-00488, DSM14391-01032, BspAI02518-00405, Bba02069-00882, BspZ00056-00873 |
| X040E-X069S-X259P | AprE-01036, Chemgen-01310, DSM14391-01033, BspAI02518-01920, Bba02069-00730, BspZ00056-00151 |
| X040E-X076D-X078N | AprE-00540, Chemgen-00761, Bpan01744-00337, DSM14391-01352, BspAI02518-00814, Bba02069-00824 |
| X040E-X076D-X166Q | AprE-01032, Chemgen-00642, Bpan01744-01035, DSM14391-00272, BspAI02518-01184, Bba02069-00693 |
| X040E-X076D-X185Q | AprE-01108, Chemgen-00660, Bpan01744-01133, DSM14391-00469, BspAI02518-00802, Bba02069-00729 |
| X040E-X076D-X218S | AprE-01824, Chemgen-00641, Bpan01744-01135, DSM14391-00953, BspAI02518-00535, Bba02069-00695 |
| X040E-X076D-X259P | AprE-01031, Bpan01744-01148, DSM14391-00686, BspAI02518-00695, Bba02069-00696 |
| X040E-X078N-X166Q | AprE-01825, Bpan01744-00158, BspAI02518-01190, Bba02069-00499, BspZ00056-00297 |
| X040E-X078N-X185Q | AprE-01844, Chemgen-01465, Bpan01744-01629, DSM14391-01066, BspAI02518-01032, Bba02069-00377 |
| X040E-X078N-X218S | AprE-01030, Bpan01744-00991, DSM14391-01065, BspAI02518-00800, Bba02069-01952 |
| X040E-X078N-X259P | AprE-01035, Chemgen-00758, Bpan01744-01151, DSM14391-00659, BspAI02518-00937, Bba02069-00845, BspZ00056-00088 |
| X040E-X166Q-X185Q | AprE-01107, Chemgen-00872, Bpan01744-00369, BspAI02518-02195, Bba02069-00692, BspZ00056-00257 |
| X040E-X166Q-X218S | AprE-01820, Chemgen-00873, Bpan01744-00172, DSM14391-00947, BspAI02518-01002, Bba02069-00691, BspZ00056-00837 |
| X040E-X166Q-X259P | AprE-01831, Chemgen-00752, Bpan01744-00048, BspAI02518-01006, Bba02069-00705, BspZ00056-00133 |
| X040E-X185Q-X218S | AprE-01054, Chemgen-00750, Bpan01744-00094, DSM14391-00281, BspAI02518-01094, Bba02069-00706, BspZ00056-01030 |
| X040E-X185Q-X259P | AprE-01105, Chemgen-00851, Bpan01744-00339, DSM14391-00293, BspAI02518-00439, Bba02069-00686, BspZ00056-00377 |
| X040E-X218S-X259P | AprE-01826, Chemgen-00845, Bpan01744-00126, DSM14391-00960, BspAI02518-00548, Bba02069-00685, BspZ00056-00491 |
| X069S-X076D-X078N | AprE-01810, Chemgen-00844, Bpan01744-00810, DSM14391-00945, BspAI02518-01243, Bba02069-00518, BspZ00056-00490 |
| X069S-X076D-X166Q | AprE-01812, Chemgen-00746, Bpan01744-01159, BspAI02518-01245, Bba02069-00708, BspZ00056-00389 |
| X069S-X076D-X185Q | AprE-00498, Chemgen-00748, Bpan01744-00291, DSM14391-01016, BspAI02518-01139, Bba02069-00883, BspZ00056-00042 |
| X069S-X076D-X218S | AprE-01403, Chemgen-01054, Bpan01744-00736, DSM14391-01013, BspAI02518-00870, Bba02069-00684, BspZ00056-00873 |
| X069S-X076D-X259P | AprE-01829, Chemgen-00744, Bpan01744-00888, DSM14391-01012, BspAI02518-01219, Bba02069-00683, BspZ00056-00151 |
| X069S-X078N-X166Q | AprE-01830, Chemgen-00861, BspAI02518-01205, Bba02069-00505 |
| X069S-X078N-X185Q | AprE-00788, Chemgen-00860, Bpan01744-01154, DSM14391-00883, Bba02069-00844 |
| X069S-X078N-X218S | AprE-01693, Chemgen-00859, Bpan01744-01162, DSM14391-01014, BspAI02518-01207, Bba02069-00736 |
| X069S-X078N-X259P | AprE-01873, Chemgen-00756, Bpan01744-01779, DSM14391-00474, Bba02069-00114 |
| X069S-X166Q-X185Q | AprE-00666, Bpan01744-00174, BspAI02518-01166, Bba02069-00703, BspZ00056-00110 |
| X069S-X166Q-X218S | AprE-00996, Chemgen-00862, Bpan01744-01885, DSM14391-01007, BspAI02518-01201, Bba02069-01832, BspZ00056-00500 |
| X069S-X166Q-X259P | AprE-01117, Chemgen-00753, BspAI02518-01151, Bba02069-00704, BspZ00056-00704 |
| X069S-X185Q-X218S | AprE-00594, Chemgen-00659, Bpan01744-00963, DSM14391-01105, BspAI02518-01215, Bba02069-01679 |
| X069S-X185Q-X259P | AprE-00758, Chemgen-00863, DSM14391-00882, Bba02069-00930, BspZ00056-00693 |
| X069S-X218S-X259P | AprE-01807, Chemgen-00864, Bpan01744-01174, DSM14391-00264, BspAI02518-01202, Bba02069-00700, BspZ00056-00705 |
| X076D-X078N-X166Q | AprE-01805, Chemgen-00645, Bpan01744-00228, BspAI02518-01199, Bba02069-00247, BspZ00056-00297 |
| X076D-X078N-X185Q | AprE-00774, Bpan01744-01182, DSM14391-01018, BspAI02518-00999, Bba02069-00822 |
| X076D-X078N-X218S | AprE-01407, Chemgen-00865, Bpan01744-01173, DSM14391-01021, BspAI02518-00507, Bba02069-00815 |
| X076D-X078N-X259P | AprE-01118, Chemgen-00866, Bpan01744-01957, DSM14391-01019, BspAI02518-01218, Bba02069-00423, BspZ00056-00088 |
| X076D-X166Q-X185Q | AprE-00920, BspAI02518-01210, Bba02069-00699, BspZ00056-00257 |
| X076D-X166Q-X218S | AprE-01802, Chemgen-00770, Bpan01744-01170, DSM14391-01100, BspAI02518-01211, Bba02069-00698, BspZ00056-00837 |

TABLE 41-continued

Variants of AprE, Chemgen, DSM14391, BspZ00056, Bba02069, BspAI02518, and Bpan01744 subtilisins with shared features

| Shared feature in BPN' numbering | Variants with shared feature |
|---|---|
| X076D-X166Q-X259P | AprE-01819, Chemgen-01542, BspAI02518-01212, Bba02069-01319, BspZ00056-00133 |
| X076D-X185Q-X218S | AprE-00912, Chemgen-00771, Bpan01744-01292, DSM14391-00473, BspAI02518-01124, Bba02069-01333, BspZ00056-01030 |
| X076D-X185Q-X259P | AprE-01836, Bpan01744-01289, BspAI02518-01132, Bba02069-01321, BspZ00056-00377 |
| X076D-X218S-X259P | AprE-01817, Chemgen-00846, DSM14391-00162, BspAI02518-01122, Bba02069-01323, BspZ00056-00491 |
| X078N-X166Q-X185Q | AprE-00974, Chemgen-00847, BspAI02518-02142, Bba02069-00190 |
| X078N-X166Q-X218S | AprE-01722, Chemgen-00763, Bpan01744-01294, DSM14391-01090, BspAI02518-01128, Bba02069-00817 |
| X078N-X166Q-X259P | AprE-01816, BspAI02518-01119, Bba02069-00043 |
| X078N-X185Q-X218S | AprE-00904, Bpan01744-01717, DSM14391-00170, BspAI02518-01114, Bba02069-00493 |
| X078N-X185Q-X259P | AprE-00891, Chemgen-00849, Bpan01744-00034, DSM14391-01086, BspAI02518-01263, Bba02069-00005 |
| X078N-X218S-X259P | AprE-01112, Chemgen-00768, Bpan01744-01952, DSM14391-00263, BspAI02518-01115, Bba02069-00051 |
| X166Q-X185Q-X218S | AprE-00698, Chemgen-00765, Bpan01744-00899, DSM14391-00893, BspAI02518-01265, Bba02069-01324 |
| X166Q-X185Q-X259P | AprE-00694, Chemgen-00870, BspAI02518-01117, Bba02069-01335, BspZ00056-00710 |
| X166Q-X218S-X259P | AprE-01815, Chemgen-00880, DSM14391-01445, BspAI02518-01116, Bba02069-01328, BspZ00056-00238 |
| X185Q-X218S-X259P | AprE-00646, Chemgen-00767, Bpan01744-01867, DSM14391-00872, Bba02069-01329, BspZ00056-01490 |

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

We claim:

1. A subtilisin variant having subtilisin protease activity and sharing at least 70% amino acid sequence identity with any one of SEQ ID NO: 8, 9, 10, 11, 12, 13, 14, 15, 16, 17, 18, 19, or 22, wherein the variant comprises the mutations X040E, X078N, and X166Q, wherein the positions are numbered by correspondence with the amino acid sequence of SEQ ID NO: 1, wherein the variant does not have 100% sequence identity to a naturally-occurring amino acid sequence.

2. The subtilisin variant of claim 1, wherein the variant has at least one, two, or more additional mutations selected from the group consisting of X003V, X009E, X024Q, X069S, X076D, X079I, X087D, X118R, X124I, X128S, X129P, X130S, X145R, X182E, X185Q, X210I, X217L, X218S, X248D, and X259P, wherein the positions are numbered by correspondence with the amino acid sequence of SEQ ID NO: 1, wherein the variant does not have 100% sequence identity to a naturally-occurring amino acid sequence.

3. The subtilisin variant of claim 1, wherein said variant is derived from a parent or reference polypeptide sharing at least 70%, 75%, 80%, 85%, 86%, 87%, 88%, 89%, 90%, 91%, 92%, 93%, 94%, 95%, 96%, 97%, 98%, 99%, or 100% amino acid sequence identity with any one of SEQ ID NO: 8, 9, 10, 11, 12, 13, 14, 15, 16, 17, 18, 19, or 22.

4. The subtilisin variant of claim 1, wherein said variant comprises an amino acid sequence sharing at least 75%, 80%, 85%, 86%, 87%, 88%, 89%, 90%, 91%, 92%, 93%, 94%, 95%, 96%, 97%, 98%, or 99% amino acid sequence identity with any one of SEQ ID NO: 8, 9, 10, 11, 12, 13, 14, 15, 16, 17, 18, 19, or 22.

5. The subtilisin variant of claim 1, wherein said variant has improved stability when compared to a reference subtilisin lacking the mutations X040E, X078N, and X166Q numbered by correspondence with the amino acid sequence of SEQ ID NO: 1.

6. The subtilisin variant of claim 5, wherein the improved stability is measured as (i) a performance index (PI) of 1.1 or greater after 20 minutes at 30-70 degrees Celsius in a 10% detergent solution in comparison to a respective parent from which the variant is derived or (ii) an improved residual activity of at least 10% greater in comparison to the respective parent from which the variant is derived under the same assay conditions.

7. The subtilisin variant of claim 6, wherein the improved stability is measured as (i) a PI of 1.1 or greater after 20 minutes at 30-70 degrees Celsius in 10% detergent solution without protease-stabilizers in comparison to the respective parent from which the variant is derived or (ii) an improved residual activity of at least 10% greater in comparison to the respective parent from which the variant is derived under the same assay conditions in a 10% detergent solution without protease-stabilizers.

8. The subtilisin variant of claim 1, wherein the subtilisin variant has a cleaning performance index (PI) value of 1.0 or greater in comparison to a reference subtilisin.

9. A polynucleotide comprising a nucleotide sequence that encodes the subtilisin variant of claim 1, wherein said polynucleotide is optionally isolated.

10. An expression vector or cassette comprising the polynucleotide of claim 9.

11. The expression vector or cassette of claim 10, wherein the polynucleotide is operably linked to a promoter.

12. A recombinant host cell comprising the expression vector or cassette of claim 10.

13. A composition comprising one or more subtilisin variant according to claim 1.

14. The composition according to claim 13, wherein said composition is selected from the group consisting of an enzyme composition and a detergent composition.

15. The composition according to claim 14, wherein said detergent composition is selected from the group consisting of a laundry detergent, a fabric softening detergent, a dish-washing detergent, and a hard-surface cleaning product.

16. The composition of claim 13, wherein said composition further comprises one or more ions selected from calcium and/or zinc; one or more enzyme stabilizer from 0.001 to 1.0 weight % of said subtilisin variant; one or more bleaching agent; one or more adjunct material; and/or one or more additional enzymes or enzyme derivatives selected from the group consisting of acyl transferases, alpha-amylases, beta-amylases, alpha-galactosidases, arabinosidases, aryl esterases, beta-galactosidases, carrageenases, catalases, cellobiohydrolases, cellulases, chondroitinases, cutinases, DNase or nuclease, endo-beta-1, 4-glucanases, endo-beta-mannanases, esterases, exo-mannanases, galactanases, glucoamylases, hemicellulases, hyaluronidases, keratinases, laccases, lactases, ligninases, lipases, lipoxygenases, lysozymes, mannanases, oxidases, pectate lyases, pectin acetyl esterases, pectinases, pentosanases, perhydrolases, peroxidases, phenoloxidases, phosphatases, phospholipases, phytases, polygalacturonases, proteases, pullulanases, reductases, rhannogalacturonases, beta-glucanases, tannases, transglutaminases, xylan acetyl-esterases, xylanases, xyloglucanases, xylosidases, metalloproteases, nucleases, additional serine proteases, and combinations thereof.

17. The composition of claim 13, wherein said composition contains phosphate or is phosphate-free and/or contains boron or is boron-free.

18. The composition of claim 13, wherein said composition does not contain a protease stabilizer.

19. The composition of claim 13, wherein said composition is a granular, powder, solid, bar, liquid, tablet, gel, paste or unit dose composition.

20. A method of cleaning, comprising contacting a surface or an item in need of cleaning with the subtilisin variant of claim 1; and optionally further comprising the step of rinsing said surface or item after contacting said surface or item with said variant, wherein, optionally, said item is dishware or fabric.

21. The composition according to claim 14, wherein said enzyme composition is an enzyme granule.

* * * * *